(12) United States Patent
Levy et al.

(10) Patent No.: US 8,173,624 B2
(45) Date of Patent: *May 8, 2012

(54) METHODS OF USING SUBSTITUTED TETRACYCLINE COMPOUNDS TO MODULATE RNA

(75) Inventors: Stuart B. Levy, Boston, MA (US); Michael Draper, Plaistow, NH (US); Mark L. Nelson, Norfolk, MA (US); Graham Jones, Needham, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 1496 days.

This patent is subject to a terminal disclaimer.

(21) Appl. No.: 10/692,764

(22) Filed: Oct. 24, 2003

(65) Prior Publication Data

US 2004/0214800 A1    Oct. 28, 2004

Related U.S. Application Data

(60) Provisional application No. 60/421,248, filed on Oct. 24, 2002.

(51) Int. Cl.
- *A61K 31/65* (2006.01)
- *A61K 31/535* (2006.01)
- *A61K 31/16* (2006.01)
- *A01N 37/18* (2006.01)

(52) U.S. Cl. ............... 514/152; 514/231.5; 514/616

(58) Field of Classification Search .............. None
See application file for complete search history.

(56) References Cited

U.S. PATENT DOCUMENTS

| | | | |
|---|---|---|---|
| 5,563,130 A | 10/1996 | Backer et al. | |
| 5,567,963 A | 10/1996 | Rao | |
| 5,574,026 A | 11/1996 | Backer et al. | |
| 5,668,122 A | 9/1997 | Fife et al. | |
| 5,837,696 A | 11/1998 | Golub et al. | |
| 5,843,925 A | 12/1998 | Backer et al. | |
| 5,843,995 A | 12/1998 | Rana et al. | |
| 5,856,315 A | 1/1999 | Backer et al. | |
| 5,900,235 A | 5/1999 | Gosselin et al. | |
| 6,100,248 A | 8/2000 | Golub et al. | |
| 6,500,812 B2 | 12/2002 | Nelson et al. | |
| 6,617,318 B1 | 9/2003 | Nelson et al. | |
| 6,624,168 B2 | 9/2003 | Nelson et al. | |
| 6,642,270 B2 | 11/2003 | Nelson et al. | |
| 6,683,068 B2 | 1/2004 | Nelson et al. | |
| 6,818,634 B2 | 11/2004 | Nelson et al. | |
| 6,818,635 B2 | 11/2004 | Nelson et al. | |
| 6,833,365 B2 | 12/2004 | Levy et al. | |
| 6,841,546 B2 | 1/2005 | Draper et al. | |
| 6,846,939 B2 | 1/2005 | Nelson et al. | |
| 6,849,615 B2 | 2/2005 | Nelson et al. | |
| 7,001,918 B2 | 2/2006 | Huss et al. | |
| 7,045,507 B2 | 5/2006 | Draper et al. | |
| 7,935,687 B2 * | 5/2011 | Berniac et al. | 514/152 |
| 2002/0045603 A1 | 4/2002 | Golub et al. | |
| 2002/0128237 A1 | 9/2002 | Nelson et al. | |
| 2002/0128238 A1 | 9/2002 | Nelson et al. | |
| 2002/0132798 A1 | 9/2002 | Nelson et al. | |
| 2003/0166585 A1 | 9/2003 | Draper et al. | |
| 2003/0186281 A1 | 10/2003 | Hillen | |
| 2003/0215873 A1 | 11/2003 | Alekshun et al. | |
| 2003/0219407 A1 | 11/2003 | Ding et al. | |
| 2004/0033996 A1 | 2/2004 | Nelson et al. | |
| 2004/0048835 A1 | 3/2004 | Nelson et al. | |
| 2004/0063674 A1 | 4/2004 | Levy et al. | |
| 2004/0092490 A1 | 5/2004 | Draper et al. | |
| 2004/0138183 A1 | 7/2004 | Nelson et al. | |
| 2004/0152674 A1 | 8/2004 | Levy et al. | |
| 2004/0157806 A1 | 8/2004 | Nelson et al. | |
| 2004/0214801 A1 | 10/2004 | Nelson et al. | |
| 2004/0242548 A1 | 12/2004 | Draper et al. | |
| 2004/0266740 A1 | 12/2004 | Huss et al. | |
| 2005/0020545 A1 | 1/2005 | Draper et al. | |
| 2005/0026875 A1 | 2/2005 | Nelson et al. | |
| 2005/0026876 A1 | 2/2005 | Nelson et al. | |
| 2005/0038002 A1 | 2/2005 | Nelson et al. | |
| 2005/0070510 A1 | 3/2005 | Draper et al. | |
| 2005/0119235 A1 | 6/2005 | Nelson et al. | |
| 2005/0137174 A1 | 6/2005 | Ohemeng et al. | |
| 2005/0143352 A1 | 6/2005 | Nelson et al. | |
| 2005/0143353 A1 | 6/2005 | Nelson et al. | |
| 2005/0148551 A1 | 7/2005 | Nelson et al. | |
| 2005/0187198 A1 | 8/2005 | Nelson et al. | |
| 2005/0215532 A1 | 9/2005 | Levy et al. | |
| 2005/0250744 A1 | 11/2005 | Levy et al. | |
| 2005/0288262 A1 | 12/2005 | Bandarage et al. | |
| 2009/0118269 A1 | 5/2009 | Berniac et al. | 514/231.5 |

FOREIGN PATENT DOCUMENTS

| | | |
|---|---|---|
| EP | 1241160 A1 | 9/2002 |
| WO | WO-92/12717 A2 | 8/1992 |
| WO | WO-98/31224 A1 | 7/1998 |
| WO | WO-99/30720 A1 | 6/1999 |
| WO | WO-99/49871 A1 | 10/1999 |
| WO | WO-00/28983 A1 | 5/2000 |
| WO | WO-01/87823 A1 | 11/2001 |
| WO | WO 03/005971 A2 | 1/2003 |
| WO | WO-03/030819 A2 | 4/2003 |
| WO | WO-2004014434 A1 | 2/2004 |
| WO | WO-2004026246 A2 | 4/2004 |
| WO | WO-2004032843 A2 | 4/2004 |

OTHER PUBLICATIONS

Liu et al (The lipophilicity, Pharmacokinetics, and Cellular Uptake of Different Chemically-Modified Tetracyclines (CMTs). Current medicinal Chemistry, 2001. 8:243-252).* Yrjanheikki et al (Tetracyclines Inhibit Microglial Activation and are Neuroprotective in Global Brain Ischemia. PNAS, 1998. 95:15769-15574).*

Pruss et al (Inducible nitric oxide synthase does not mediate brain damage after transient focal cerebral ischemia in mice. Journal of Cerebral Blood Flow and Metabolism, 2007).*

Fonager et al (Transcription and alternative splicing in the yir multigene family of the malaria parasite Plasmodium y. yoelii: identification of motifs suggesting epigenetic and post-transcriptional control of RNA expression. Molecular Biochemical Parasitology, 2007, 156(1):1-11).*

(Continued)

*Primary Examiner* — Janet Epps-Smith
(74) *Attorney, Agent, or Firm* — Mintz Levin Cohn Ferris Glovsky and Popeo, P.C.; Heidi A. Erlacher

(57) ABSTRACT

A method for modulating RNA with tetracycline compounds is described.

17 Claims, 1 Drawing Sheet

OTHER PUBLICATIONS

Chakkalakal et al (Molecular, cellular and pharmacological therapies for Duchenne/Becker muscular dystrophies. The FASEB Journal, 2005. 19(8):880-91).*

Hertweck et al (inhibition of nuclear pre-mRNA splicing by antibiotics in vitro. European Journal of Biochemistry, 2002. 269:175-183).*

Gentamicin C-PubChem; http://pubchem.ncbi.nlm.nih.gov/summary/summary.cgi?cid=72396.*

Andreassi et al. Human Molecular Genetics, 2001, vol. 10, No. 24, pp. 2841-2849.*

Amin, A.R. et al, "Post-transcriptional regulation of inducible nitric oxide synthase mRNA in murine macrophages by doxycycline and chemically modified tetracyclines," *FEBS*, vol. 410(2):259-264 (1997).

Friedman, Kenneth J. et al, "Correction of Aberrant Splicing of the Cystic Fibrosis Transmembrane Conductance Regulator (*CFTR*) Gene by Antisense Oligonucleotides," *The Journal of Biological Chemistry*, vol. 274(51):36193-36199 (1999).

Hertweck, Maren et al, "Inhibition of nuclear pre-mRNA splicing by antibiotics in vitro," *Eur. J. Biochem.*, vol. 269:175-183 (2002).

Karras, James G. et al, "Deletion of Individual Exons and Induction of Soluble Murine Interleukin-5 Receptor-α Chain Expression through Antisense Oligonucleotide-Mediated Redirection of Pre-mRNA Splicing," *Molecular Pharmacology*, vol. 58:380-387 (2000).

Krawczak, Michael et al, "The mutational spectrum of single base-pair subsititutions in mRNA splice junctions of human genes: Causes and consequences," *Human Genetics*, vol. 90(1-2):41-54 (1992).

Lim, Sharlene R. et al, "Modulation of Survival Motor Neuron Pre-mRNA Splicing by Inhibition of Alternative 3' Splice Site Pairing," *The Journal of Biological Chemistry*, vol. 276(48):45476-45483 (2001).

Liu, Y. et al, "Inhibition of in vitro splicing of a group I intron of Pneumocystis camii," *J. Euk. Microbiol.*, vol. 41:31-38 (1994).

Nakai, K. et al, "Construction of a novel database containing aberrant splicing mutations of mammalian genes," *Gene*, vol. 141(2):171-177 (1994).

Nelson, M. et al, "Tetracyclines in Biology, Chemistry and Medicine," Published by Birkhäuser, pp. 177-196 (2001).

Philips, A.V. et al, "RNA processing and human disease," *Cellular and Molecular Life Sciences*, vol. 57(2):235-249 (2000).

Sazani, Peter et al, "Systemically delivered antisense oligomers upregulate gene expression in mouse tissue," *Nature Biotechnology*, vol. 20:1228-1233 (2002).

Sazani, Peter et al, "Nuclear antisense effects of neutral, anionic and cationic oligonucleotide analogs," *Nucleic Acids Research*, vol. 29(19):3965-3974 (2001).

Schroeder, Renée et al, "Modulation of RNA function by aminoglycoside antibiotics," *The EMBO Journal*, vol. 19(1):1-9 (2000).

Stoss, Oliver et al, "Misregulation of pre-mRNA splicing that causes human diseases. Concepts and therapeutic strategies," *Gene Therapy and Molecular Biology*, vol. 5:9-30 (2000).

Wei, Yi et al, "Tetracycline Induces Stabilization of mRNA in *Bacillus subtilis*," *Journal of Bacteriology*, vol. 184(4):889-894 (2002).

Wilton, S.D. et al, "Specific removal of the nonsense mutation from the mdx dystrophin mRNA using antisense oligonucleotides," *Neuromuscular Disorders*, vol. 9(5):330-338 (1999).

"Families of Spinal Muscular Atrophy and Paratek Pharmaceuticals Expand Drug Discovery Collaboration for Spinal Muscular Atrophy", http://www.paratekpharm.com/m_press.html, XP-002492415, 2 pages (2007).

"SMA Summit on Drug Development, Session 7: Identification of Tetracycline Compounds That Correct Defective SMN2 Splicing", http://www.fsma.org/research/clinical/smadrugsummit/smadrugsummitslides/, (2007).

Sumner, C.J. "Therapeutics Development for Spinal Muscular Atrophy", *J. Am. Soc. Exp. NeuroTherap.*, 3(2):235-245 (2006).

Attur, Mukundan G., "Tetracycline Up-Regulates COX-2 Expression and Prostaglandin $E_2$ Production Independent of its Effect on Nitric Oxide", *Journal of Immunology*, 162, 3160-3167 (1999).

Kloppenburg, Margreet, "The Tetracycline Derivative Minocycline Differentially Affects Cytokine Production by Monocytes and T Lymphocytes", *Antimicrobial Agents and Chemotherapy*, 40(4), 934-940 (1996).

Rasmussen, Beth, "Molecular Basis of Tetracycline Action: Identification of Analogs whose Primary Target is not the Bacterial Ribosome", *Antimicrobial Agents and Chemotherapy*, 35(11), 2306-2311 (1991).

Wilson, R. G., et al., "Comparative Inhibition of Nuclear RNA Synthesis in Cultured Mouse Leukemia L1210 Cells by Adriamycin and 4'-Epi-Adriamyclin", *Chemico-Biological Interactions*, 37(3), pp. 351-363 (1981).

Chuang, L.F., et al., "Selective Inhibition of Eukaryotic RNA Polymerase: A Possible New Mechanism of Antitumor Drug Action", *Database Medline (Online)*, US National Library of Medicine (*NLM*), Bethesda, MD, US (1984).

* cited by examiner

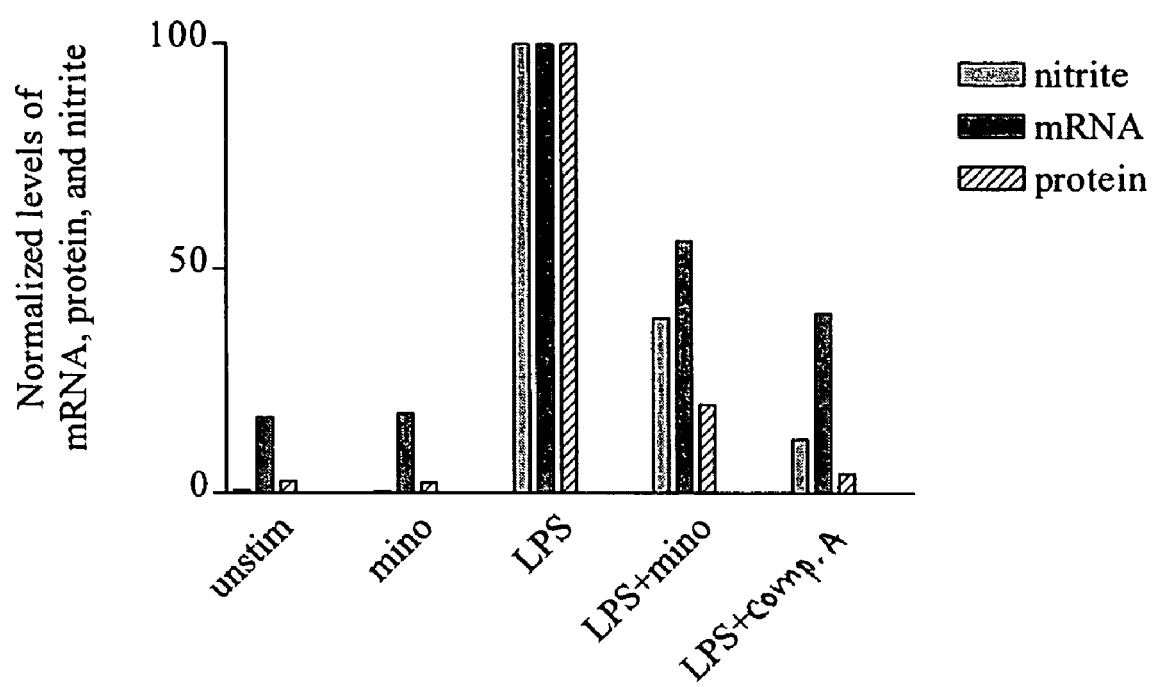

METHODS OF USING SUBSTITUTED TETRACYCLINE COMPOUNDS TO MODULATE RNA

RELATED APPLICATIONS

This application claims priority to U.S. Provisional Patent Application Ser. No. 60/421,248, filed Oct. 24, 2002, incorporated herein by reference in its entirety.

BACKGROUND

Molecules of RNA are transcribed from DNA. RNA molecules are relatively short compared to DNA molecules. RNA transcripts that direct the synthesis of protein molecules are called messenger RNA (mRNA) molecules, while other RNA transcripts serve as transfer RNAs (tRNAs) or form the RNA components of ribosomes (rRNA) or smaller ribonucleoprotein particles.

The amount of RNA-made from a particular region of DNA is controlled by gene regulatory proteins that bind to specific sites on DNA close to the coding sequence of a gene. In any cell at any given time, some genes are used to make RNA in very large quantities while other genes are not transcribed at all. For an active gene thousands of RNA transcripts can be made from the same DNA segment in each cell generation. Because each mRNA molecule can be translated into many thousands of copies of a polypeptide chain, the information contained in a small region of DNA can direct the synthesis of millions of copies of a specific protein.

In eukaryotes, a primary RNA transcript is synthesized; this transcript contains both introns and exons. Intron sequences are cut out and exon sequences on either side of an intron are joined together by RNA splicing.

The translation of mRNA into protein depends on a set of small RNA molecules known as transfer RNAs (tRNAs), each about 80 nucleotides in length. A tRNA molecule has a folded three-dimensional conformation that is held together in part by noncovalent base-pairing interactions like those that hold together the two strands of the DNA helix. In the single-stranded tRNA molecule, however, the complementary base pairs form between nucleotide residues in the same chain, which causes the tRNA molecule to fold up in a unique way.

The codon recognition process by which genetic information is transferred from mRNA via tRNA to protein depends on the same type of base-pair interactions that mediate the transfer of genetic information from DNA to DNA and from DNA to RNA. The mechanics of ordering the tRNA molecules on the mRNA require a ribosome. Each ribosome is a large protein-synthesizing machine on which tRNA molecules position themselves so as to read the genetic message encoded in an mRNA molecule. The ribosome first finds a specific start site on the mRNA that sets the reading frame and determines the amino-terminal end of the protein. Then, as the ribosome moves along the mRNA molecule, it translates the nucleotide sequence into an amino acid sequence one codon at a time, using tRNA molecules to add amino acids to the growing end of the polypeptide chain. When a ribosome reaches the end of the message, both it and the freshly made carboxyl end of the protein are released from the 3' end of the mRNA molecule into the cytoplasm.

Although most tRNAs are initially synthesized as a larger precursor RNA, an RNA molecule has been shown to play the major catalytic role in an RNA-protein complex that recognizes these precursors and cleaves them at specific sites. A catalytic RNA sequence also plays an important part in the life cycle of many plant viroids. Most remarkably, ribosomes are now suspected to function largely by RNA-based catalysis, with the ribosomal proteins playing a supporting role to the ribosomal RNAs (rRNAs), which make up more than half the mass of the ribosome. The large rRNA by itself, for example, has peptidyl transferase activity and catalyzes the formation of new peptide bonds.

The development of compositions and methods for modulation of RNA would be of great benefit in modulating numerous cellular processes and in the treatment of disorders.

SUMMARY OF THE INVENTION

In one embodiment, the invention pertains at least in part, to methods for modulating RNA. The method includes contacting an RNA molecule or a cellular component with a substituted tetracycline, such that modulation of RNA occurs.

In yet another embodiment, the invention includes a method for treating a subject for a disorder treatable by modulation of RNA or by modulation of RNA in combination with a second agent (DTMR). The method includes administering to the subject an effective amount of a tetracycline compound, or with a tetracycline compound in combination with a second agent such that the DTMR is treated. In further embodiments, the effective amount is effective to modulate translation, the half-life, message translocation, the binding of proteins, or splicing of the subject's RNA.

BRIEF DESCRIPTION OF THE DRAWINGS

FIG. 1 is a bar graph depicting variations of iNOS mRNA, protein, and nitrite levels in LPS stimulated mouse macrophages.

DETAILED DESCRIPTION OF THE INVENTION

I. Methods for Modulating RNA

In one embodiment, the invention pertains at least in part, to methods for modulating RNA. The method includes contacting an RNA molecule, or a cellular component, with a tetracycline compound, such that modulation of RNA occurs. In certain embodiments, the RNA molecule is located within a subject.

The term "modulate," "modulating" or "modulation" includes increasing, decreasing, or otherwise changing the level, amount, function, structure, and/or activity of a particular molecule of RNA.

The term "modulating RNA" or "modulation of RNA" includes modulation of all functions, structures, amounts, and/or activities of RNA which can be modulated by substituted tetracycline compounds of the invention. Modulation of RNA includes, for example, modulation of transcription, translation, translocation, catalysis, secondary structure, splicing, stability, etc. The term also includes modulations of the half-life of RNA. RNA can be modulated within an organism, cell, intracellular space, nucleus and/or other cellular compartment.

In one embodiment, a specific RNA molecule can be modulated, e.g., a specific type of RNA (such as mRNA or rRNA) and/or an mRNA specifying a particular protein can be modulated, while other mRNA molecules are not affected. In another embodiment, RNA molecules in general, e.g., several different types of RNA can be modulated and/or a plurality of mRNA molecules specifying different proteins, can be modulated according to the invention.

Modulation of RNA can occur directly, e.g., by modulation of RNA itself, for example by binding of tetracycline to the RNA (for example to alter its secondary structure) or indirectly, e.g., by binding of a molecule to a component of a cell, e.g., a protein with which the RNA interacts. For example, the tetracycline compound may interact with a particular protein necessary for the synthesis of an RNA molecule or with a protein molecule with which the RNA molecule interacts (e.g., a ribosomal protein), and thus modulate the RNA without directly binding to the RNA itself.

Examples of RNA molecules which may be modulated using the methods of the invention include, but are not limited to, hnRNA, mRNA, tRNA, ribosomal RNA, nuclear RNA, snRNA, and small RNA aptamers.

The RNA may also be e.g., RNA from a prokaryotic cell, a eukaryotic cell or may be viral RNA.

The term "cellular component" includes cells (in vivo and in vitro), cellular organelles (e.g., ribosomes, nuclei, mitochondria, chloroplasts, etc.), cytoplasm, etc. In a further embodiment, the cells are located within a subject. In another embodiment, the cells are in vitro. In another further embodiment, the cellular component comprises RNA. In a further embodiment, the cellular component is a cell which is associated with (e.g., derived from a subject having or present in a subject having) a particular disorder treatable by modulation of RNA or by modulation of RNA in combination with a second agent (DTMR). For example, when the DTMR is a tumor, the cellular component may be a cell of the tumor.

RNA modulation can occur via a variety of different mechanisms. Exemplary mechanisms are listed below.

In one embodiment, RNA is modulated by direct interaction with a tetracycline molecule (e.g., Berens. 2001. Tetracyclines in Biology, Chemistry and Medicine ed. By M. Nelson, W. Hillen and R. A. Greenwald, pp 177-196). Preferably, "modulation of RNA" as used herein excludes interaction of a tetracycline molecule with the 30S ribosomal subunit of a bacterial cell. In another preferred embodiment, binding to 16S RNA and the proteins S4, S7, S9, and S17 are preferentially excluded from the term "modulation of RNA".

In one embodiment, the RNA is modulated by altering RNA transcription. For example, tetracycline compound may inhibit or decrease the transcription of an mRNA. In another embodiment, a tetracycline compound may inhibit transcription.

Levels of transcription can be measured in the presence and the absence of a tetracycline compound using techniques that are known in the art. Transcription of a specific gene can be measured or genome-wide transcription (transcription of many genes) can be detected. For example, in one embodiment, transcription levels can be detected by performing nascent-chain run-on analysis. This technique is known in the art and requires using $P^{32}$ labeled nucleotides; genes with high transcription levels can be detected by intensity. In another example, transcription of a reporter gene, e.g., luciferase which is easily detectable, can be operably linked to a gene of interest. Detection of light will indicate transcription of the gene of interest. Other exemplary methods for measuring transcription include Northern blots and in situ hybridization. Detection of transcription levels of more than one gene can be performed using, e.g., microarrays (e.g., cDNA or synthetic oligonucleotide arrays) or PCR.

In one embodiment, the RNA is modulated by altering RNA translation. For example, tetracycline compound may inhibit or decrease the translation of a mRNA. In one embodiment, a tetracycline compound may inhibit RNA translation by inhibiting its initiation. In another embodiment, a tetracycline compound may inhibit translation by altering the point at which translation terminates. For example, in one embodiment a tetracycline compound can cause a ribosome to skip a termination codon and continue translation.

In one embodiment, the level of a specific protein translated from mRNA can be measured using standard techniques. For example, in vitro or in situ analysis of enzyme activity can be measured, if the protein is an enzyme. In vitro analysis can include activity in bulk protein extracts, or after electrophoresis to partially separate the enzyme from other proteins. In another example, in vitro or in situ analysis can be performed using immunochemical methods, i.e., employing a labeled antibody specific for the protein. Quantification/visualization of the antibody can the be performed. Western blots can be performed after electrophoresis or cellular extracts or components can be assayed directly, e.g., by ELISA or immunoprecipitation. If the protein is sufficiently abundant, it can also be directly visualized after 1D or 2D electrophoresis if it can be separated sufficiently from other proteins by this method.

In one embodiment, the level of mRNA specifying a particular protein can be measured. In another embodiment, the level of total mRNA can be measured. Such measurements can be made using techniques described herein or other techniques known in the art.

In another embodiment, the half-life of RNA is modulated by contacting the cellular component with the tetracycline compound. For example, in one embodiment, the half-life of mRNA is increased. In one embodiment, a tetracycline compound of the invention increases the binding of RNA to a ribosome, thereby increasing the stability of the RNA (Wei and Bechhofer. 2002. J. of Bacteriology 184: 889). In another embodiment, the half-life of mRNA is decreased. In a further embodiment, the tetracycline compound is not tetracycline or otherwise described in Wei and Bechhofer. 2002. J. of Bacteriology 184:889.

For example, in one embodiment, a tetracycline molecule of the invention increases the degradation of a specific mRNA molecule. For example, the half-life of mRNA specifying a protein such as iNOS (Amin et al. 1997. FEBS Letters 410: 259) can be measured. In a further embodiment, the tetracycline compound is not doxycycline, minocycline, or a tetracycline compound described in Amin et al. 1997. FEBS Letters 410:259.

In one embodiment, the half-life of RNA can be measured using in vitro nuclear run-on transcription assays known in the art. Nuclei can be isolated from cells and incubated in vitro with radioactive precursors under conditions where nascent RNA pol II will continue elongation off of the native gene, but will not initiate transcription. The fraction of total incorporated radioactivity in a specific transcript can be measured and a degradation rate constant can be generated. In another embodiment, a kinetic analysis can be performed. For example, radioactive precursors can be provided and, over time, amounts of radioactivity (specific activity) in a particular mRNA can be measured by hybridization with unlabeled cloned DNA. The concentration of mRNA can be followed over time using this method.

In another embodiment, the Kd can be independently assayed by performing a pulse-chase experiment where radioactive precursor is chased out of the cell, and then the decline in radioactivity of mRNA molecules made during the pulse is followed. In yet another example, synthesis and/or degradation rates can be estimated using transcription reporters.

In another embodiment, the RNA can be modulated by modulating the translocation of the RNA. For example, in one embodiment, a tetracycline molecule may interfere with the translocation of an RNA molecule to or from the nucleus of a cell.

Translocation of RNA to the nucleus can be measured, e.g., by nuclear translocation assays in which the emission of two or more fluorescently-labeled species is detected simultaneously. For example, the cell nucleus can be labeled with a known fluorophore specific for DNA, such as Hoechst 33342. The RNA can be directly or indirectly labeled, e.g., fluorescently-labeled antibody specific for RNA. The amount of RNA that translocates to or from the nucleus can be determined by determining the amount of a first fluorescently-labeled species, i.e., the nucleus, that is distributed in a correlated or anti-correlated manner with respect to a second fluorescently-labeled species, i.e., the RNA as described in U.S. Pat. No. 6,400,487, the contents of which are hereby incorporated by reference.

Modulation of RNA also includes modulation of the processing of a particular RNA molecule by splicing. The tetracycline compound may affect the arrangement, or the inclusion, or the exclusion of sections of the RNA by affecting the mechanisms governing splicing. For example, in the case of mRNAs, the tetracycline compound may, for example, promote the inclusion of a particular exon, or promote the exclusion of a particular exon, or cause a particular exon size to become altered, for example, by inclusion of a sequence at the 5' or the 3' ends of the exon. The tetracycline compound may promote the inclusion or the exclusion of an exon containing, for example, a premature stop codon. The tetracycline compound may modulate splicing by, for example, activating cryptic splice sites, or silencing consensus splice sites, or silencing exonic or intronic splicing enhancers (ESEs or ISEs) or by silencing exonic or inronic splicing silencers (ESSs or ISSs), or altering the binding orf a component of the splicing machinery to the RNA, or by affecting the intermolecular interactions between components of the splicing machincery. Examples of RNA splicing are discussed in Stoss et al. (2000), *Gene Ther. Mol. Biol.* 5:9-30; Liu et al. (1994) *J. Euk. Microbiol.* 41:31; Hertweck et al., 2002. *Eur. J. Biochem* 269:1.75.

In another embodiment, the amount of spliced mRNA specifying a particular protein can be measured. In another embodiment, the effect of a tetracycline compound on splicing of RNA can be measured, e.g., using standard assays such as β globin splicing assays (Hertweck et al. 2002. *Eur. J. Biochem.* 269:175). In one embodiment, a particular form of RNA (e.g., an mRNA molecule comprising a particular exon) can be measured in a cell. In a further embodiment, the tetracycline compound is not tetracycline, chlortetracycline, or other tetracycline compounds described in Hertweck et al. 2002. *Eur. J. Biochem.* 269:175 or Liu et al. 1994. *J. Euk. Microbiol.* 41(1):31.

Various spliced forms of mRNA can be detected in a cell using techniques known in the art. For example, in one embodiment, PCR can be performed using primer sets that specifically amplify the products to be detected (see, e.g., Lim and Hertel. 2001 *J. Biol. Chem* 276:45476). In another embodiment, a reporter cell line is used to detect changes in RNA splicing. For example, a cell line such as the 654 EGFP reporter cell line (which comprises a C to T mutation at nucleotide 654 of the human β-globin intron 2 (see, e.g., Sazani et al. 2001. *Nucleic Acids Research* 29:3965). Treatment of these cells with an agent that modulates RNA splicing can restore proper splicing and translation of EGFP, thereby providing a rapid and positive readout for identification of such agents.

In another embodiment, the RNA is modulated by altering the interactions of proteins with the RNA molecule. Examples of proteins which interact with RNA include hnRNP proteins, snRNP proteins, ribosomal proteins, endonucleases, and other enzymes. The substituted tetracycline compound may either promote or inhibit the interactions of particular proteins with RNA. In certain embodiments, the interaction of RNA with another nucleic acid molecule may also be modulated by the interaction of the tetracycline compound.

The ability of the tetracycline compound to modulate binding of an RNA molecule to one or more proteins can also be determined. Determining the ability of the test compound to binding can be accomplished, for example, by coupling the RNA molecule or the protein(s) with a radioisotope or enzymatic label such that binding of the RNA to the protein can be determined by detecting the labeled molecule in a complex. For example, RNA or protein can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product. Alternatively, if the protein with which the RNA interacts is an enzyme, it can be detected without labeling.

In one embodiment, the amount of binding of RNA to the protein target molecule in the presence of the tetracycline compound is greater than the amount of binding of RNA to the target molecule in the absence of the tetracycline compound, in which case the tetracycline compound is identified as a compound that enhances binding of RNA. In another embodiment, the amount of binding of the RNA to the target molecule in the presence of the tetracycline compound is less than the amount of binding of the RNA to the target molecule in the absence of the tetracycline compound, in which case the tetracycline compound is identified as a compound that inhibits the binding of RNA to protein.

In more than one embodiment of the above assay methods of the present invention, it may be desirable to immobilize either RNA or a target protein molecule, for example, to facilitate separation of complexed from uncomplexed forms of one or both of the molecules, or to accommodate automation of the assay. Binding of a tetracycline compound to an RNA molecule, or interaction of an RNA molecule with a protein molecule in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix.

In one embodiment, RNA modulation can be detected in a cell by measuring the effect of a tetracycline compound on the amount or activity of one or more proteins in a cell. Preferably the protein is one associated with a particular disorder in a subject, i.e., is a therapeutically relevant protein.

In another aspect, the invention pertains to a method for treating a subject for a disorder treatable by modulation RNA or by modulation of RNA in combination with a second agent (DTMR). The method includes administering to the subject an effective amount of a substituted tetracycline compound or an effective amount of a substituted tetracycline compound and a second agent (e.g., a chemotherapeutic agent) such that the DTMR is treated.

The term "disorders treatable by modulation of RNA" or "DTMR" includes viral, neurodegenerative and other disorders which are caused or related to RNA function, structure, amounts and/or other activities of RNA which are lower or higher than desired and those disorders treatable by compounds described herein. Examples of DTMR include viral disorders (e.g., retroviral disorders (e.g., HIV, etc.), disorders caused by human rhinovirus RNA and proteins, VEE virus, Venezuelan equine encephalitis virus, eastern X disease, West Nile virus, bacterial spot of peach, camelpox virus, potato leafroll virus, stubborn disease and infectious variegations of citrus seedlings, viral protein synthesis in *Escherichia coli* infected with coliphage MS2, yellow viruses, citrus greening disease, ratoon stunting disease, European yellows of plants, inclusion conjunctivitis virus, meningopneumonitis virus, trachoma virus, hog plague virus, ornithosis virus, influenza virus, rabies virus, viral abortion in ungulates, pneumonitis, and cancer.

Other exemplary DTMRs include disorders caused by, or associated with splicing. For example, some disorders associated with defects in pre-mRNA processing result from a loss of function due to mutations in regulatory elements of a gene. Examples of such mutations are described in Krawczak et al. (1992) *Hum. Genet,* 90:41-54; and Nakai et al. (1994) *Gene* 14:171-177. Other DTMR include disorders which have been attributed to a change in trans-acting factors.

Examples of DTMRs which are associated with splicing include those described in Philips et al. (2000), *Cell. Mol. Life. Sci.,* 57:235-249[()]], for example, spinal muscular atrophy (SMA), as well as, FTDP-17 (frontotemporal dementia with parkinsonism) and β-thalassemia.

Certain DTMRs associated with splicing include those which are generated by point mutations that either destroy splice-sites or generate new cryptic sites in the vicinity of normally used exons. Examples of such DTMRs include cystic fibrosis (Friedman et al. (1999) *J. Biol. Chem.* 274:36193-36199), muscular dystrophy (Wilton et al. (1999) *Neuromuscul. Disord.* 0.9:330-338), and eosinophilic diseases (Karras et al., (2000) *Mol. Pharamcol.* 58:380-387).

Other DTMRs include cancers which may change splicing patterns during cancer formation and progression. Example of such cancers include, but are not limited to leukemia, colon/rectal cancer, myeloid leukemia, breast cancer, gastric carcinomas, acute leukemia, multiple myeloma, myeloid cell leukemia, lung cancer, prostate cancer, etc. Addition DTMRs associated with splicing are discussed in Stoss et al., (2000), *Gene Ther. Mol. Biol.* 5:9-30).

Another example of a DTMR is a cancer in which treatment of the cancer cells with a tetracycline compound results in the modulation of RNA, where the modulation of RNA increases the susceptibility of the cell to a second agent, e.g., a chemotherapeutic agent. Such DTMRs can be treated using a combination of the tetracycline compound and a chemotherapeutic agent. Exemplary cancers include those in which the tetracycline compound modulates the form of BCL expressed by the cells.

Other DTMRs include disorders wherein particular ribozymes are present in aberrant quantities. Examples include breast cancer, hepatitis C virus (HCV), liver cirrhosis, and heptacellular carcinoma.

In a further embodiment, the tetracycline compounds for treating cancer do not include, for example, the tetracycline compounds described in U.S. Pat. Nos. 6,100,248; 5,843,925; 5,837,696; 5,668,122; WO 98/31224; US 20020045603; WO 99/49871; WO 01/87823; WO 00/28983; U.S. Pat. No. 5,574,026; incorporated herein by reference in their entirety.

Other DTMRs include, but are not limited to, asthma, arthritis, anemia, Alzheimer's, Huntington's disease, aortic aneurysm, diabetes, ischemia, hyperlipidemia, and obesity.

In an embodiment, when the DTMR is an aortic aneurysm, the tetracycline compound is not doxycycline. In another embodiment, when the DTMR is Huntington's disease, the tetracycline compound is not minocycline. In another embodiment, when the DTMR is cerebral ischemia, the tetracycline compound is not tetracycline. In other embodiments, when the DTMR is asthma, the tetracycline compound is not minocycline or doxycycline.

In other embodiments, the DTMRs of the invention do not include aortic aneurysm, Huntington's disease, asthma or cerebral ischemia.

The term "subject" with reference to treatment includes humans and other organisms and viruses which have RNA such as plants, animals (e.g., mammals, e.g., cats, dogs, horses, pigs, cows, sheep, rodents, rabbits, squirrels, bears, primates (e.g., chimpanzees and gorillas)).

The language "effective amount" of the tetracycline compound is that amount necessary or sufficient to treat or prevent a DTMR or modulate RNA in a subject. The effective amount can vary depending on such factors as the size and weight of the subject, the particular DTMR, or the particular tetracycline compound. For example, the choice of the tetracycline compound can affect what constitutes an "effective amount". One of ordinary skill in the art would be able to study the aforementioned factors and make the determination-regarding the effective amount of the tetracycline compound without undue experimentation.

The regimen of administration can affect what constitutes an effective amount. The tetracycline compound can be administered to the subject either prior to or after the onset of a disease which is treatable. Further, several divided dosages, as well as staggered dosages, can be administered daily or sequentially, or the dose can be continuously infused, orally administered, administered by inhalation, or can be a bolus injection. Further, the dosages of the tetracycline compound(s) can be proportionally increased or decreased as indicated by the exigencies of the therapeutic or prophylactic situation.

The term "treated," "treating" or "treatment" includes therapeutic- and/or prophylactic treatment. The treatment includes the diminishment or alleviation of at least one symptom associated or caused by the DTMR. For example, treatment can be diminishment of one or several symptoms of a disorder or complete eradication of the DTMR.

In another aspect, the invention pertains to methods for identifying tetracycline compounds for treating DTMR, comprising: contacting a cellular component with a tetracycline compound; measuring the ability of the tetracycline compound to modulate RNA, to thereby identify a tetracycline compound for treating DTMR, either alone or in combination with a second agent.

In one embodiment, the ability of the compound to modulate RNA translation is measured. In another embodiment, the ability of the compound to modulate the half-life of RNA is measured. In another embodiment, the ability of the compound to modulate translocation of RNA is measured. In another embodiment, the ability of the compound to modulate the interaction of RNA with proteins is measured. In another embodiment, modulation of RNA splicing is measured. Modulation of RNA can be detected using any of the methods described herein or other art recognized methods.

II. Substituted Tetracycline Compounds

In one embodiment, the tetracycline compound is a substituted tetracycline compound.

The term "tetracycline compound" includes substituted tetracycline compounds and compounds with a similar ring structure to tetracycline, including minocycline, doxycycline, tetracycline, chlortetracycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

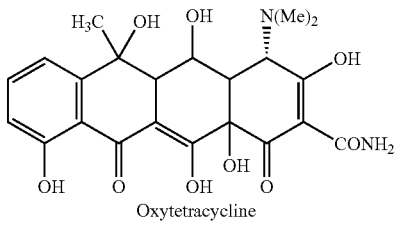
Oxytetracycline

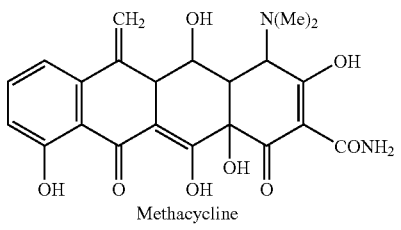
Methacycline

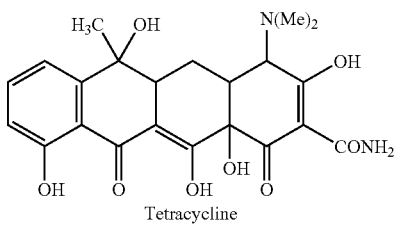
Tetracycline

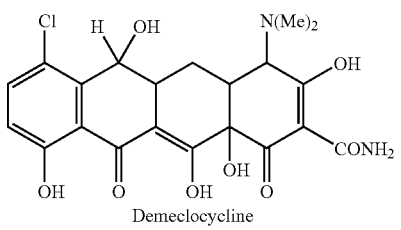
Demeclocycline

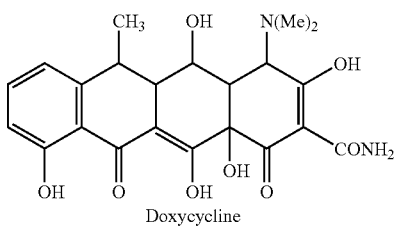
Doxycycline

TABLE 1-continued

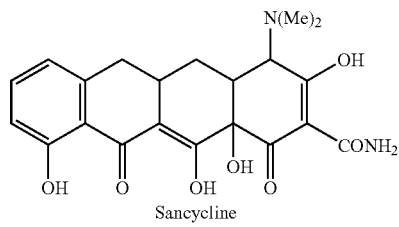
Sancycline

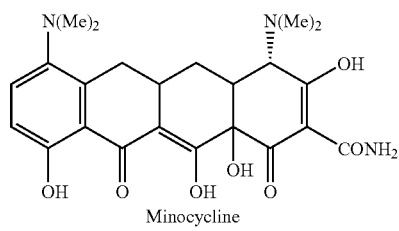
Minocycline

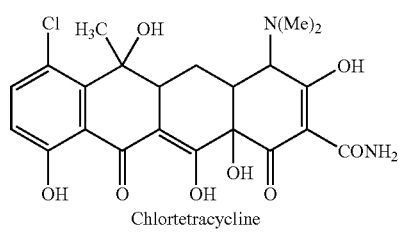
Chlortetracycline

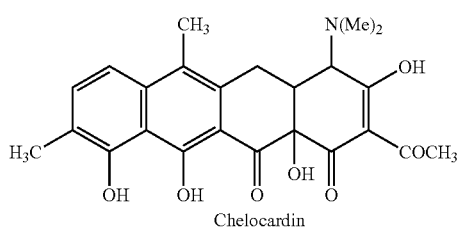
Chelocardin

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a Cl-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a, 6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a,11a dehydro tetracyclines; 11a Cl-6,12 hemiketal tetracyclines; 11a Cl-6-methylene tetracyclines; 6,13 diol tetracyclines; 6-benzylthiomethylene tetracyclines; 7,11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines; 6-α acetoxy-6-demethyl tetracyclines; 6-β acetoxy-6-demethyl tetracyclines; 7,13-epithiotetracyclines; oxytetracyclines; pyrazolotetracyclines; 11a halogens of tetracyclines; 12a formyl and other esters of tetracyclines; 5,12a esters of tetracyclines; 10,12a-diesters of tetracyclines; isotetracycline; 12-a-deoxy-anhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines. In certain embodiments, the term tetracycline compound does not include 7-chlorotetracycline, minocycline, doxycycline, or tetracycline.

The term "tetracycline compounds" includes substituted tetracycline compounds as defined below, and as described in the specification. The tetracycline compounds may or may not have antibacterial or antiinfective activity. In certain embodiments of the invention, the tetracycline compound has antiinfective, antiinflammatory and/or antibacterial activity. In other embodiments of the invention, the tetracycline compound does not have significant antiinfective, antiinflammatory or antibacterial therapeutic activity.

Examples of substituted tetracycline compounds include compounds described in U.S. Pat. Nos. 6,165,999; 5,834,450; 5,886,175; 5,567,697; 5,567,692; 5,530,557; 5,512,553; 5,430,162 each of which is incorporated herein by reference in its entirety. Other examples of substituted tetracycline compounds include those described in, for example, WO 99/37307, WO 02/12170, WO 02/04407, WO 02/04406, WO 02/04404, WO 01/98260, WO 01/98259, WO 01/98236, WO 01/87824, WO 01/74761, WO 01/52858, WO 01/19784, WO 84/01895, U.S. S. No. 60/367,050, U.S. Ser. No. 09/895,797, U.S. S. No. 60/305,546, U.S. S. No. 60/346,930, U.S. S. No. 60/346,929, U.S. S. No. 60/347,065, U.S. S. No. 60/346,956, U.S. S. No. 60/367,049, U.S. Ser. No. 10/097,095, U.S. Ser. No. 10/097,135, U.S. S. No. 60/362,654, U.S. S. No. 60/367, 045, U.S. S. No. 60/366,915, U.S. S. No. 60/367,048, and 10/196,010. Other examples of substituted tetracycline compounds are described in EP 0582810 B1; EP 0536 515B1; EP 0582 789B1; EP 0582 829B1; EP 0582788B1; U.S. Pat. No. 5,530,117; U.S. Pat. No. 5,495,030; U.S. Pat. No. 5,495,018; U.S. Pat. No. 5,494,903; U.S. Pat. No. 5,466,684; EP 0535 346B1; U.S. Pat. No. 5,457,096; U.S. Pat. No. 5,442,059; U.S. Pat. No. 5,430,162; U.S. Pat. No. 5,420,272; U.S. Pat. No. 5,401,863; U.S. Pat. No. 5,401,729; U.S. Pat. No. 5,386, 041; U.S. Pat. No. 5,380,888; U.S. Pat. No. 5,371,076; EP 618 190; U.S. Pat. No. 5,326,759; EP 582 829; EP 528 810; EP 582 790; EP 582 789; EP 582 788; U.S. Pat. No. 5,281, 628; EP 536 515; EP 535 346; WO 96/34852; WO 95/22529A1; U.S. Pat. No. 4,066,694; U.S. Pat. No. 3,862, 225; U.S. Pat. No. 3,622,627; WO 01/87823A1; and WO 00/28983A1. Each of these aforementioned applications and patents are hereby incorporated herein by reference in its entirety. In addition, the invention pertains to each of the compounds described herein, methods of using each of the compounds, and pharmaceutical compositions comprising each of the compounds.

The term "substituted tetracycline compound" includes tetracycline compounds with one or more additional substituents, e.g., at the 1, 2, 3, 4, 5, 6, 7, 8, 9, 10, 11, 11a, 12, 12a or 13 position or at any other position which allows the substituted tetracycline compound of the invention to perform its intended function, e.g., to modulate RNA or treat a DTMR. In certain embodiments, the substituted tetracycline compound is a 7-substituted sancycline compound, a 9-substituted minocycline compound, or a 7,9-substituted sancycline compound. In certain embodiments, the term "substituted tetracycline compound" does not include tetracycline compounds with a chlorine, hydrogen or dimethylamino substituent at the 7-position. In other embodiments, the term "substituted tetracycline compound" does not include compounds with a hydrogen as a 9-position substituent. In other embodiments, the term substituted tetracycline does not include 5-hydroxy tetracycline, 7-chlorotetracycline, 6-demethyl-7-chlorotetracycline, anhydrochlorotetracycline, 4-epi-anhydrochlorotetracycline, or β-chelocardin.

The term "substituted tetracycline compound" also includes substituted tetracycline compounds of the formula (I):

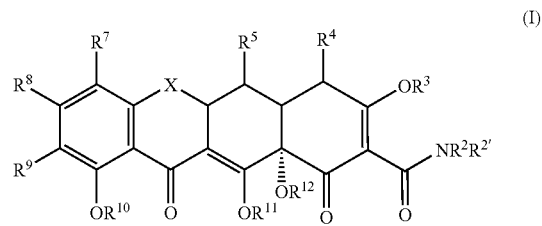

wherein
$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen, alkyl, alkenyl, alkynyl, aryl, substituted carbonyl, or a pro-drug moiety;

$R^4$ is $NR^4R^{4''}$, alkyl, alkenyl, alkynyl, hydroxyl, halogen, or hydrogen;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{7c}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —$(CH_2)_{0-3}NR^{8c}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl alkylsulfonyl, alkylamino, or an arylalkyl;

E is $CR^{8d}R^{8e}$, S, $NR^{8b}$ or O;
E' is O, $NR^{8f}$, or S;
W is $CR^{7d}R^{7e}$, S, $NR^{7b}$ or O;
W' is O, $NR^{7f}$, or S;

X is CHC($R^{13}$Y'Y), C=$CR^{13}$Y C$R^{6'}R^6$, S, N$R^6$ or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is C$R^{9d}R^{9e}$, S, N$R^{9b}$ or O;

Z' is O, S, or N$R^{9f}$, and pharmaceutically acceptable salts, esters and enantiomers thereof.

In a further embodiment, the substituted tetracycline compounds of formula (I) comprise compounds wherein $R^2$, $R^{2'}$, $R^8$, $R^{10}$, $R^{11}$, and $R^{12}$ are each hydrogen, X is C$R^6R^{6'}$, and $R^4$ is N$R^{4'}R^{4''}$, wherein $R^{4'}$ and $R^{4''}$ are each methyl. In addition, $R^9$ may be hydrogen.

In one embodiment, $R^7$ is substituted or unsubstituted aryl, e.g., phenyl or heteroaryl. In a further embodiment, $R^7$ is substituted with one or more substituents which allow the substituted tetracycline compound to perform its intended function, e.g., treat a DTMR or modulate RNA. Examples of such substituents include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl or heterocyclic moiety.

In another embodiment, $R^7$ is substituted or unsubstituted alkenyl. Examples of substituents for alkenyl $R^7$ groups include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl or heterocyclic moiety.

In another embodiment, $R^7$ is substituted or unsubstituted heteroaryl and $R^9$ is alkyl.

In another further embodiment, the substituted tetracycline compound is a substituted minocycline compound, e.g., $R^7$ is dialkylamino. In a further embodiment, $R^9$ is alkylamino. In another embodiment, $R^9$ is —N$R^{9c}$C(=Z')Z$R^{9a}$, wherein $R^{9c}$ is hydrogen, Z' is nitrogen or oxygen, Z is NH, and $R^{9a}$ is aryl or aralkyl.

Examples of tetracycline compounds include:

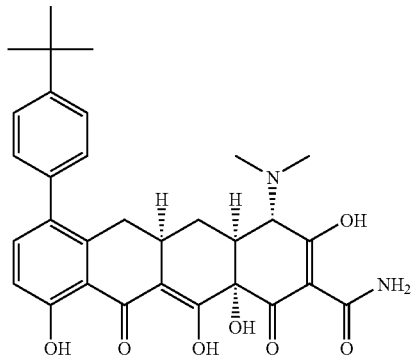

-continued

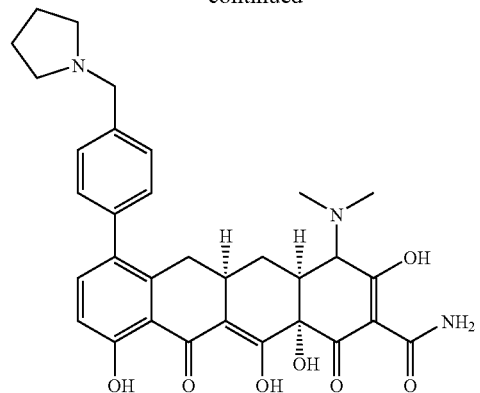

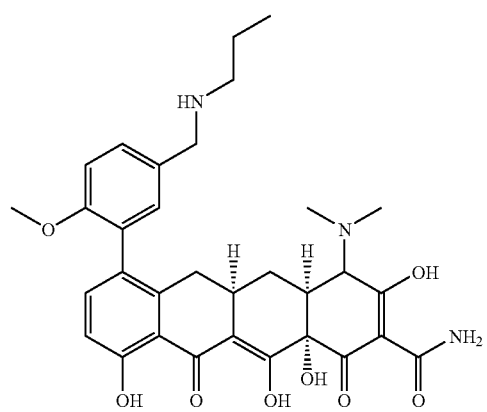

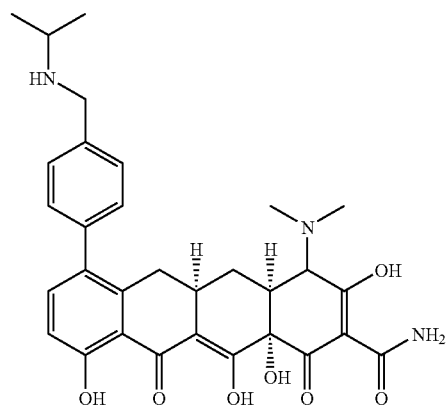

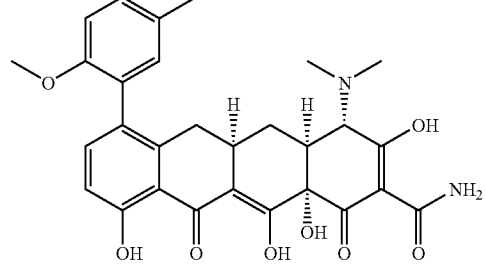

15
-continued
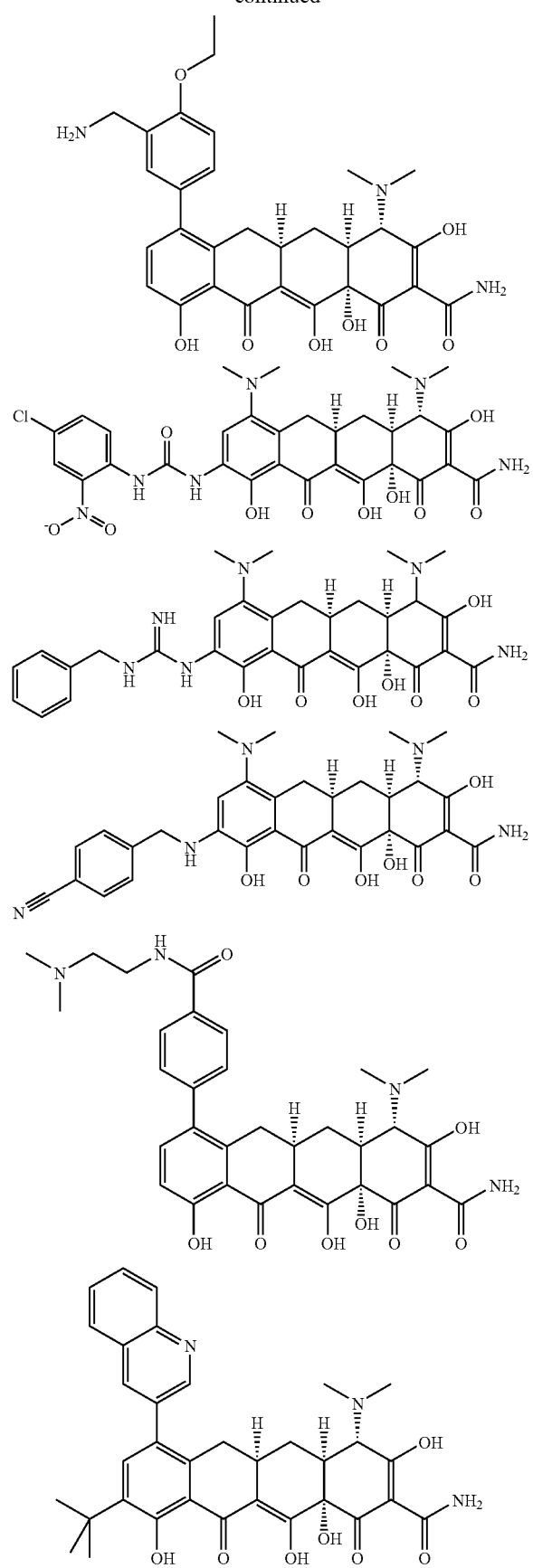
16
-continued
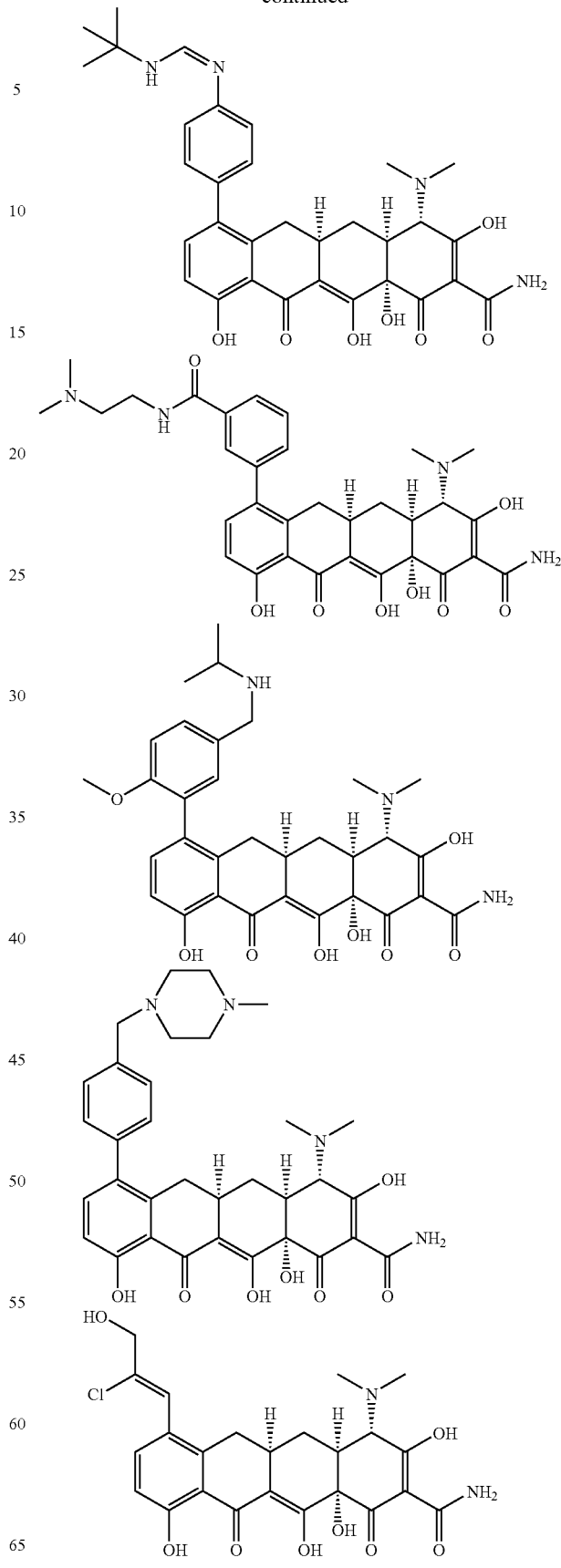

and pharmaceutically acceptable salts, esters, and prodrugs thereof. Other examples of substituted tetracycline compounds are shown in Table 2, below.
TABLE 2
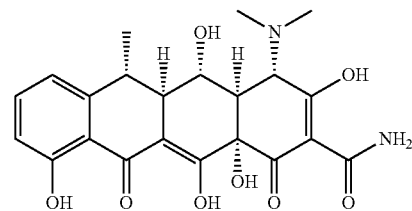
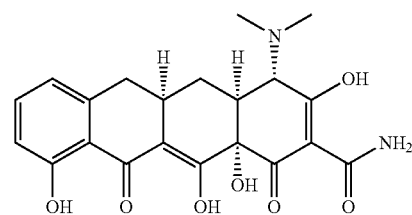
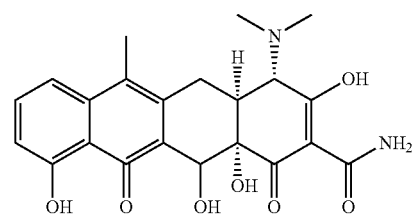
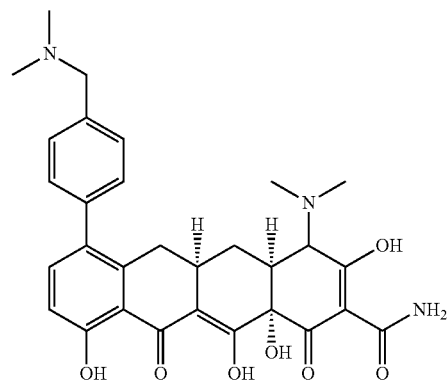
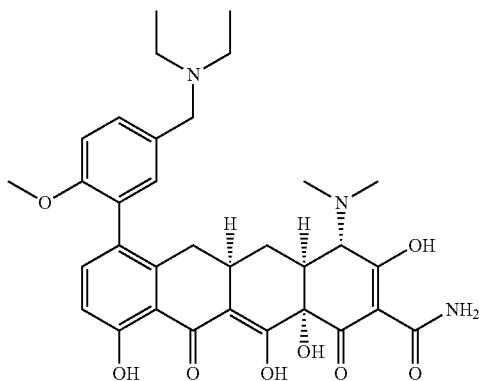

TABLE 2-continued
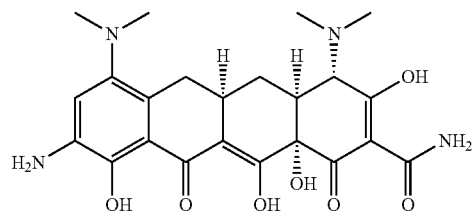
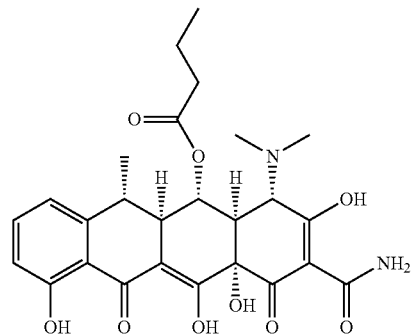
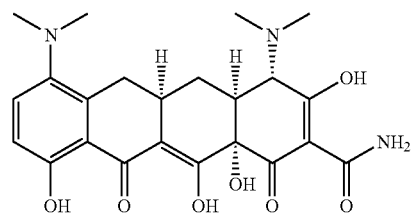
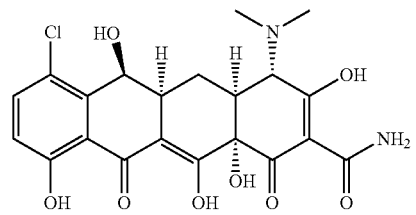
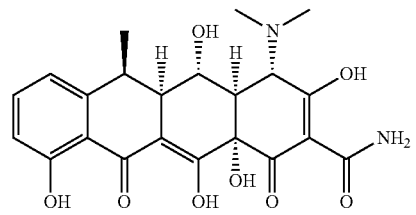
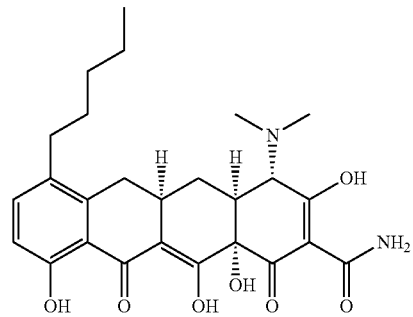

TABLE 2-continued
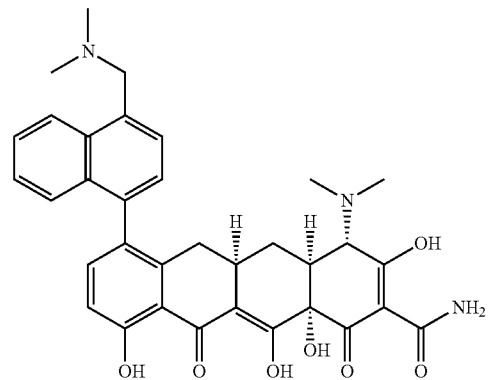
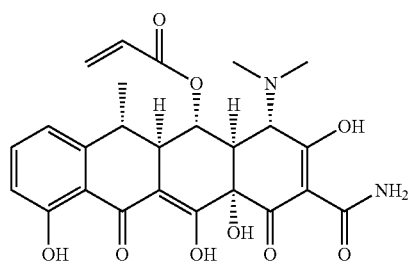
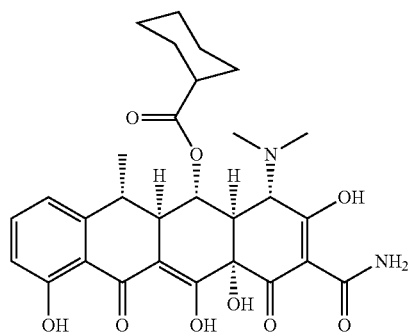
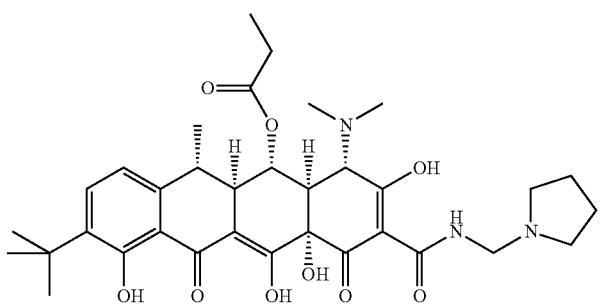
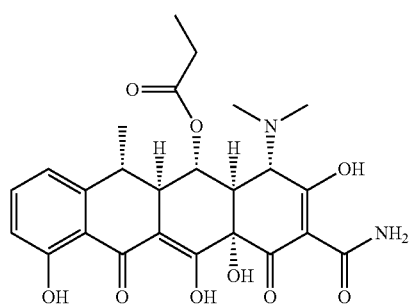

TABLE 2-continued
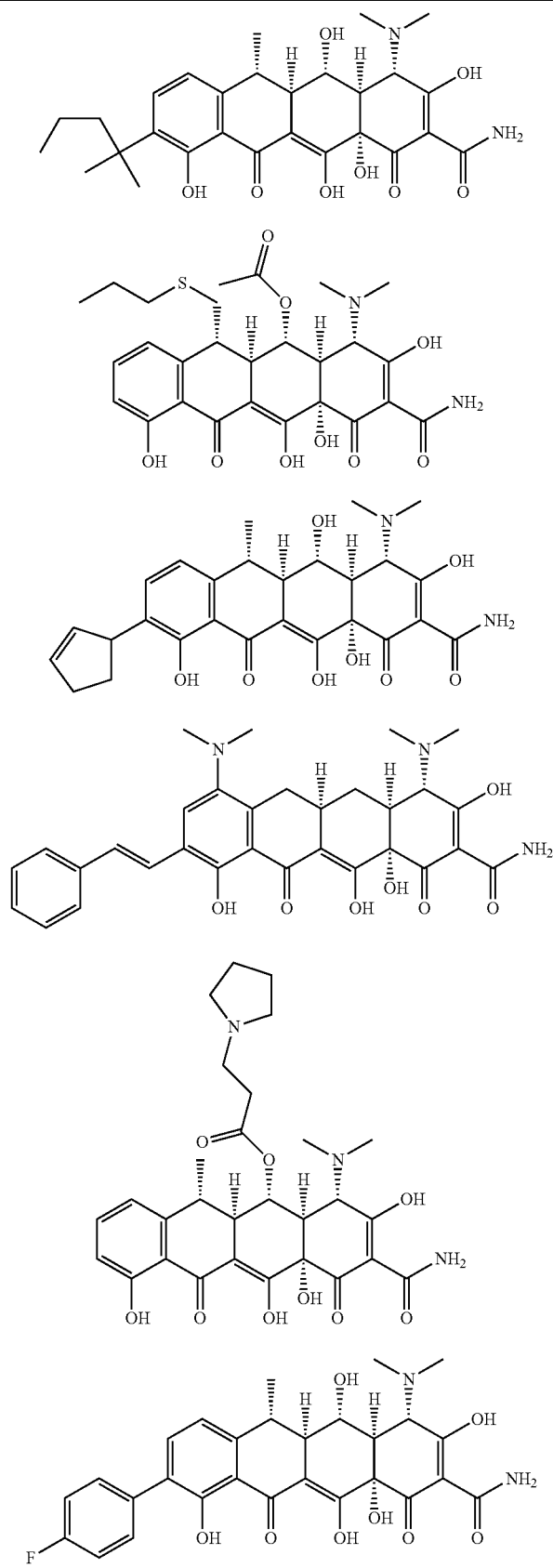

TABLE 2-continued
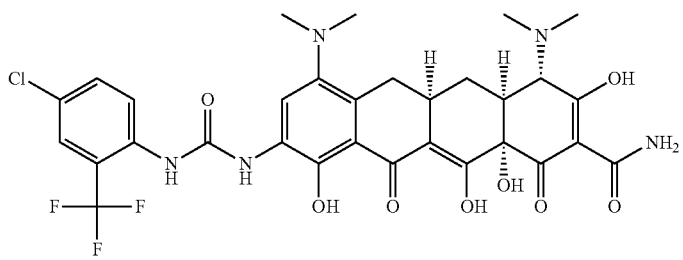
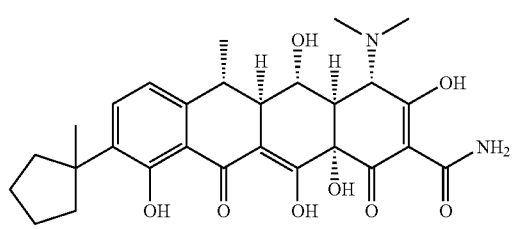
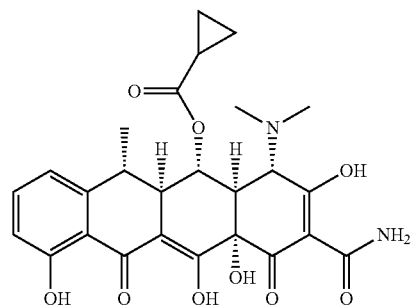
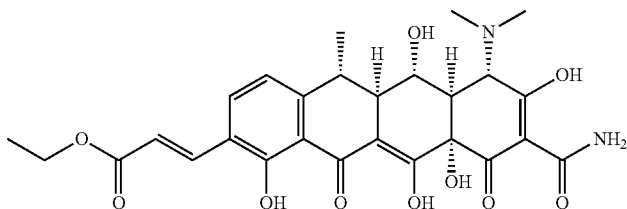
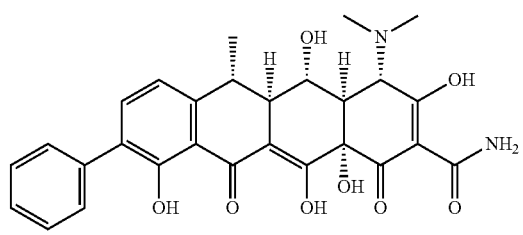
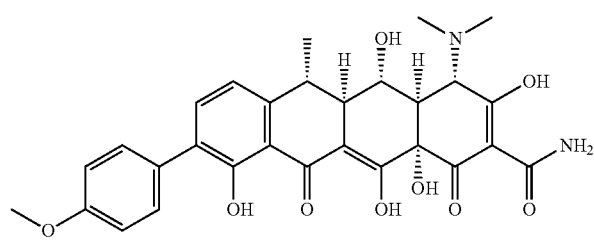

TABLE 2-continued
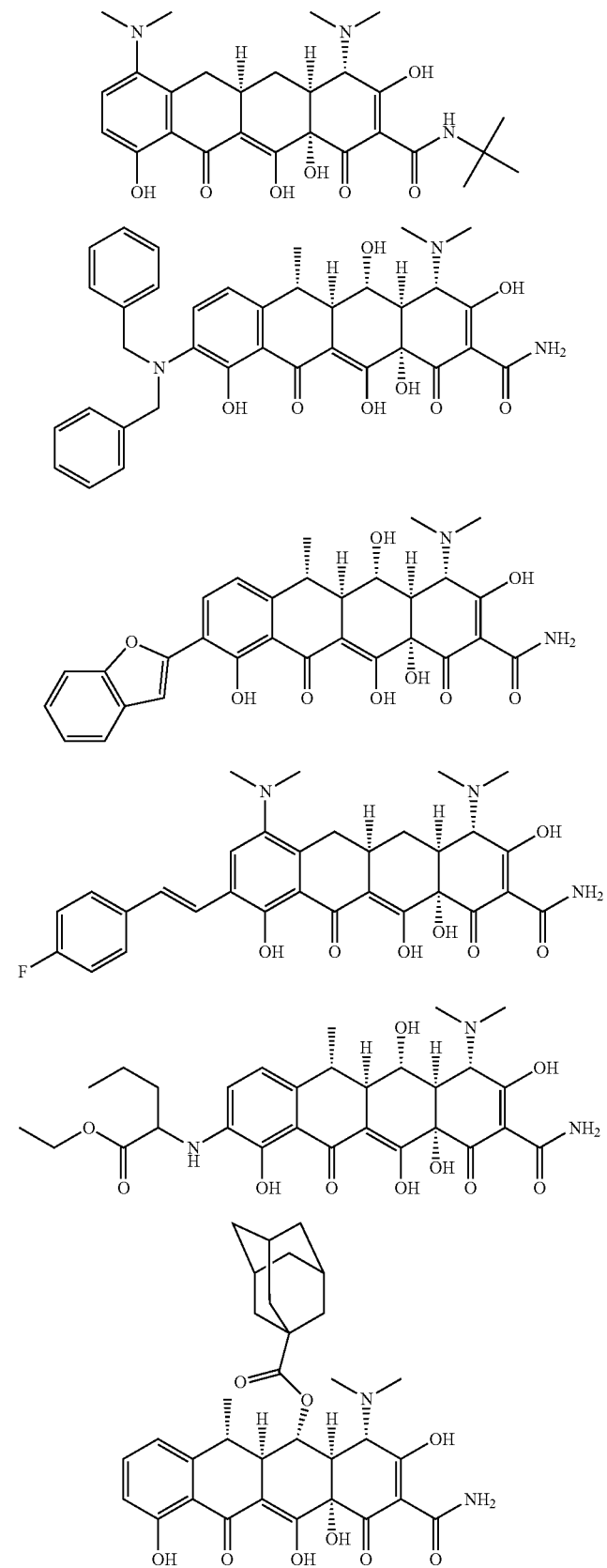

TABLE 2-continued
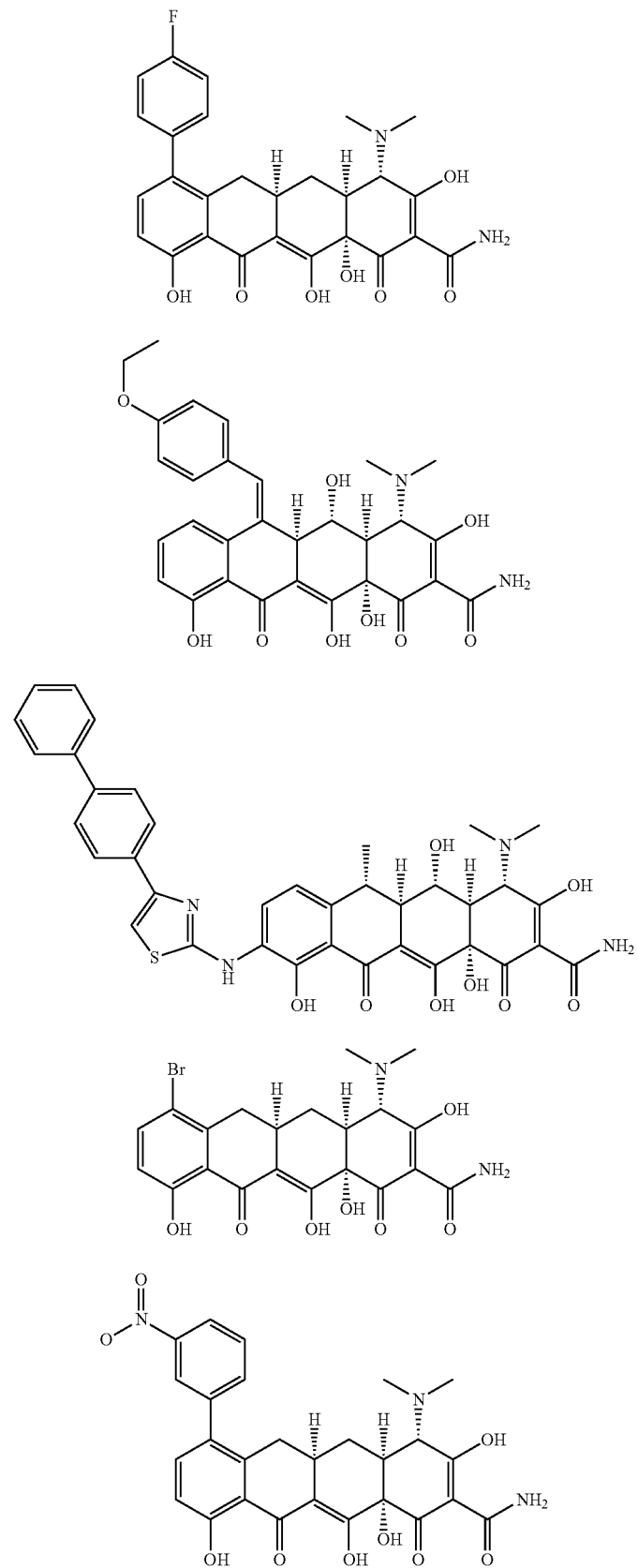

TABLE 2-continued
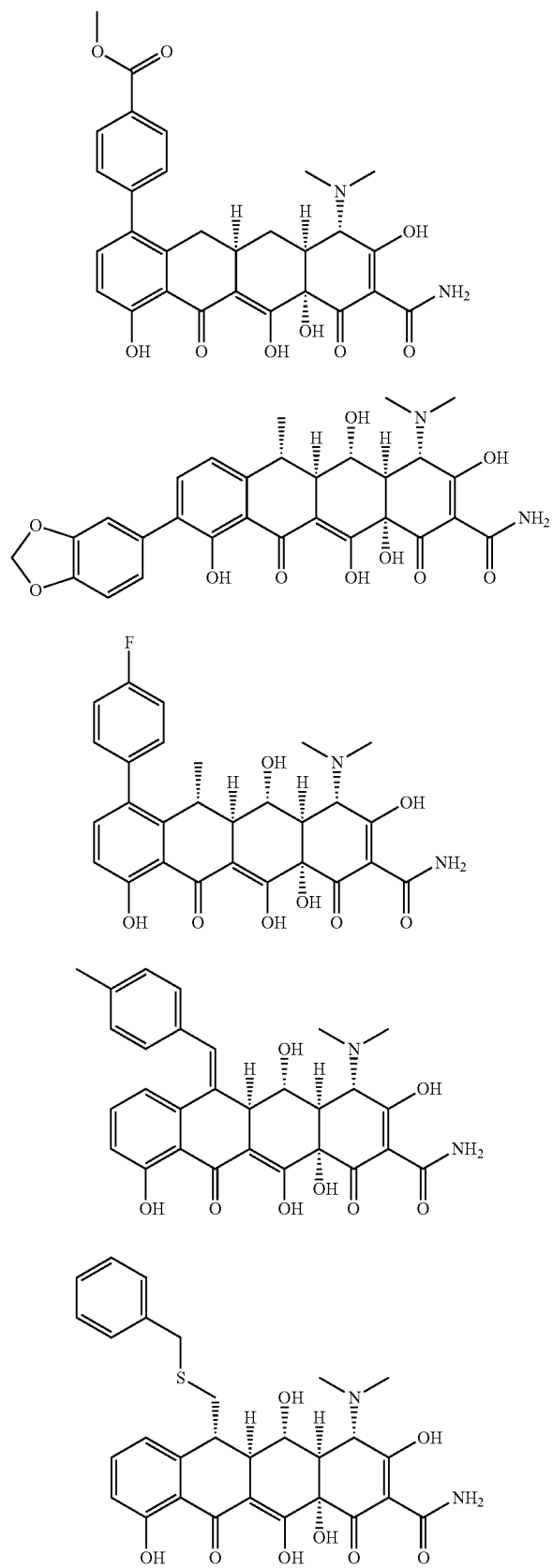

TABLE 2-continued
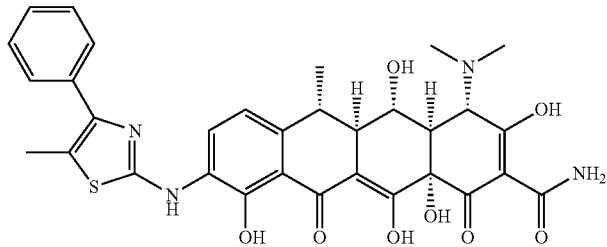
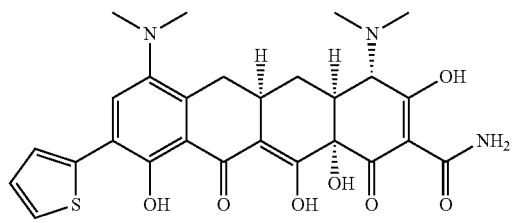
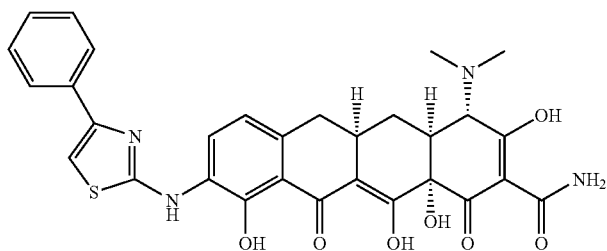
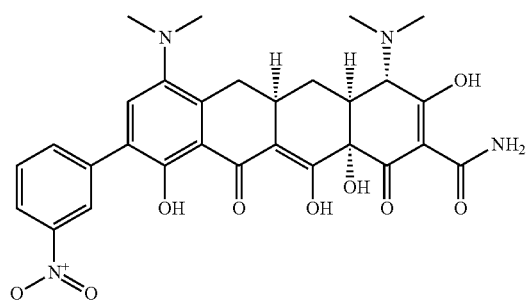
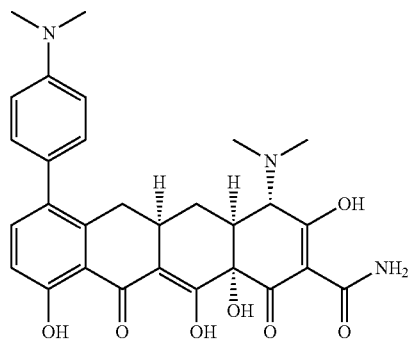

TABLE 2-continued
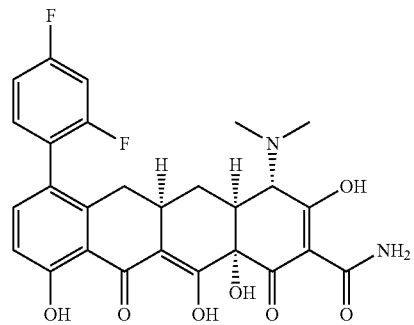
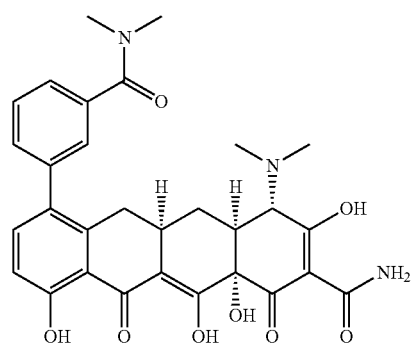
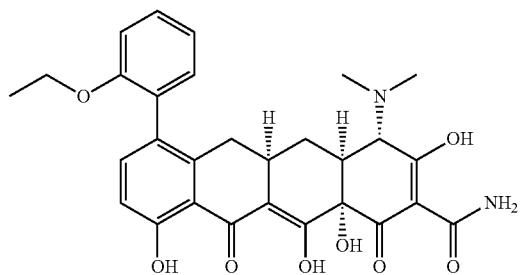
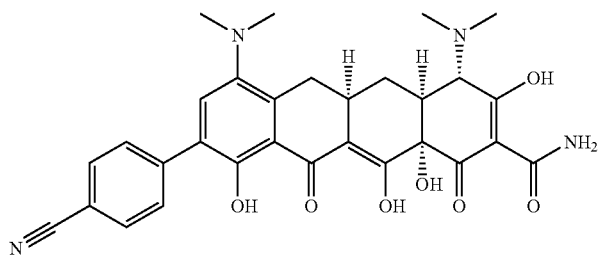
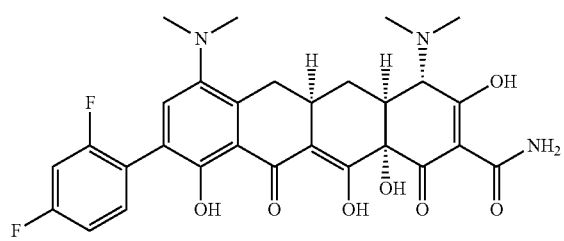

TABLE 2-continued
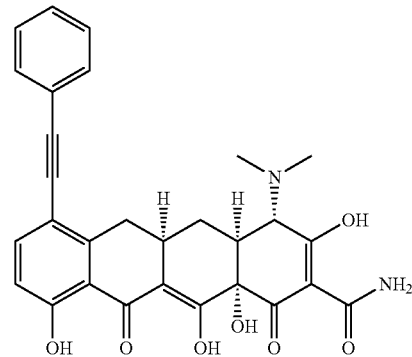
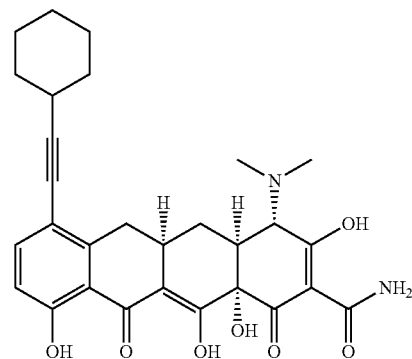
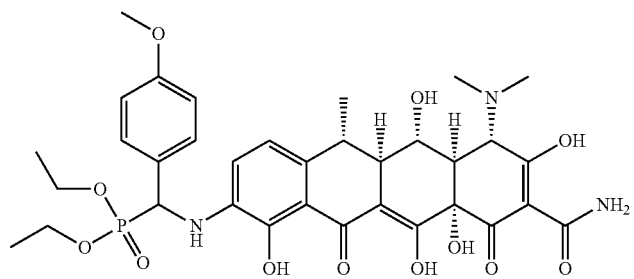
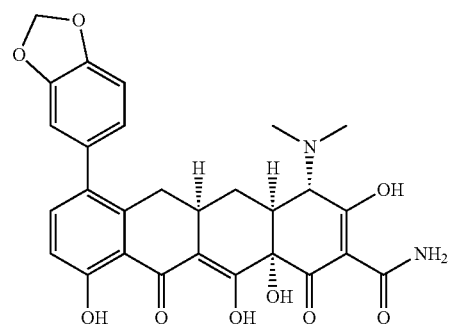
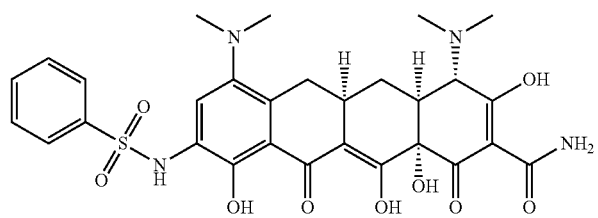

TABLE 2-continued
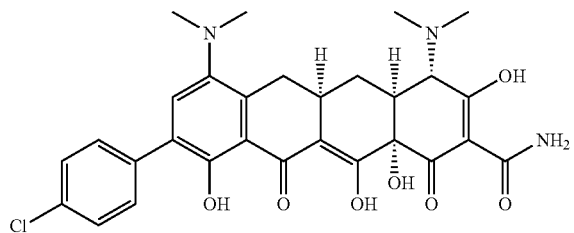
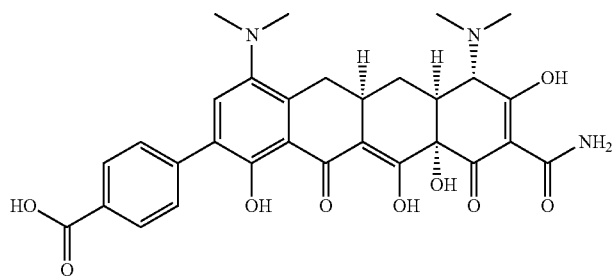
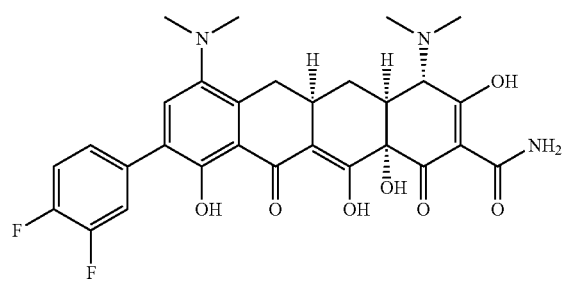
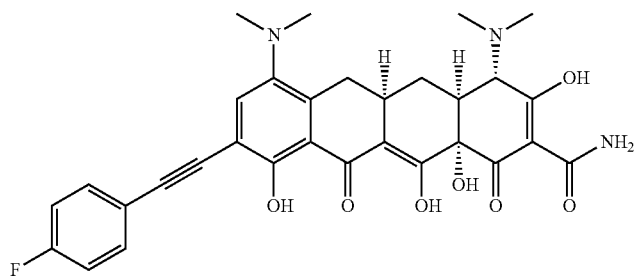
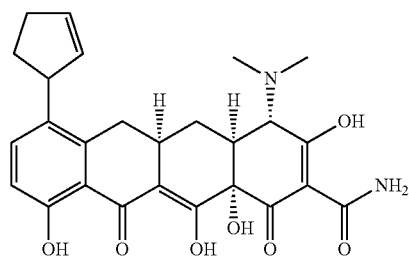

TABLE 2-continued
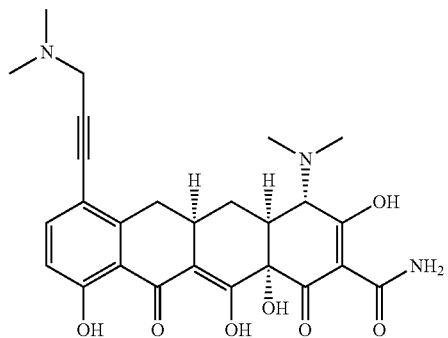
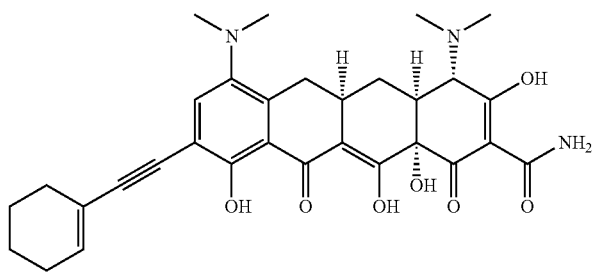
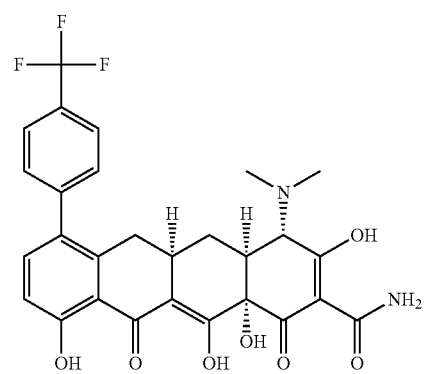
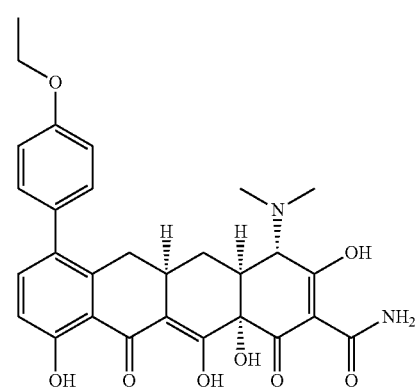

TABLE 2-continued
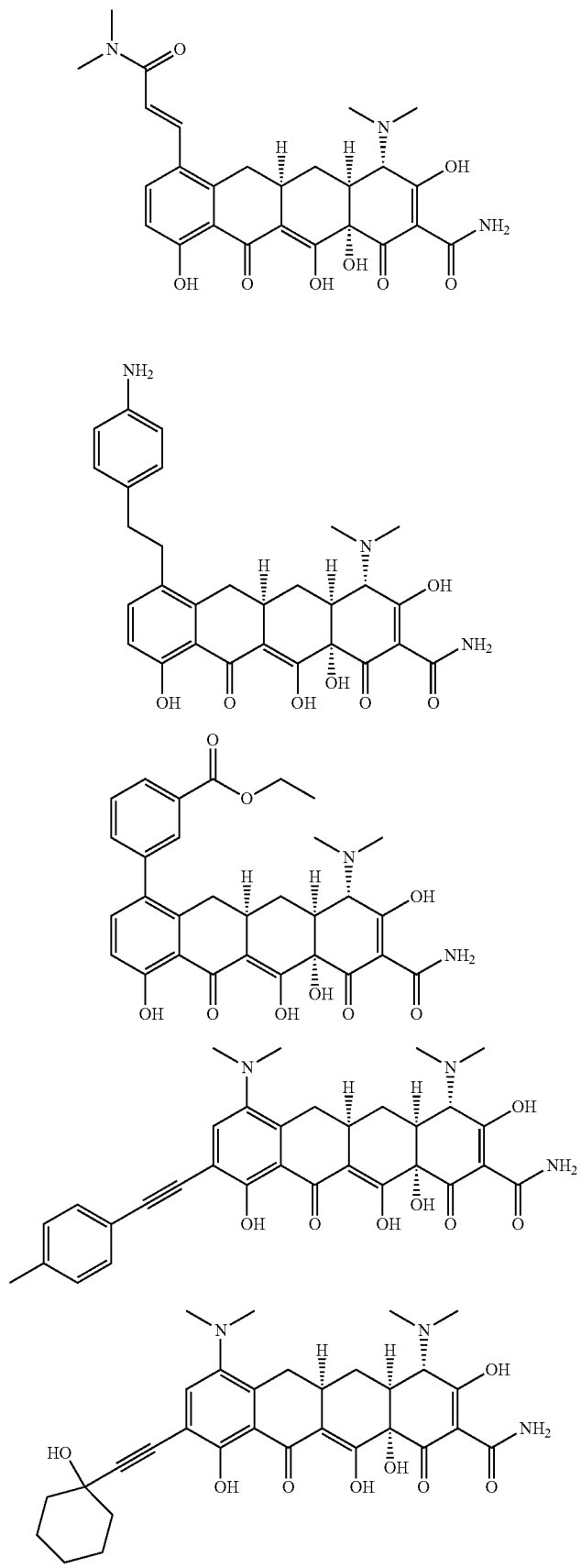

TABLE 2-continued
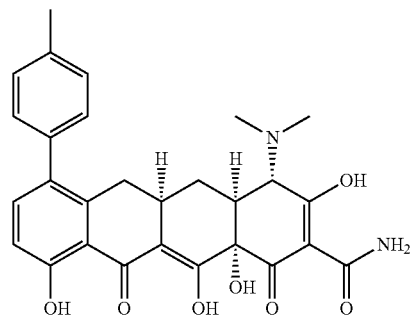
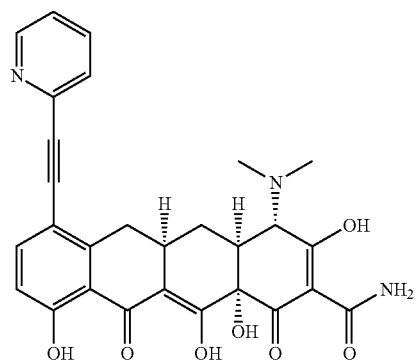
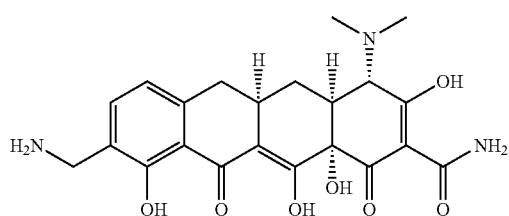
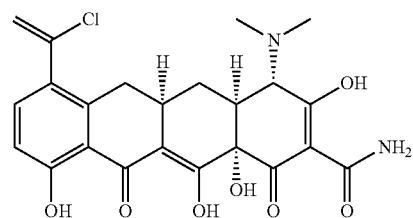
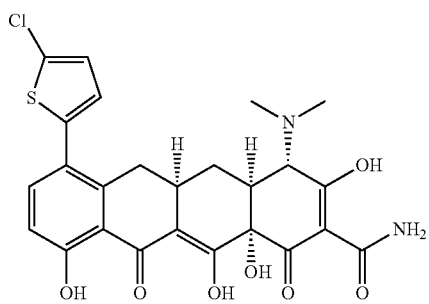

TABLE 2-continued
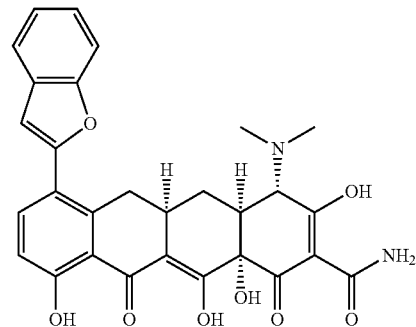
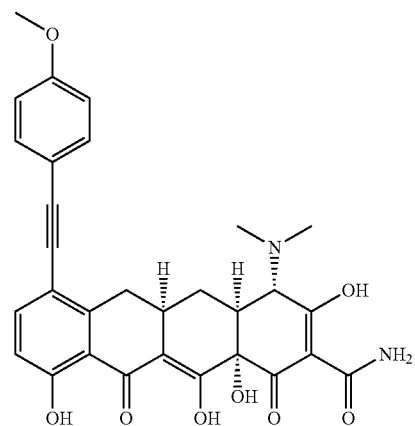
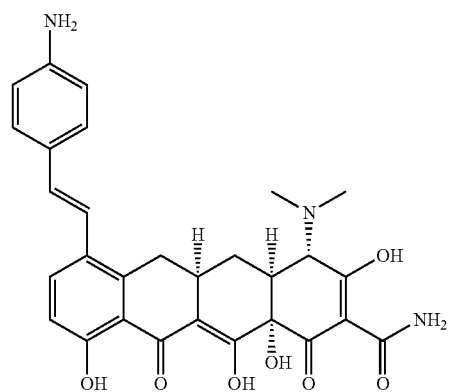
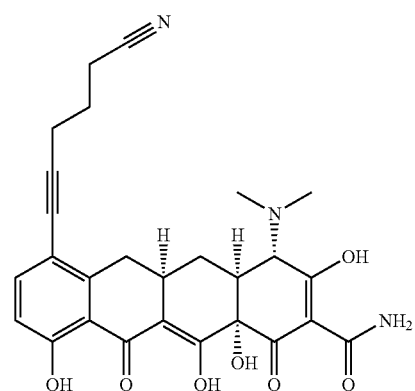

TABLE 2-continued
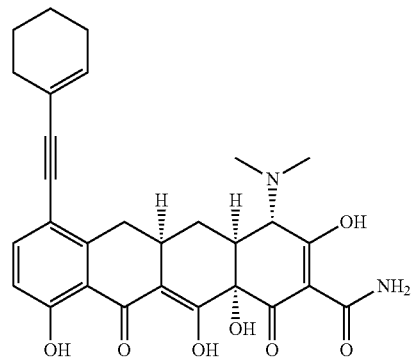
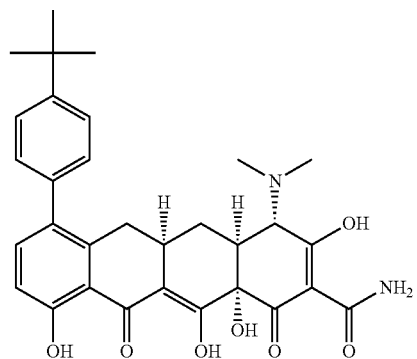
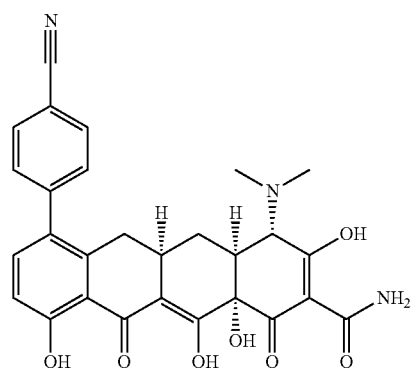
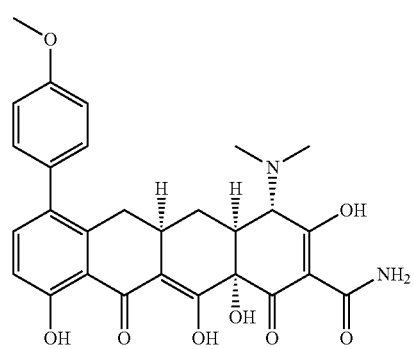

TABLE 2-continued
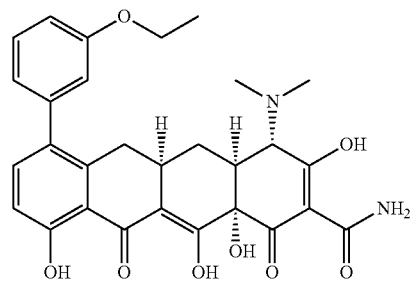
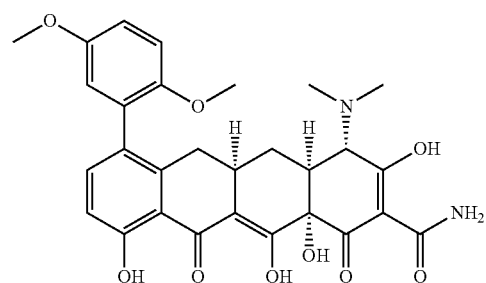
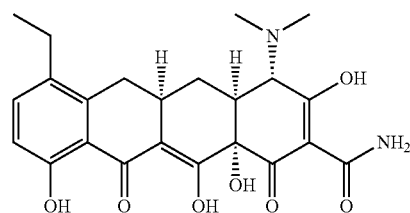
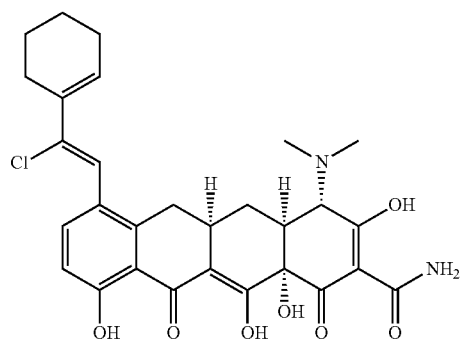
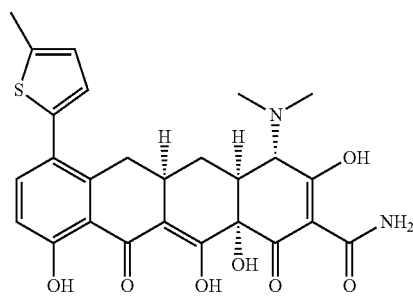

TABLE 2-continued
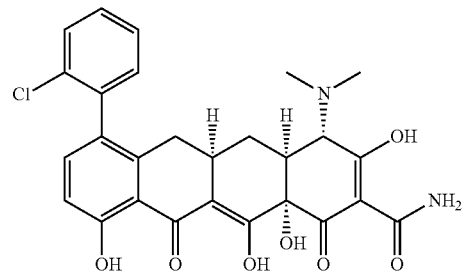
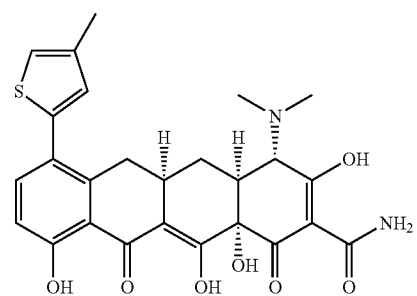
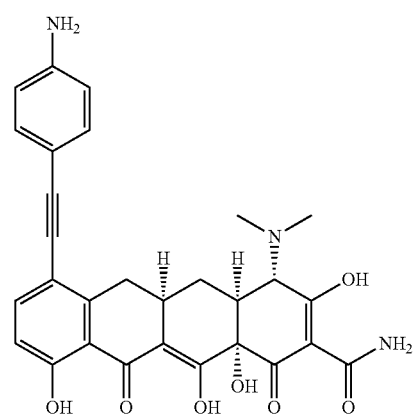
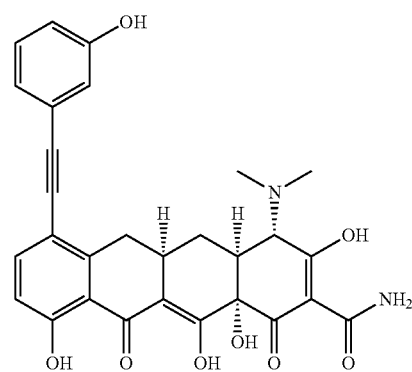

TABLE 2-continued
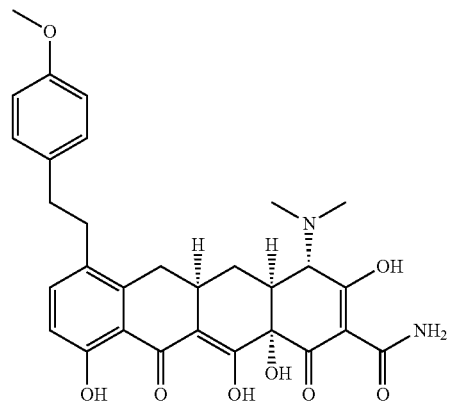
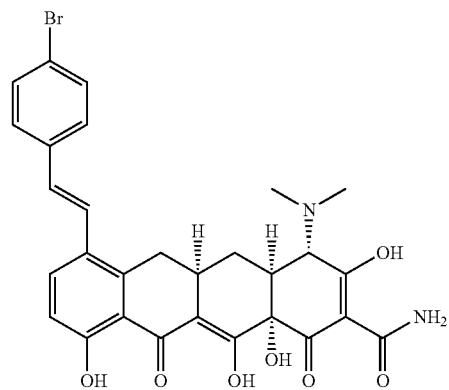
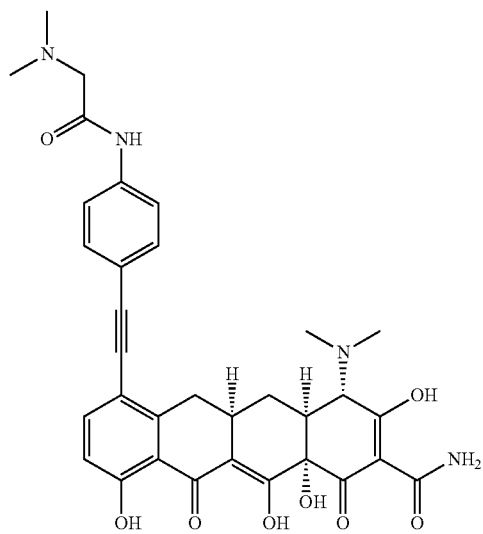
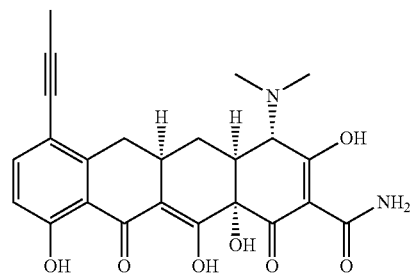

TABLE 2-continued
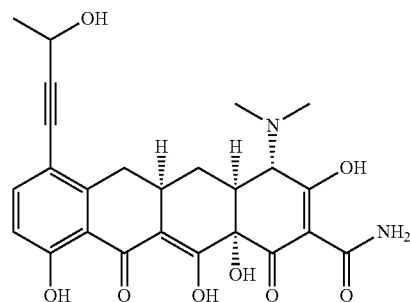
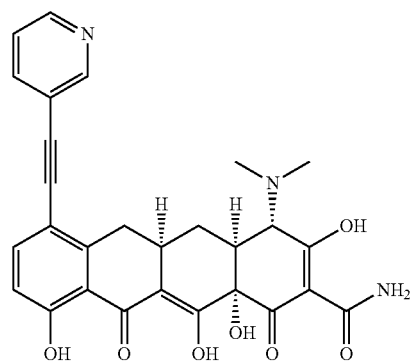
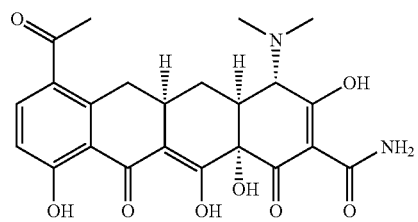
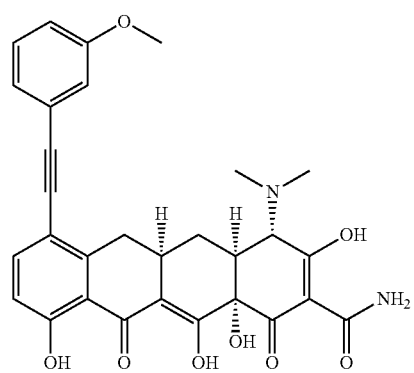
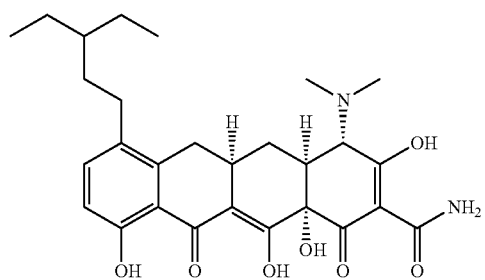

TABLE 2-continued
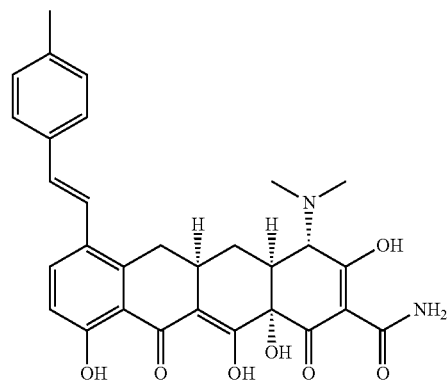
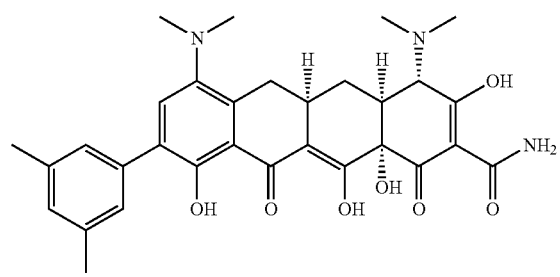
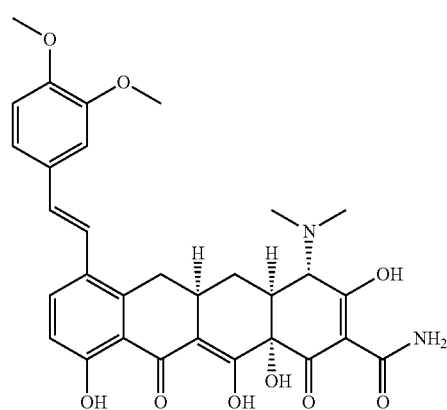
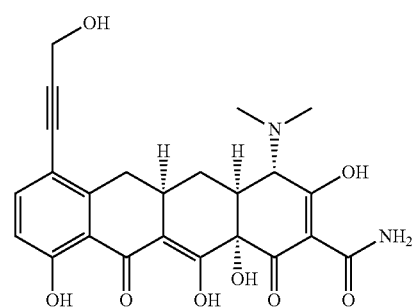

TABLE 2-continued
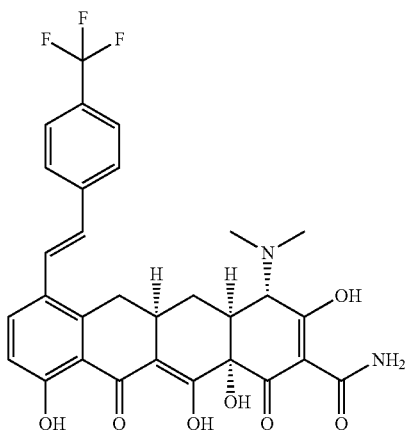
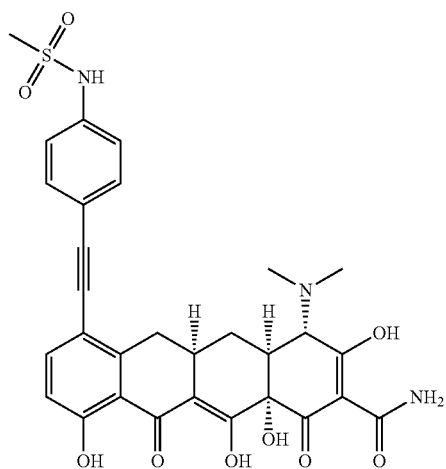
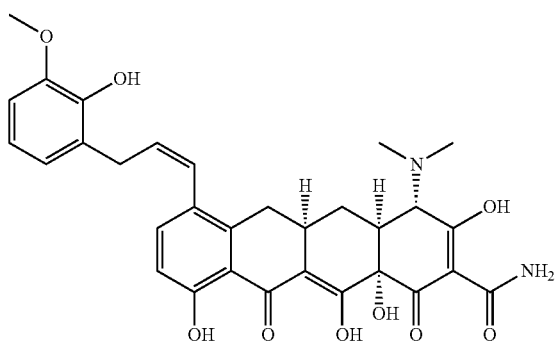
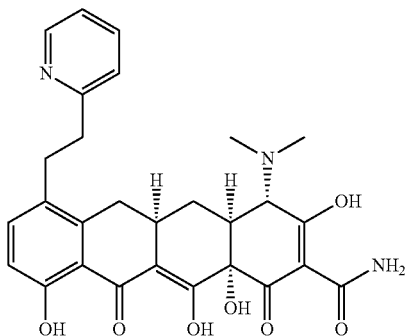

TABLE 2-continued
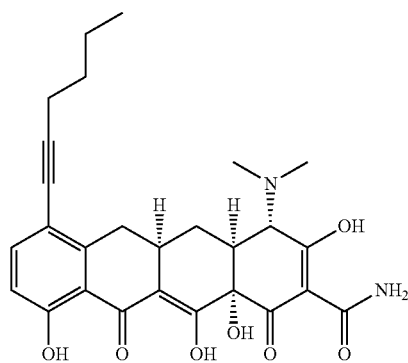
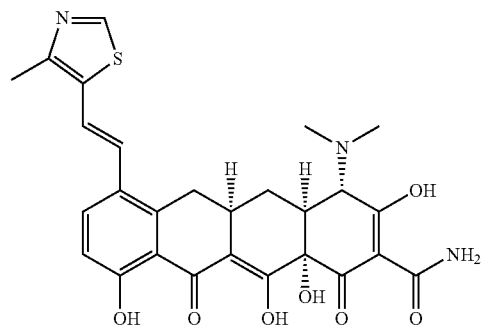
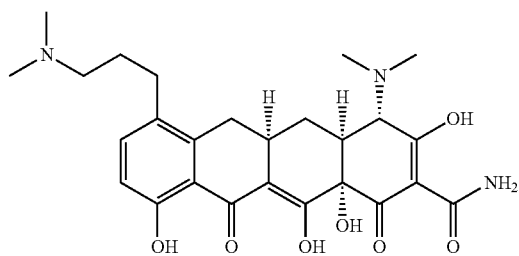
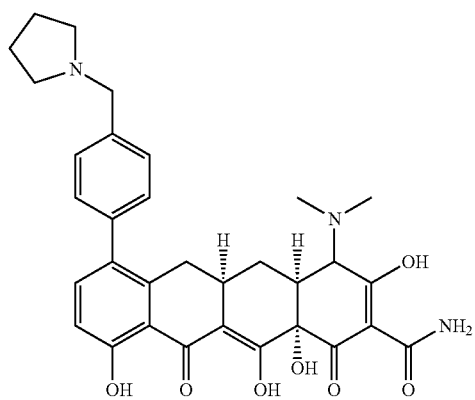

TABLE 2-continued
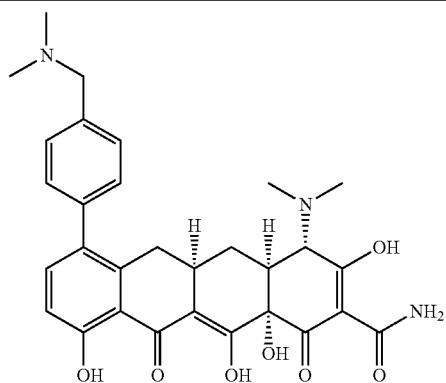
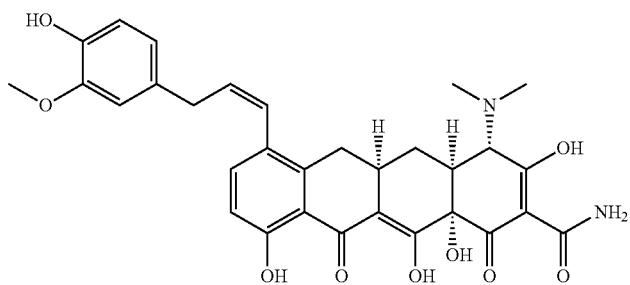
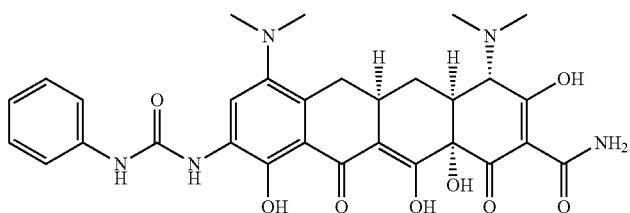
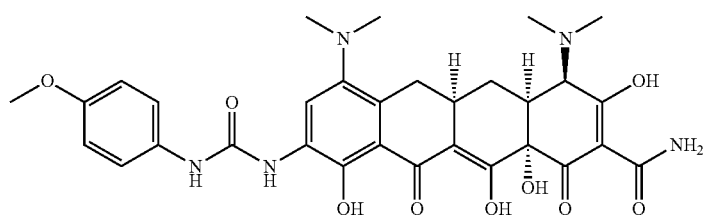
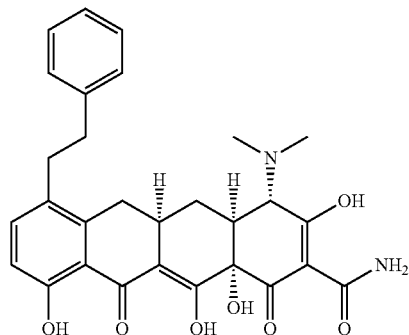

TABLE 2-continued
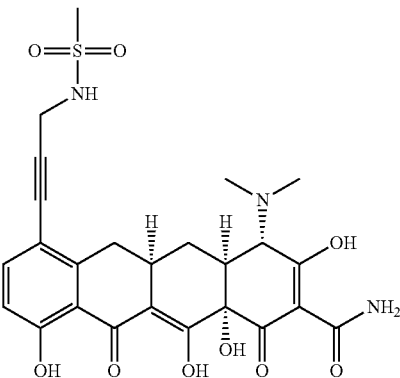
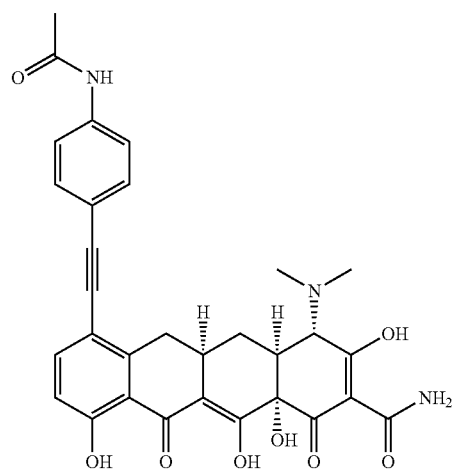
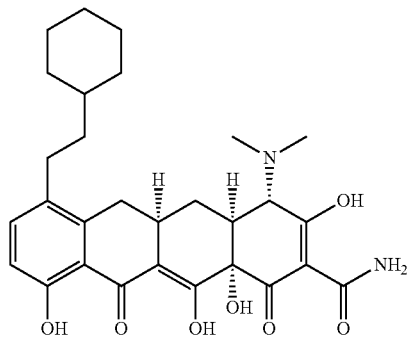
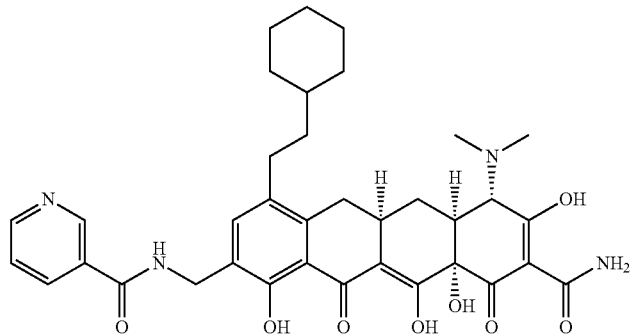

TABLE 2-continued
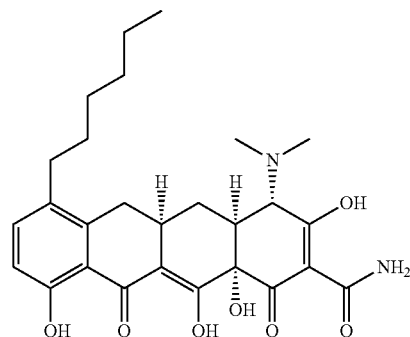
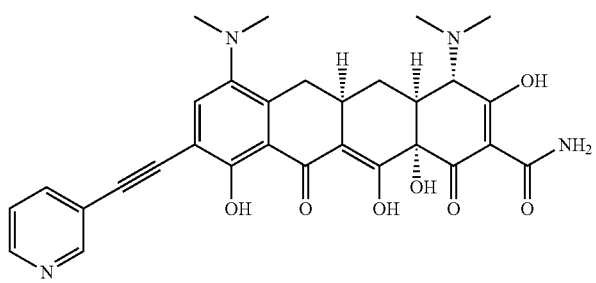
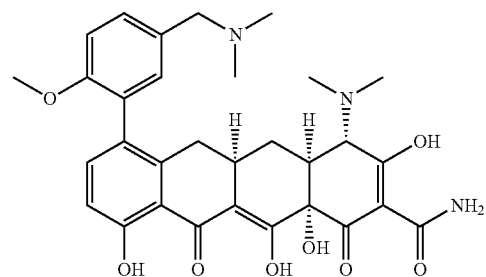
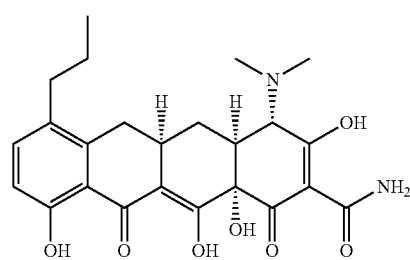
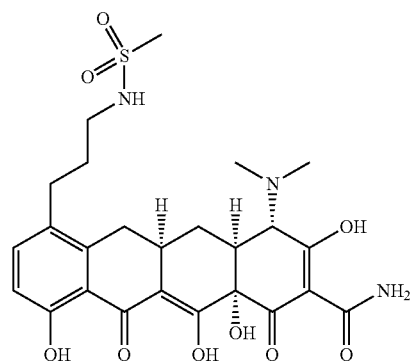

TABLE 2-continued
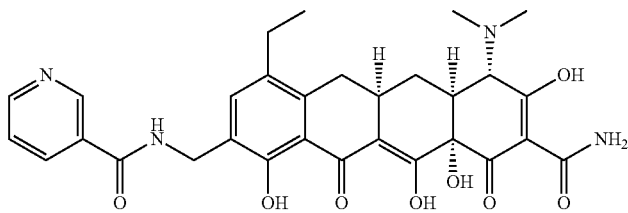
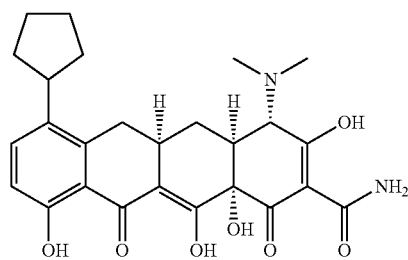
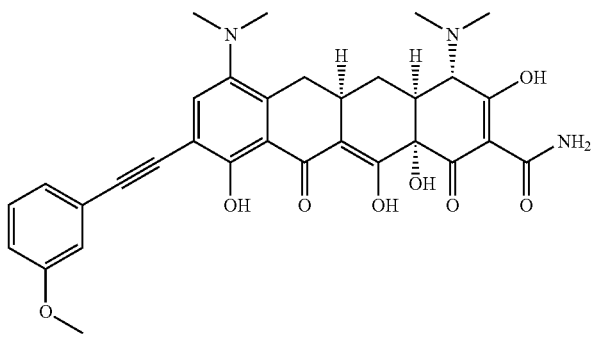
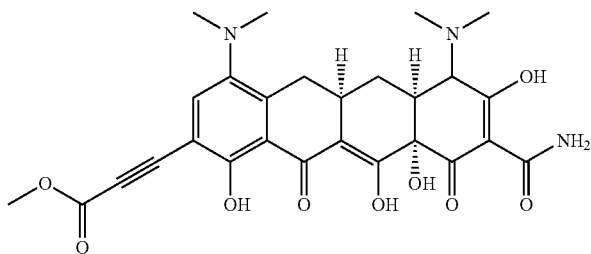
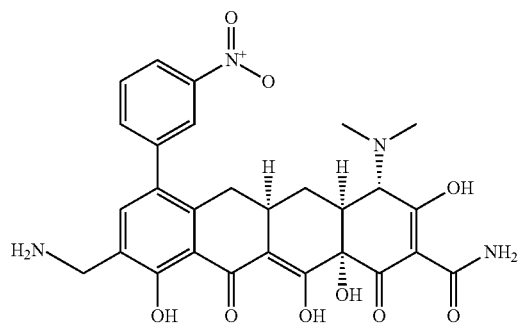

TABLE 2-continued
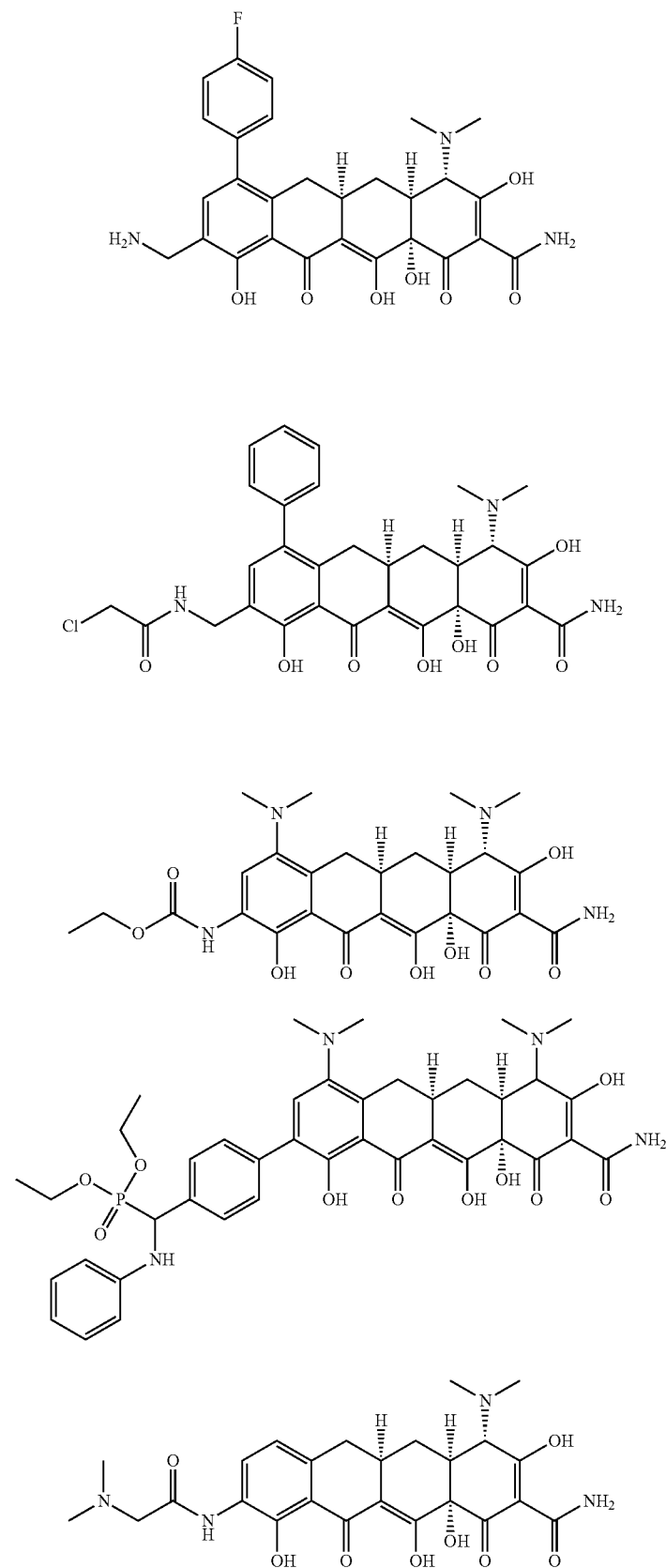

TABLE 2-continued
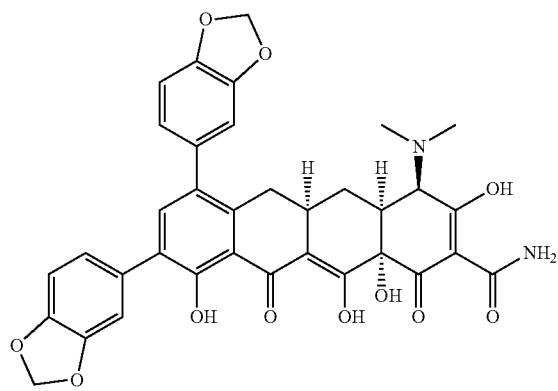
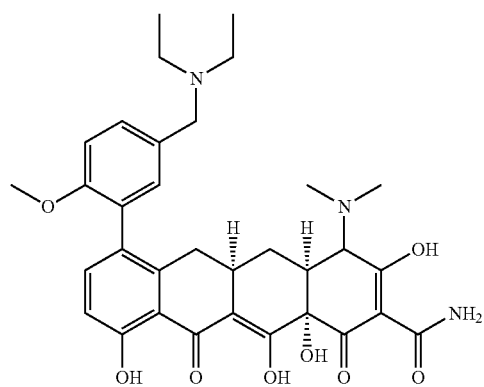
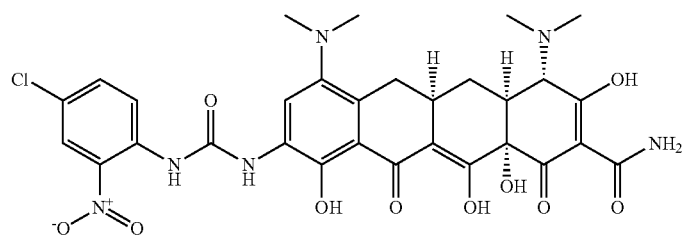
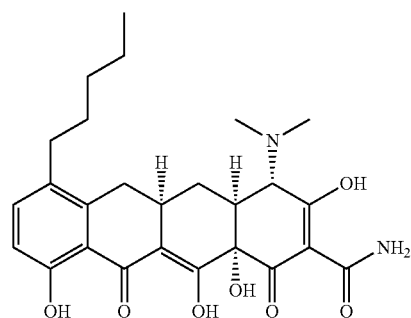
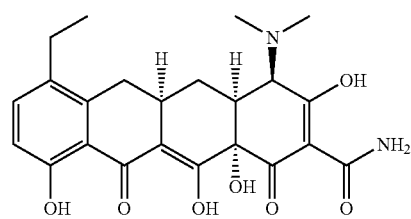

TABLE 2-continued
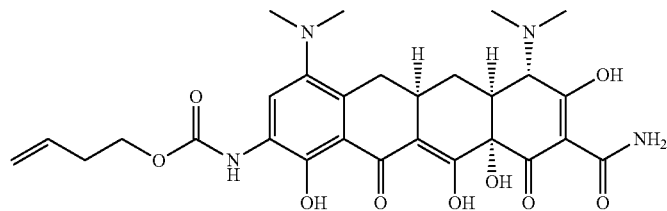
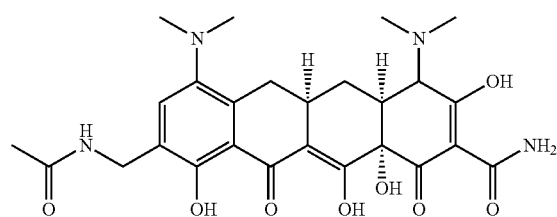
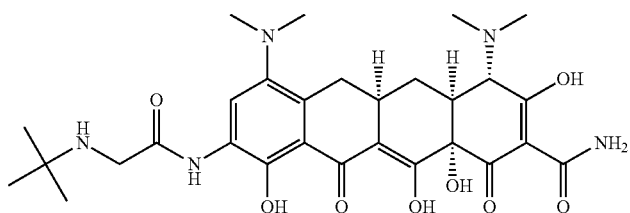
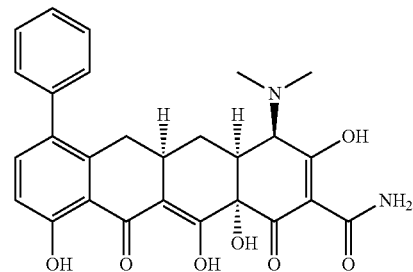
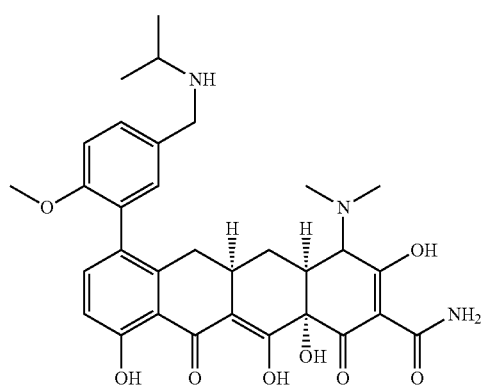

TABLE 2-continued
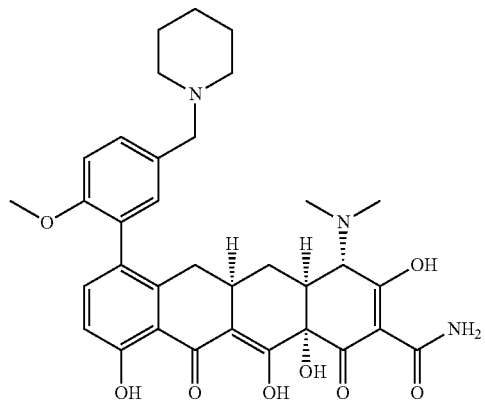
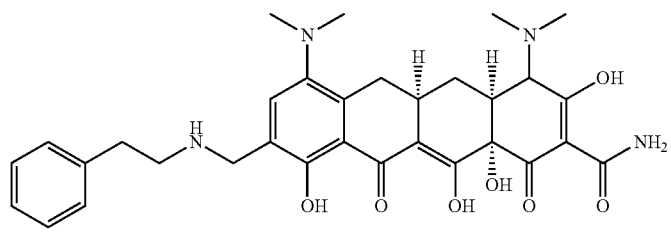
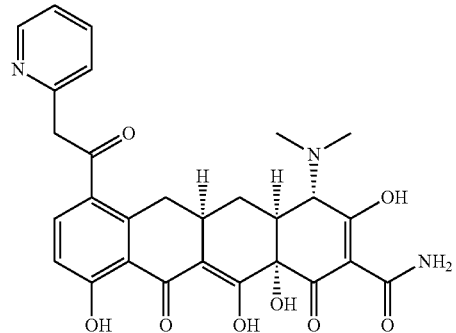
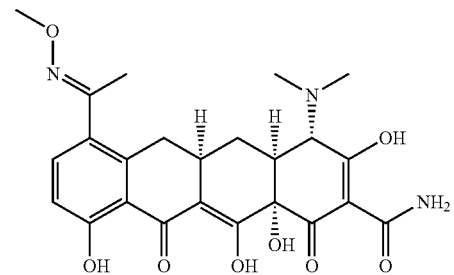
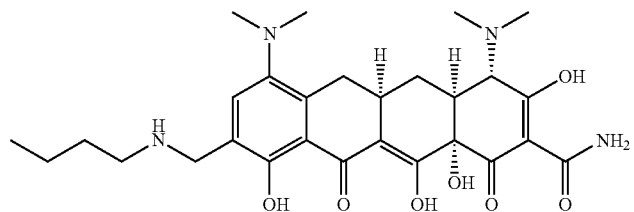

TABLE 2-continued
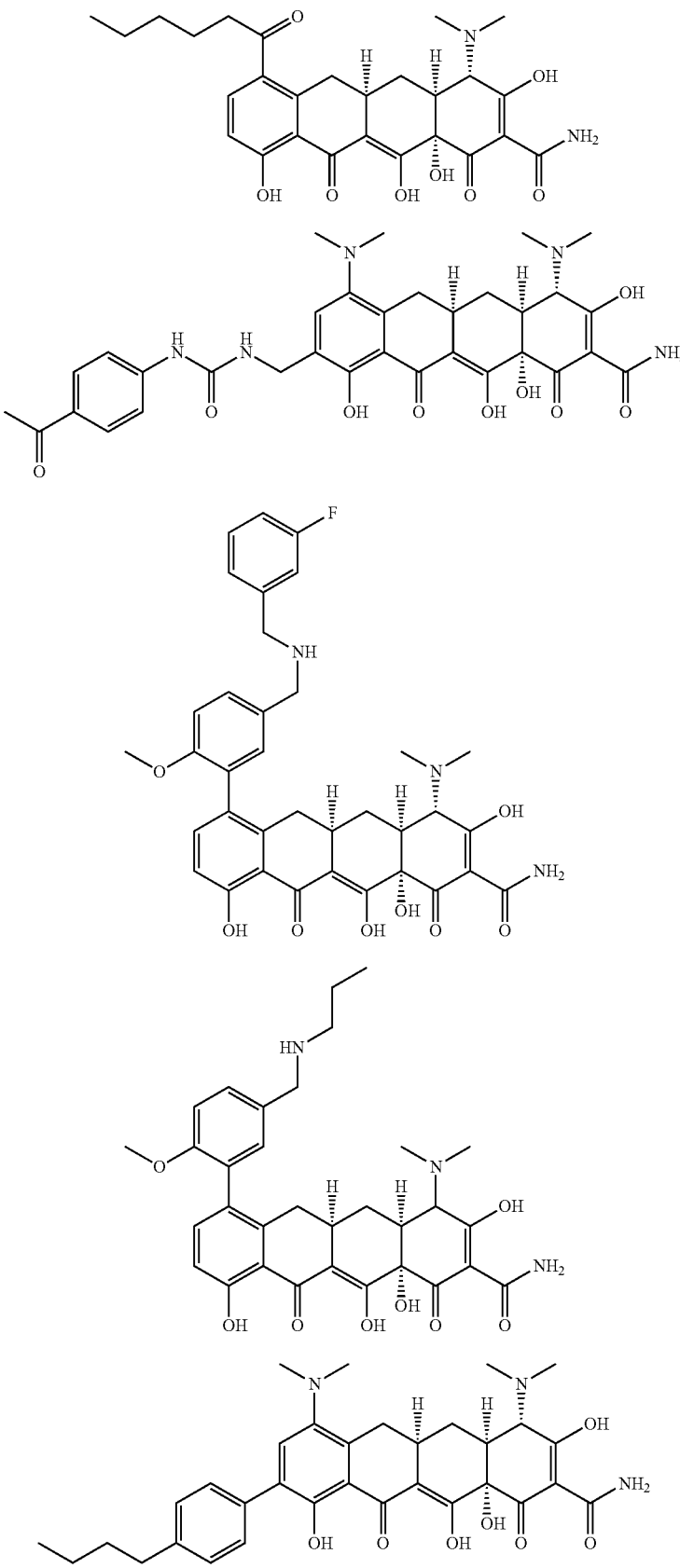

TABLE 2-continued
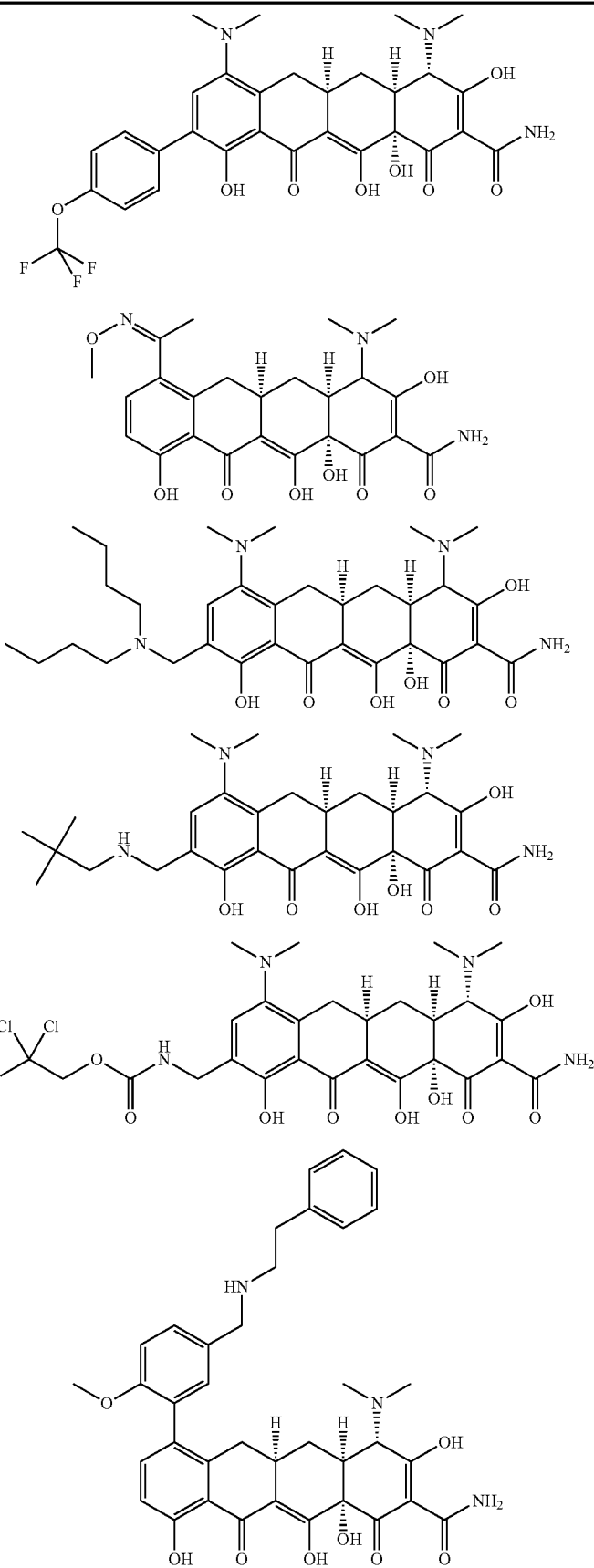

TABLE 2-continued
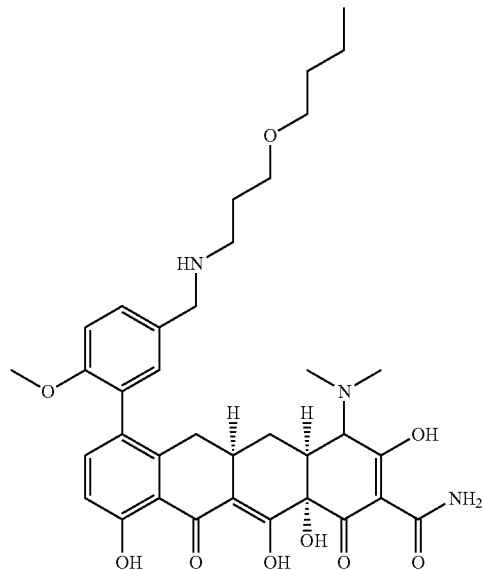
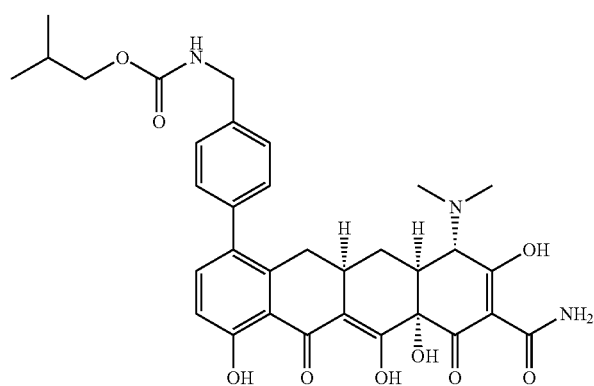
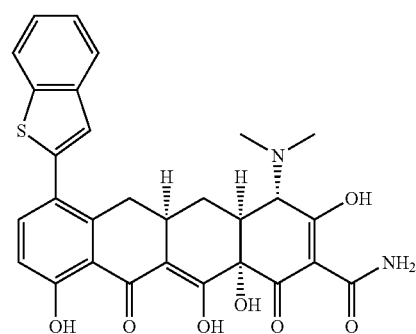

TABLE 2-continued
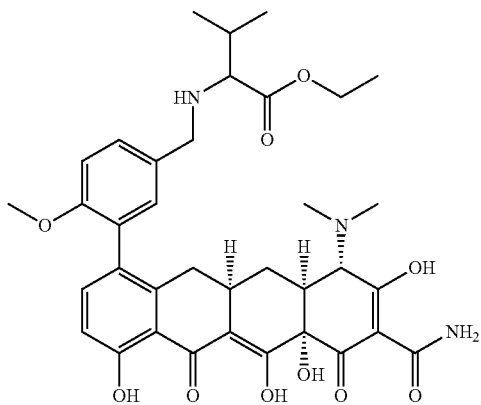
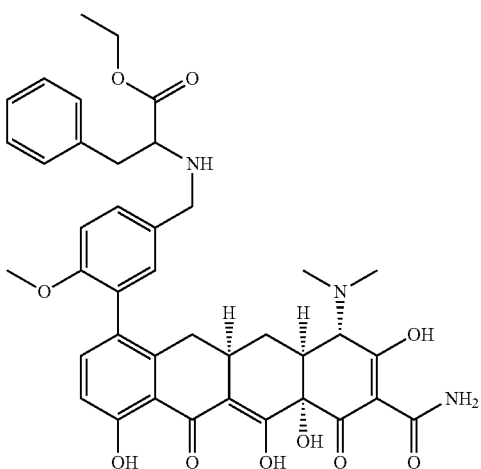
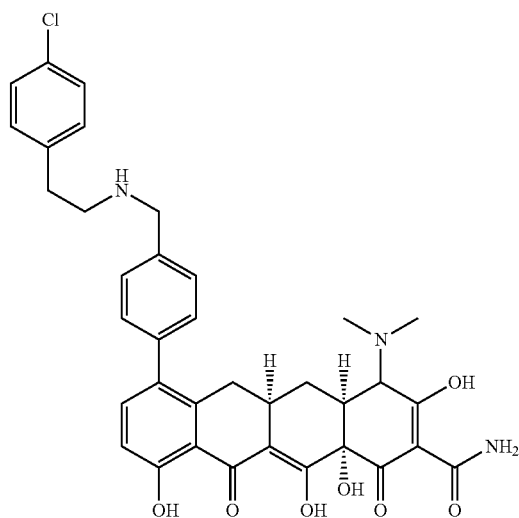

TABLE 2-continued
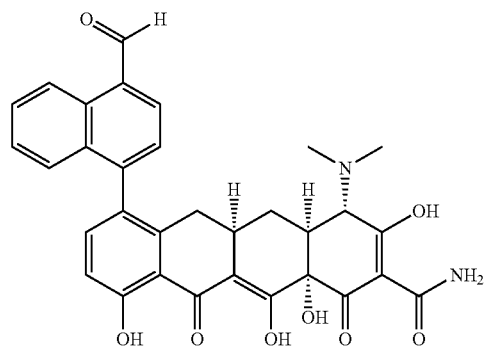
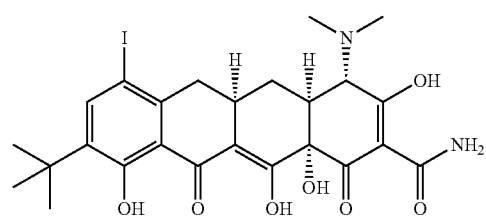
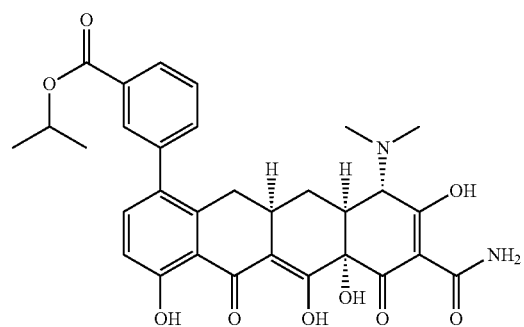
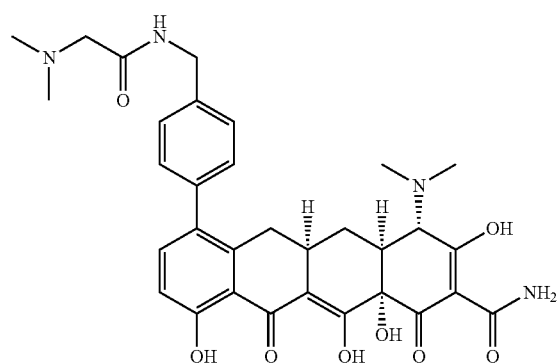

TABLE 2-continued
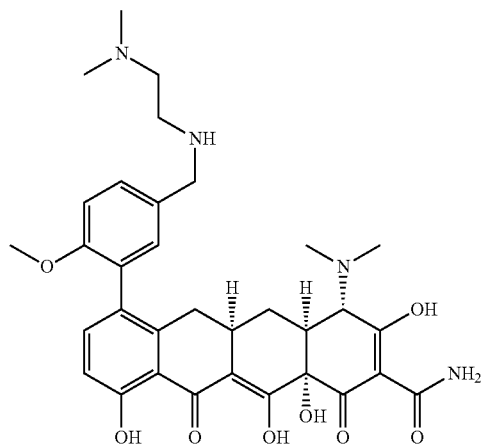
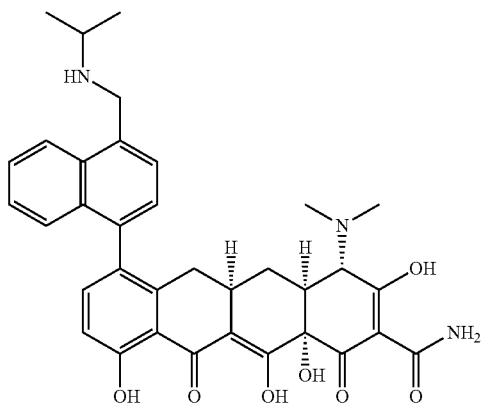
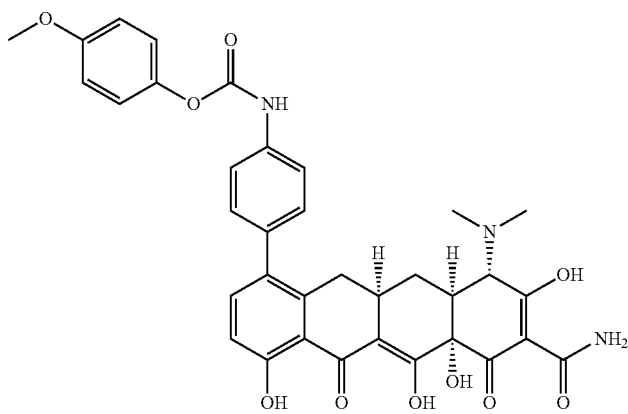
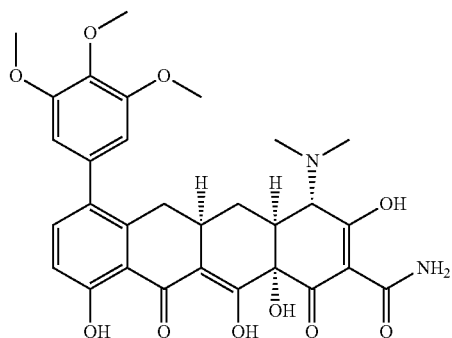

TABLE 2-continued
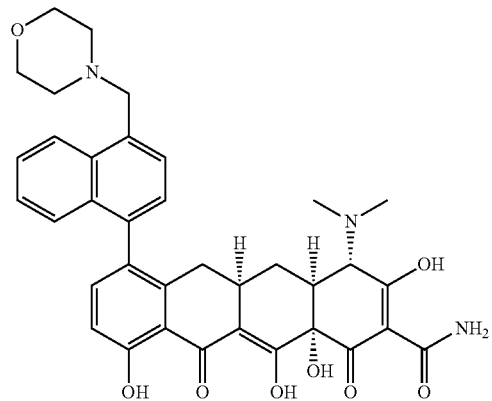
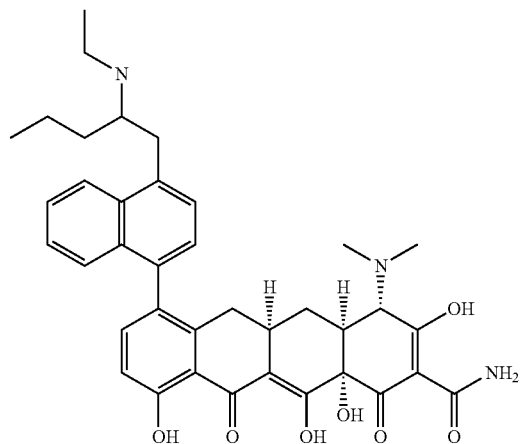
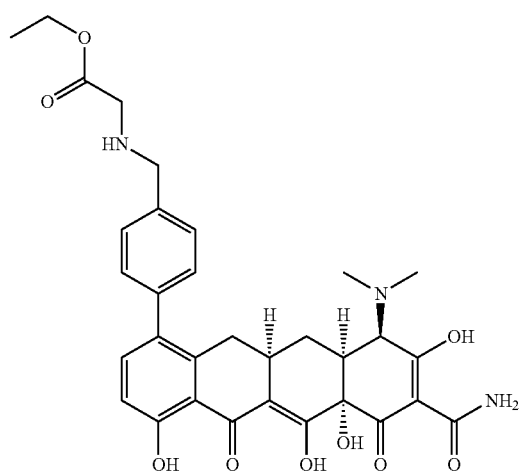

TABLE 2-continued
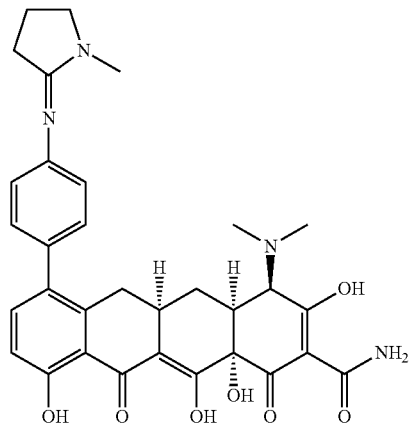
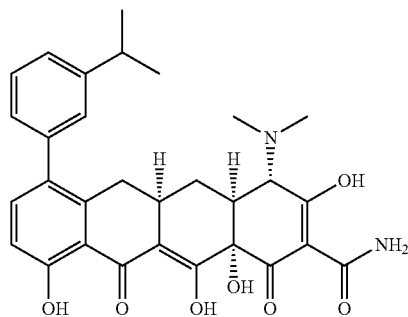
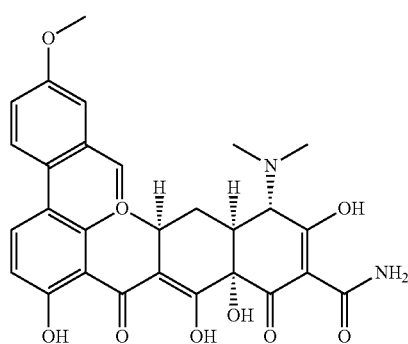
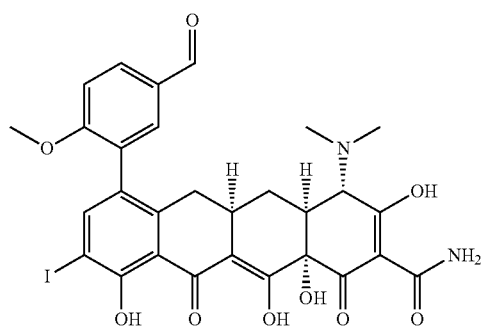

TABLE 2-continued
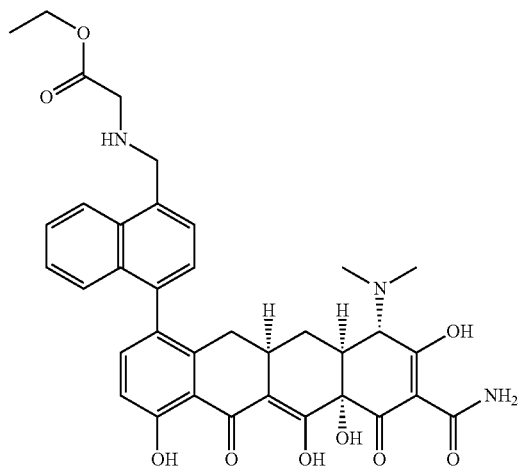
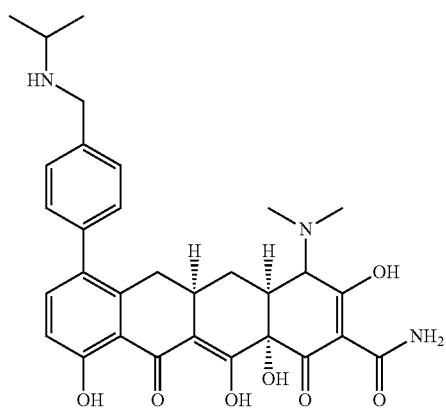
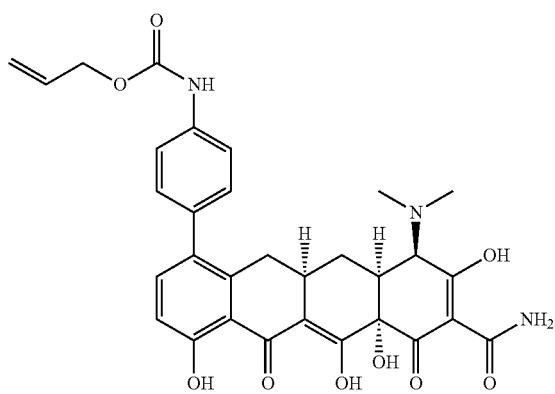
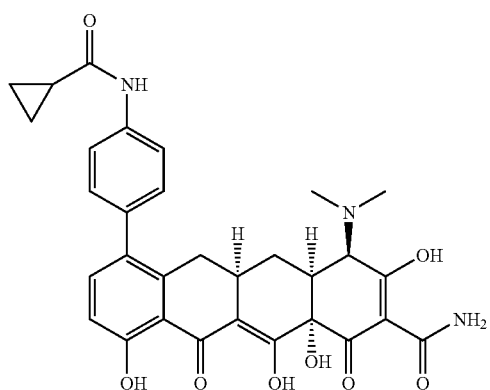

TABLE 2-continued
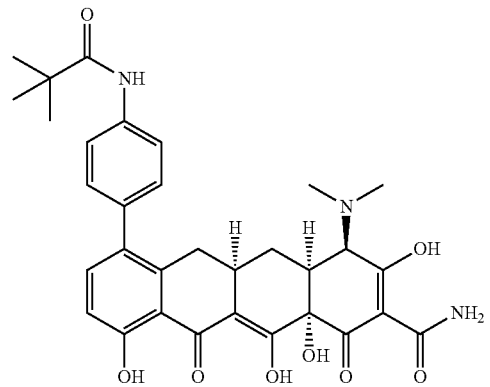
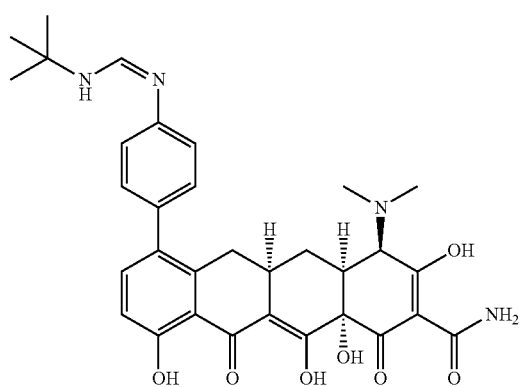
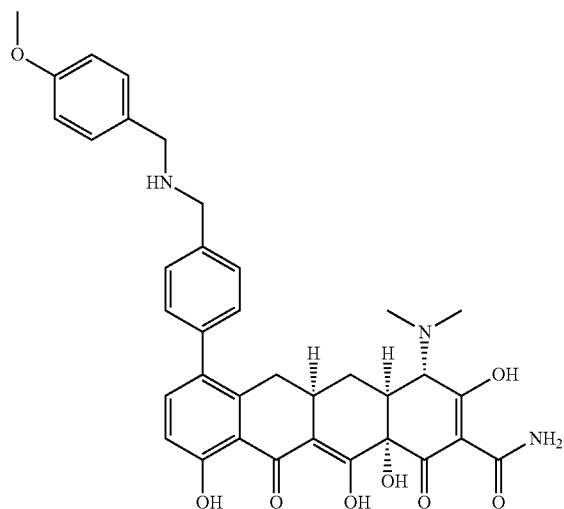
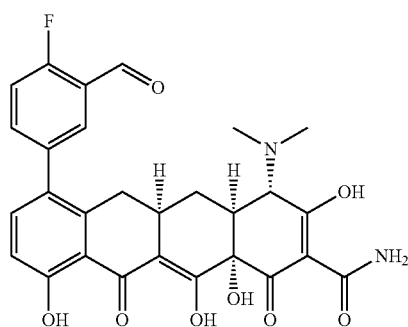

TABLE 2-continued
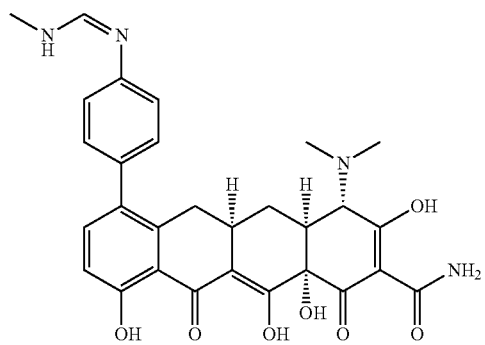
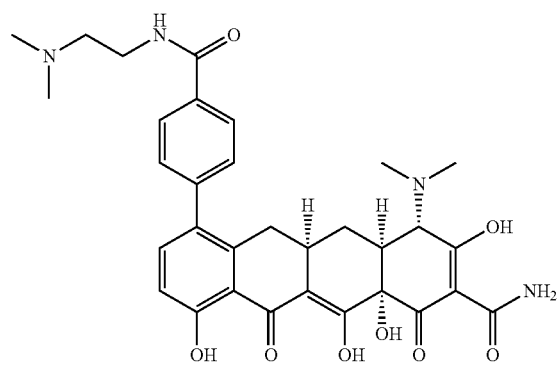
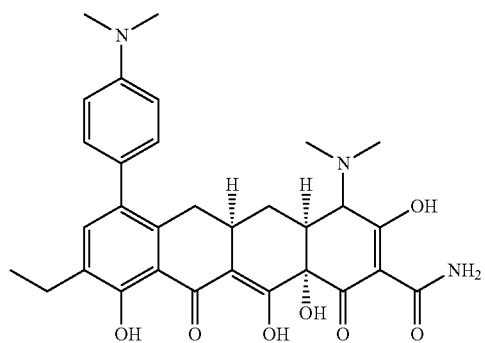
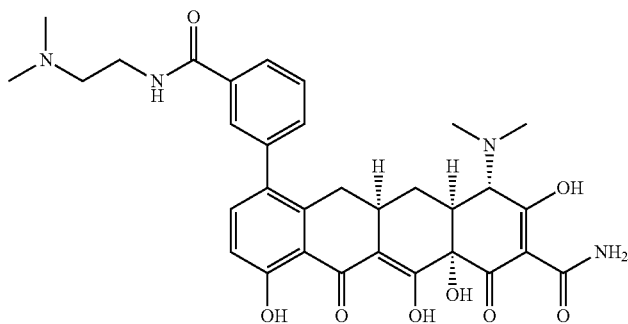

TABLE 2-continued
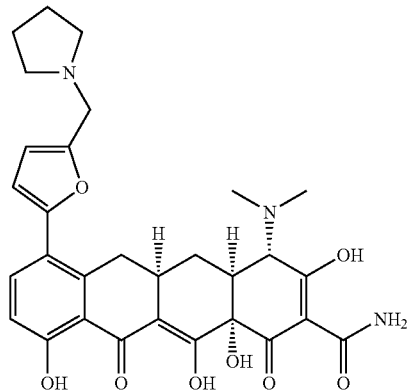
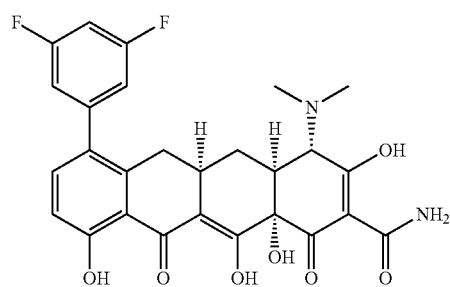
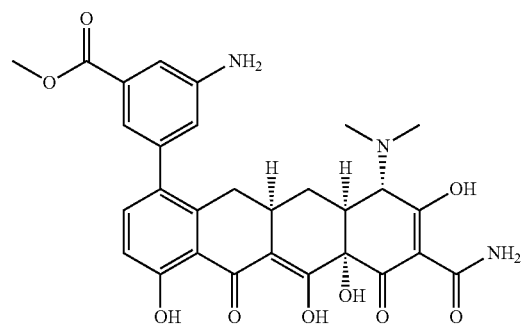
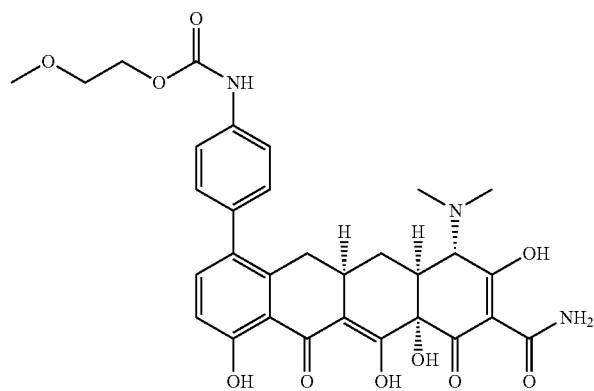

TABLE 2-continued
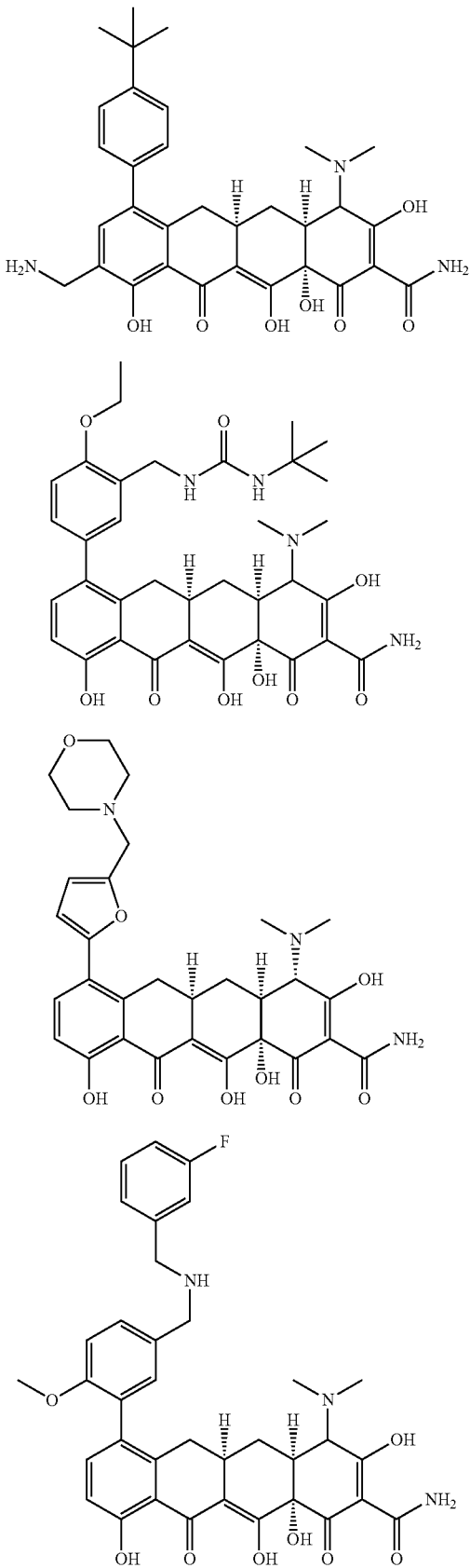

TABLE 2-continued
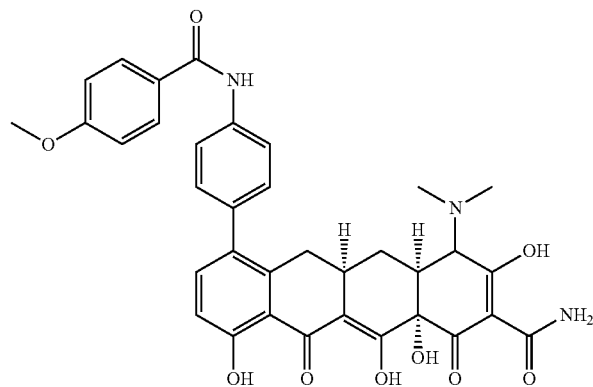
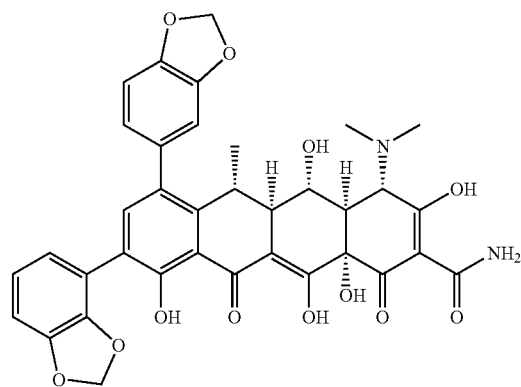
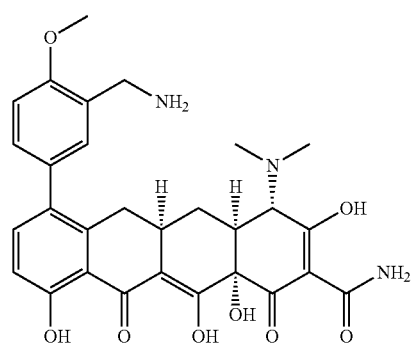
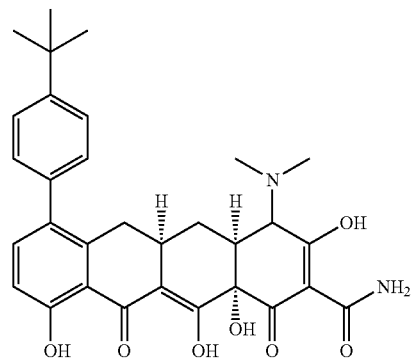

TABLE 2-continued
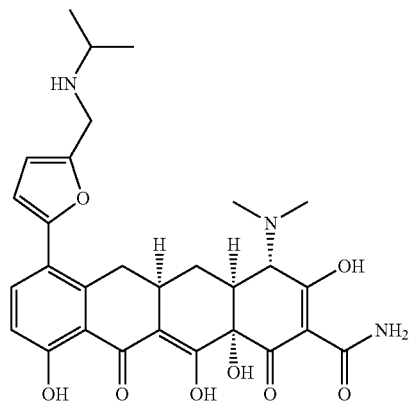
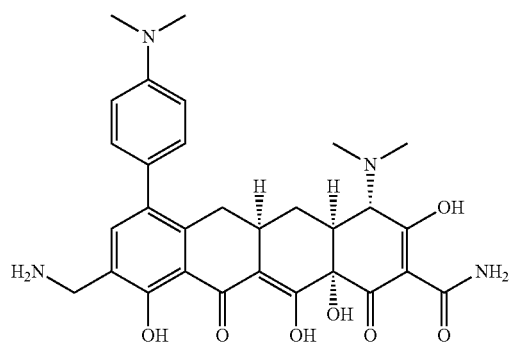
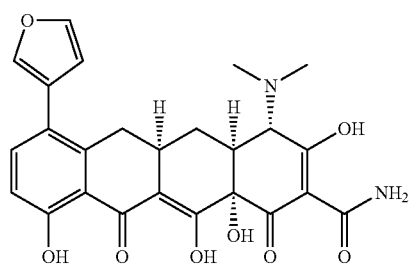
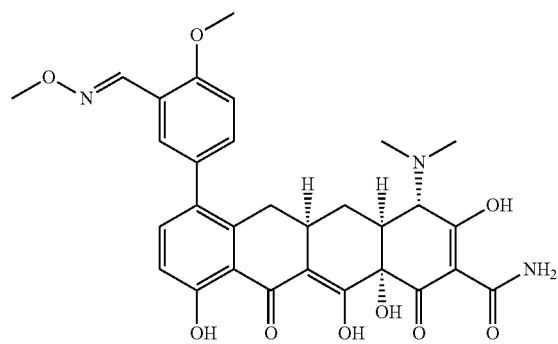

TABLE 2-continued
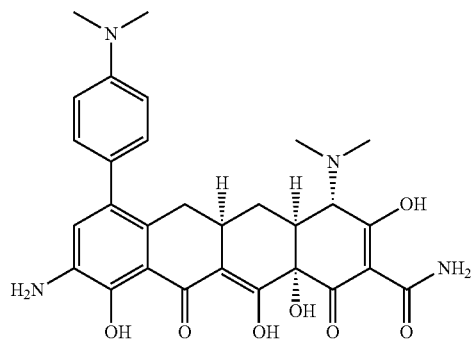
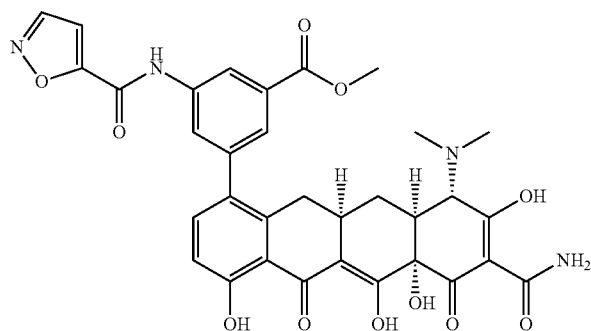
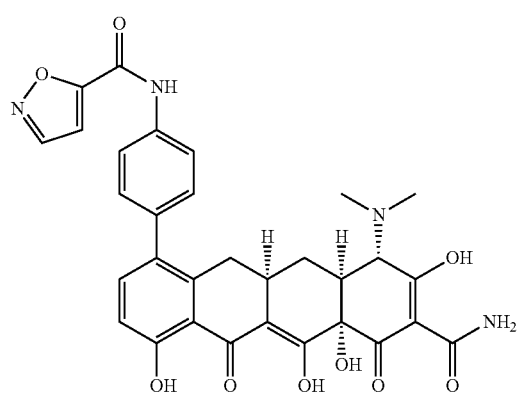
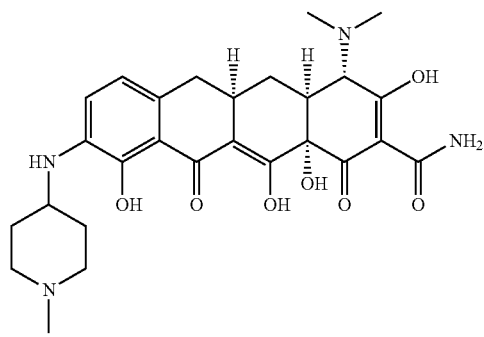

TABLE 2-continued
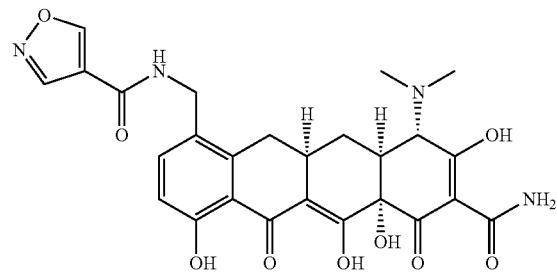
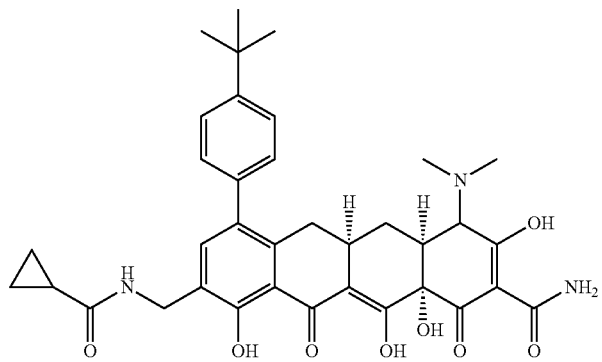
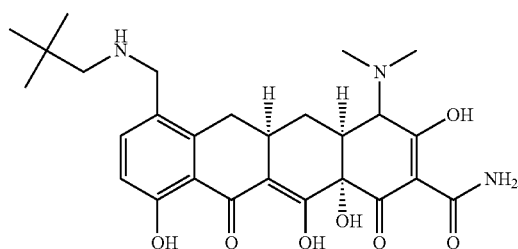
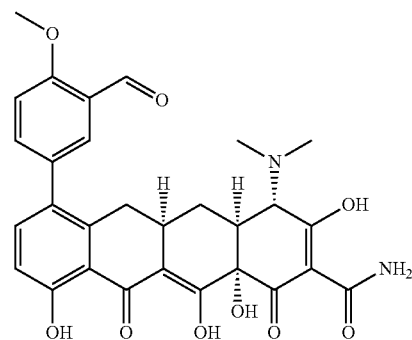
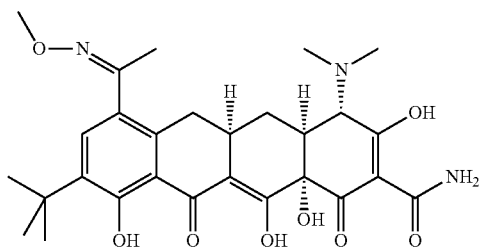

TABLE 2-continued
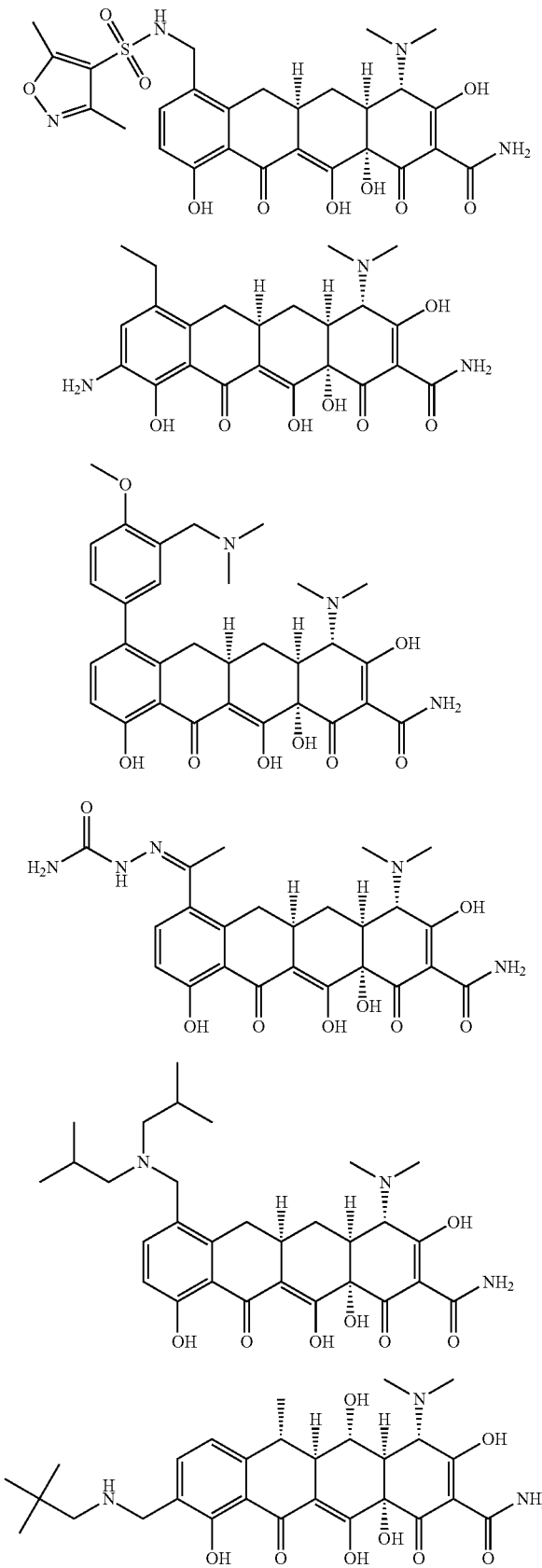

TABLE 2-continued
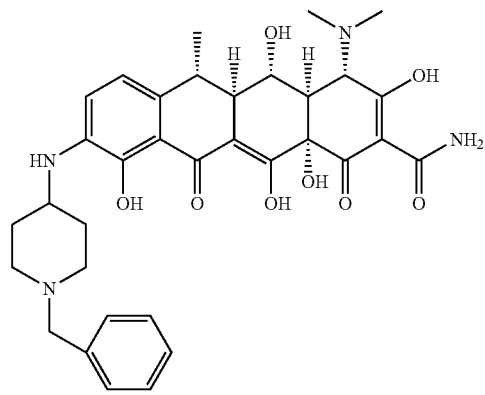
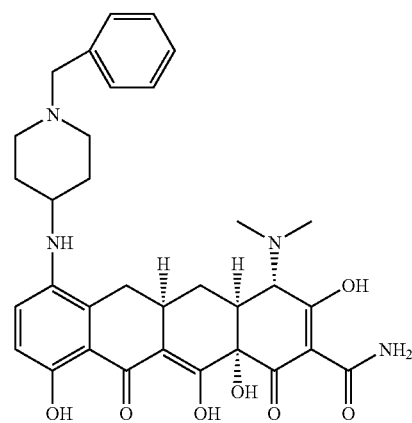
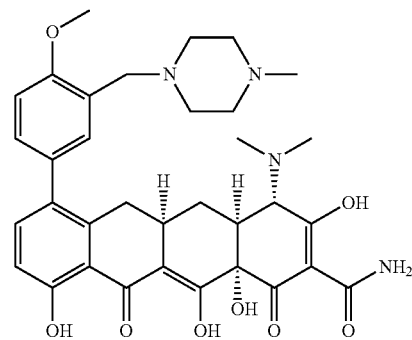
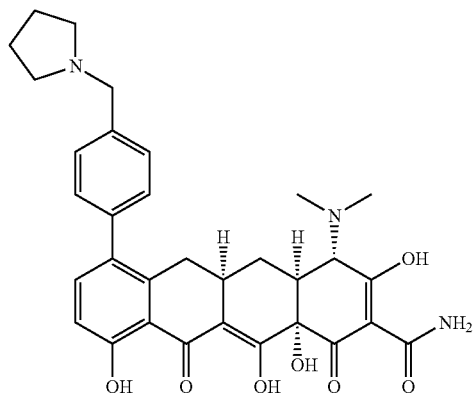

TABLE 2-continued
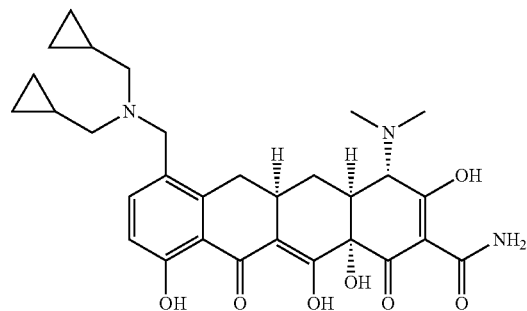
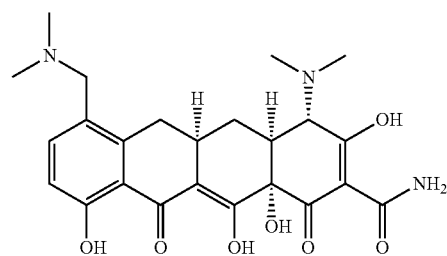
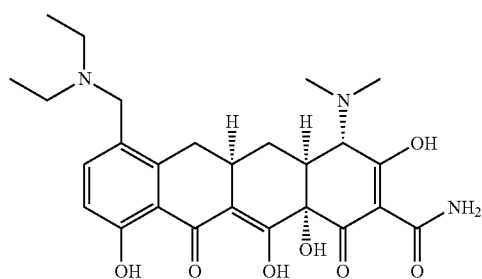
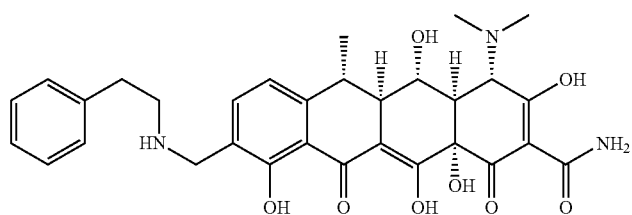
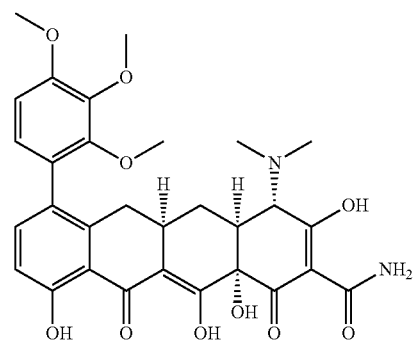

TABLE 2-continued
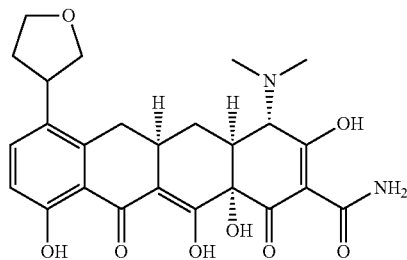
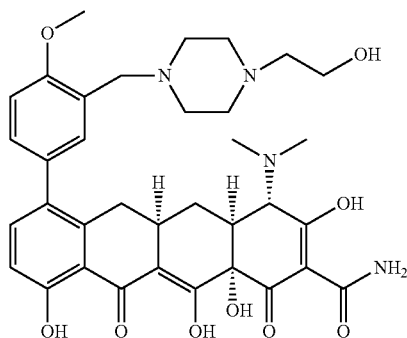
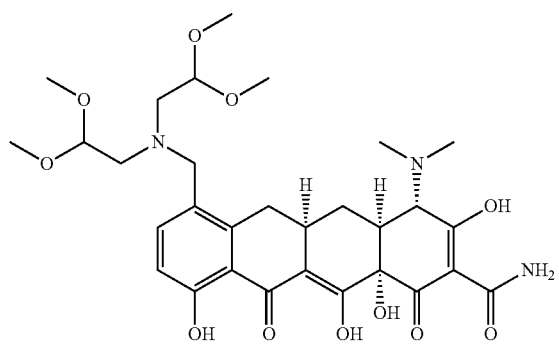
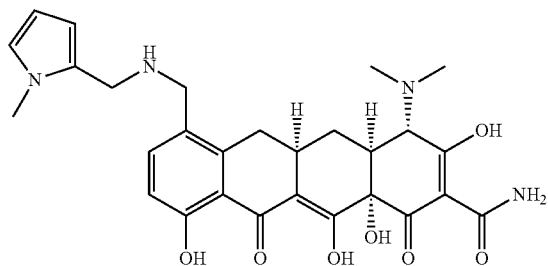
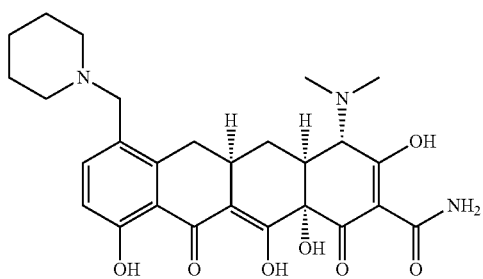

TABLE 2-continued
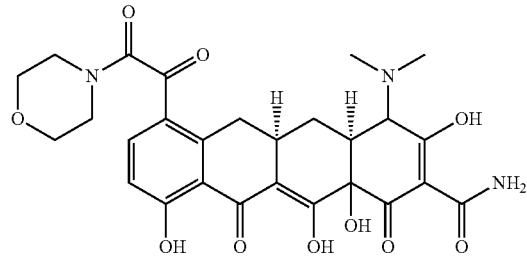
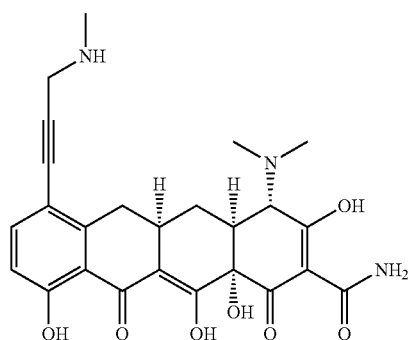
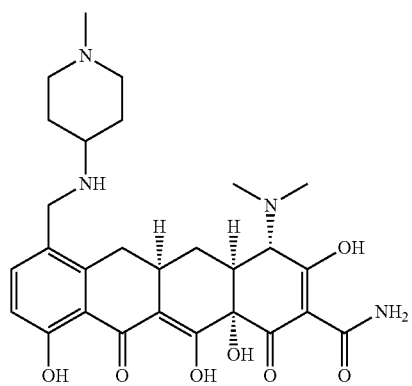

TABLE 2-continued
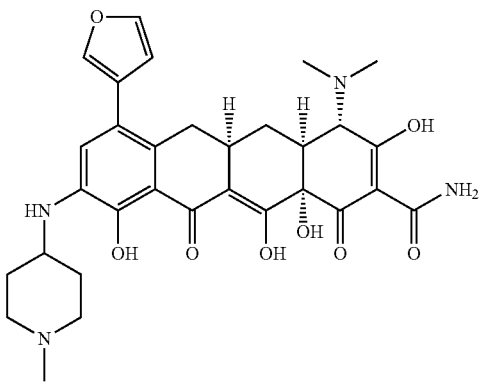
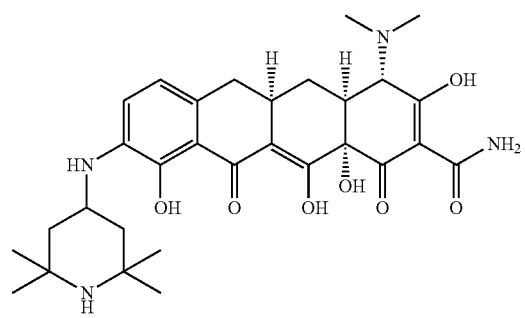
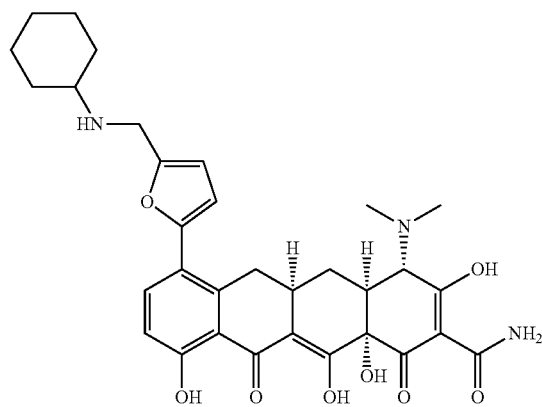
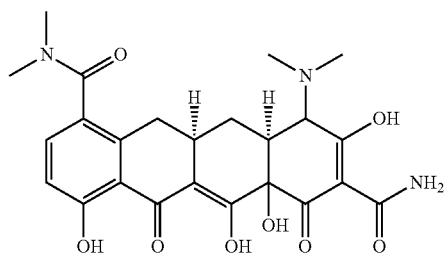
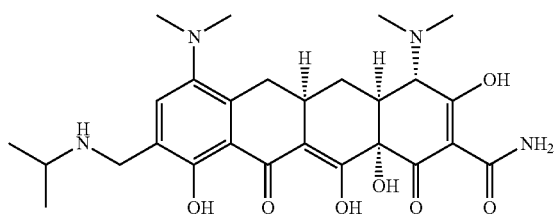

TABLE 2-continued
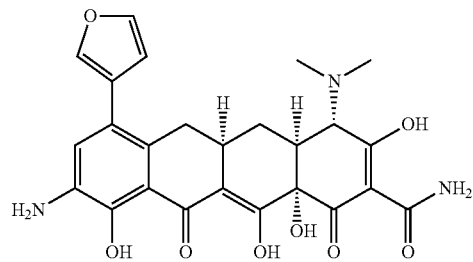
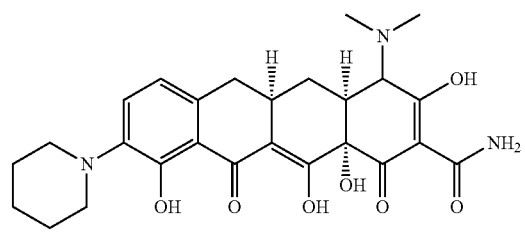
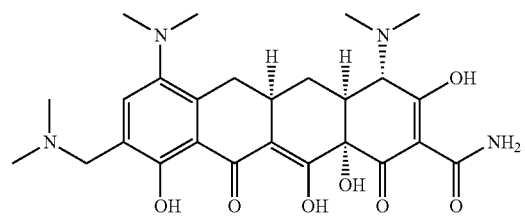
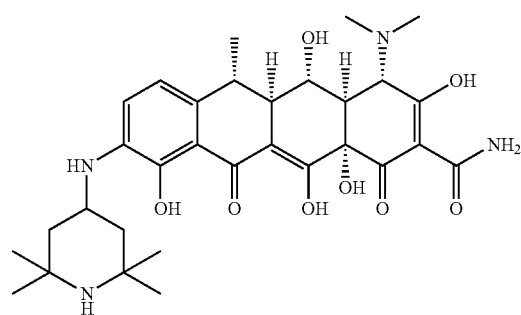
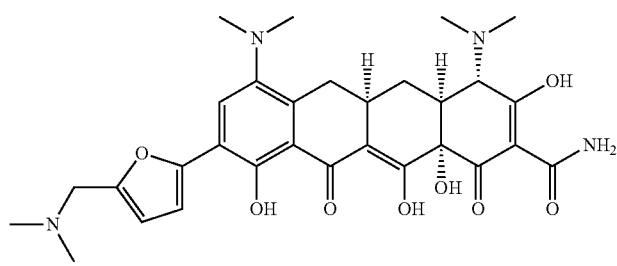

TABLE 2-continued
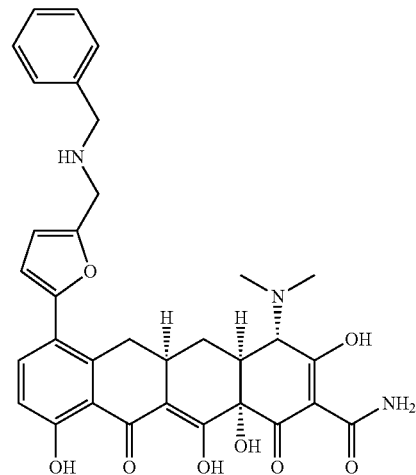
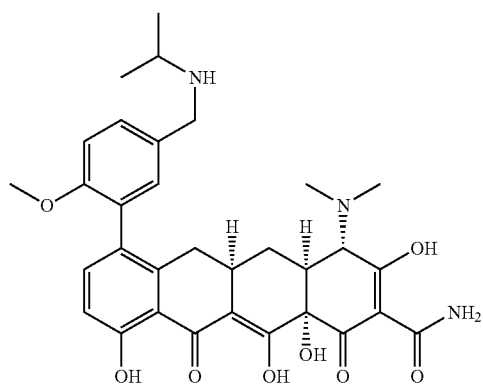
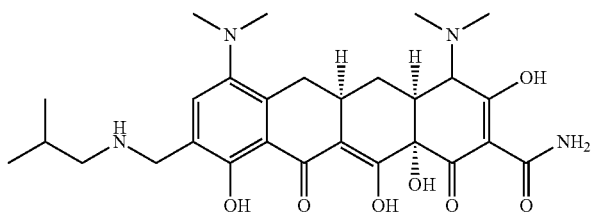
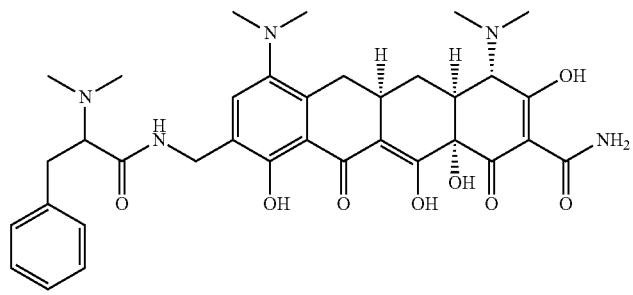

TABLE 2-continued
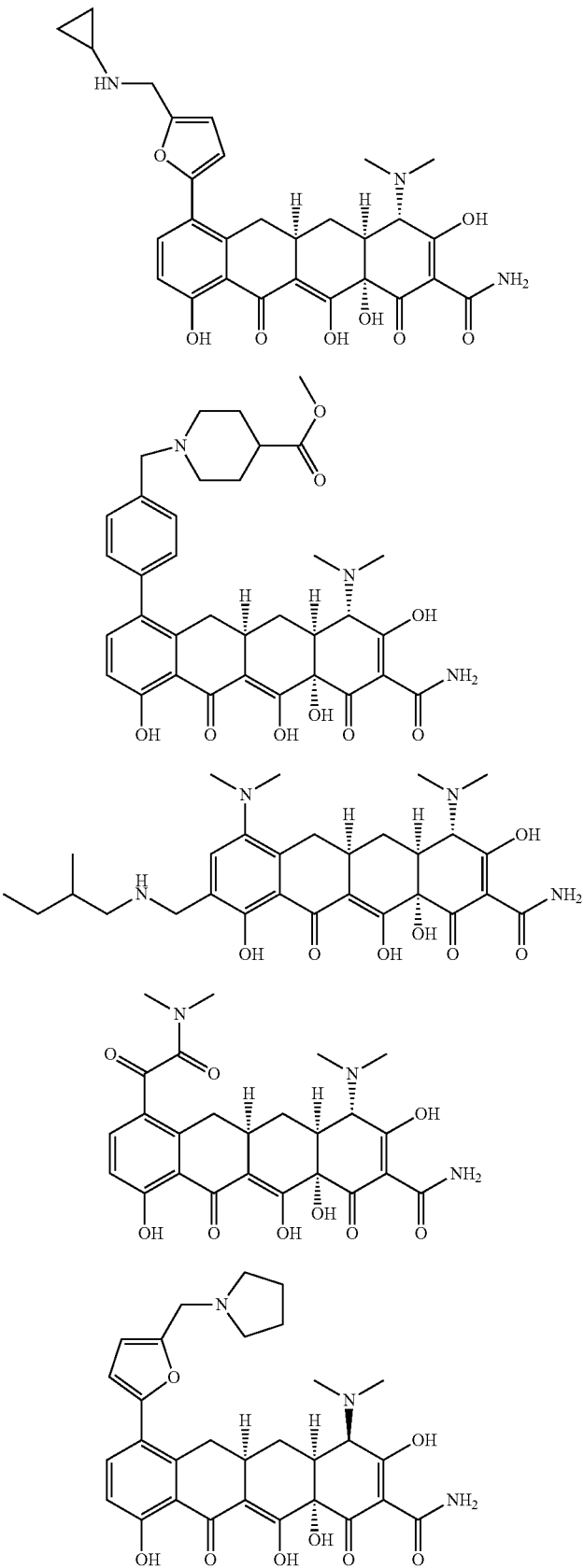

TABLE 2-continued
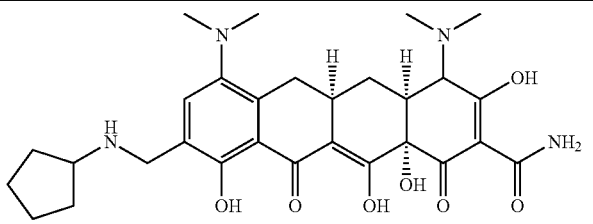
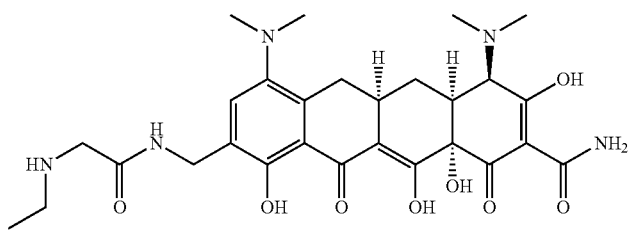
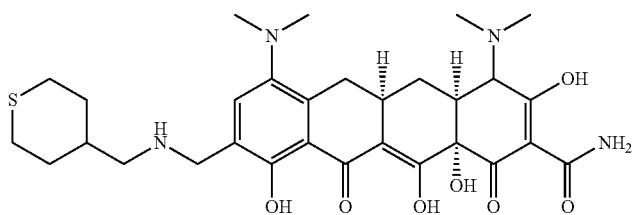
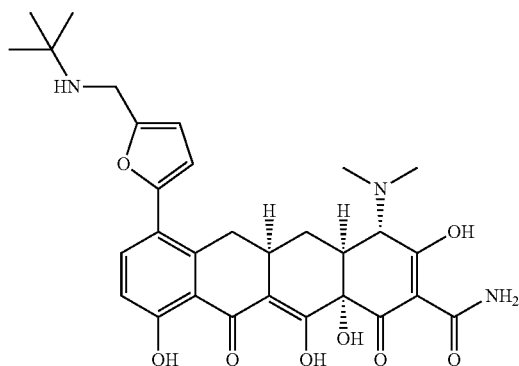
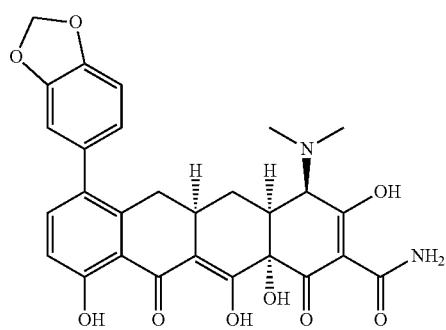
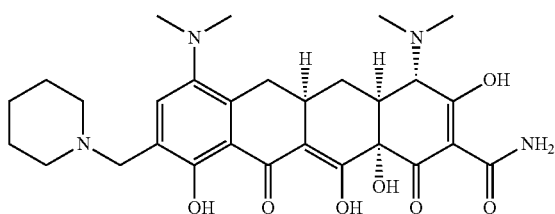

TABLE 2-continued
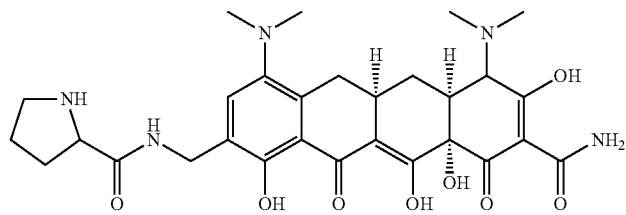
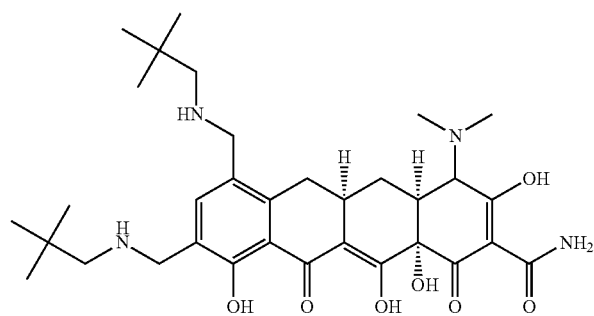
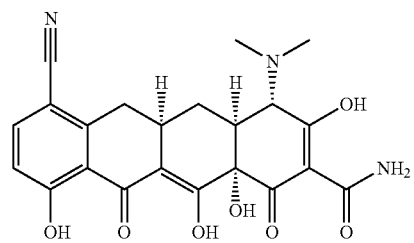
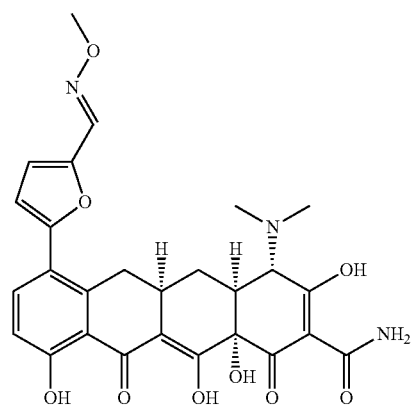
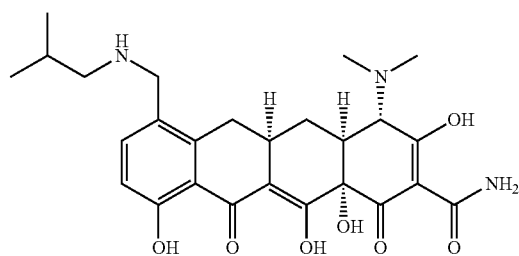

TABLE 2-continued
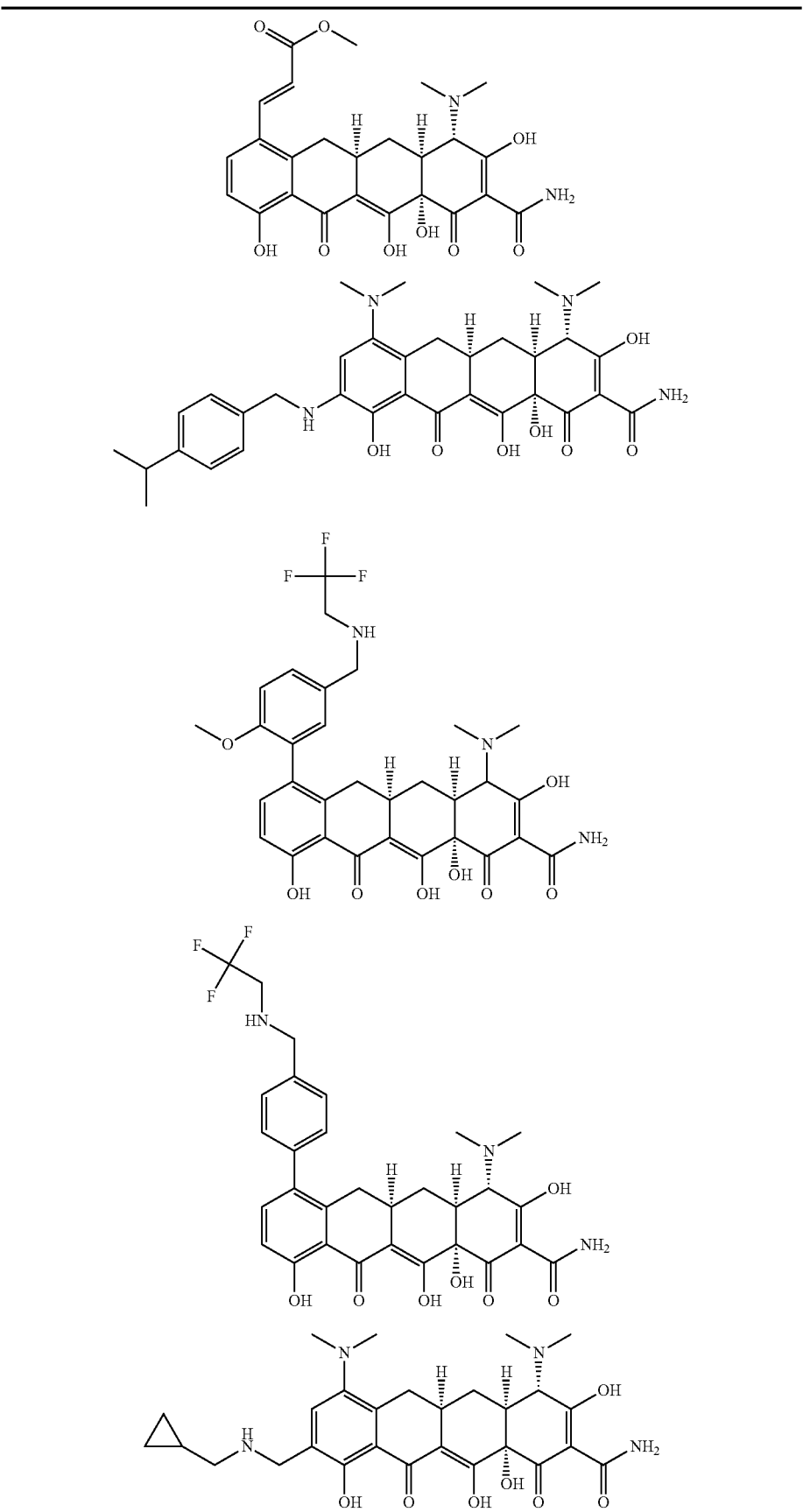

TABLE 2-continued
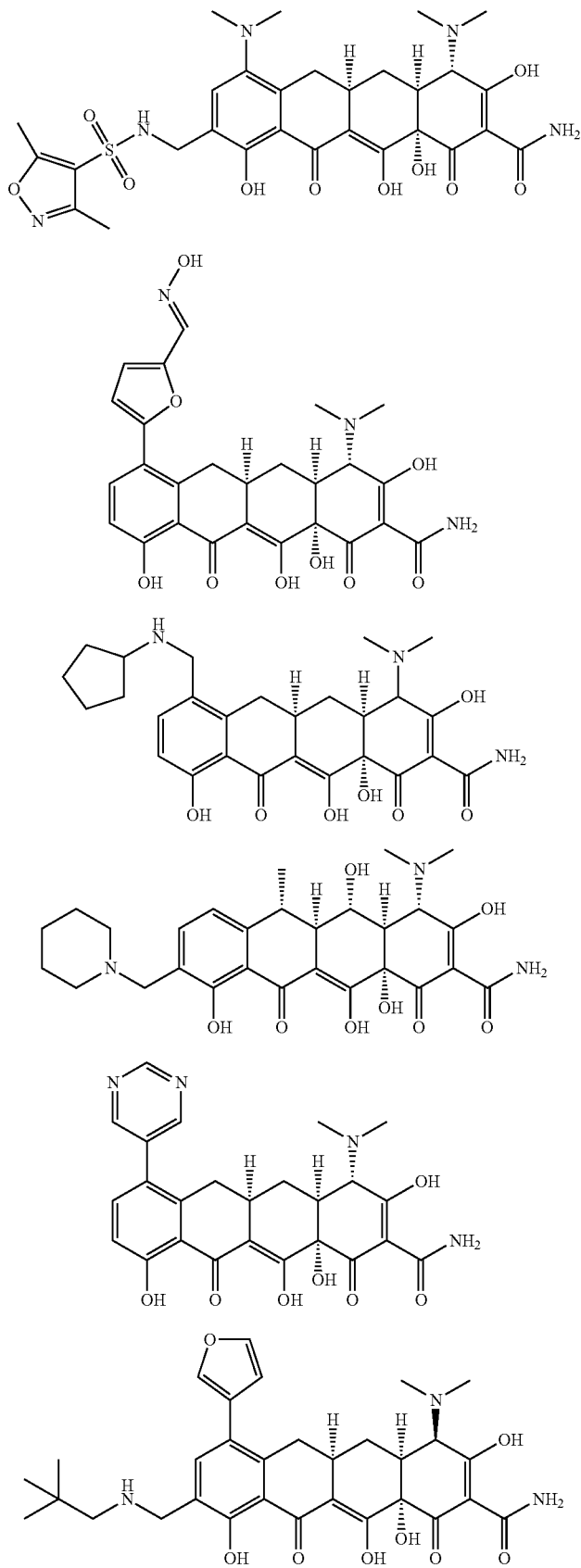

TABLE 2-continued
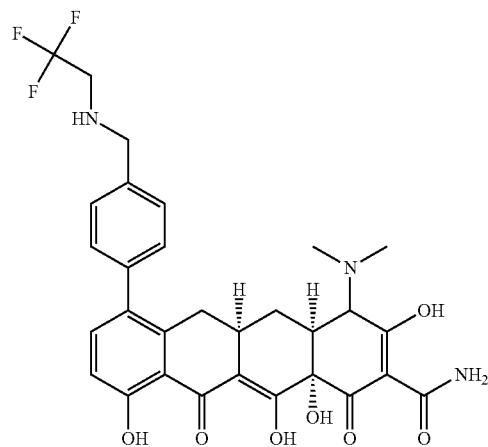
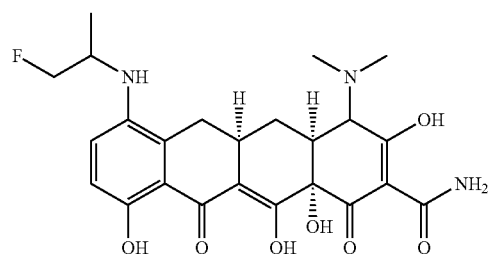
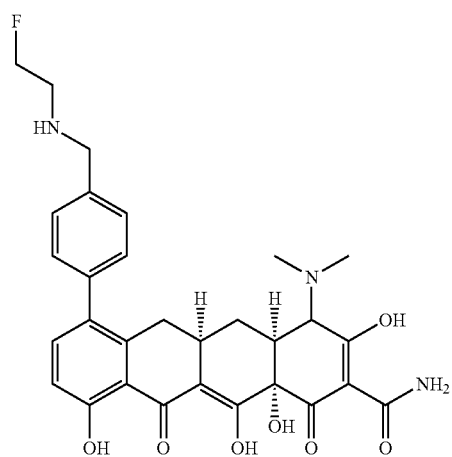

TABLE 2-continued
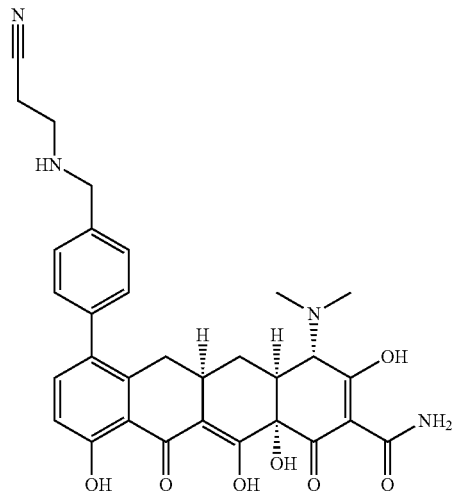
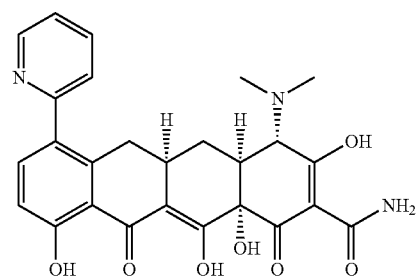
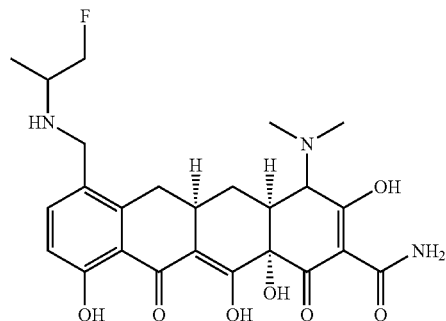
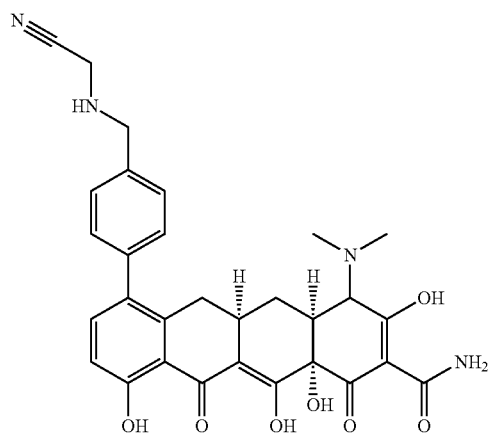

TABLE 2-continued
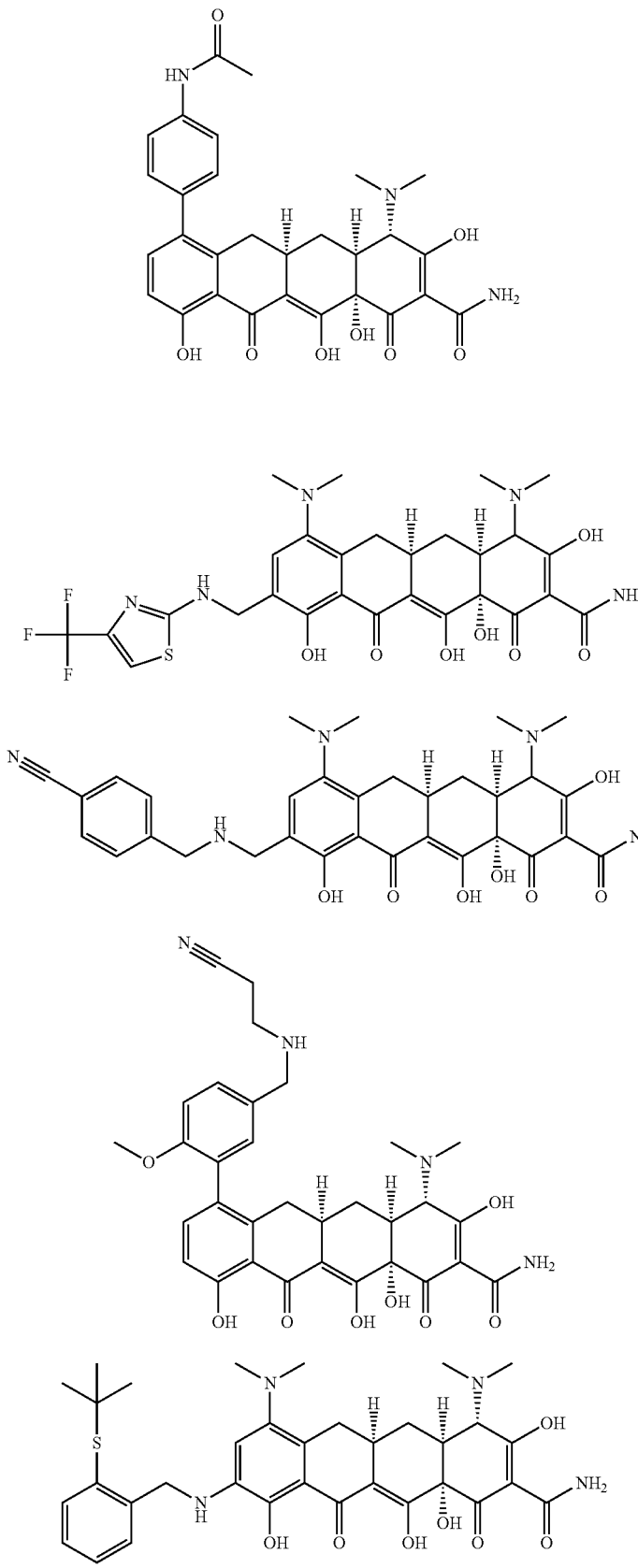

TABLE 2-continued
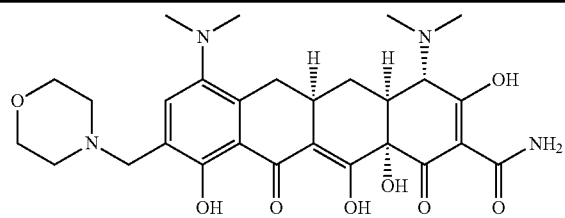
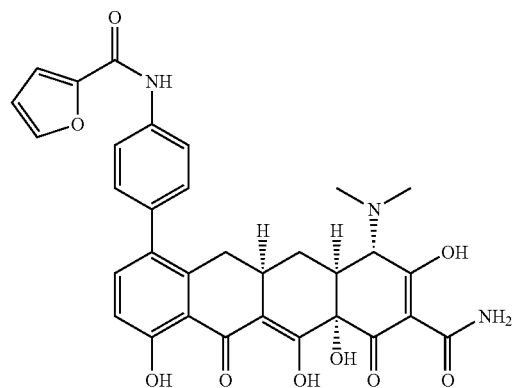
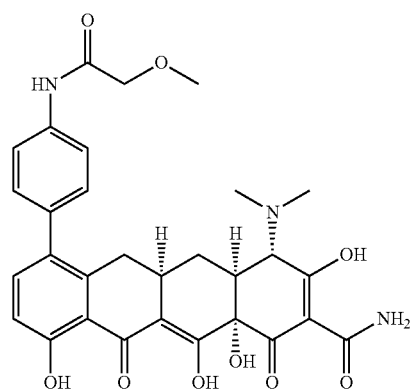
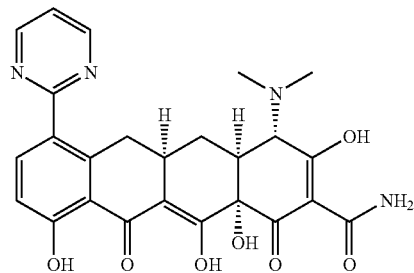
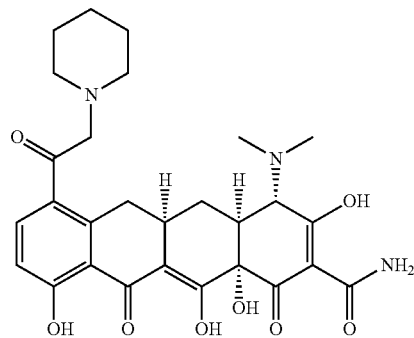

TABLE 2-continued
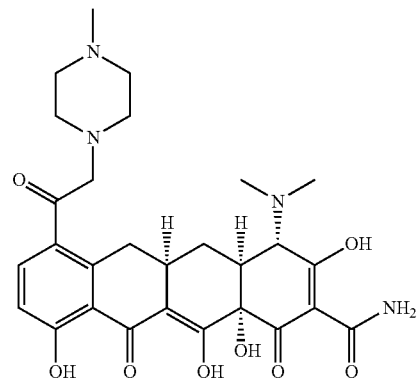
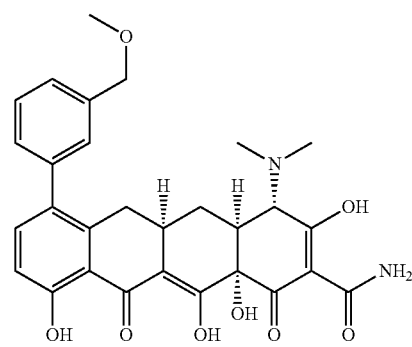
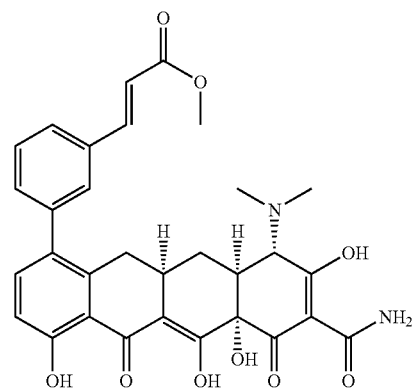
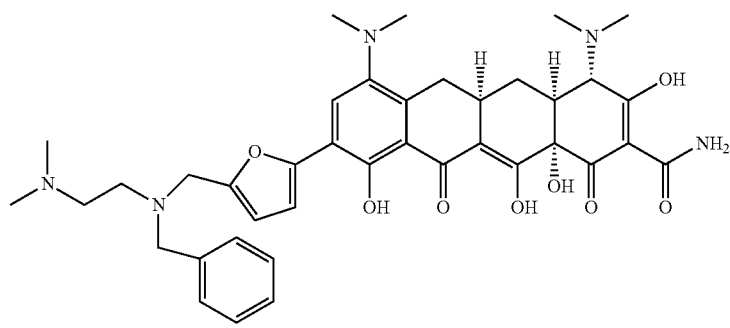

TABLE 2-continued
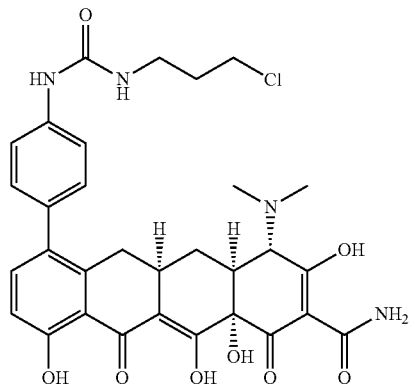
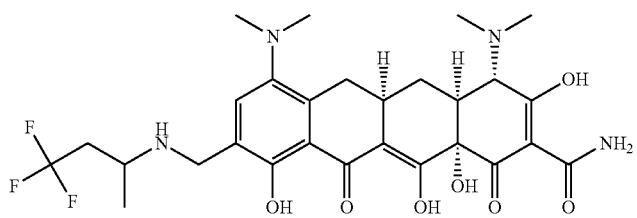
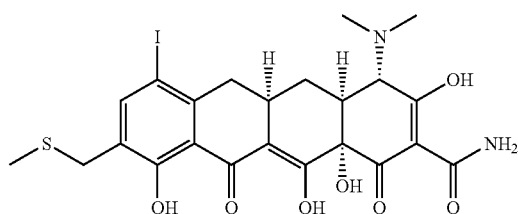
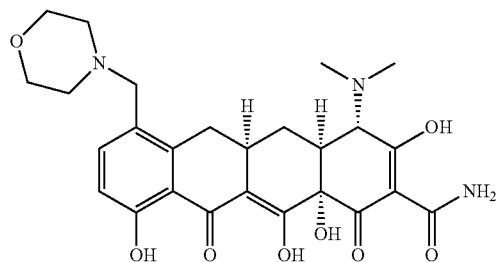
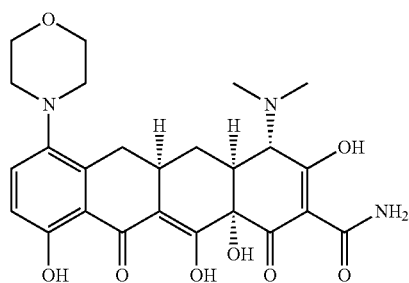

TABLE 2-continued
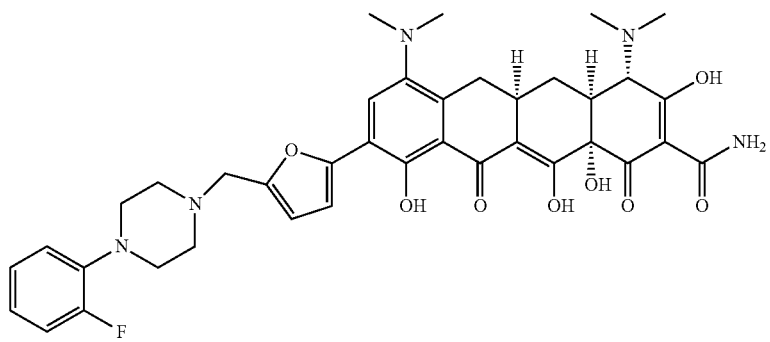
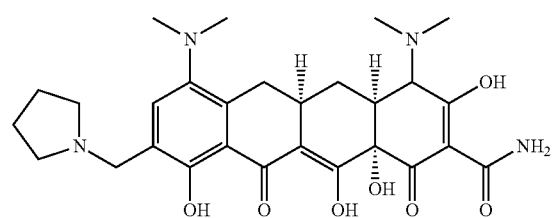
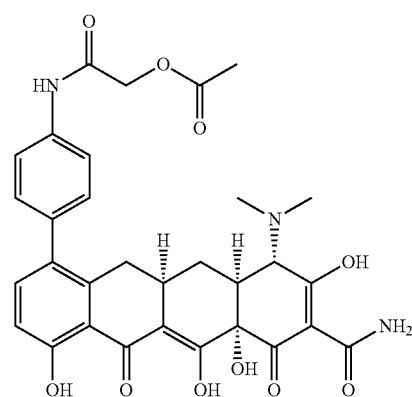
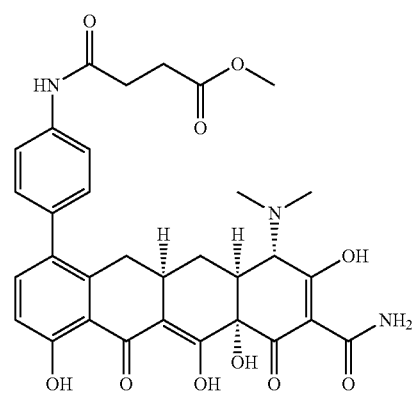

TABLE 2-continued
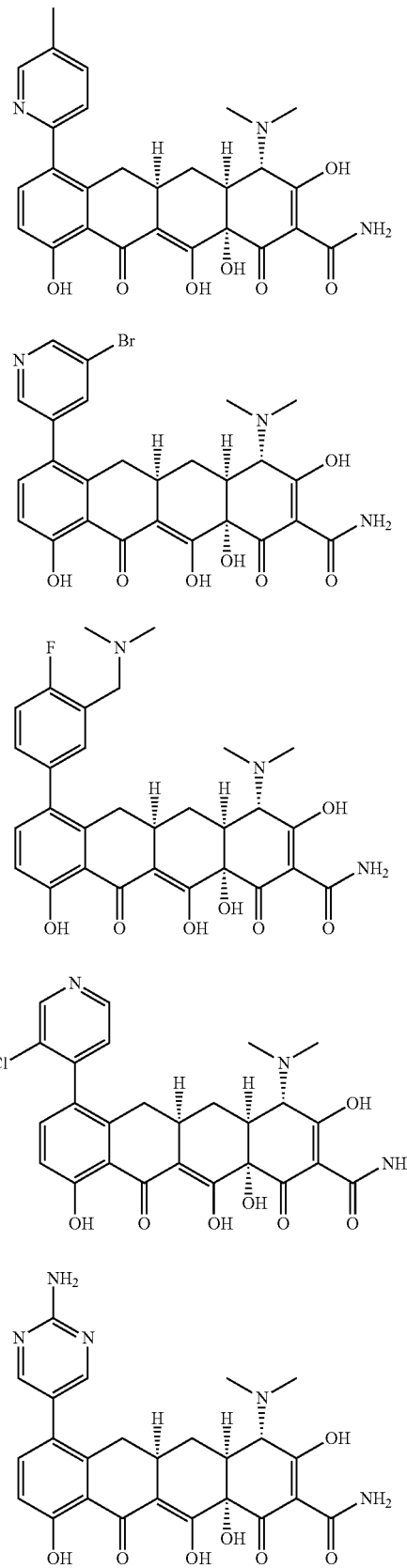

TABLE 2-continued
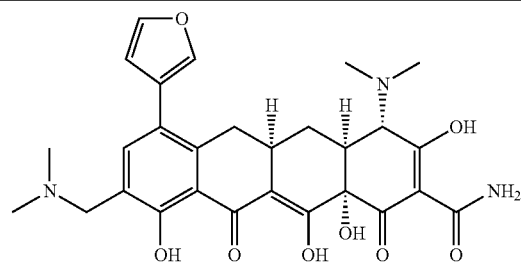
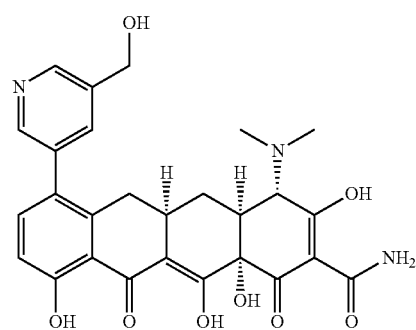
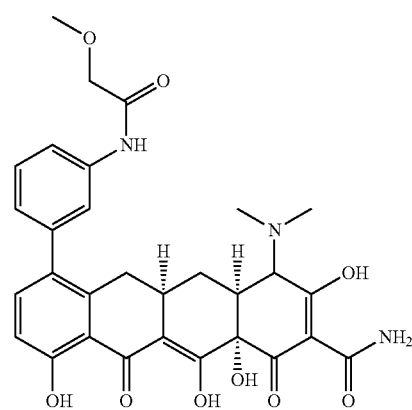
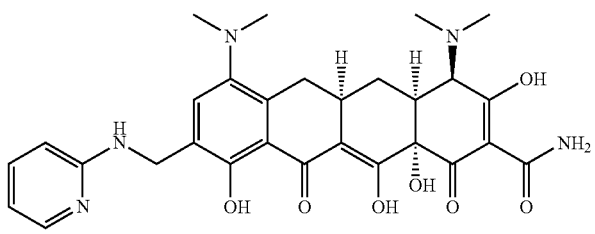
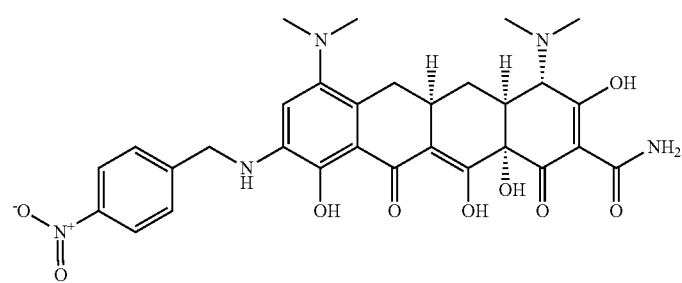

TABLE 2-continued
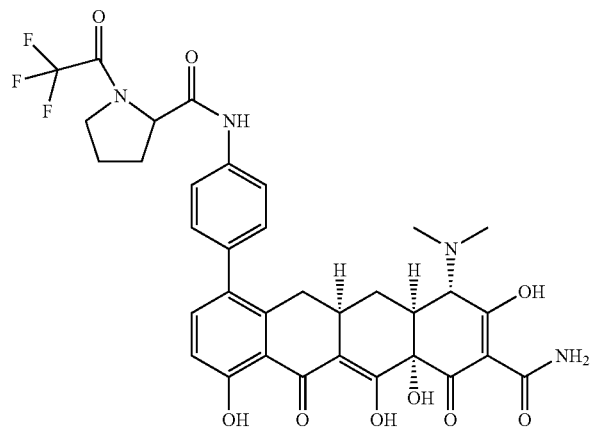
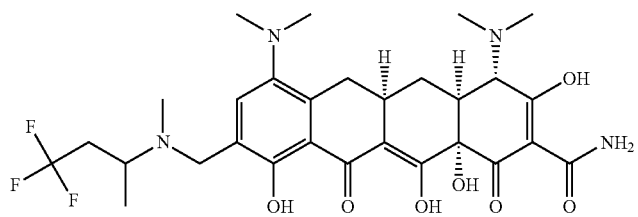
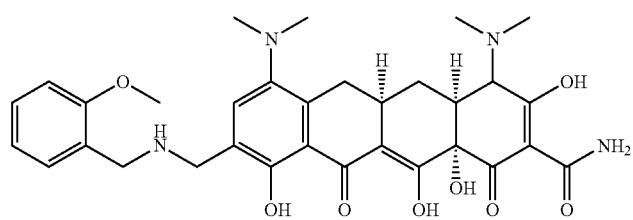
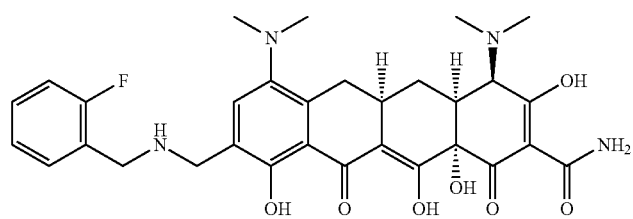
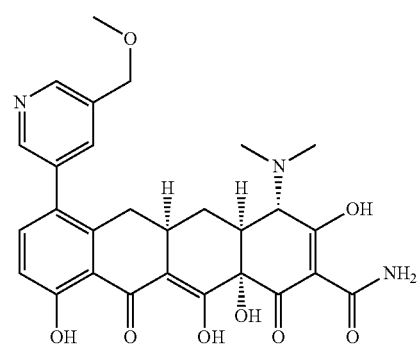

TABLE 2-continued
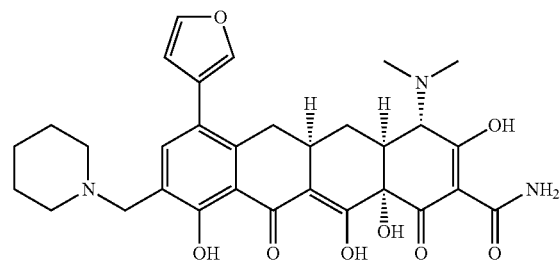
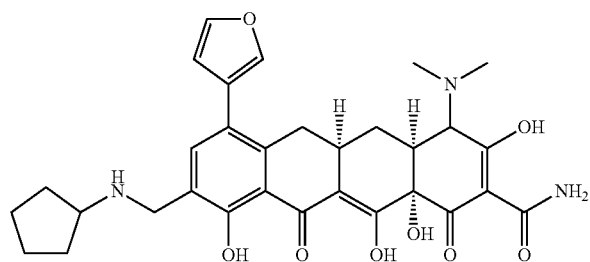
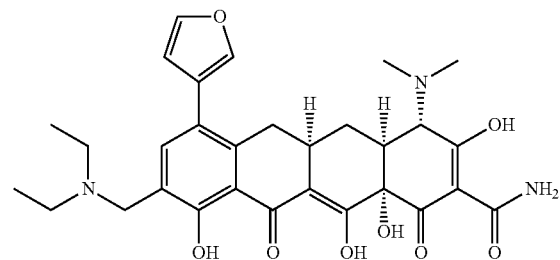
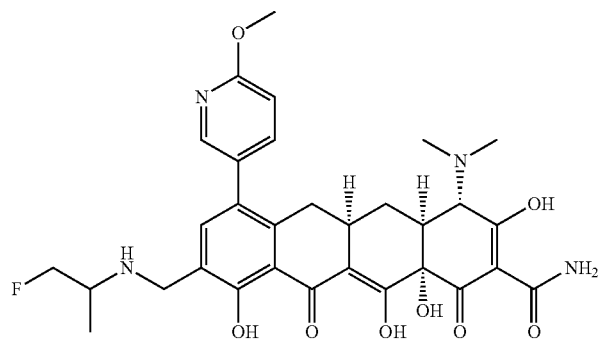
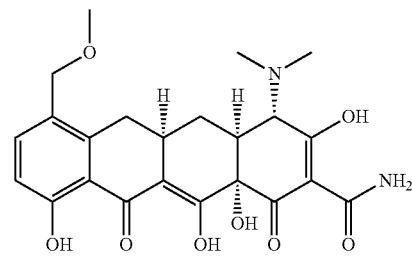

TABLE 2-continued
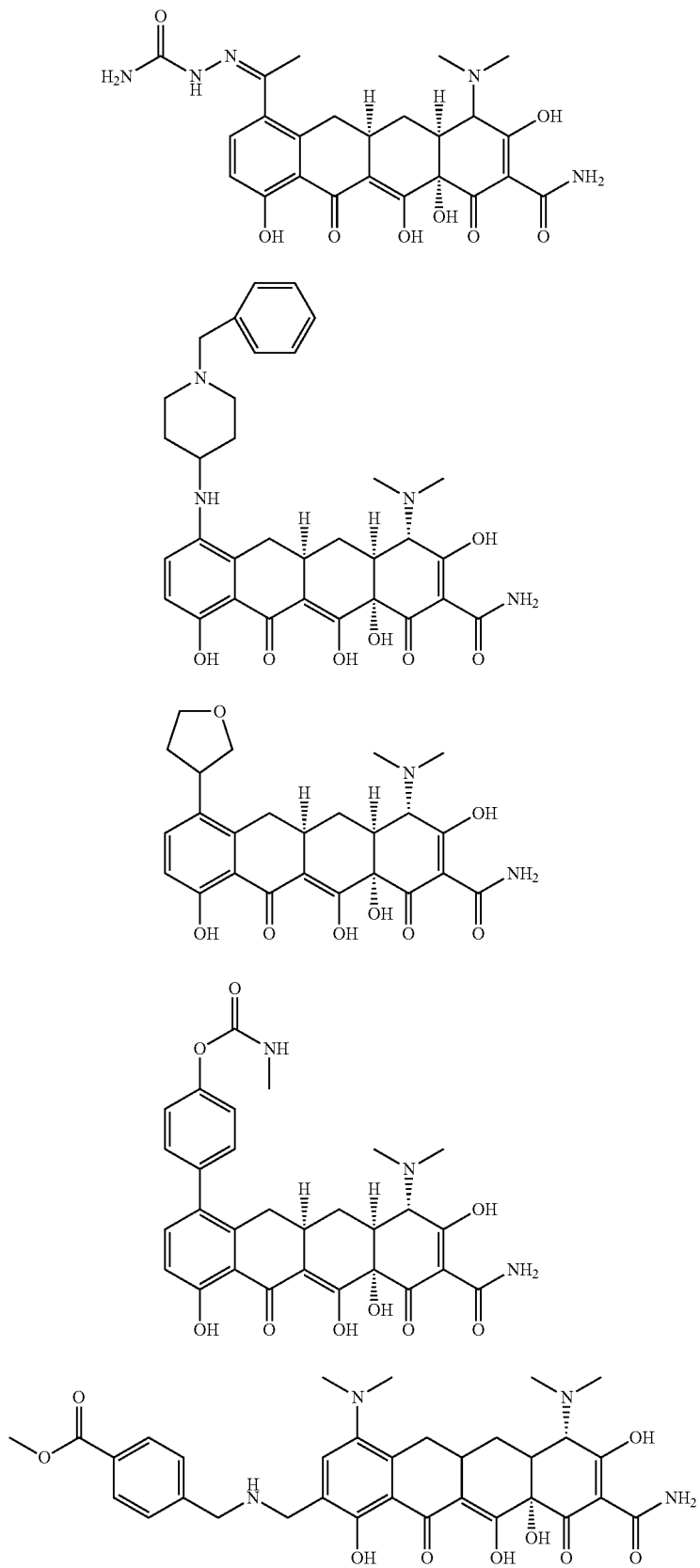

TABLE 2-continued
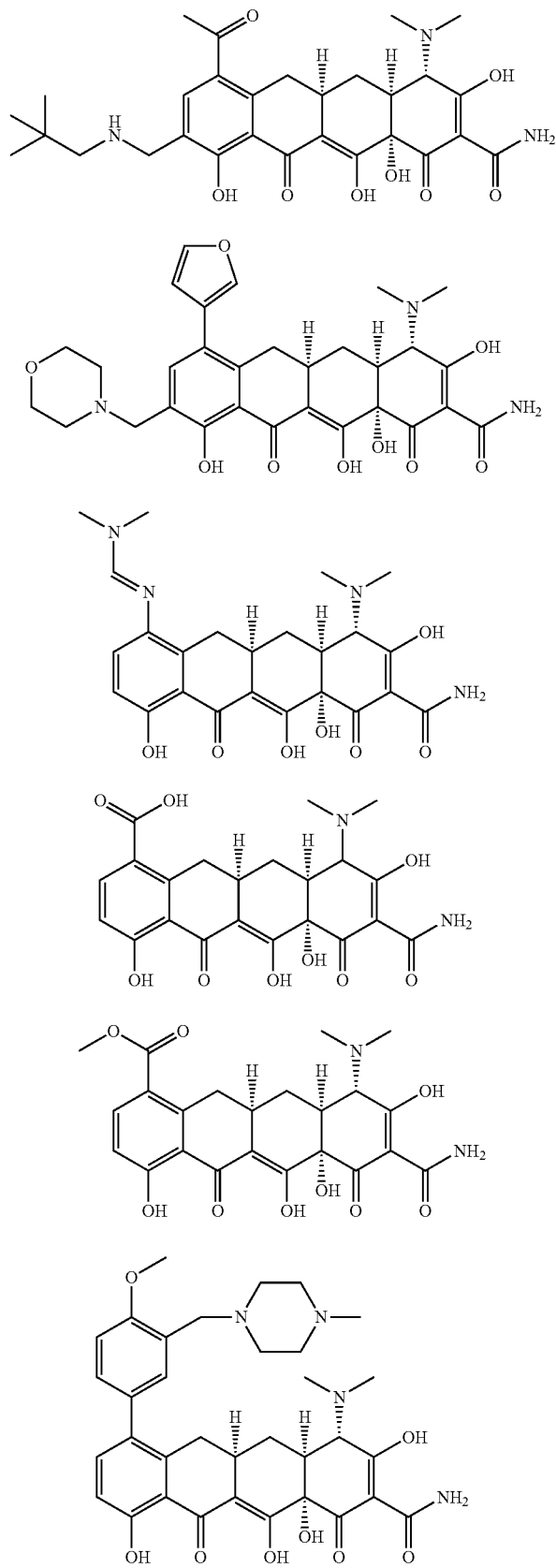

TABLE 2-continued
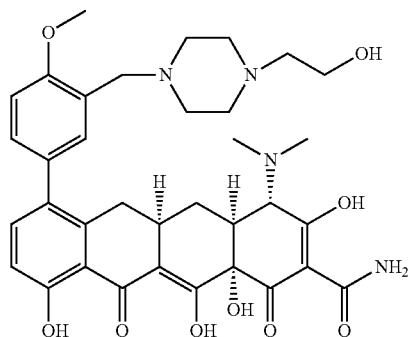
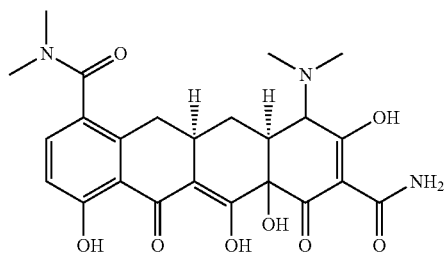
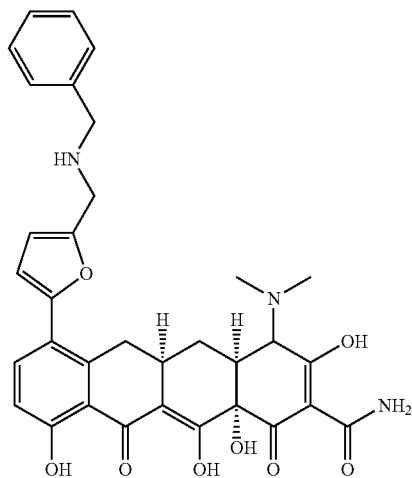
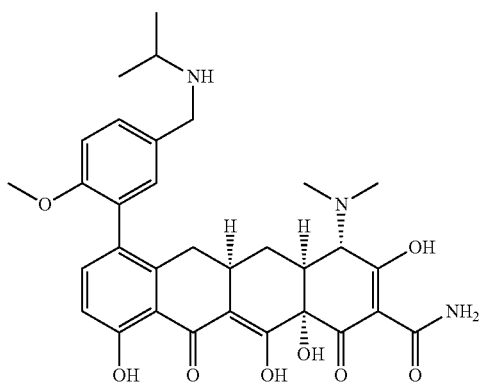

TABLE 2-continued
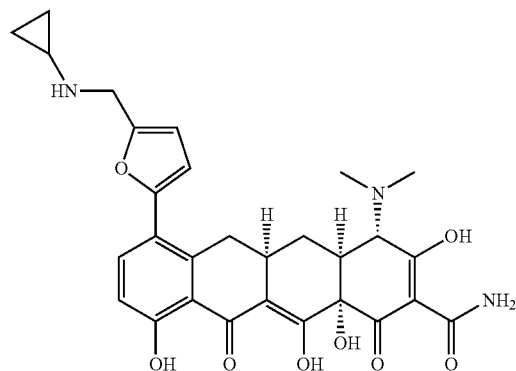
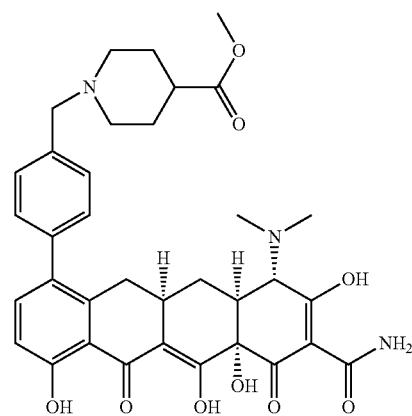
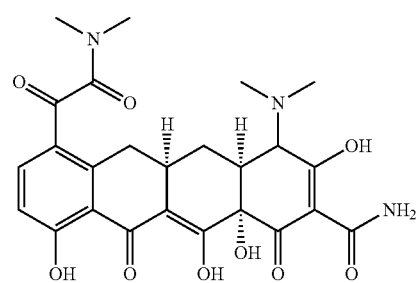
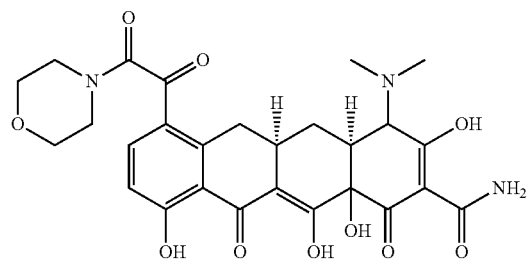

TABLE 2-continued
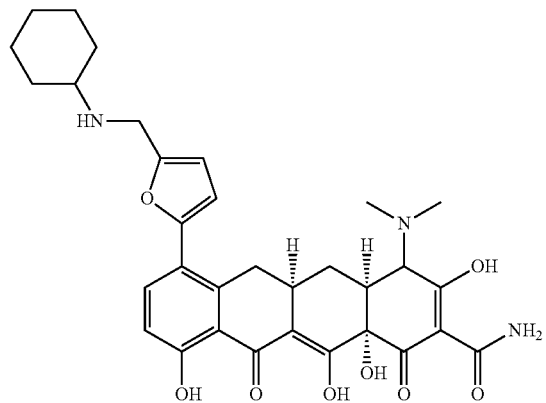
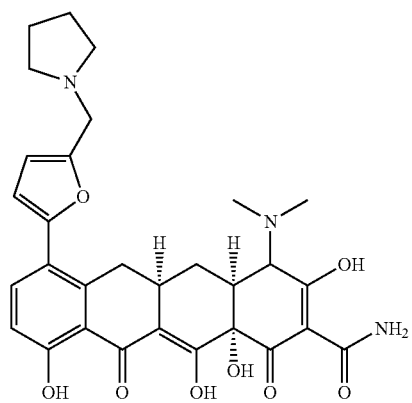
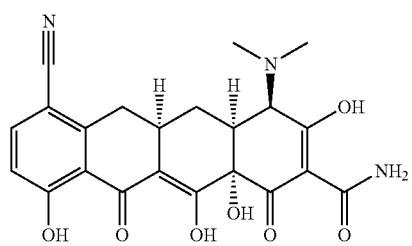
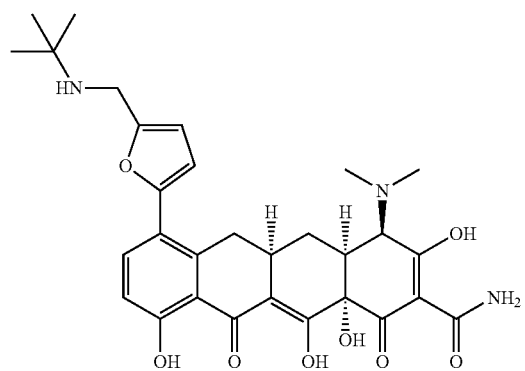

TABLE 2-continued
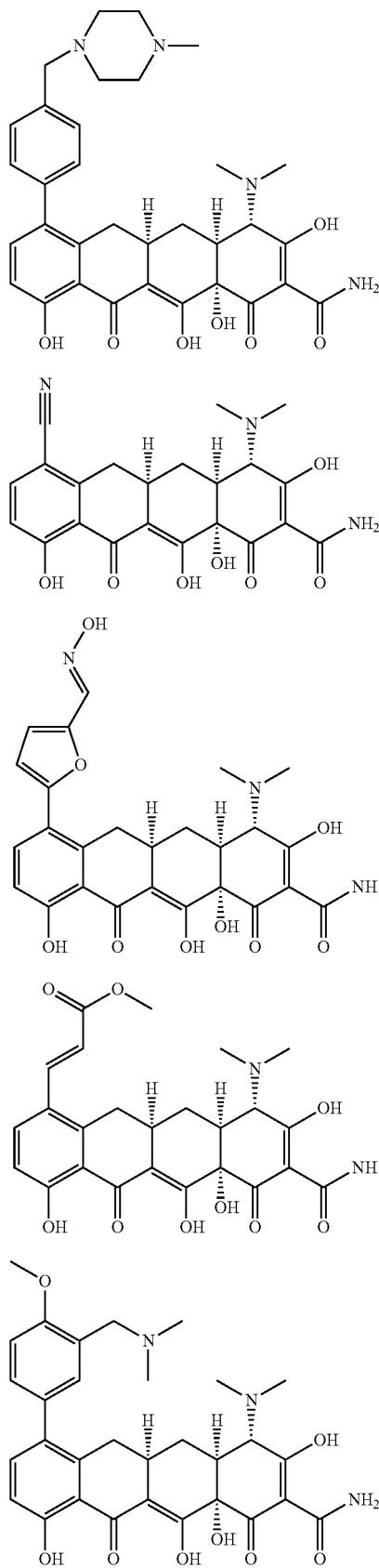

TABLE 2-continued
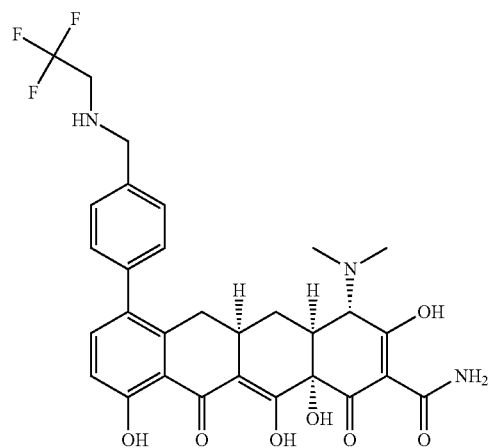
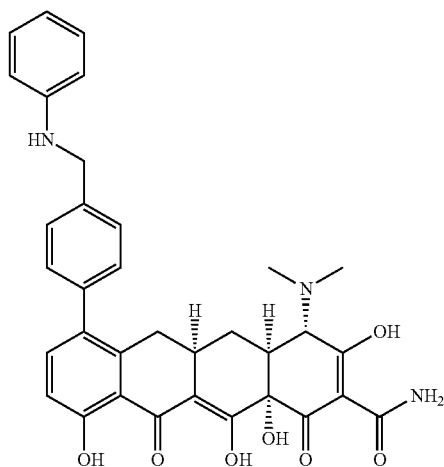
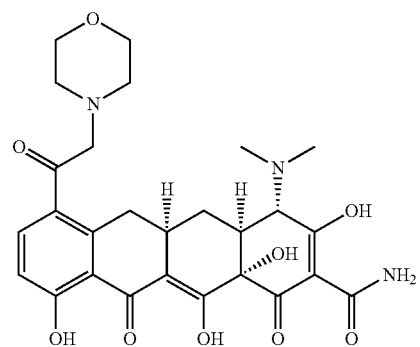
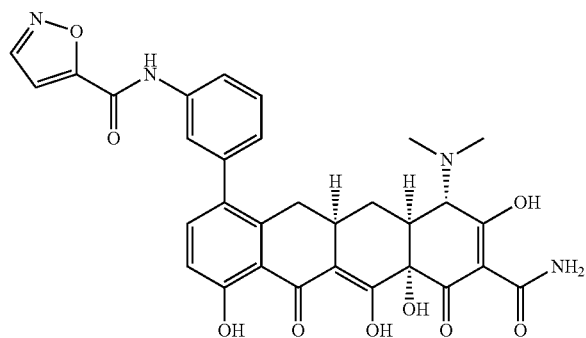

TABLE 2-continued
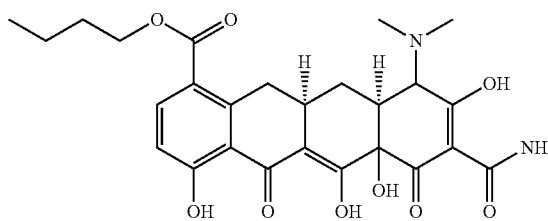
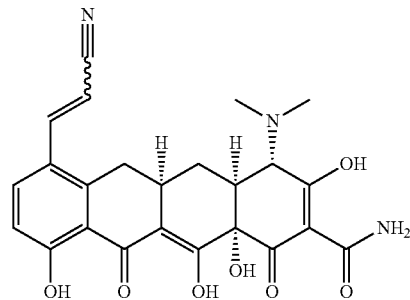
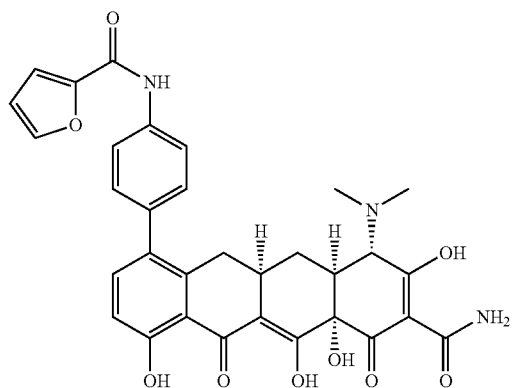
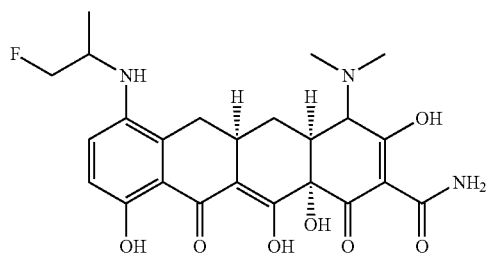
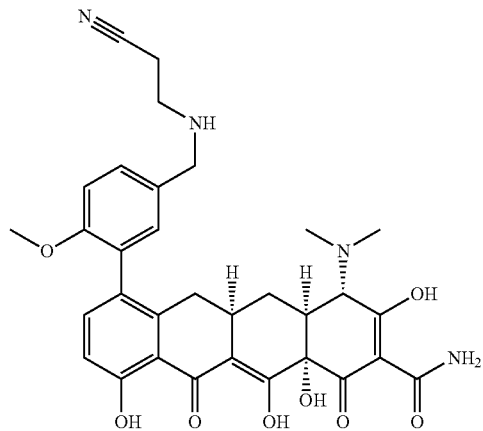

TABLE 2-continued
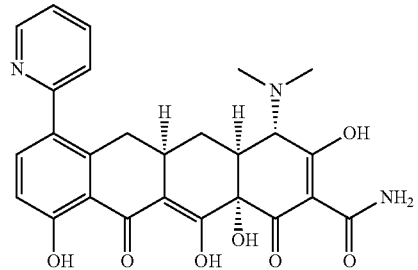
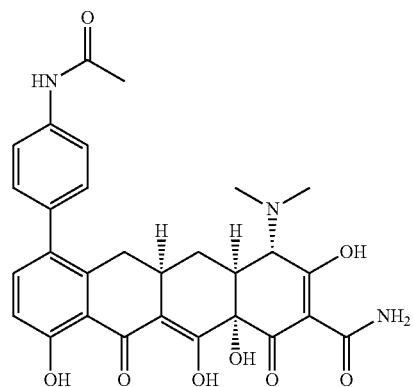
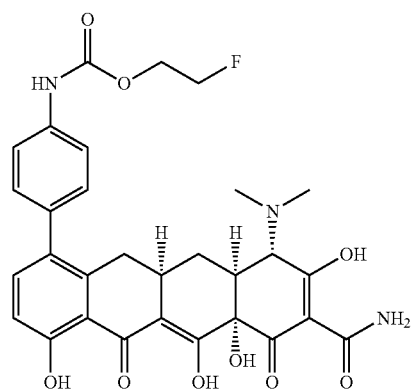
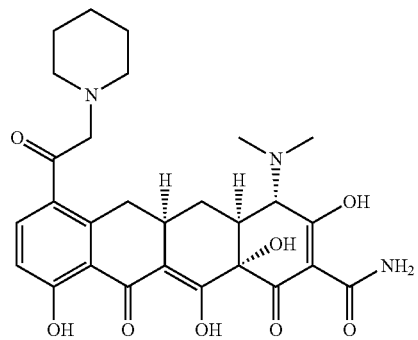

TABLE 2-continued
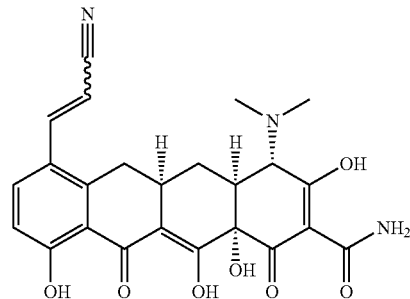
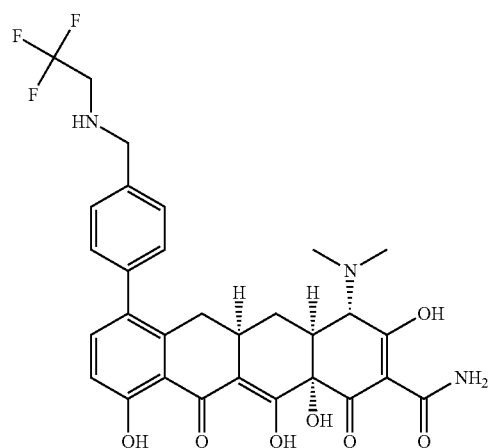
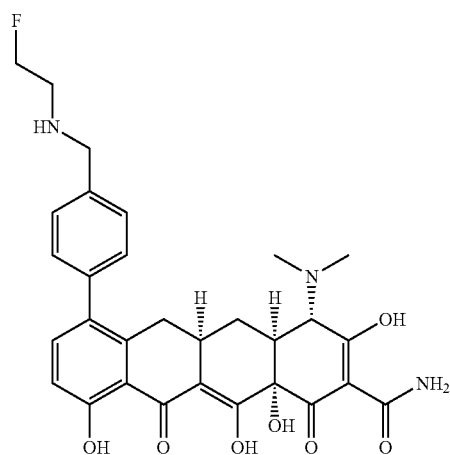

TABLE 2-continued
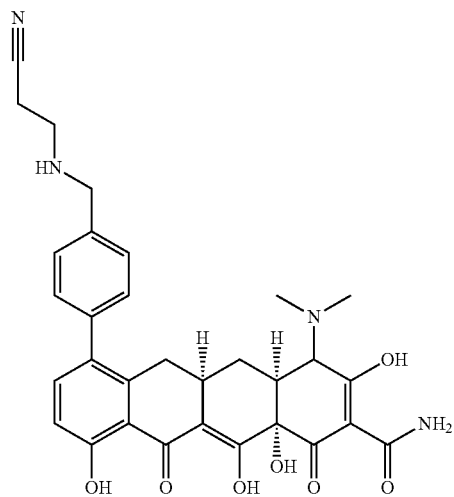
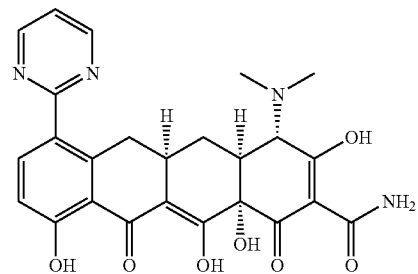
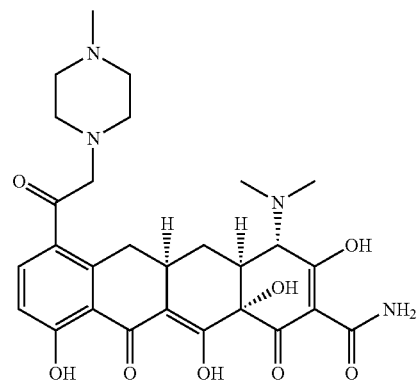
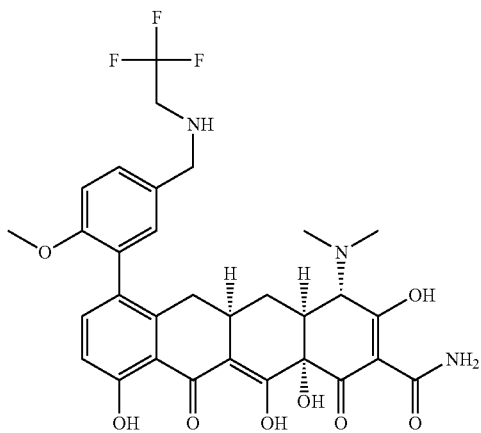

TABLE 2-continued
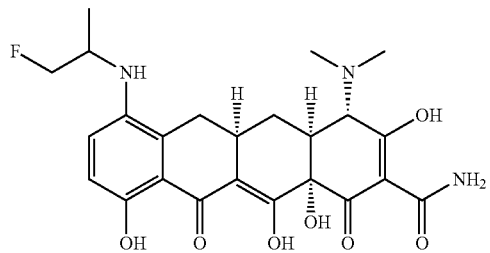
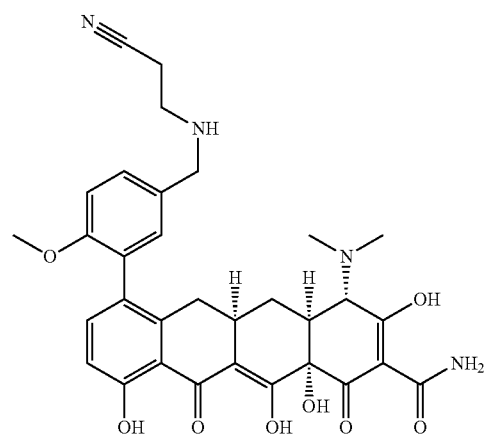
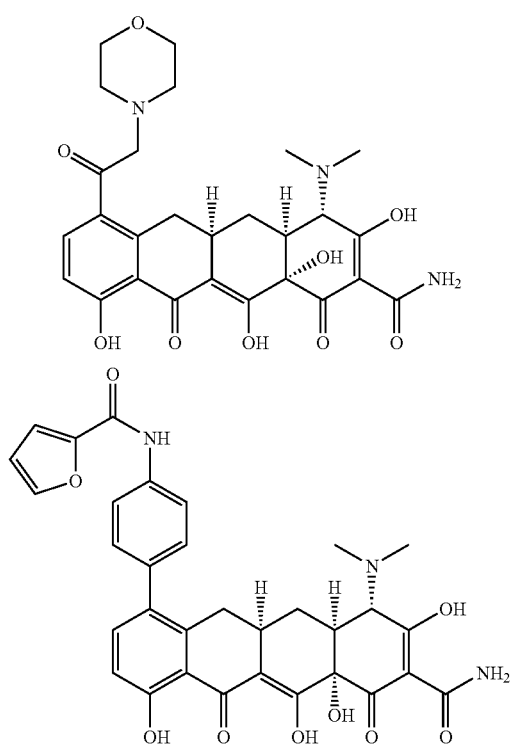

TABLE 2-continued
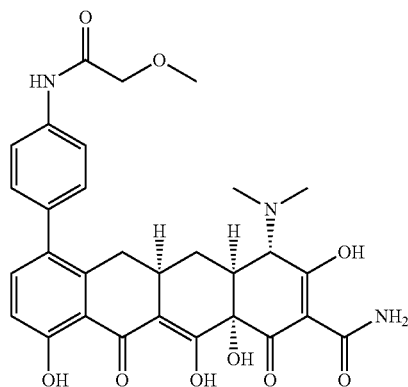
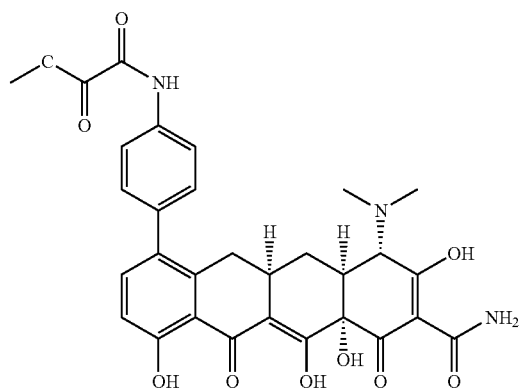
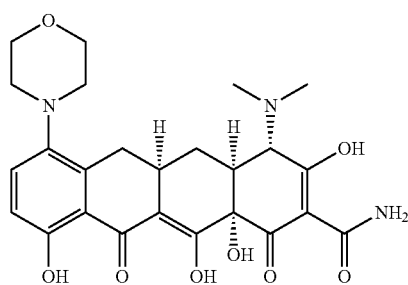
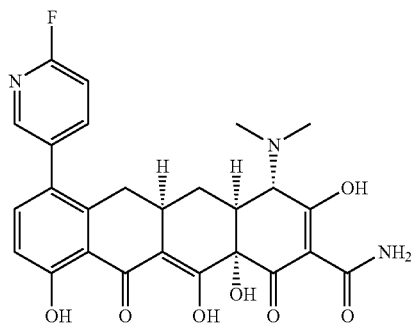

TABLE 2-continued
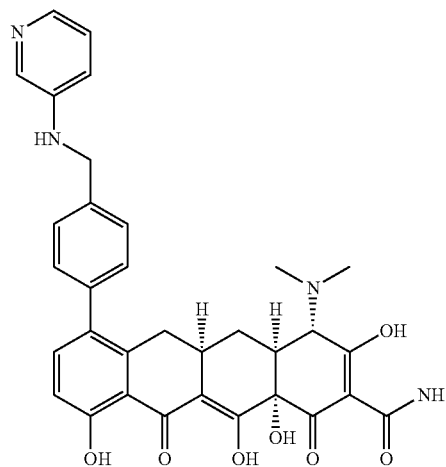
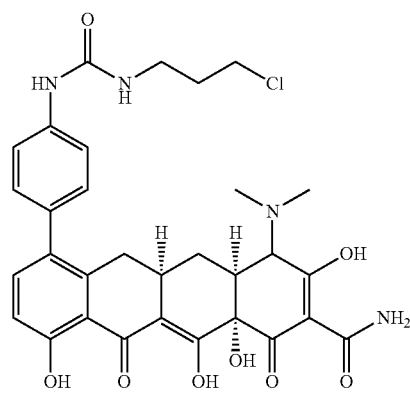
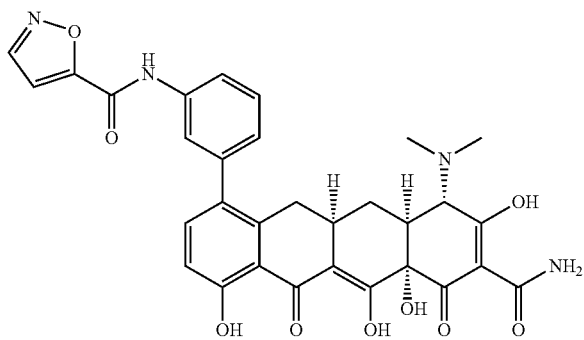
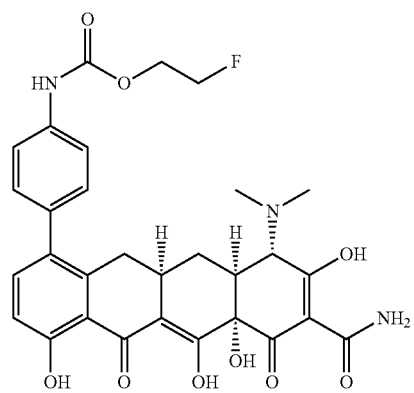

TABLE 2-continued
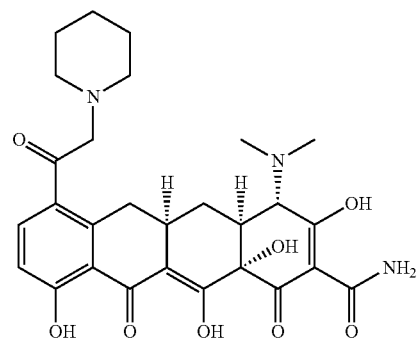
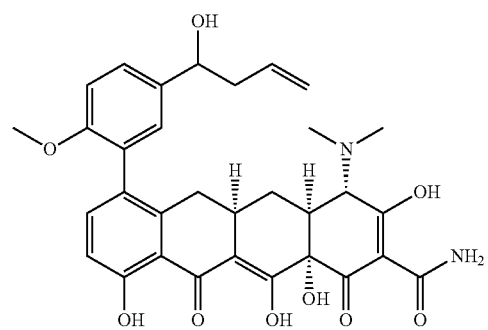
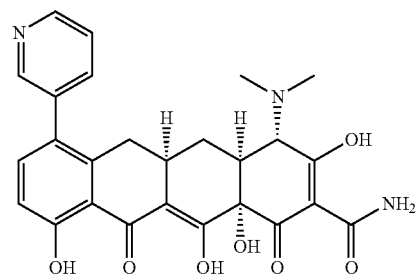
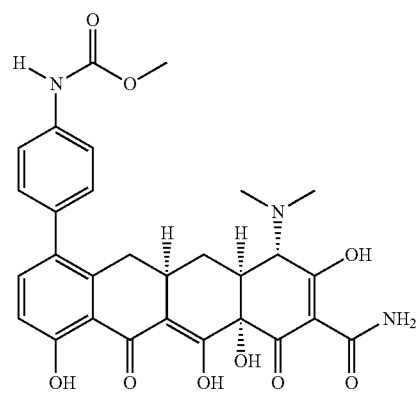

TABLE 2-continued
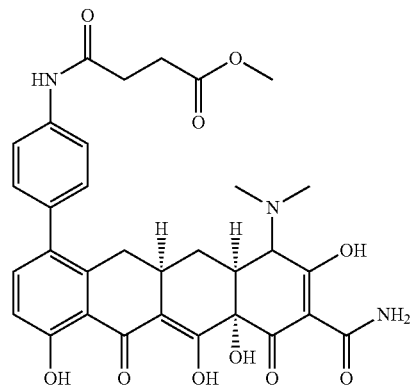
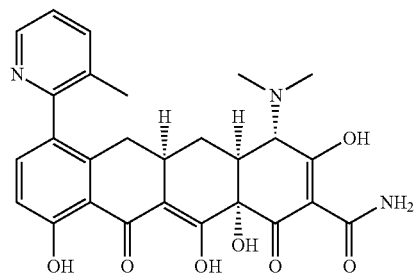
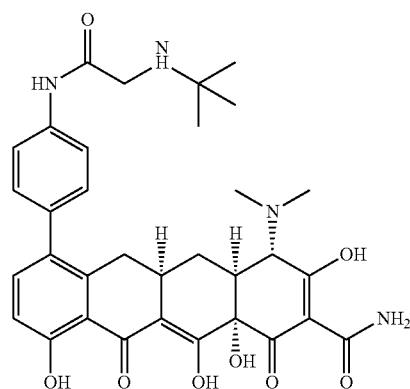
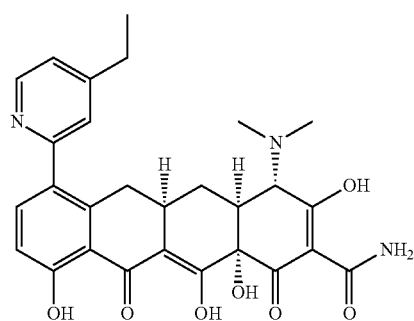

TABLE 2-continued
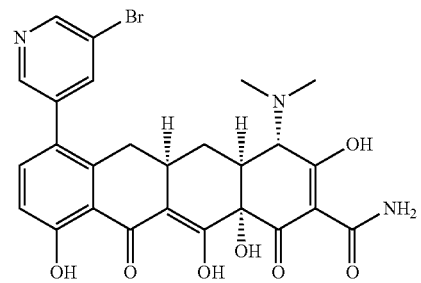
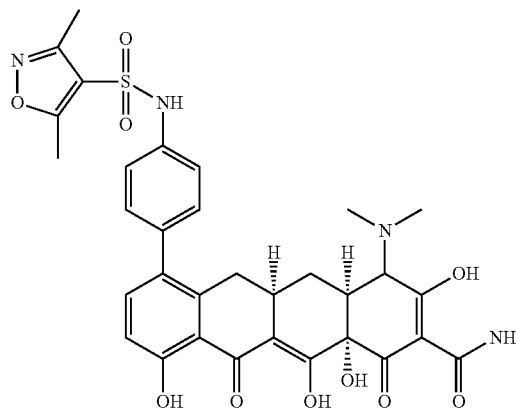
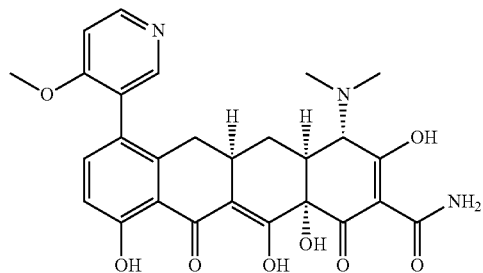
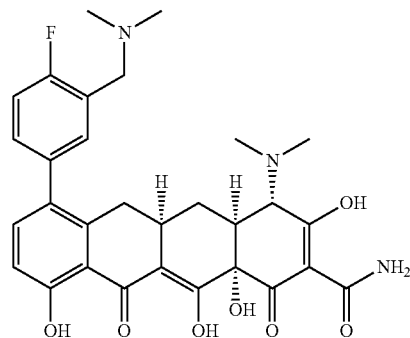
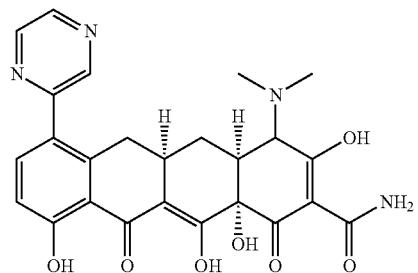

TABLE 2-continued
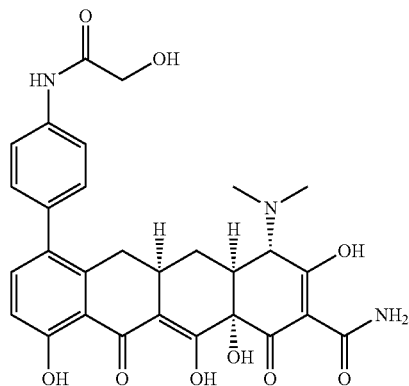
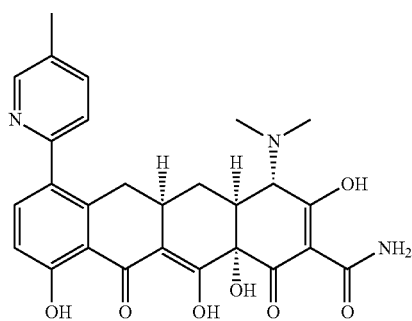
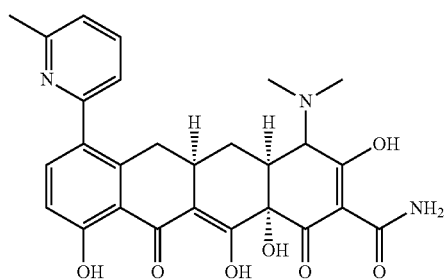
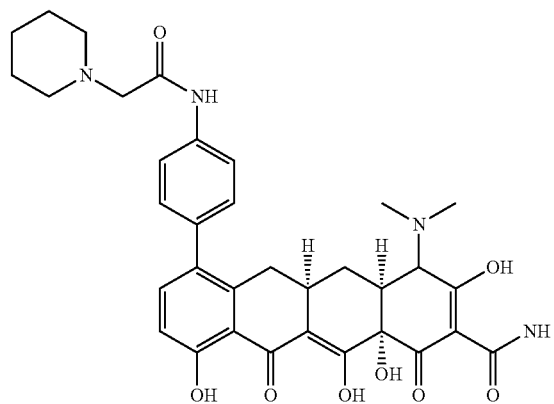

TABLE 2-continued
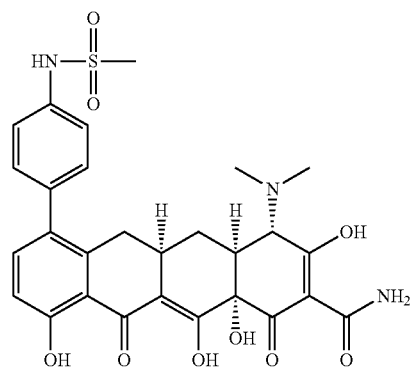
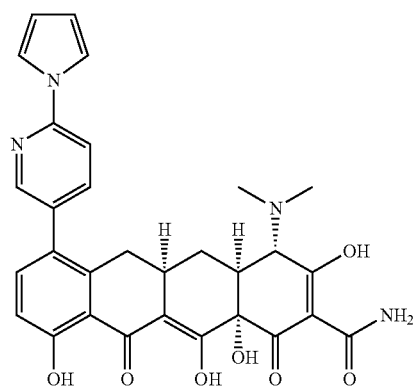
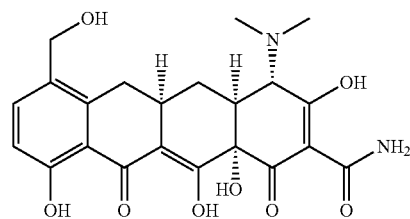
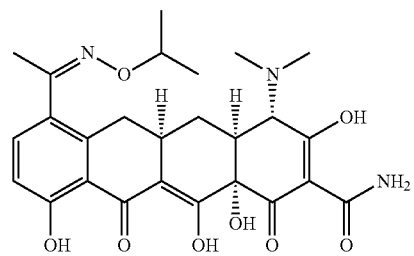
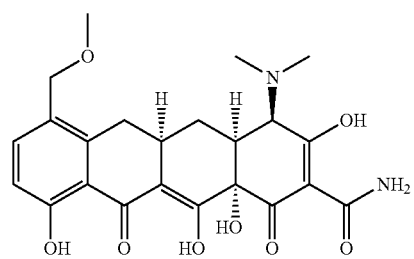

TABLE 2-continued
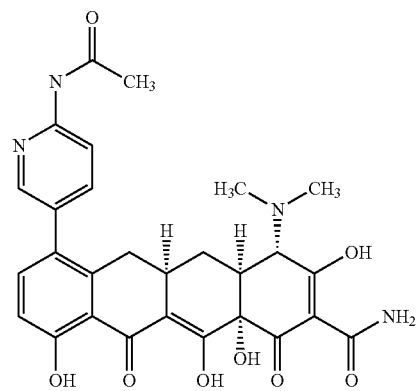
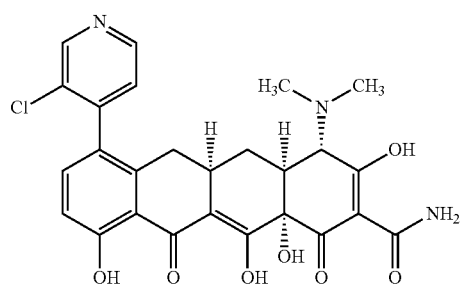
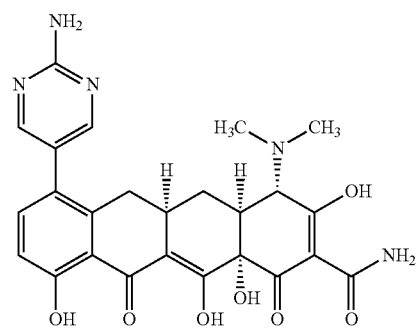
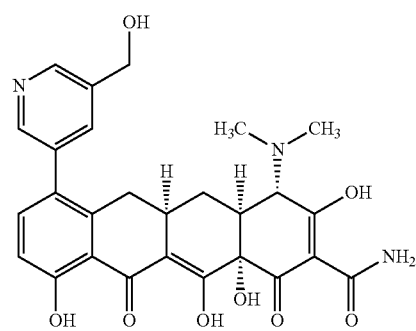
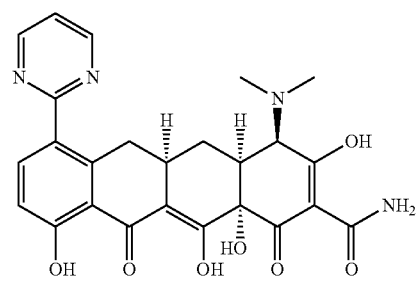

TABLE 2-continued
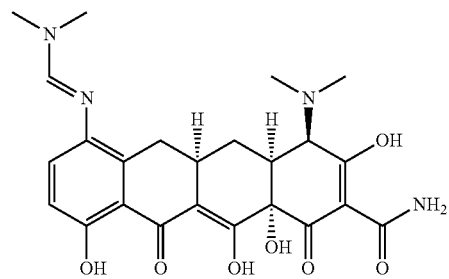
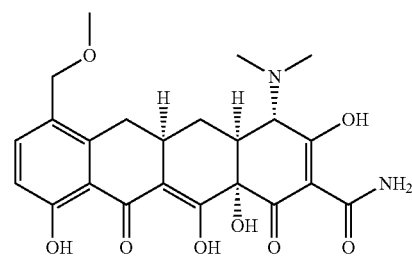
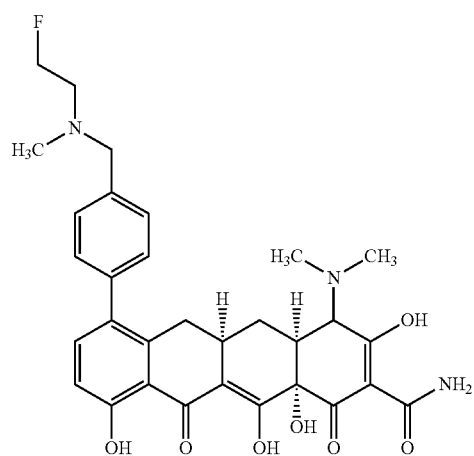
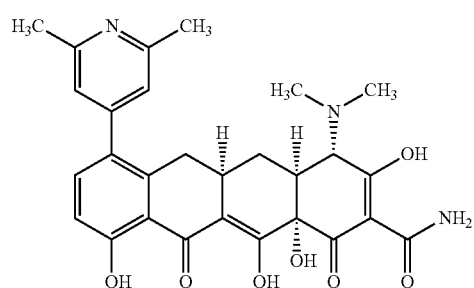

TABLE 2-continued
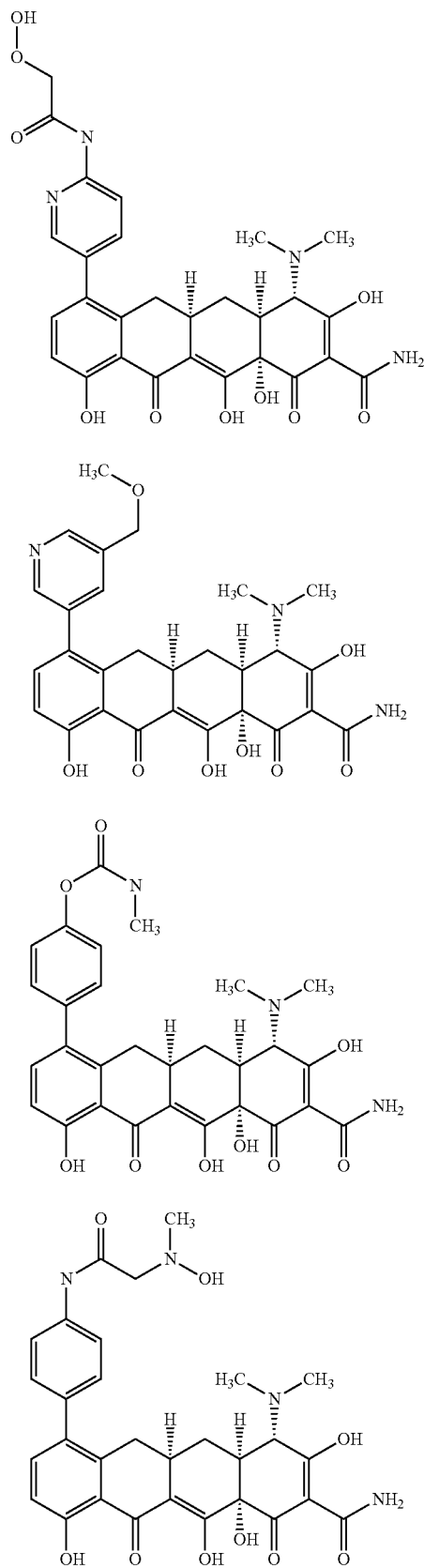

TABLE 2-continued
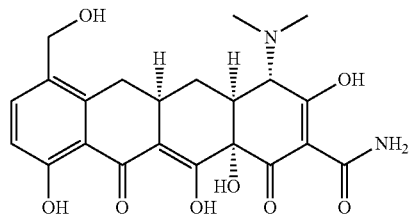
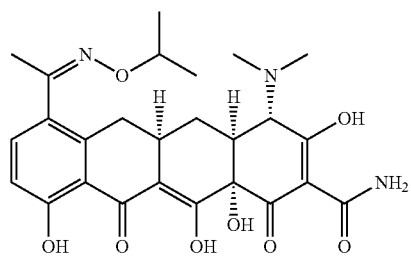
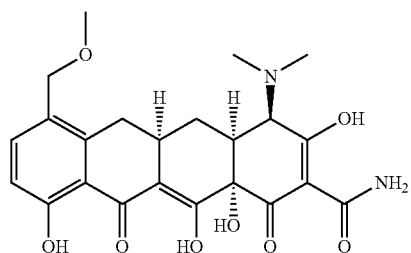
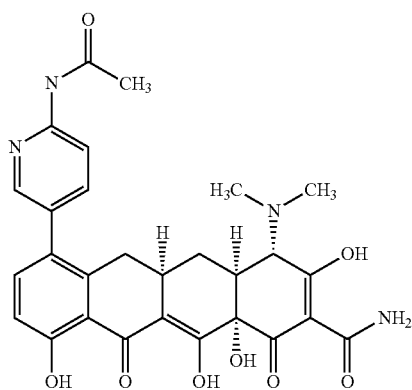
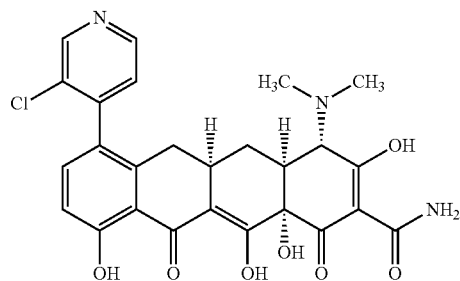

TABLE 2-continued
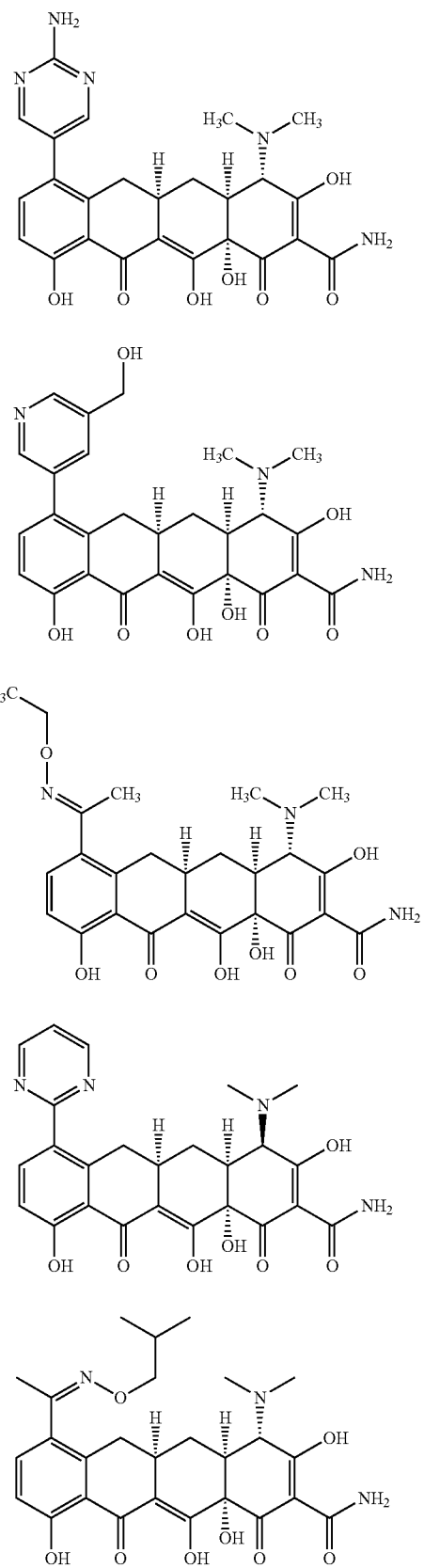

TABLE 2-continued
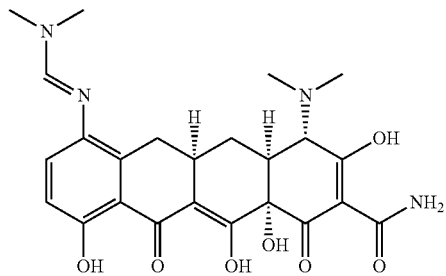
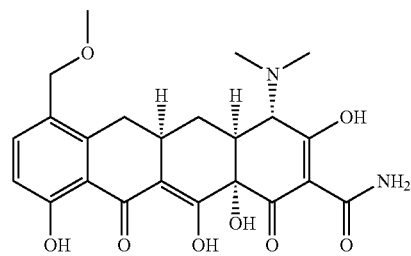
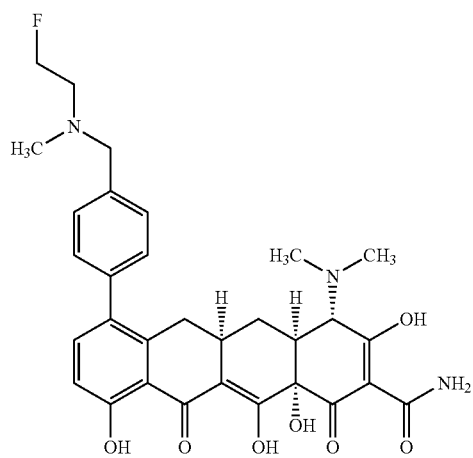
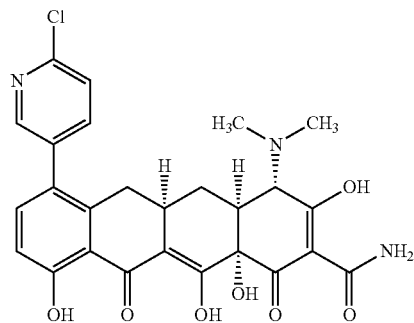

TABLE 2-continued
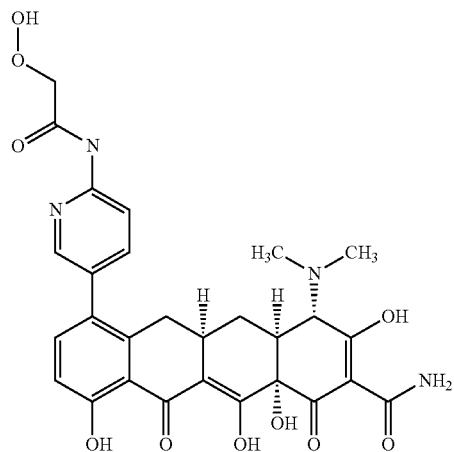
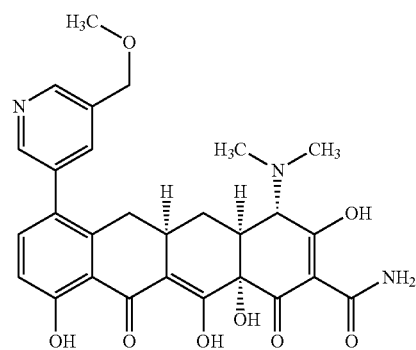
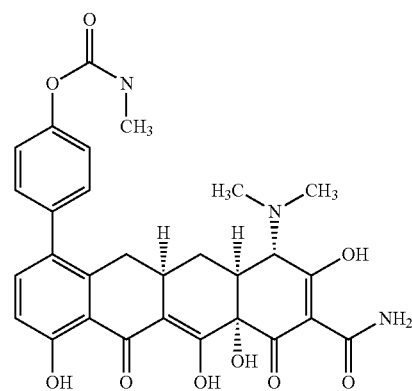
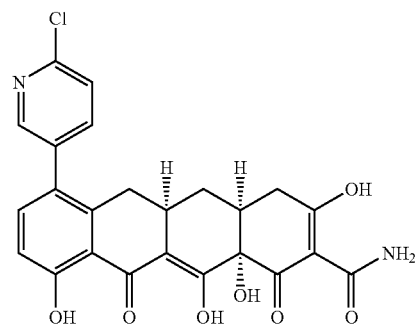

TABLE 2-continued
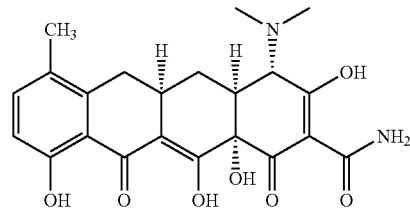
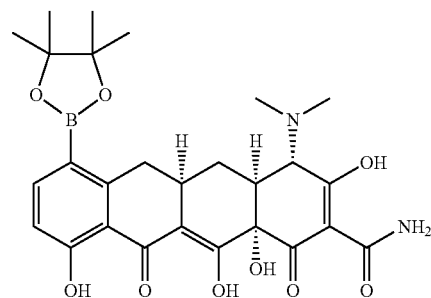
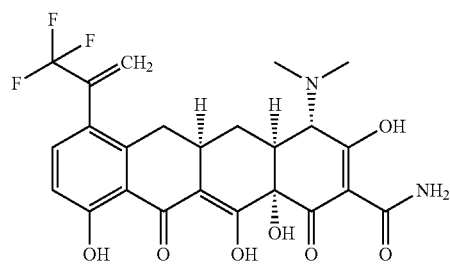
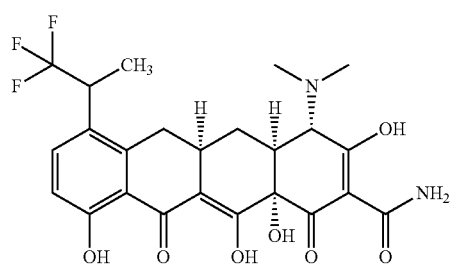
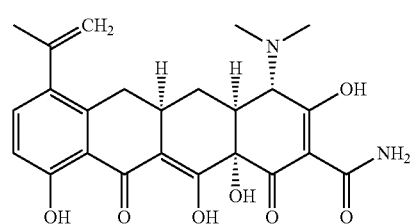

TABLE 2-continued
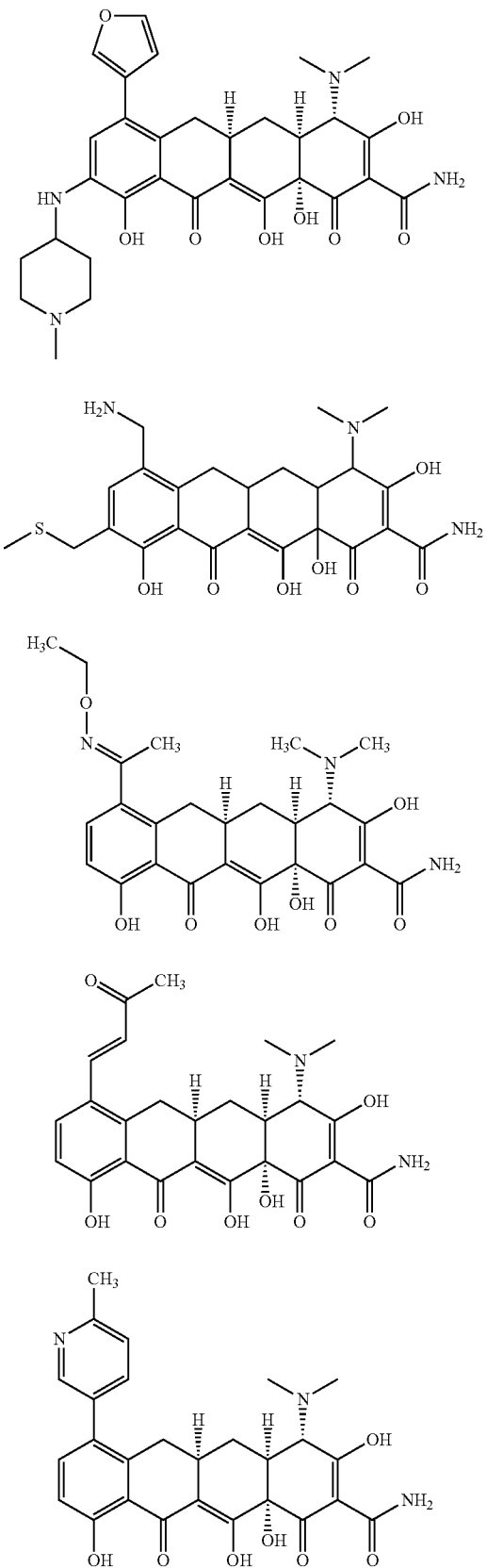

TABLE 2-continued
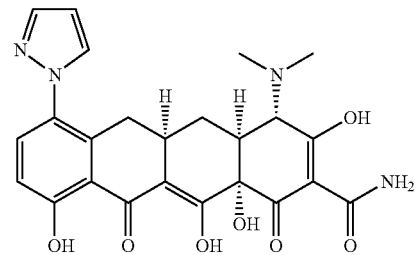
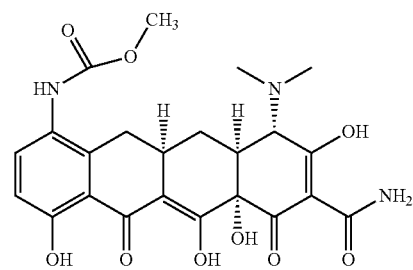
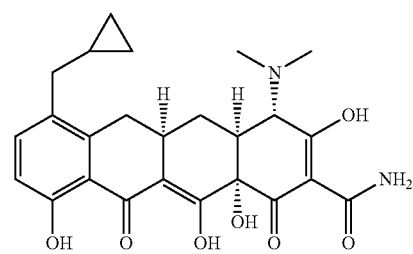
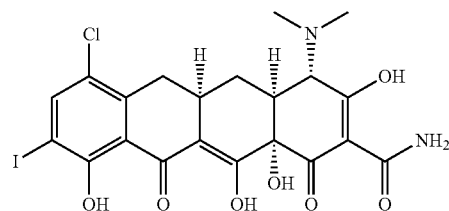
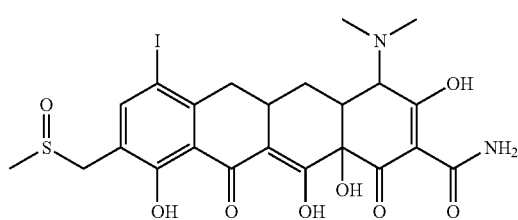
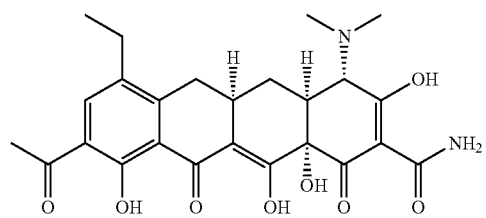

TABLE 2-continued
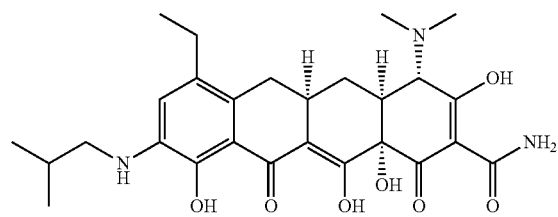
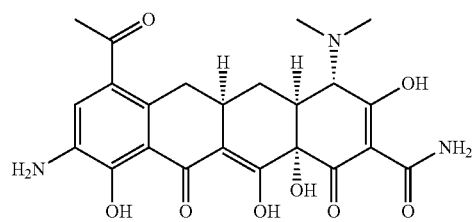
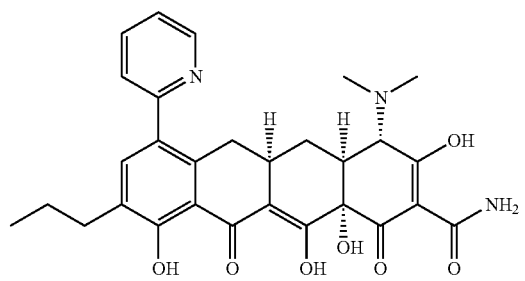
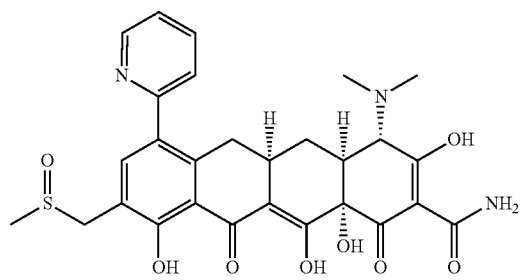
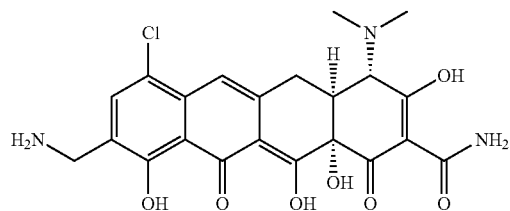
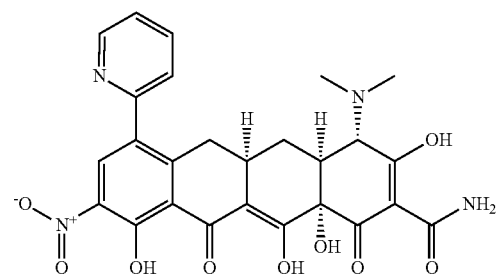

TABLE 2-continued
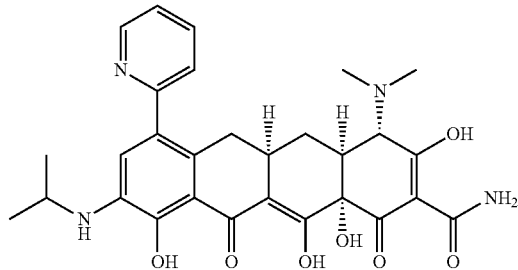
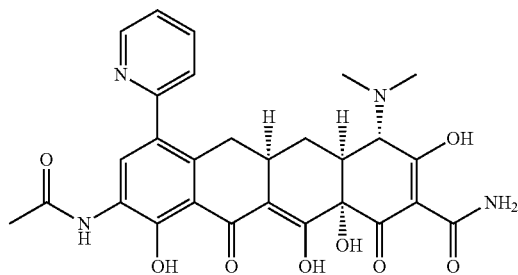
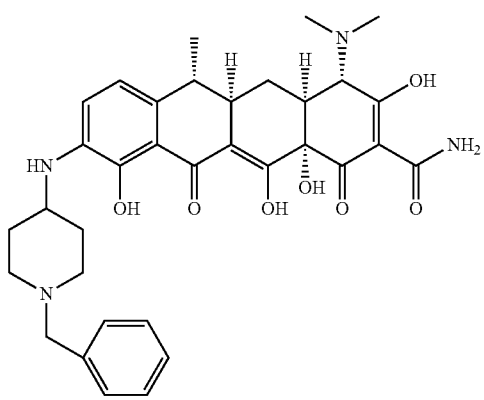
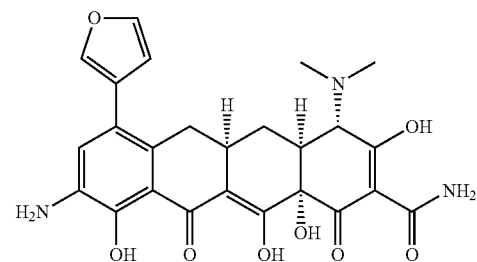
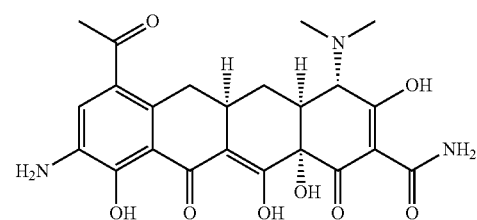

TABLE 2-continued
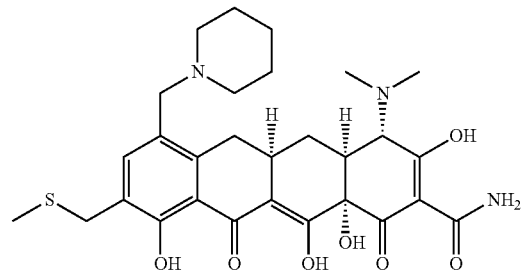
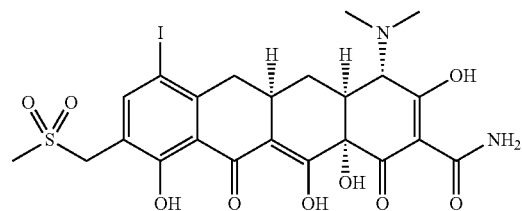
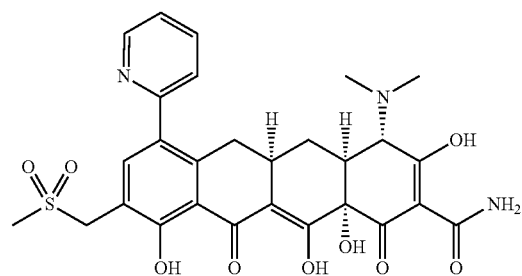
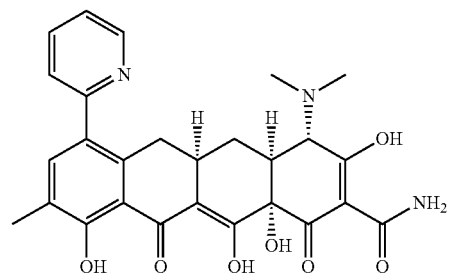
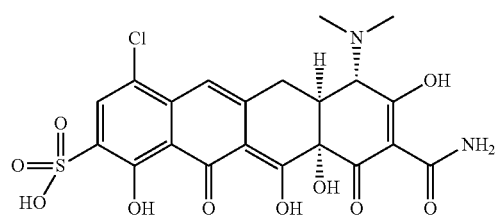
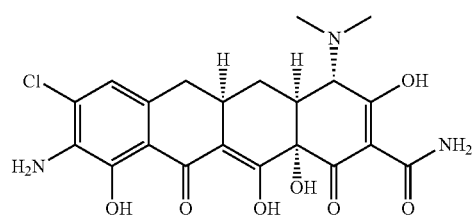

TABLE 2-continued
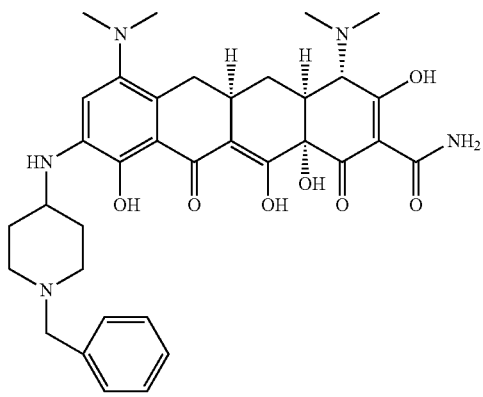
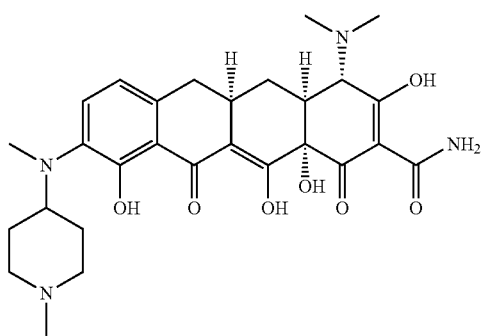
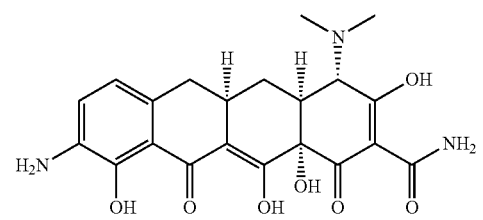
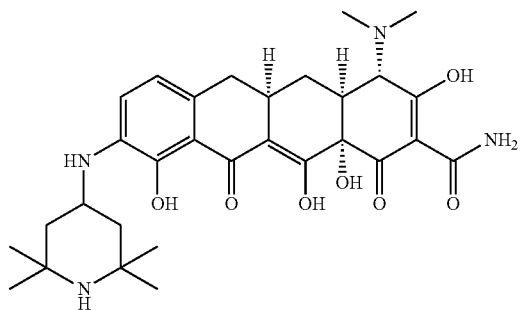
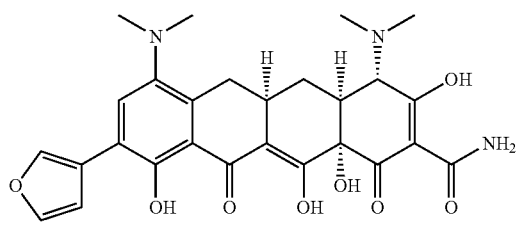

TABLE 2-continued
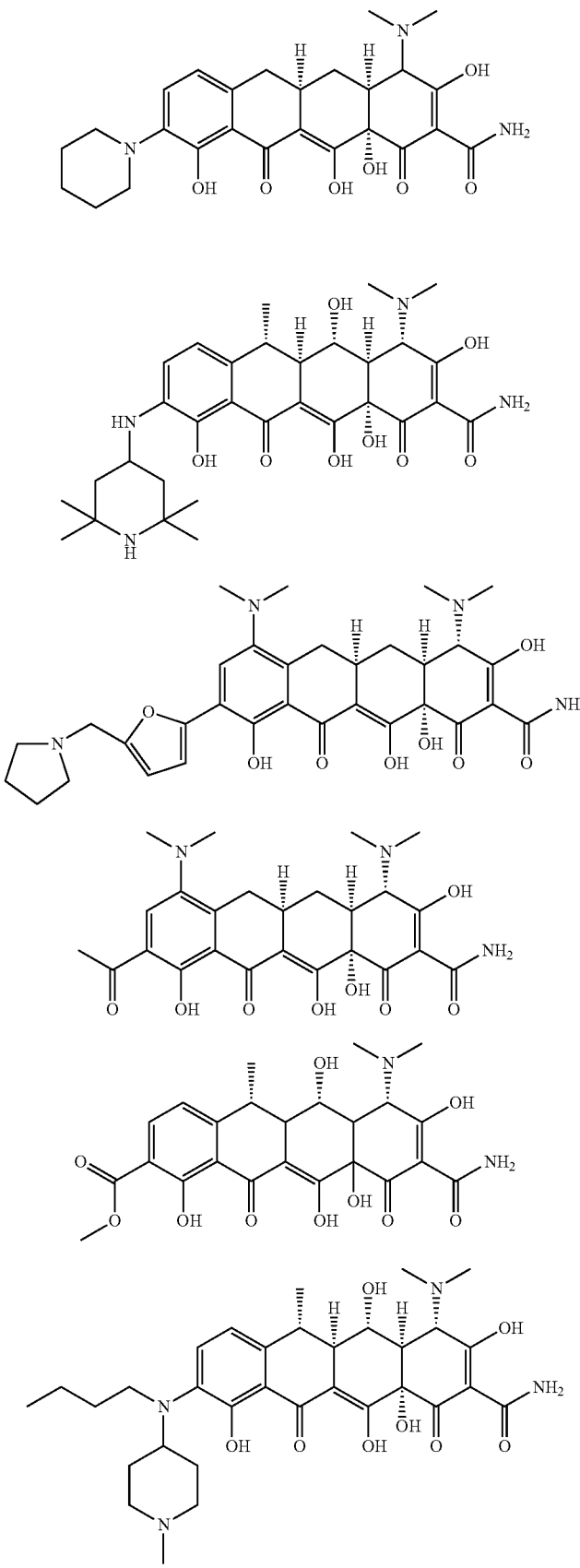

TABLE 2-continued
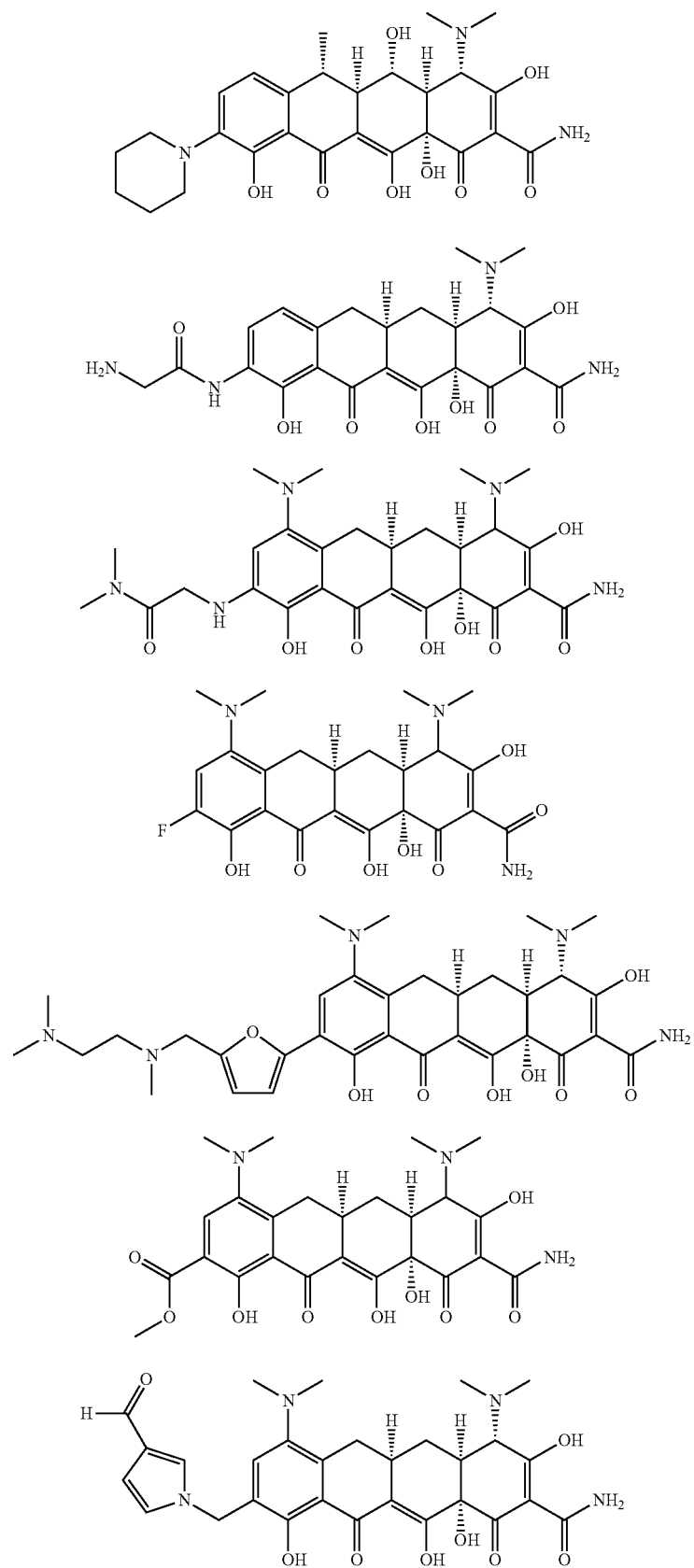

TABLE 2-continued
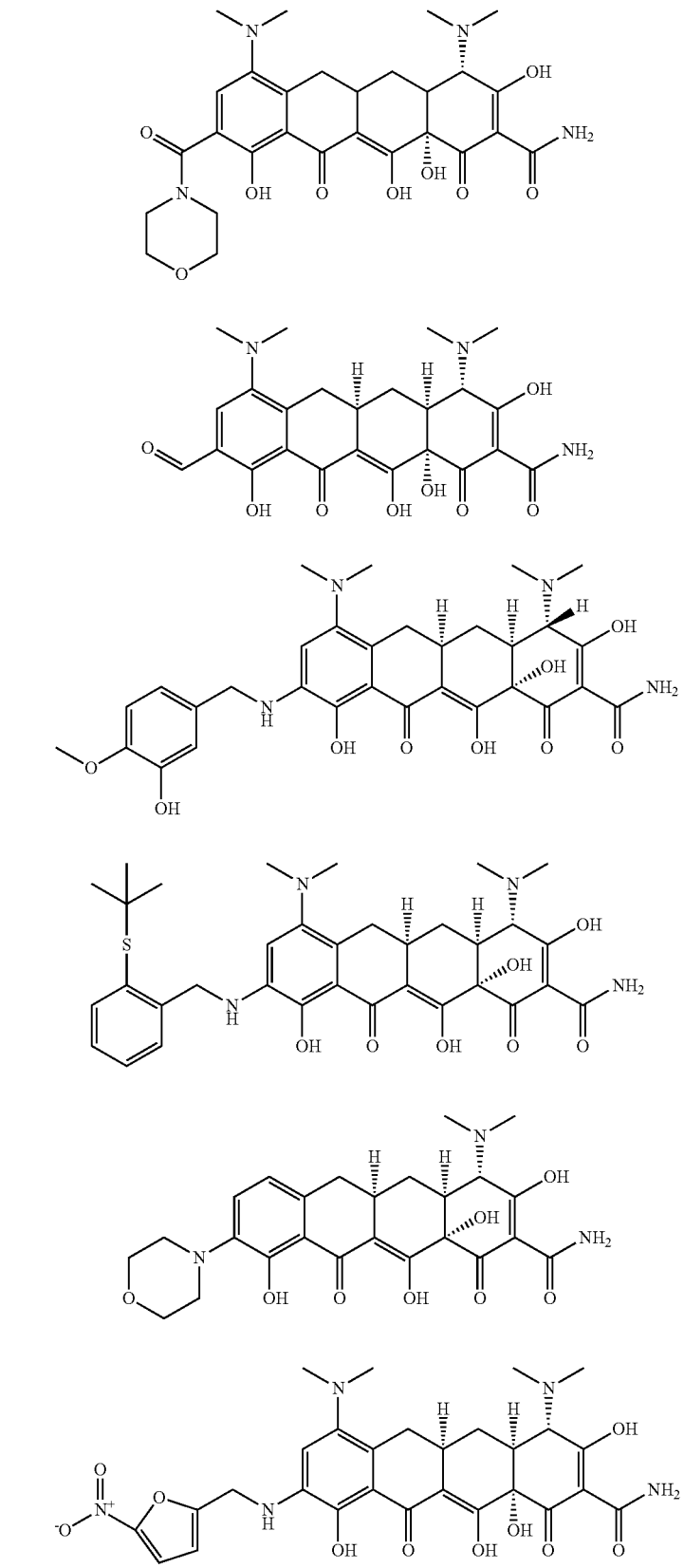

TABLE 2-continued
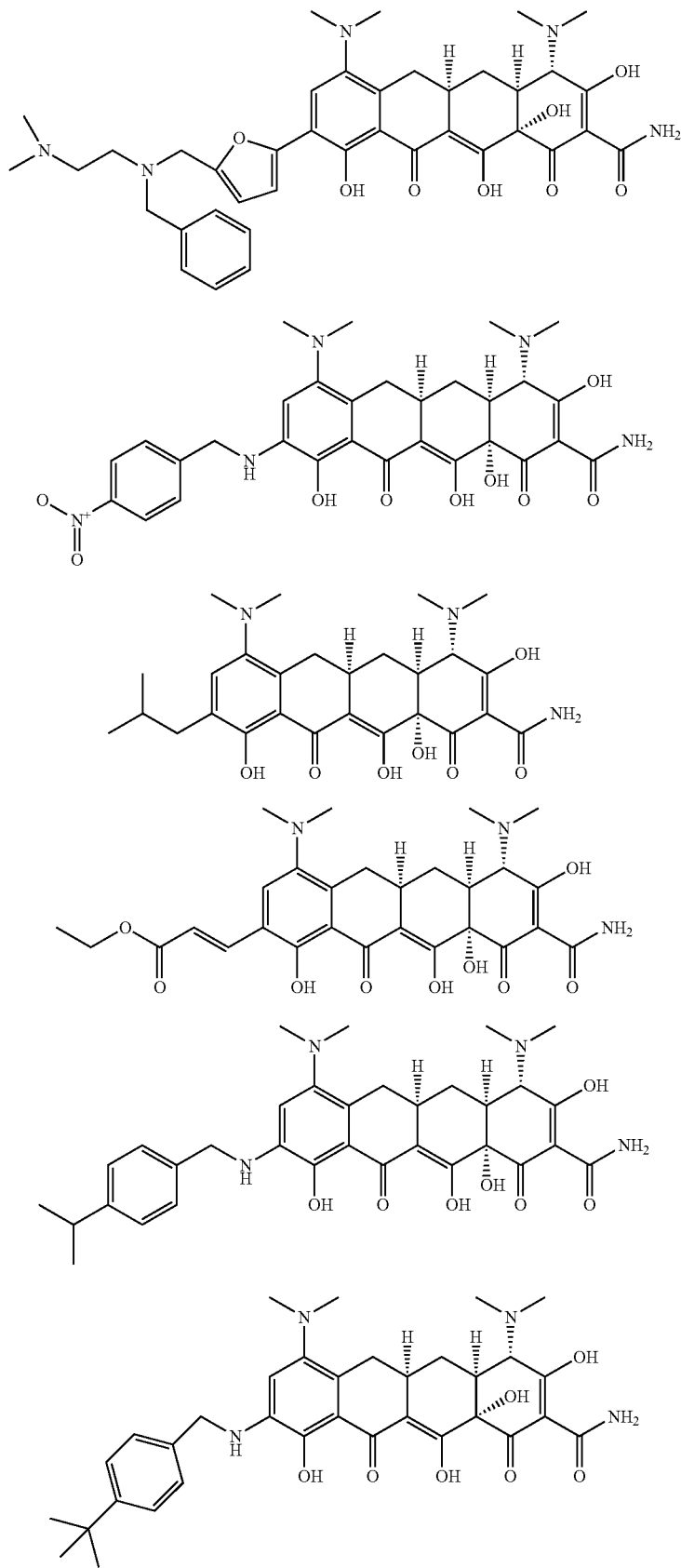

TABLE 2-continued
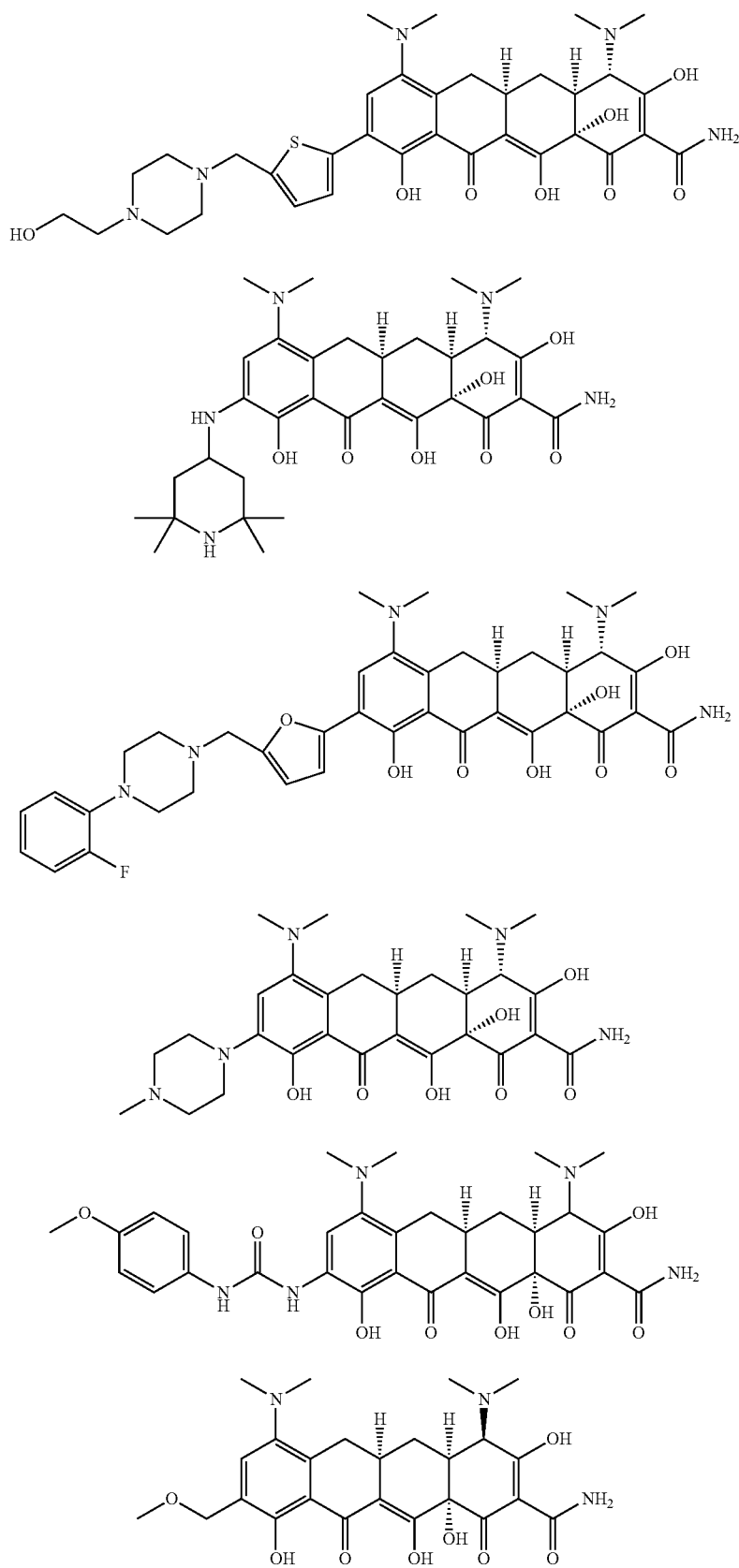

TABLE 2-continued
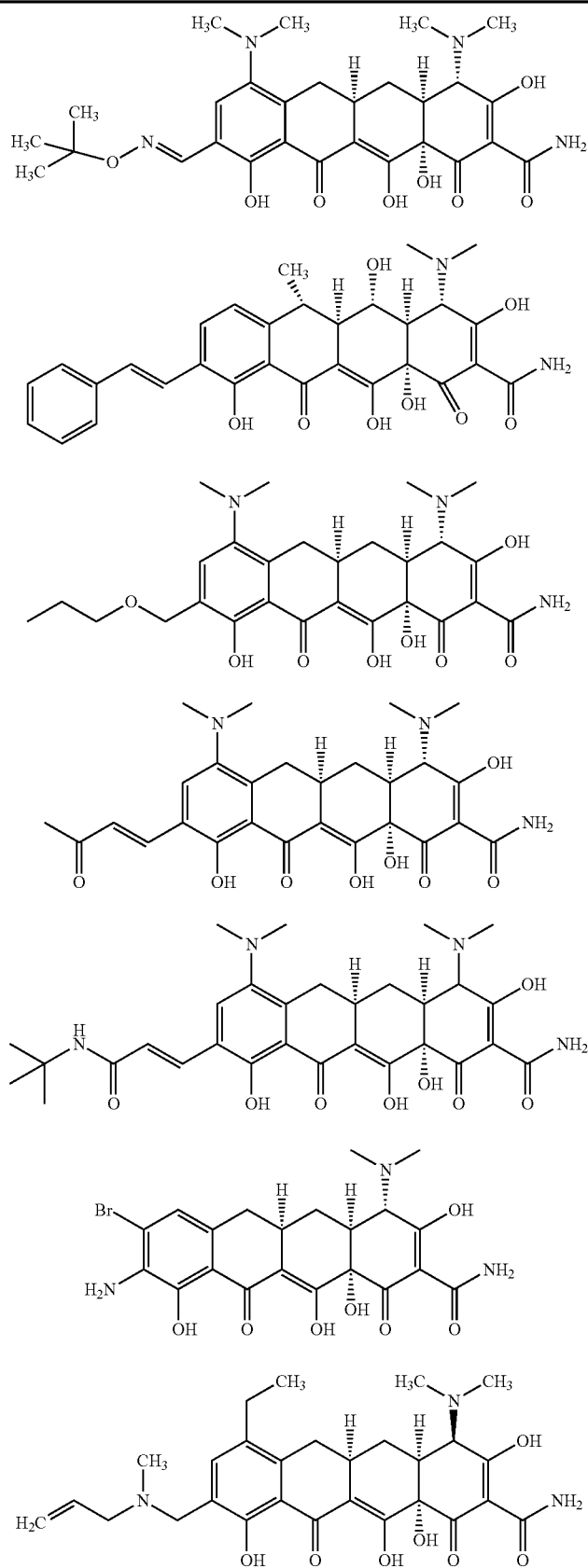

TABLE 2-continued
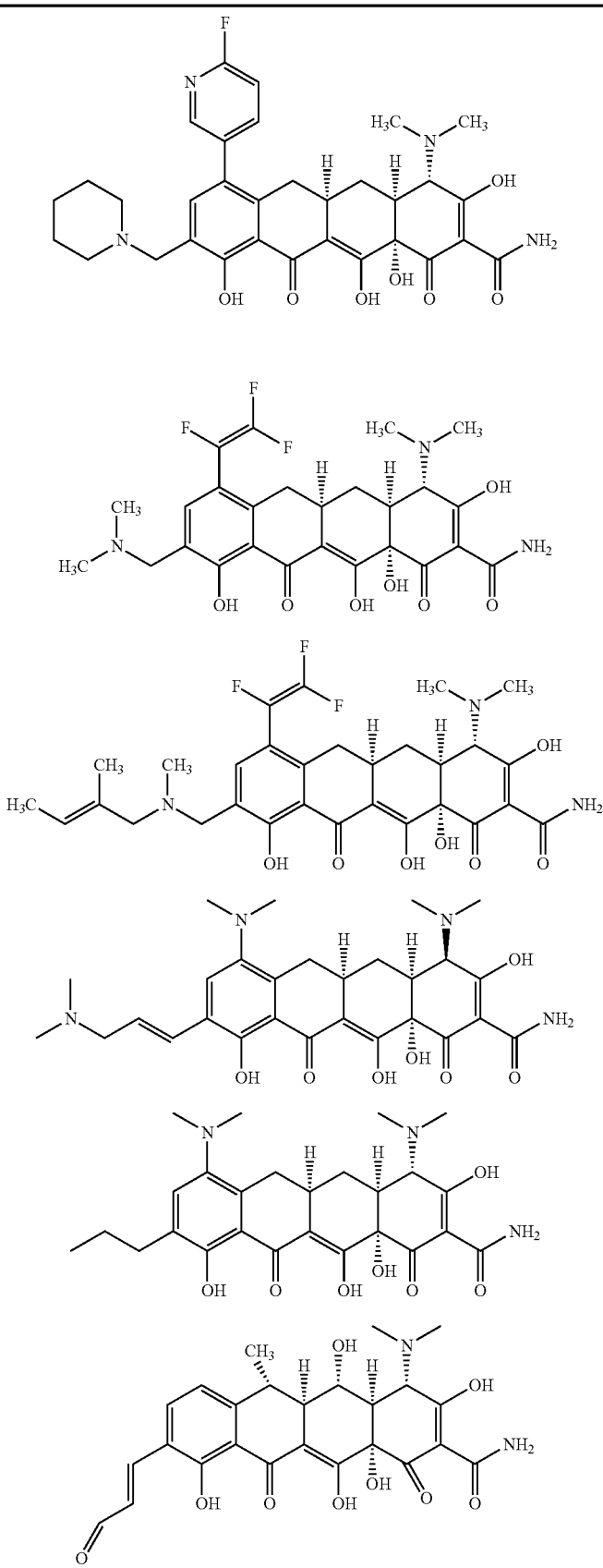

TABLE 2-continued
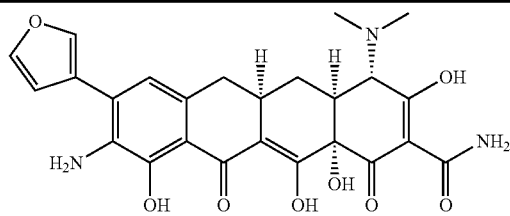
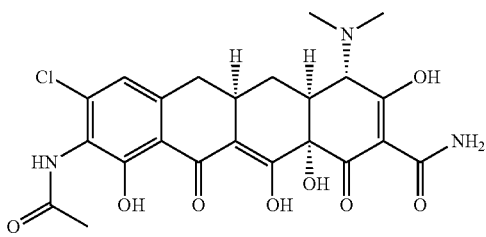
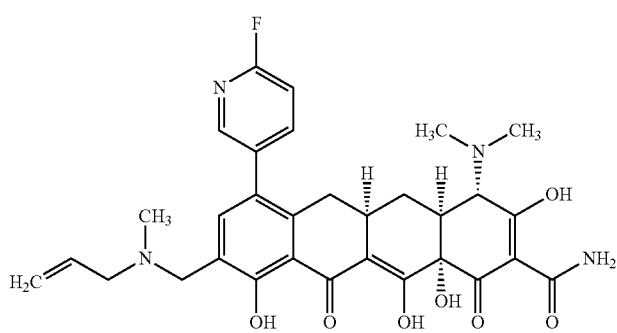
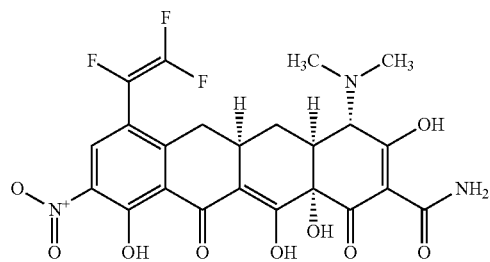
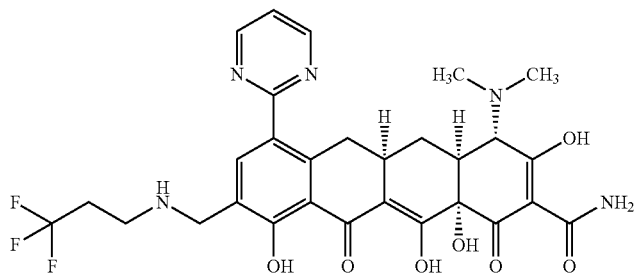
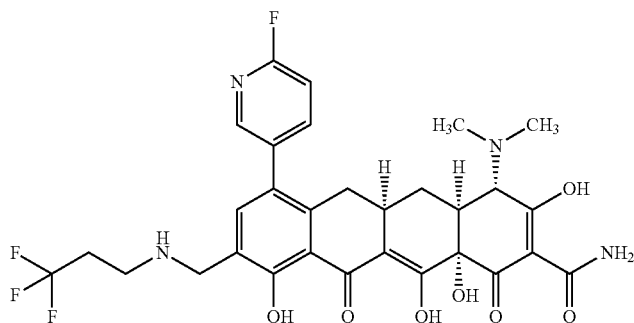

TABLE 2-continued
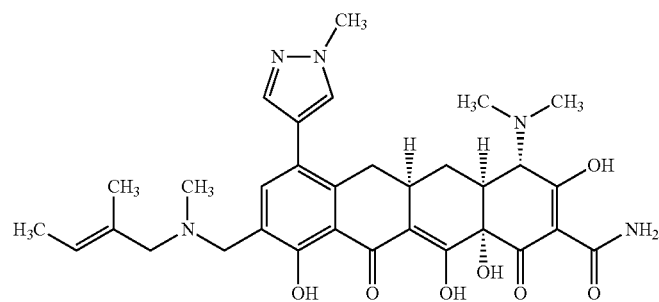
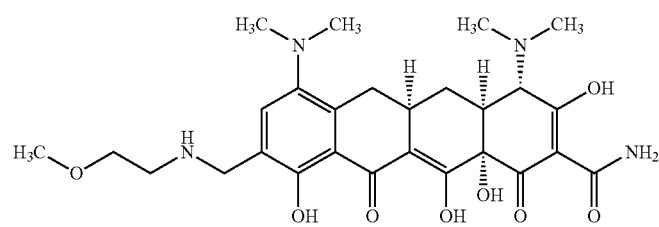
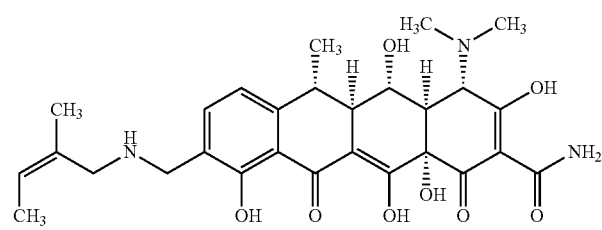
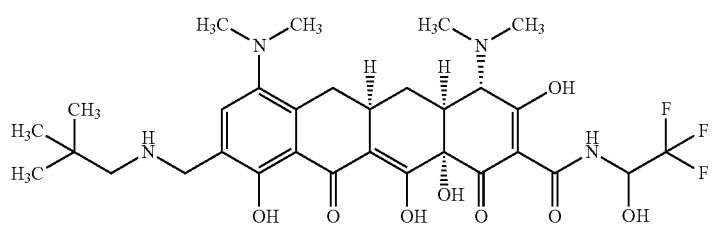
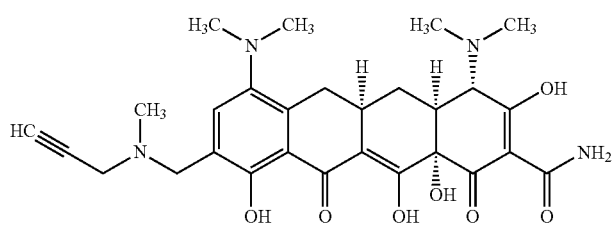
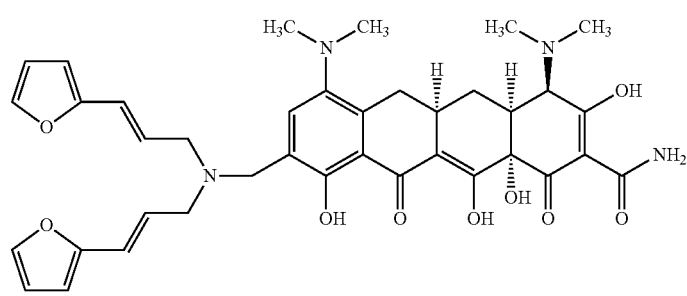

TABLE 2-continued
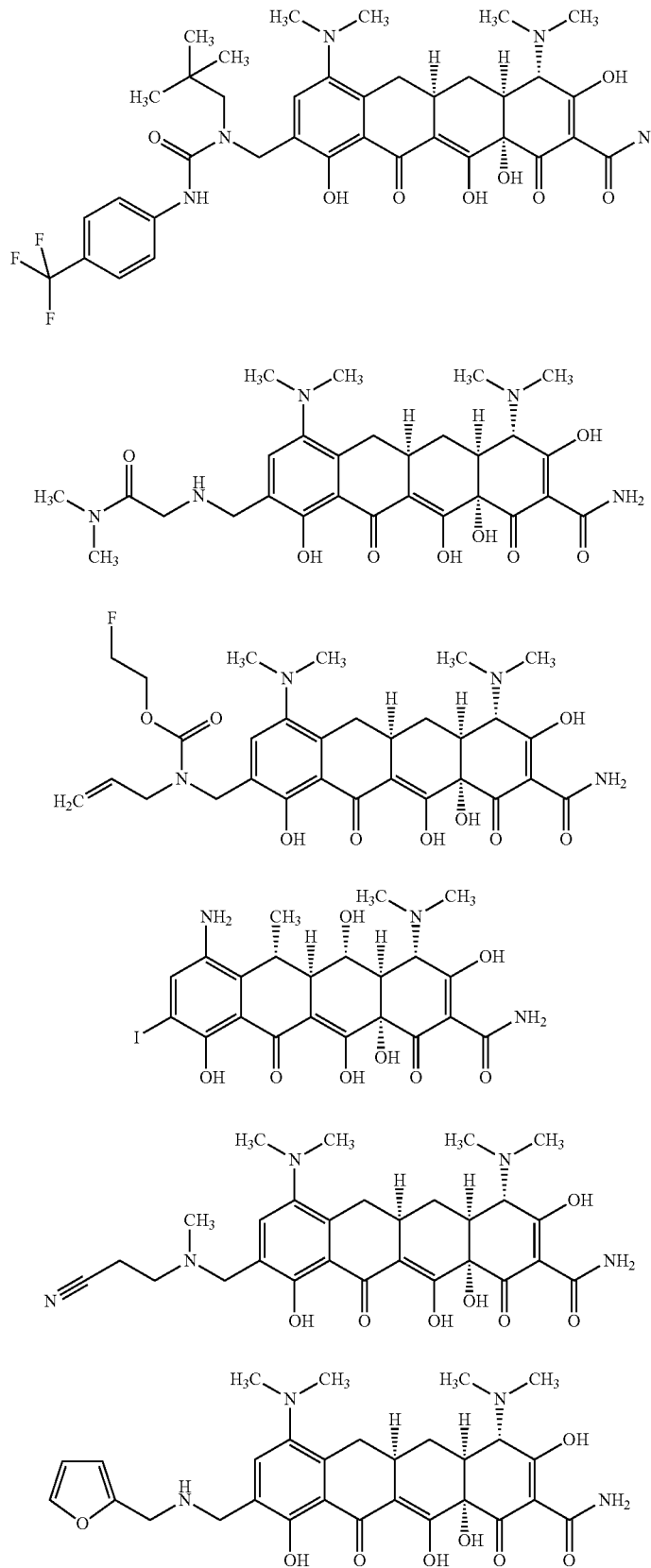

TABLE 2-continued
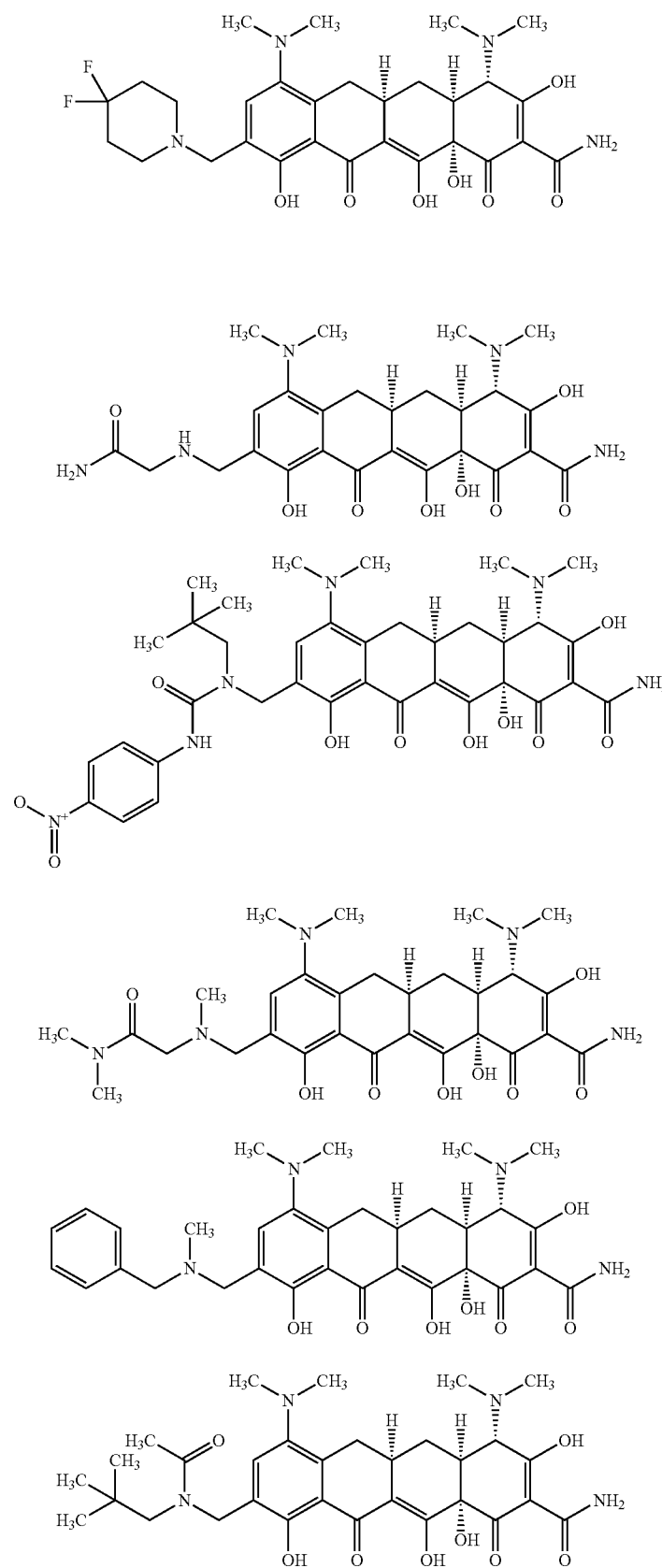

TABLE 2-continued
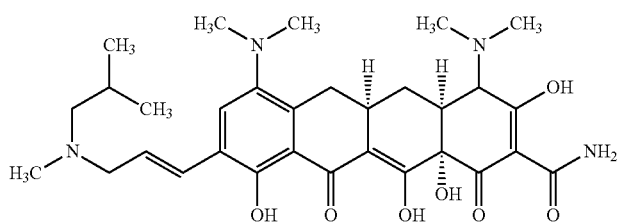
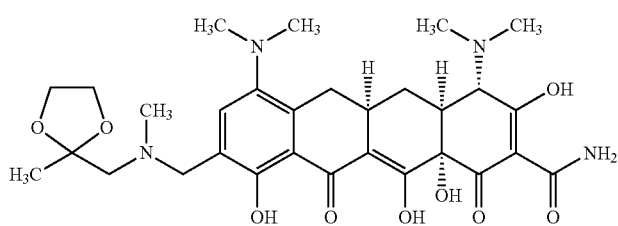
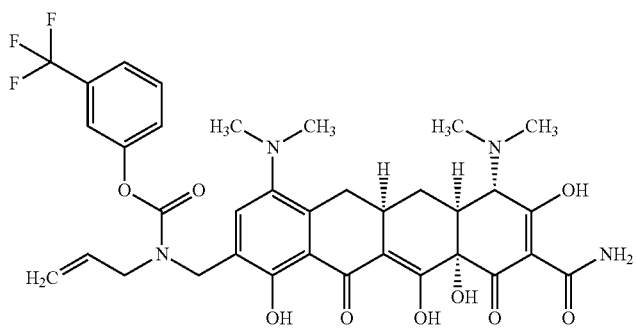
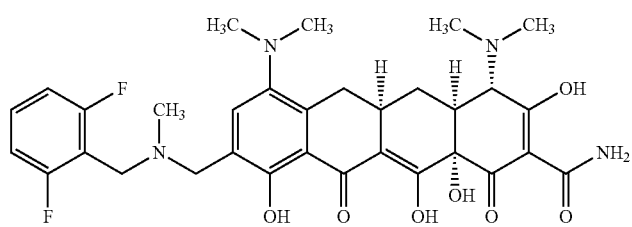
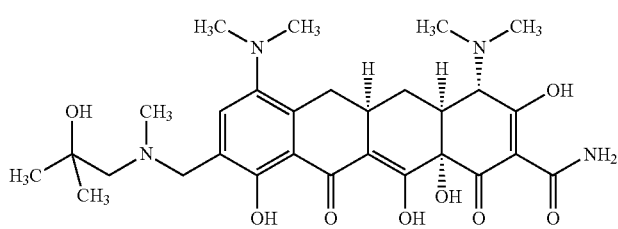
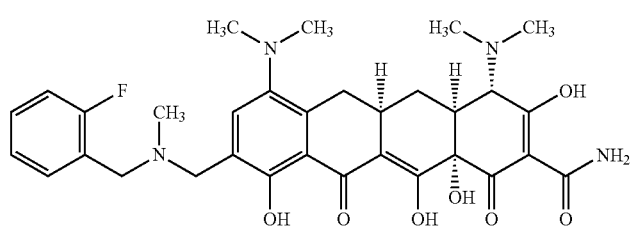

TABLE 2-continued
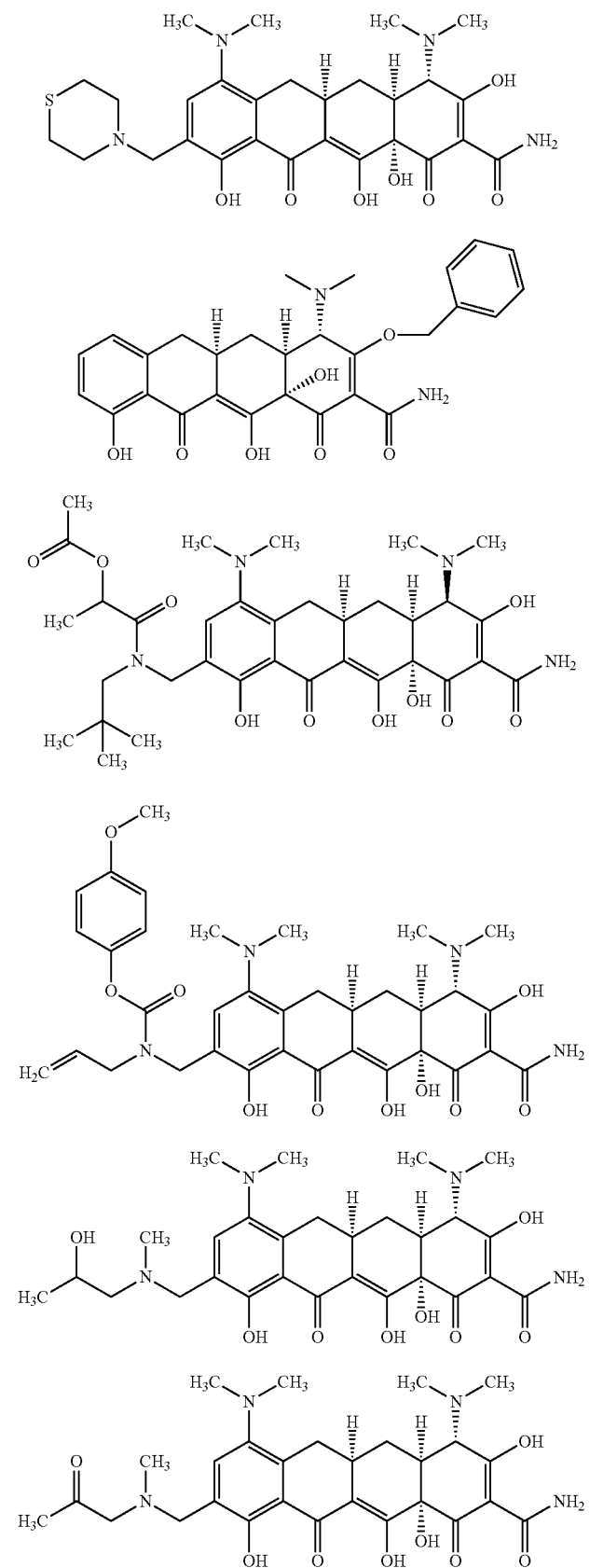

TABLE 2-continued
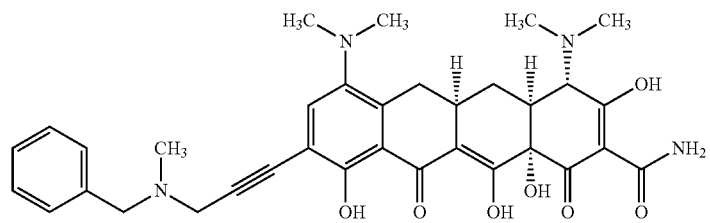
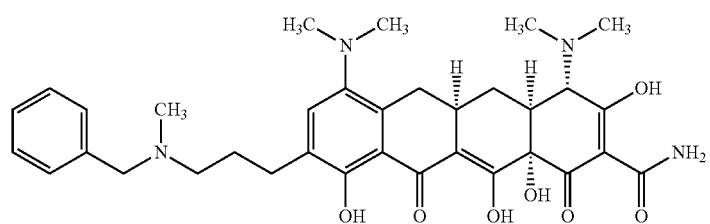
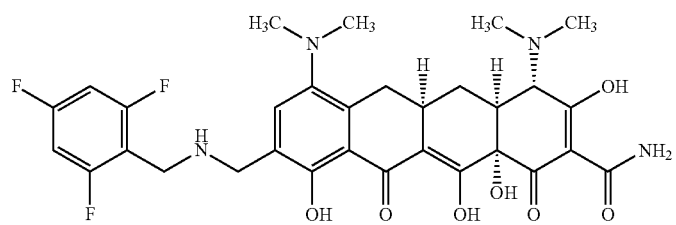
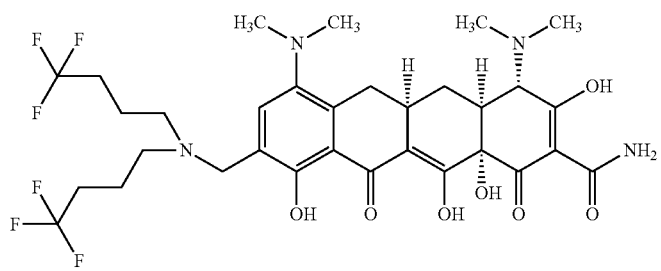
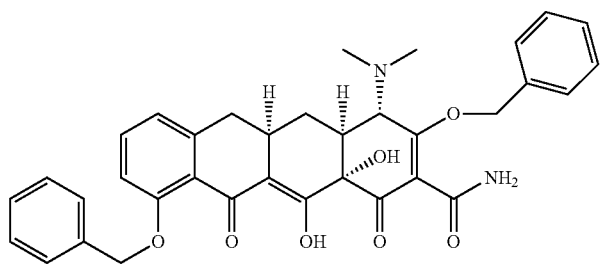
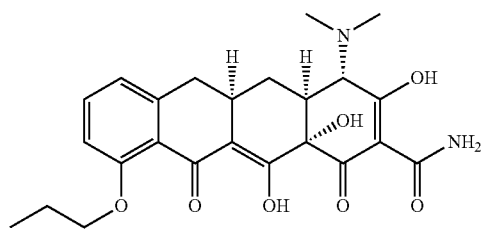

TABLE 2-continued
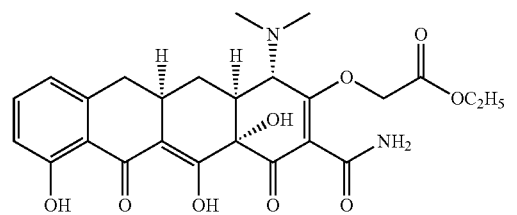
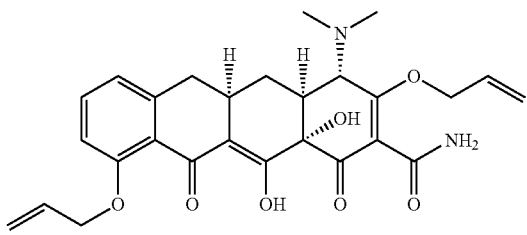
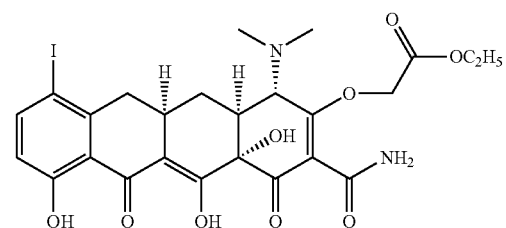
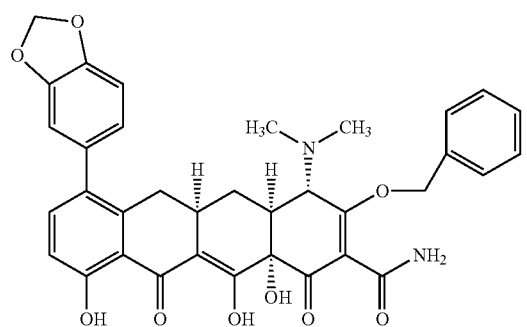
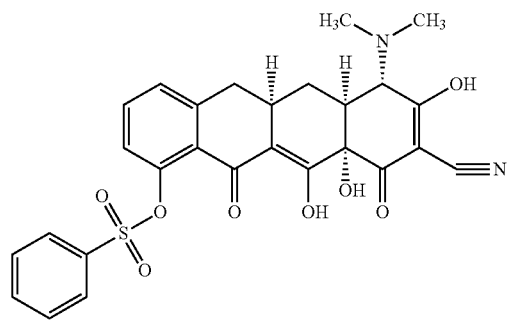
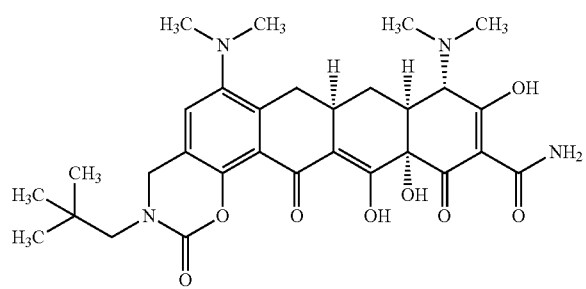

TABLE 2-continued
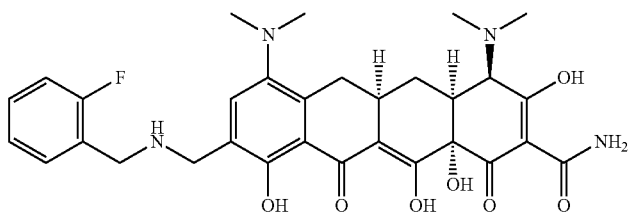
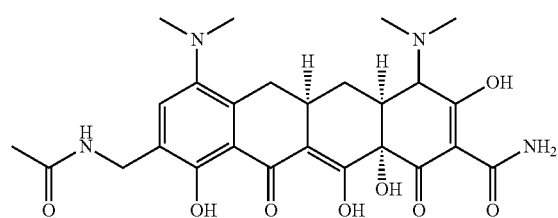
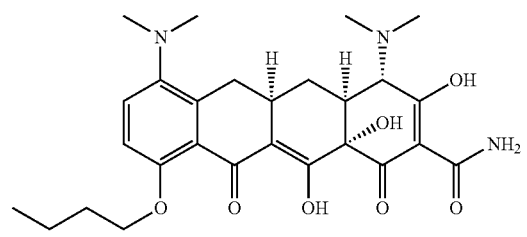
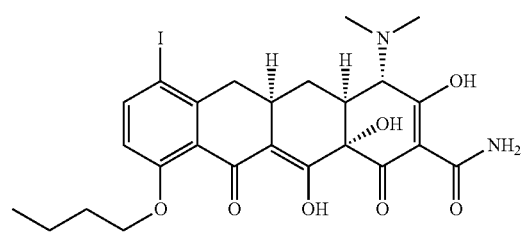
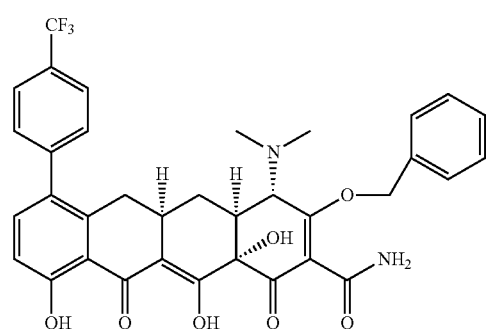
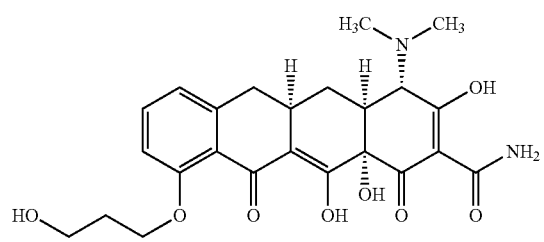

TABLE 2-continued
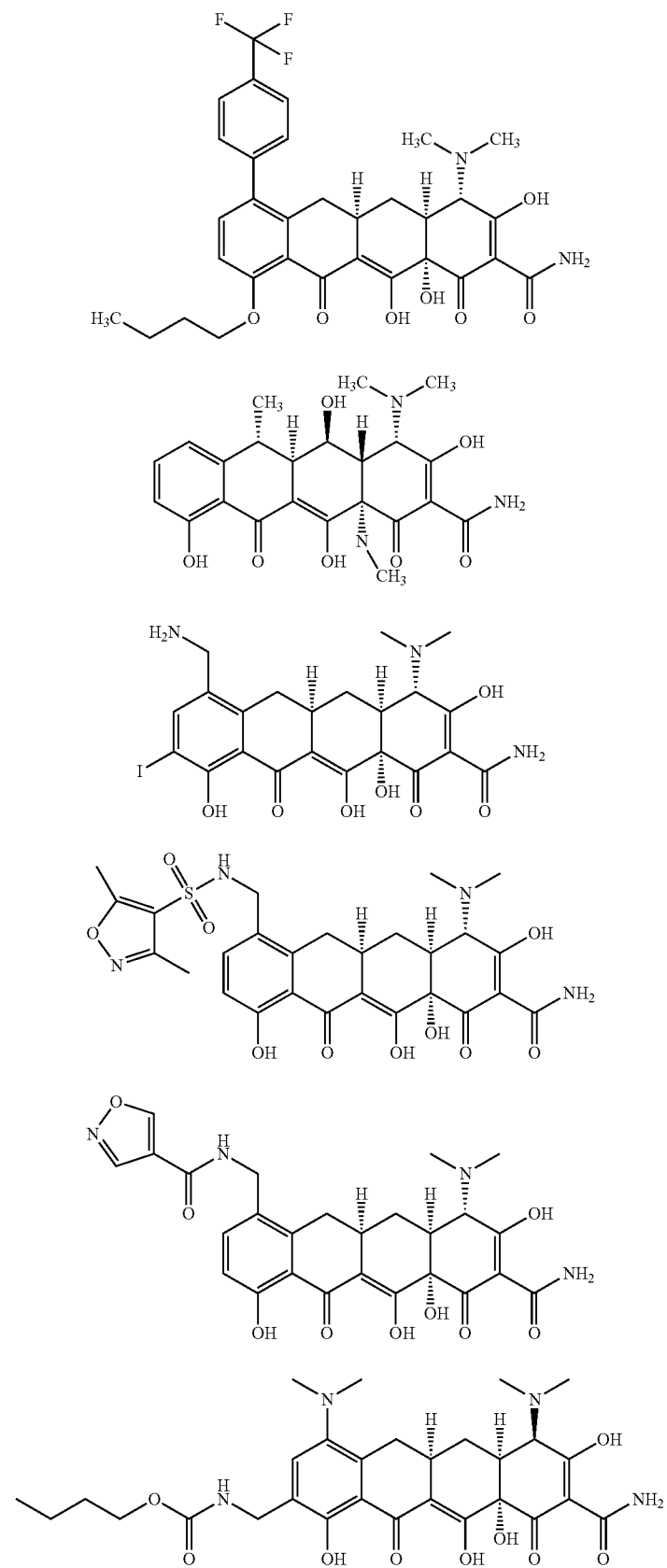

TABLE 2-continued
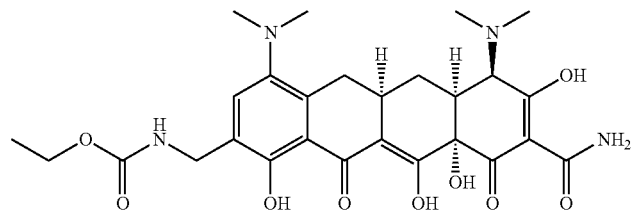
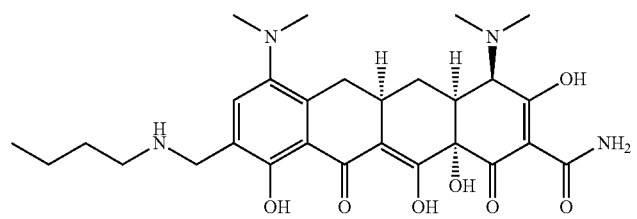
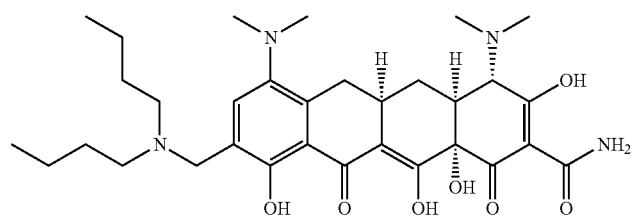
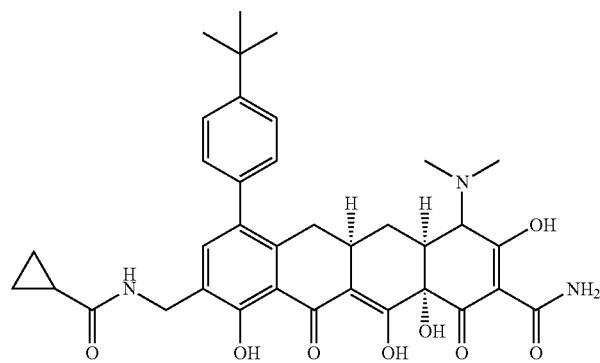
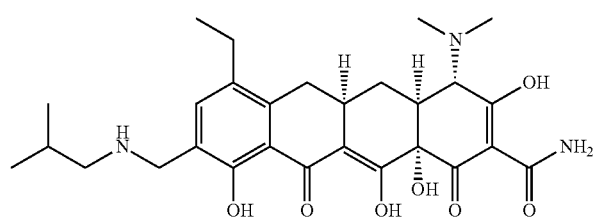
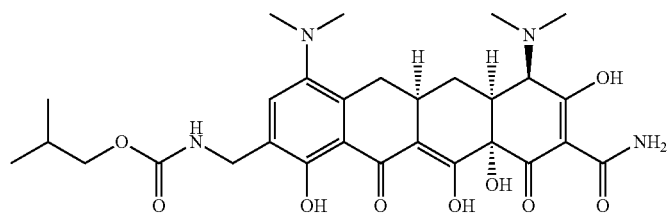

TABLE 2-continued
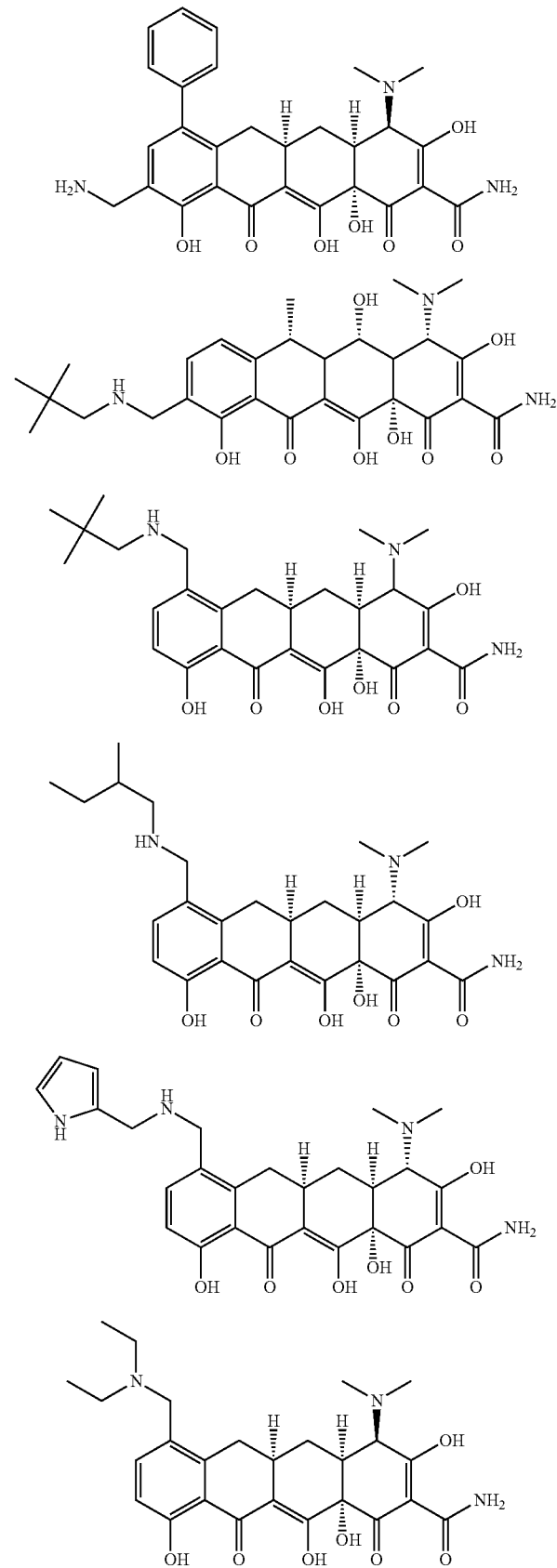

TABLE 2-continued
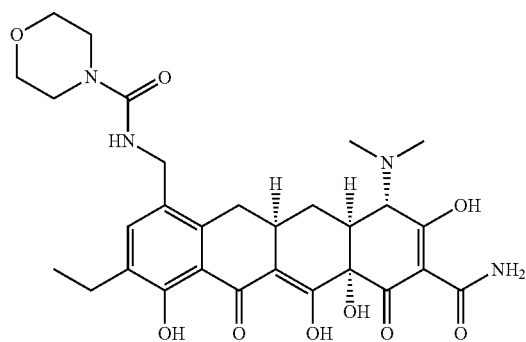
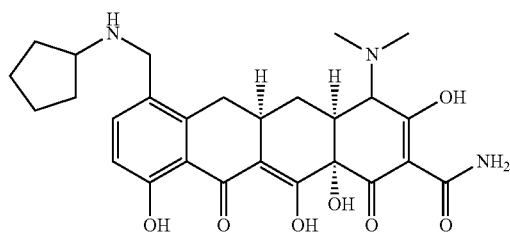
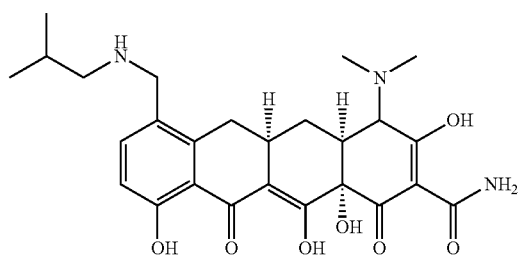
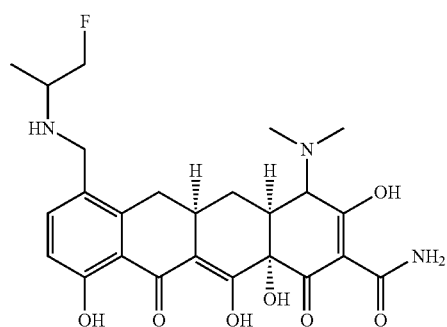
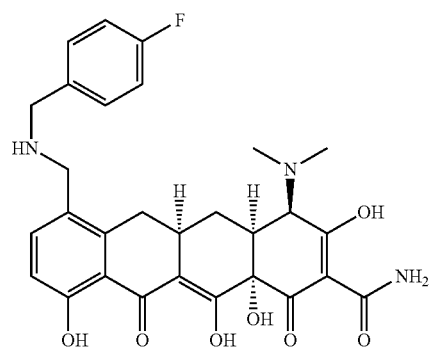

TABLE 2-continued
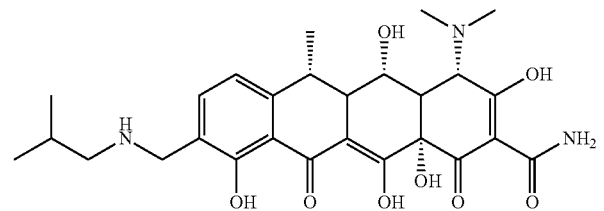
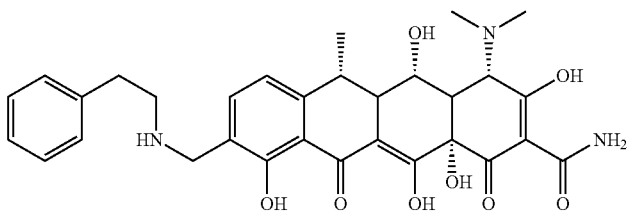
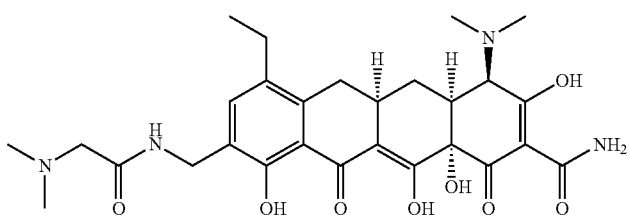
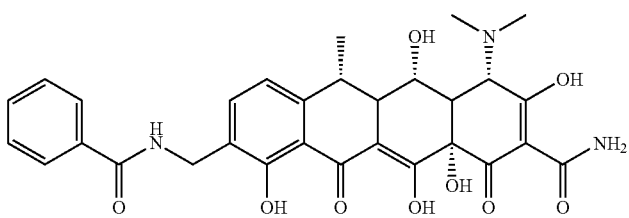
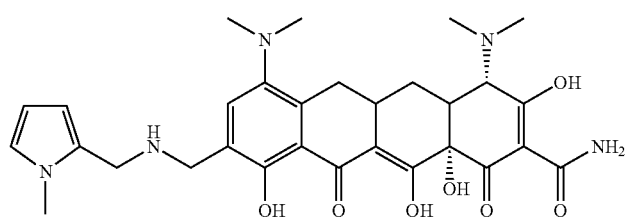
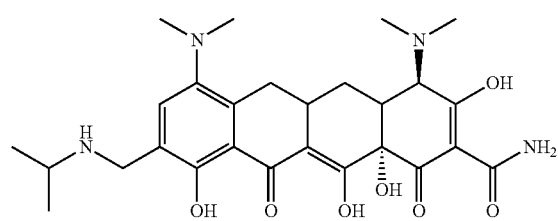
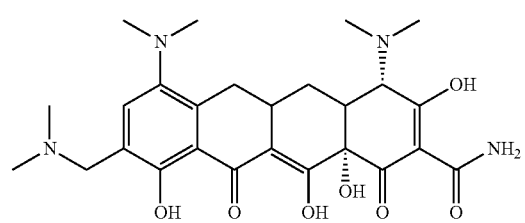

TABLE 2-continued
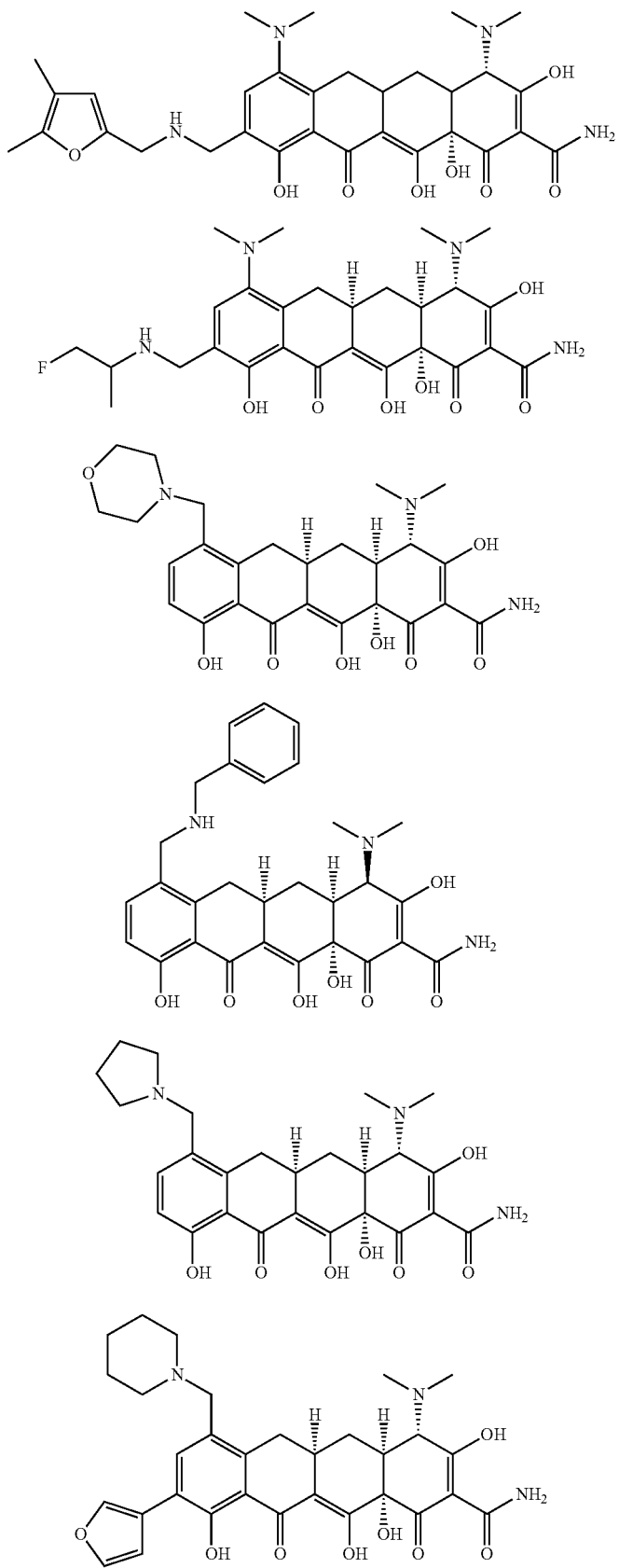

TABLE 2-continued
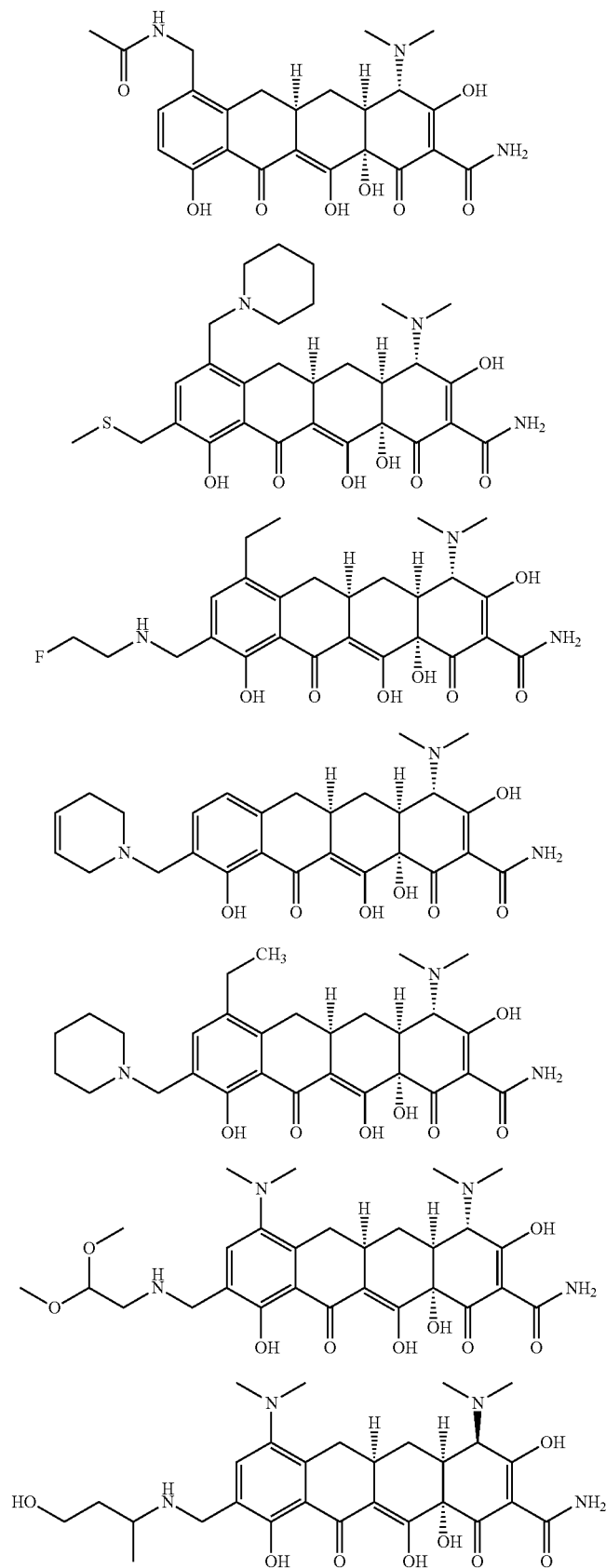

TABLE 2-continued
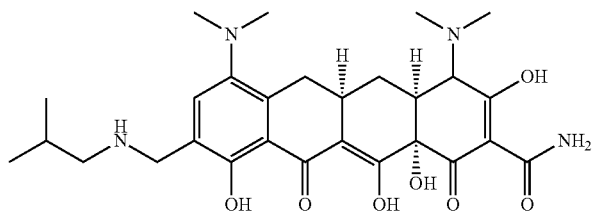
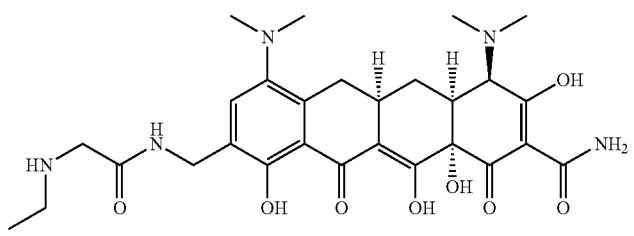
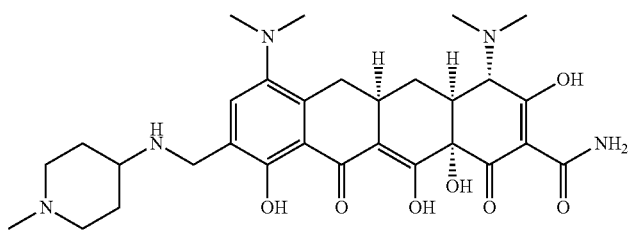
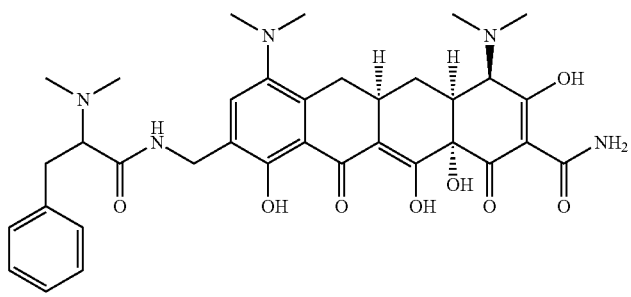
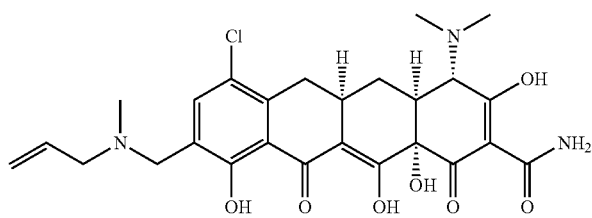
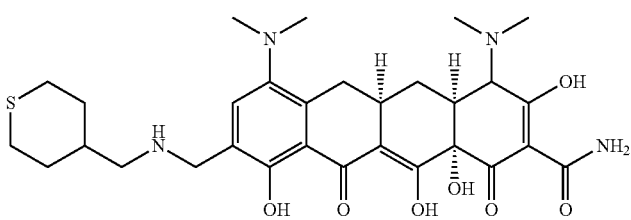

TABLE 2-continued
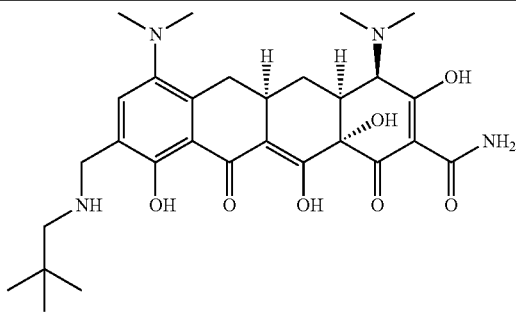
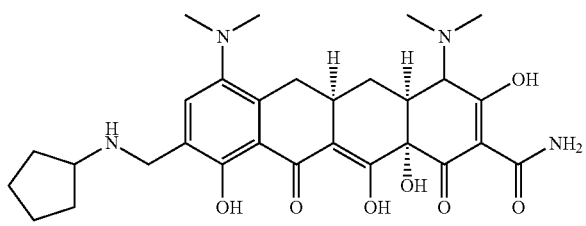
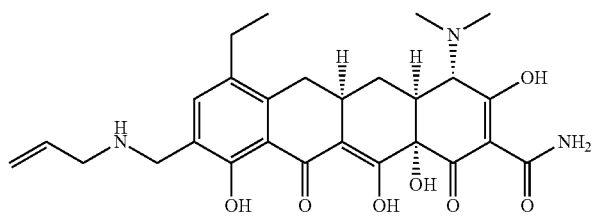
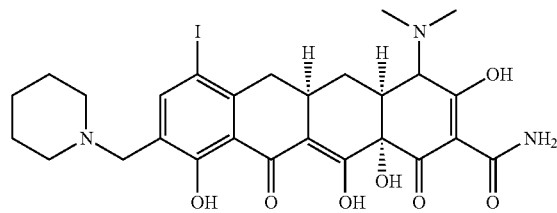
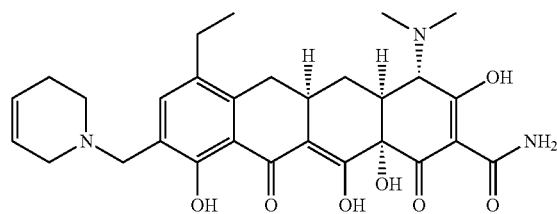
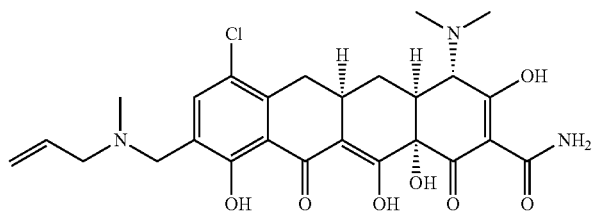
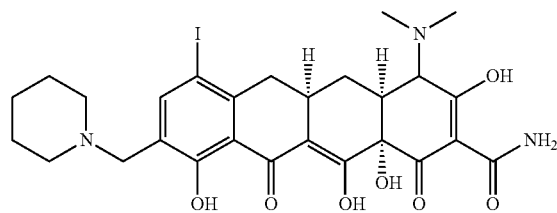

TABLE 2-continued
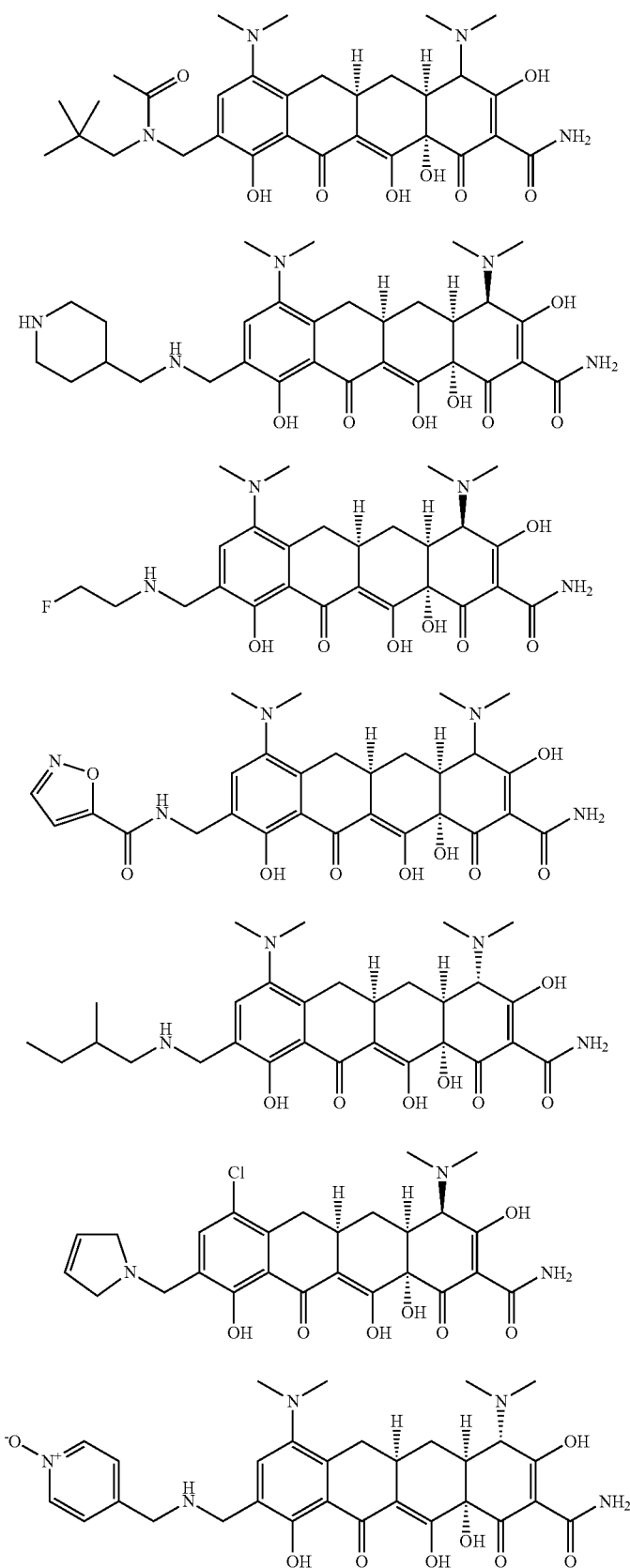

TABLE 2-continued
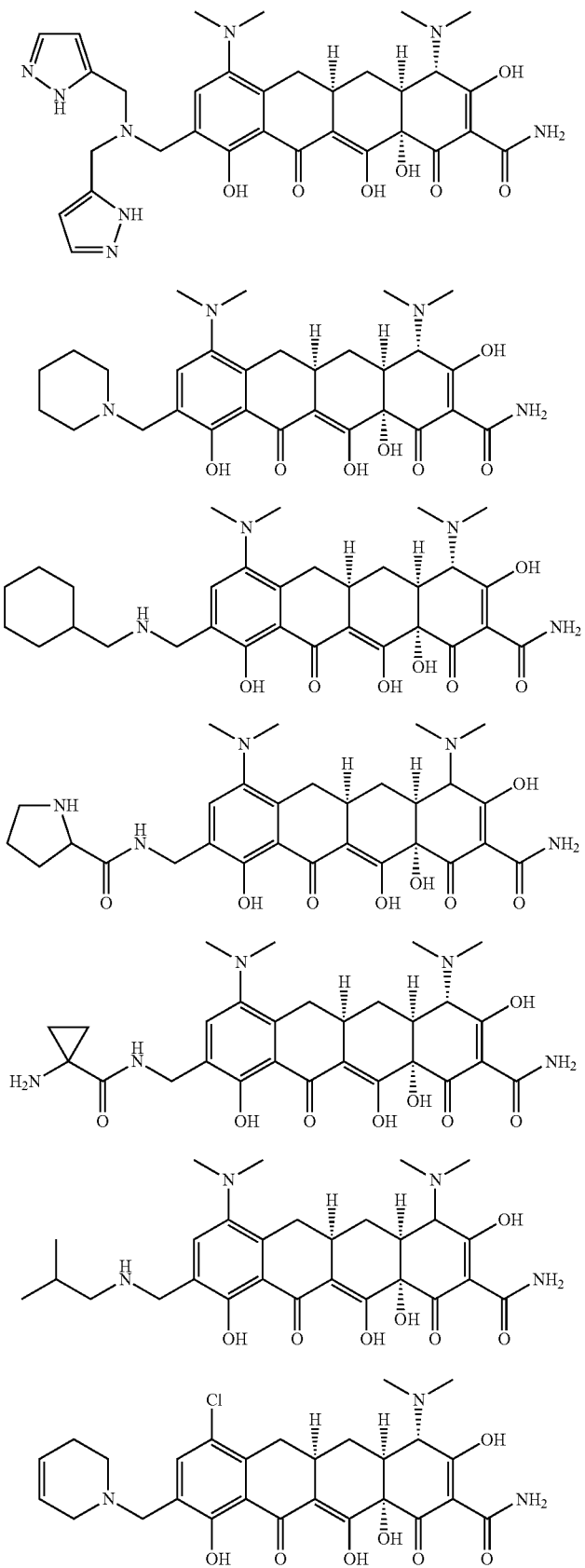

TABLE 2-continued
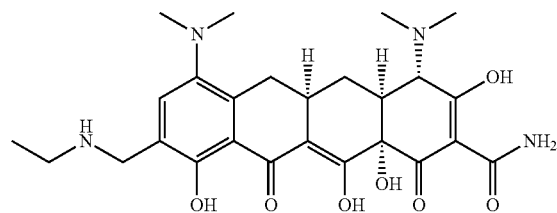
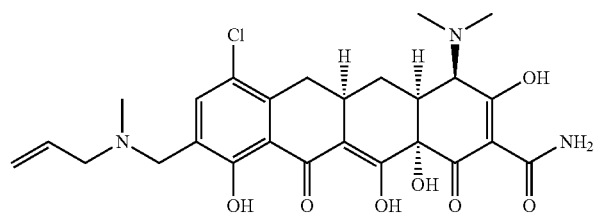
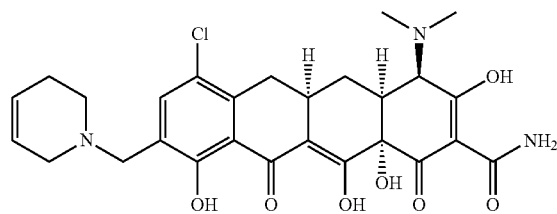
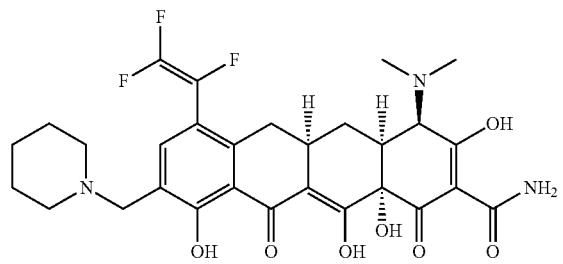
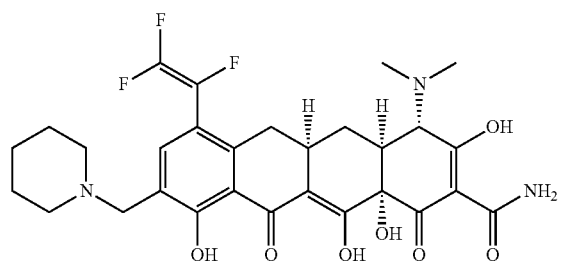
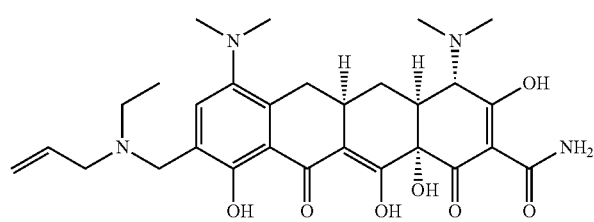

TABLE 2-continued
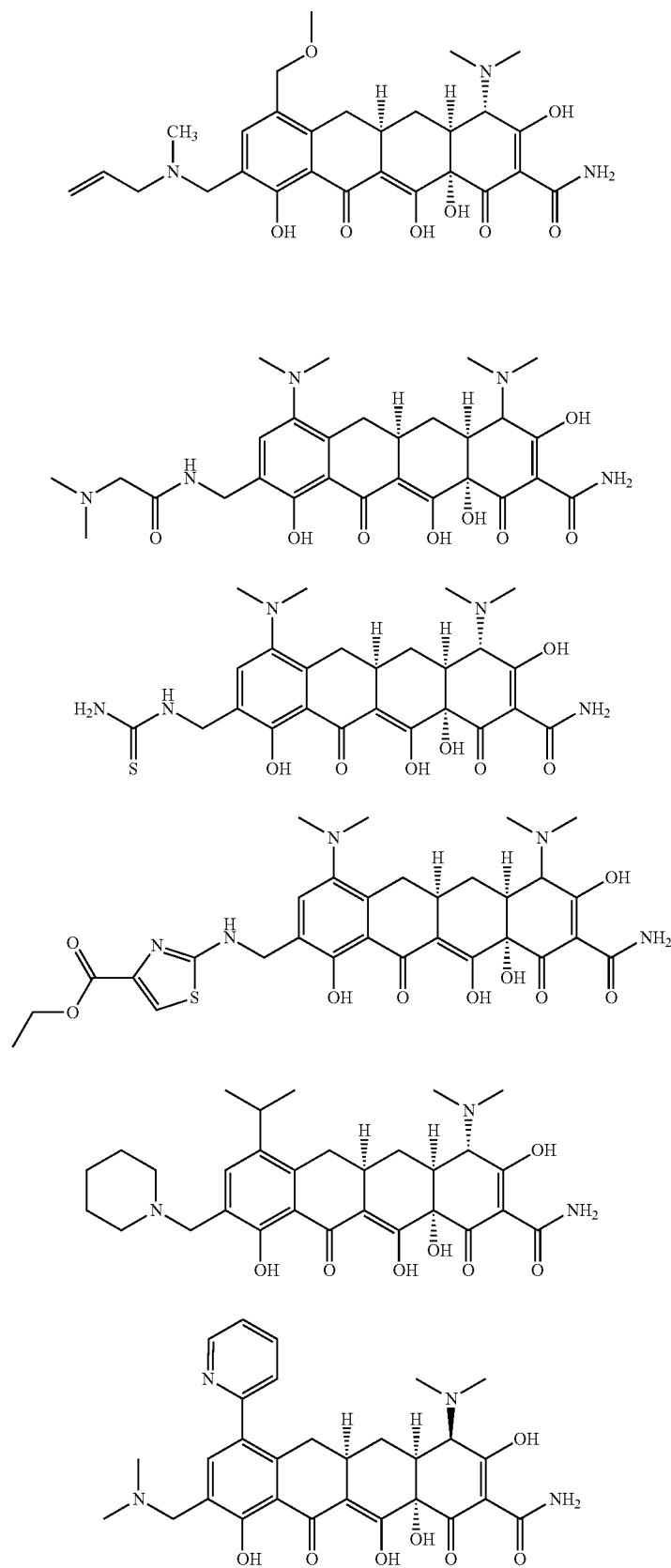

TABLE 2-continued
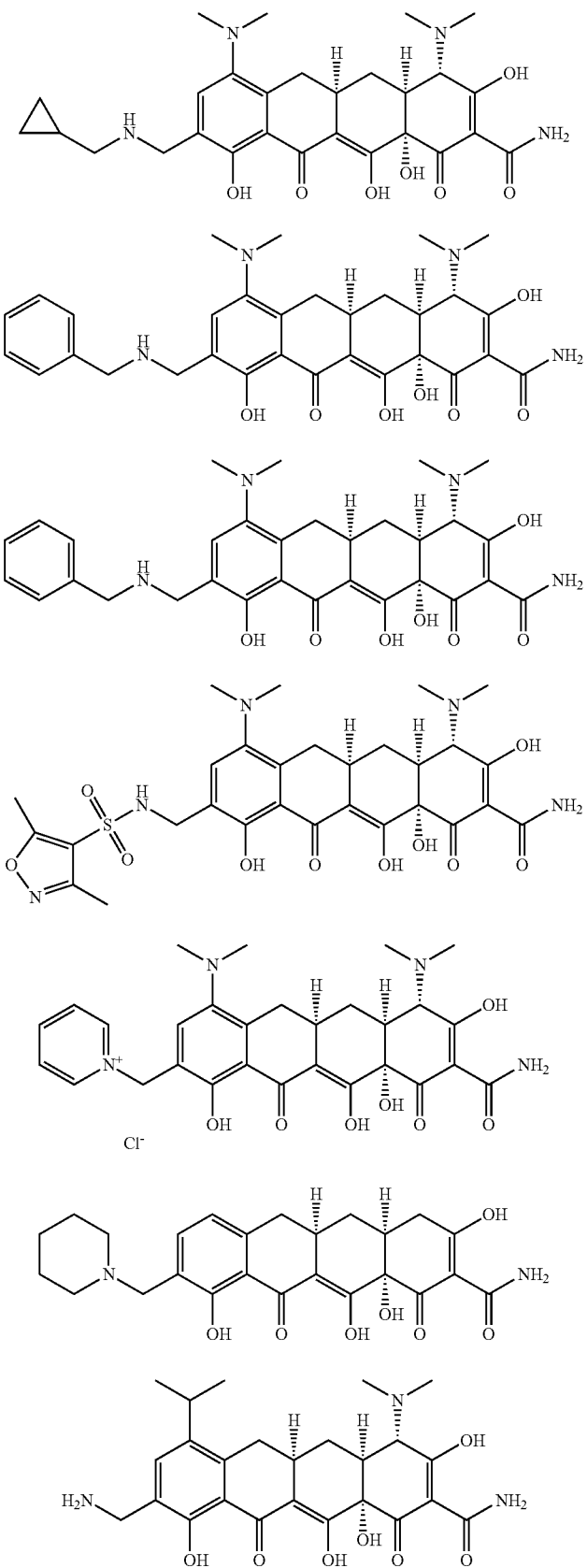

TABLE 2-continued
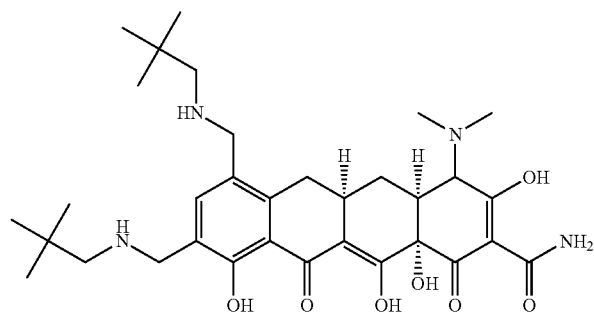
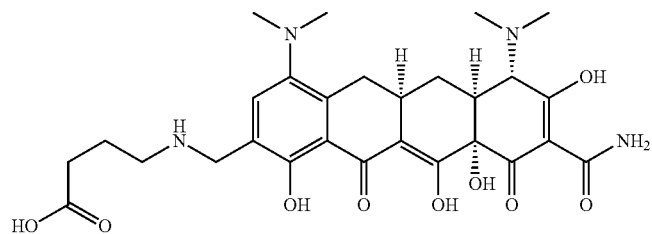
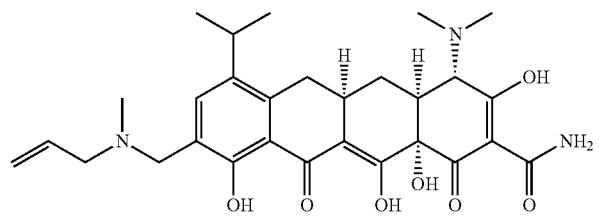
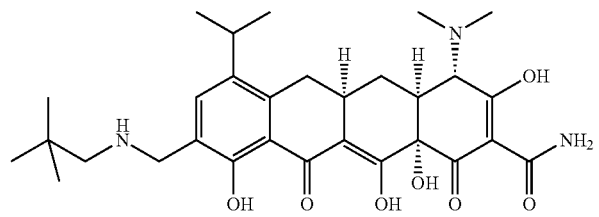
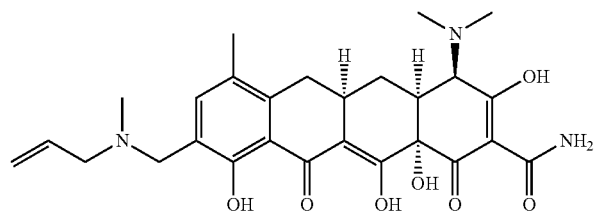
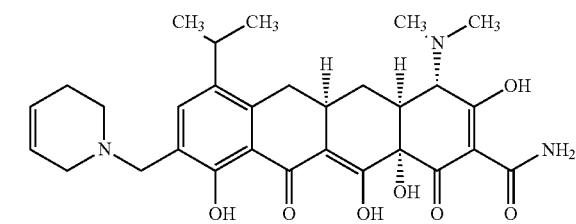

TABLE 2-continued
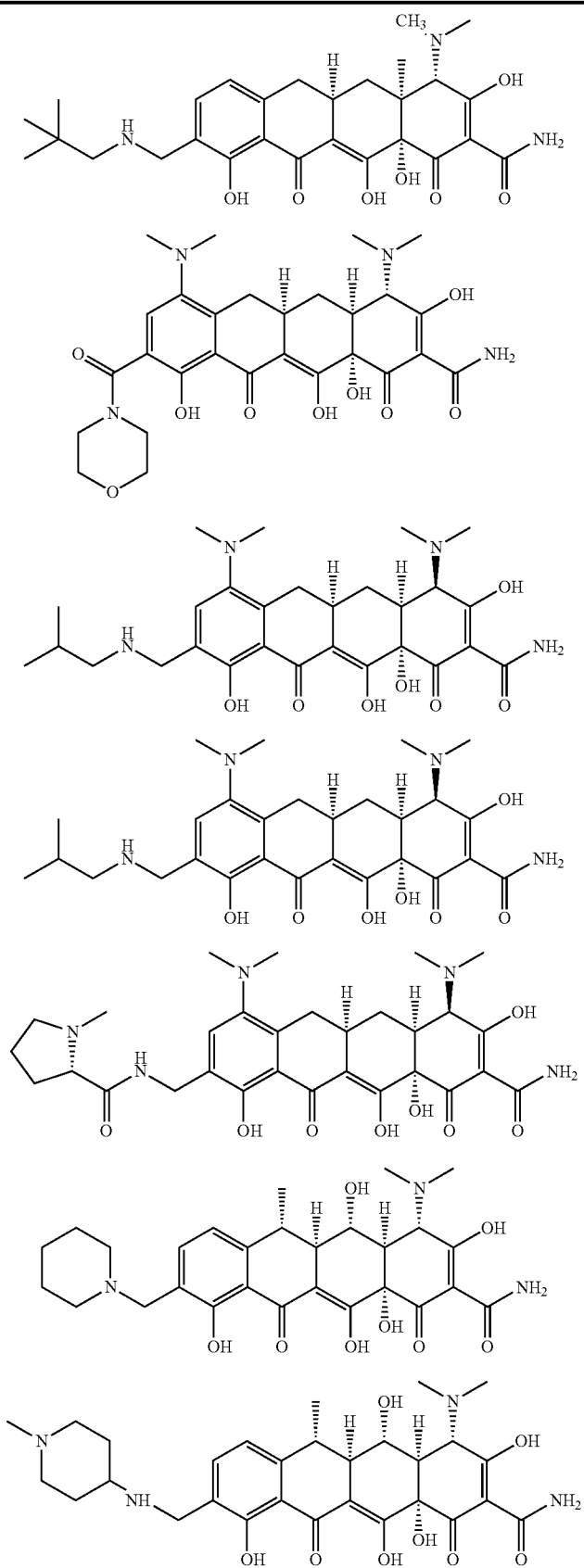

TABLE 2-continued
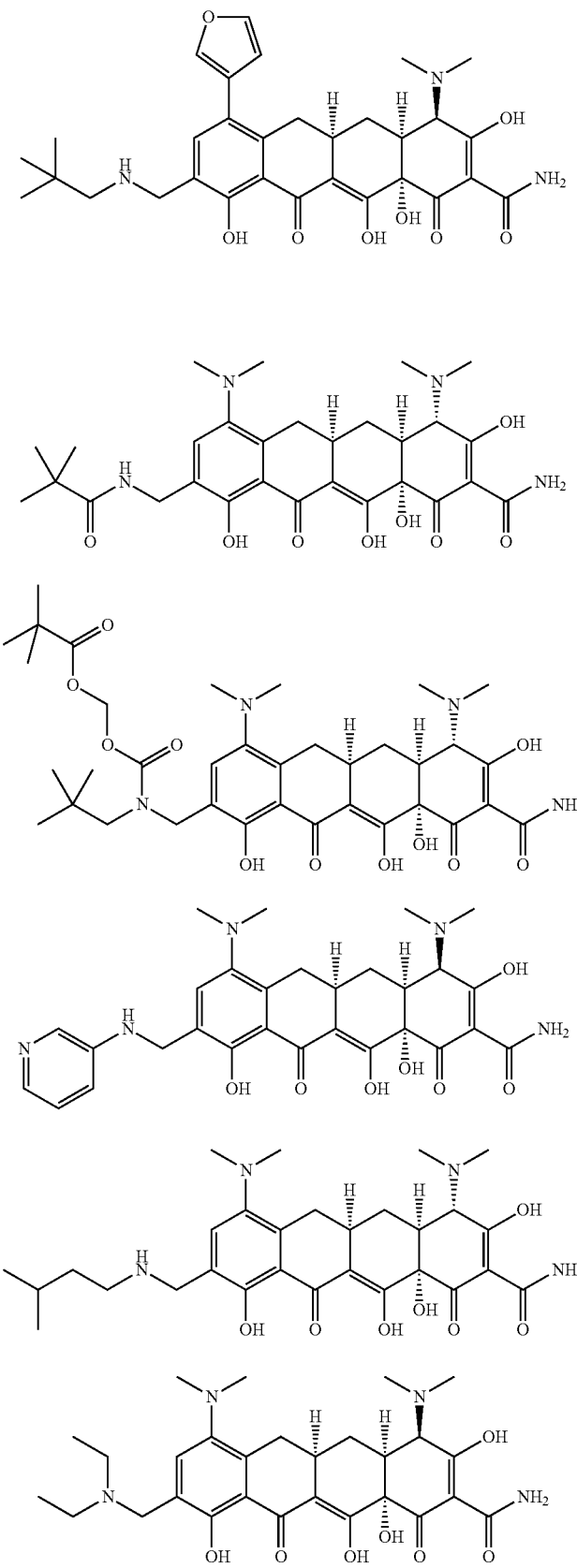

TABLE 2-continued
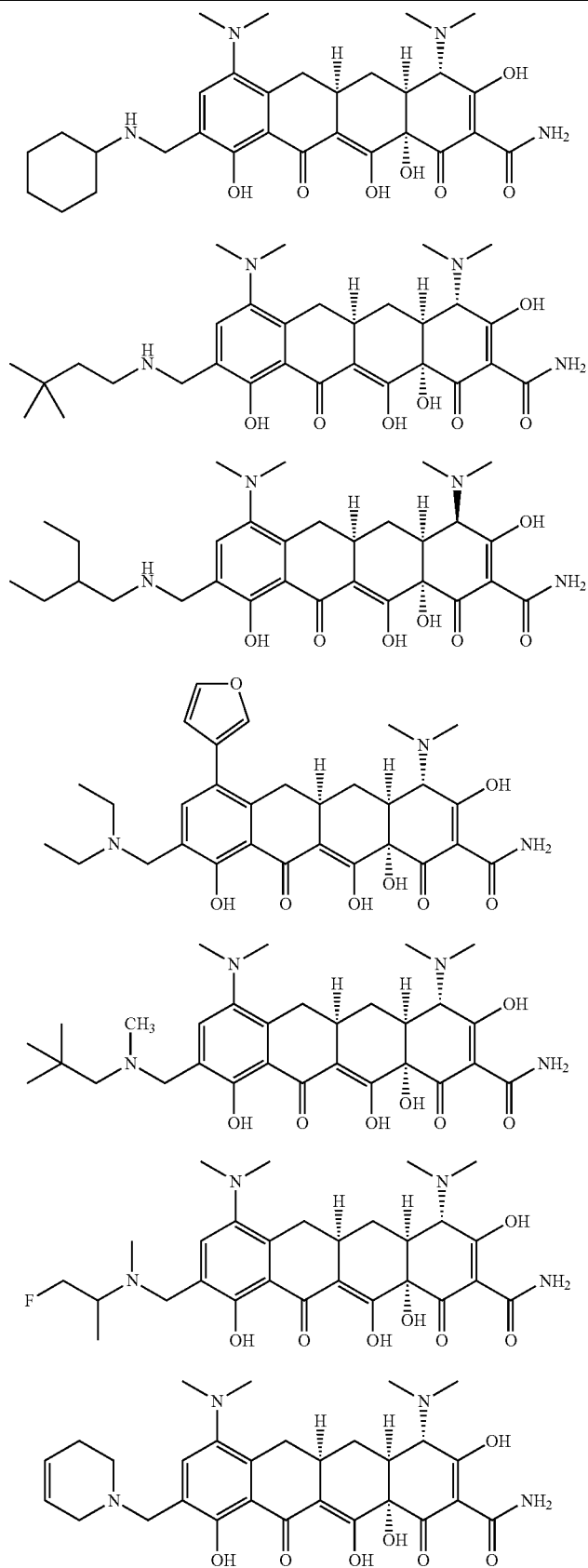

TABLE 2-continued
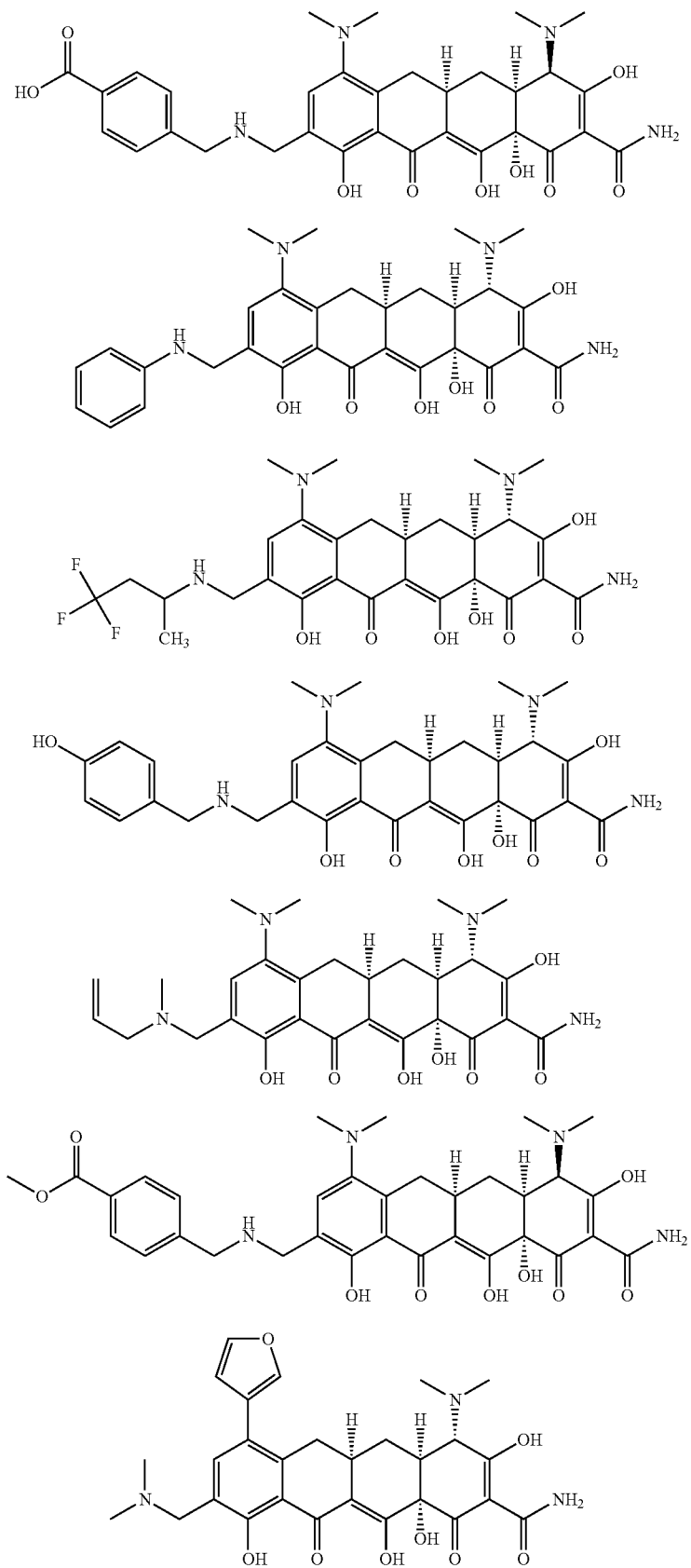

TABLE 2-continued
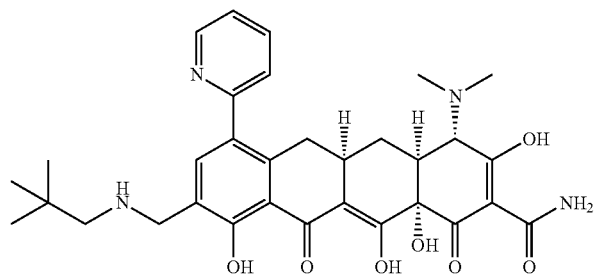
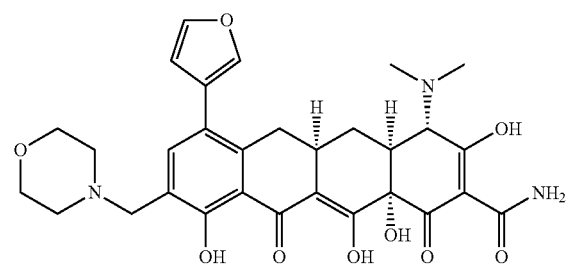
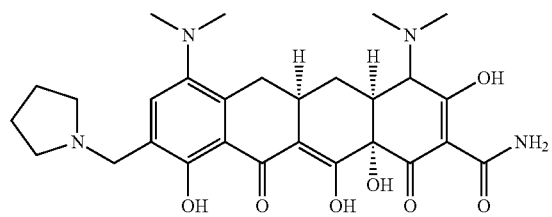
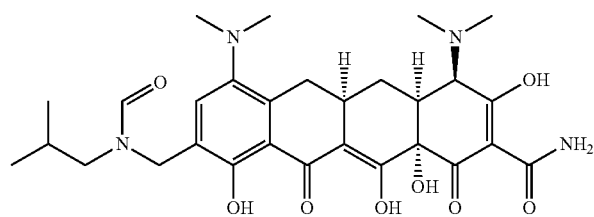
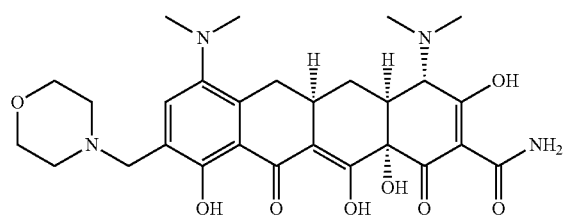
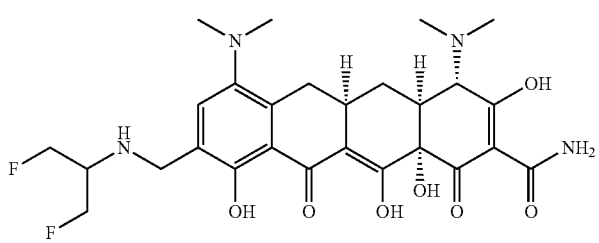

TABLE 2-continued
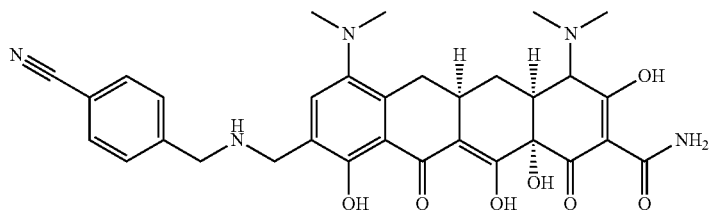
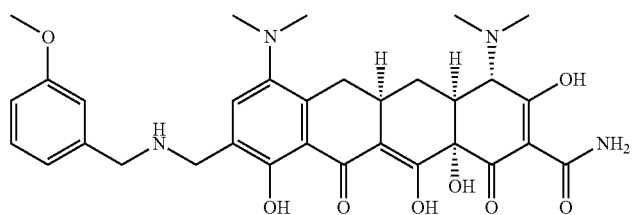
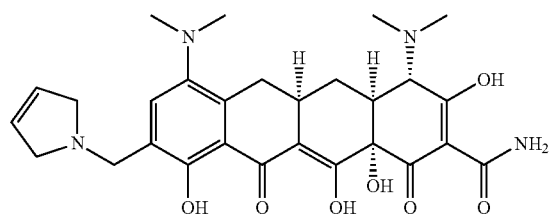
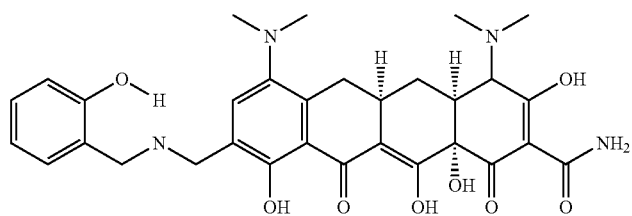
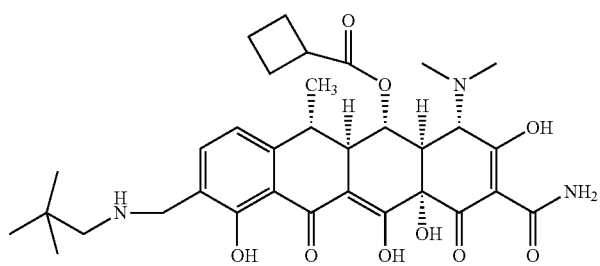
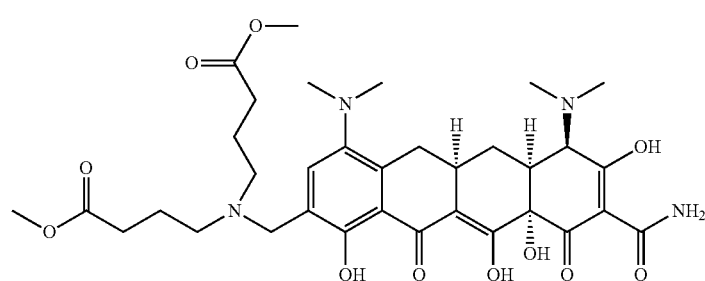

TABLE 2-continued
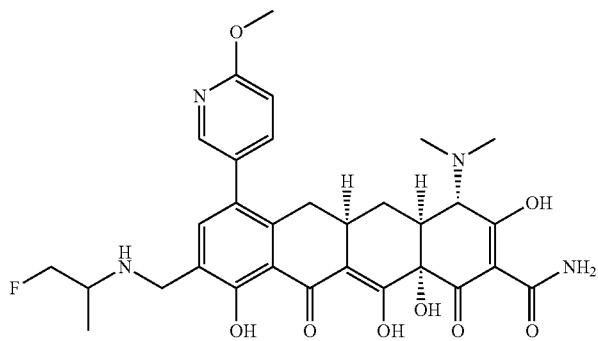
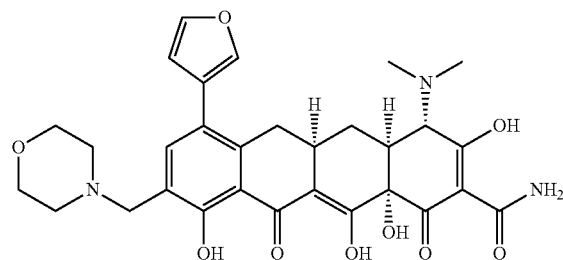
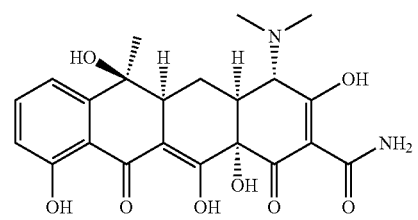
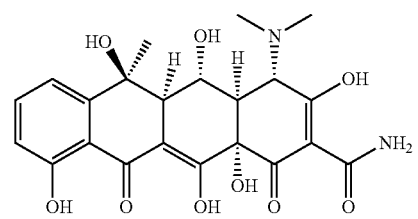
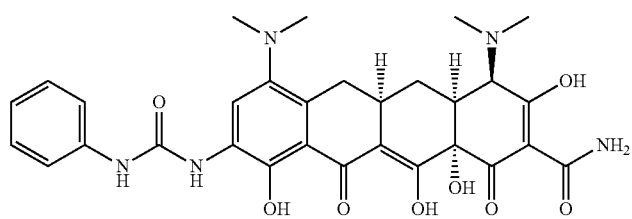
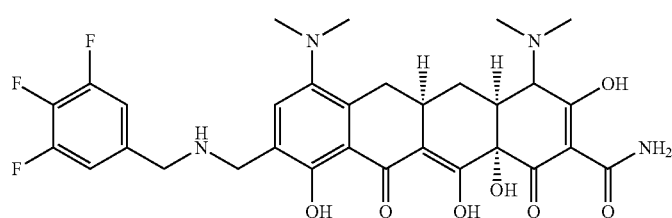

TABLE 2-continued
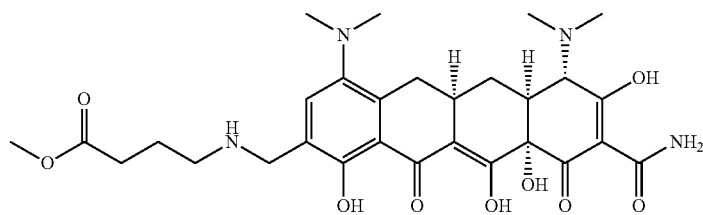
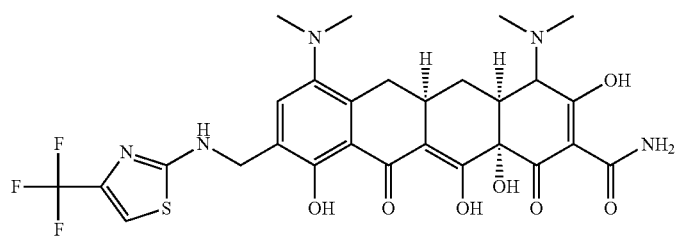
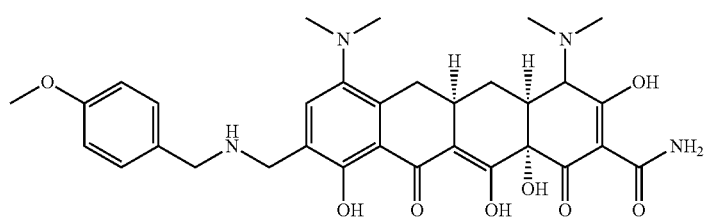
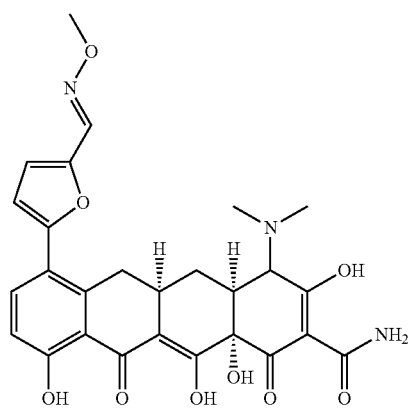
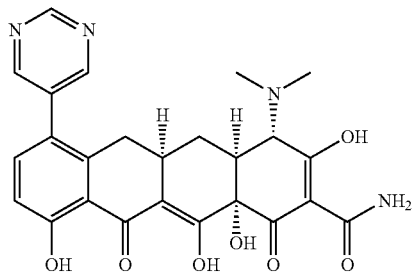

TABLE 2-continued
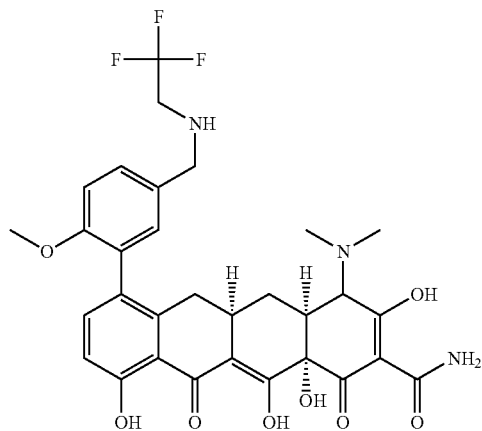
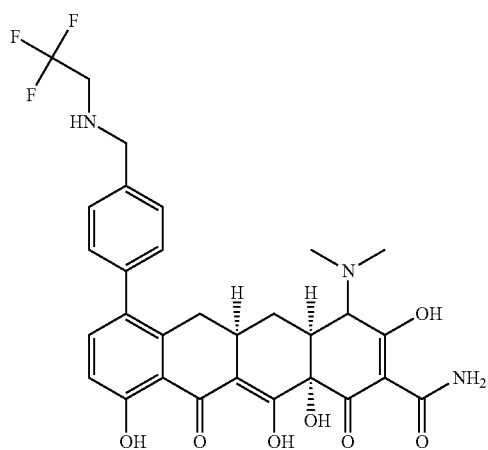
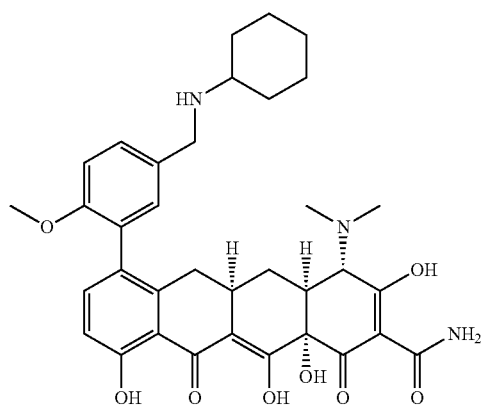

TABLE 2-continued
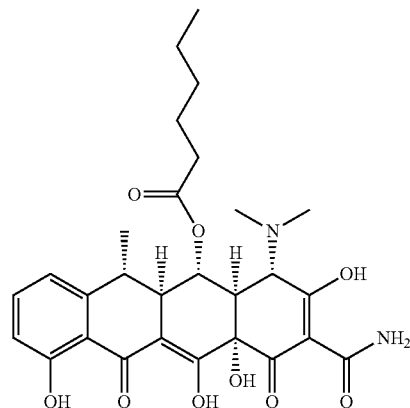
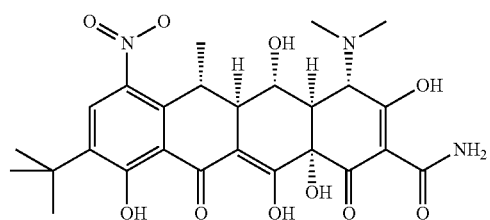
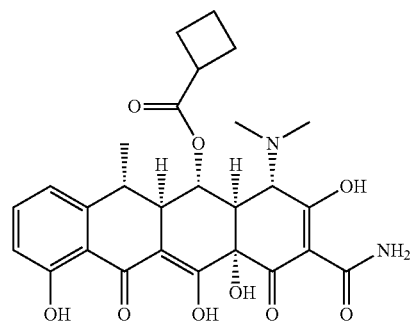
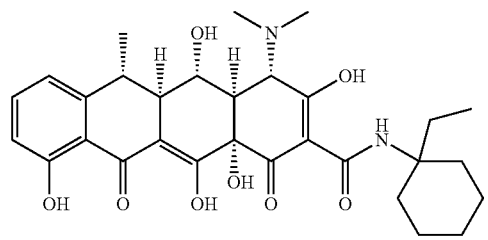
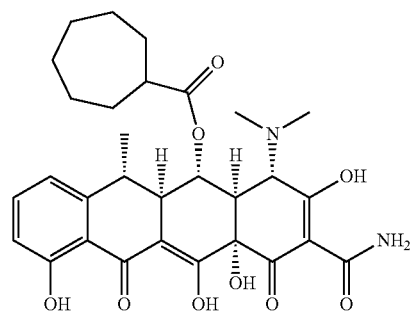

TABLE 2-continued
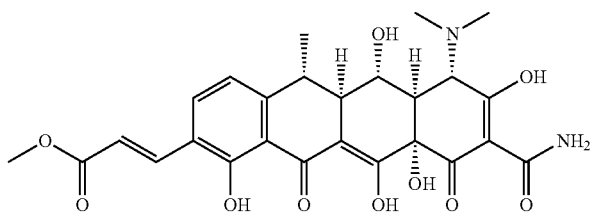
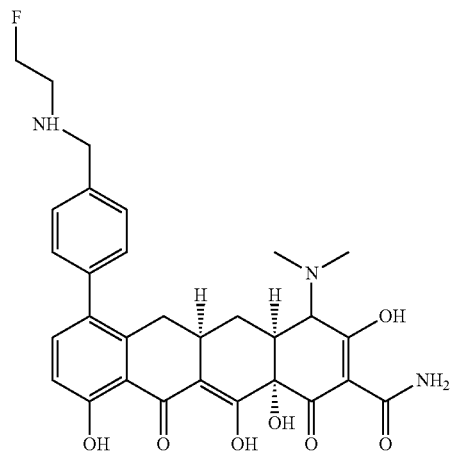
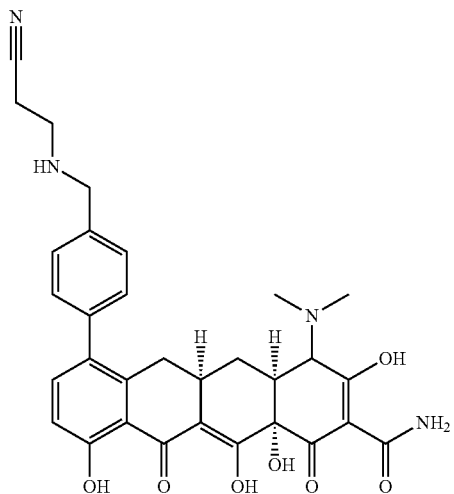
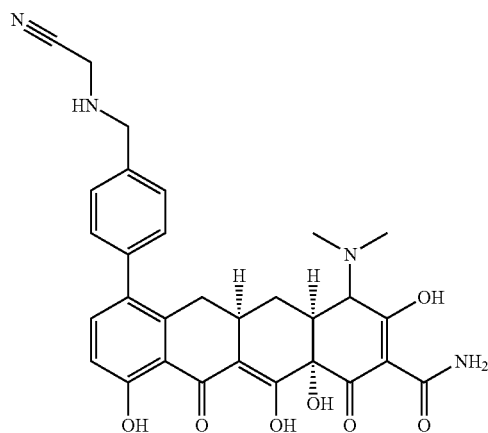

TABLE 2-continued
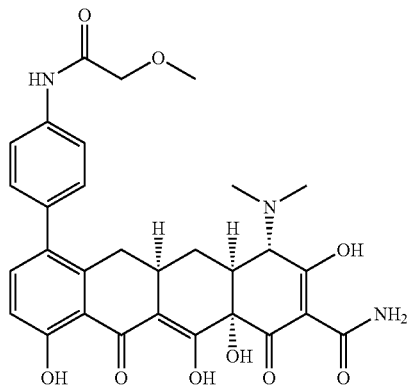
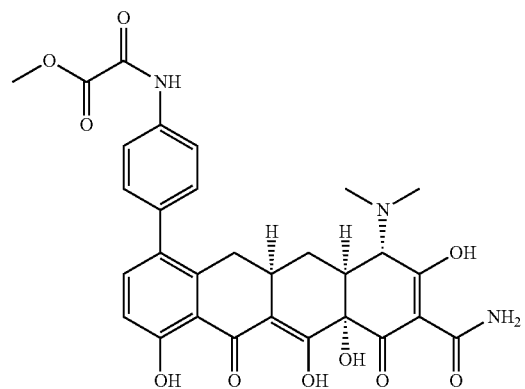
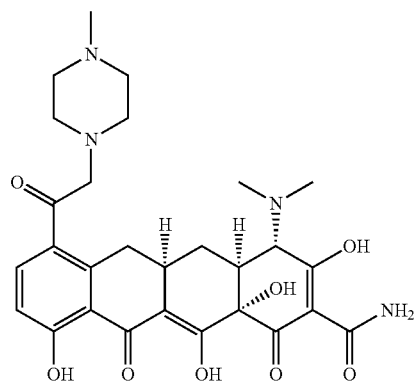
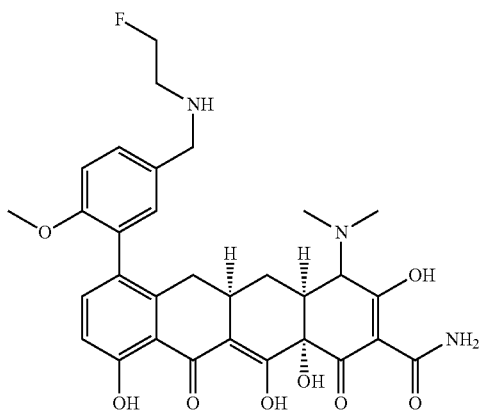

TABLE 2-continued
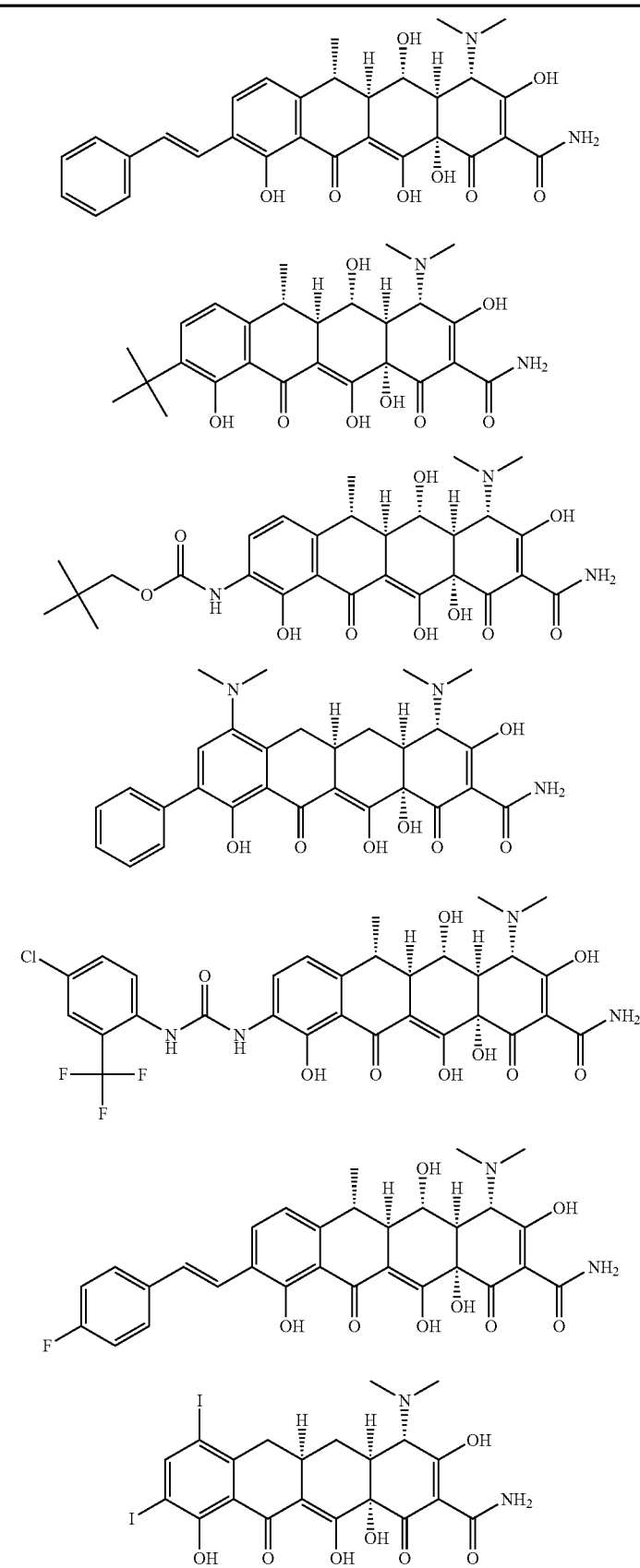

TABLE 2-continued
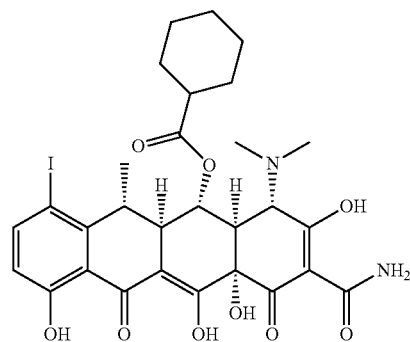
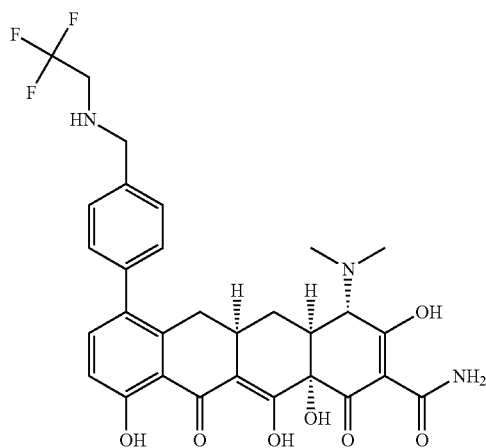
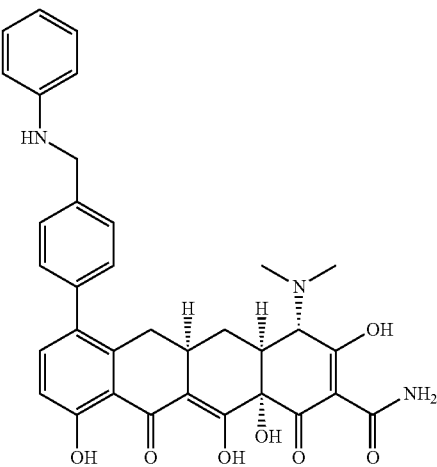
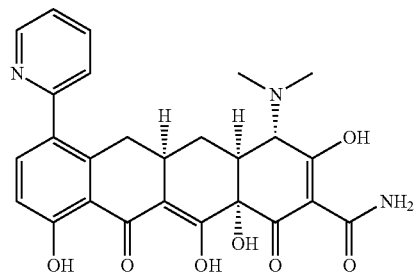

TABLE 2-continued
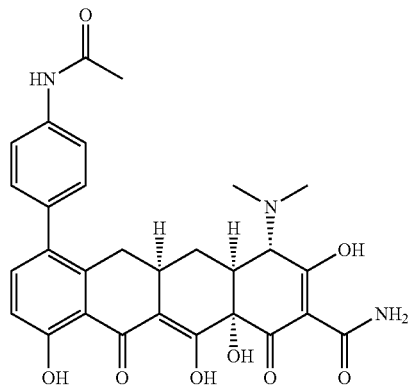
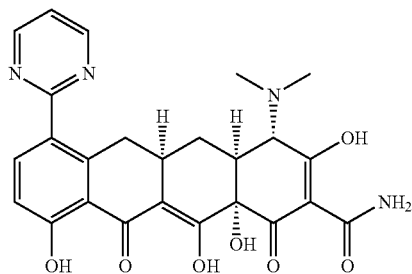
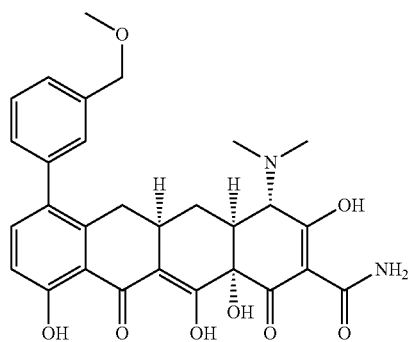
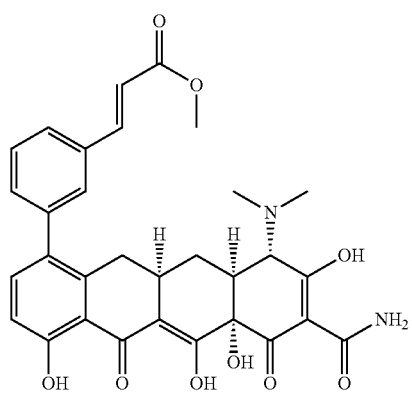

TABLE 2-continued
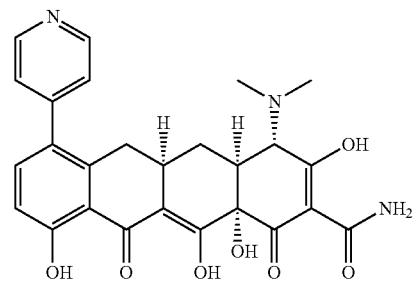
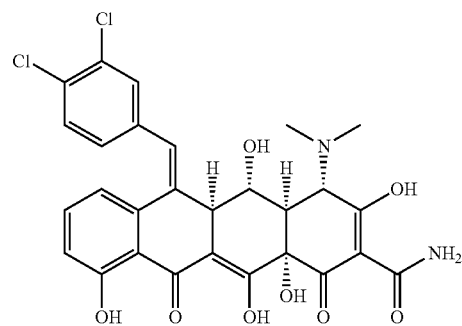
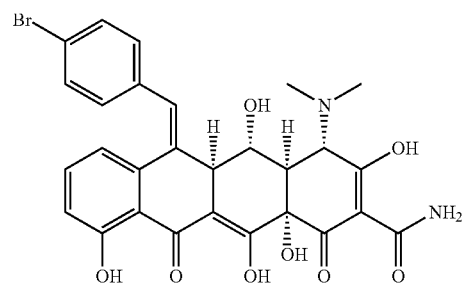
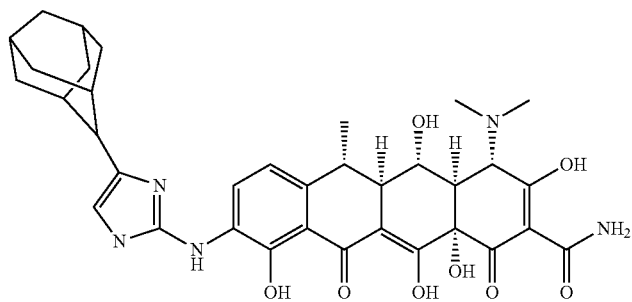
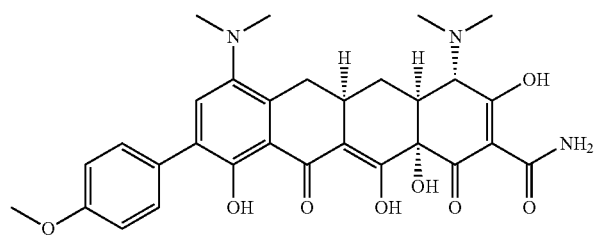

TABLE 2-continued
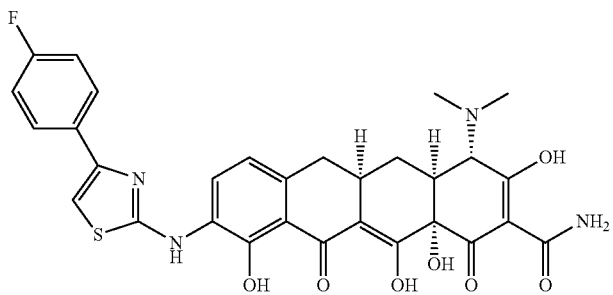
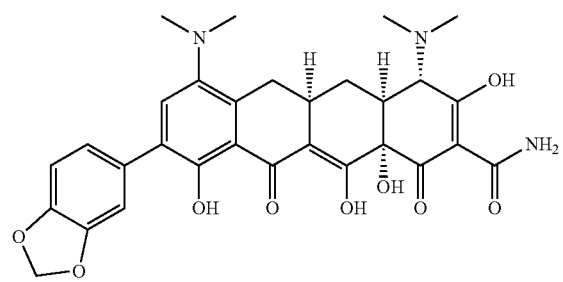
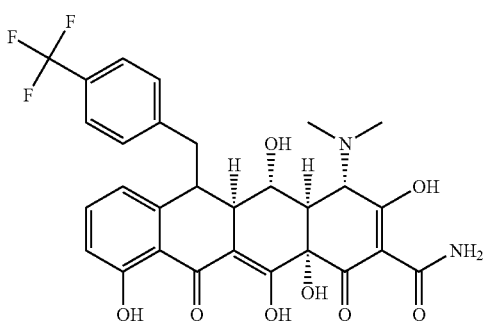

TABLE 2-continued
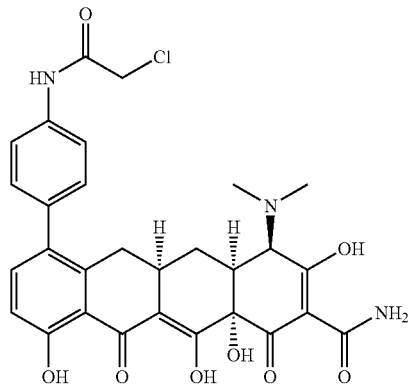
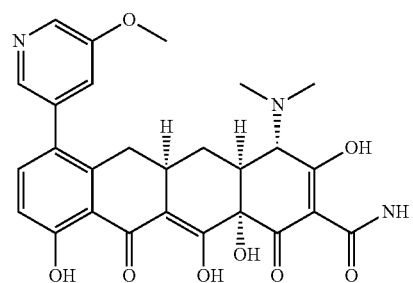
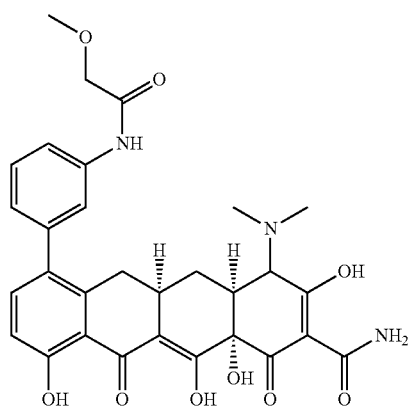
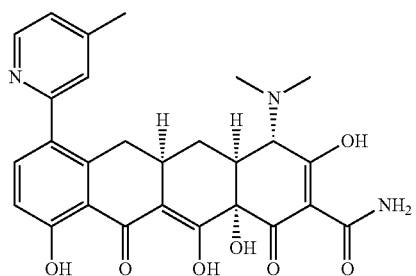

TABLE 2-continued
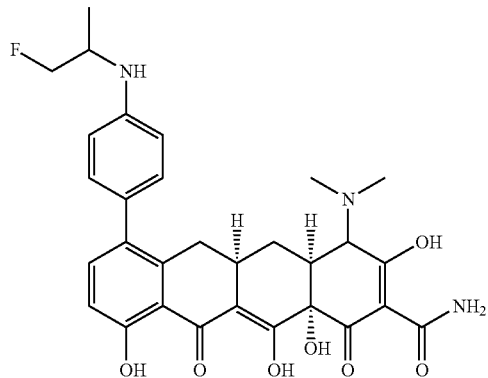
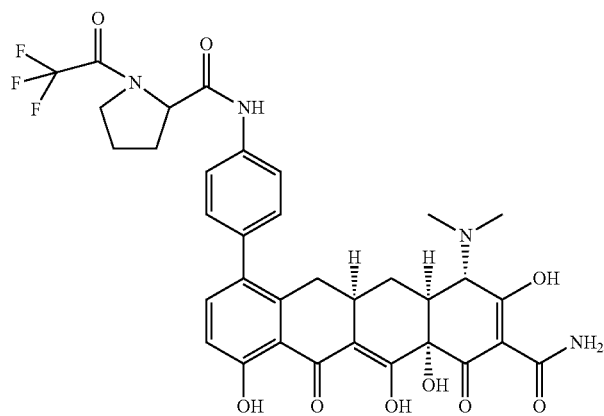
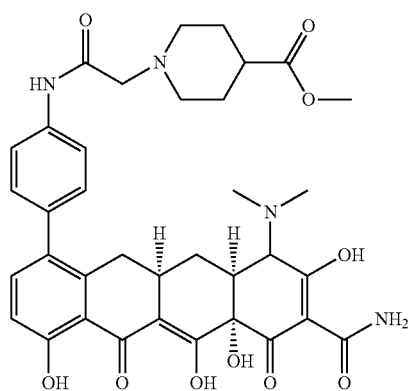
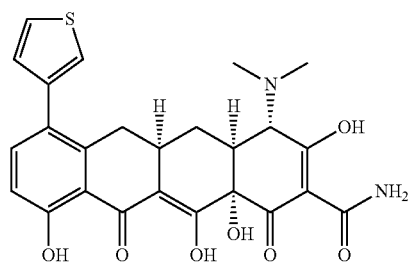

TABLE 2-continued
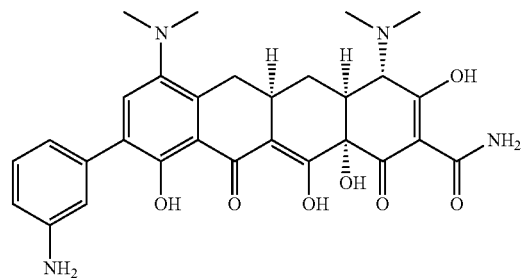
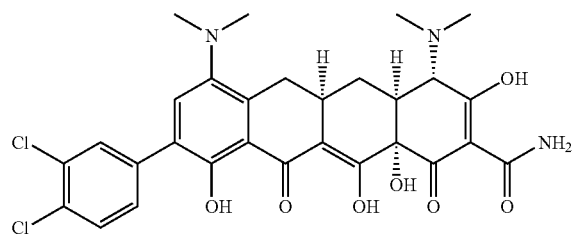
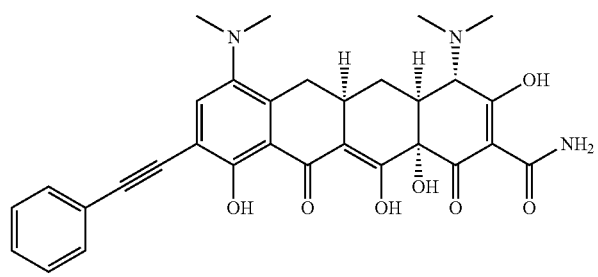
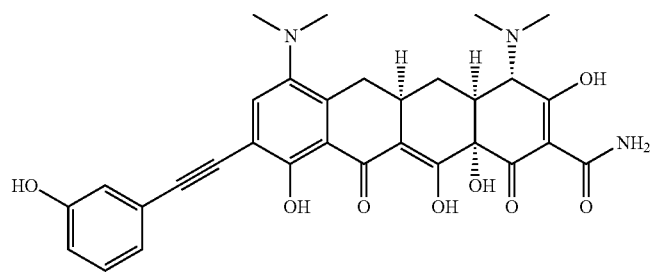
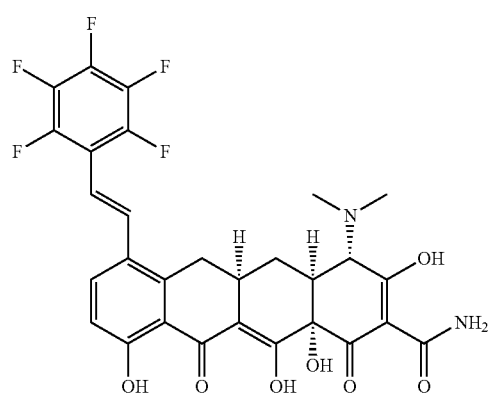

TABLE 2-continued
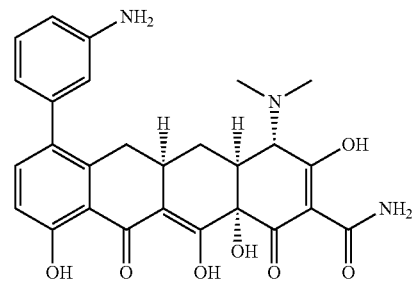
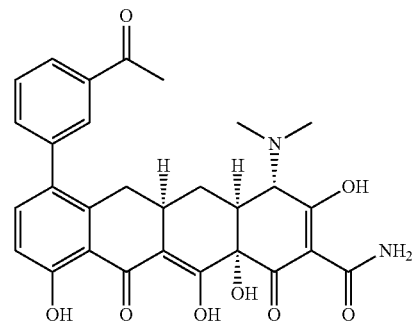
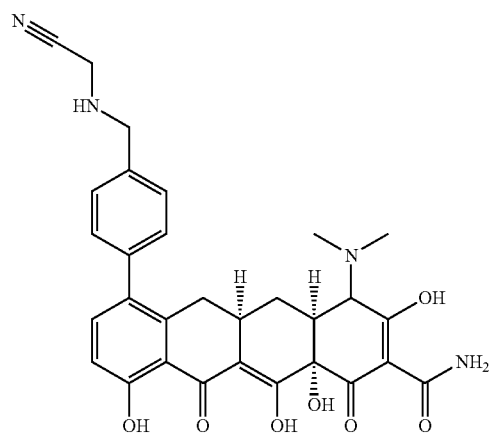
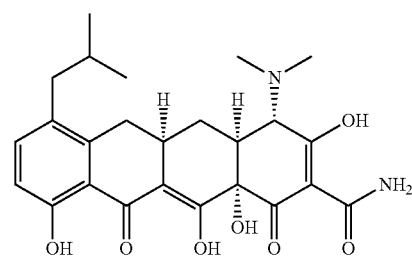
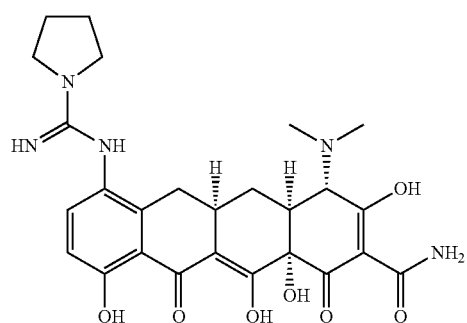

TABLE 2-continued
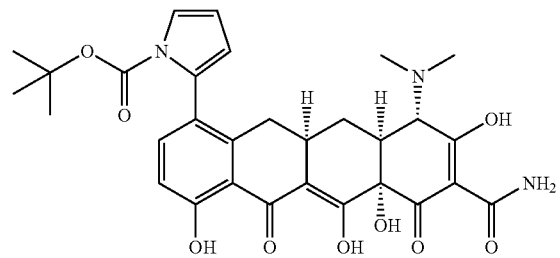
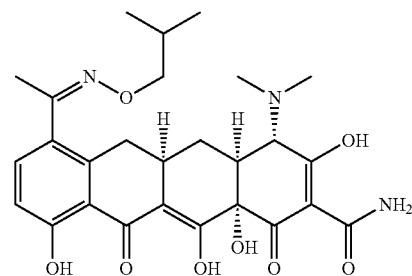
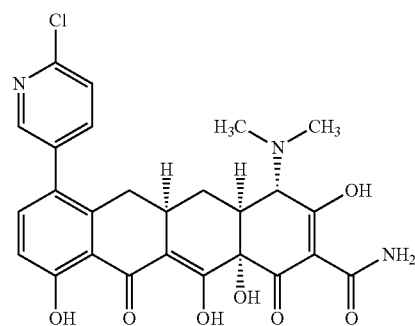
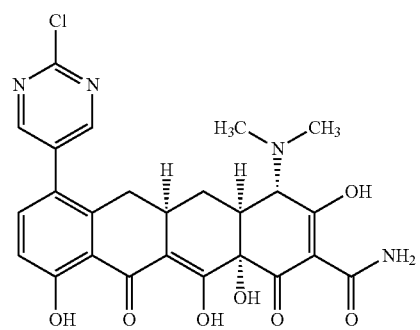
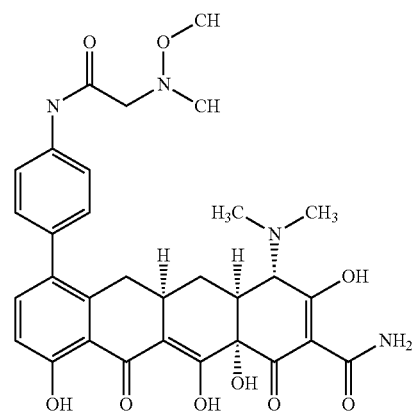

TABLE 2-continued
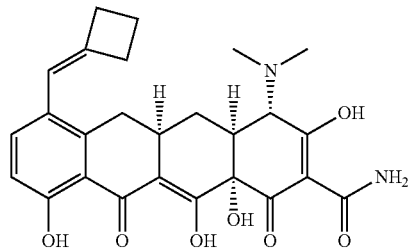
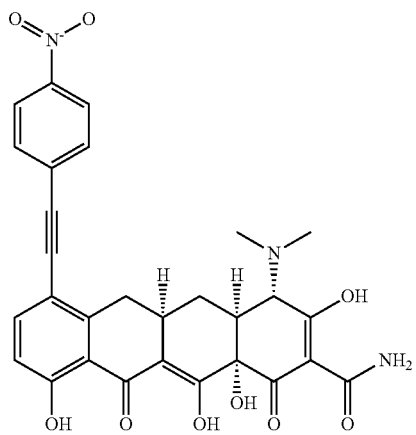
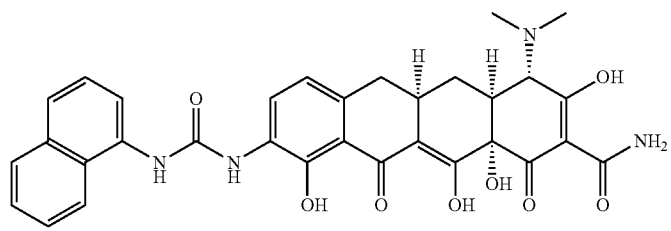
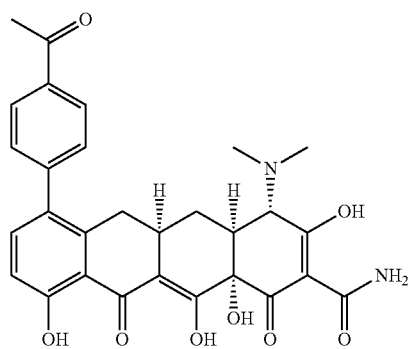
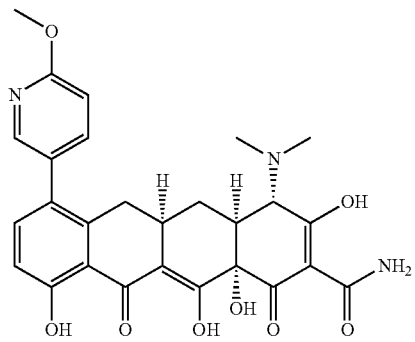

TABLE 2-continued
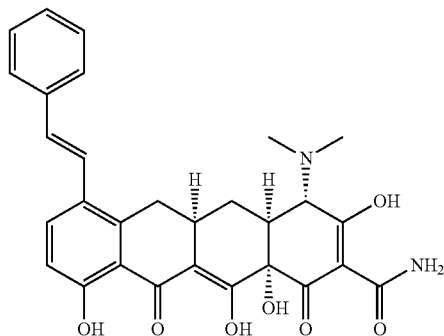
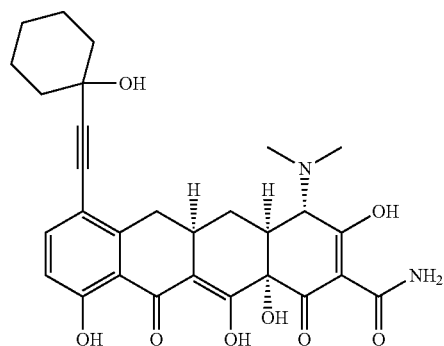
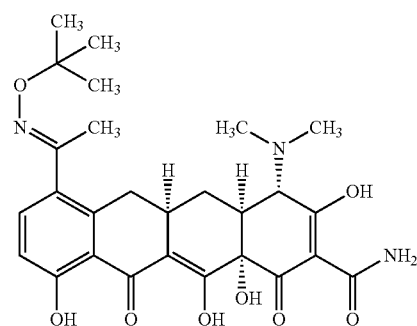
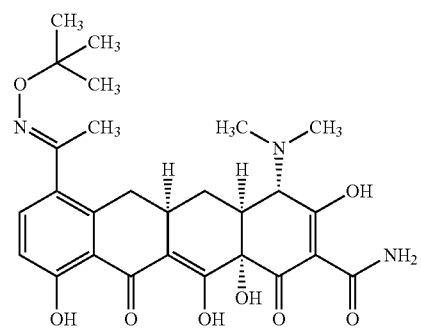
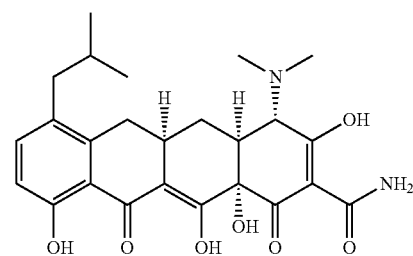

TABLE 2-continued
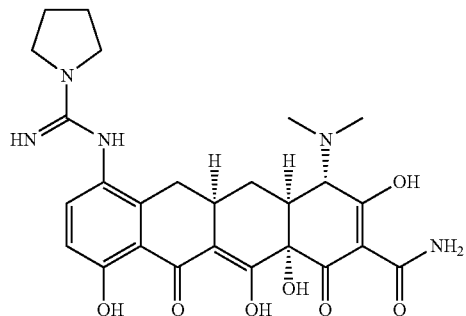
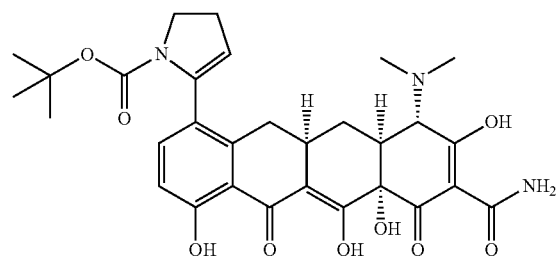
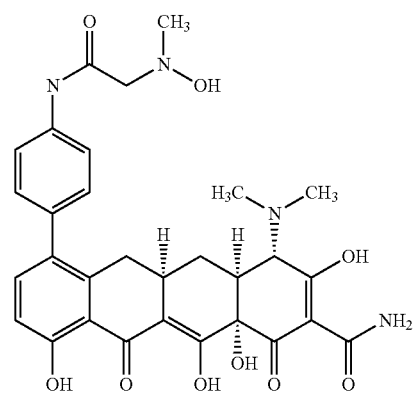
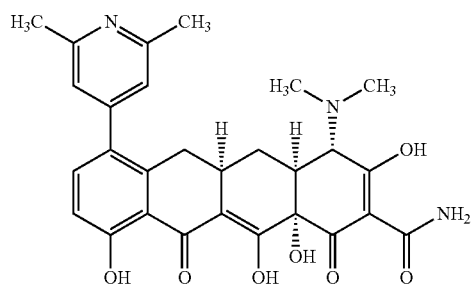
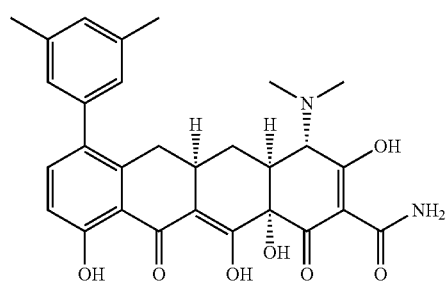

TABLE 2-continued
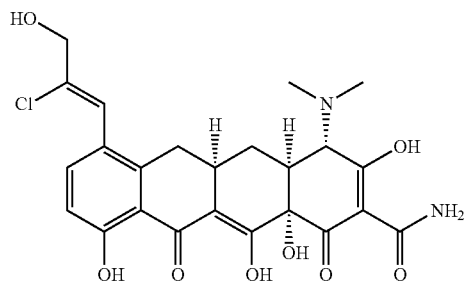
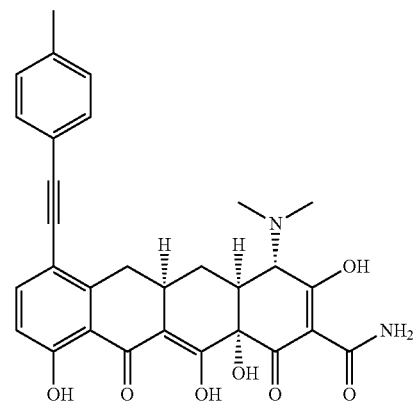
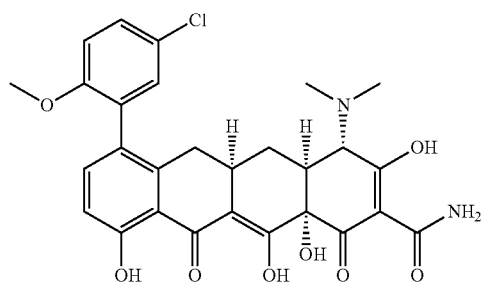
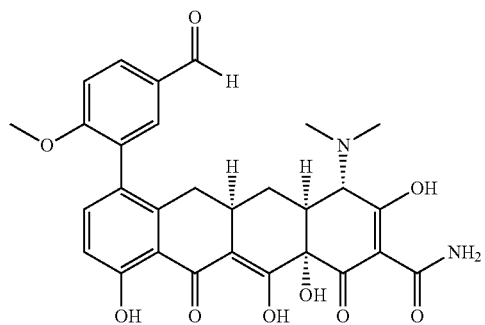
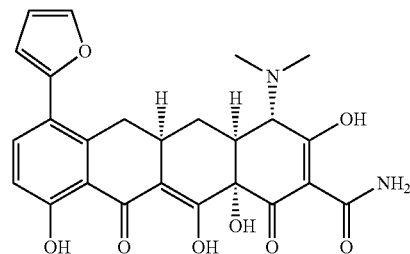

TABLE 2-continued
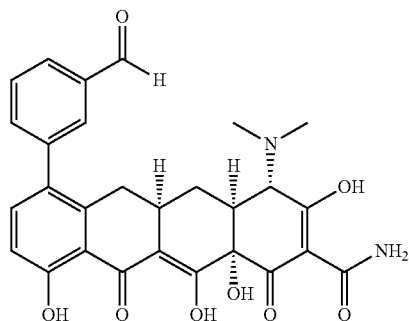
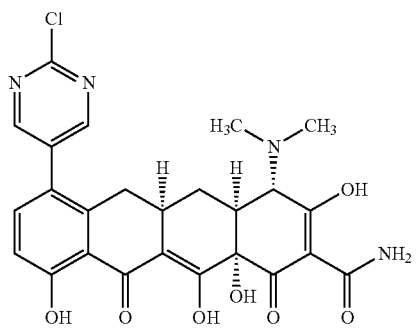
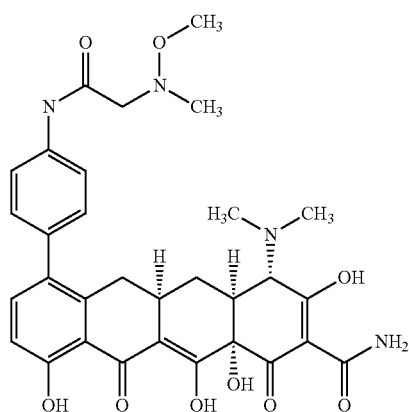
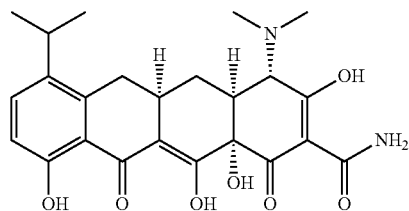
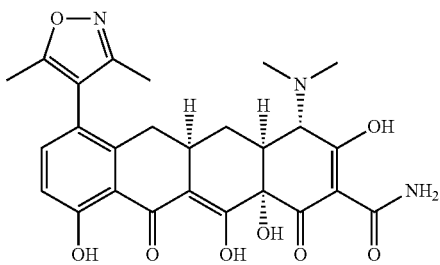

TABLE 2-continued
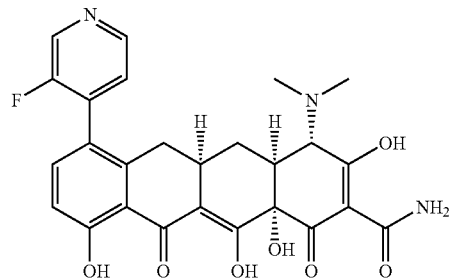
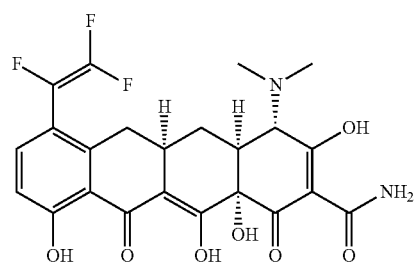
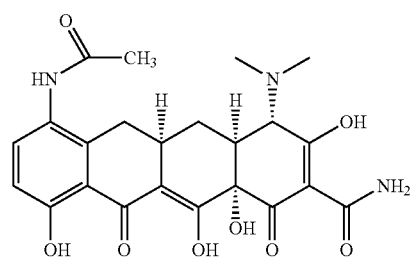
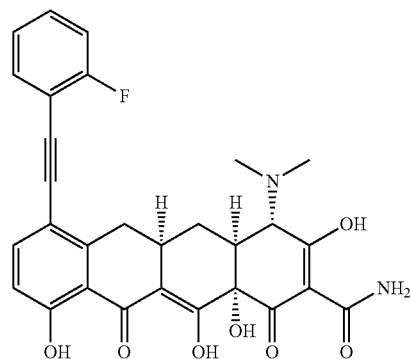
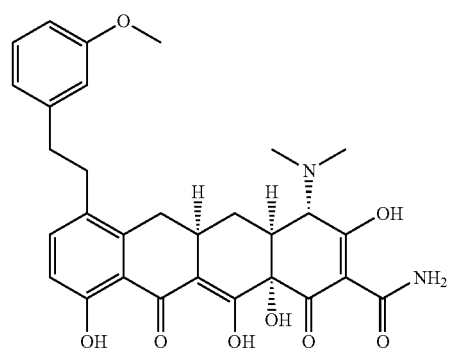

TABLE 2-continued
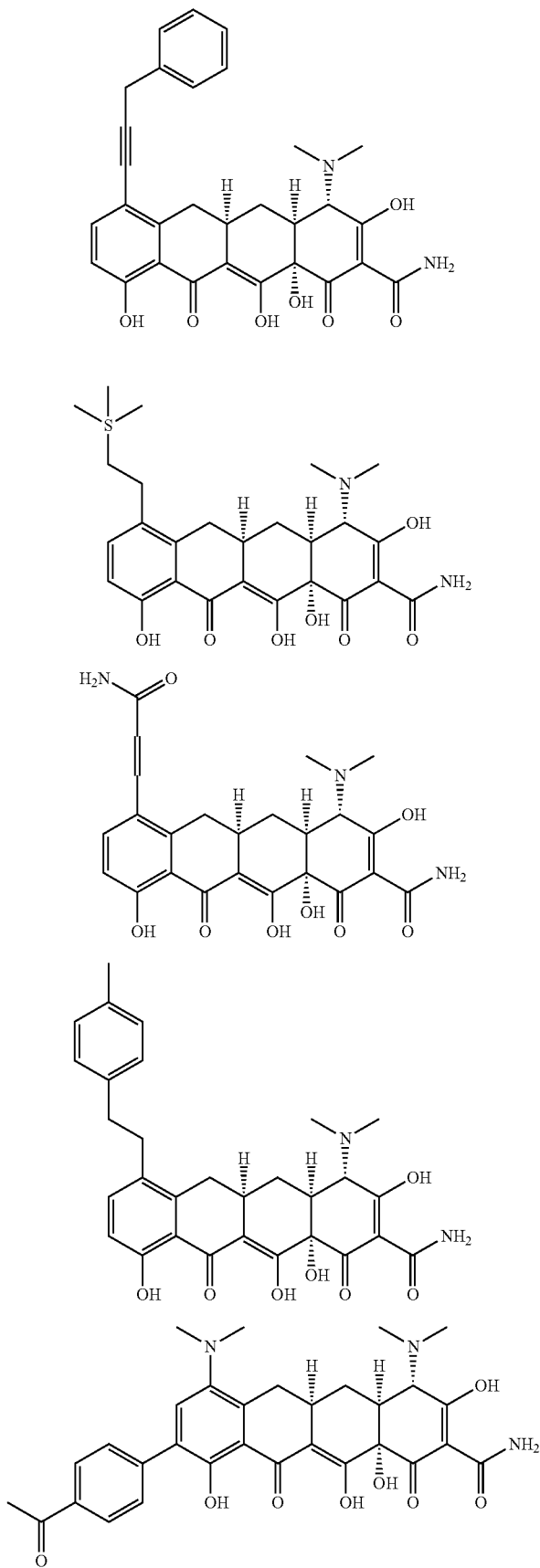

TABLE 2-continued
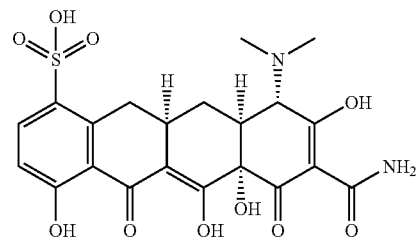
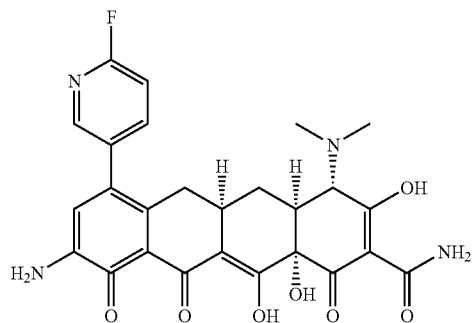
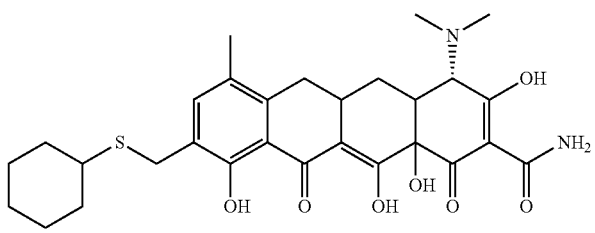
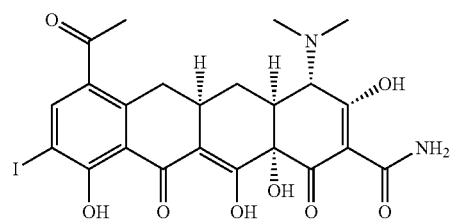
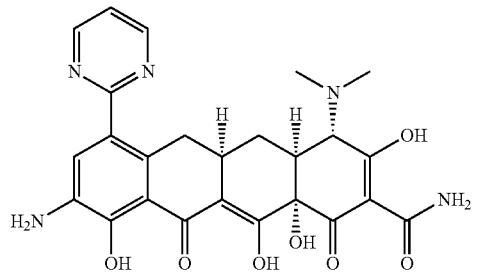
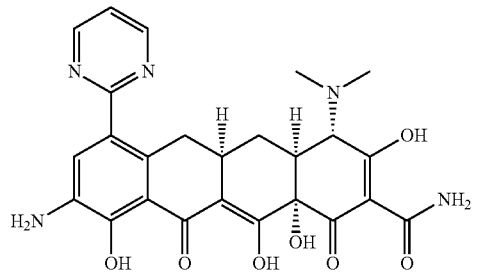

TABLE 2-continued
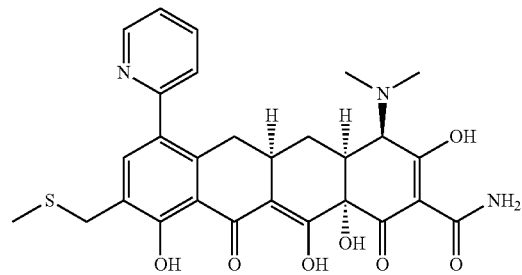
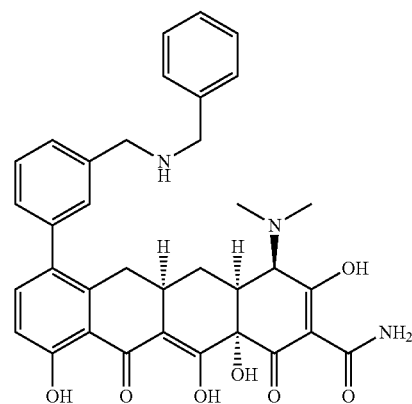
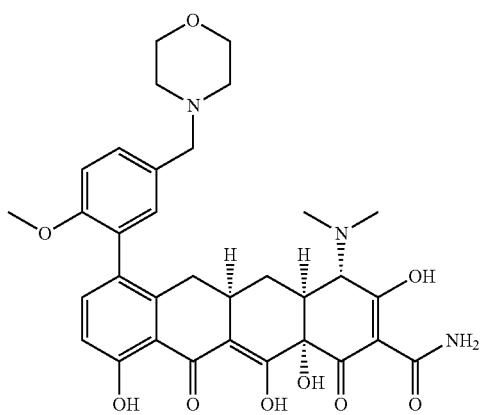
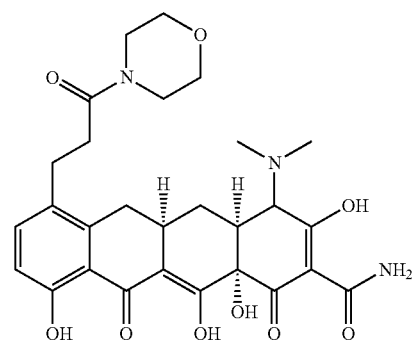

TABLE 2-continued
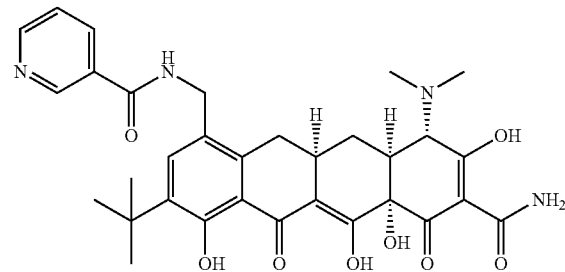
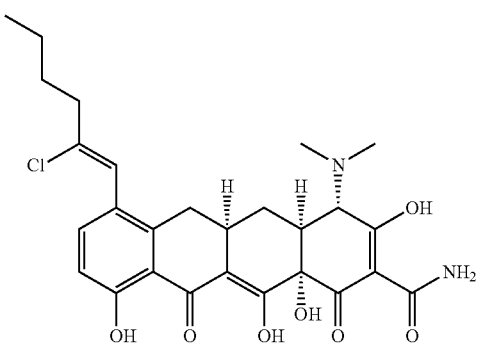
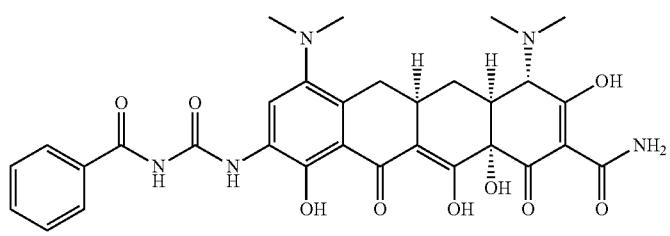
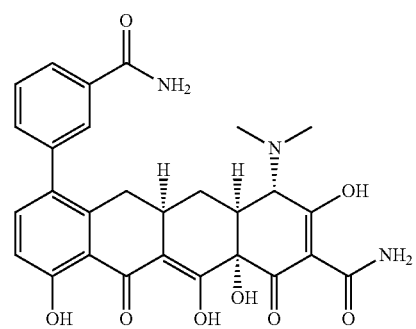
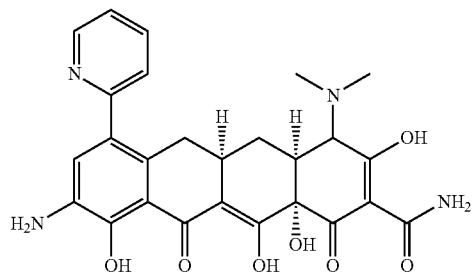

TABLE 2-continued
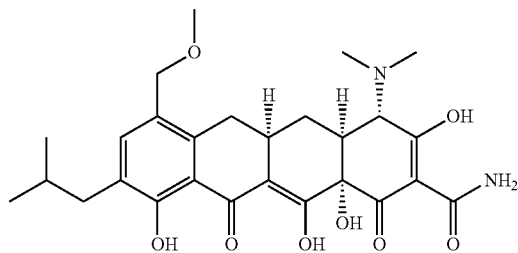
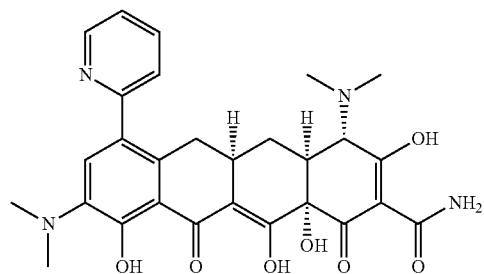
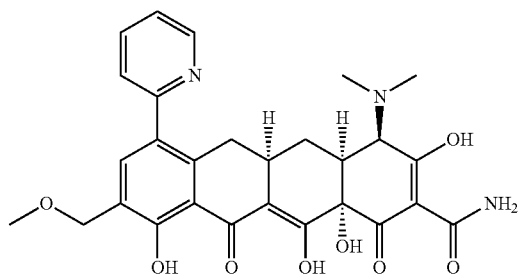
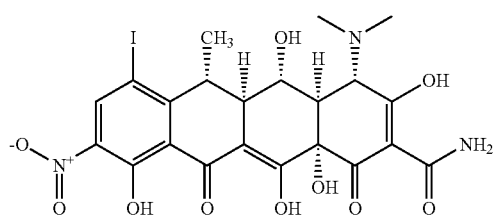
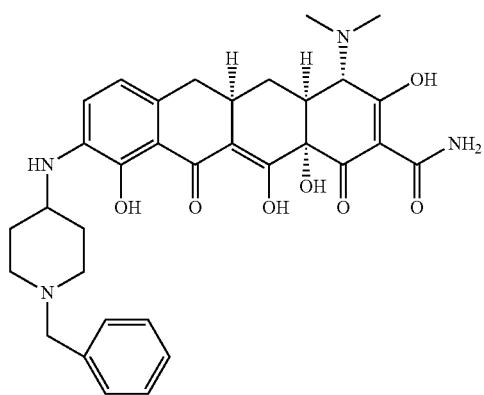

TABLE 2-continued
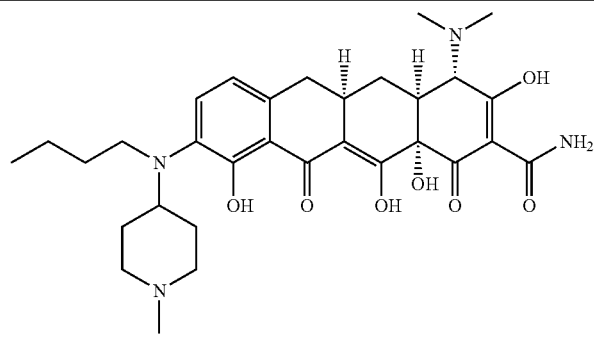
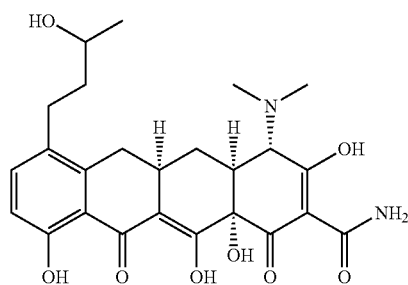
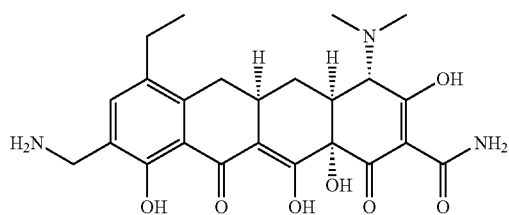
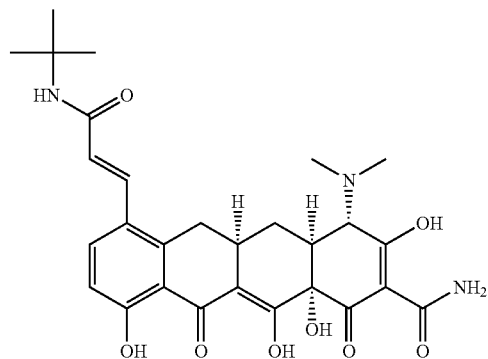
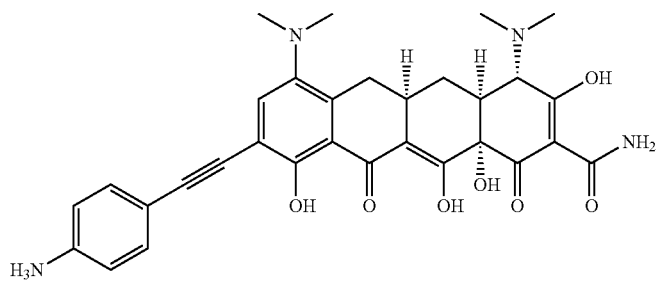

TABLE 2-continued
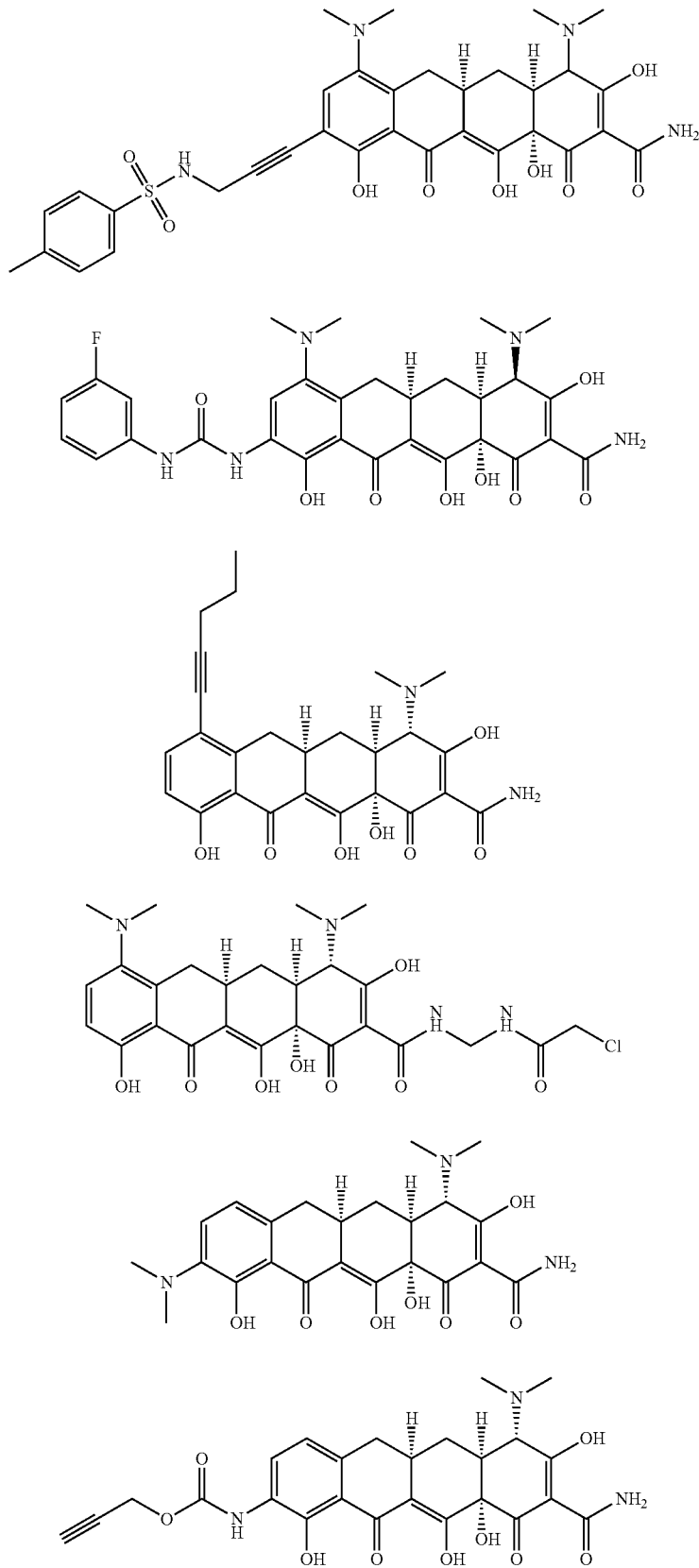

TABLE 2-continued
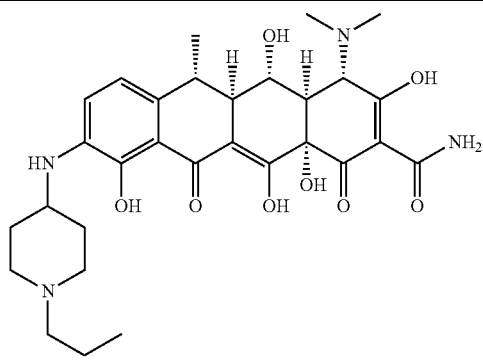
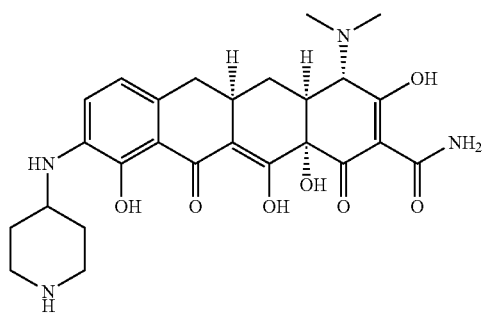
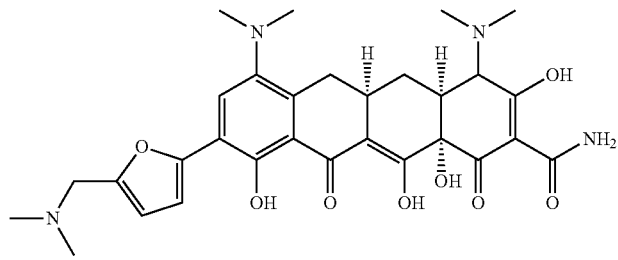
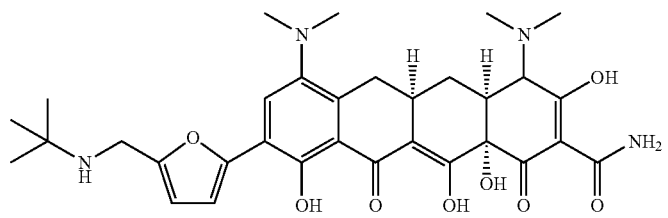
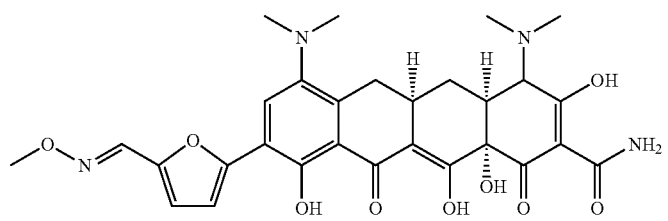
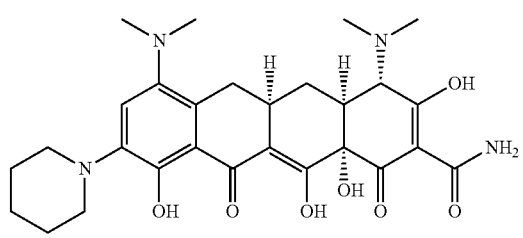

TABLE 2-continued
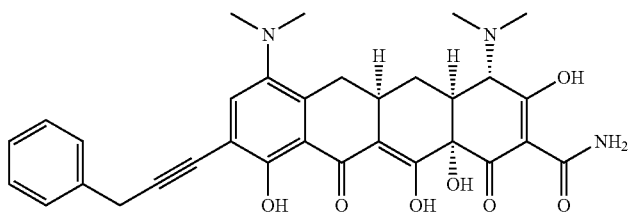
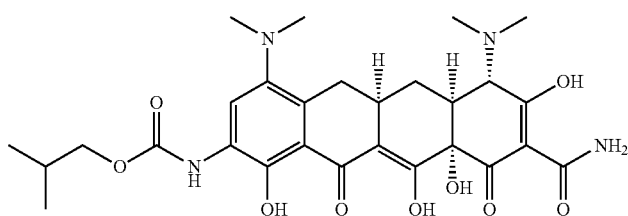
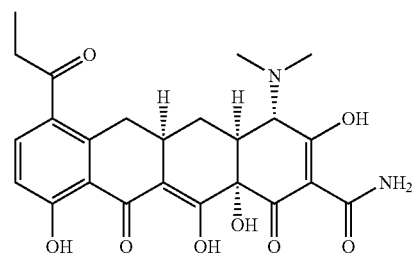
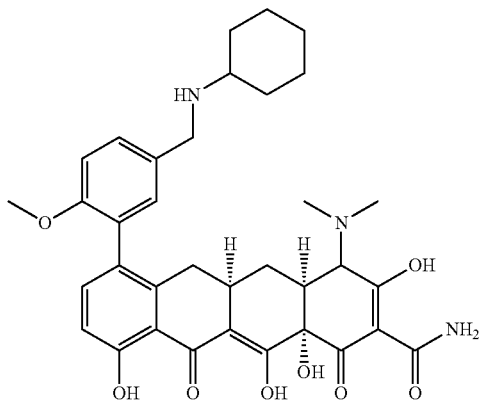
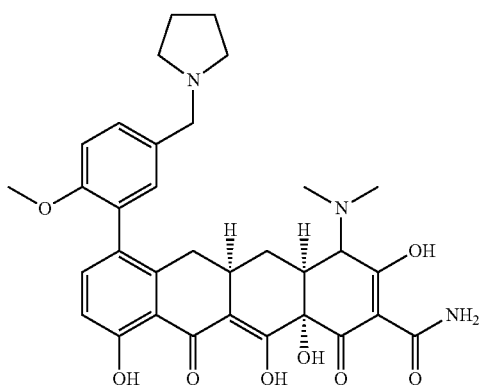

TABLE 2-continued
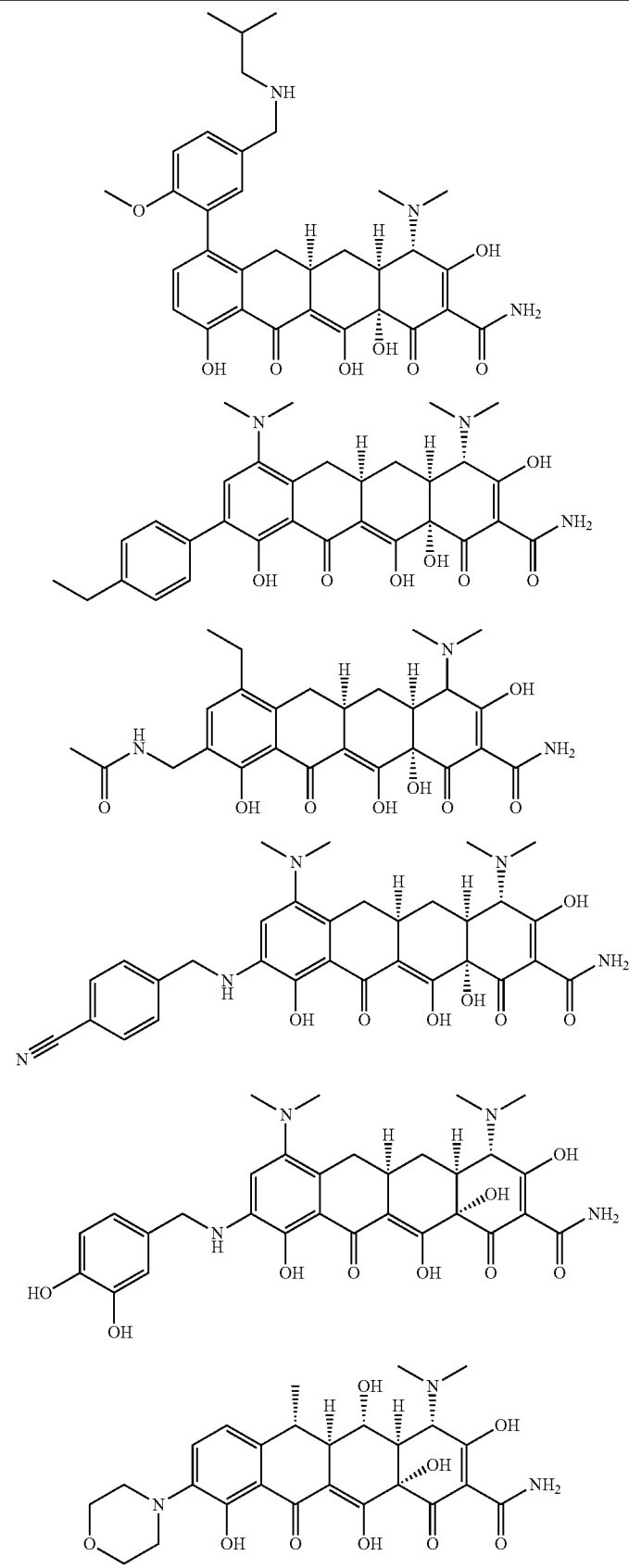

TABLE 2-continued
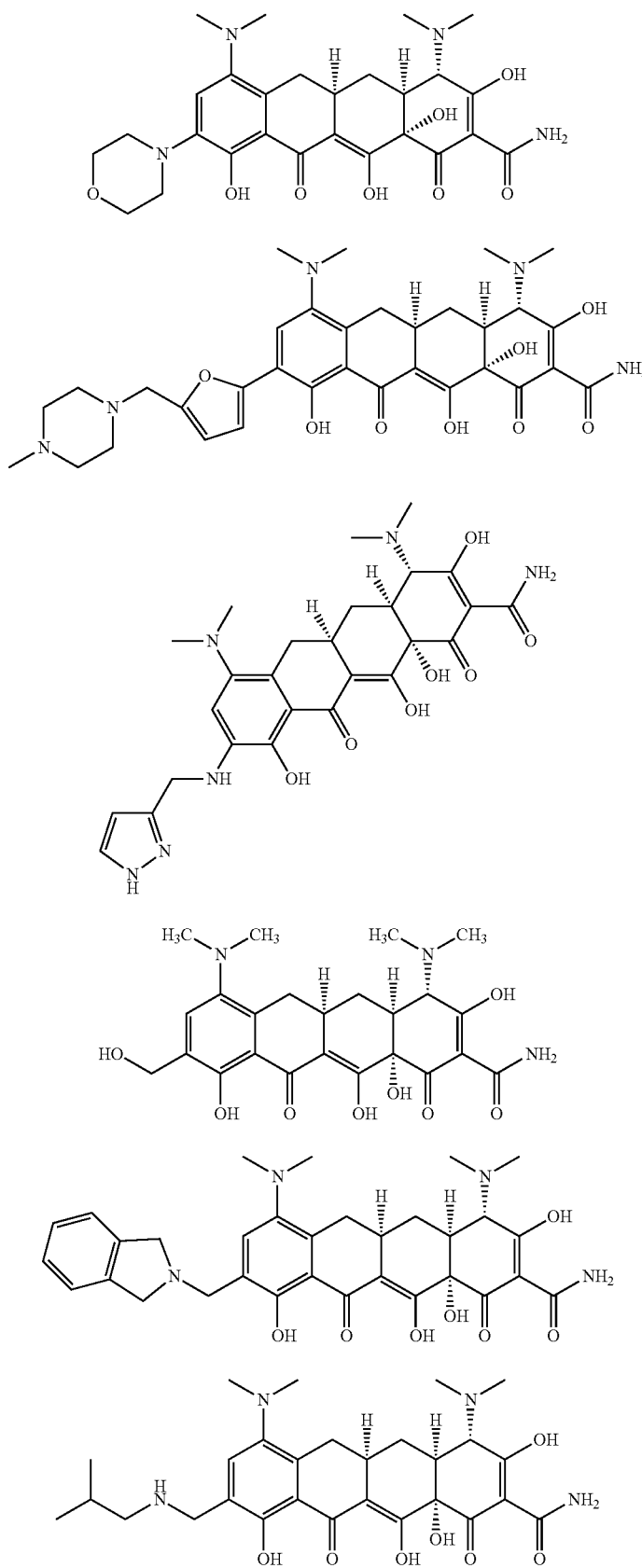

TABLE 2-continued
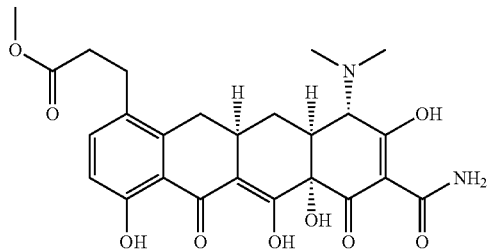
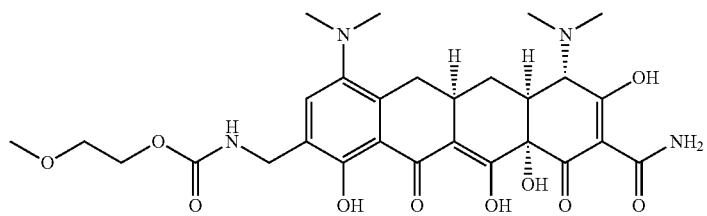
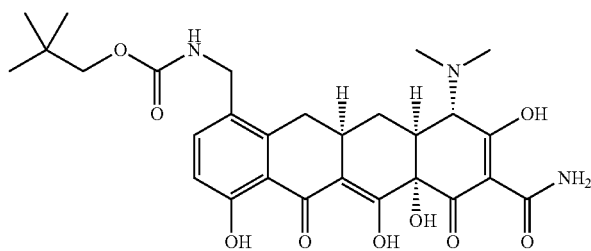
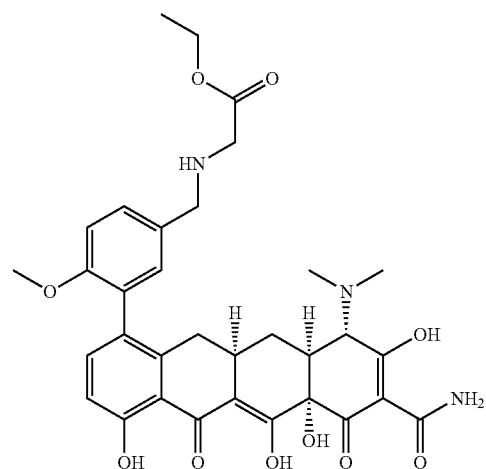
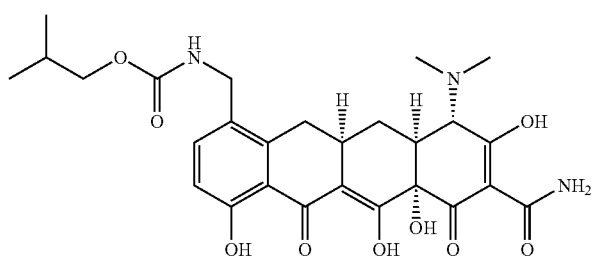

TABLE 2-continued
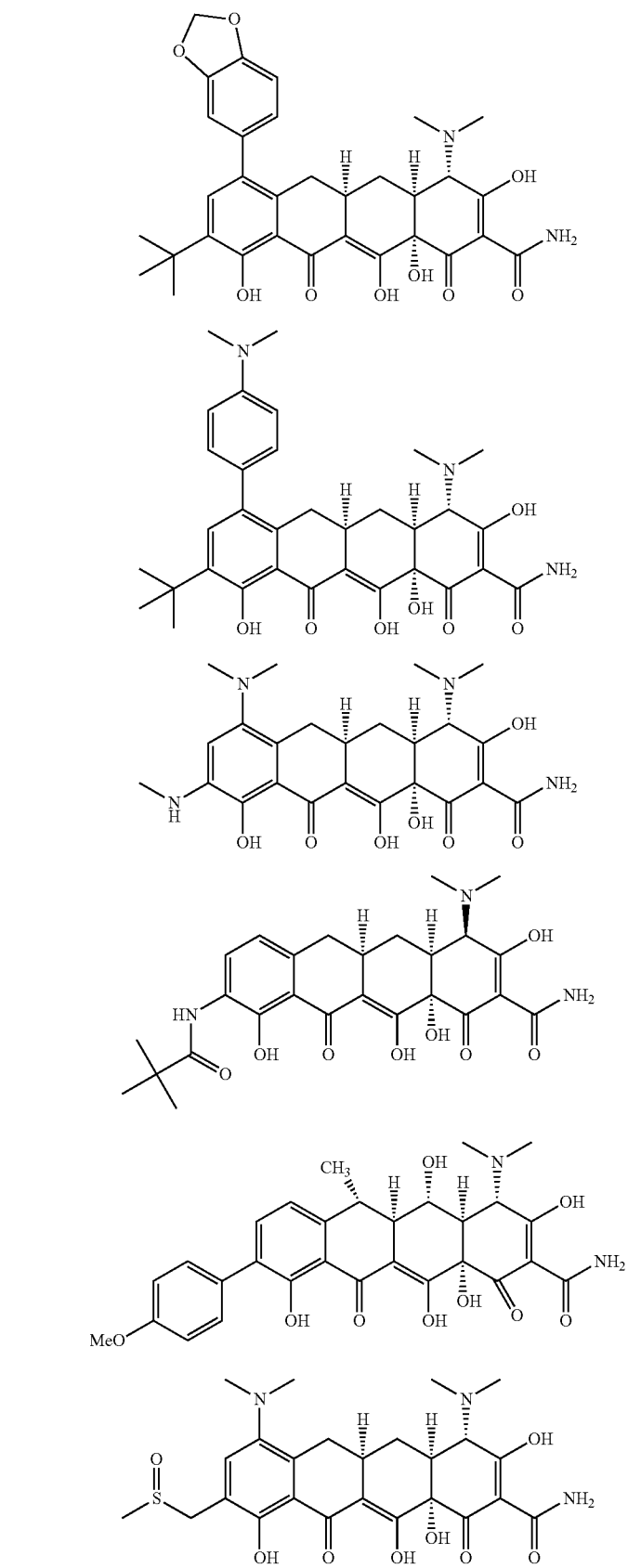

TABLE 2-continued
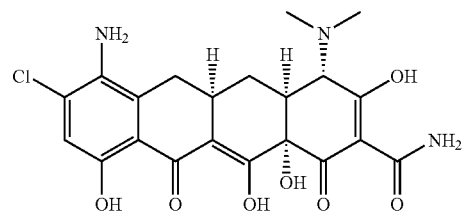
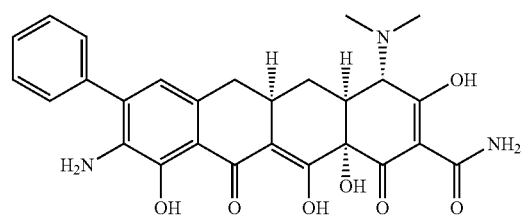
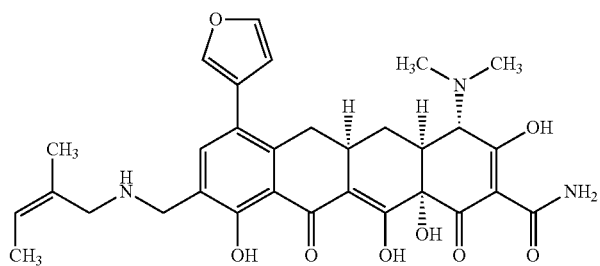
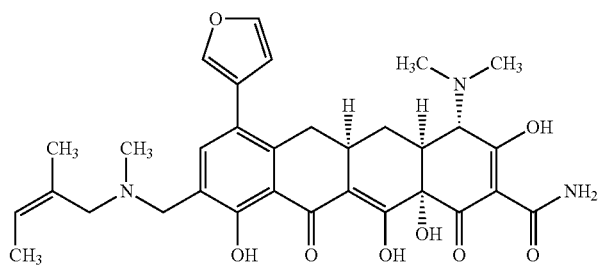
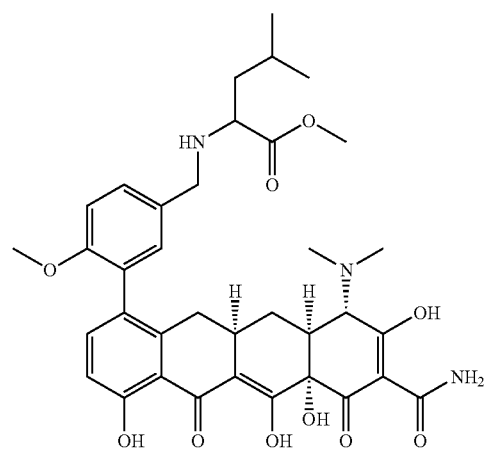

TABLE 2-continued
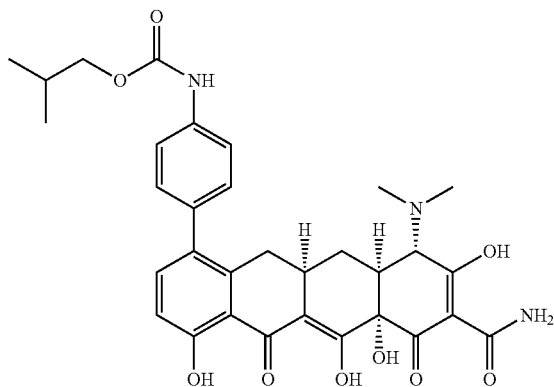
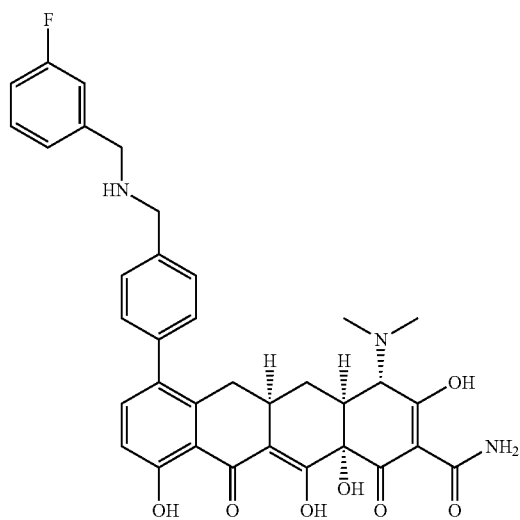
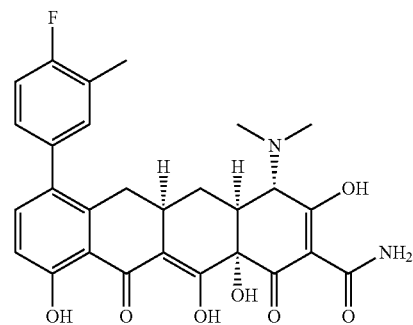
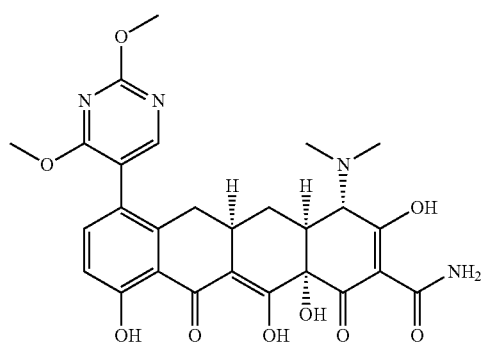

TABLE 2-continued
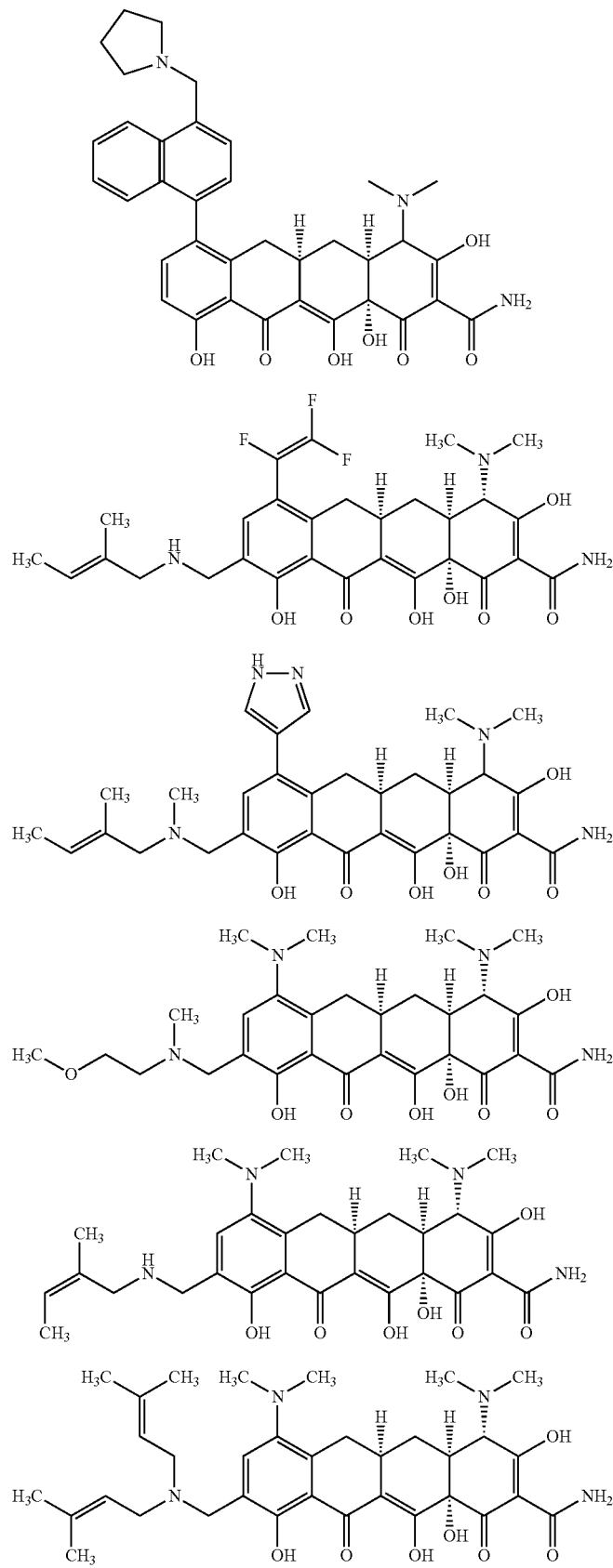

TABLE 2-continued
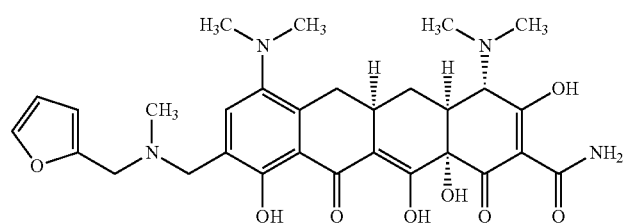
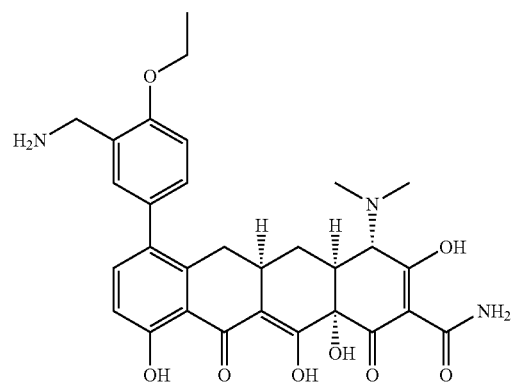
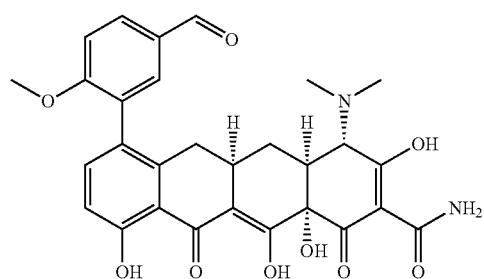
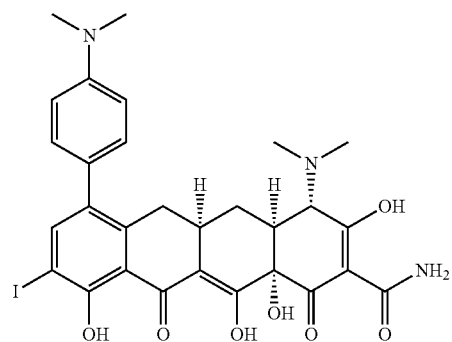
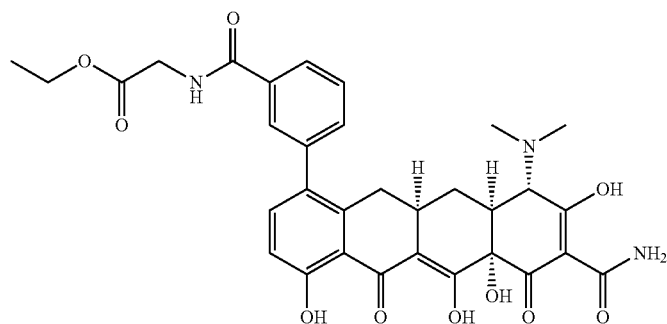

TABLE 2-continued
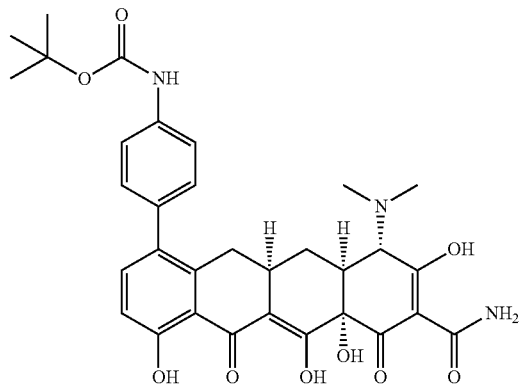
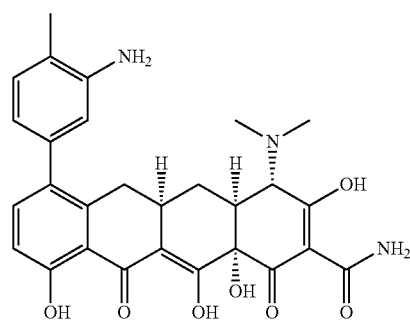
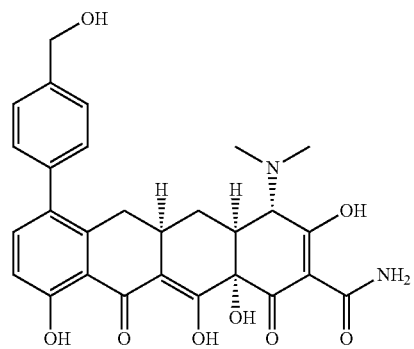
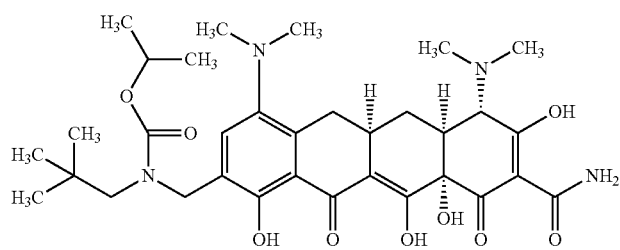
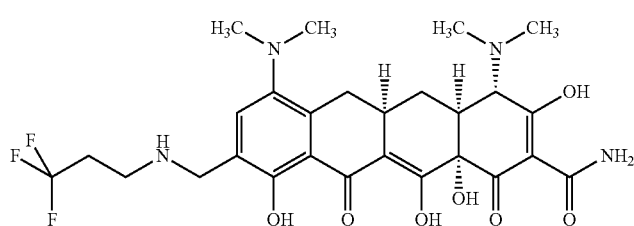

TABLE 2-continued
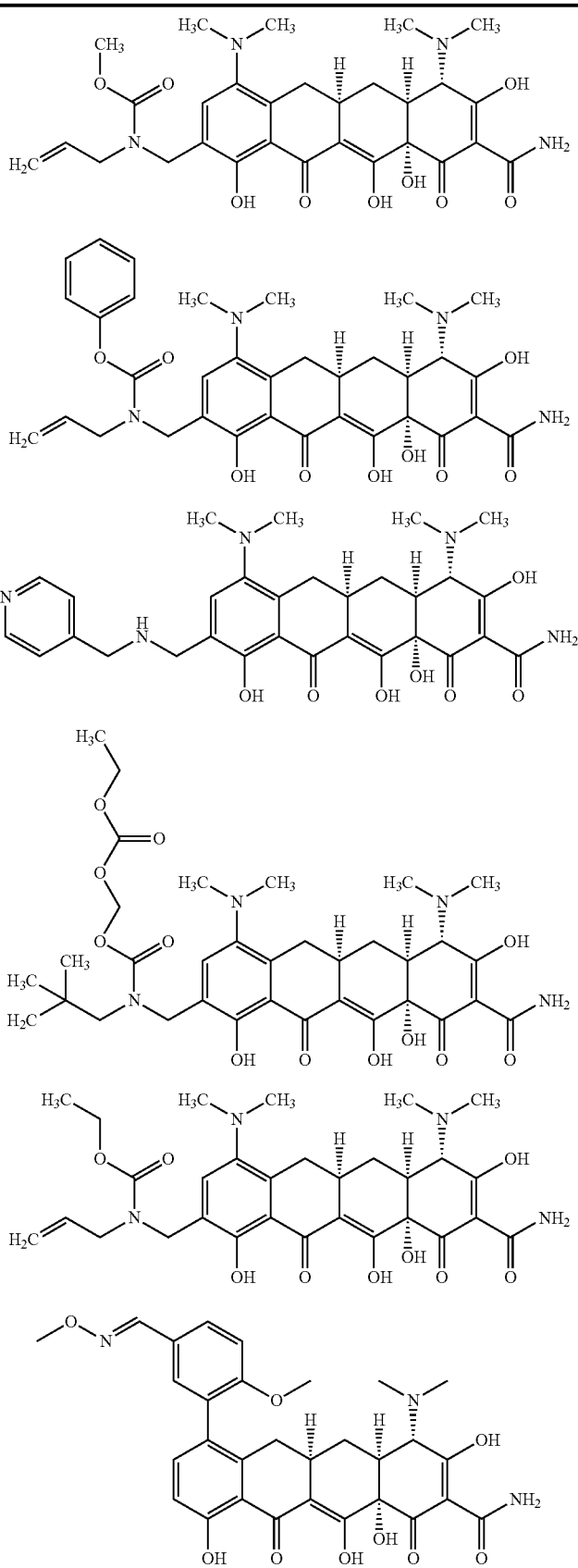

TABLE 2-continued
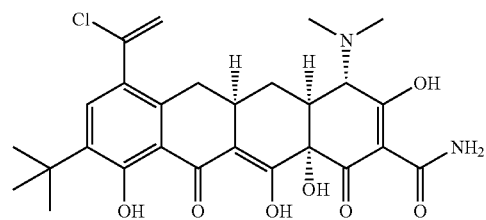
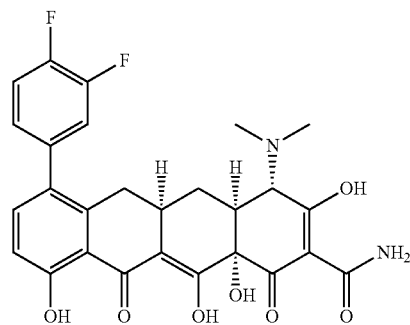
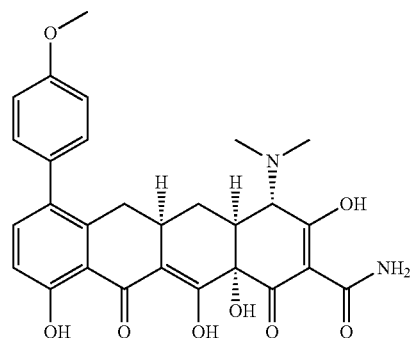
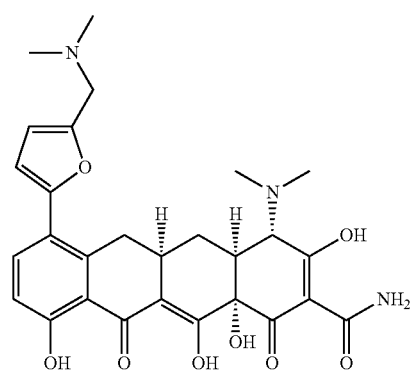
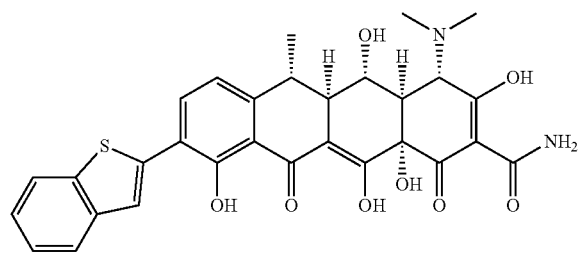

TABLE 2-continued
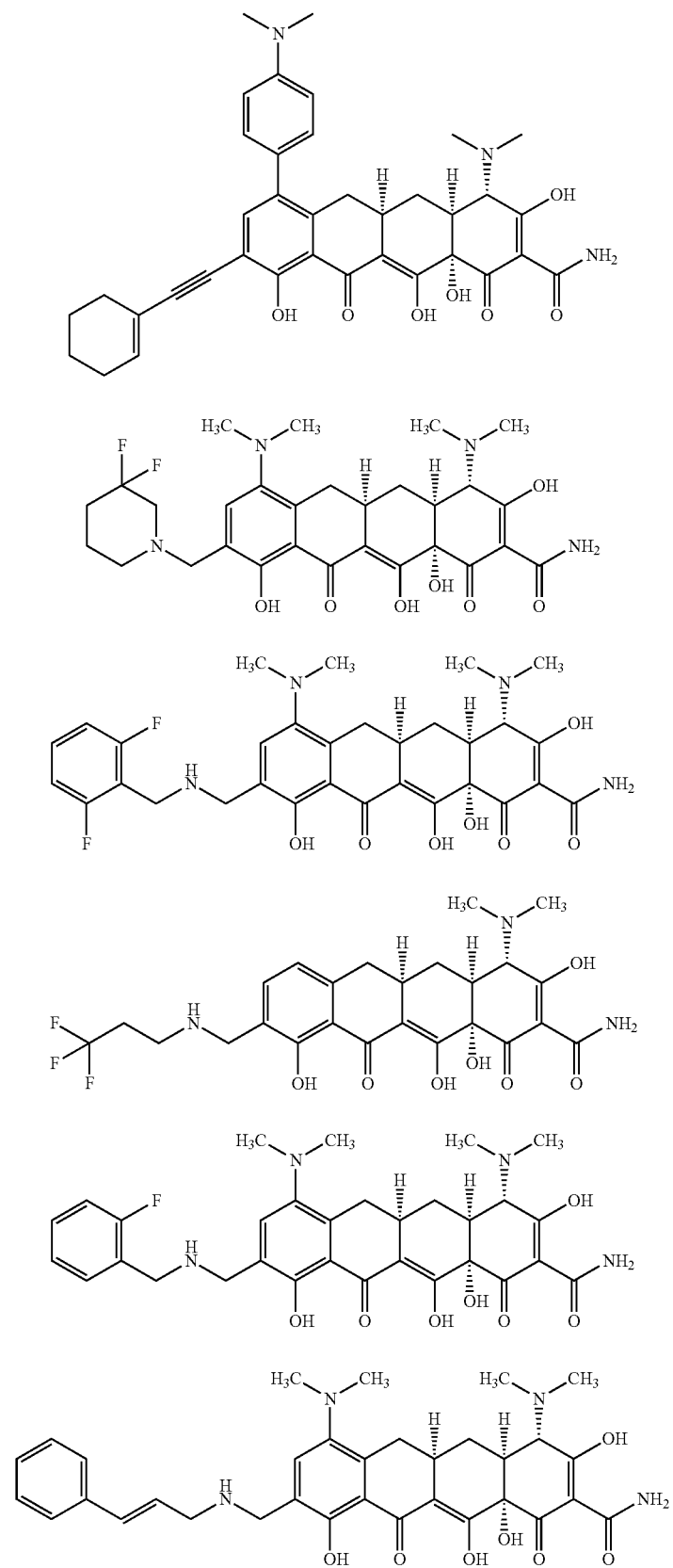

TABLE 2-continued
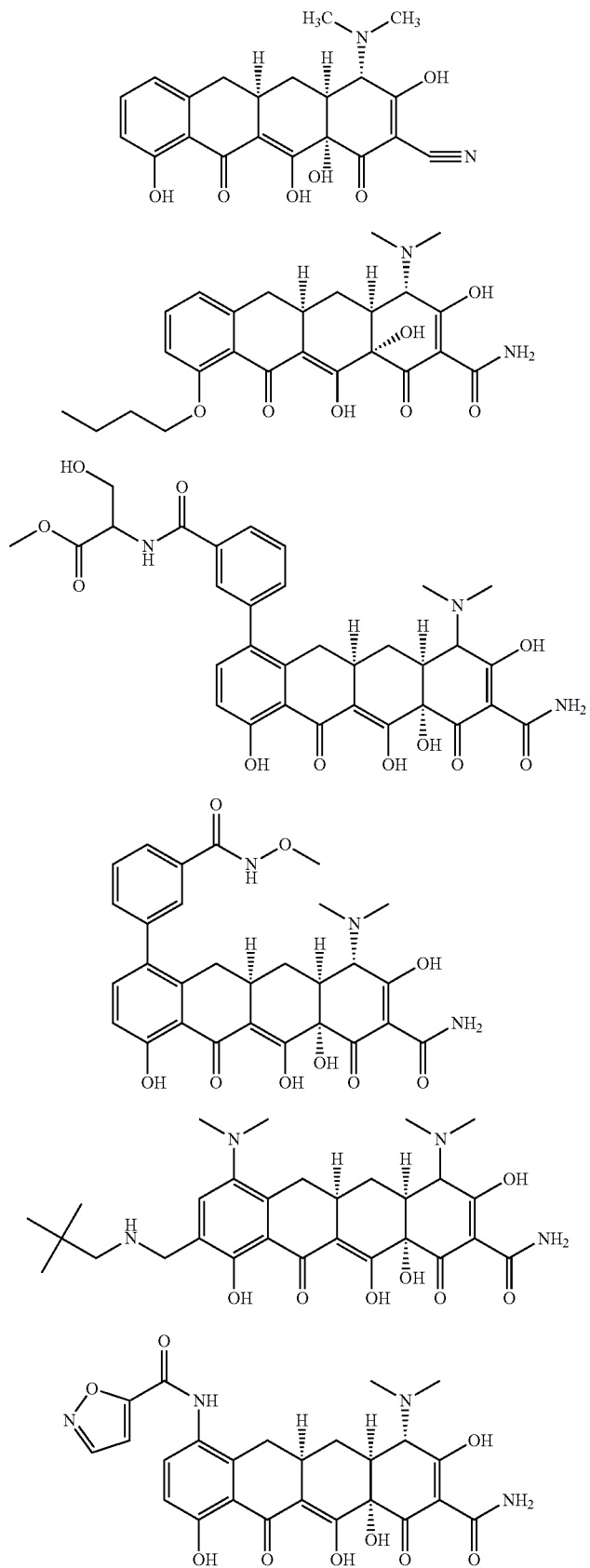

TABLE 2-continued
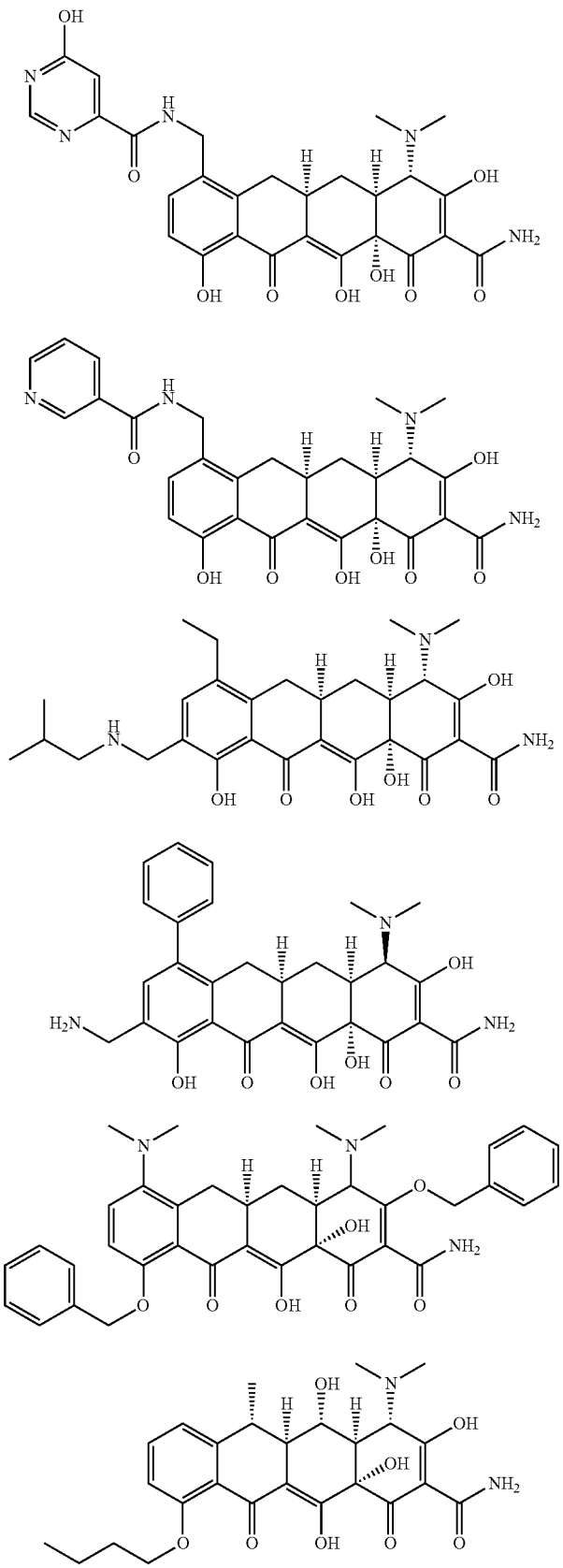

TABLE 2-continued
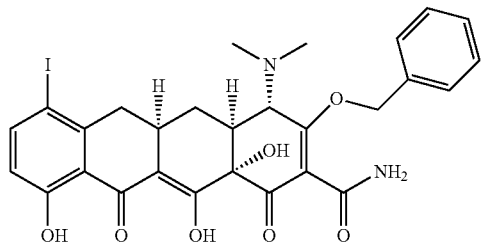
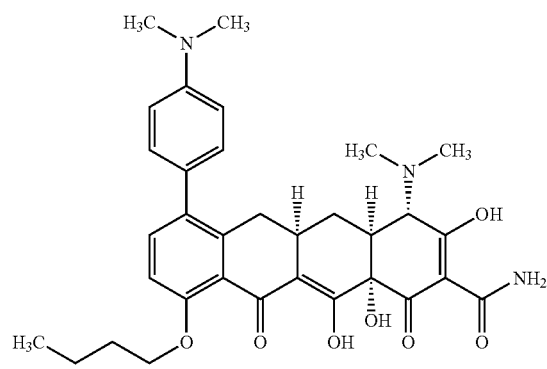
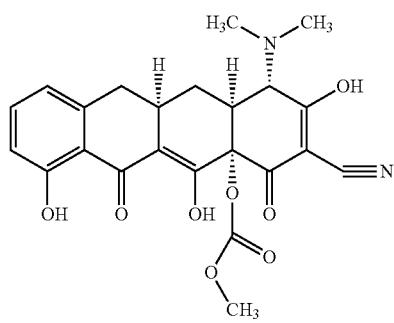
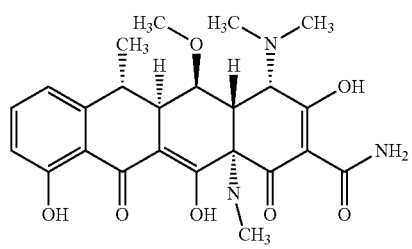
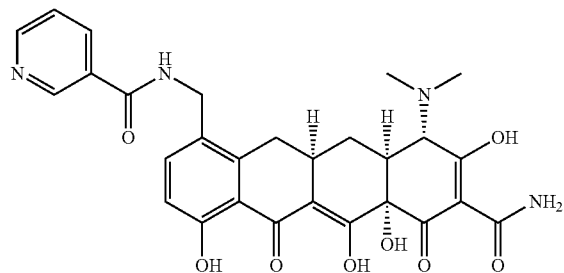

TABLE 2-continued
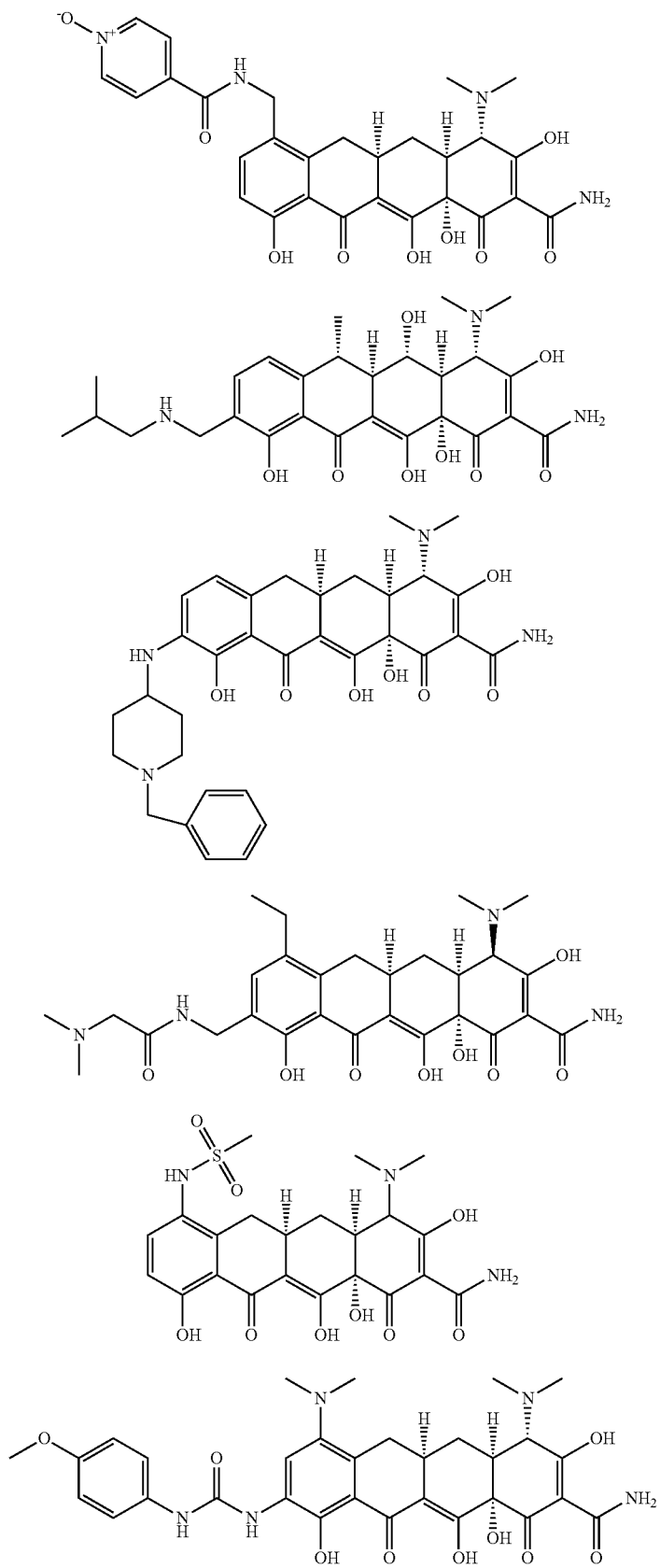

TABLE 2-continued
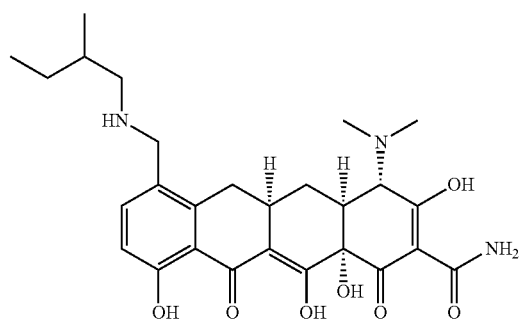
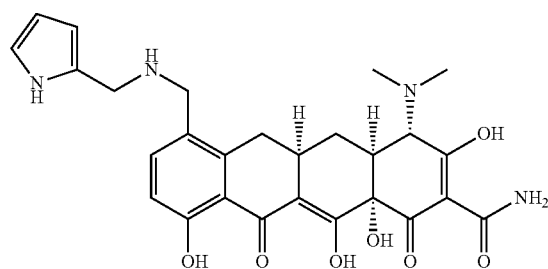
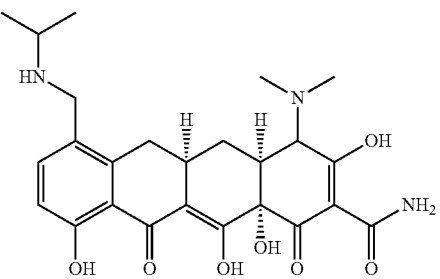
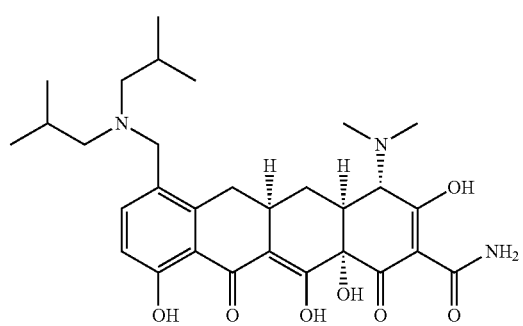
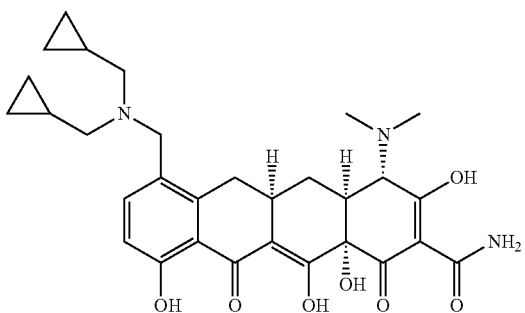

TABLE 2-continued
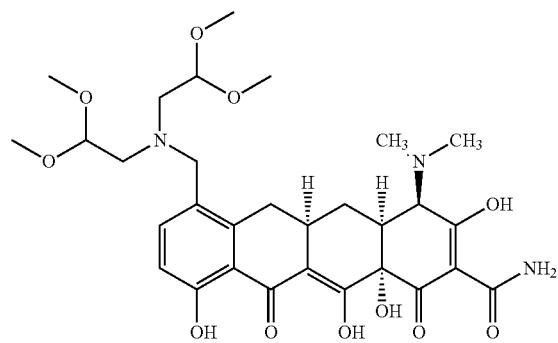
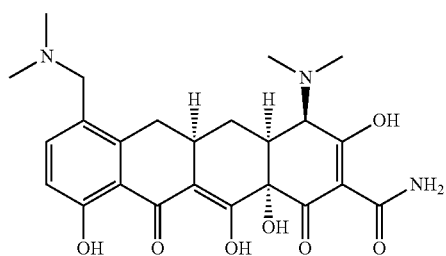
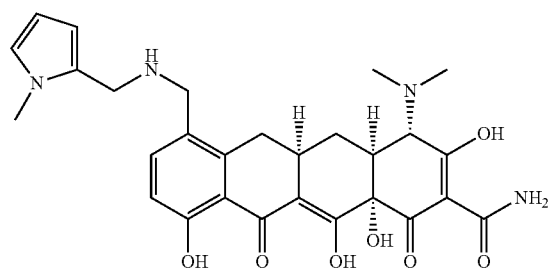
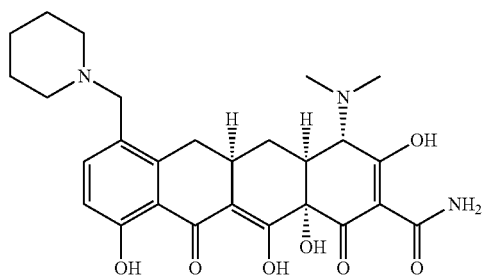
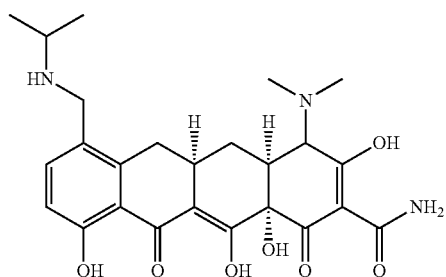

TABLE 2-continued
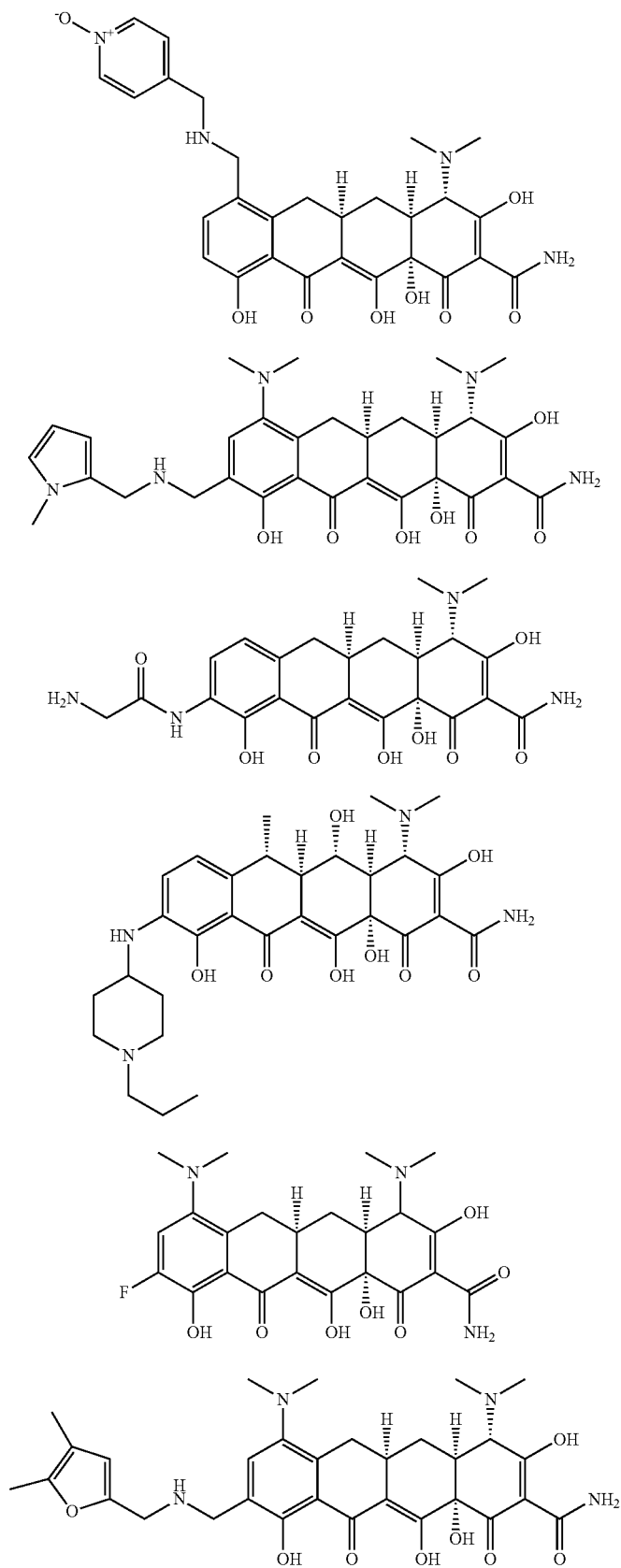

TABLE 2-continued
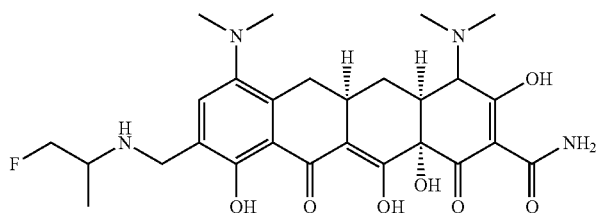
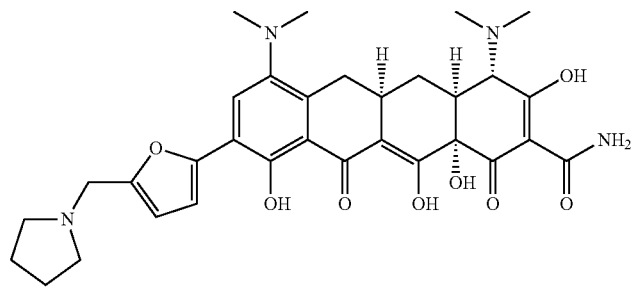
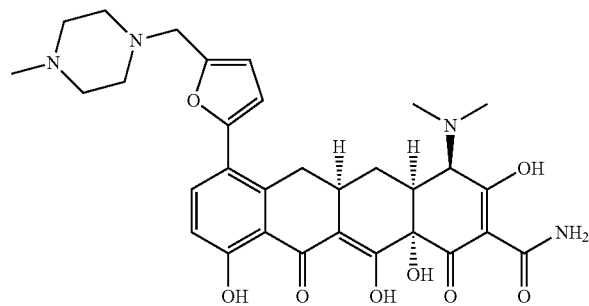
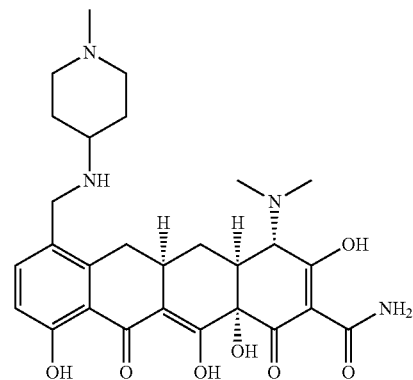
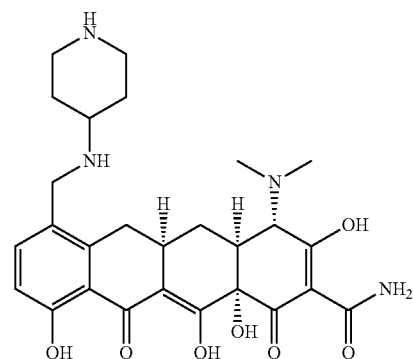

TABLE 2-continued
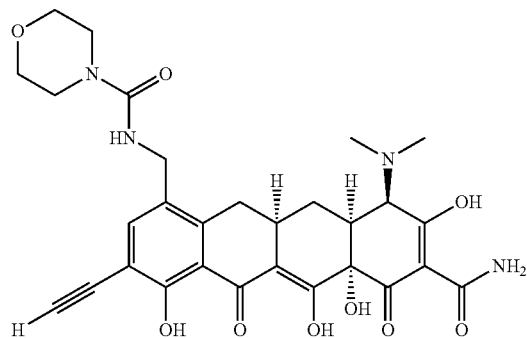
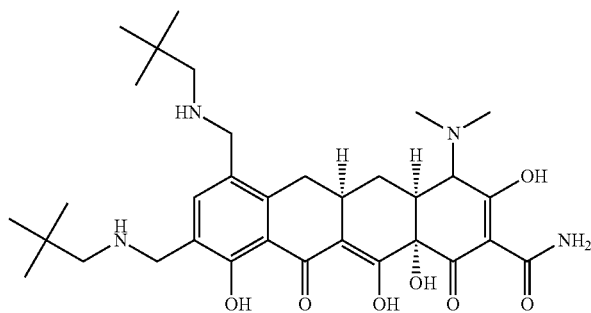
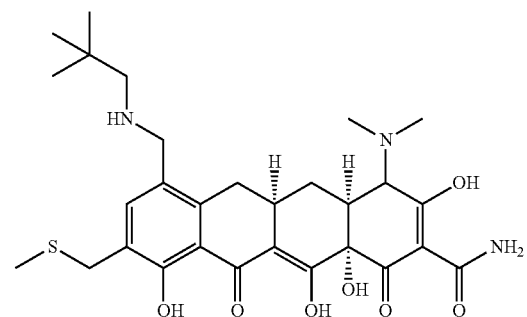
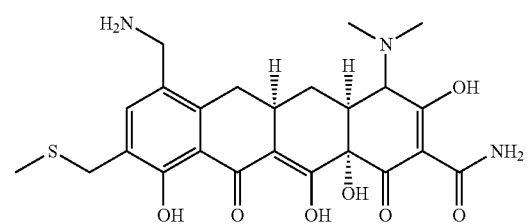
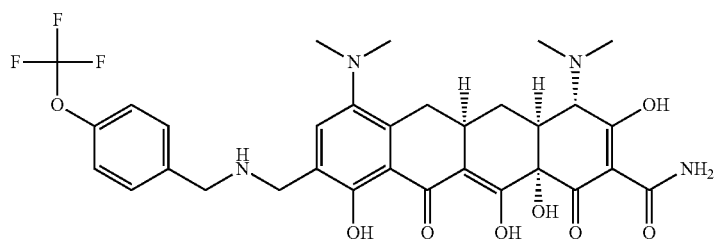

TABLE 2-continued
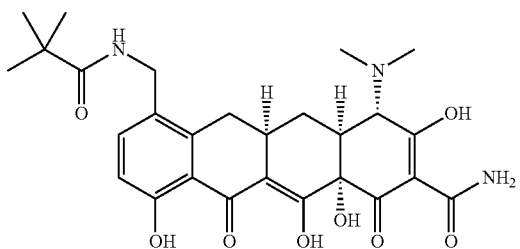
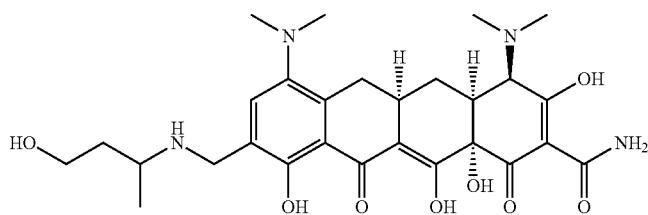
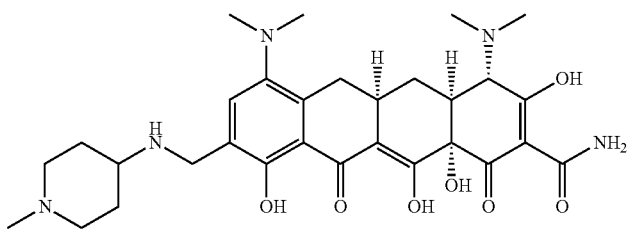
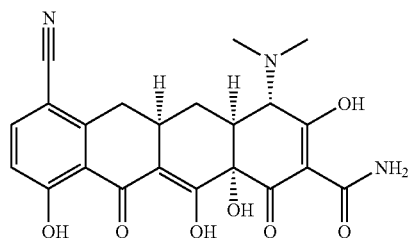
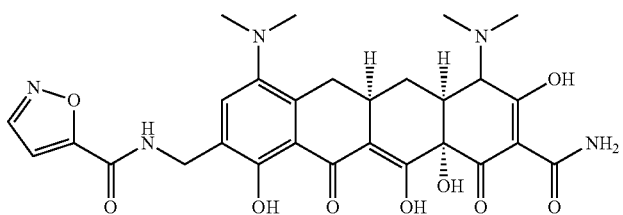
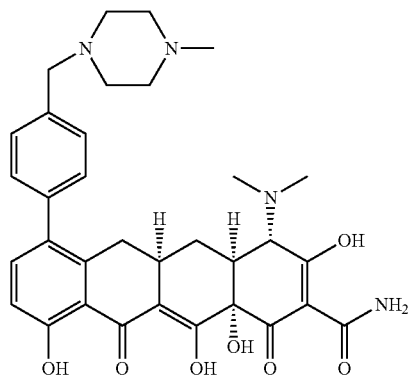

TABLE 2-continued
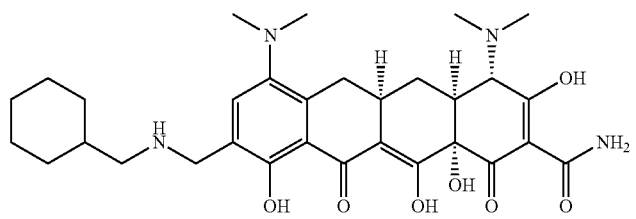
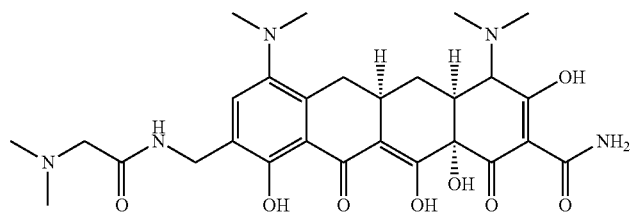
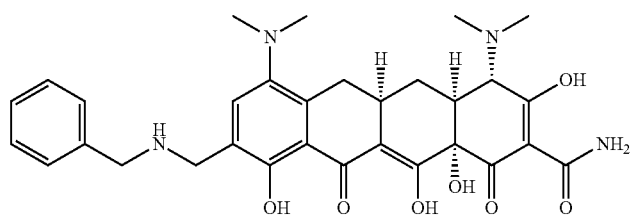
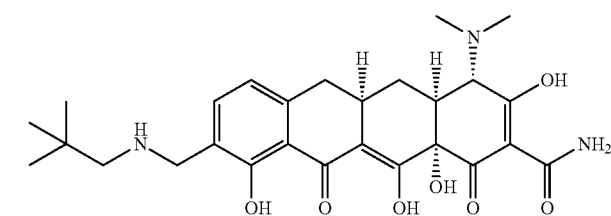
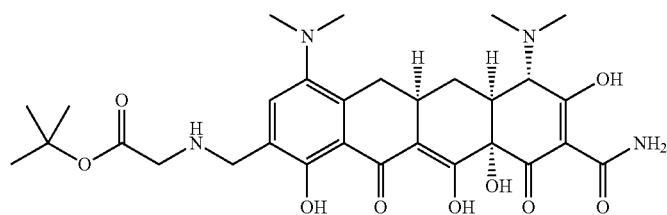
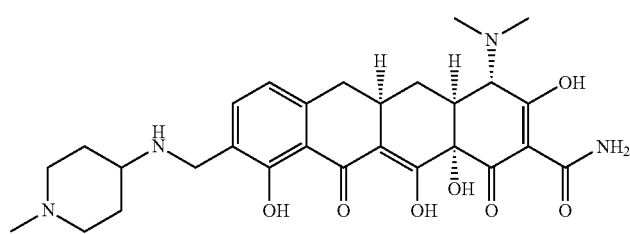
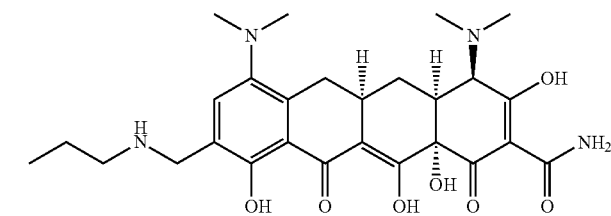

TABLE 2-continued
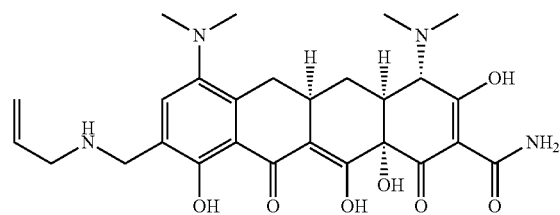
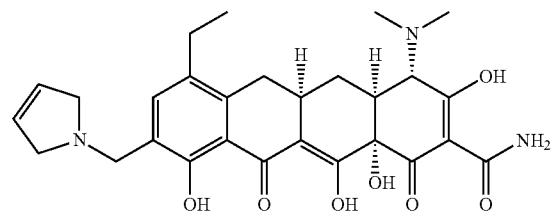
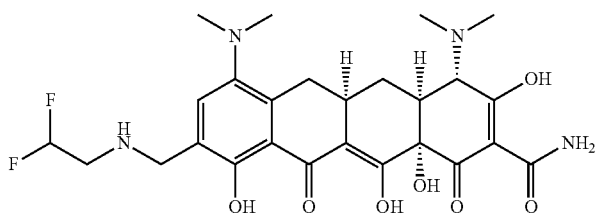
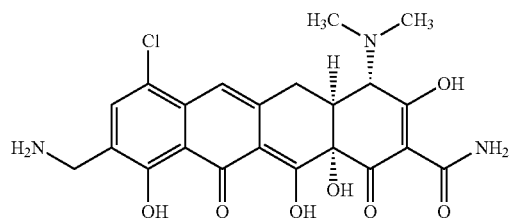
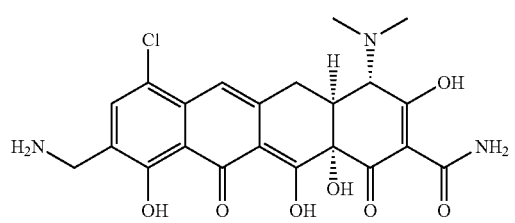
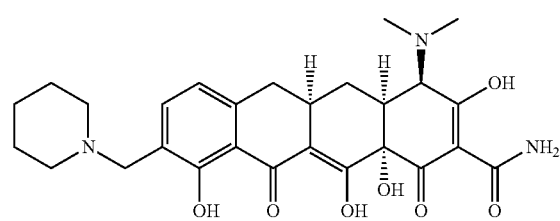
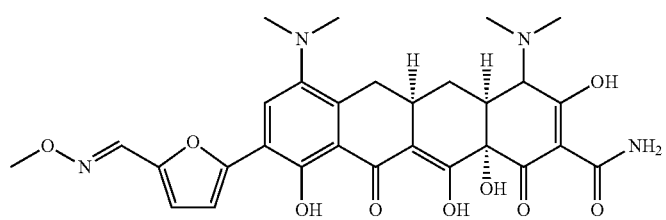

TABLE 2-continued
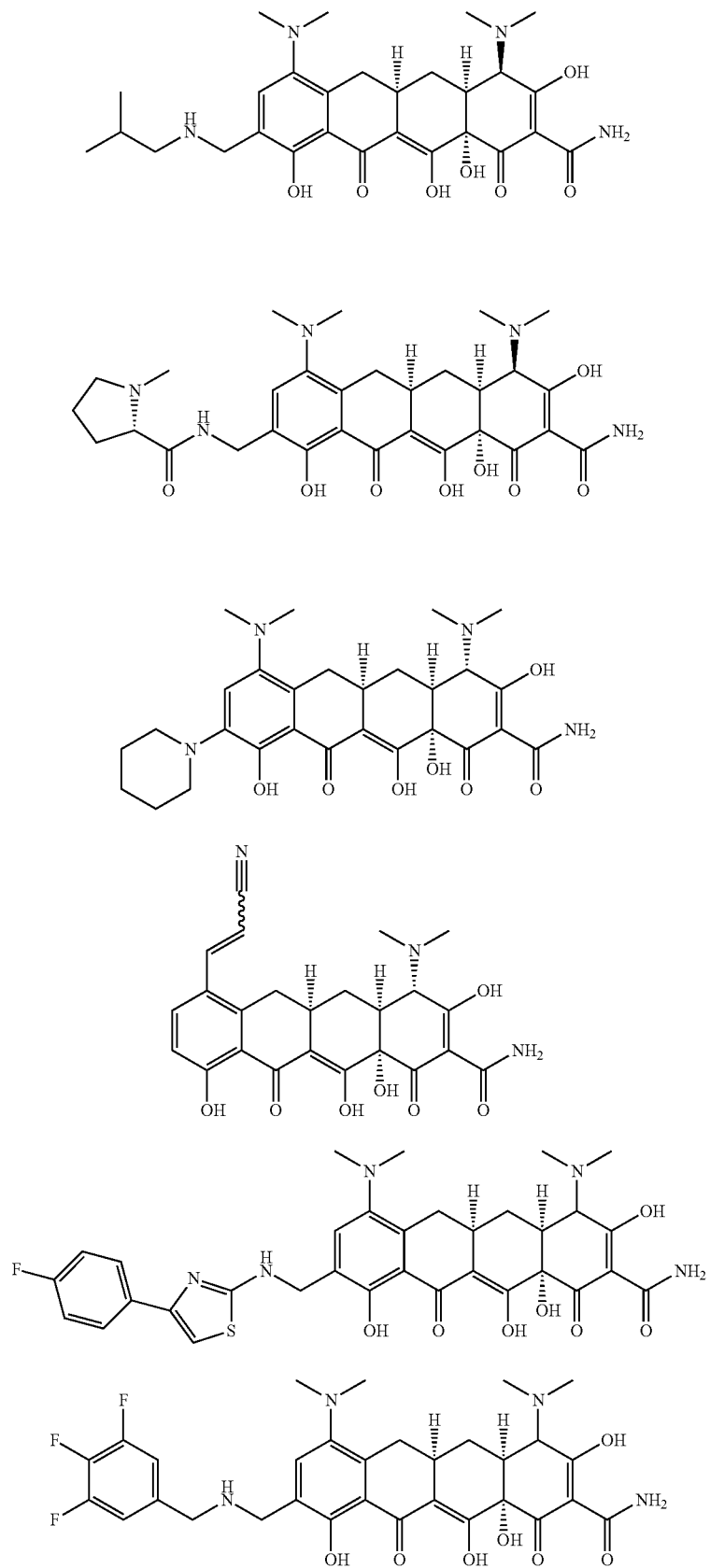

TABLE 2-continued
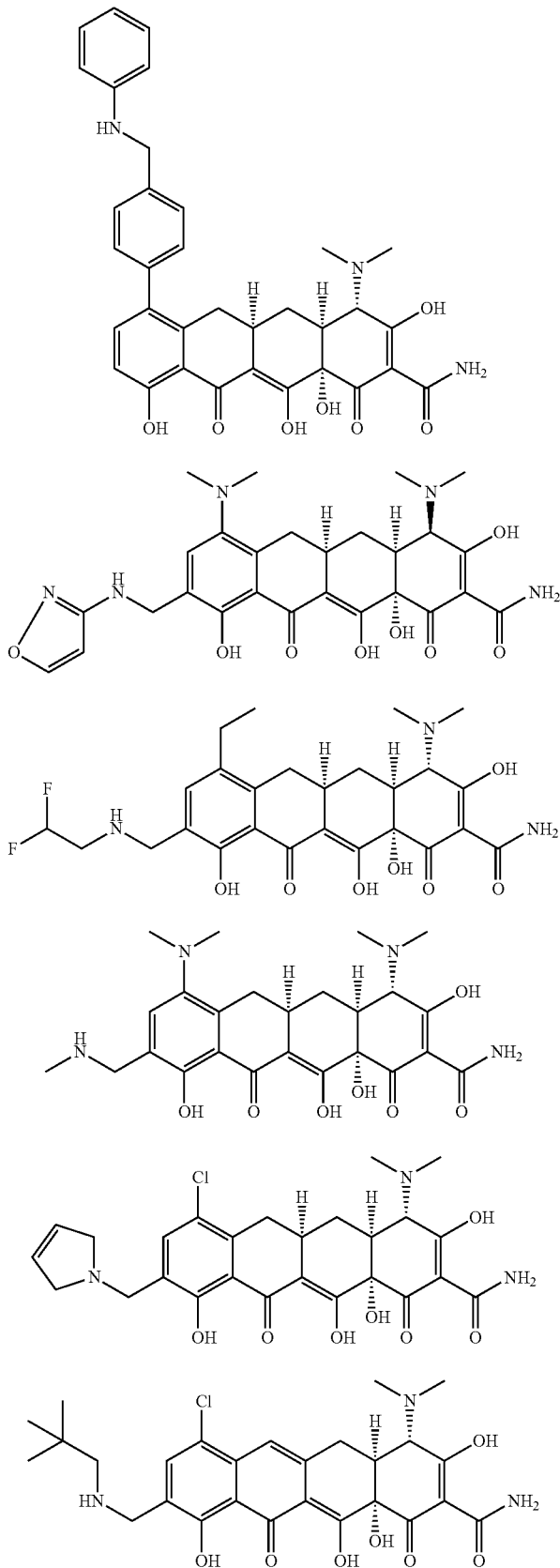

TABLE 2-continued
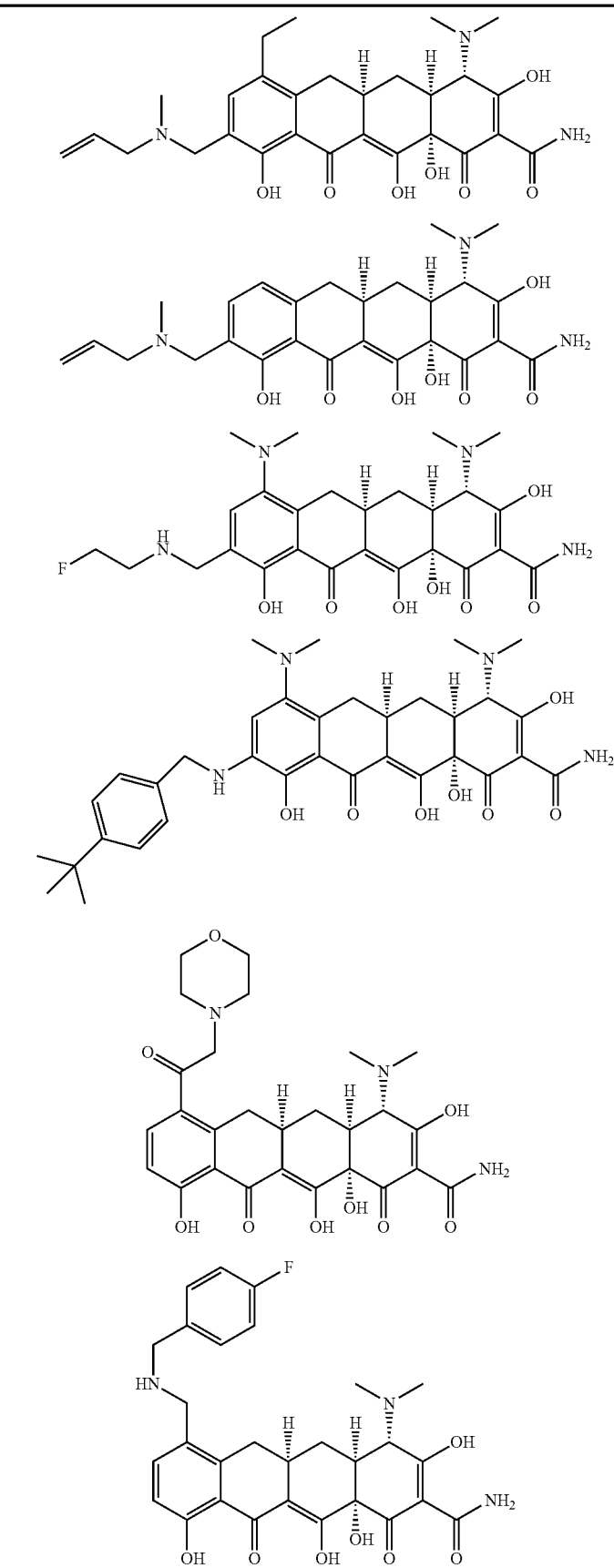

TABLE 2-continued
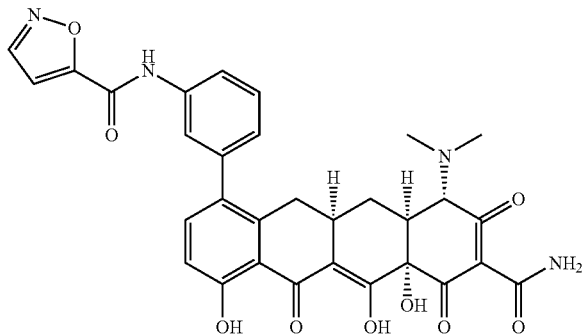
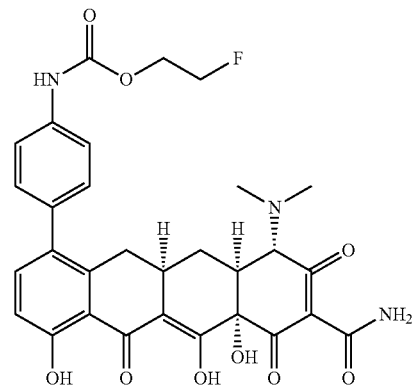
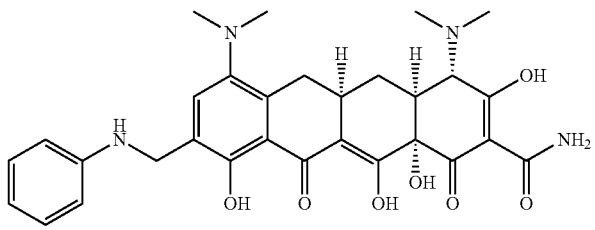
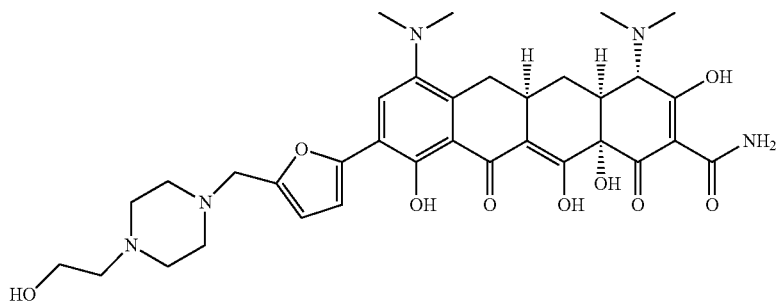
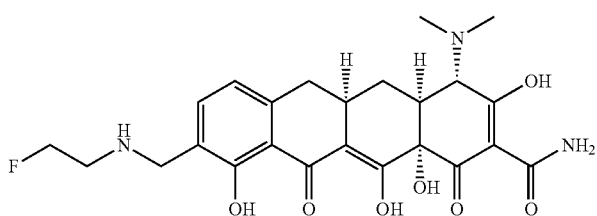

TABLE 2-continued
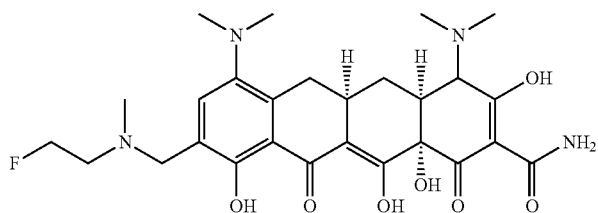
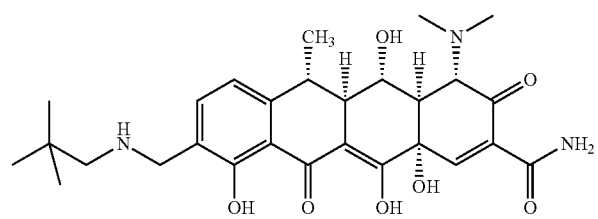
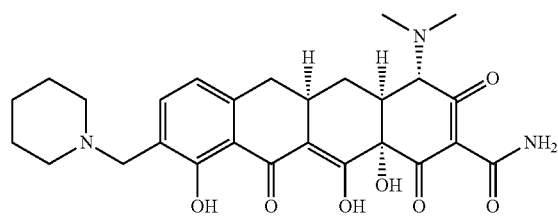
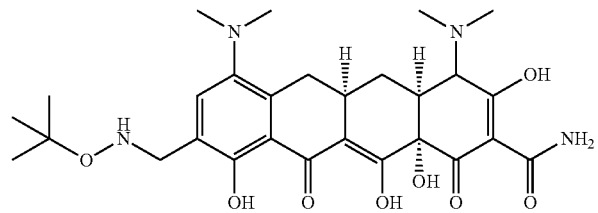
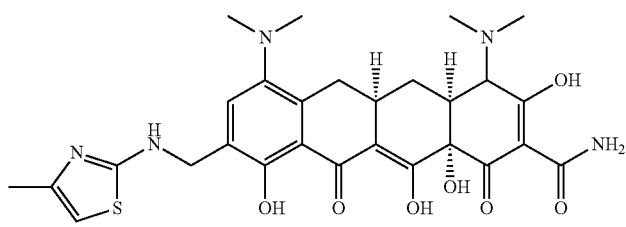
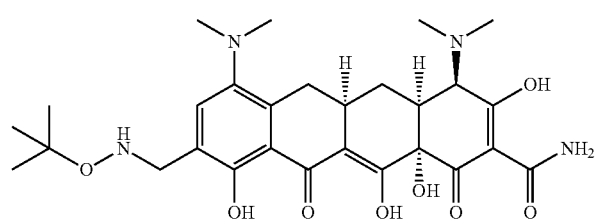

TABLE 2-continued
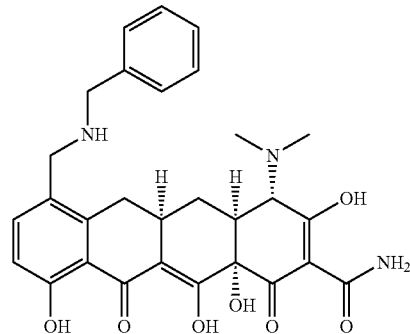
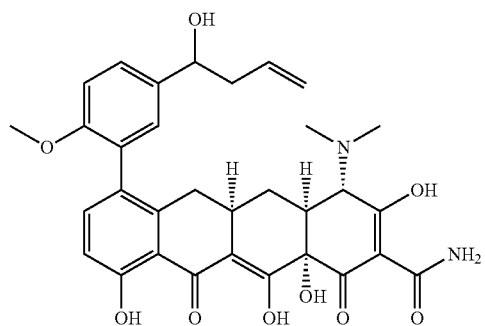
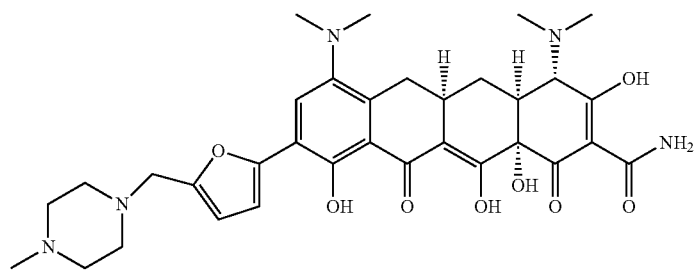
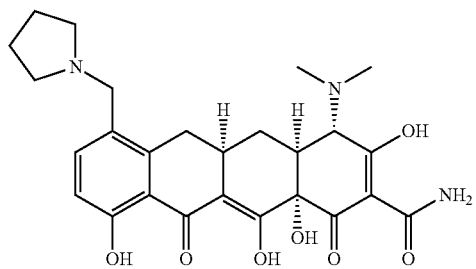
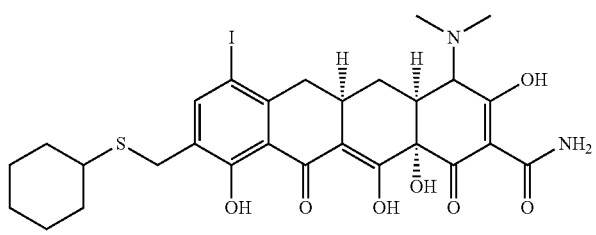

TABLE 2-continued
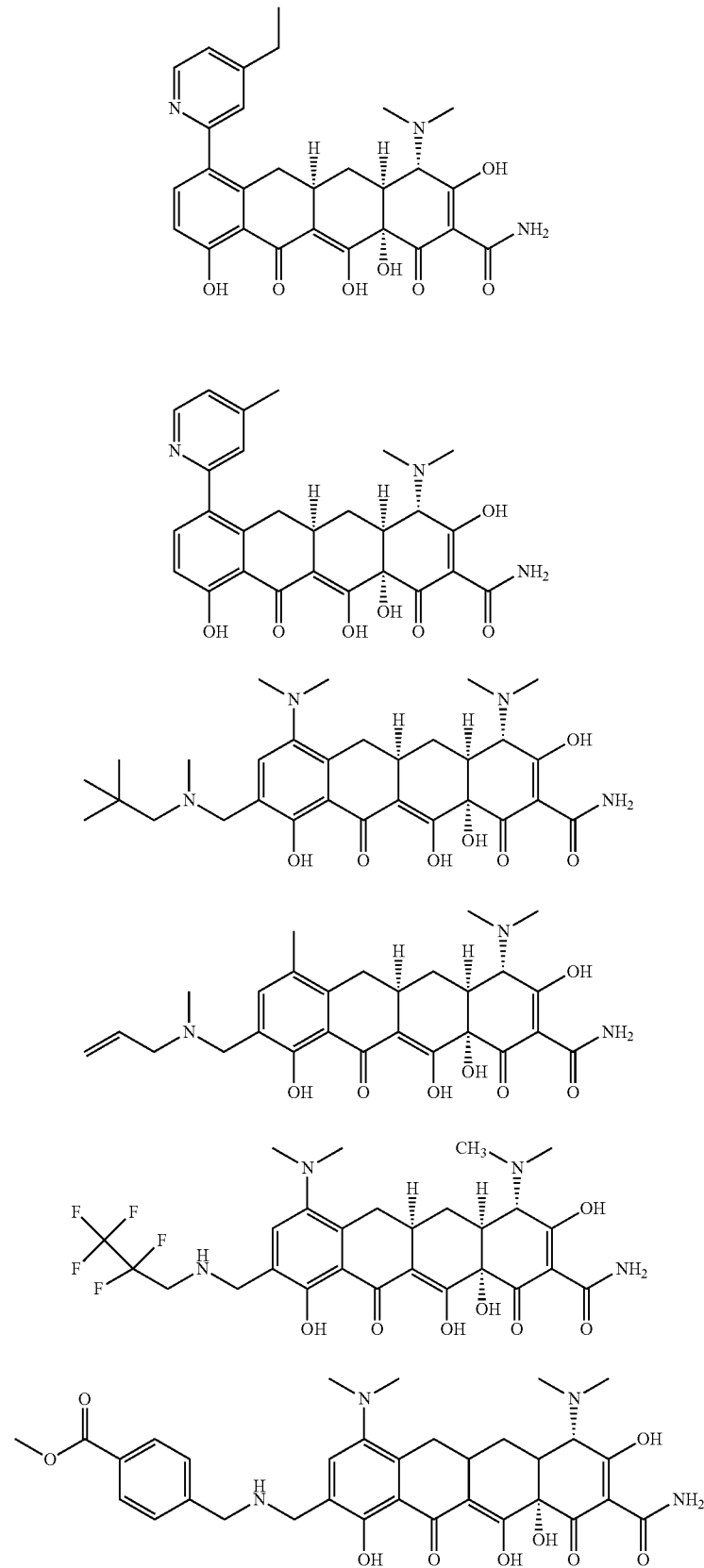

TABLE 2-continued
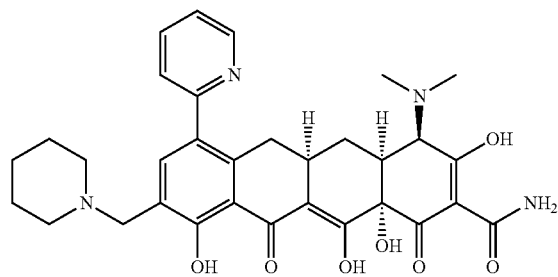
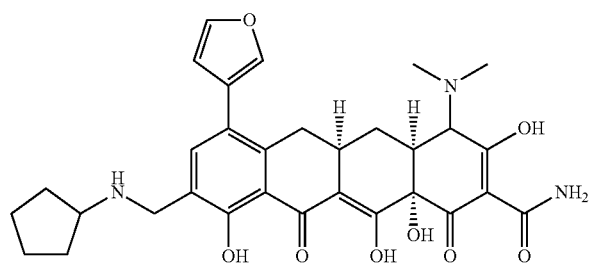
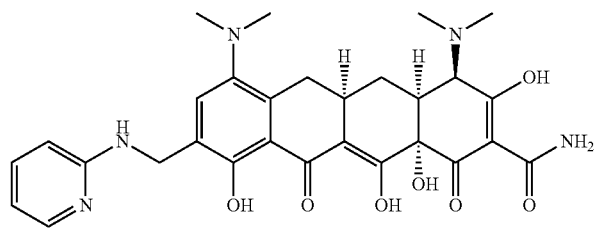
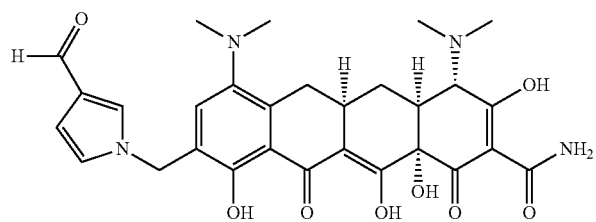
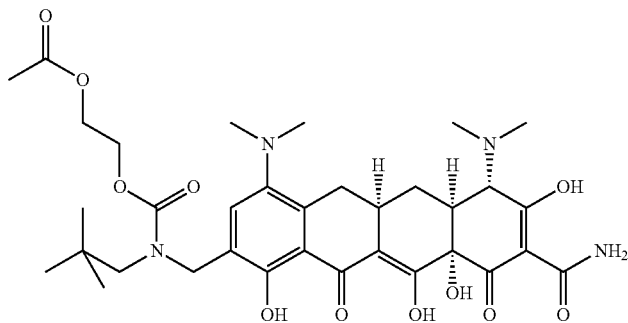

TABLE 2-continued
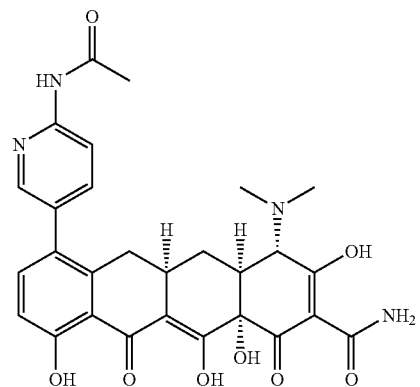
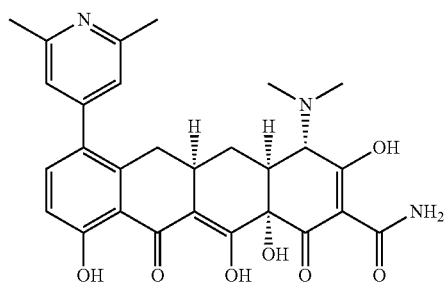
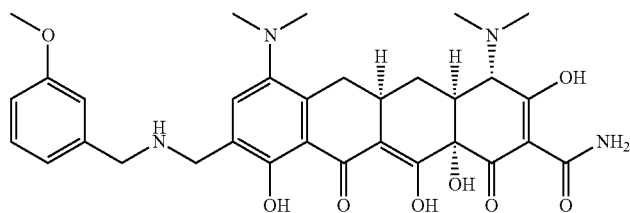
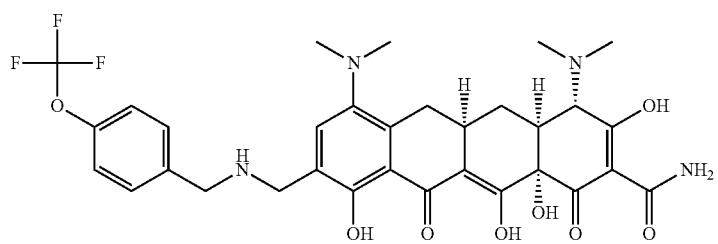
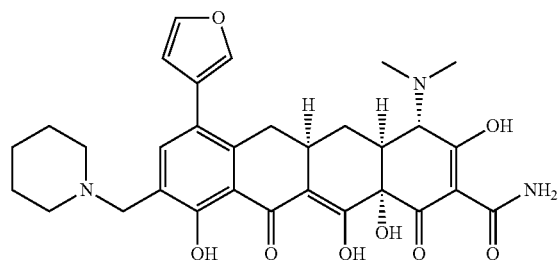

TABLE 2-continued
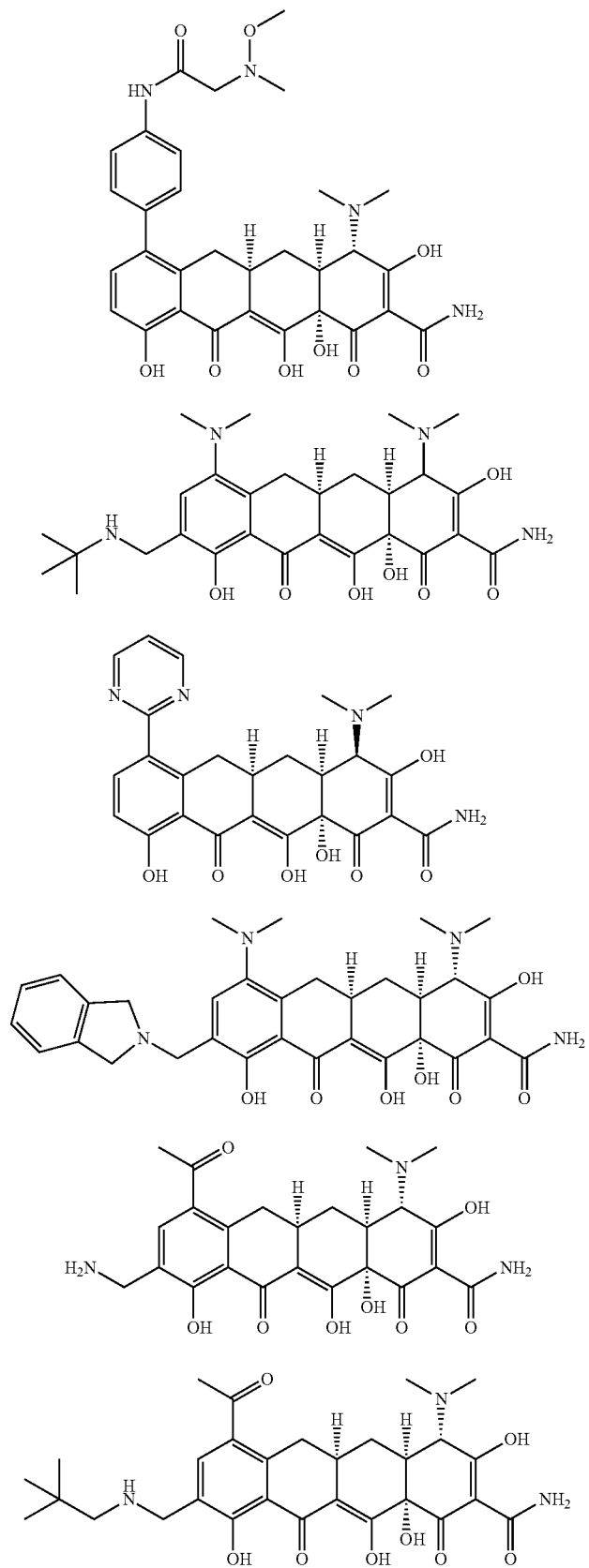

TABLE 2-continued
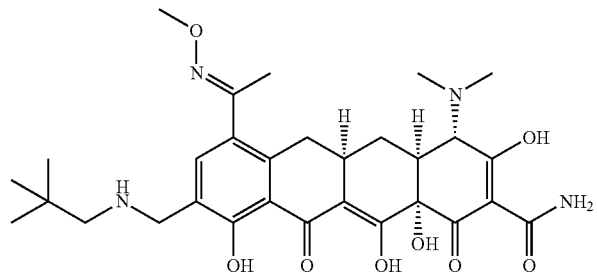
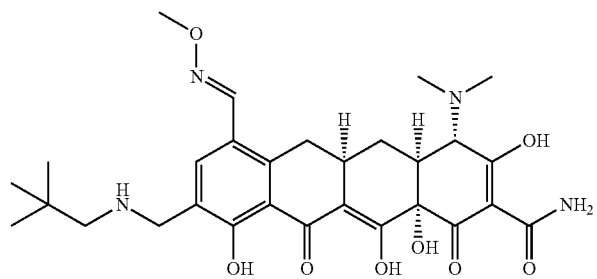
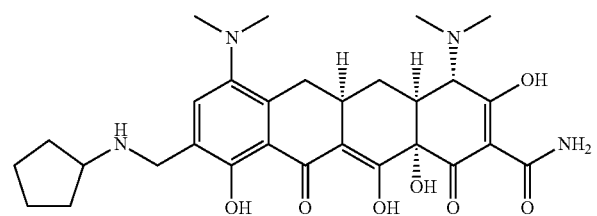
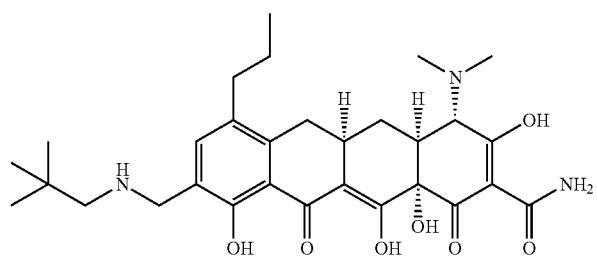
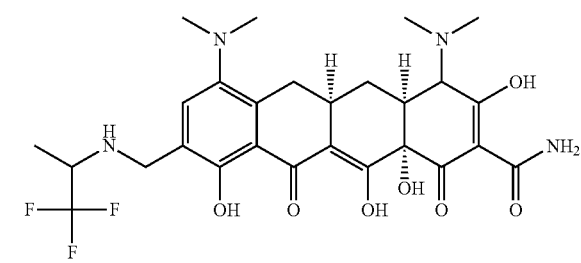
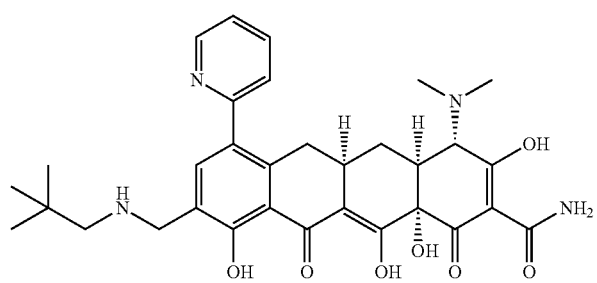

TABLE 2-continued
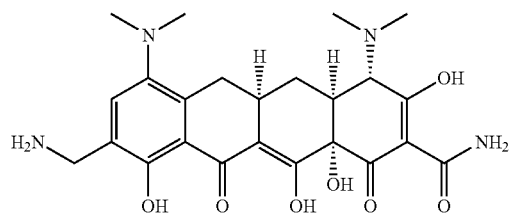
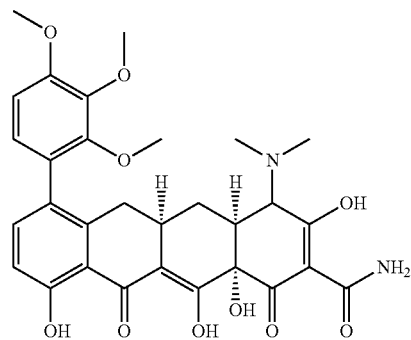
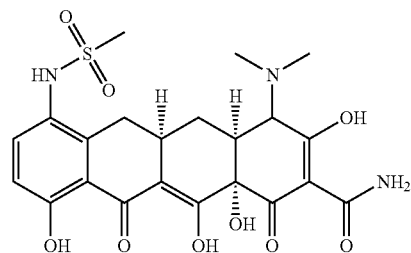
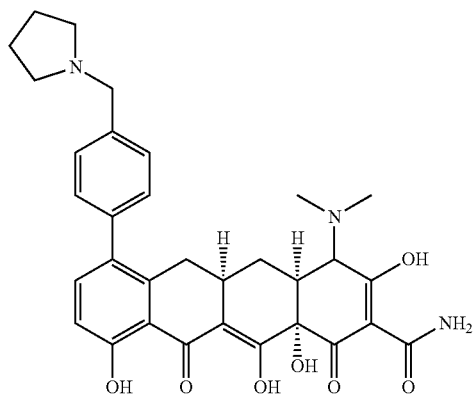
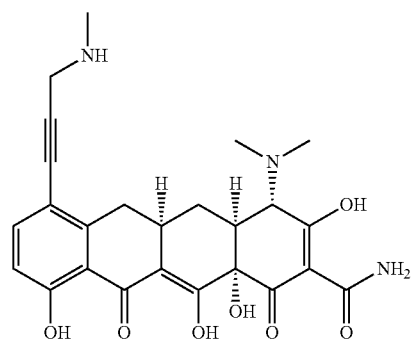

TABLE 2-continued
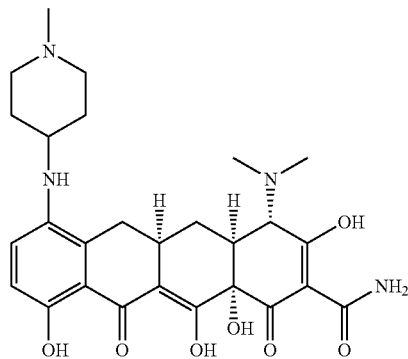
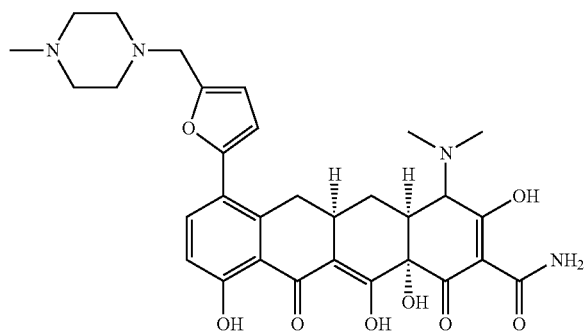
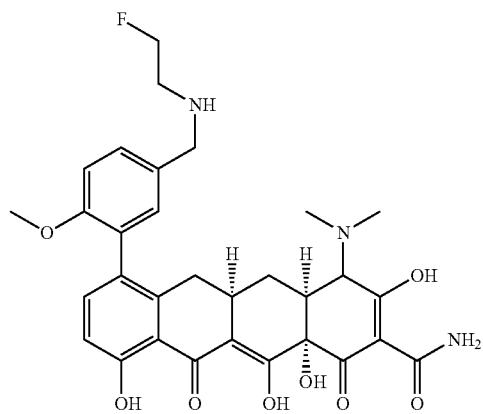
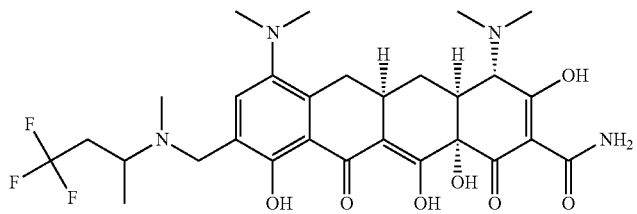
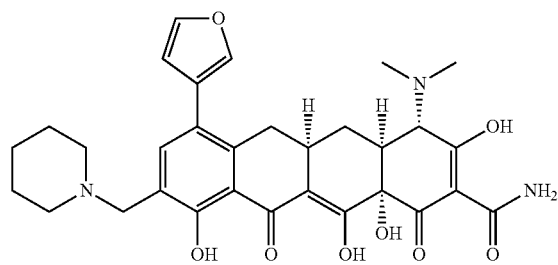

TABLE 2-continued
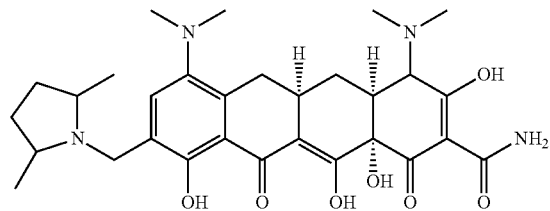
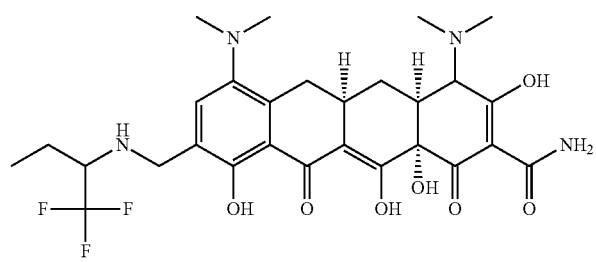
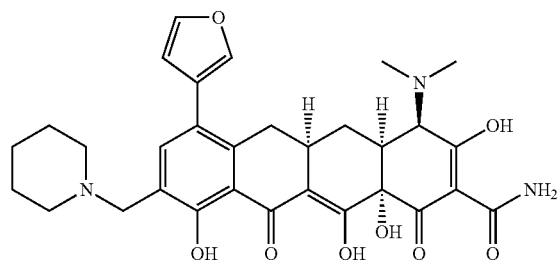
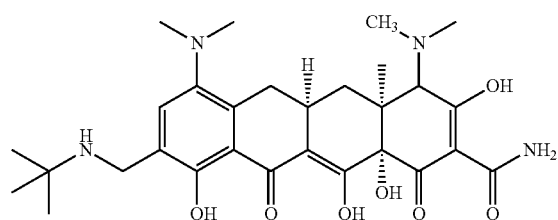
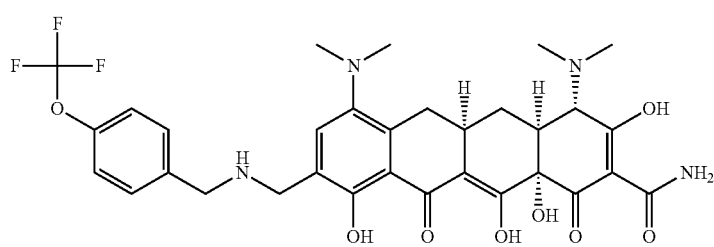
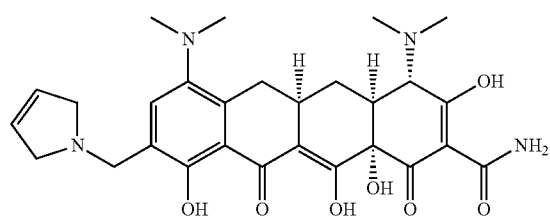

TABLE 2-continued
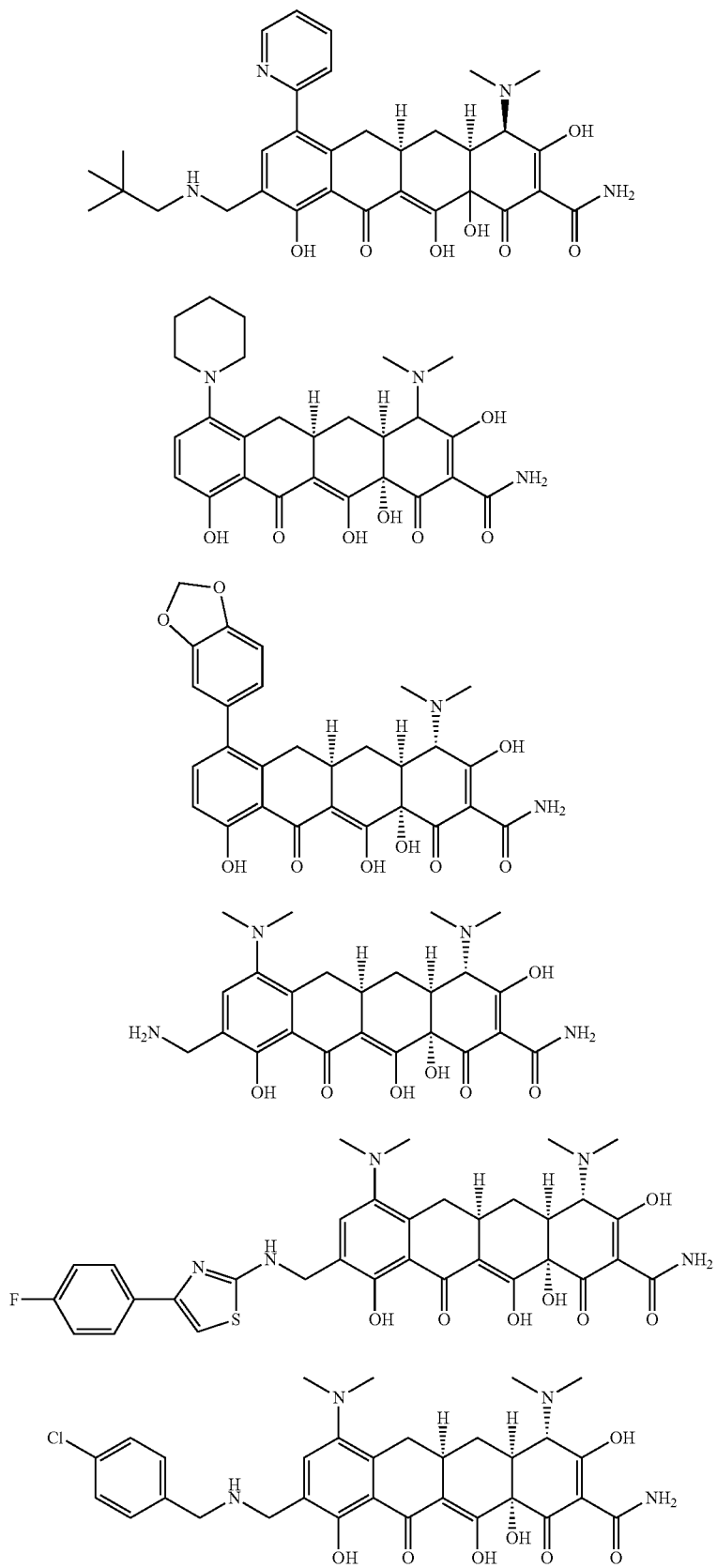

TABLE 2-continued
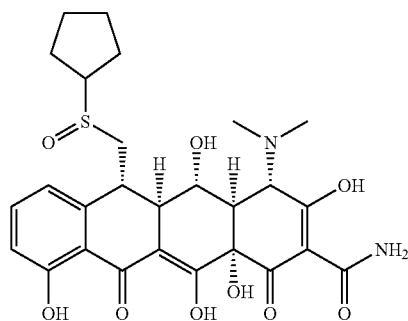
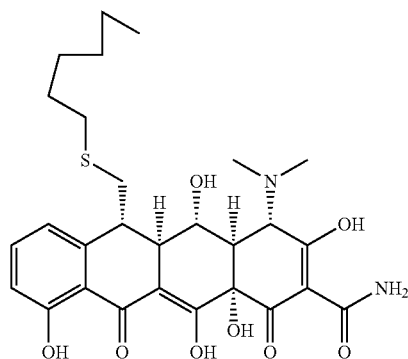
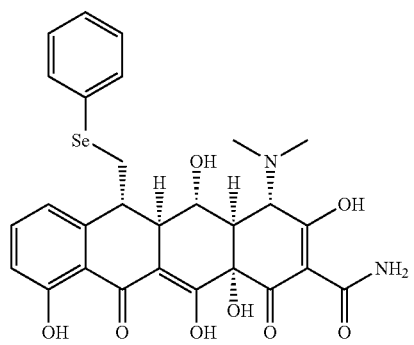
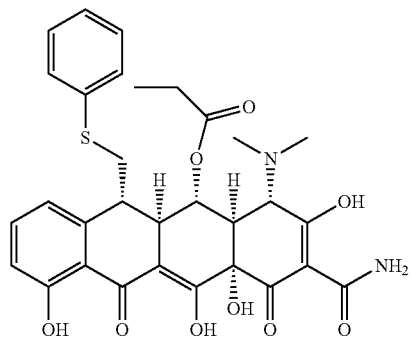

TABLE 2-continued
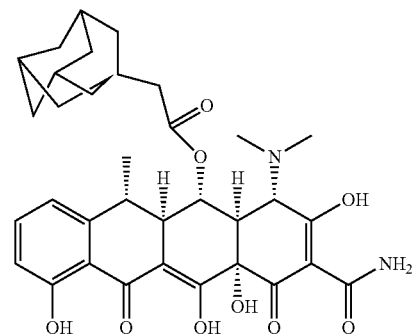
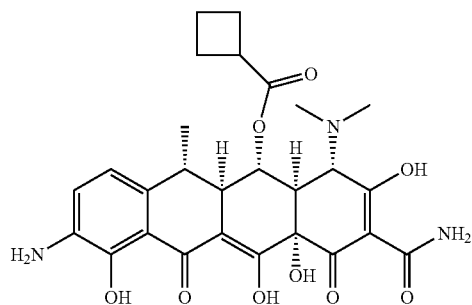
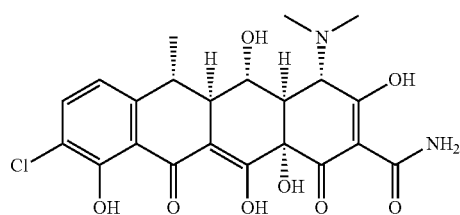
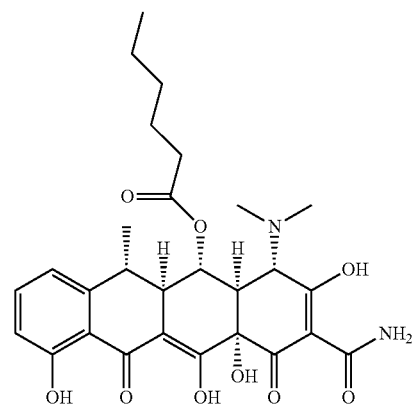
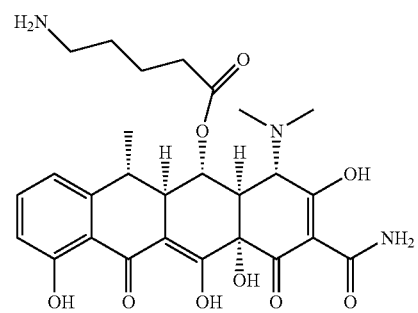

TABLE 2-continued
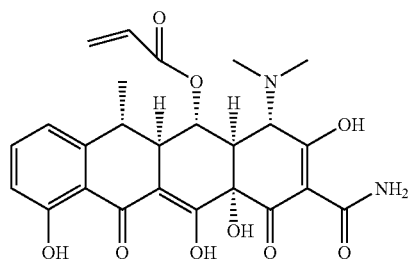
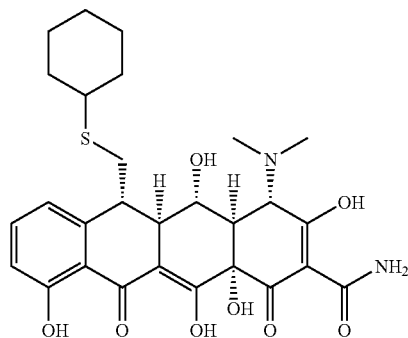
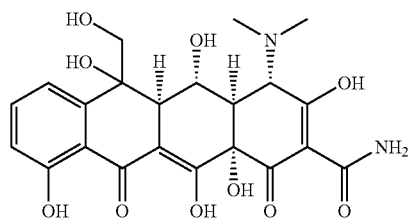
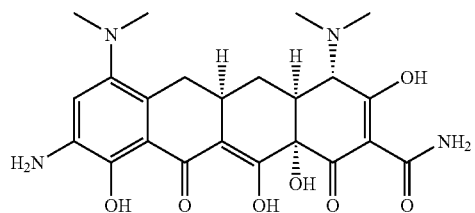
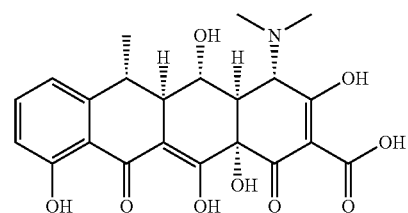
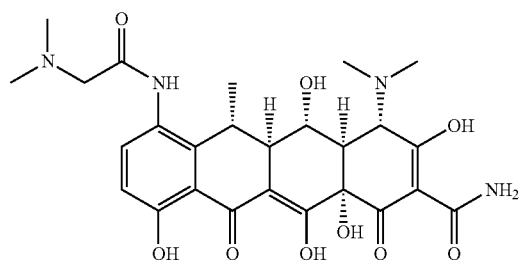

TABLE 2-continued
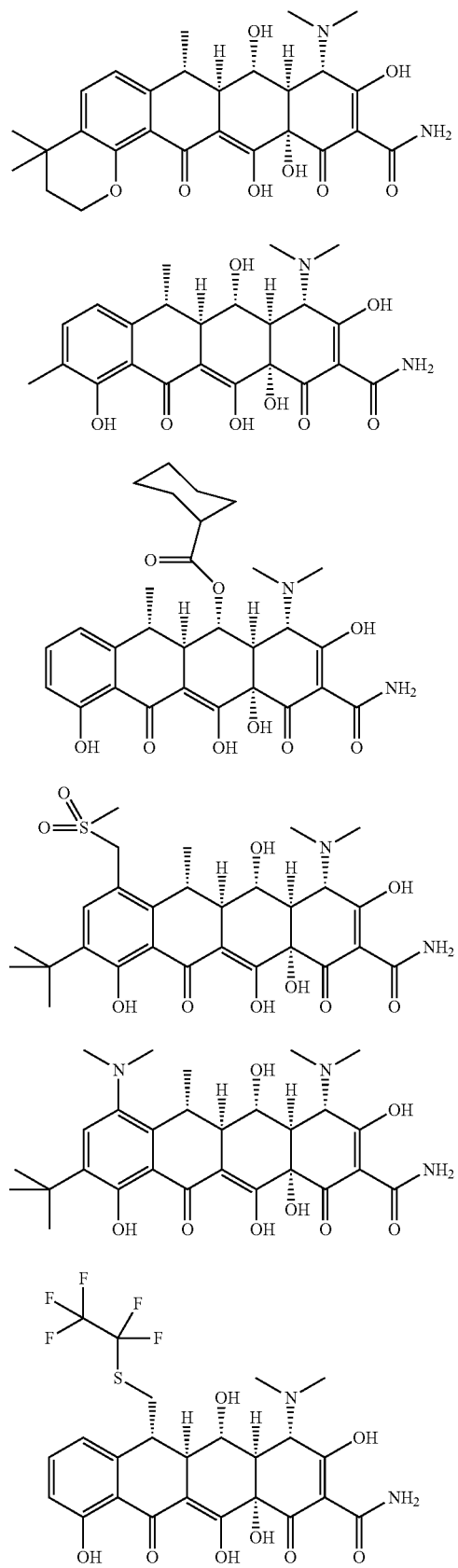

TABLE 2-continued
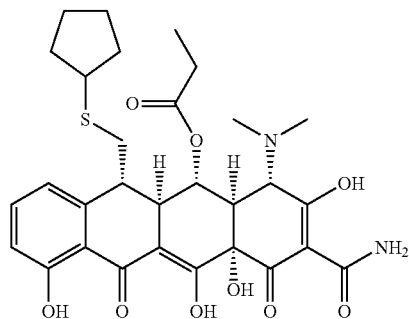
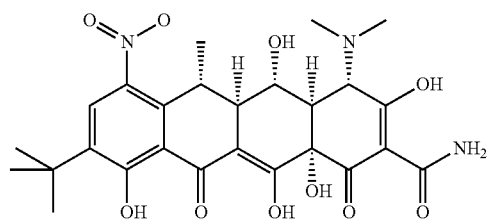
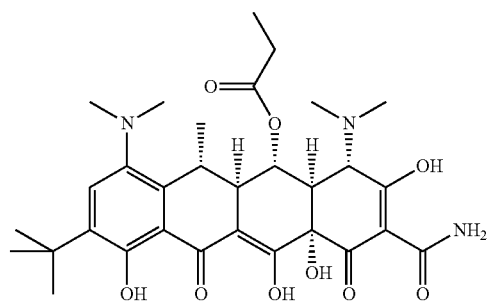
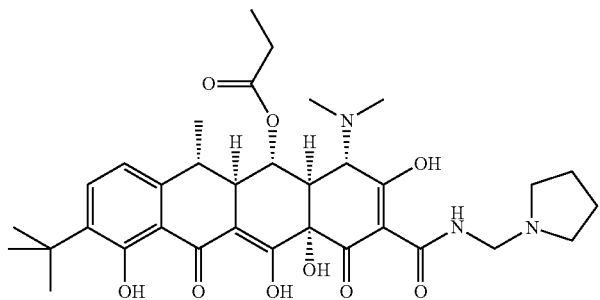
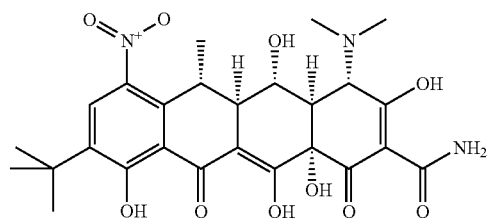

TABLE 2-continued
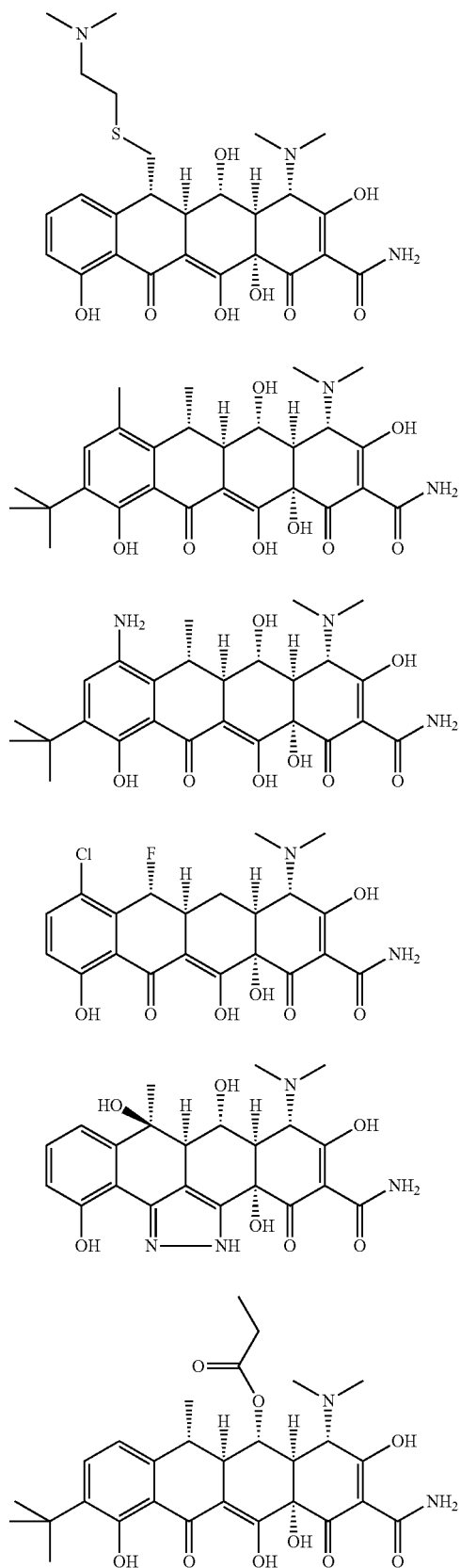

TABLE 2-continued
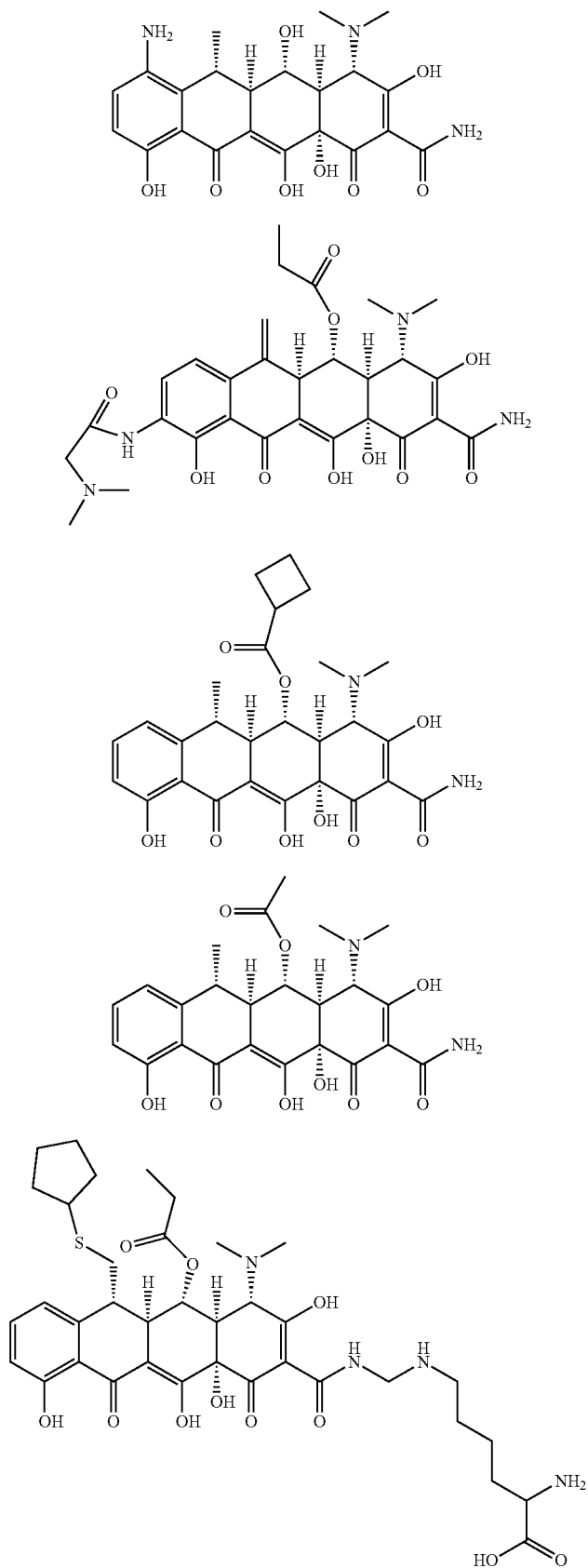

TABLE 2-continued
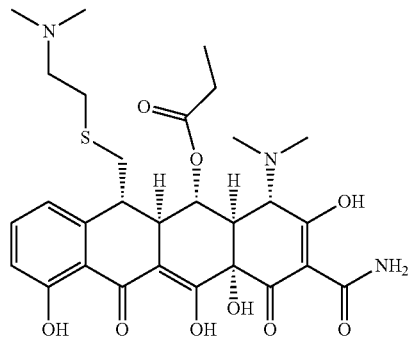
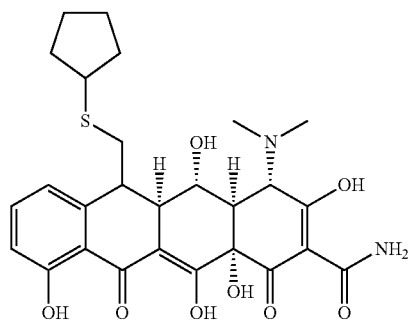
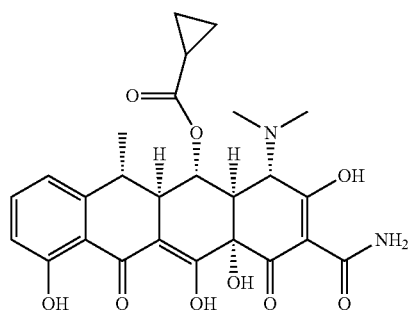
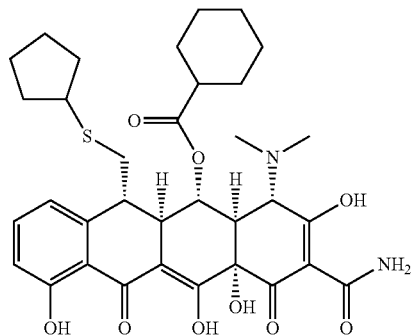
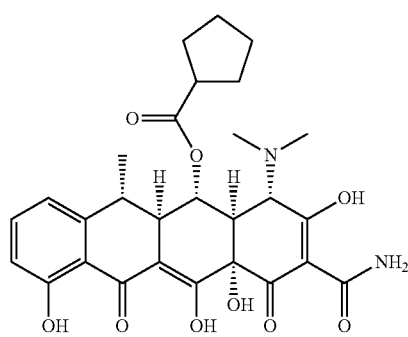

TABLE 2-continued
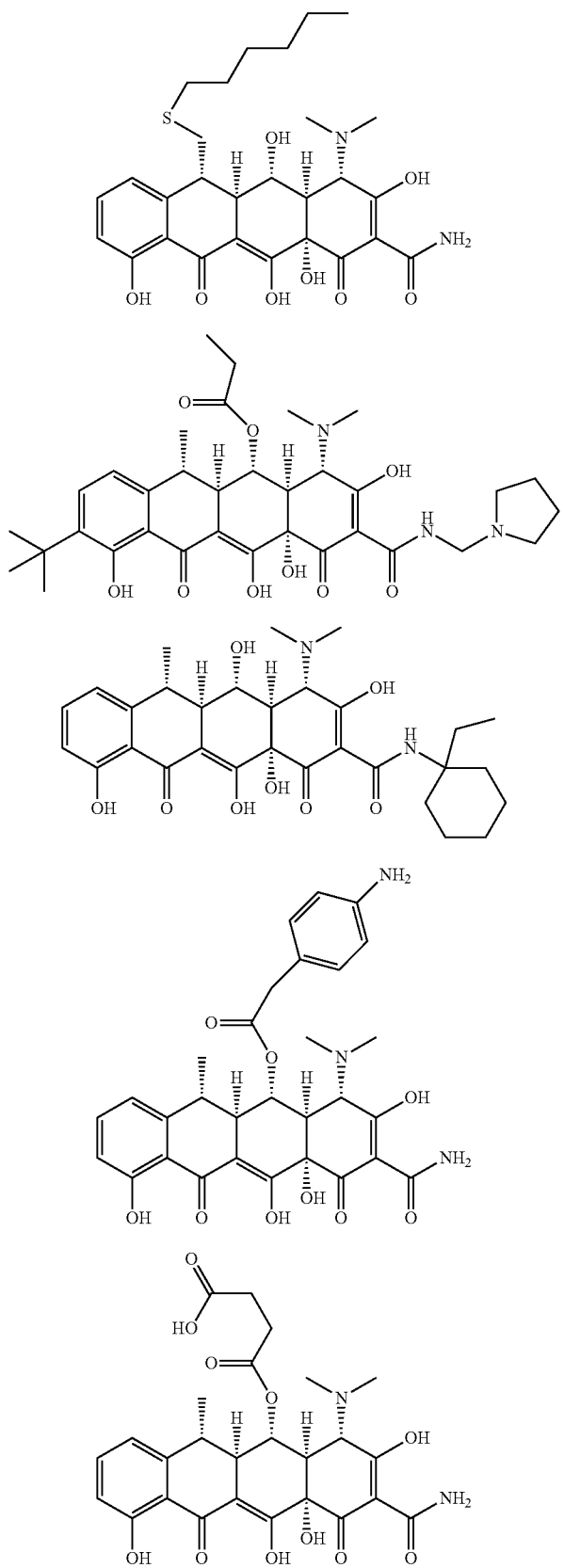

TABLE 2-continued
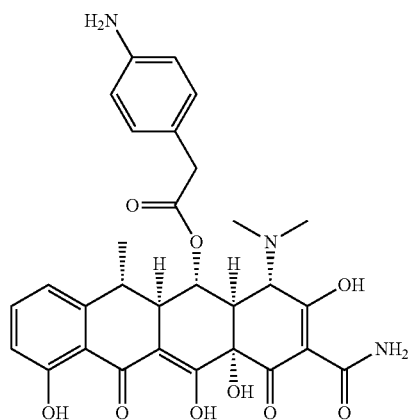
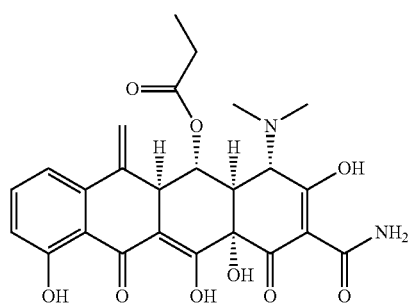
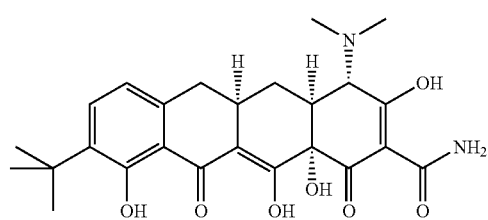
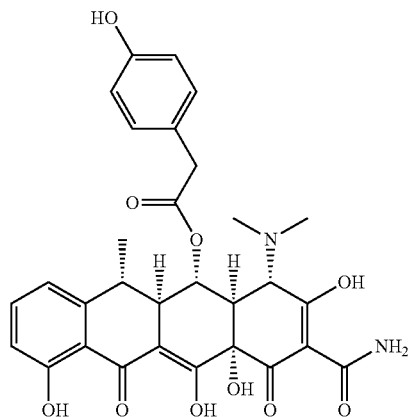

TABLE 2-continued
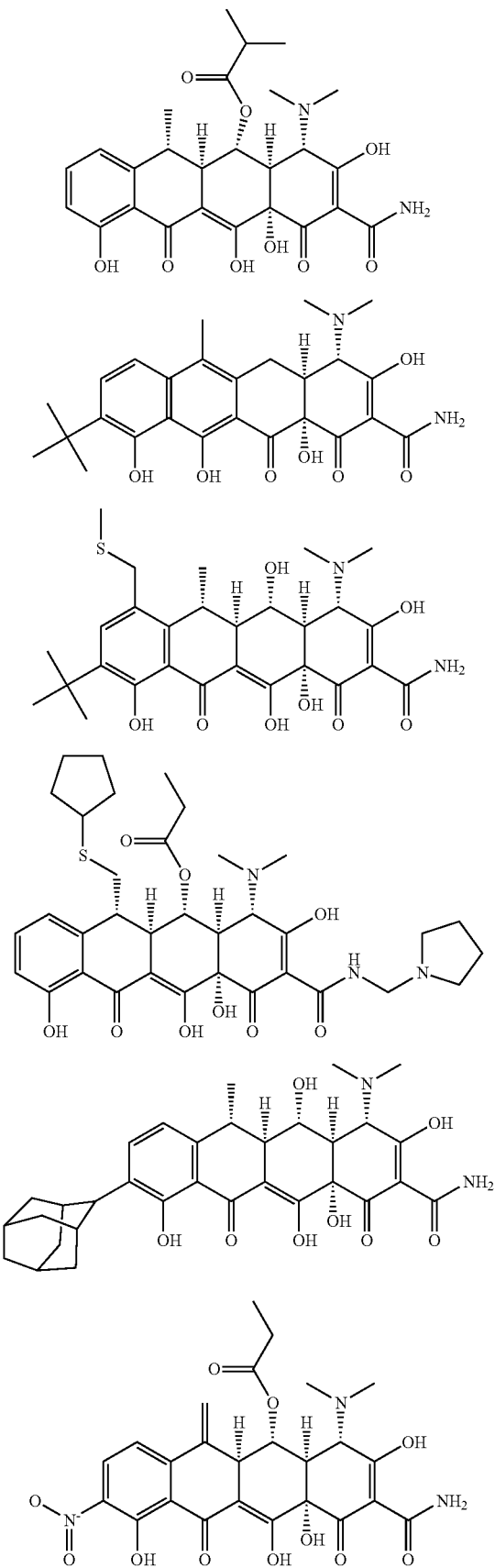

TABLE 2-continued
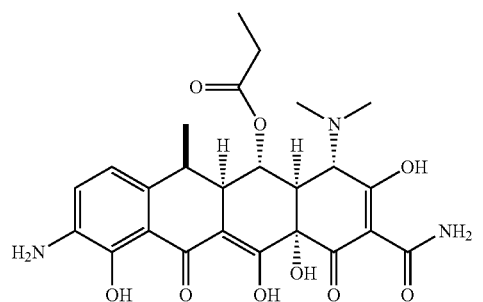
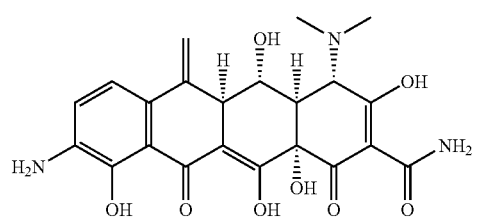
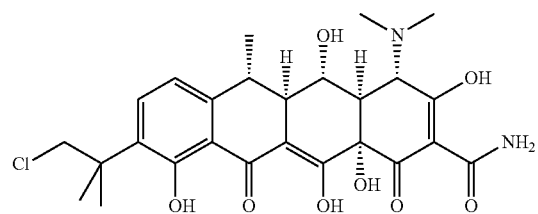
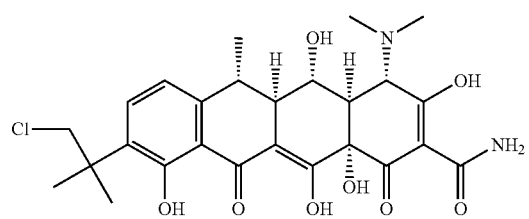
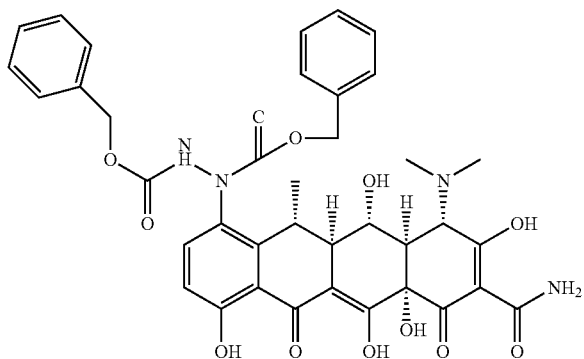
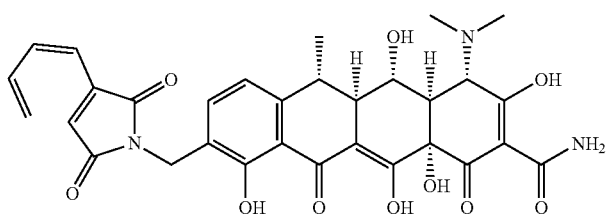

TABLE 2-continued
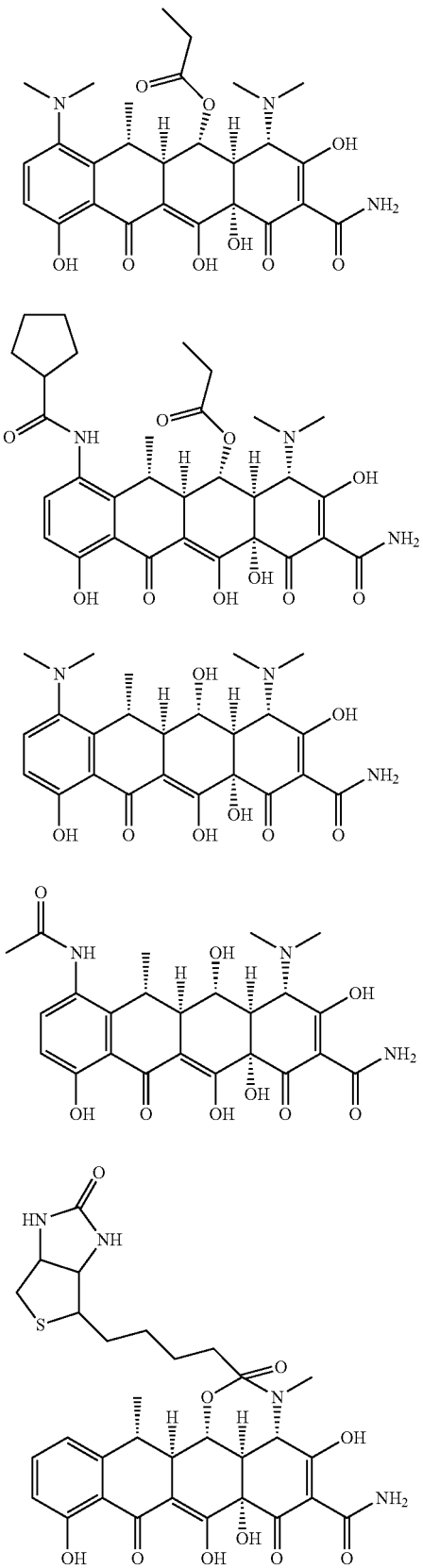

TABLE 2-continued
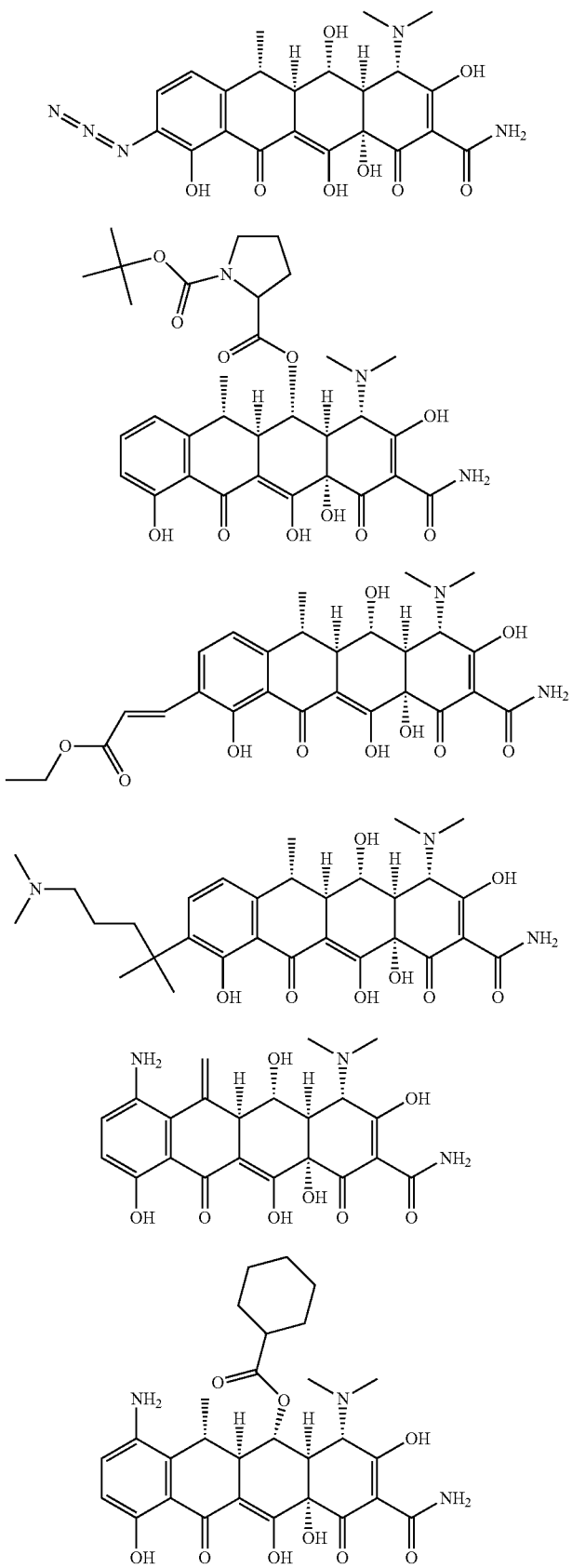

TABLE 2-continued
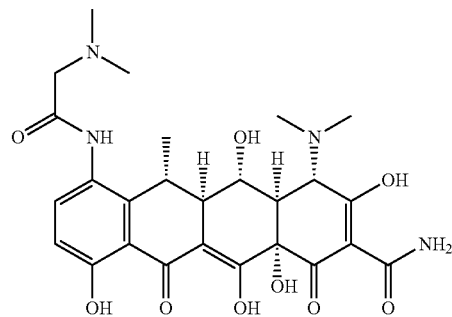
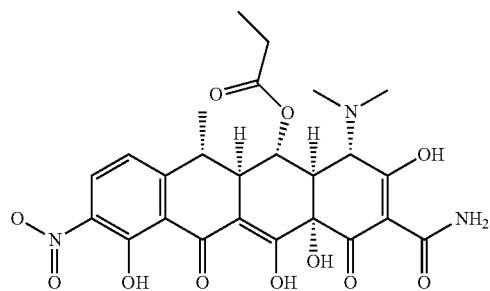
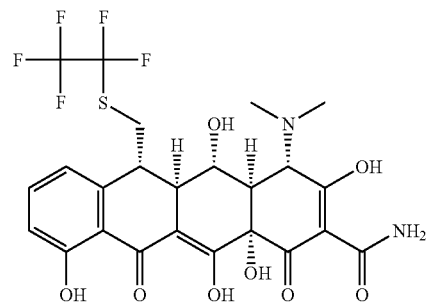
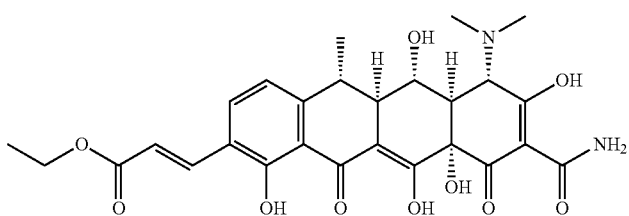
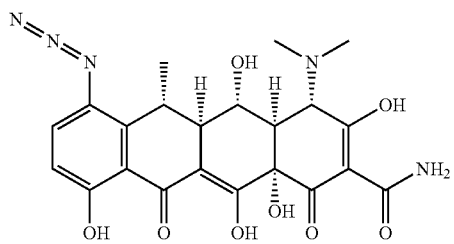
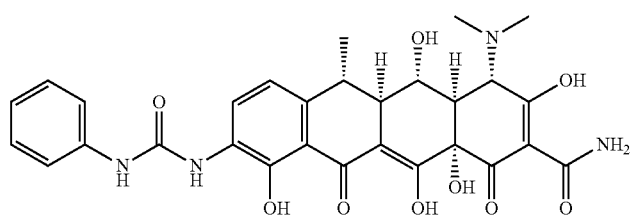

TABLE 2-continued
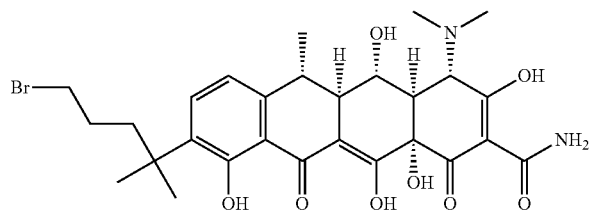
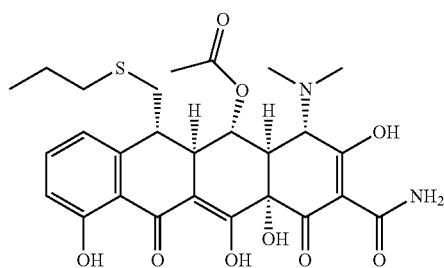
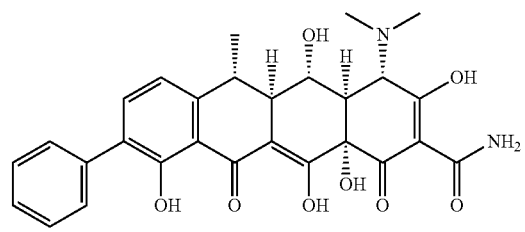
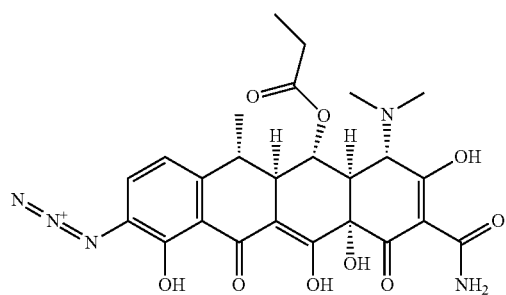
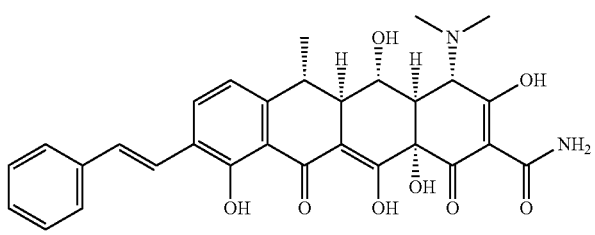
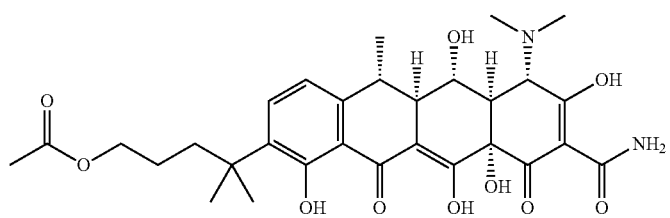

TABLE 2-continued
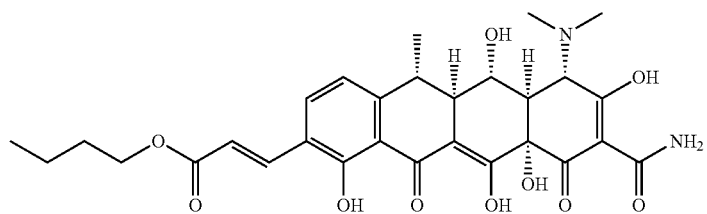
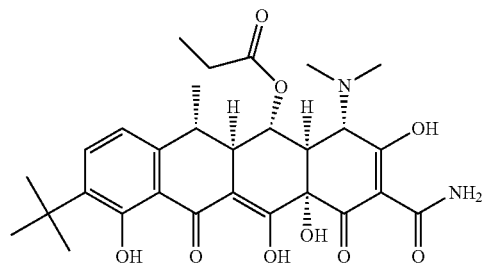
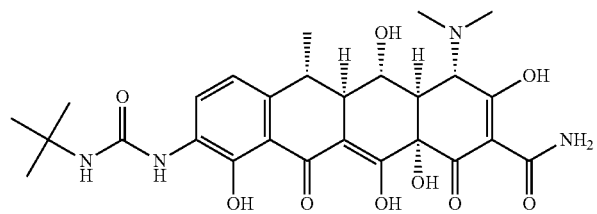
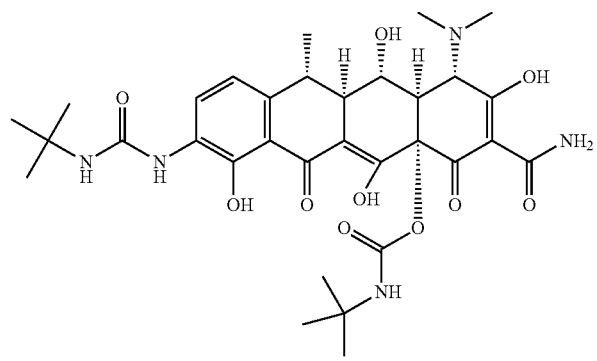
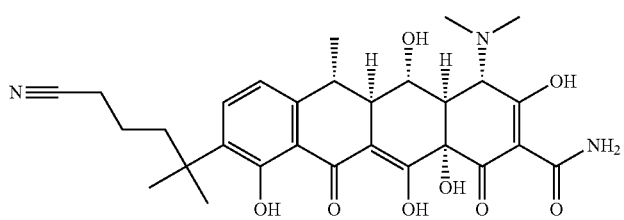
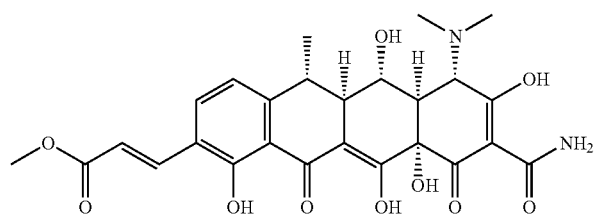

TABLE 2-continued
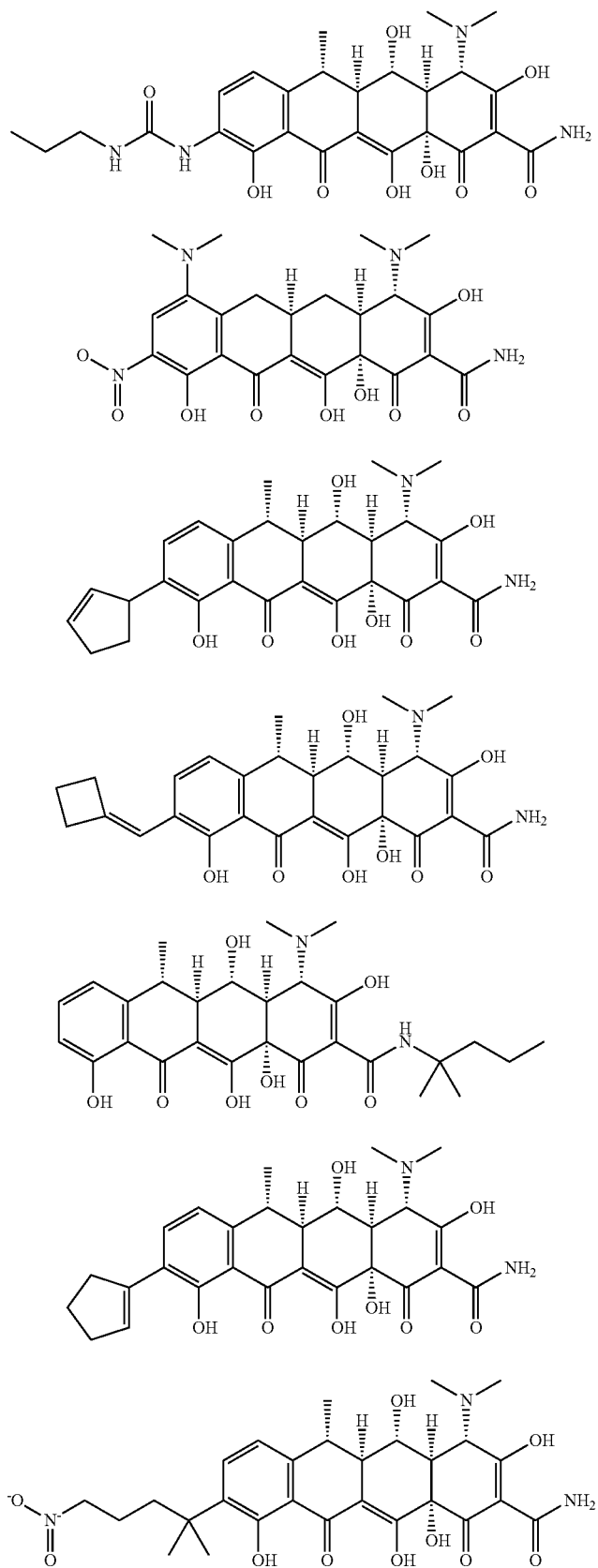

TABLE 2-continued
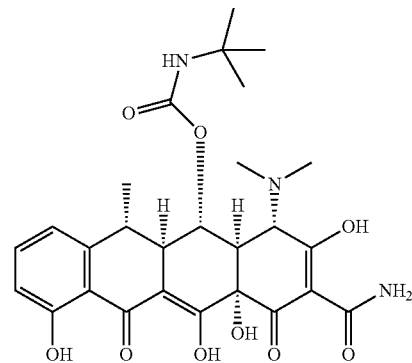
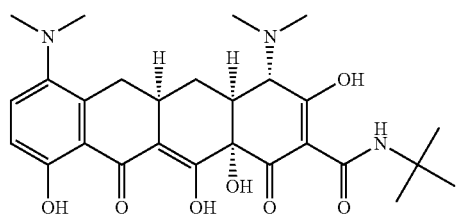
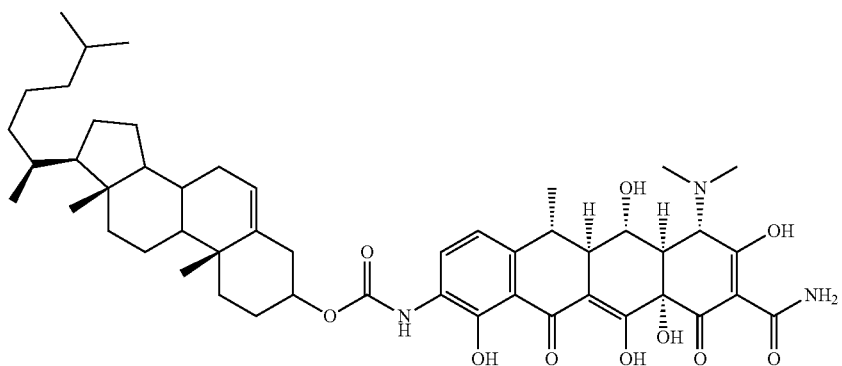
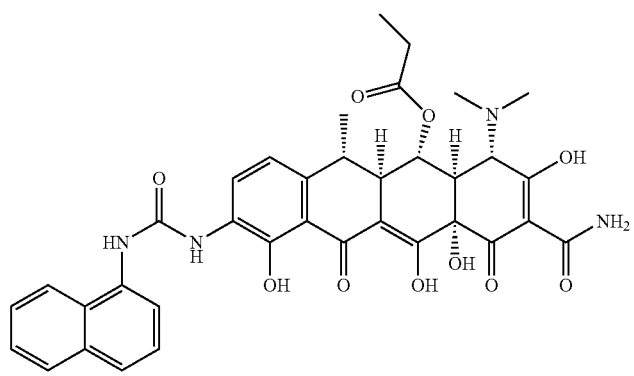

TABLE 2-continued
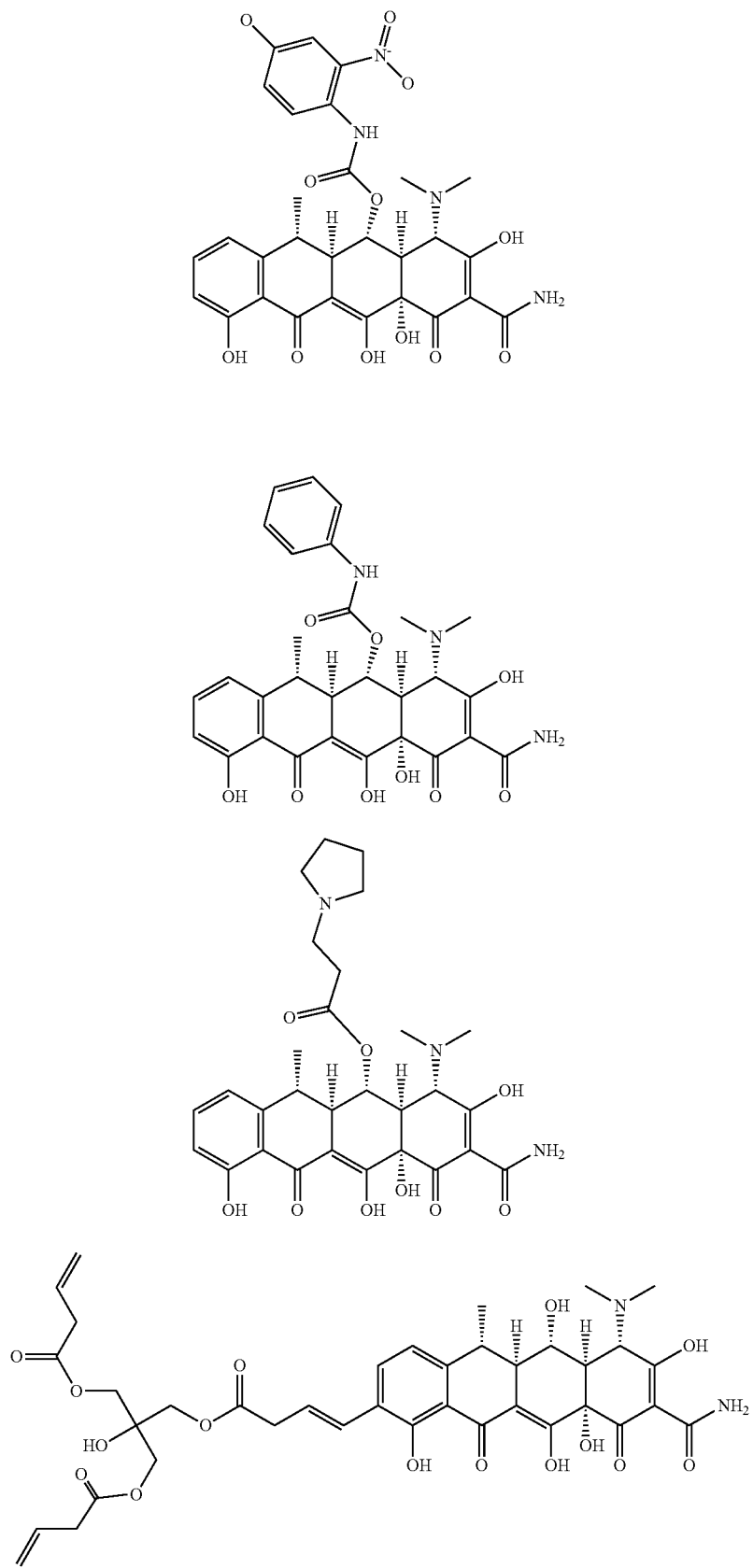

TABLE 2-continued
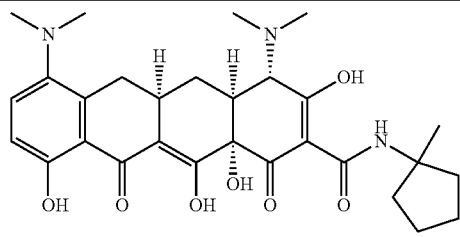
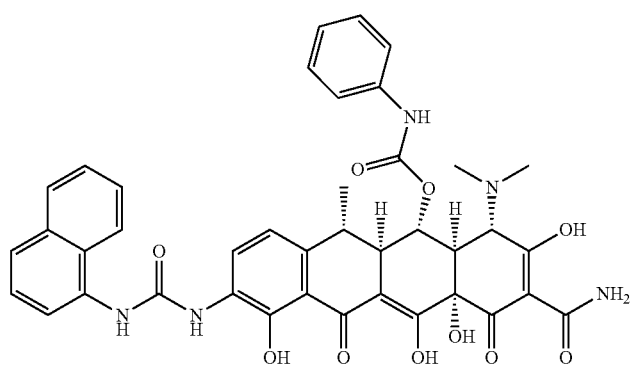
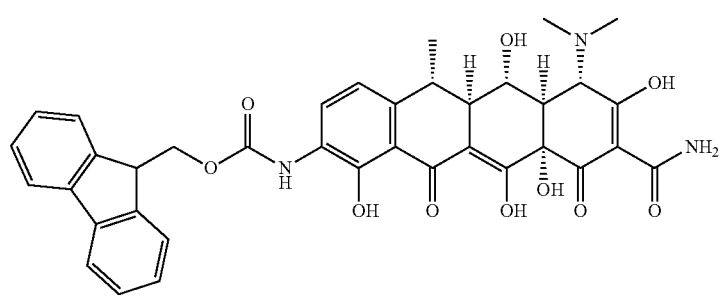
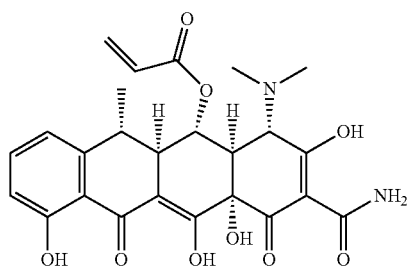
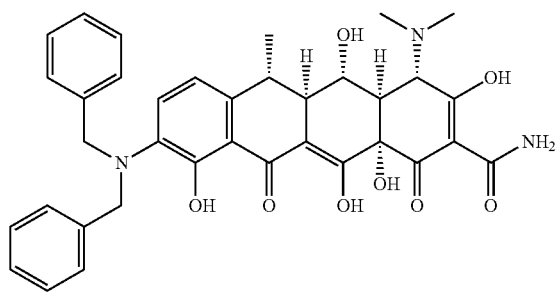

TABLE 2-continued
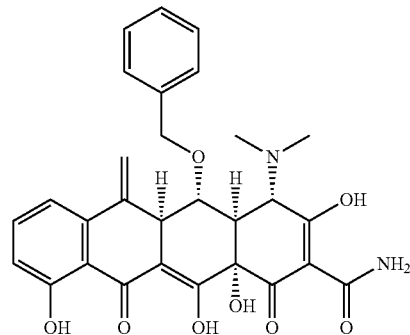
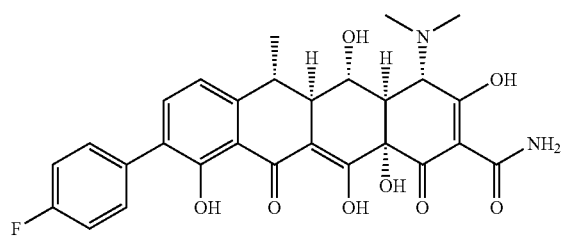
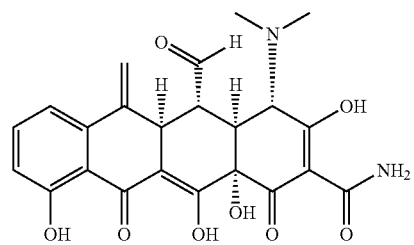
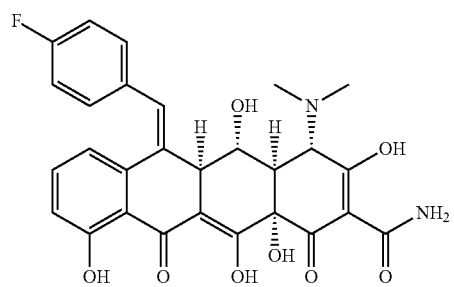
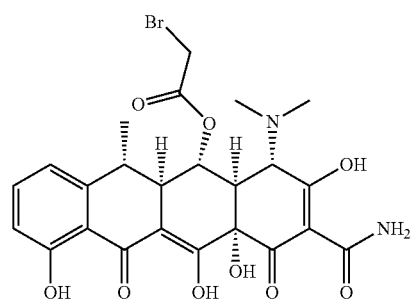

TABLE 2-continued
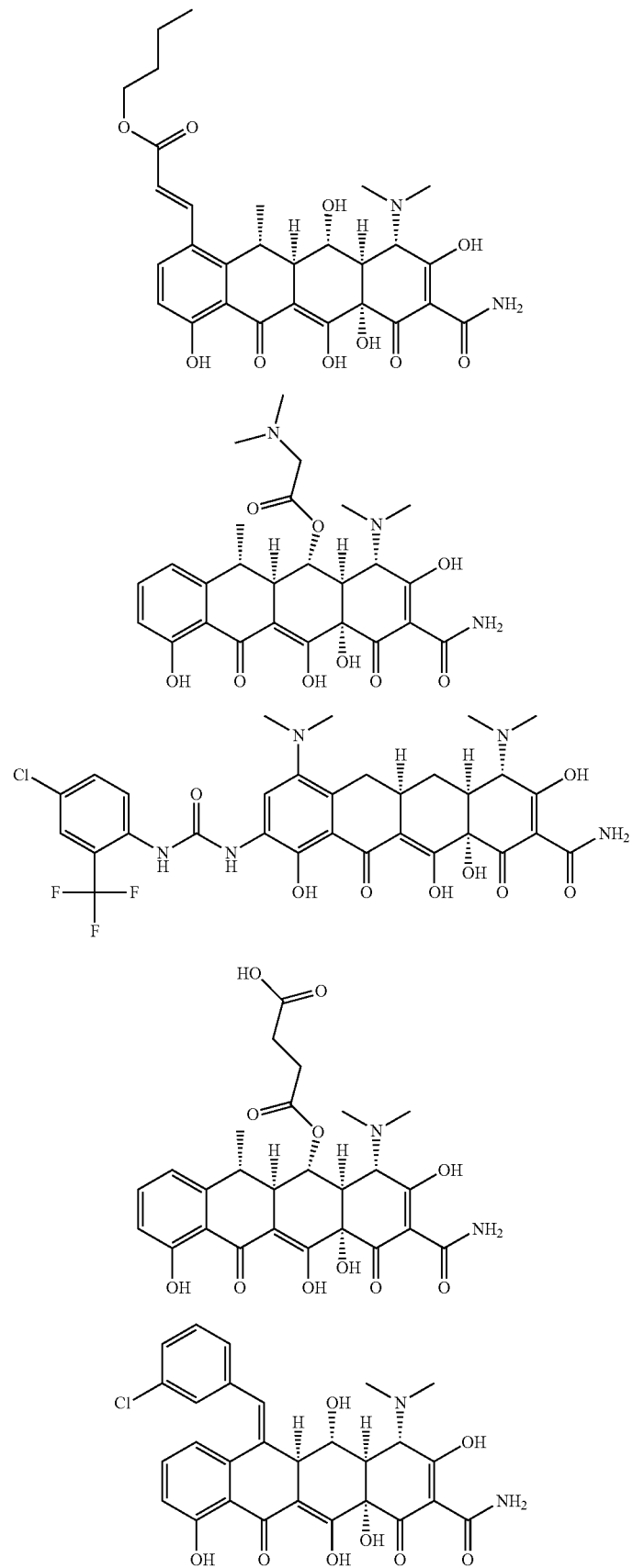

TABLE 2-continued
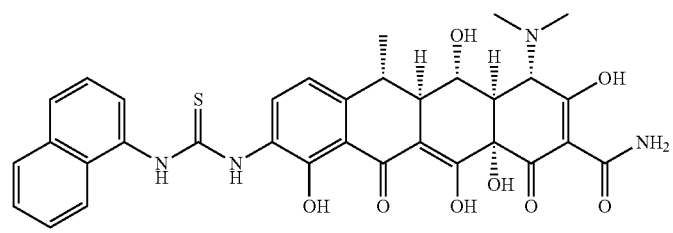
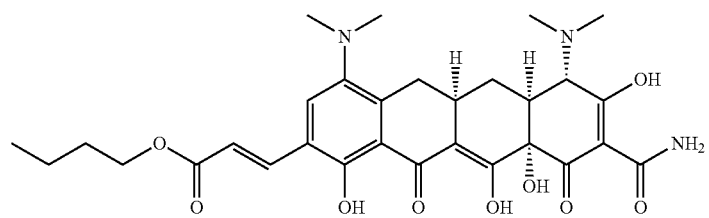
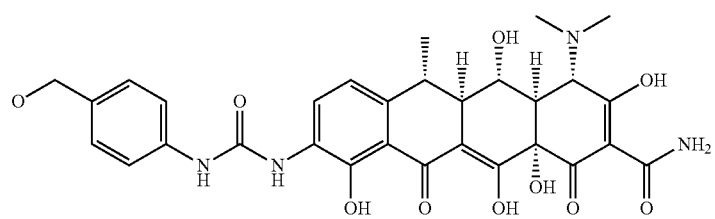
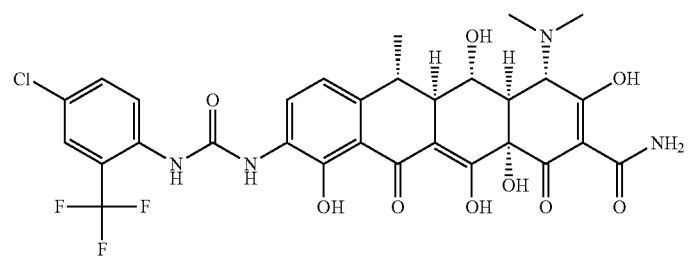
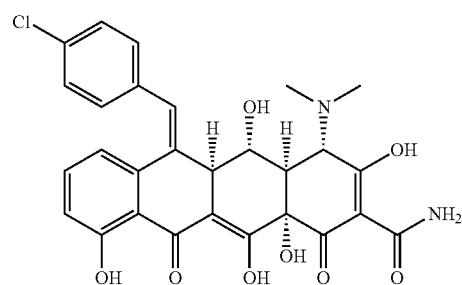
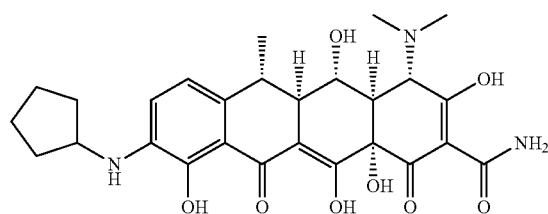

TABLE 2-continued
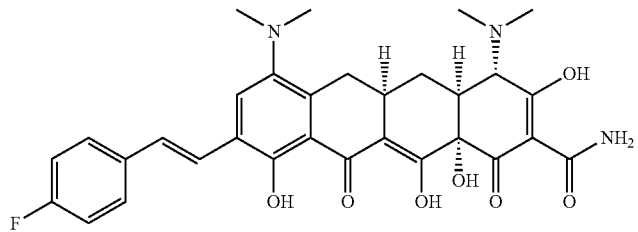
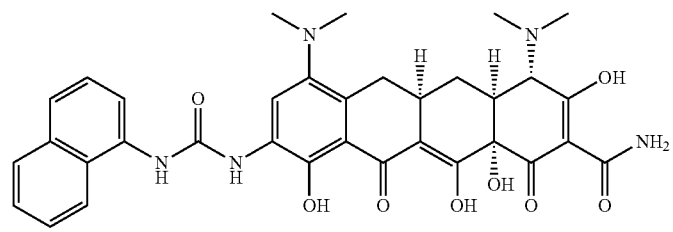
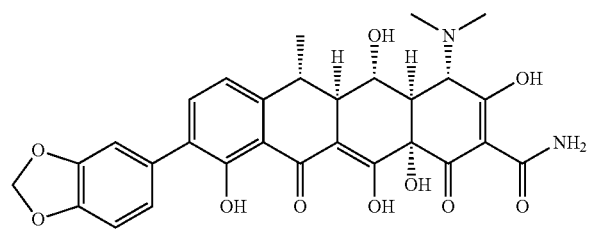
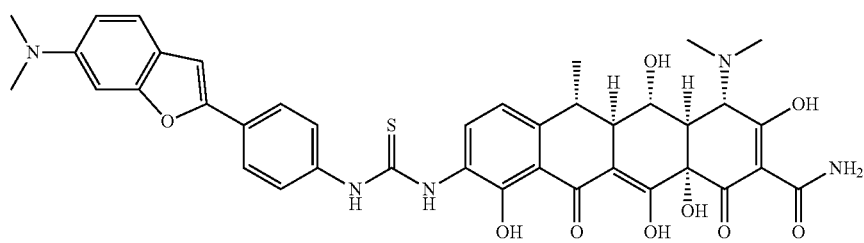
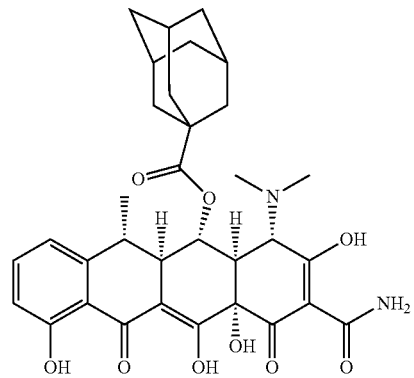

TABLE 2-continued
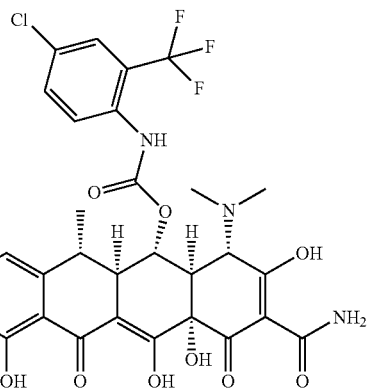
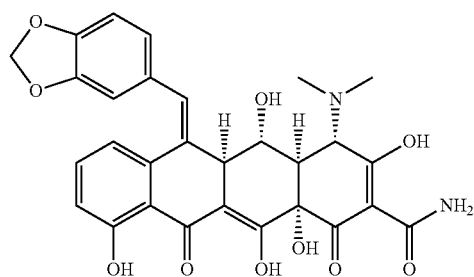
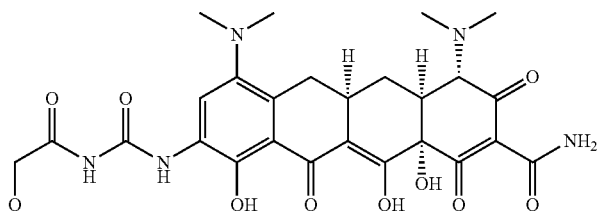
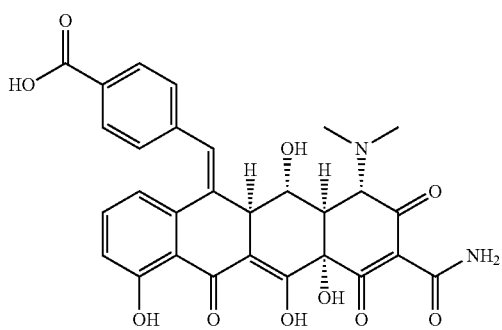
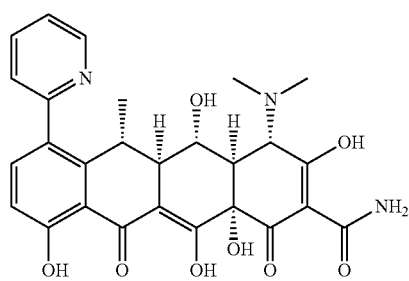

TABLE 2-continued
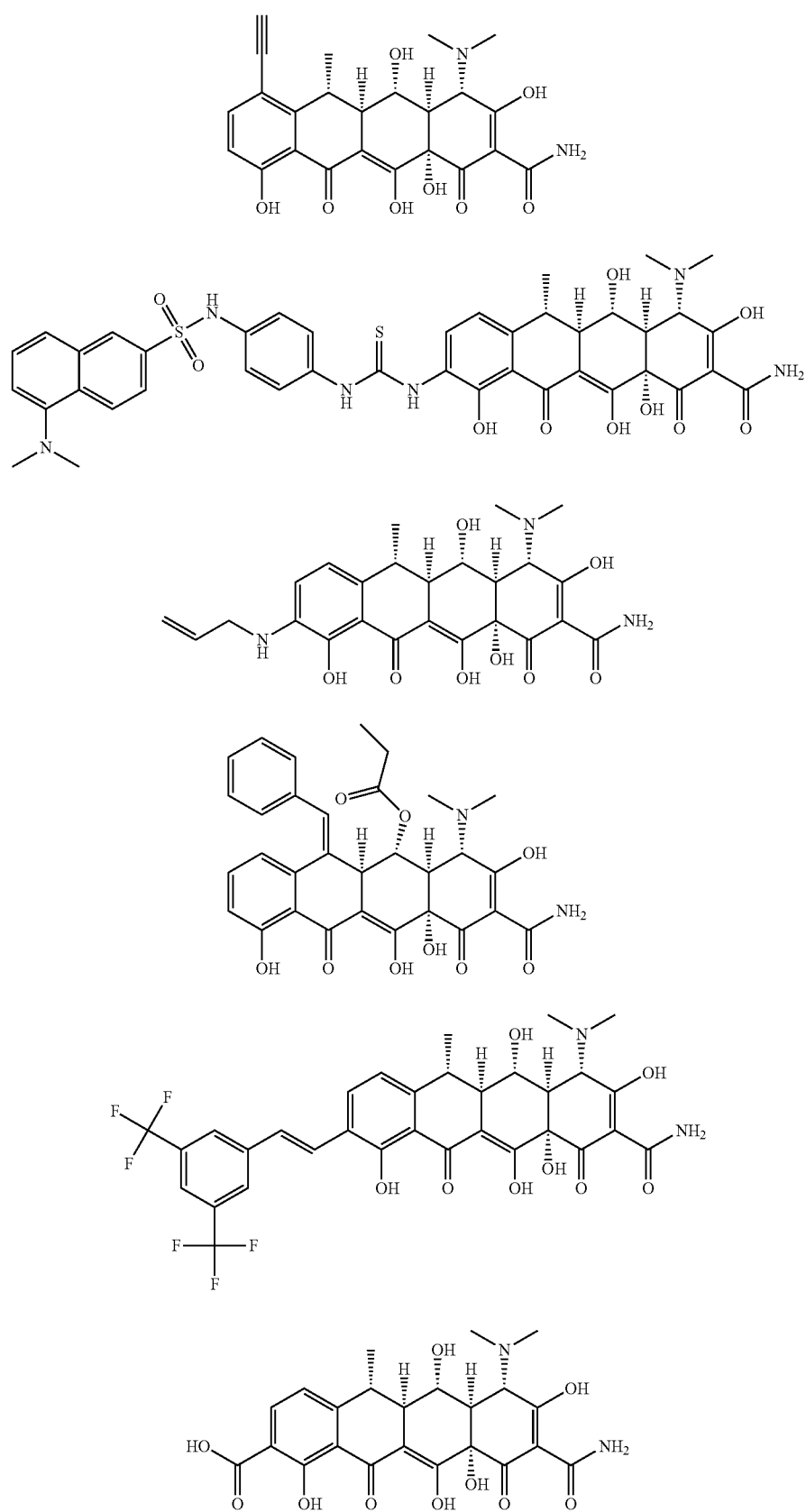

TABLE 2-continued
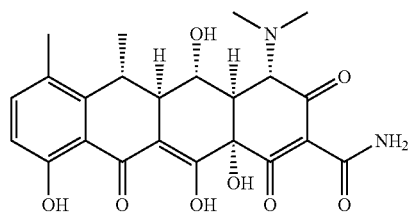
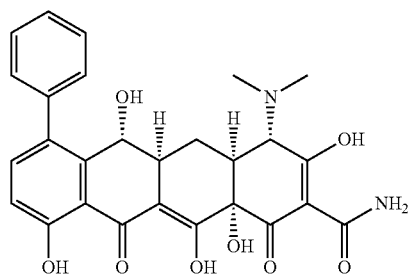
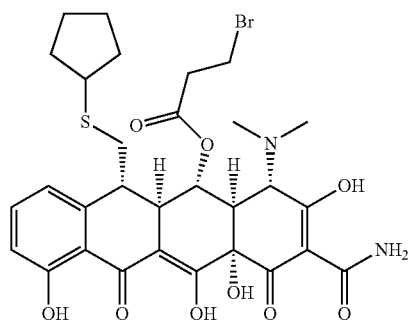
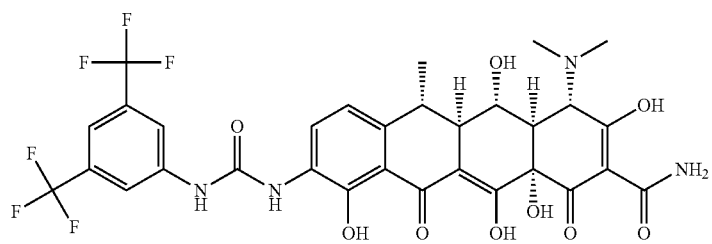
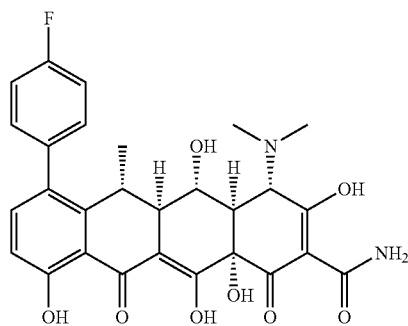

TABLE 2-continued
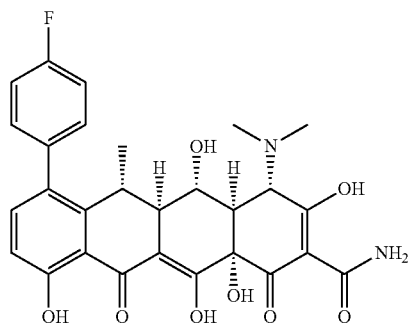
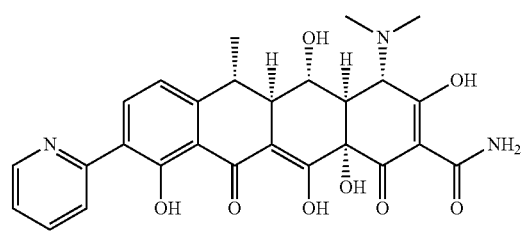
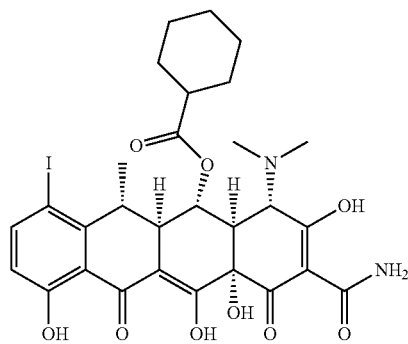
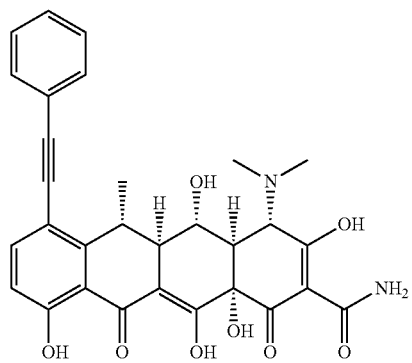
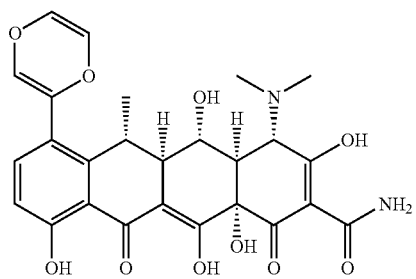

TABLE 2-continued
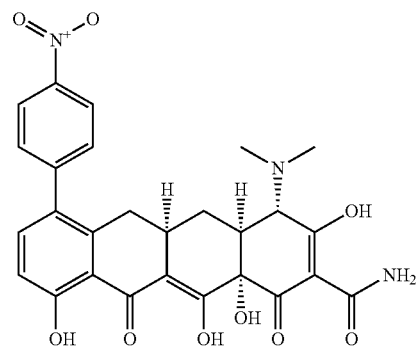
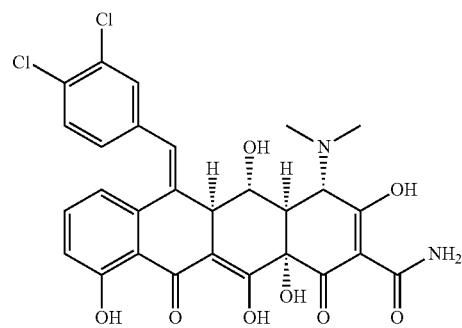
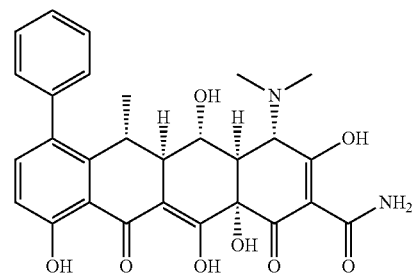
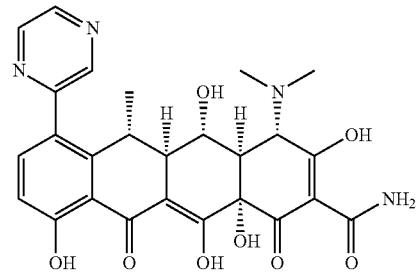
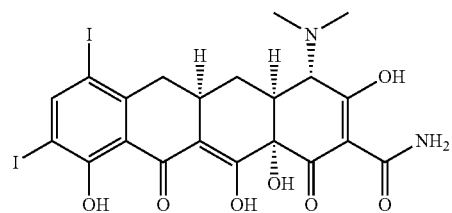

TABLE 2-continued
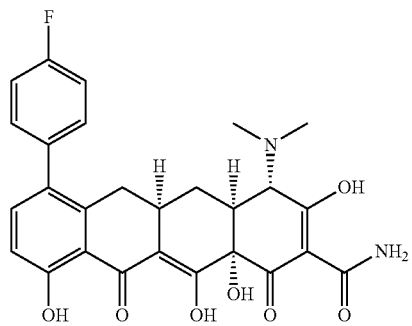
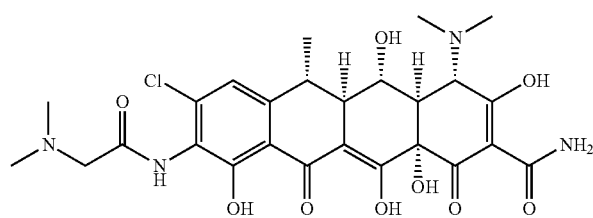
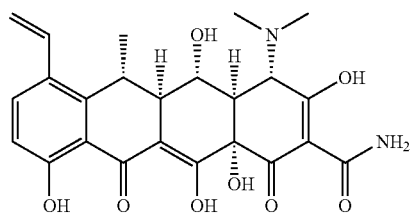
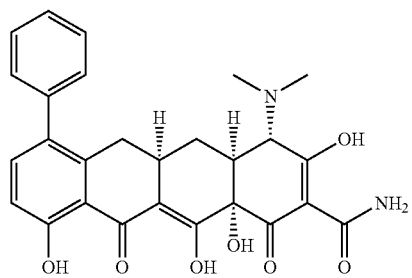
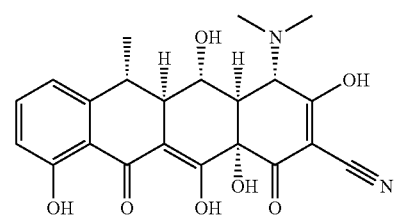
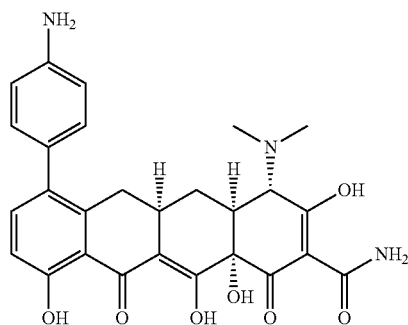

TABLE 2-continued
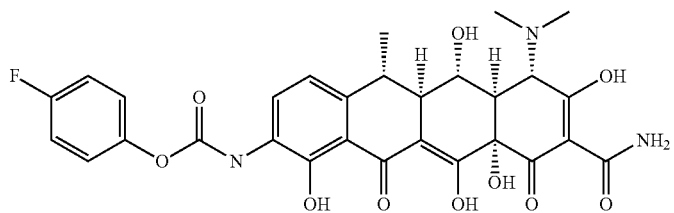
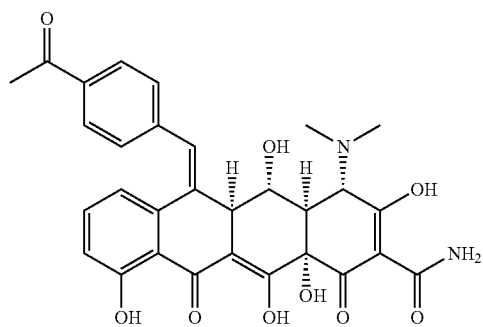
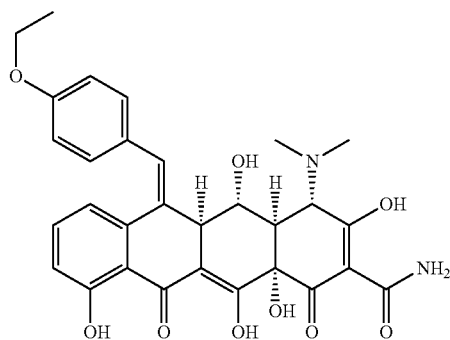
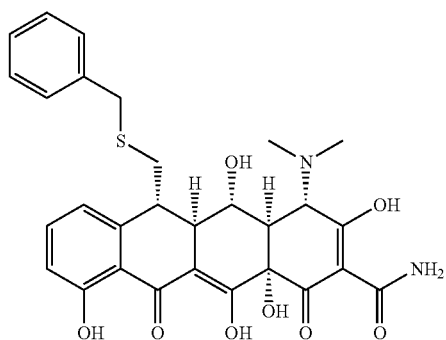
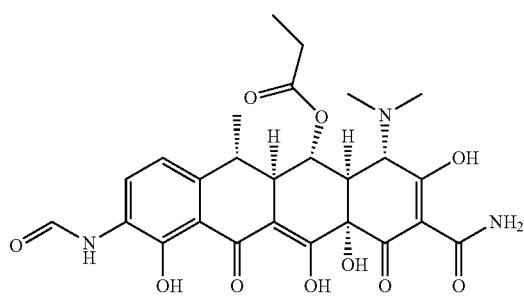

TABLE 2-continued
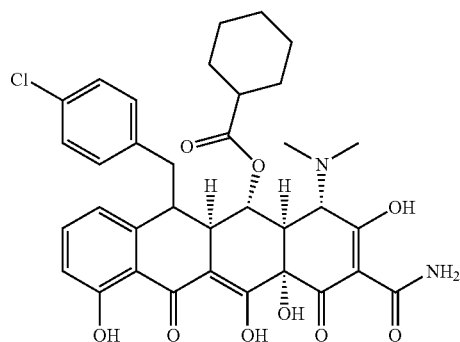
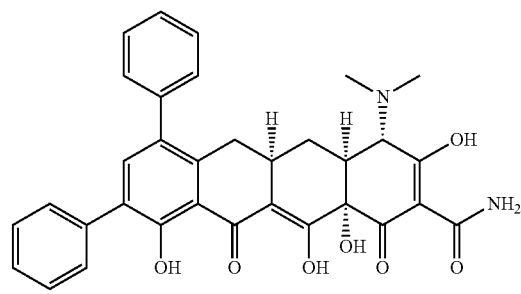
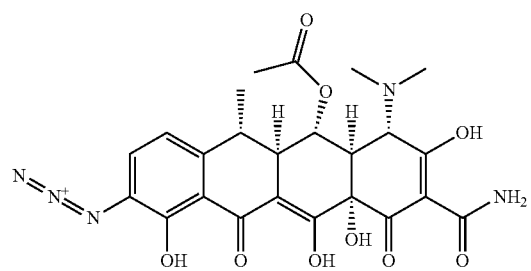
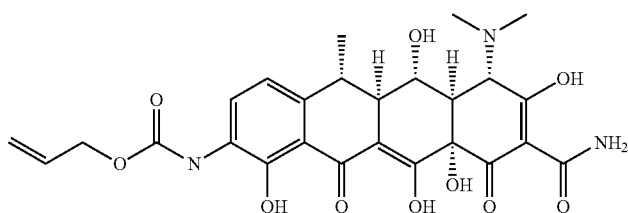
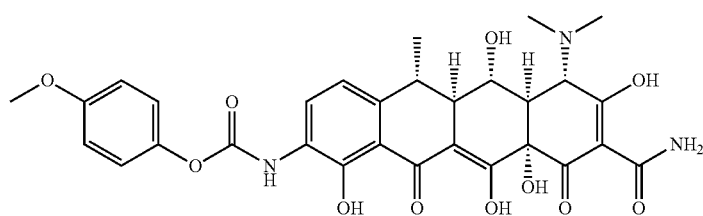
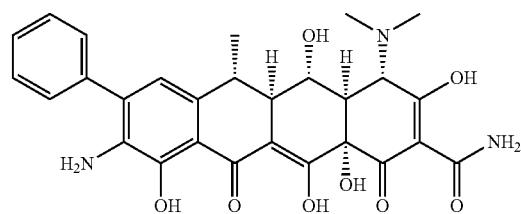

TABLE 2-continued
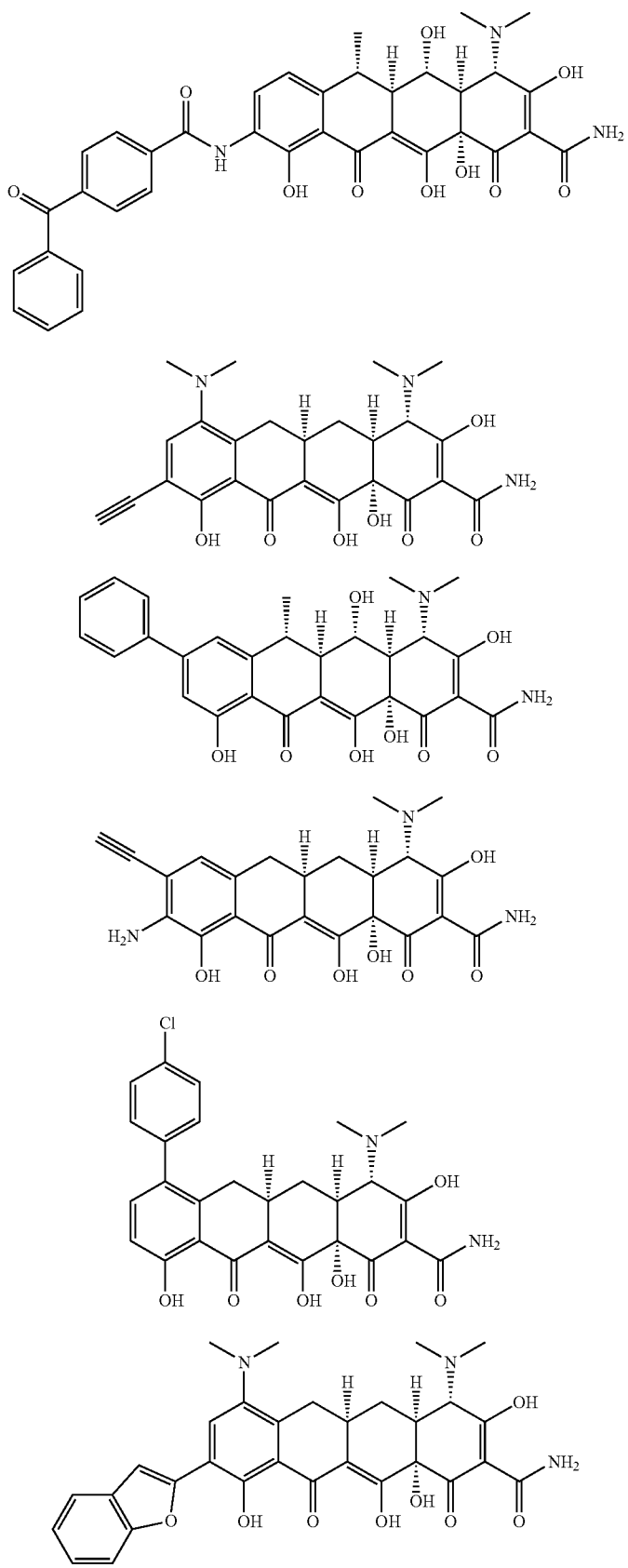

TABLE 2-continued
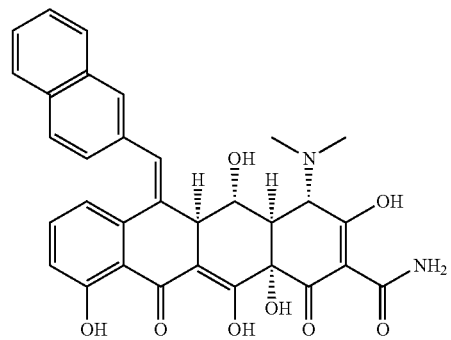
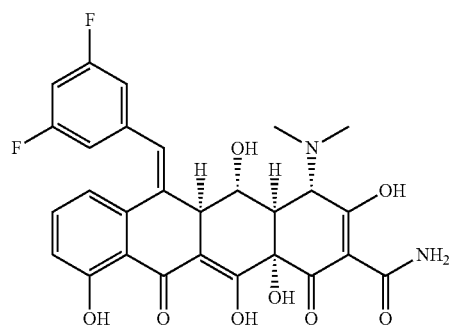
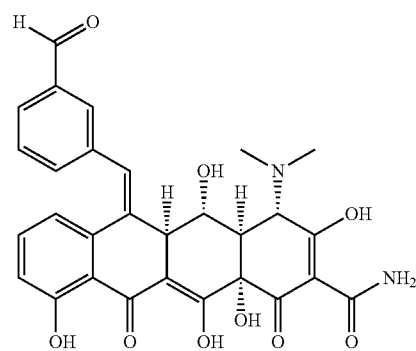
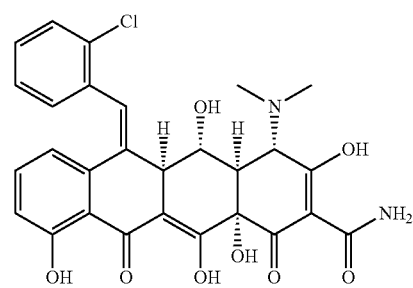

TABLE 2-continued
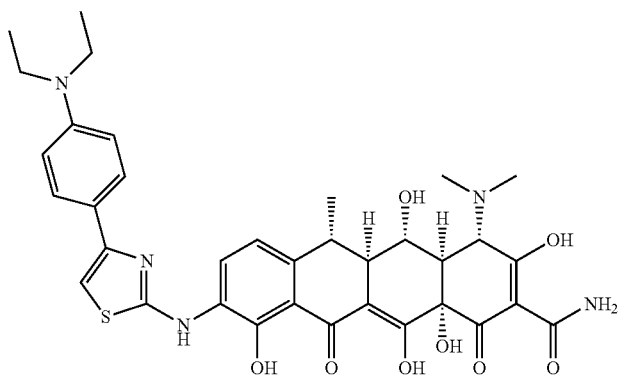
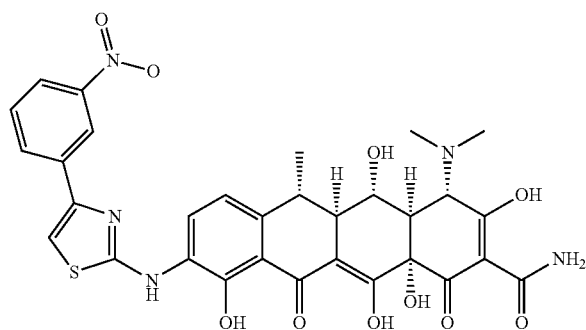
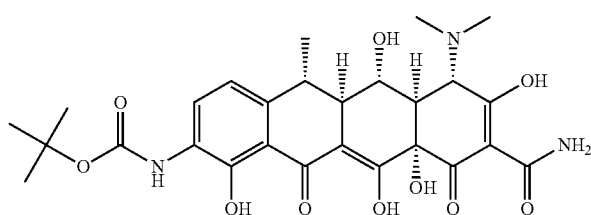
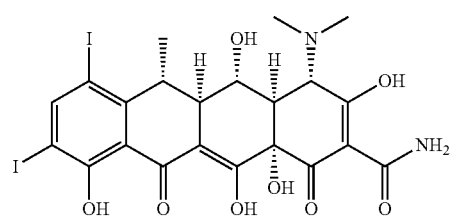
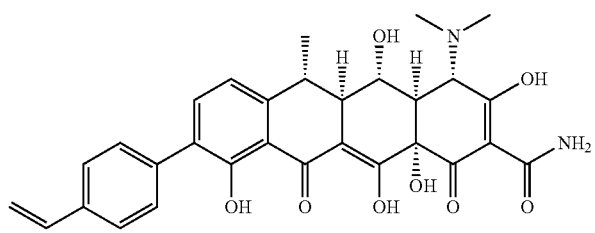

TABLE 2-continued
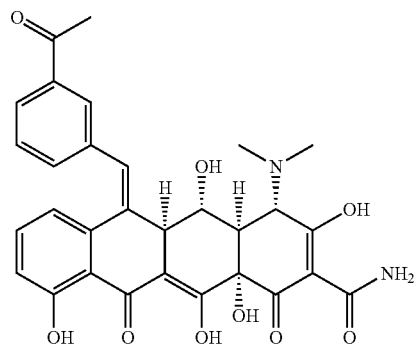
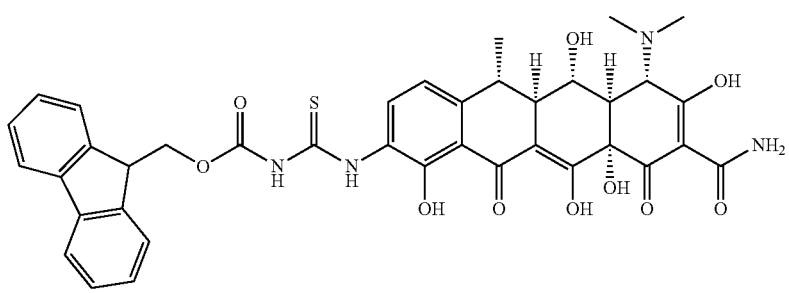
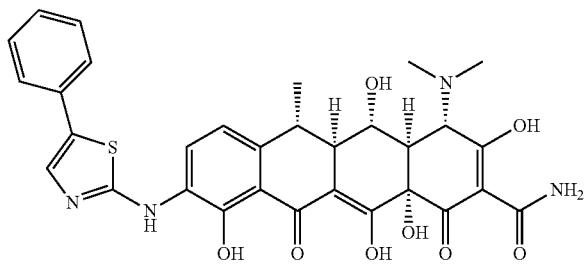
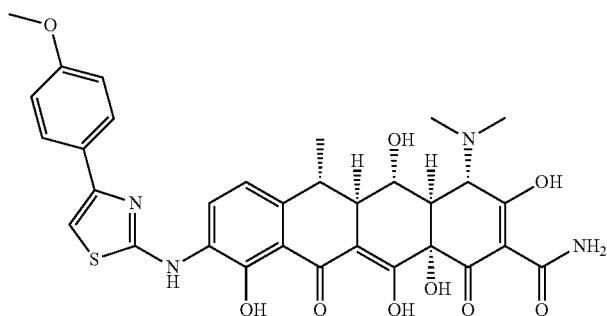
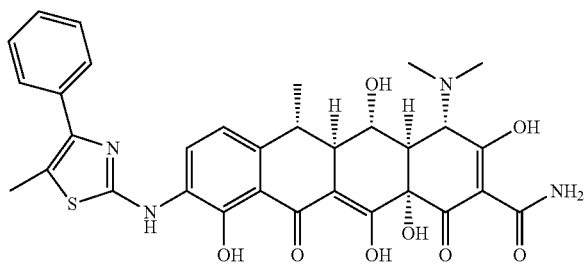

TABLE 2-continued
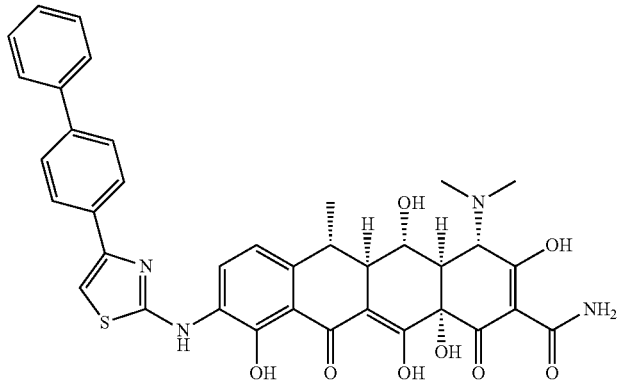
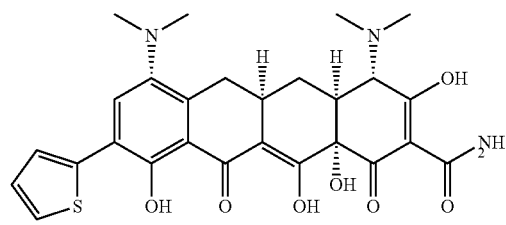
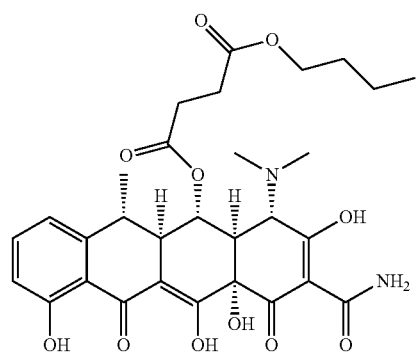
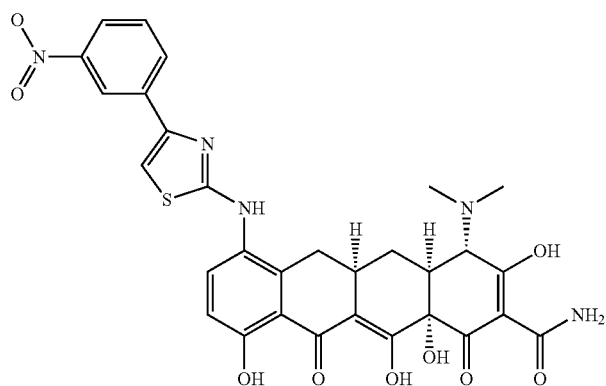

TABLE 2-continued
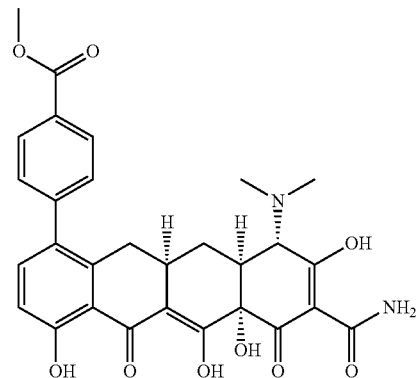
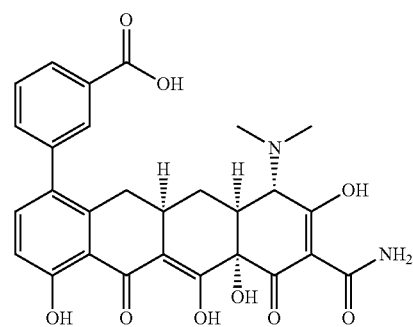
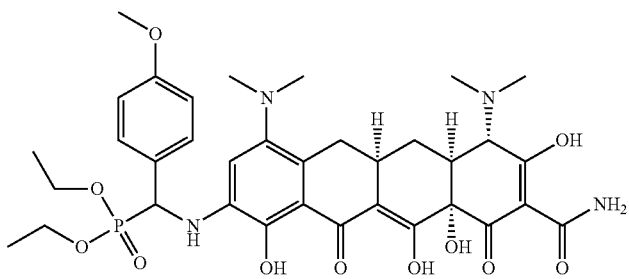
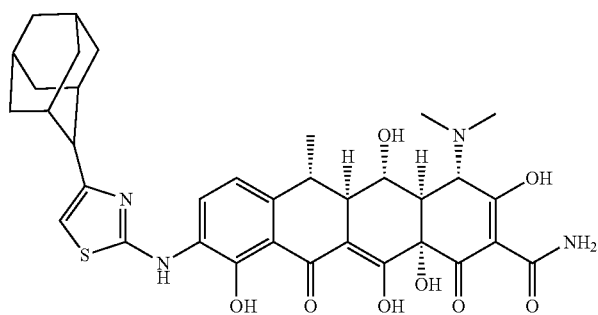
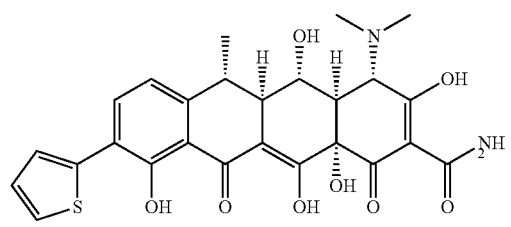

TABLE 2-continued
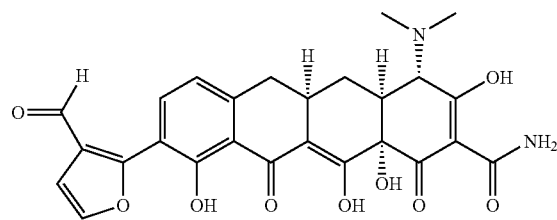
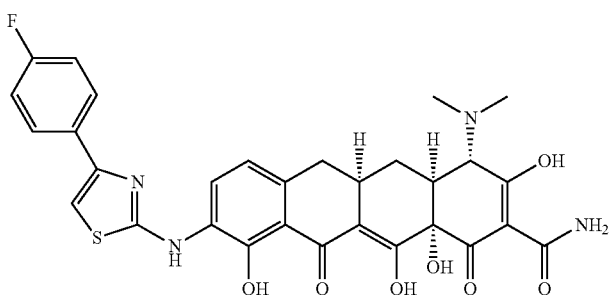
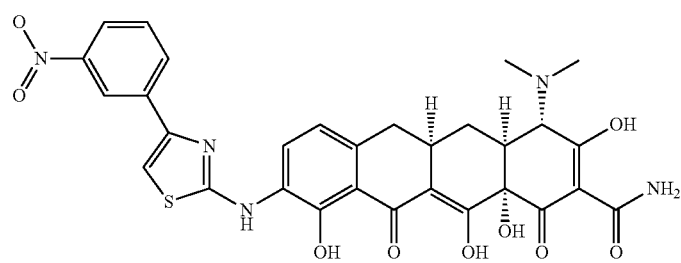
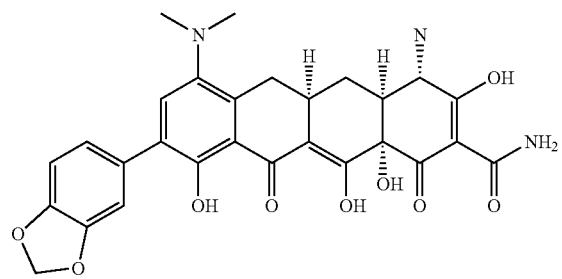
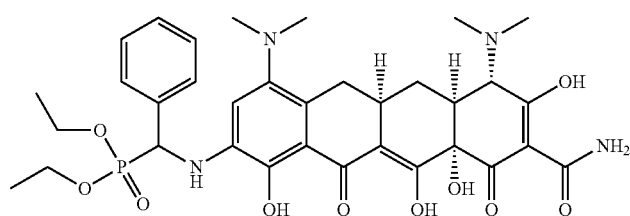

TABLE 2-continued
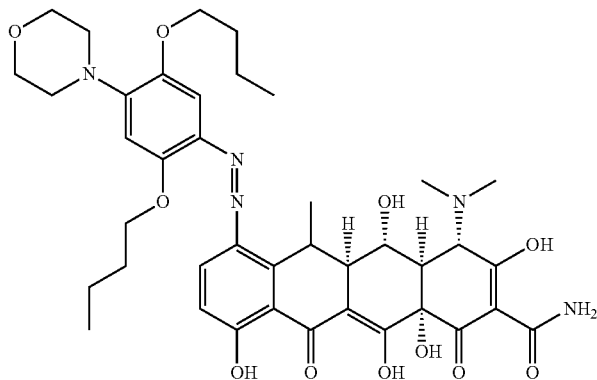
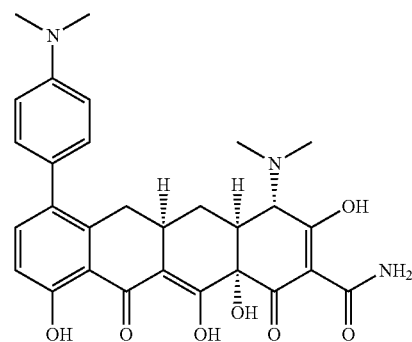
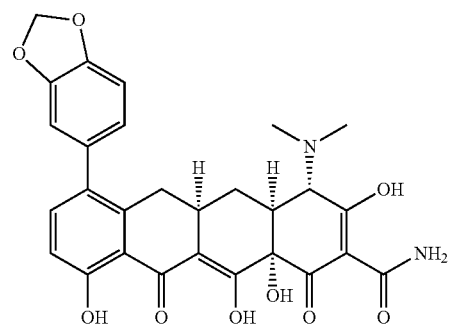

TABLE 2-continued
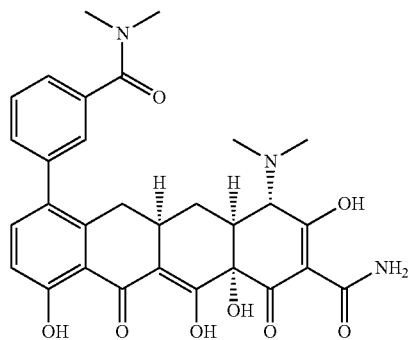
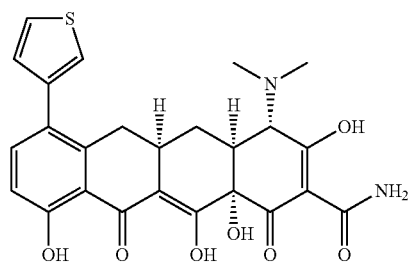
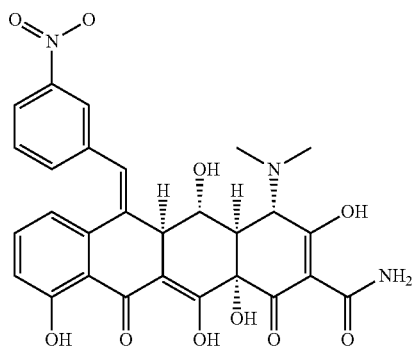
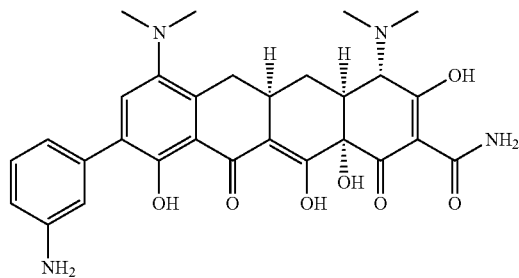
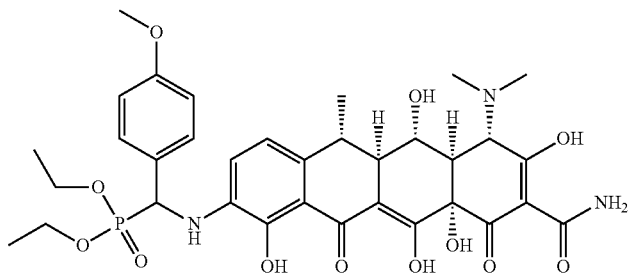

TABLE 2-continued
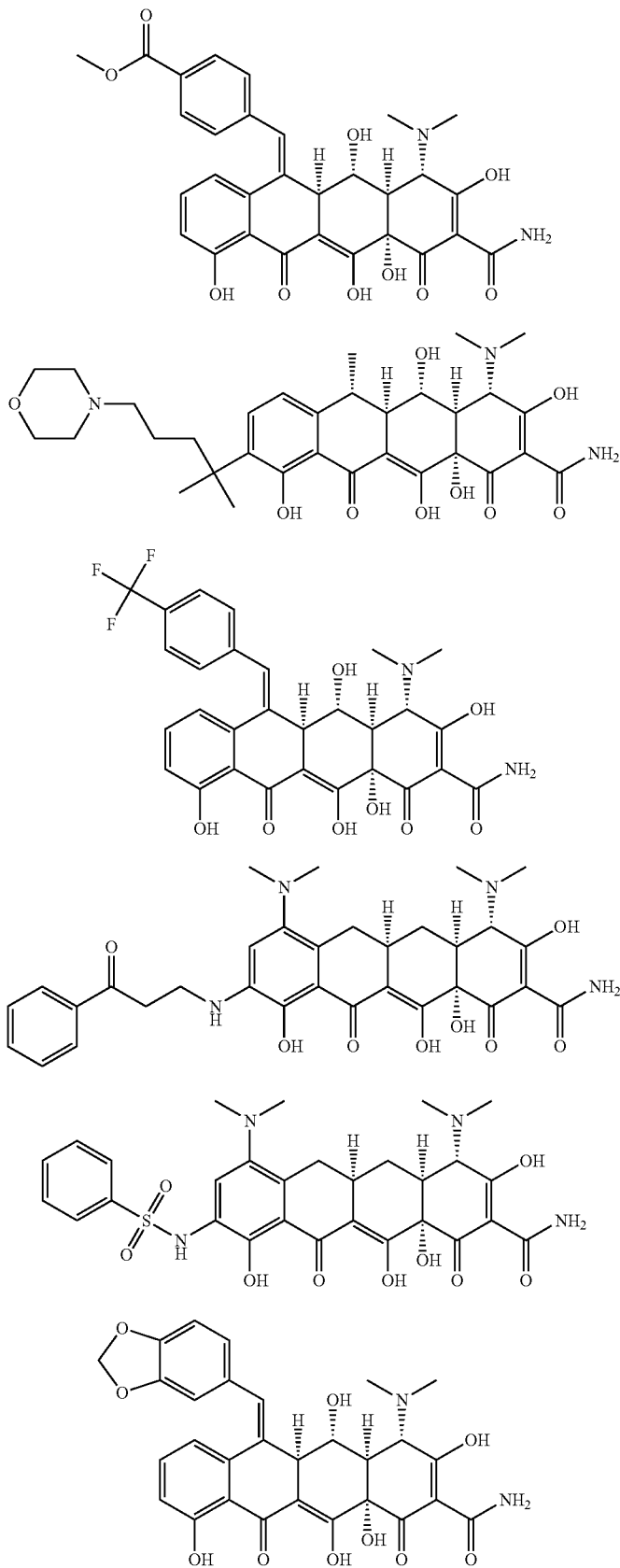

TABLE 2-continued
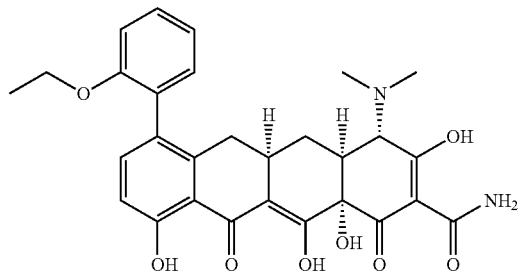
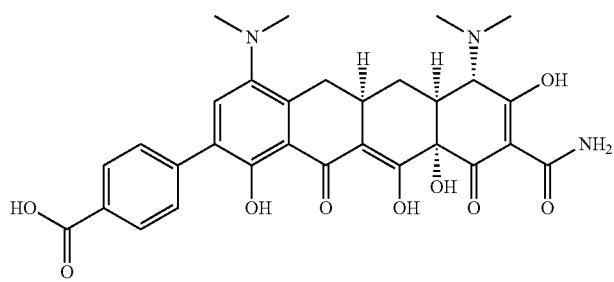
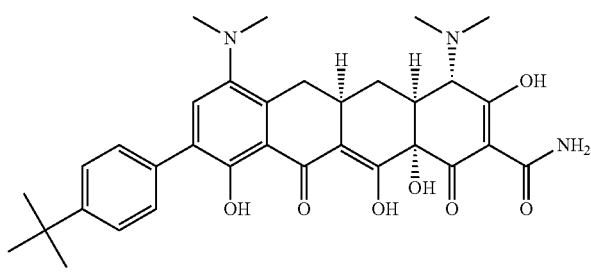
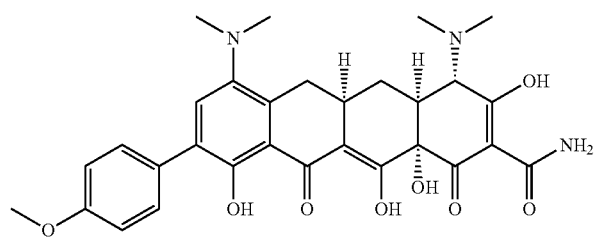
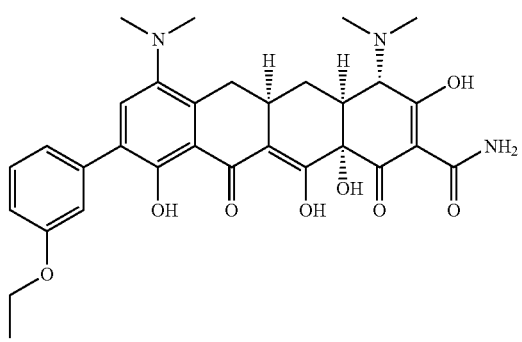

TABLE 2-continued
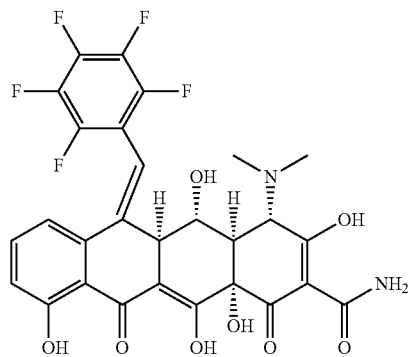
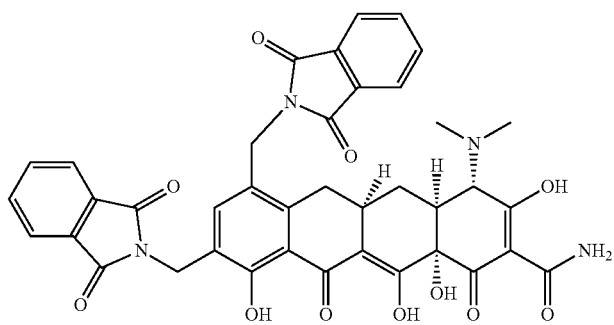
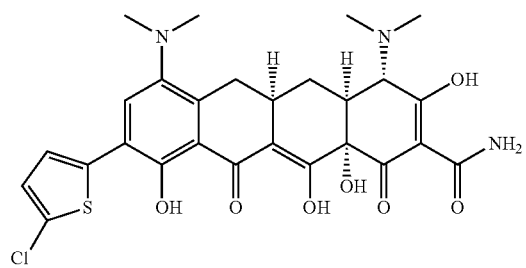
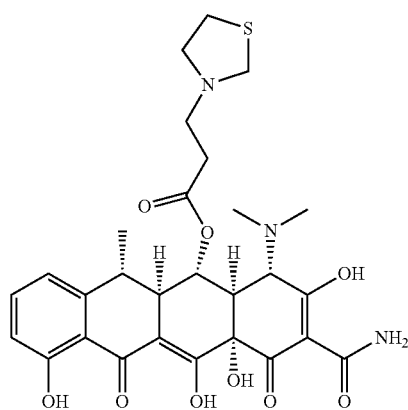
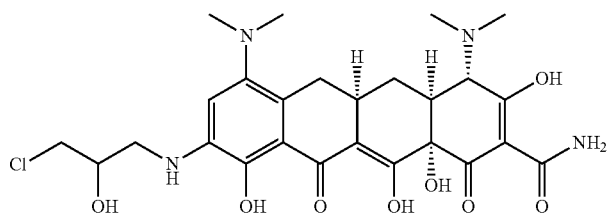

TABLE 2-continued
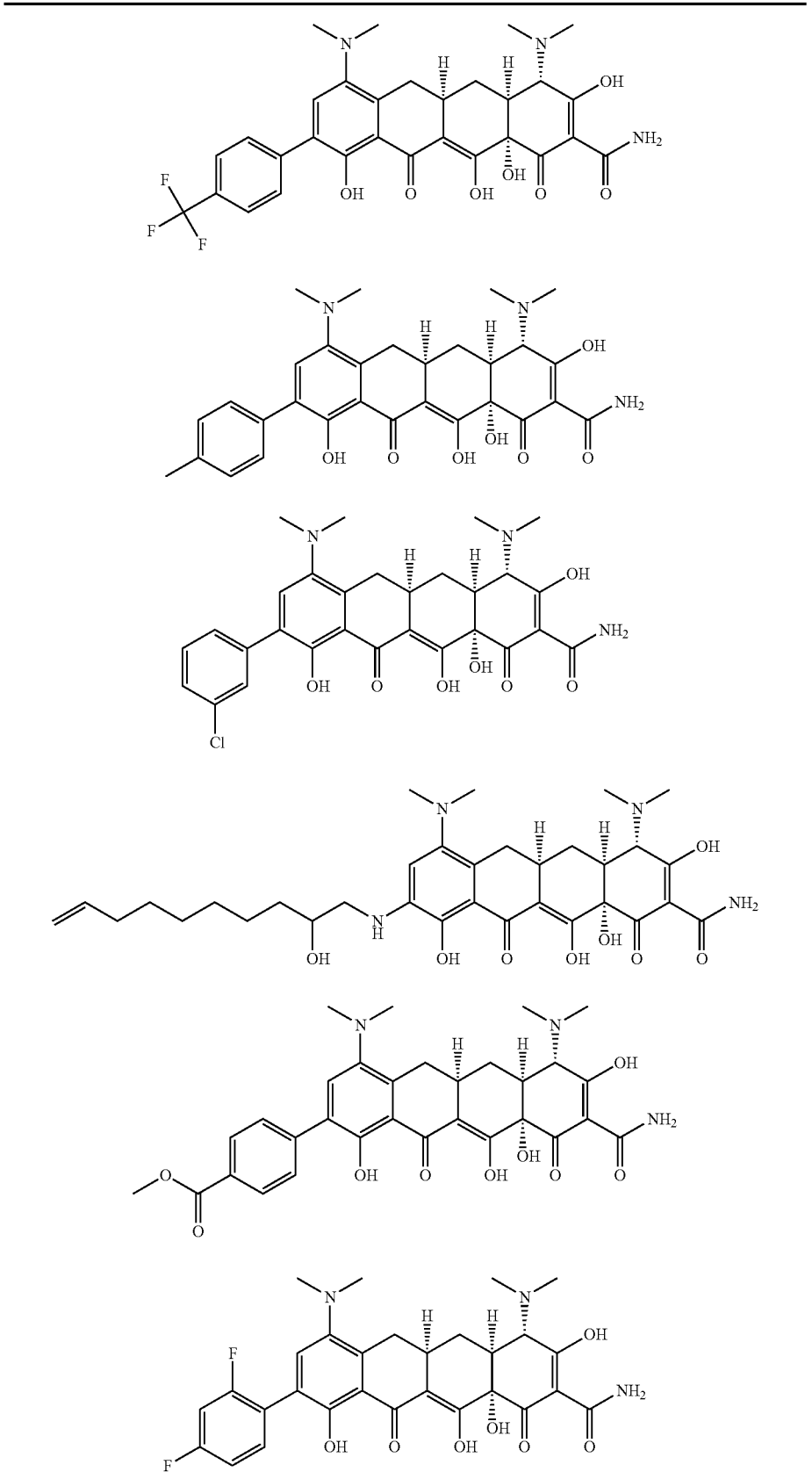

TABLE 2-continued
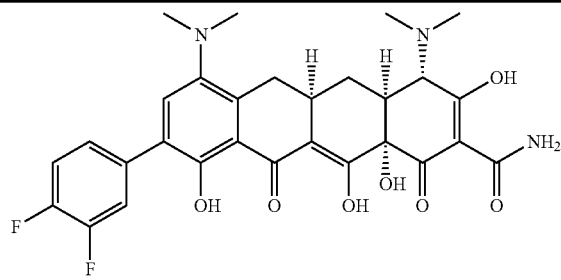
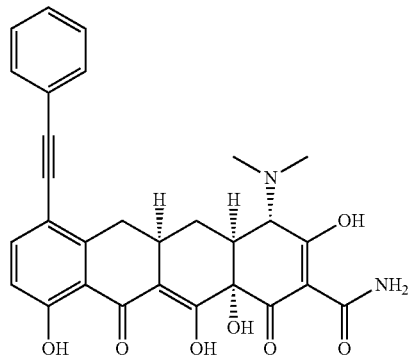
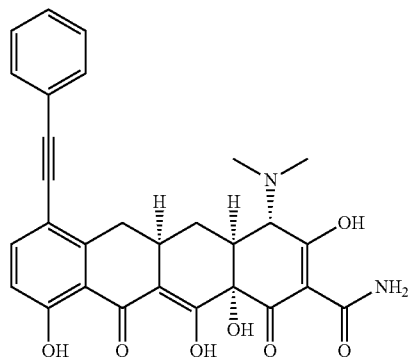
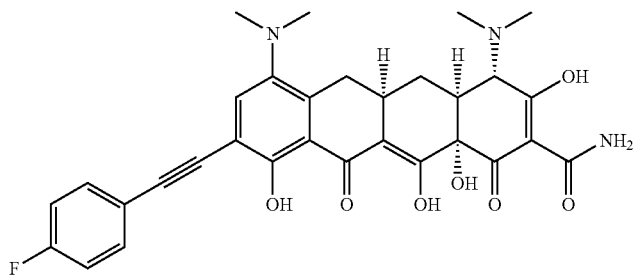
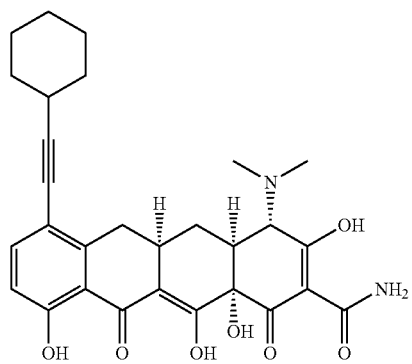

TABLE 2-continued
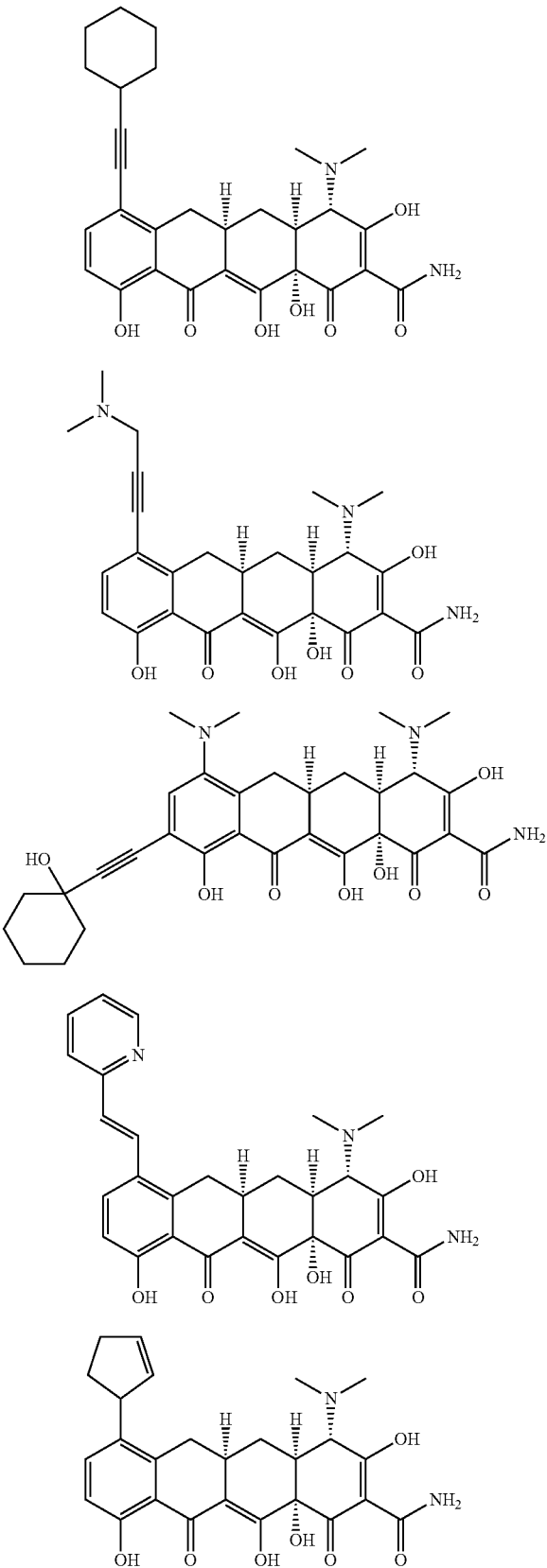

TABLE 2-continued
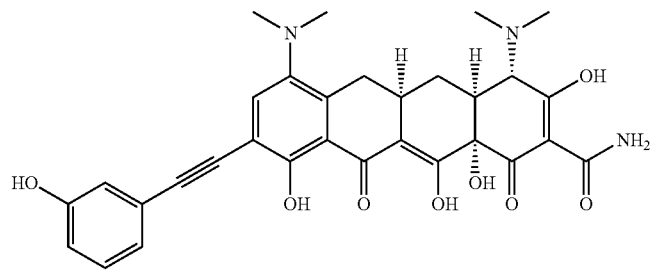
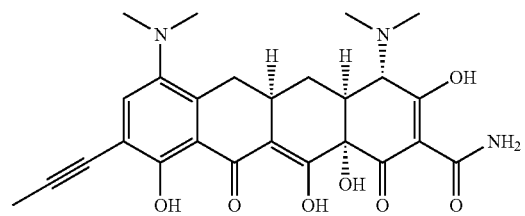
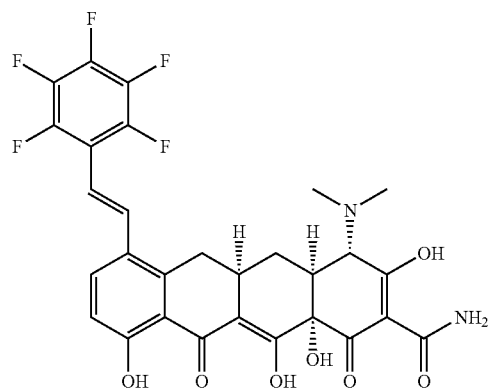
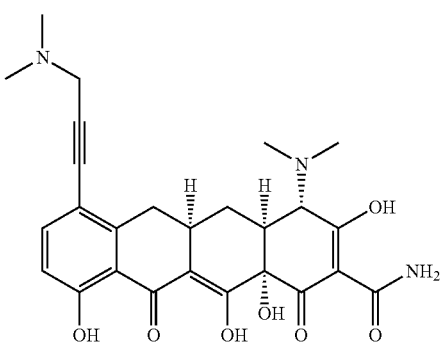
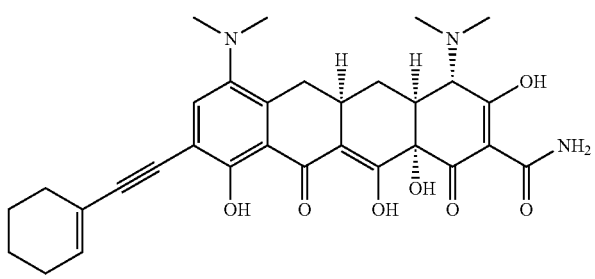

TABLE 2-continued
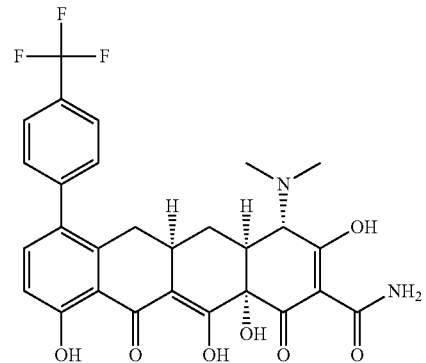
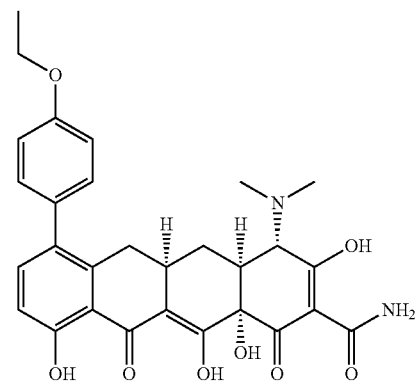
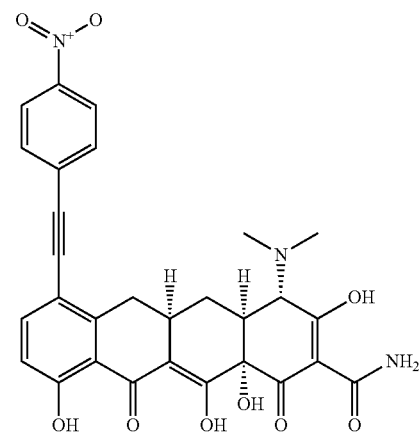
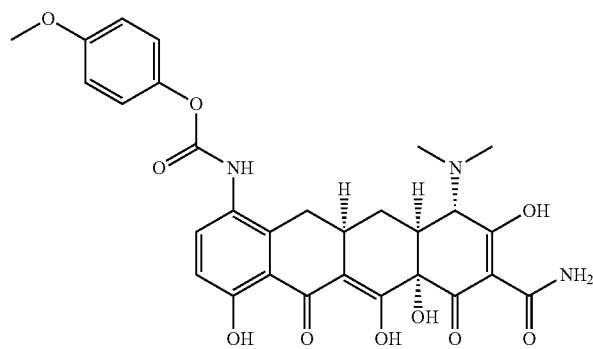

TABLE 2-continued
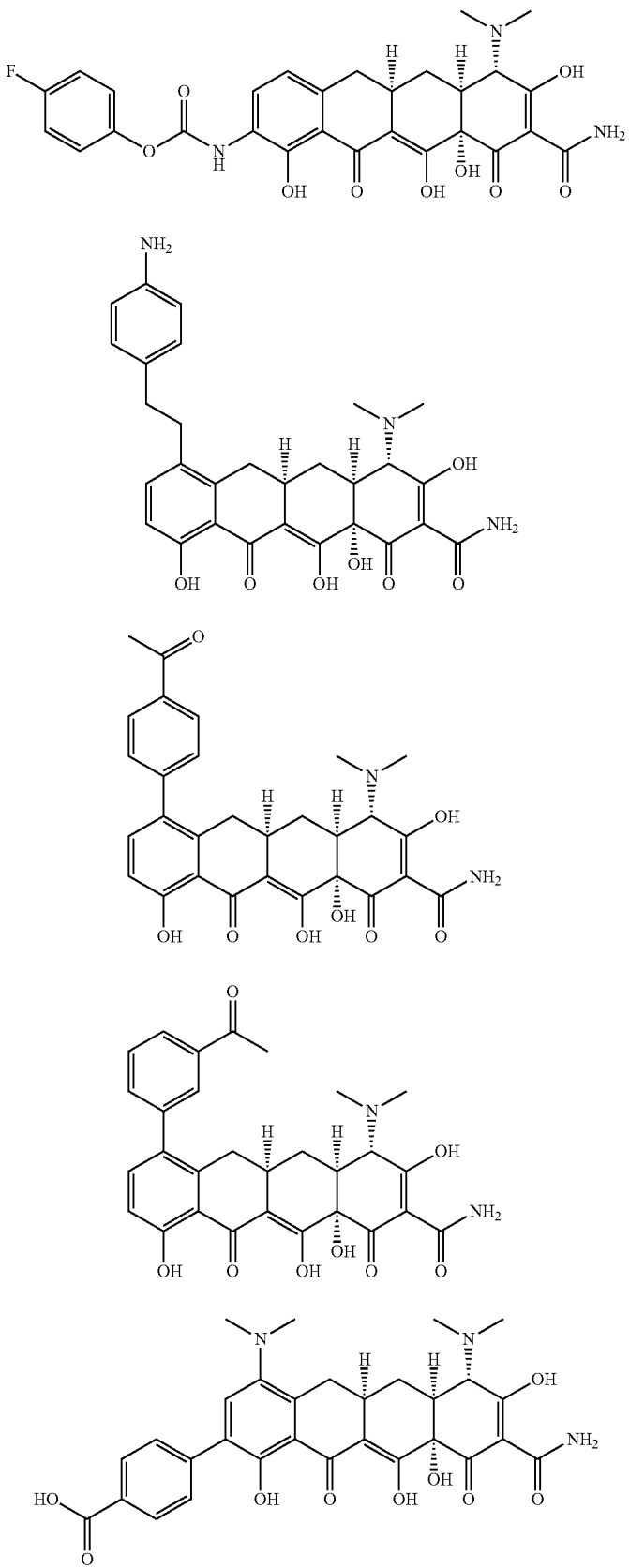

TABLE 2-continued
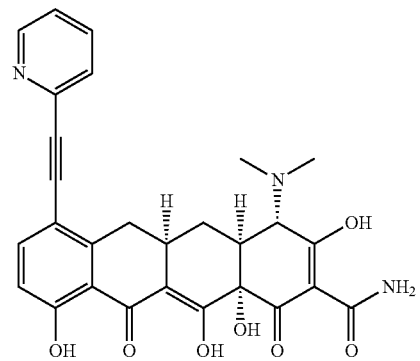
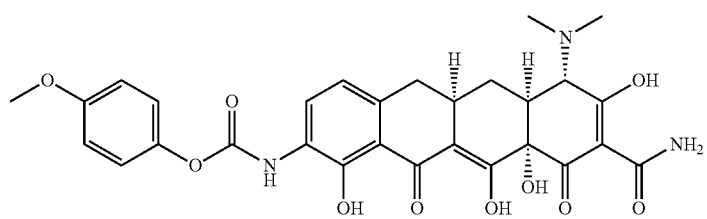
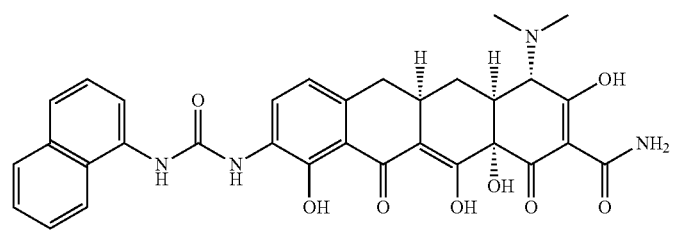
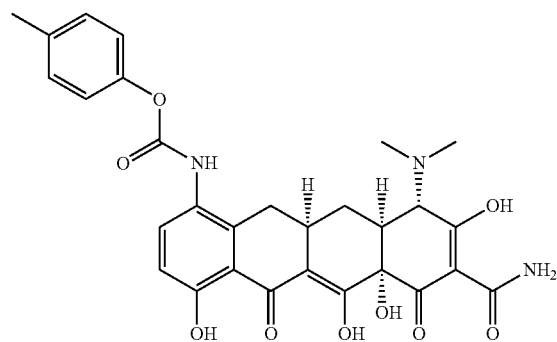
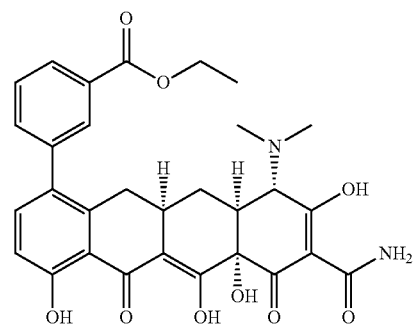

TABLE 2-continued
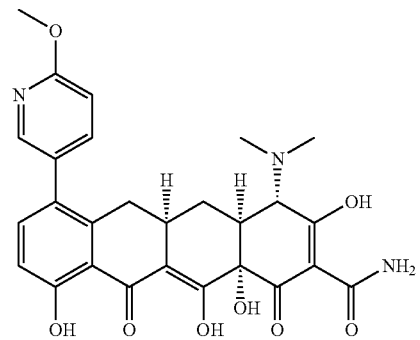
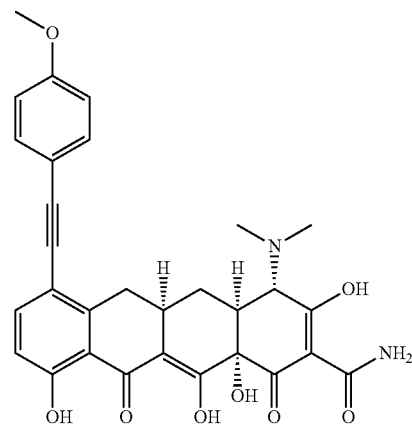
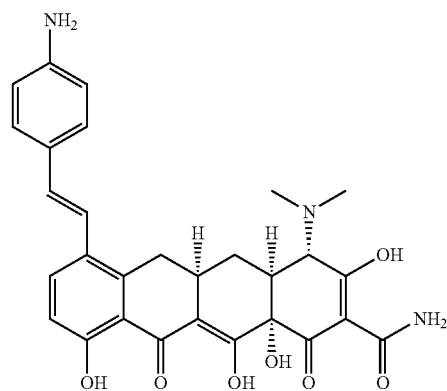
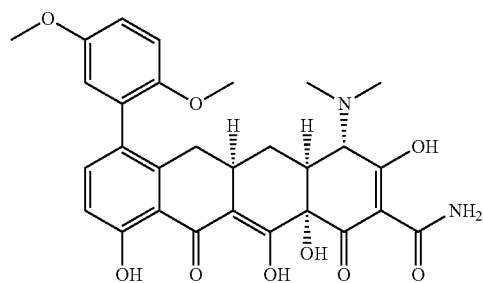

TABLE 2-continued
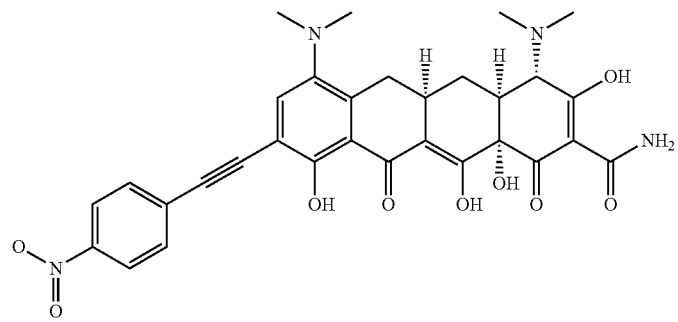
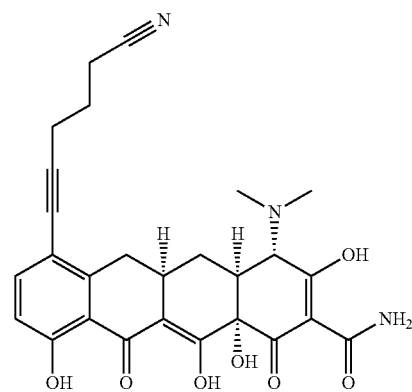
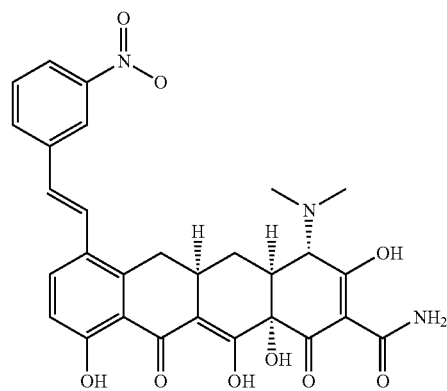
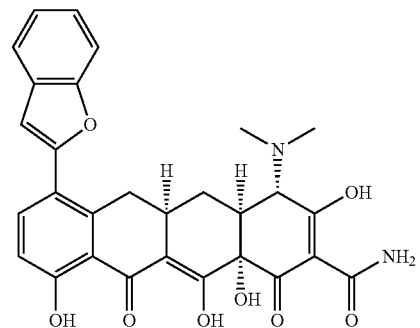

TABLE 2-continued
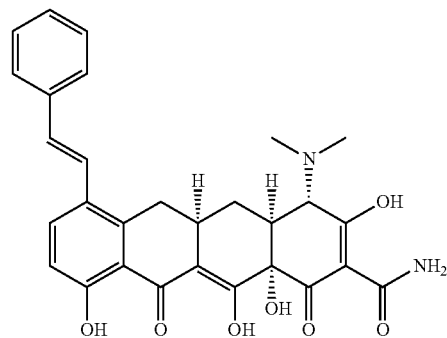
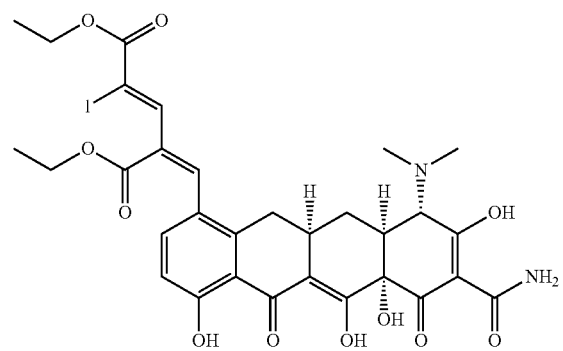
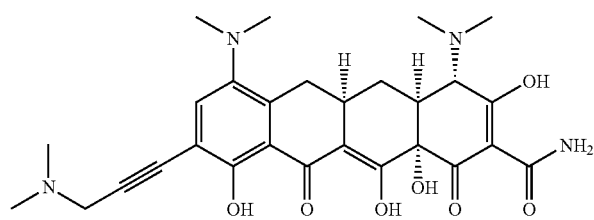
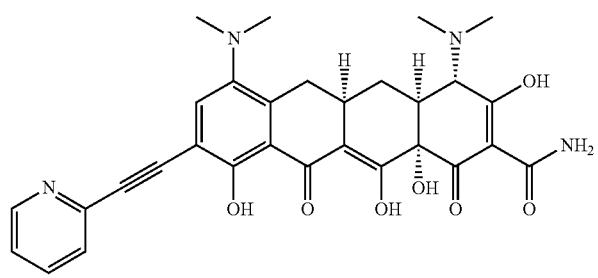
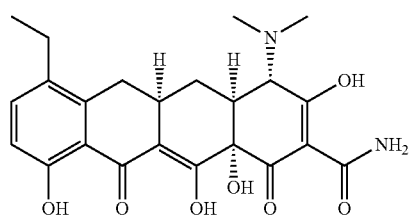

TABLE 2-continued
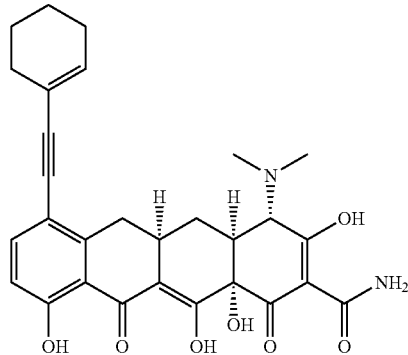
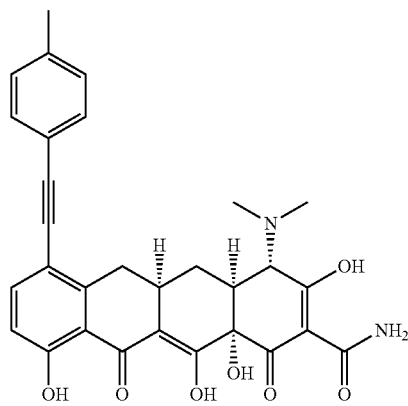
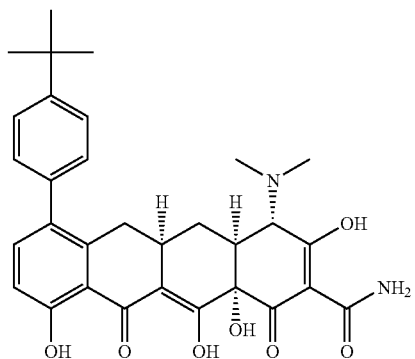
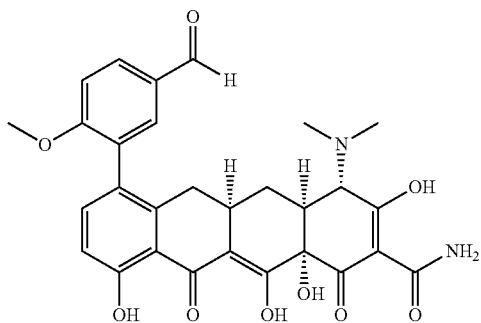

TABLE 2-continued
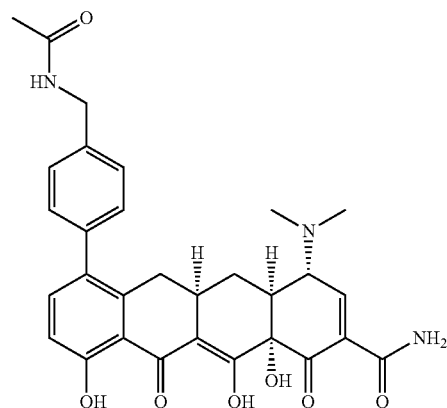
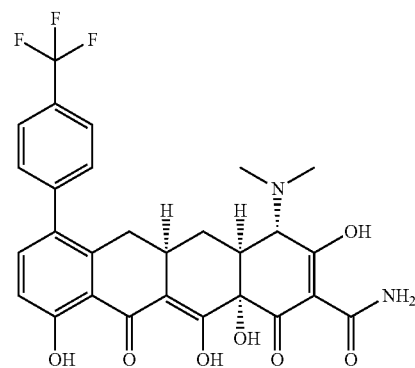
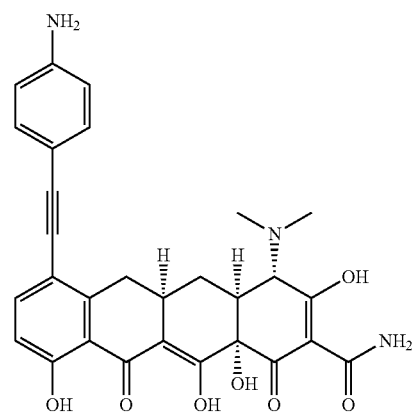
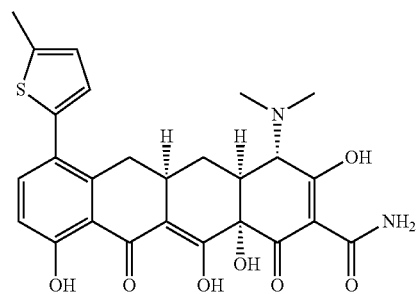

TABLE 2-continued
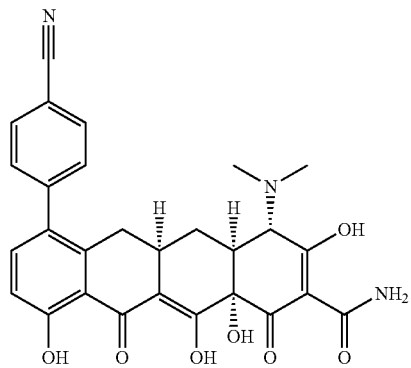
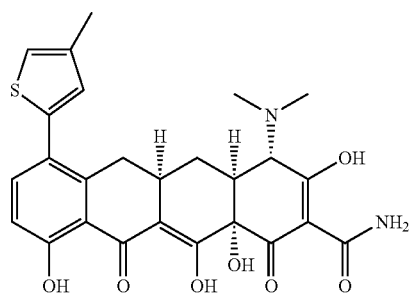
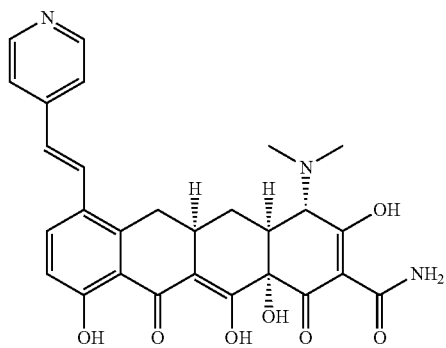
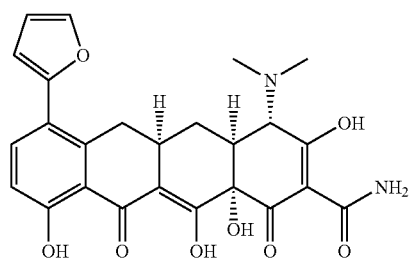
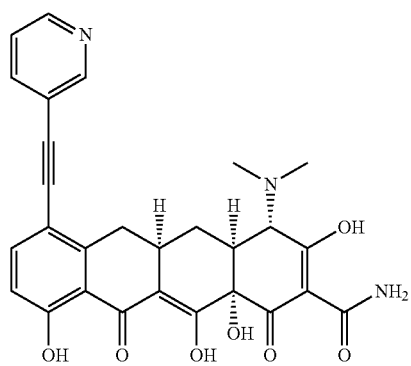

TABLE 2-continued
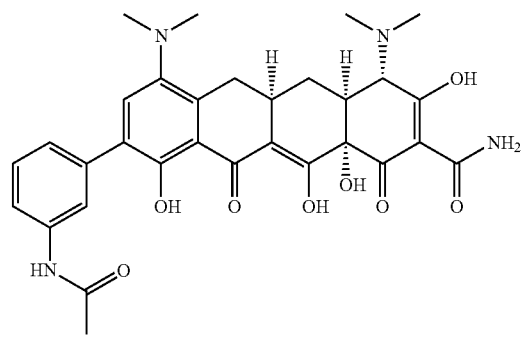
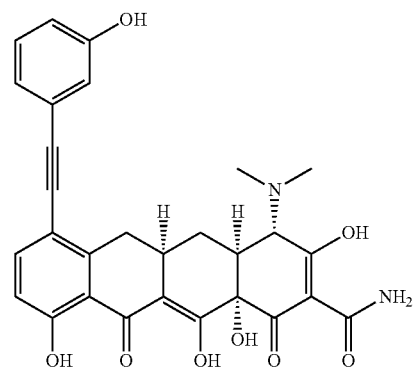
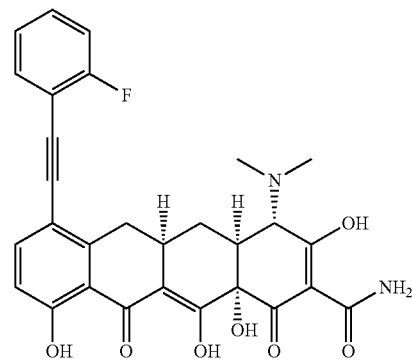
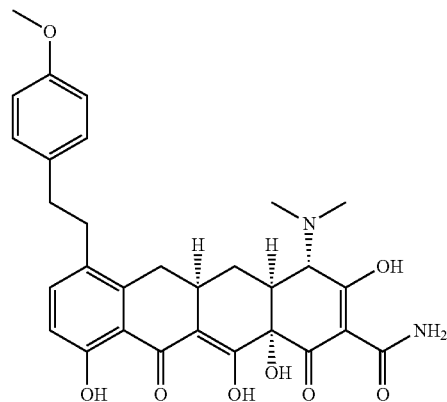

TABLE 2-continued
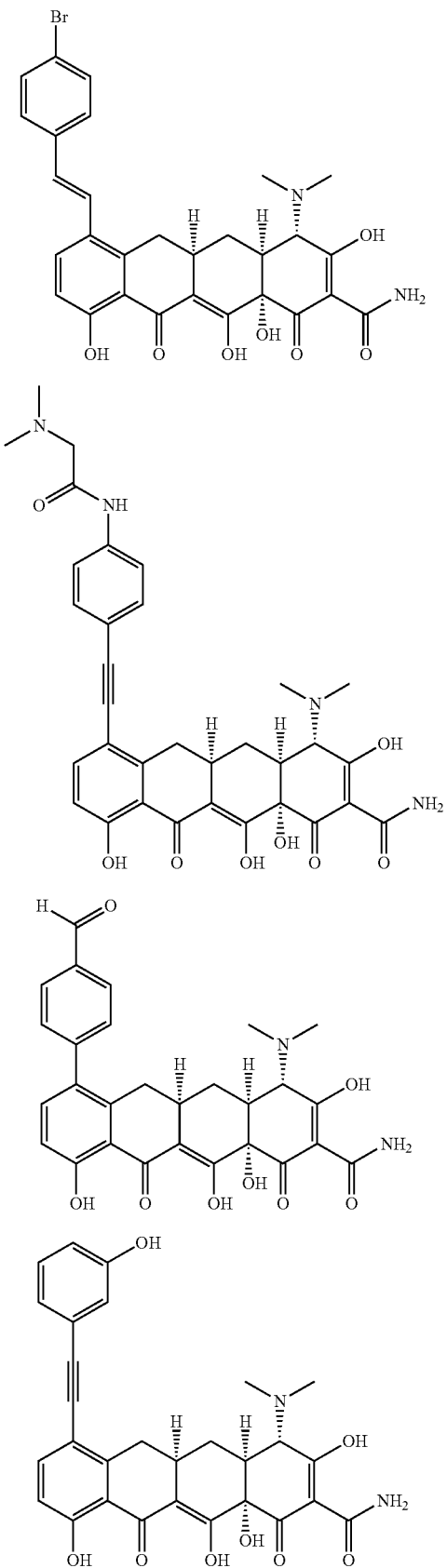

TABLE 2-continued
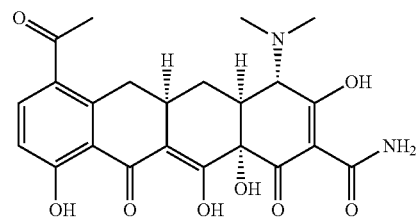
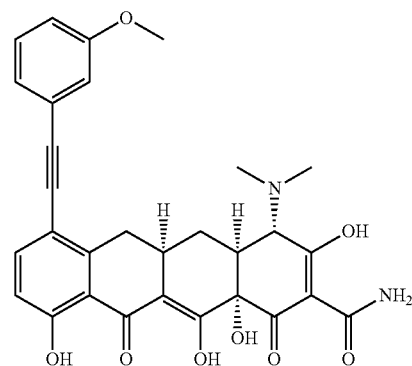
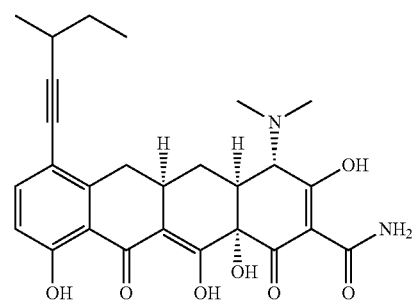
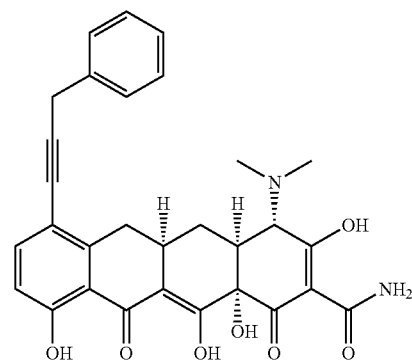
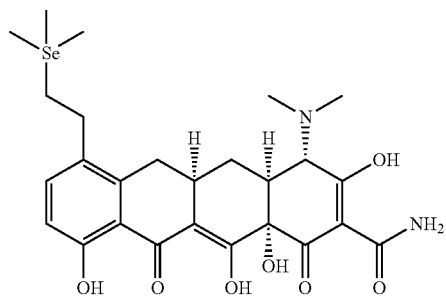

TABLE 2-continued
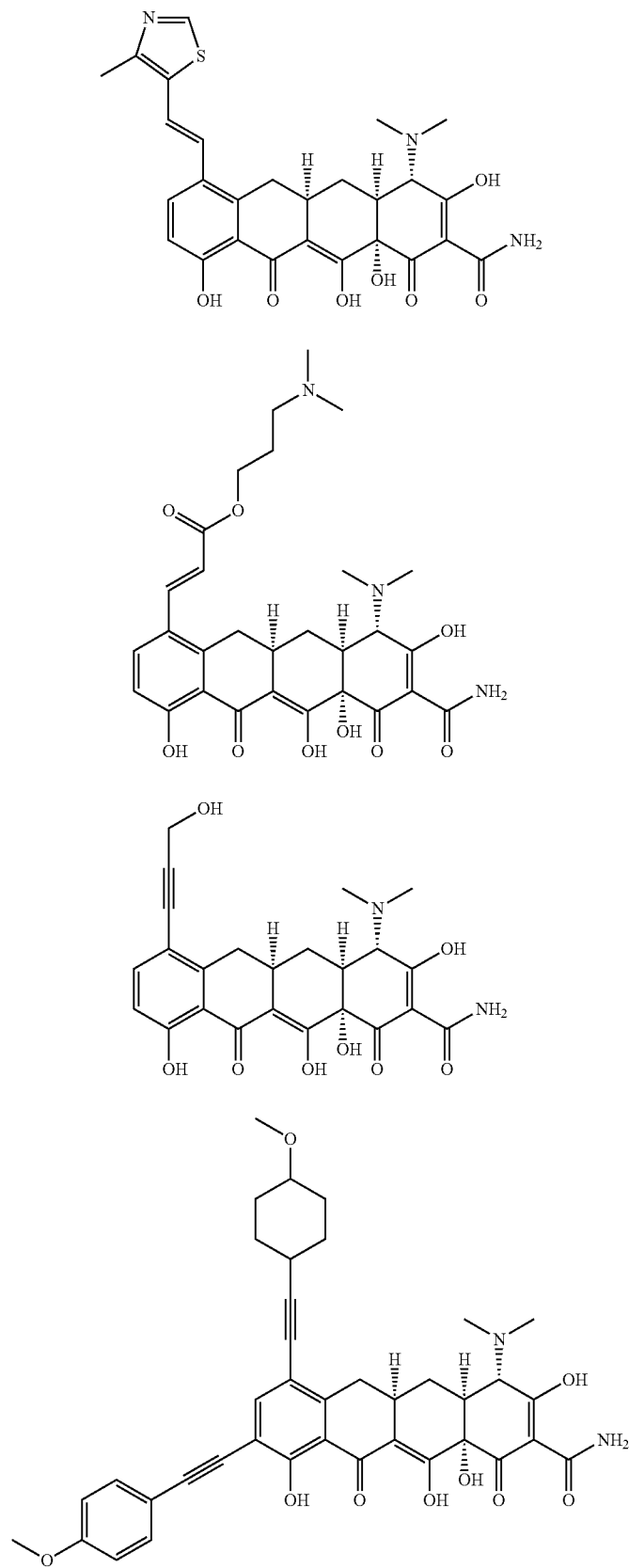

TABLE 2-continued
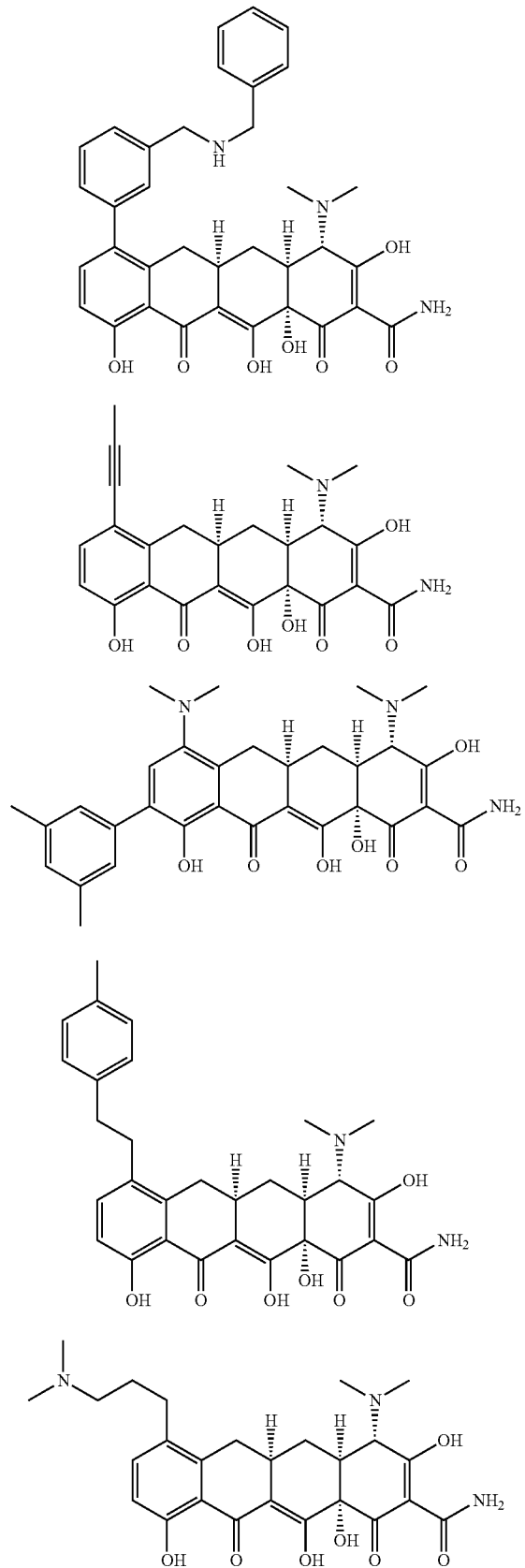

TABLE 2-continued
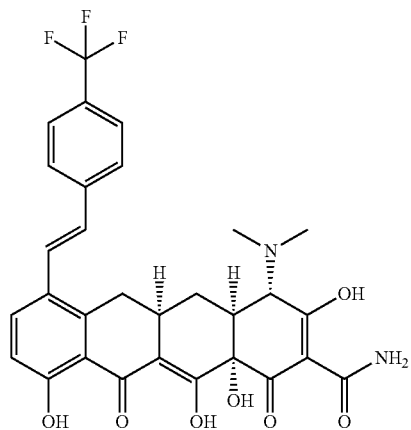
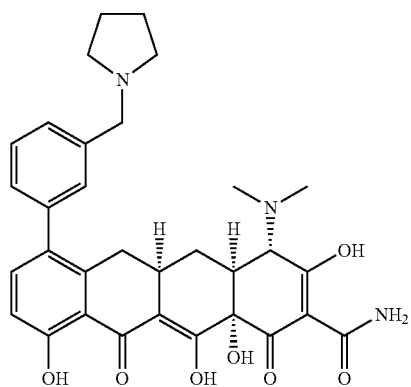
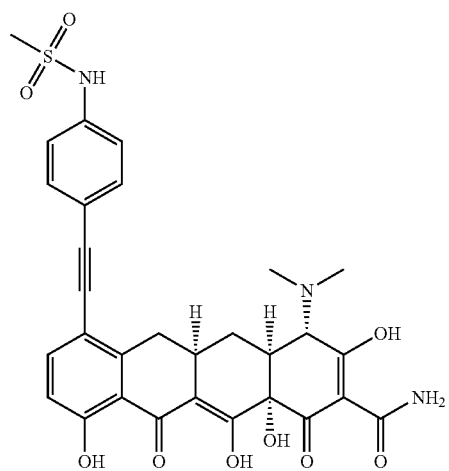

TABLE 2-continued
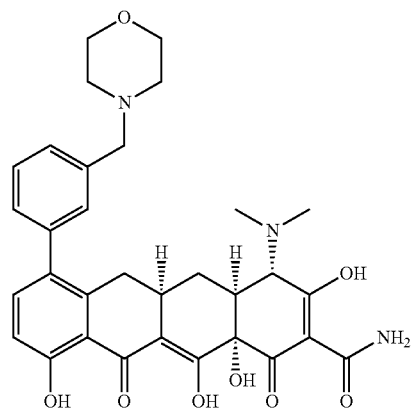
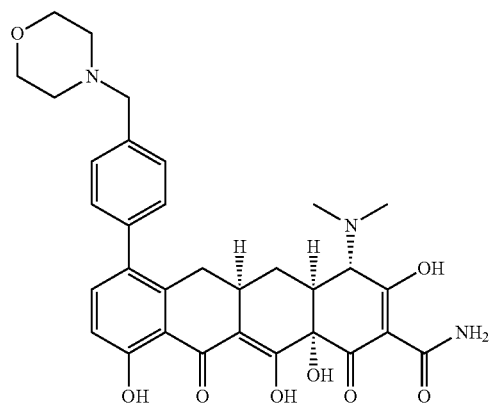
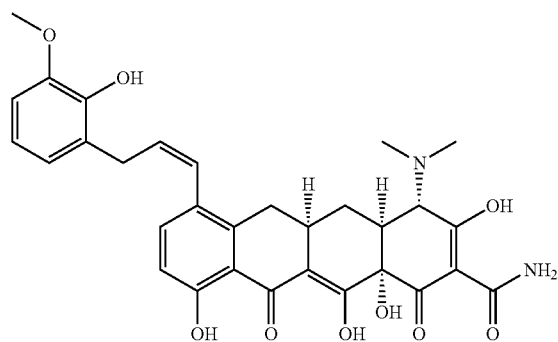
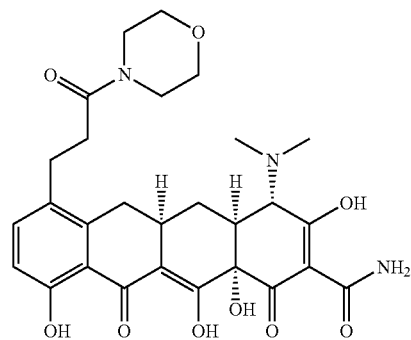

TABLE 2-continued
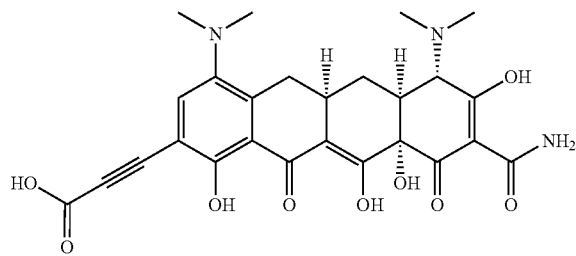
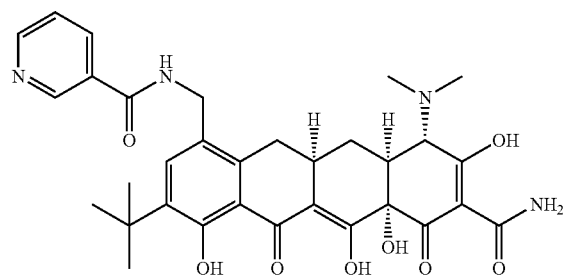
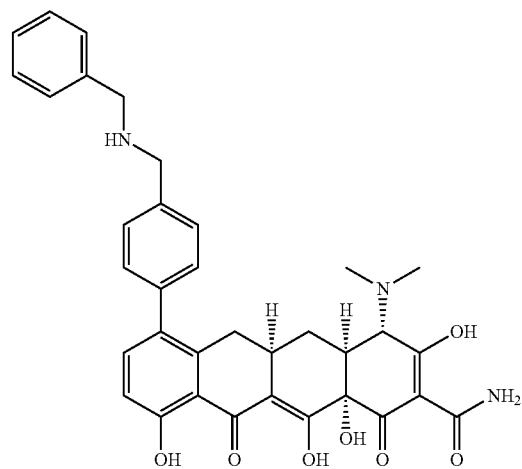
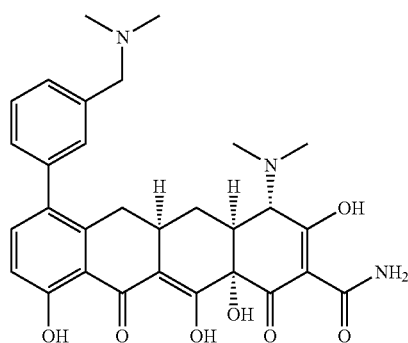

TABLE 2-continued
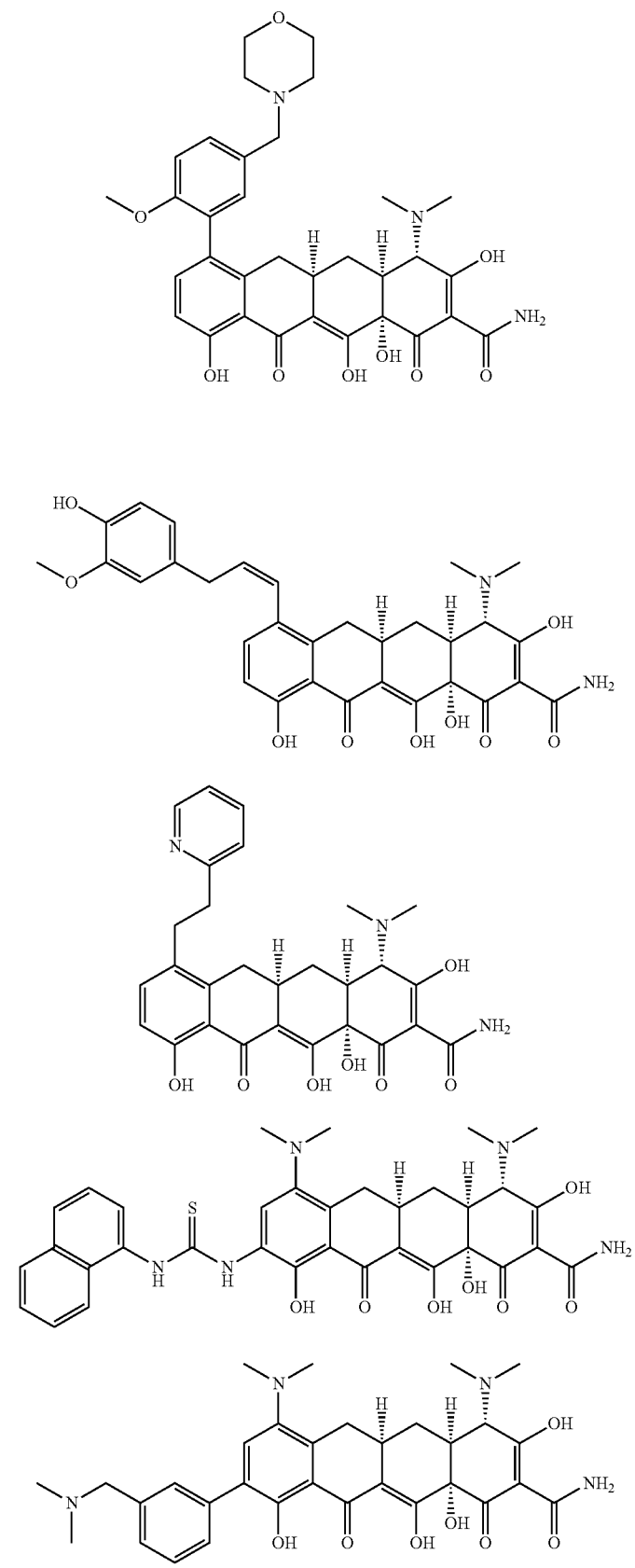

TABLE 2-continued
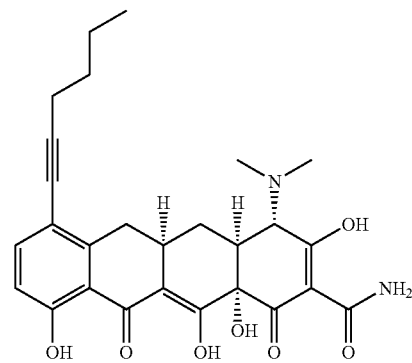
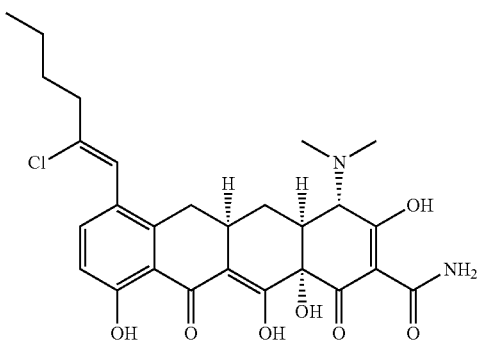
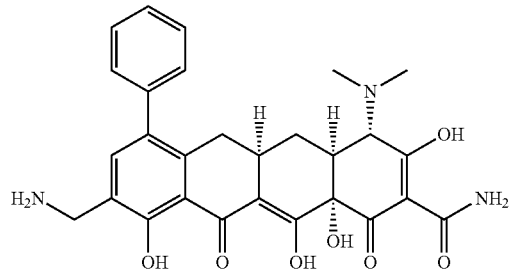
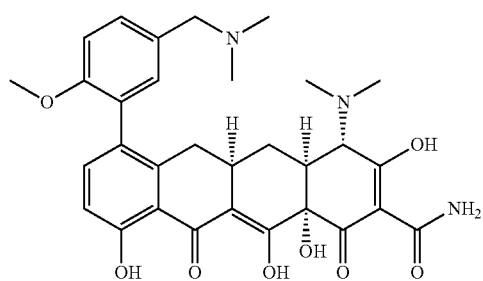
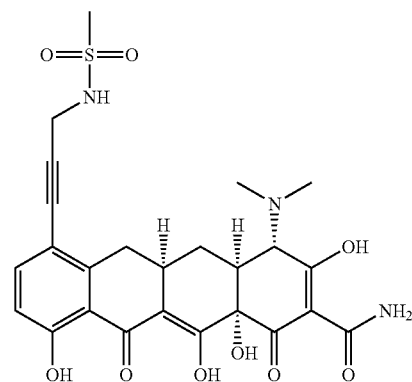

TABLE 2-continued
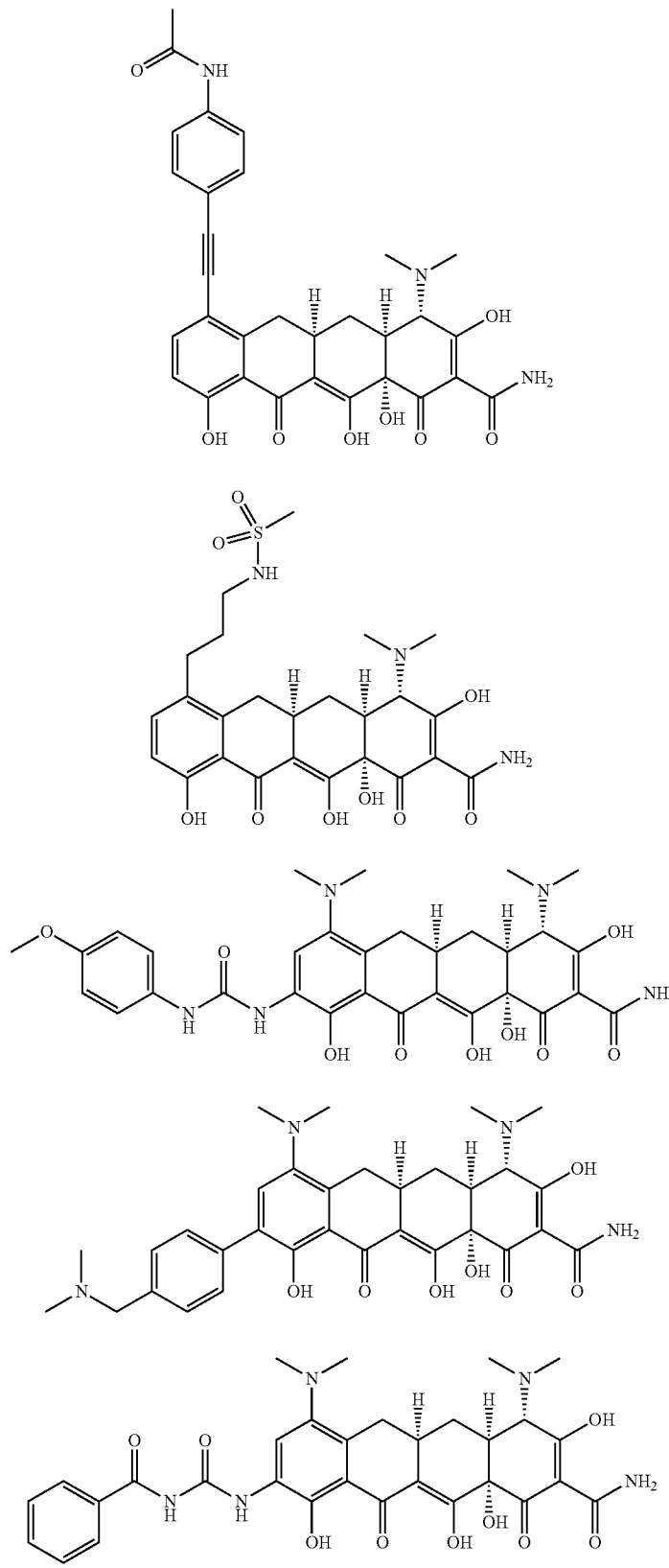

TABLE 2-continued
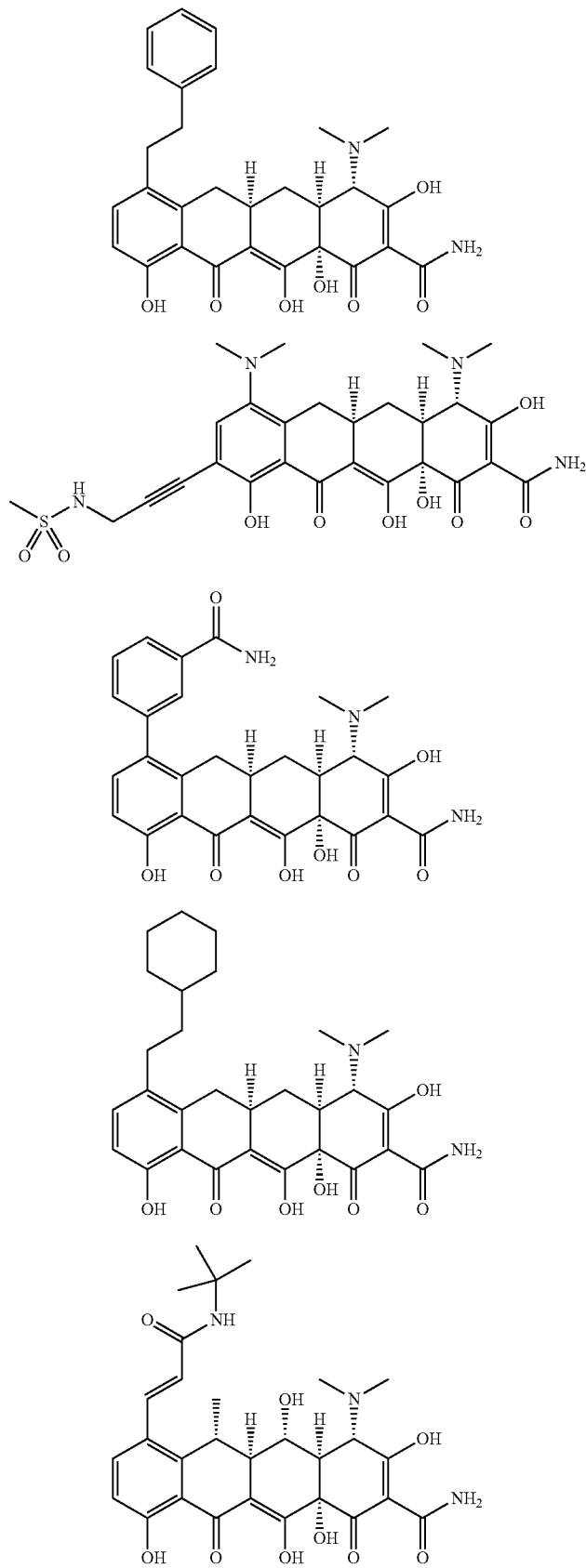

TABLE 2-continued
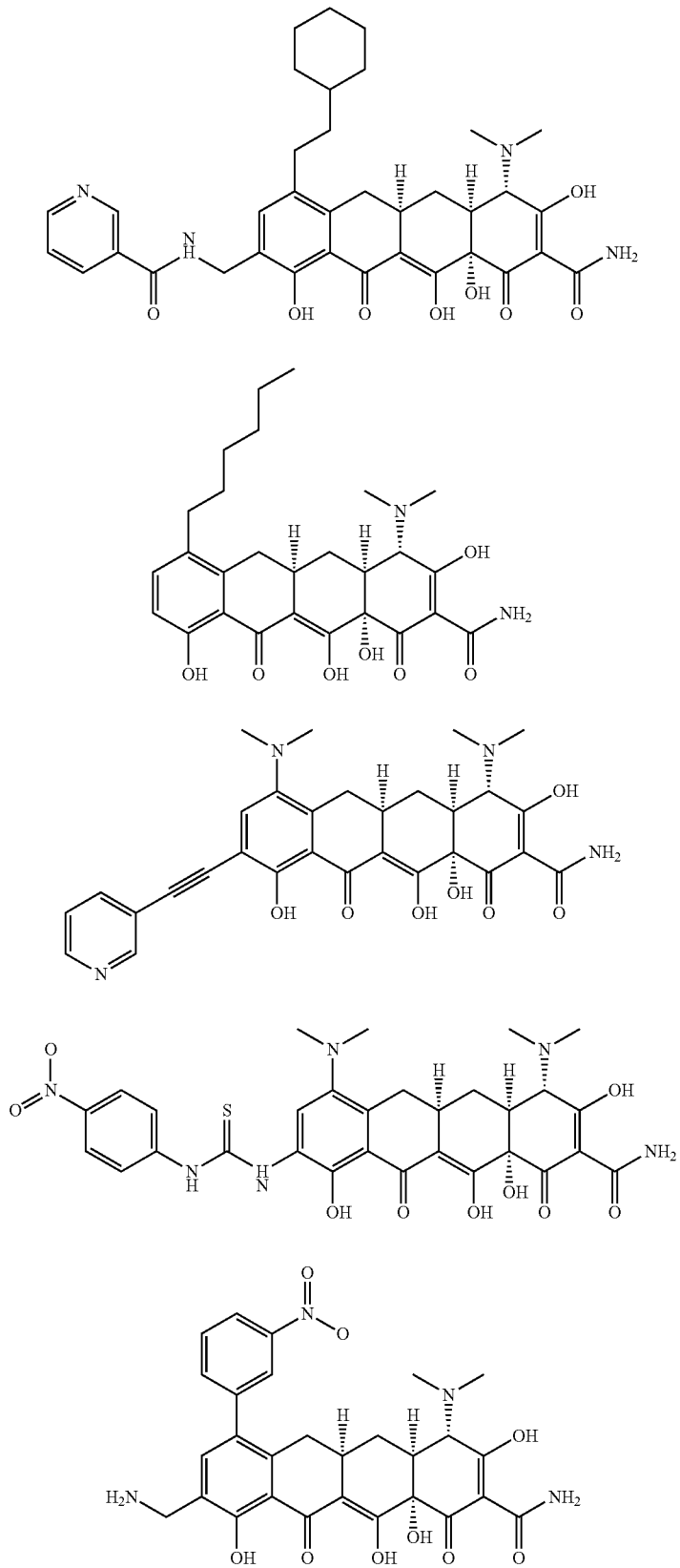

TABLE 2-continued
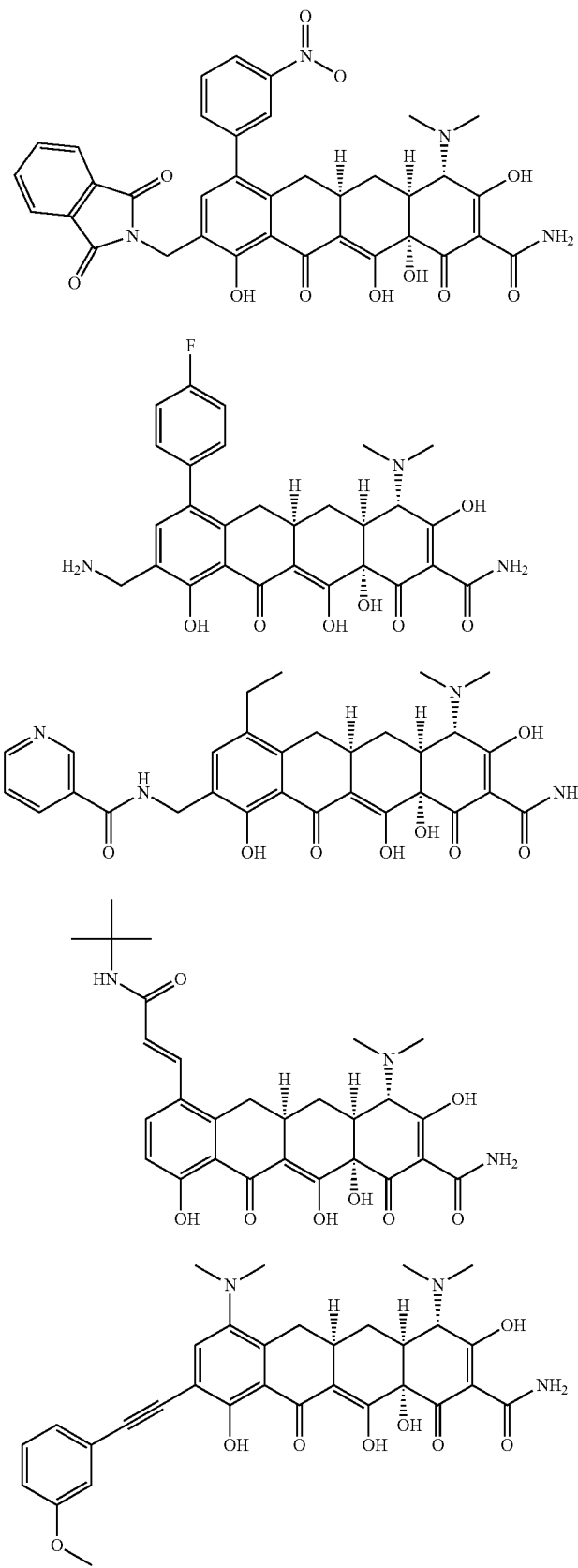

TABLE 2-continued
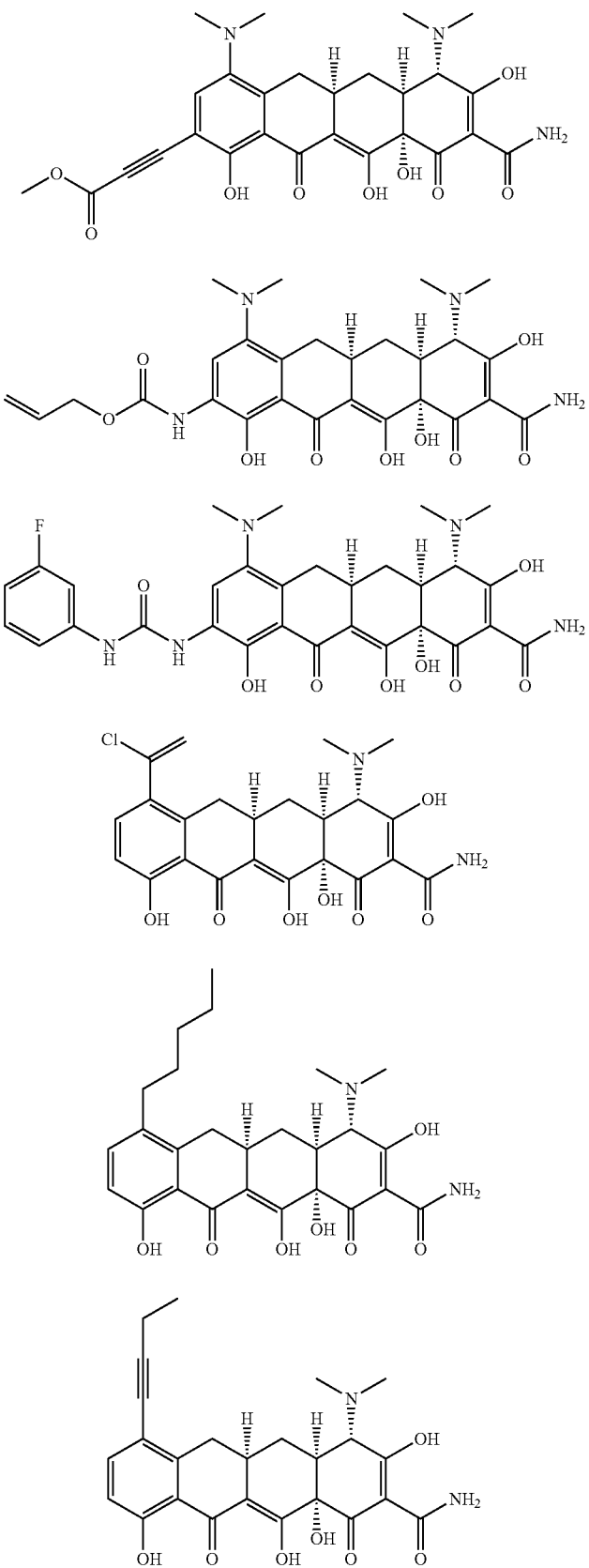

TABLE 2-continued
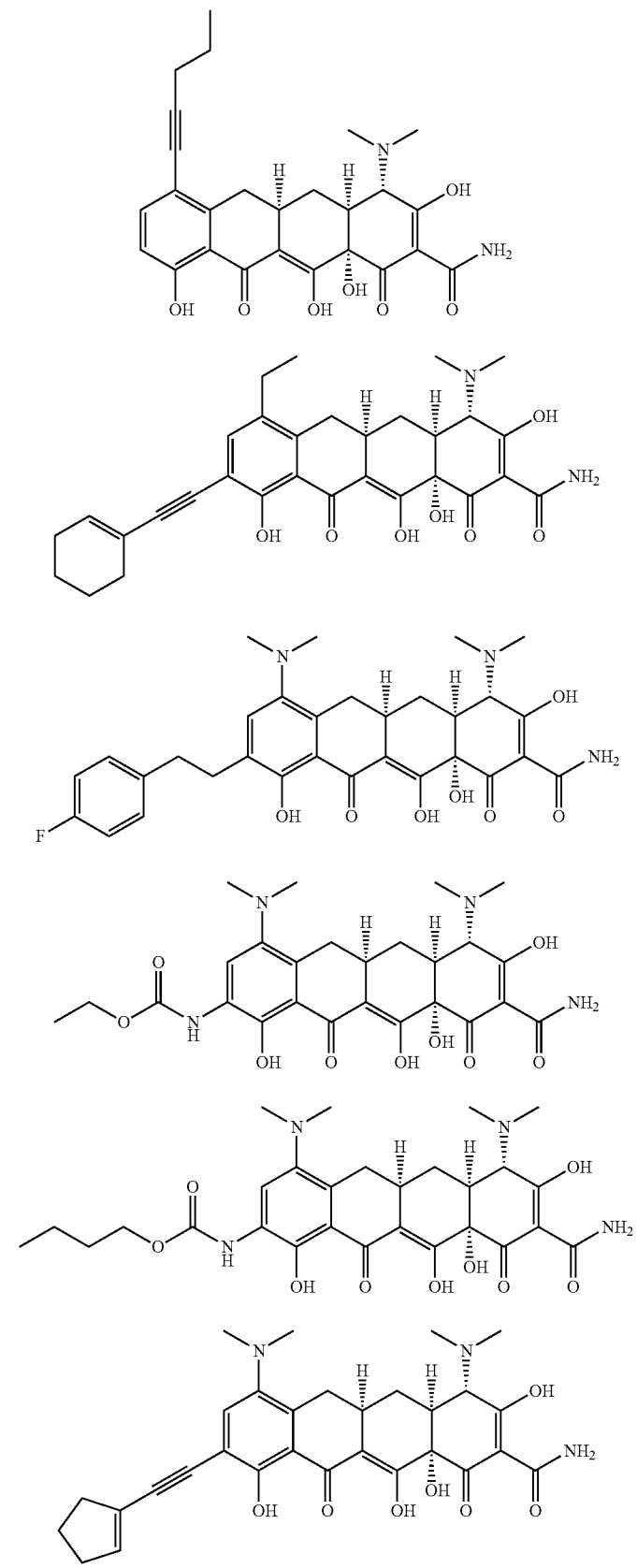

TABLE 2-continued
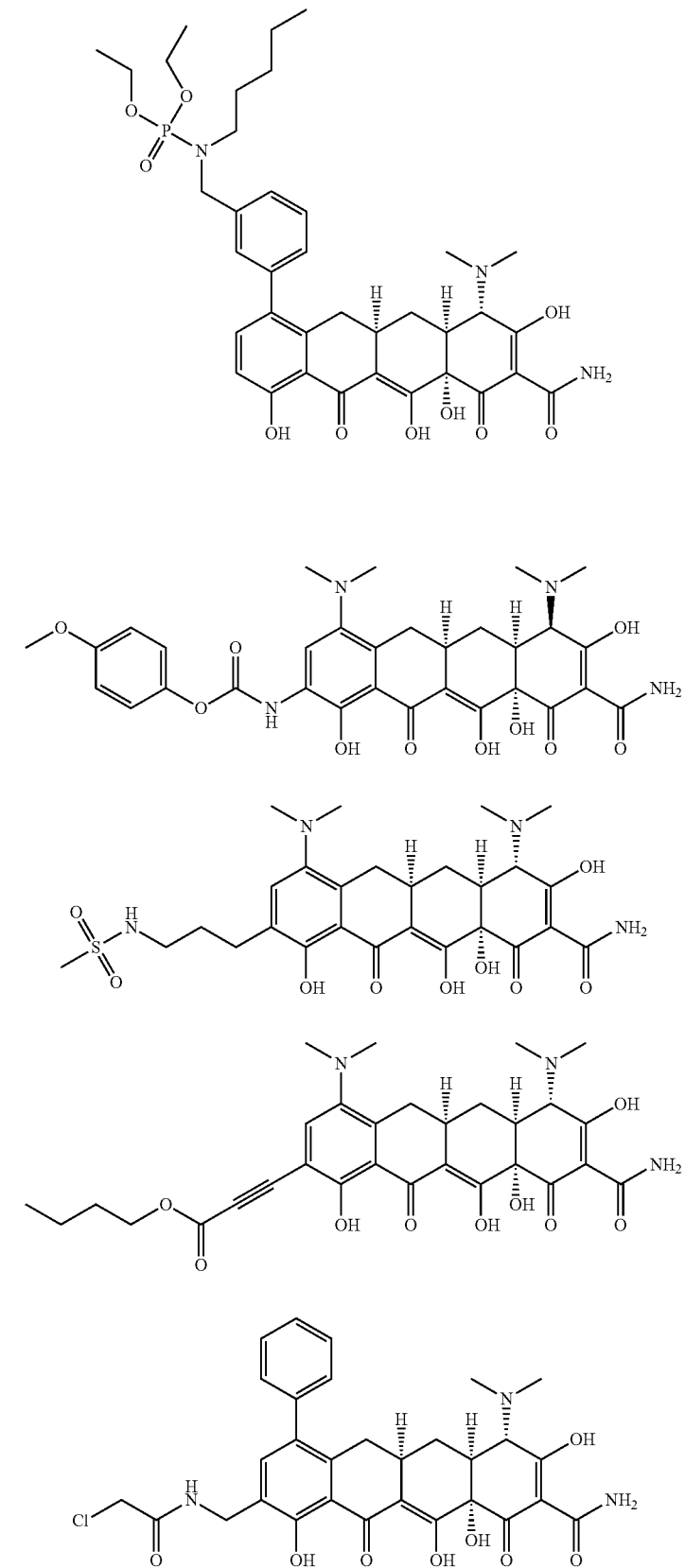

TABLE 2-continued
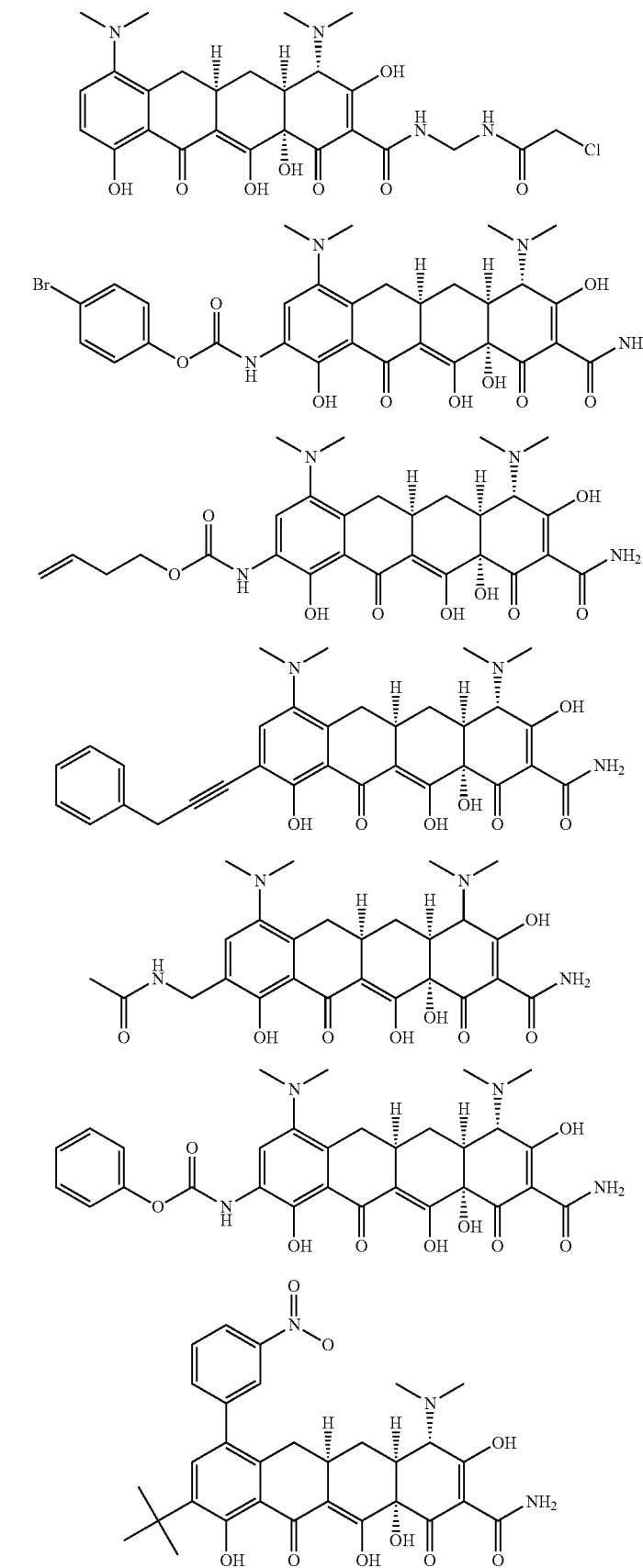

TABLE 2-continued
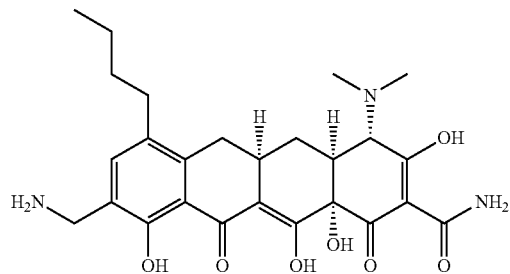
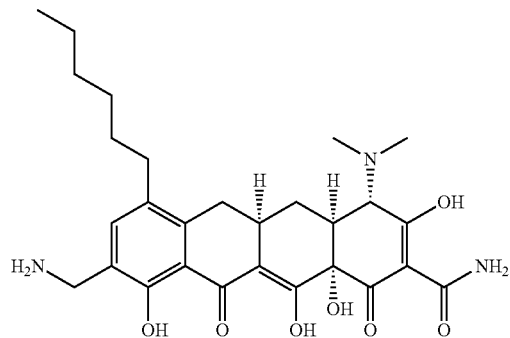
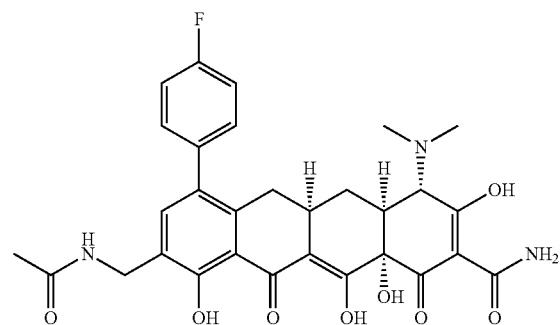
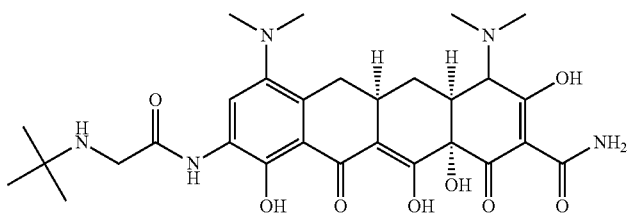
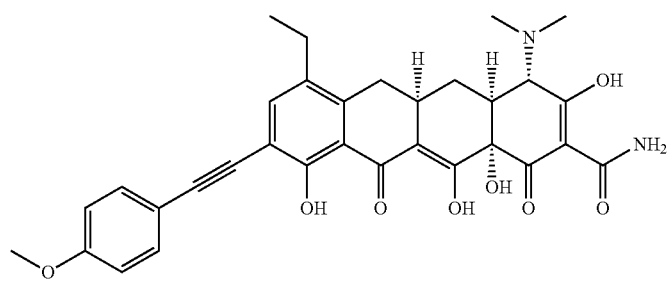

TABLE 2-continued
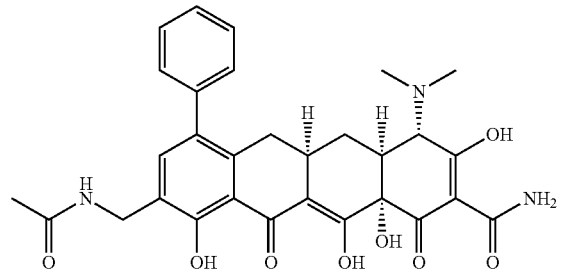
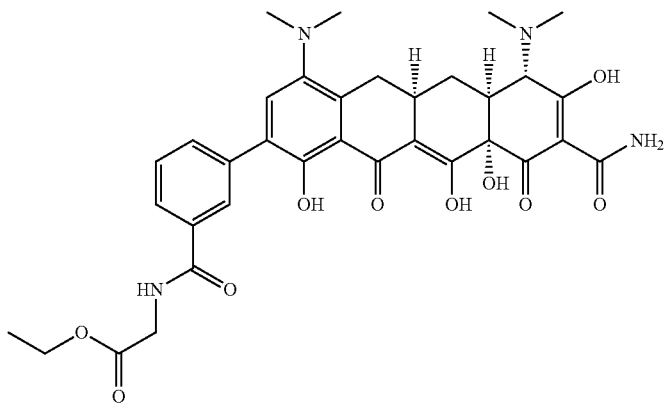
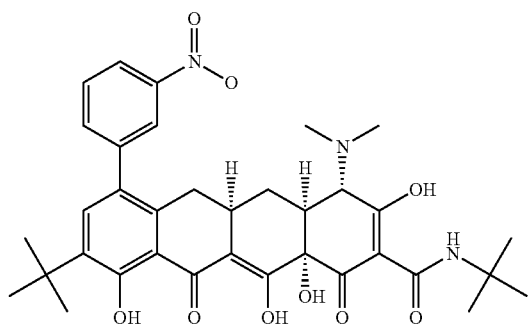
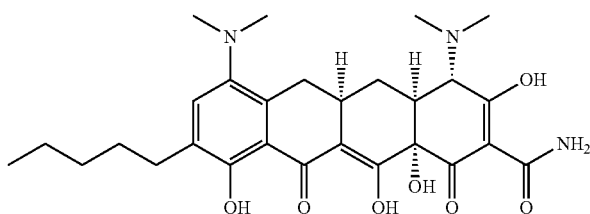
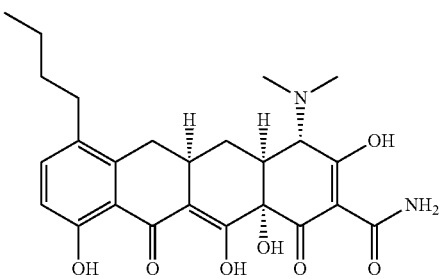

TABLE 2-continued
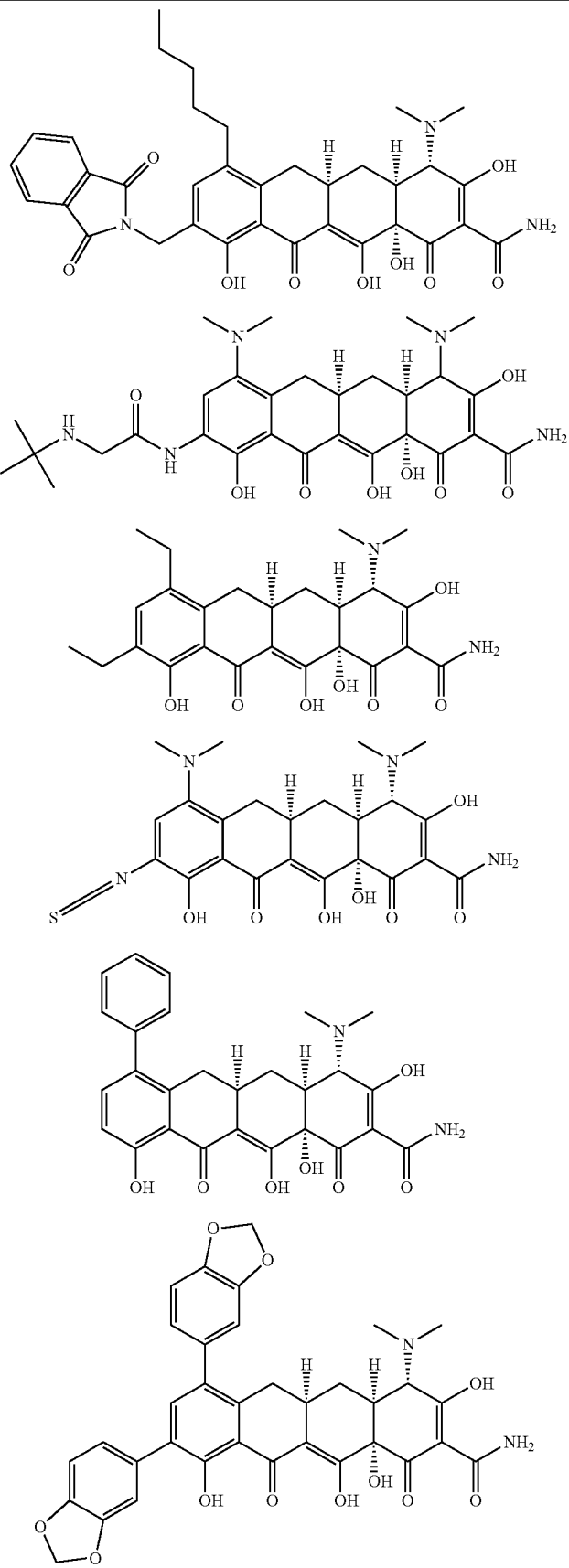

TABLE 2-continued
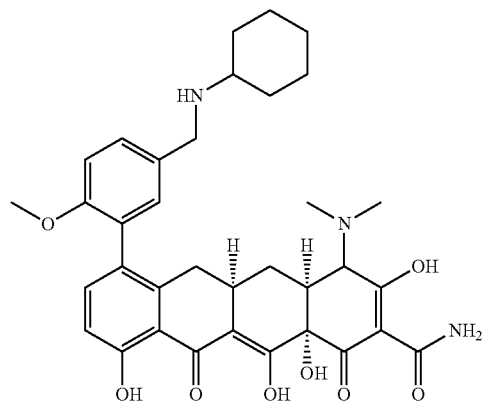
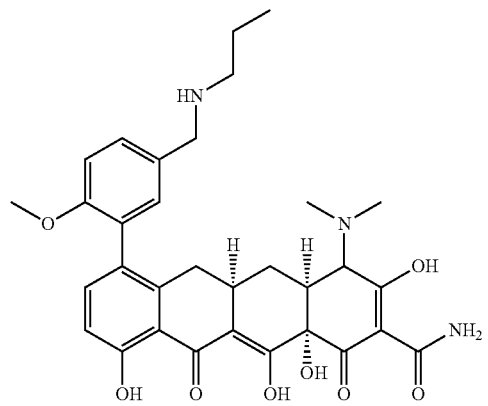
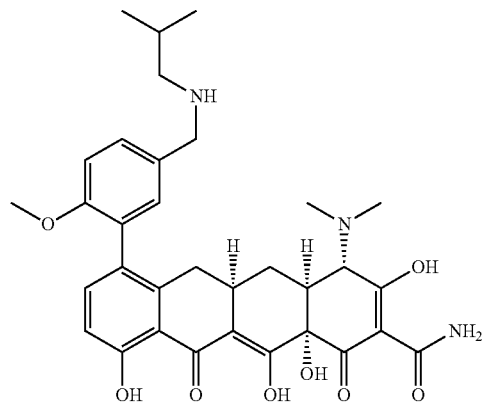
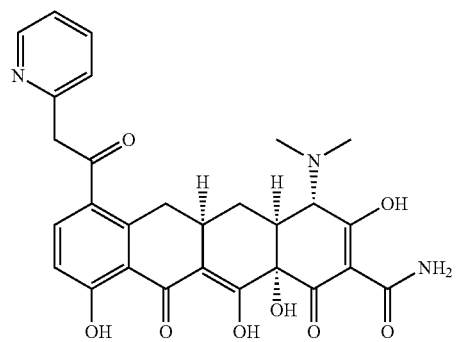

TABLE 2-continued
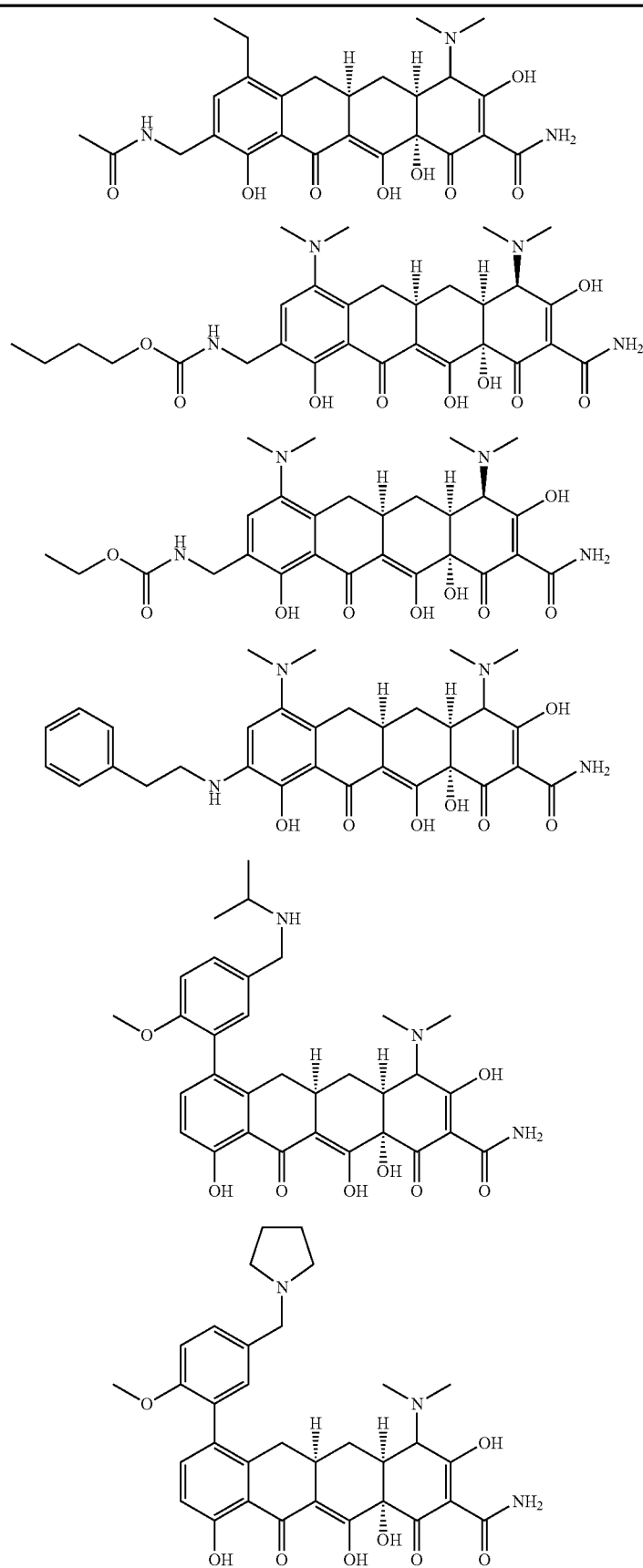

TABLE 2-continued
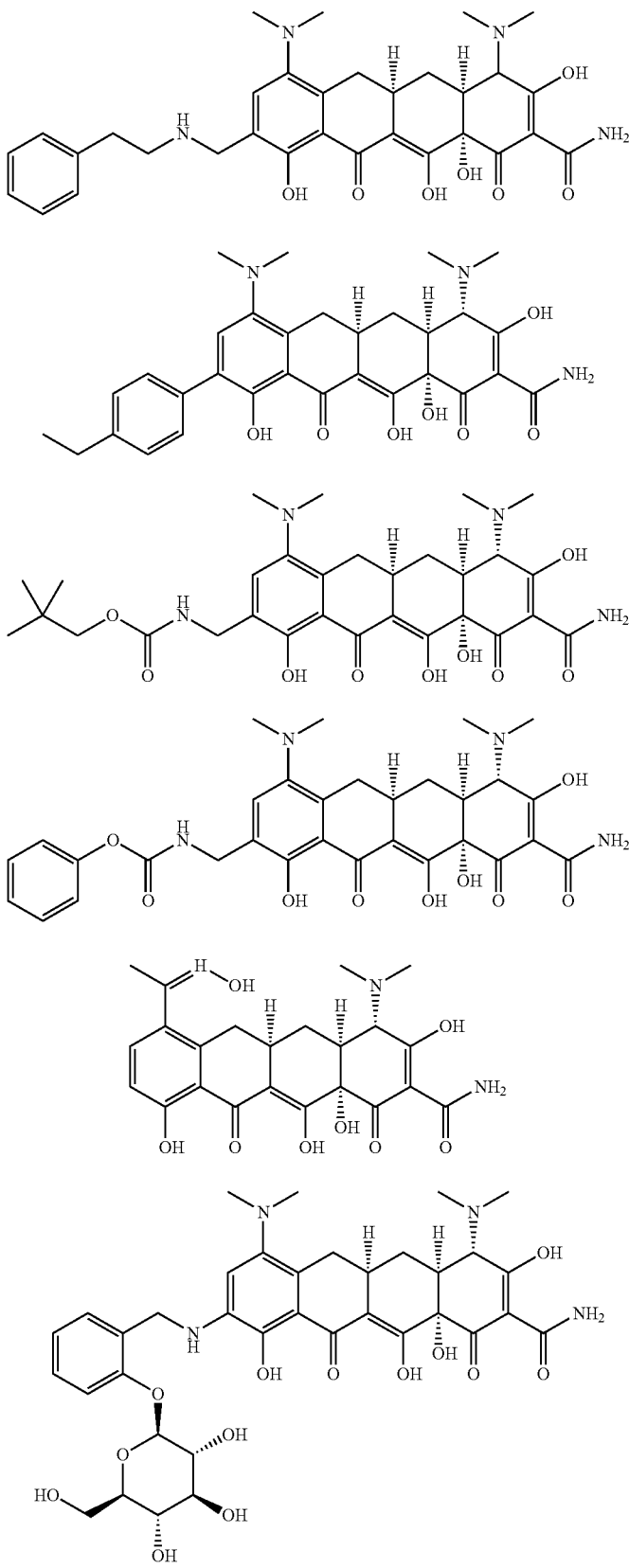

TABLE 2-continued
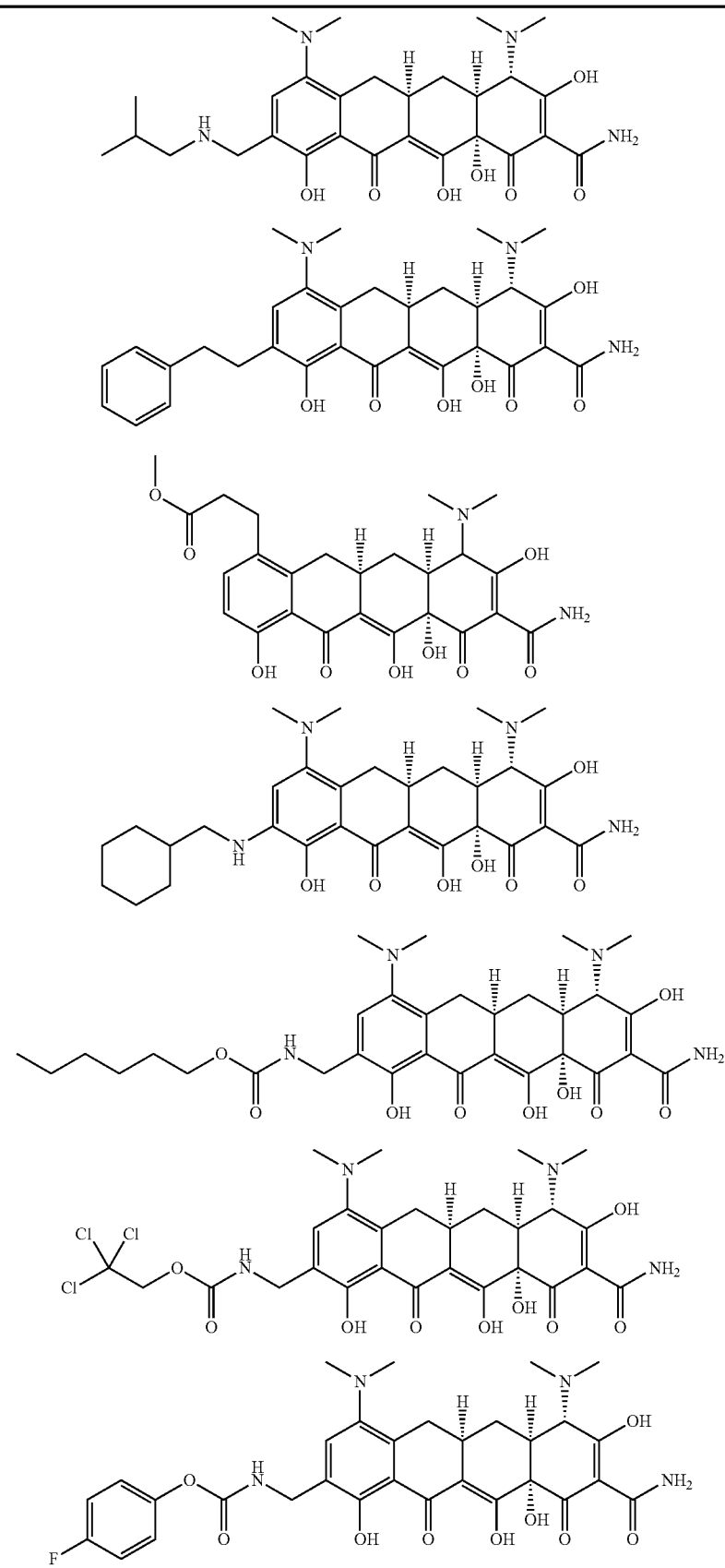

TABLE 2-continued
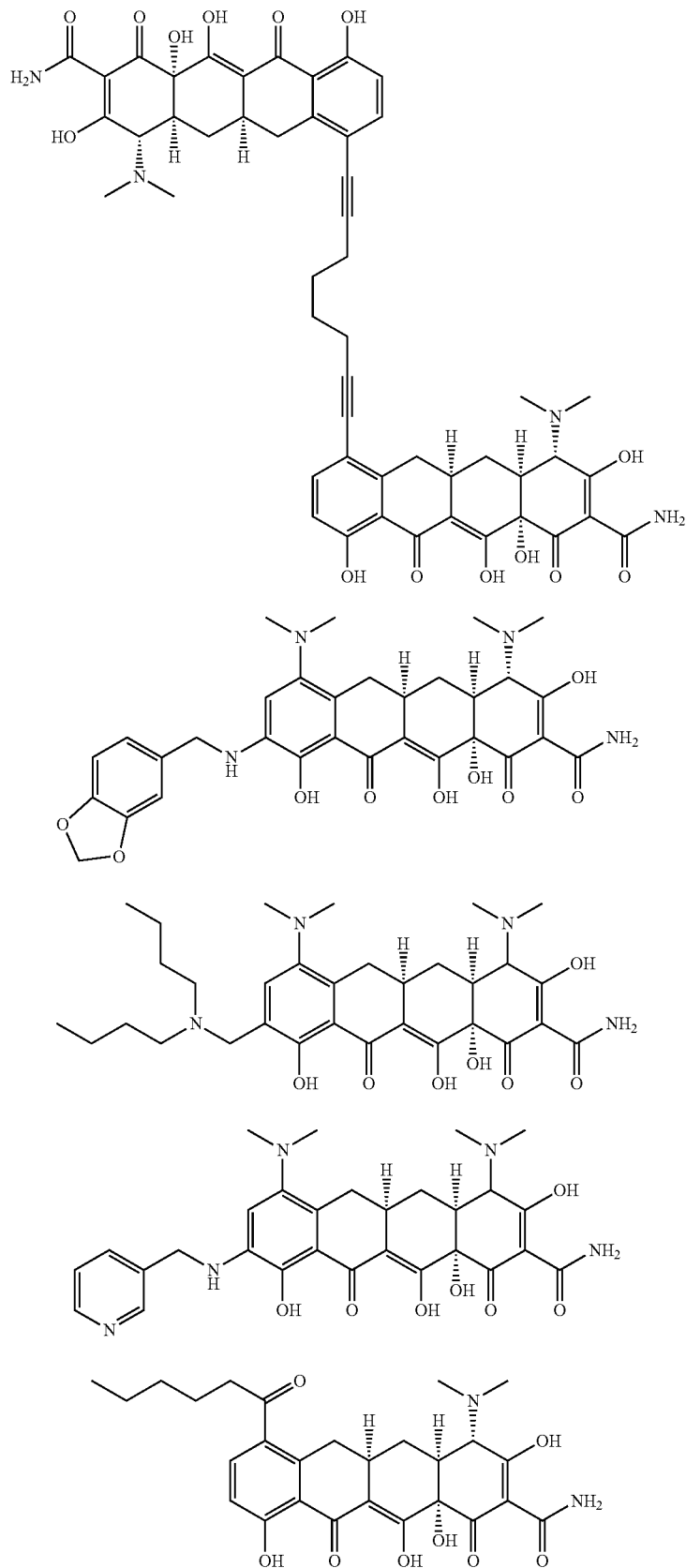

TABLE 2-continued
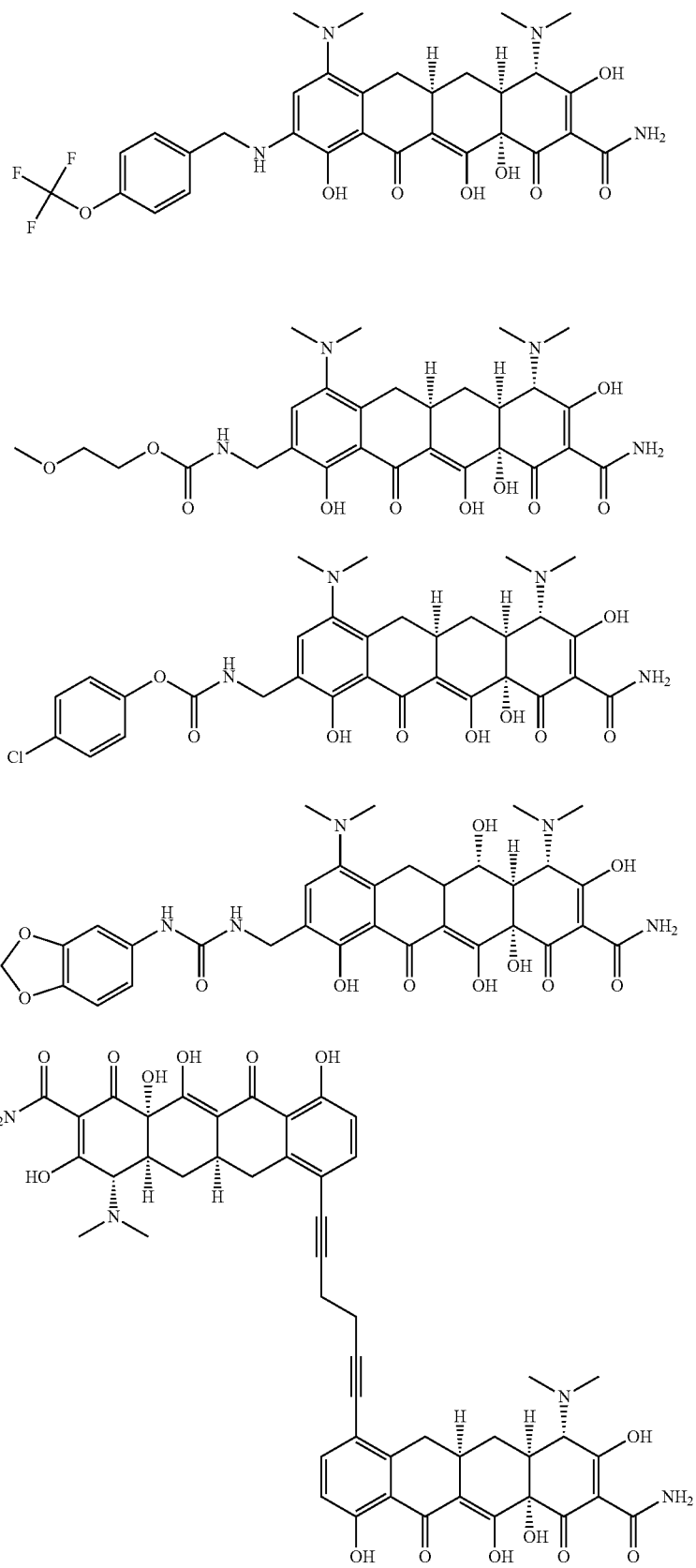

TABLE 2-continued
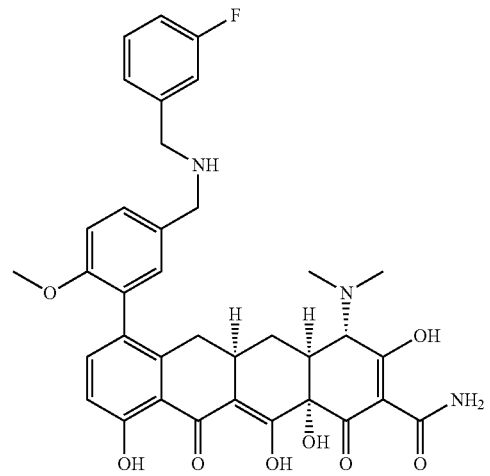
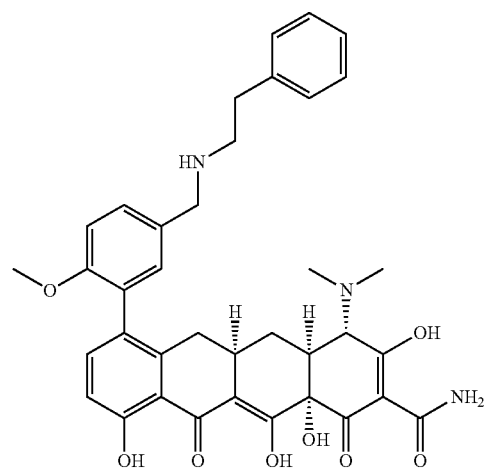
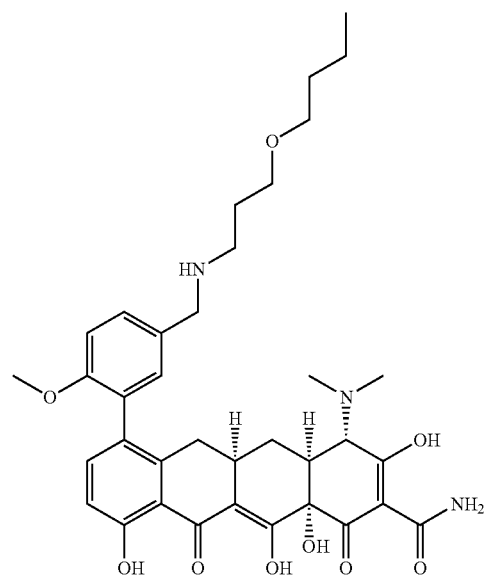

TABLE 2-continued
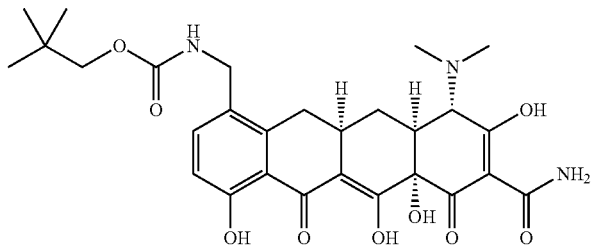
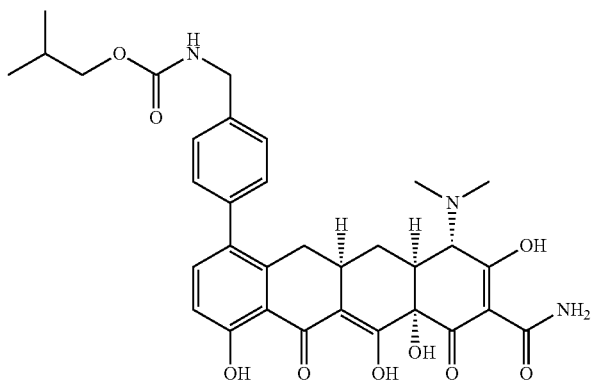
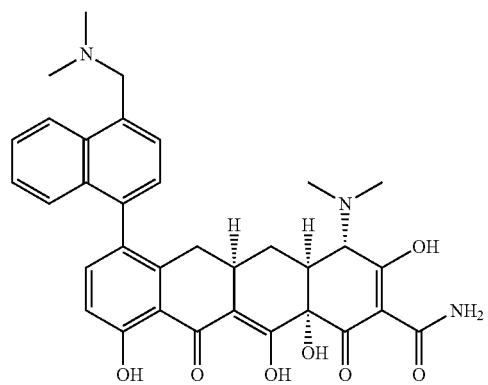
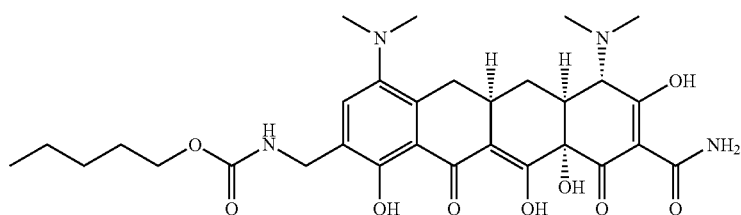
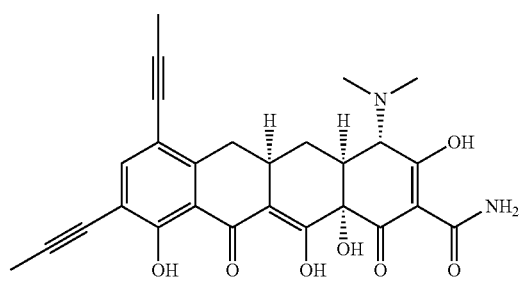

TABLE 2-continued
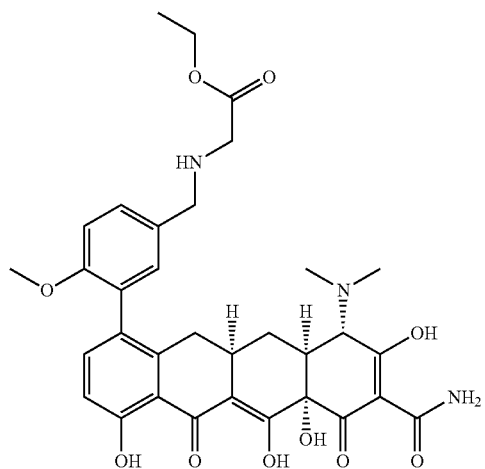
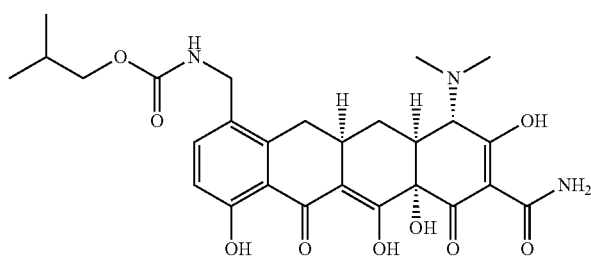
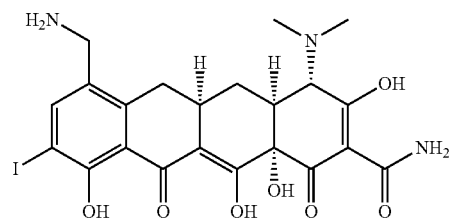
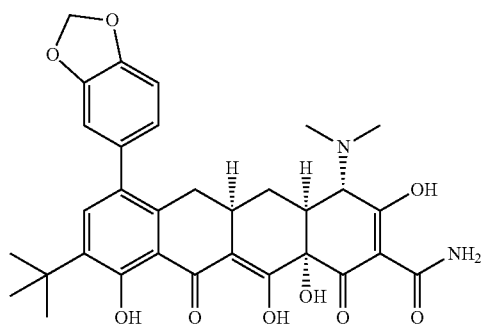
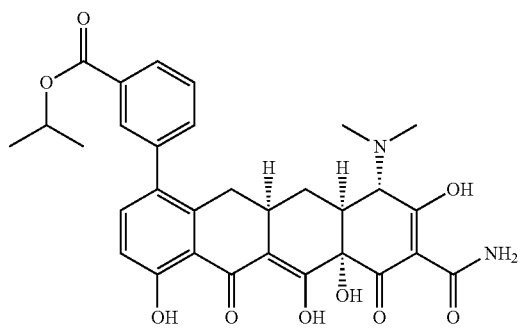

TABLE 2-continued
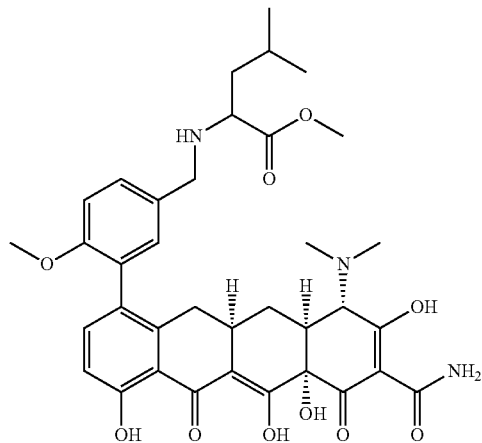
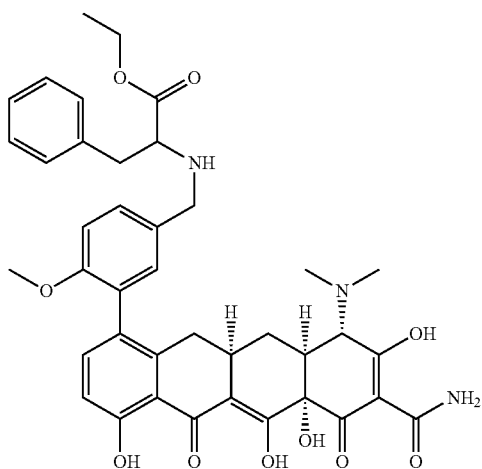
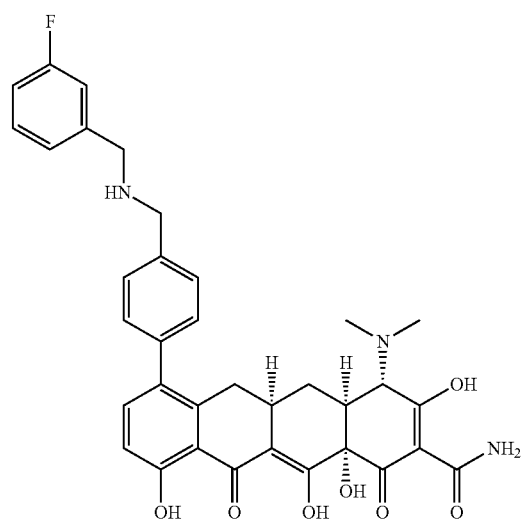

TABLE 2-continued
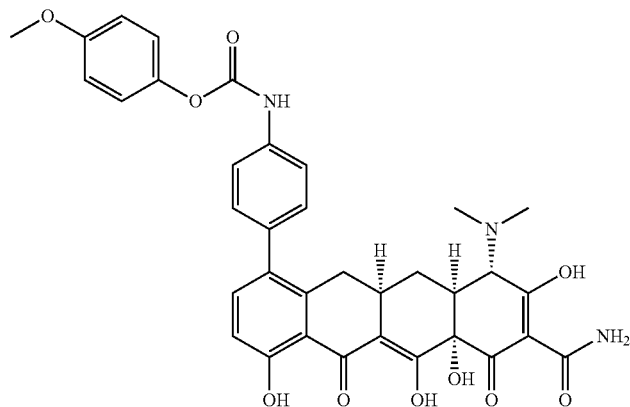
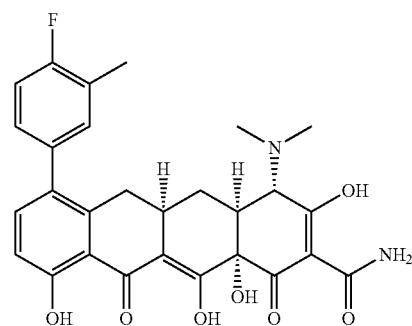
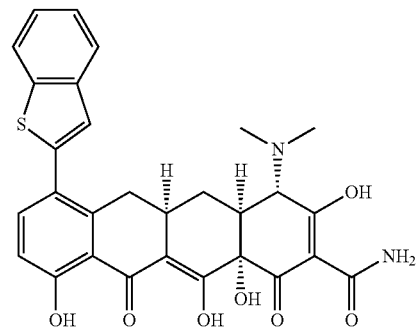
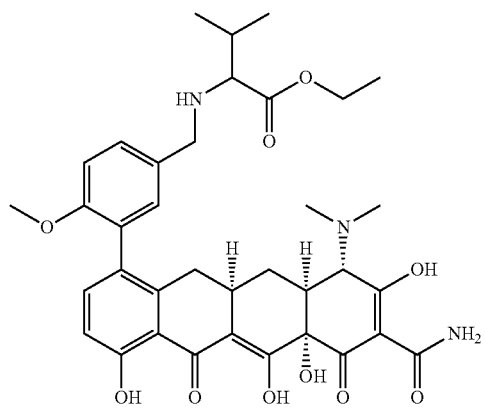

TABLE 2-continued
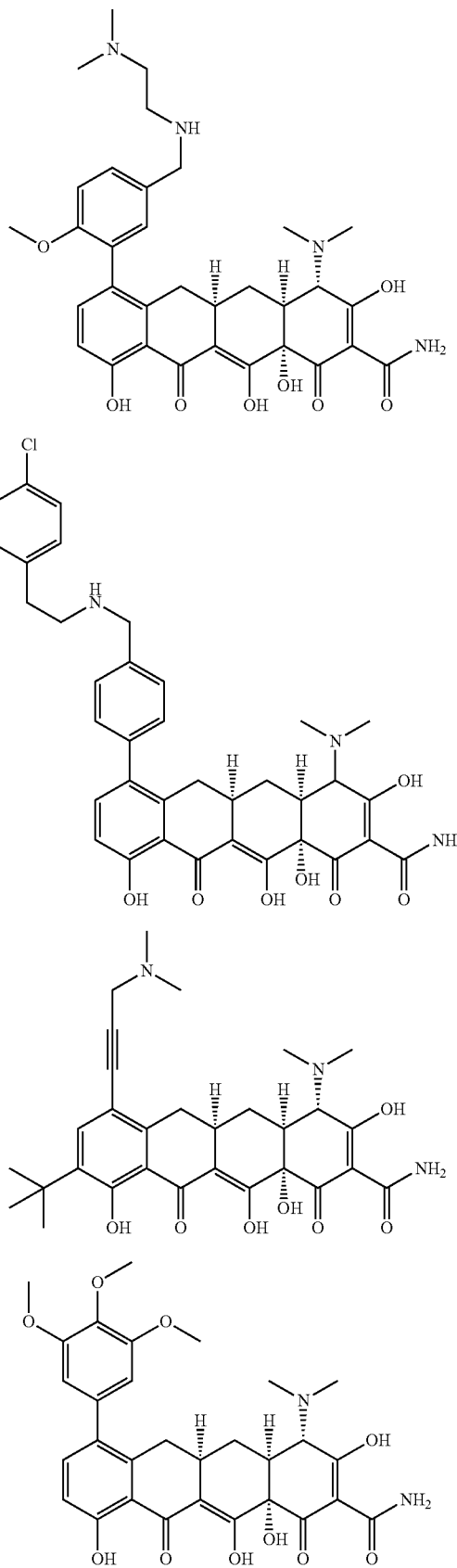

TABLE 2-continued
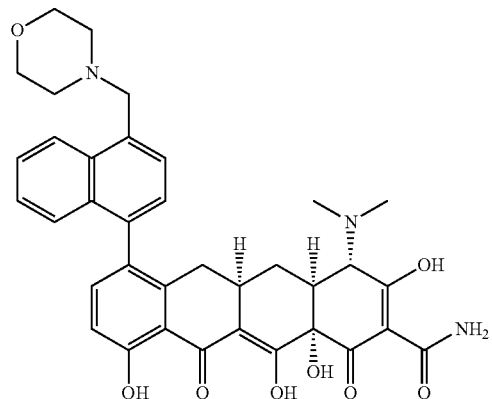
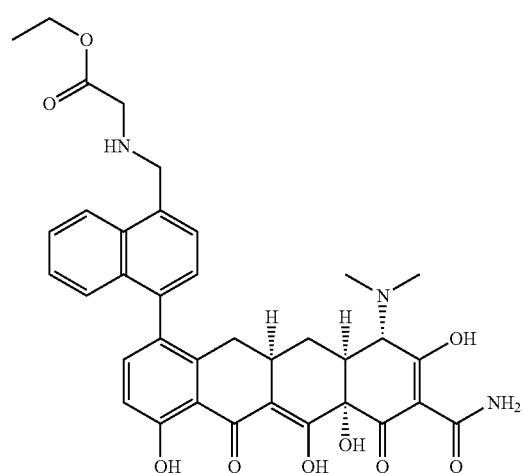
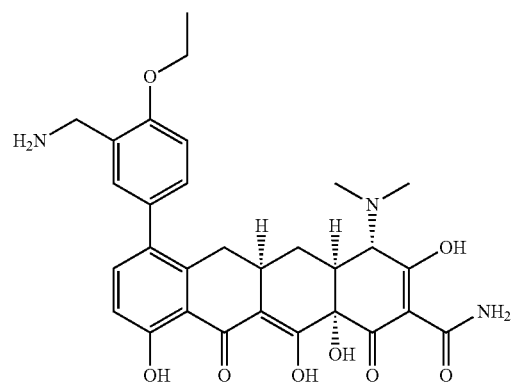

TABLE 2-continued
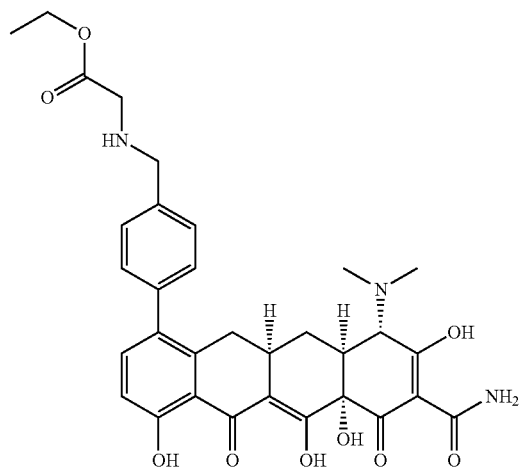
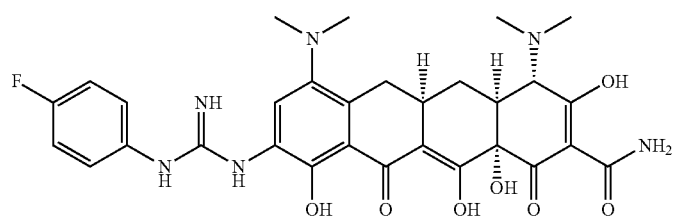
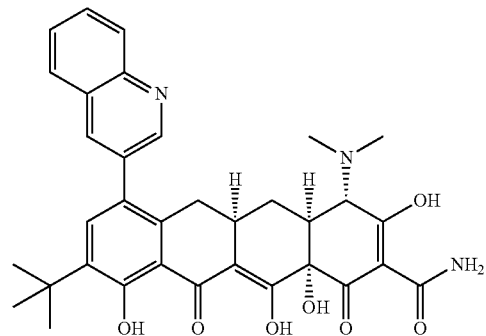
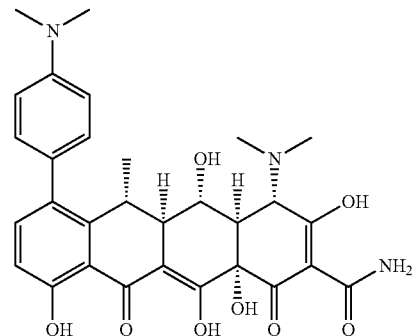

TABLE 2-continued
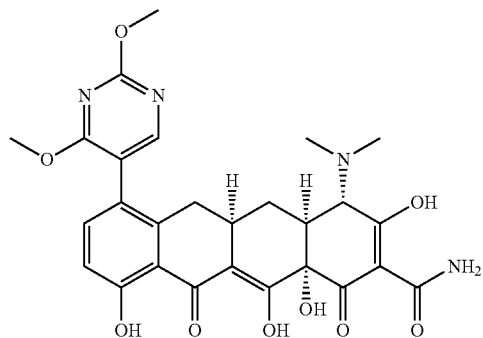
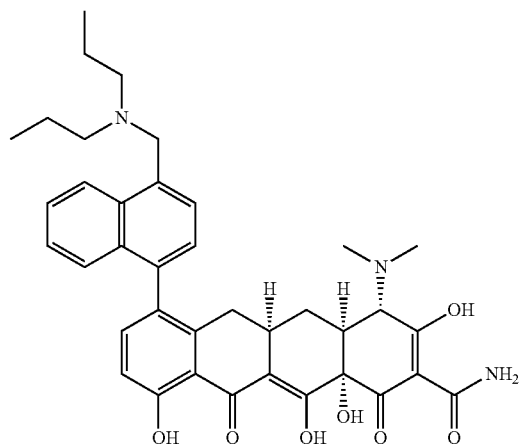
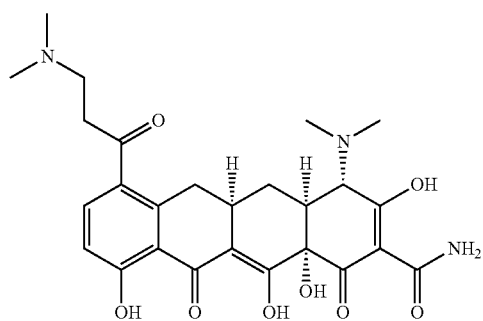
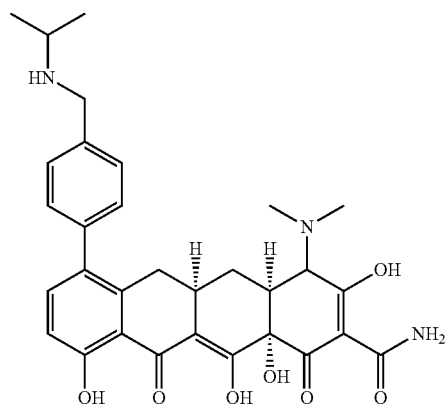

TABLE 2-continued
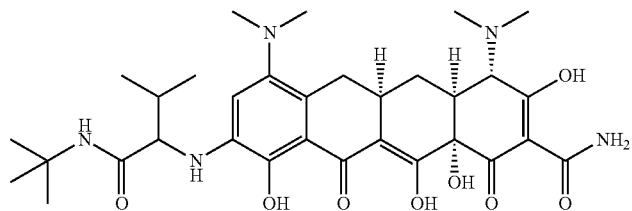
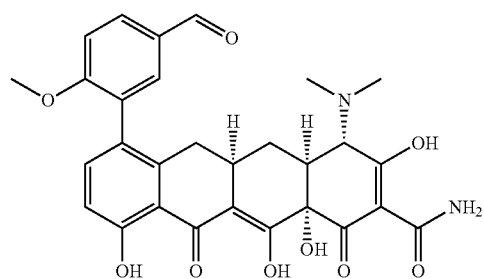
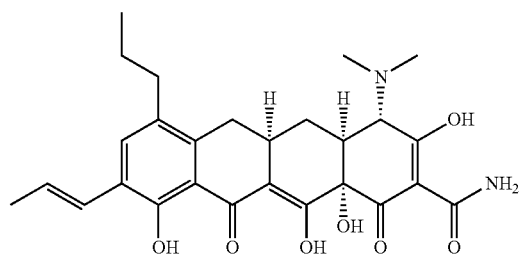
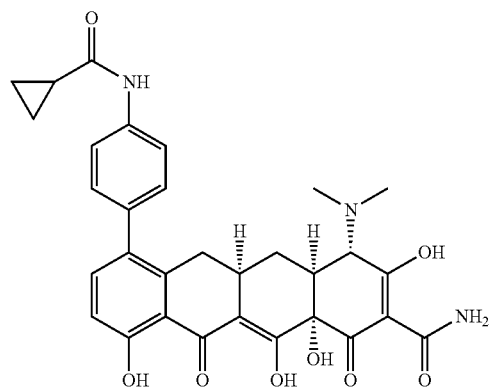
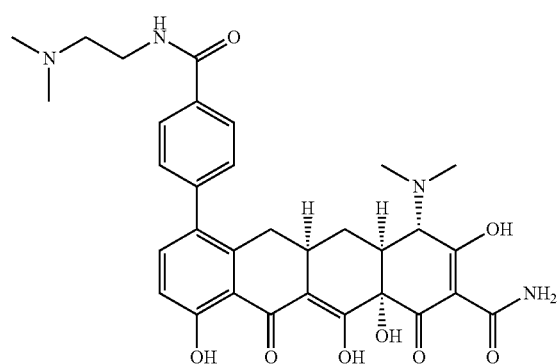

TABLE 2-continued
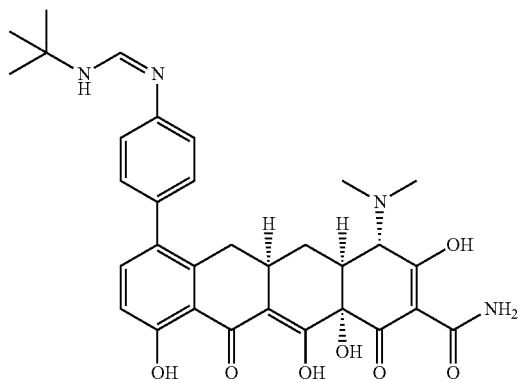
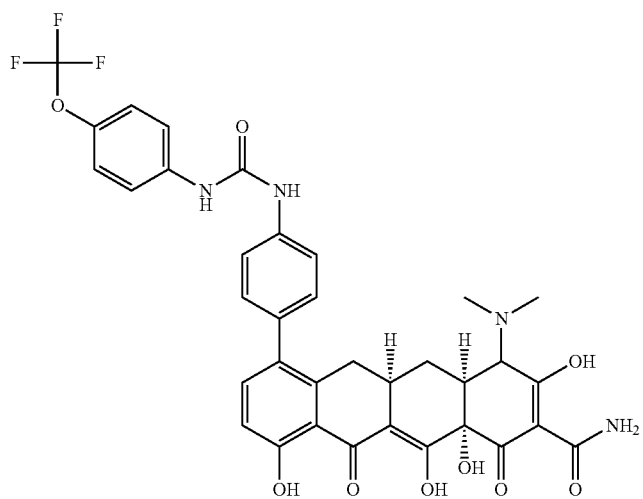
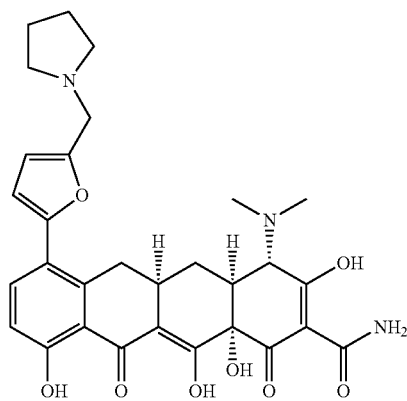
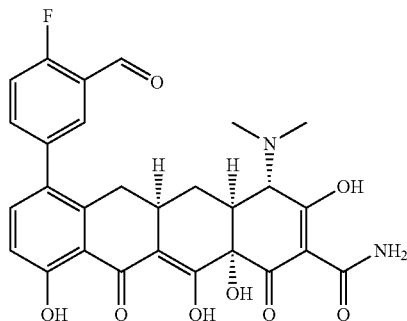

TABLE 2-continued
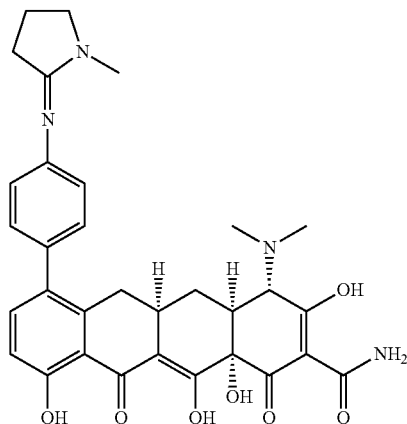
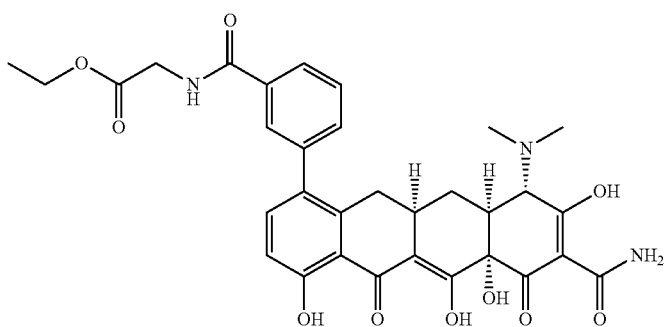
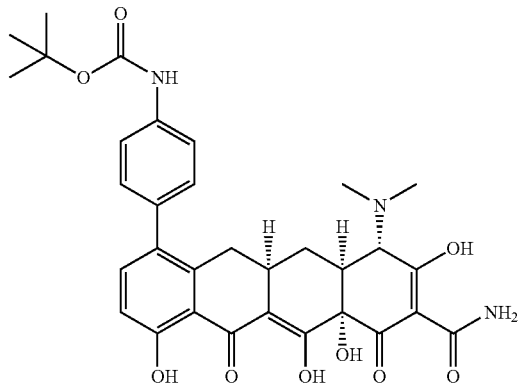
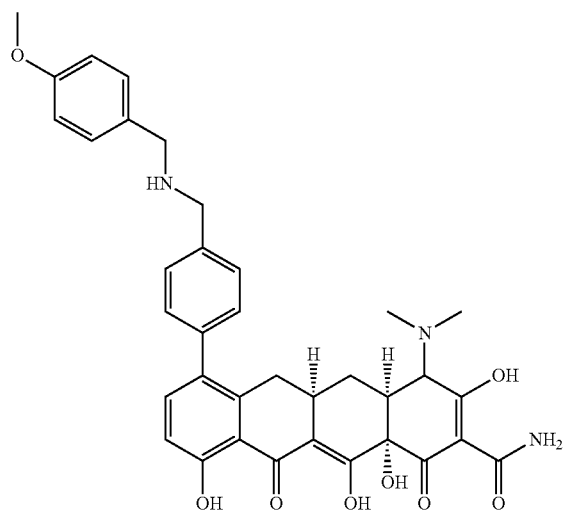

TABLE 2-continued
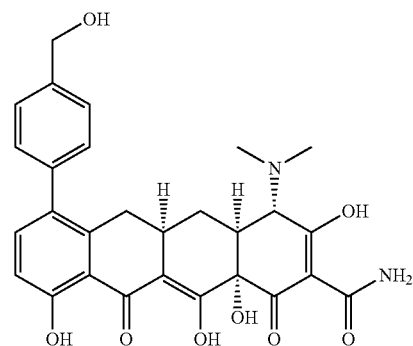
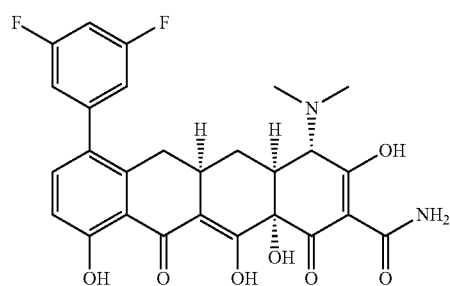
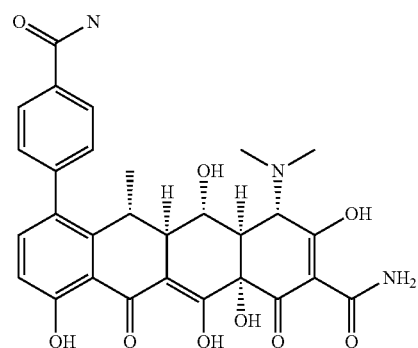
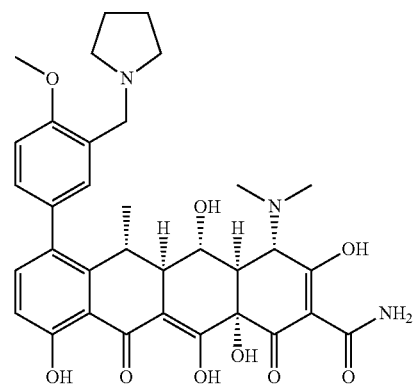

TABLE 2-continued
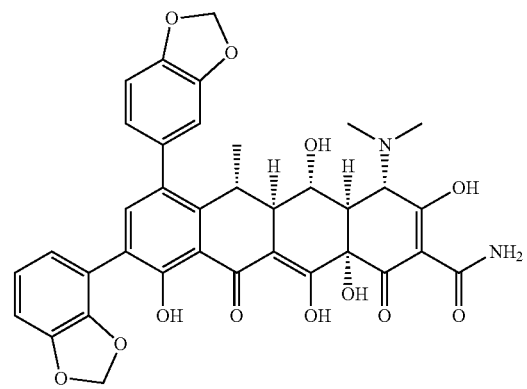
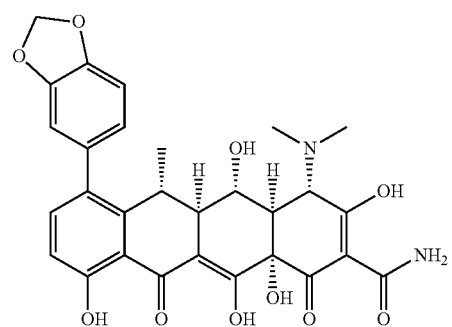
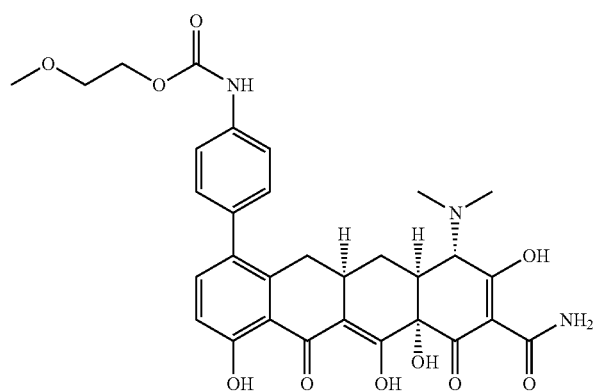
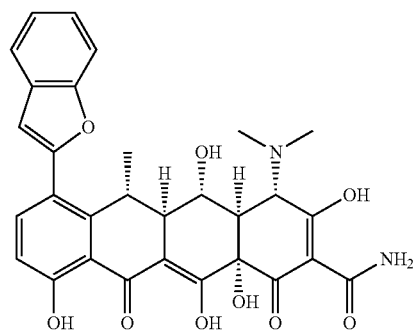

TABLE 2-continued
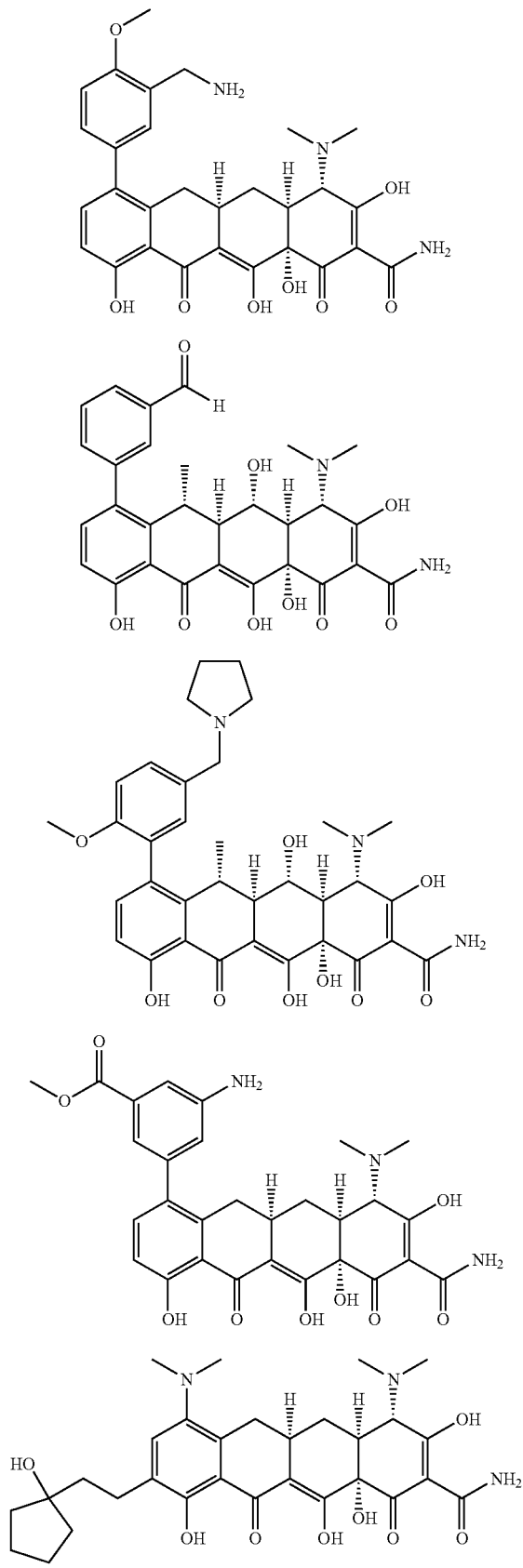

TABLE 2-continued
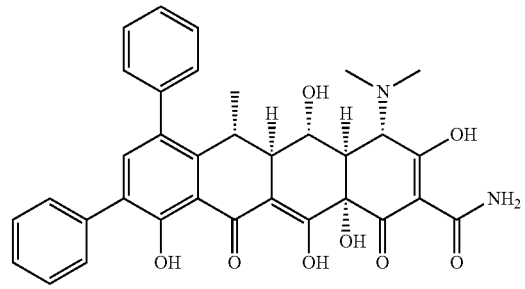
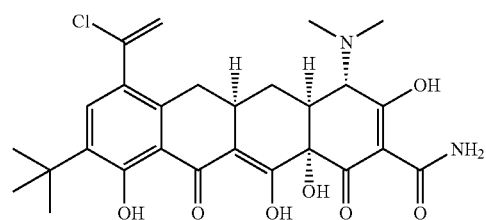
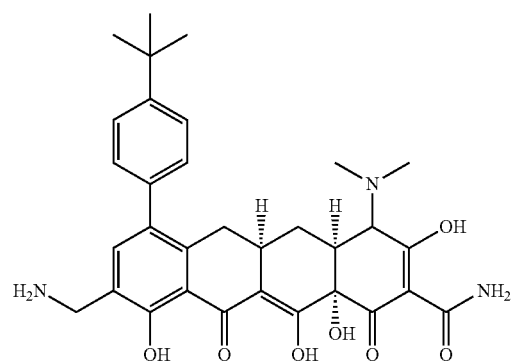
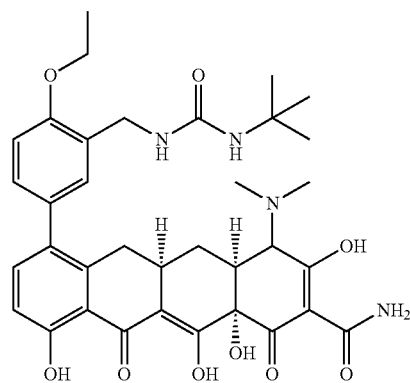

TABLE 2-continued
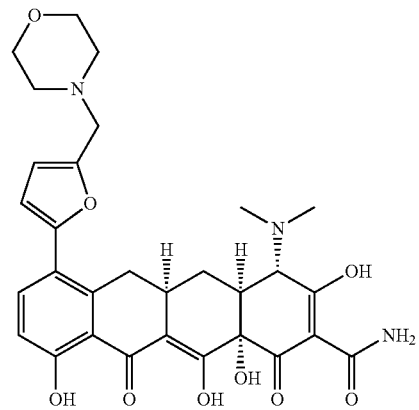
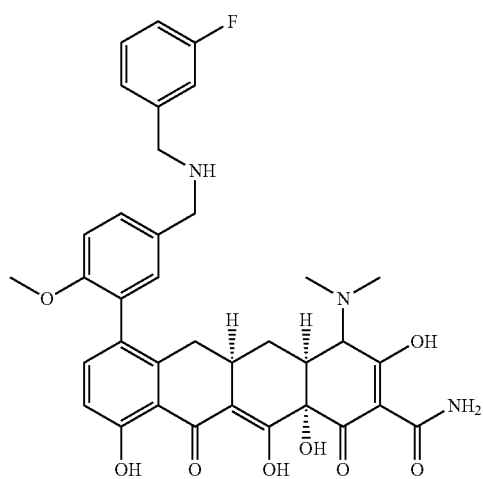
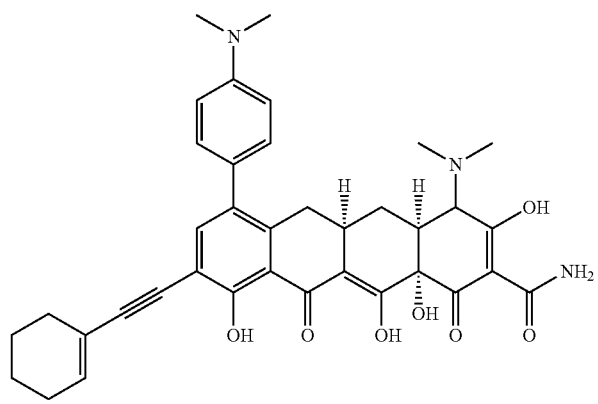

TABLE 2-continued
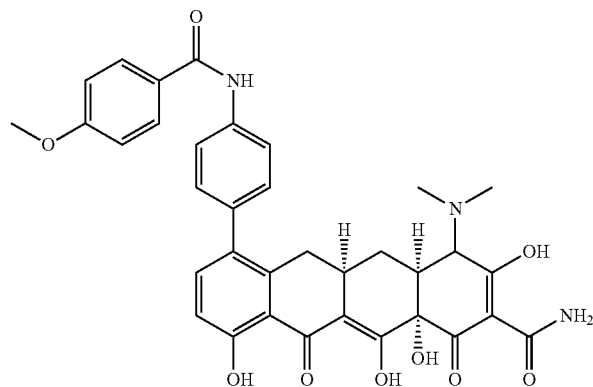
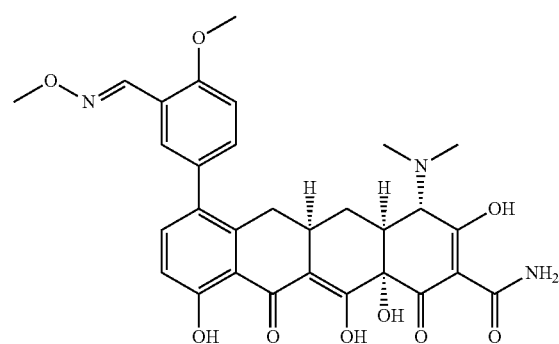
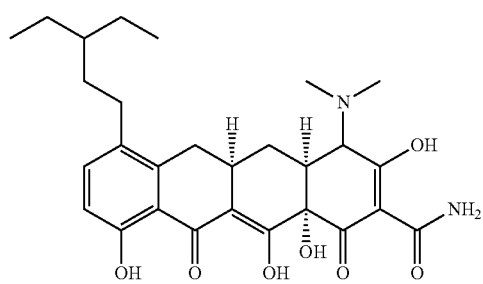
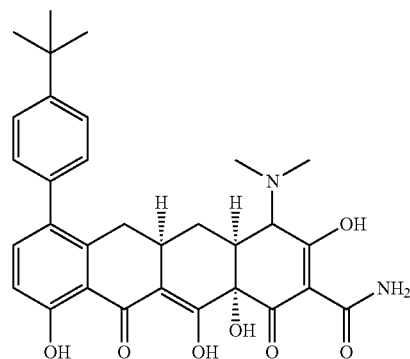

TABLE 2-continued
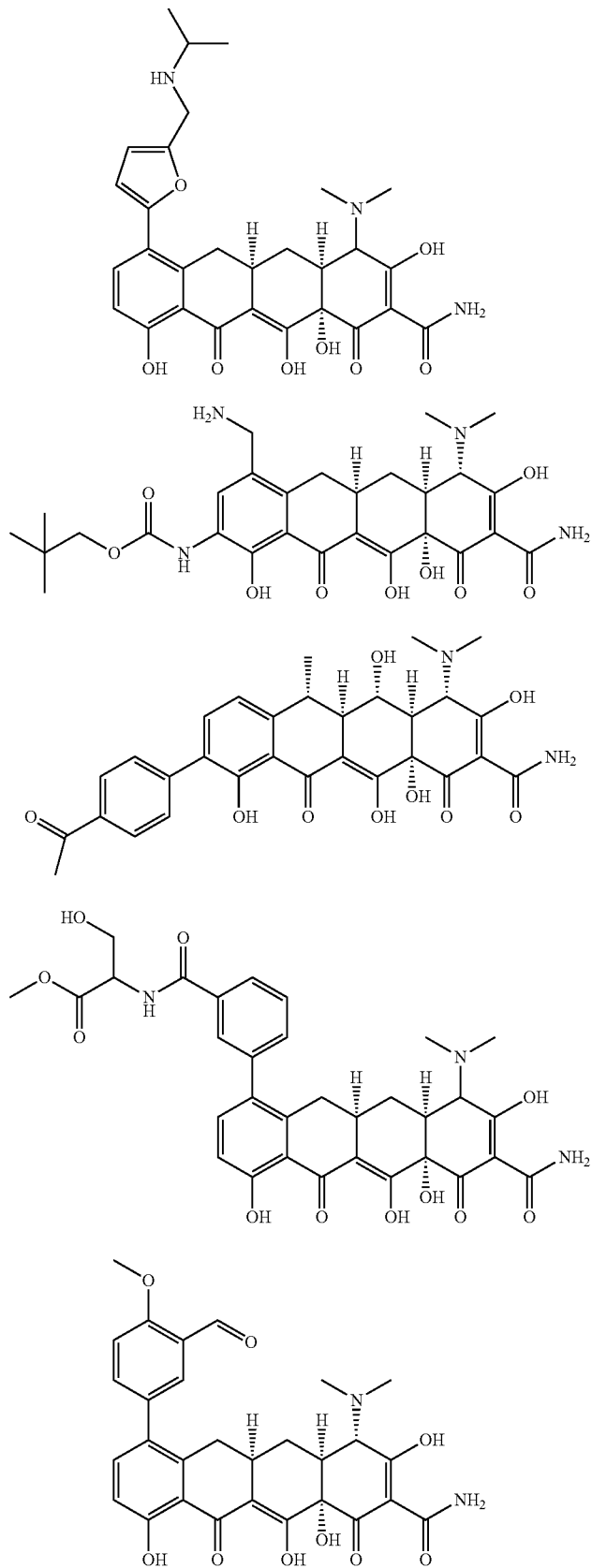

TABLE 2-continued
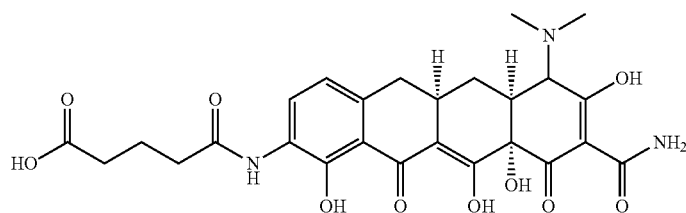
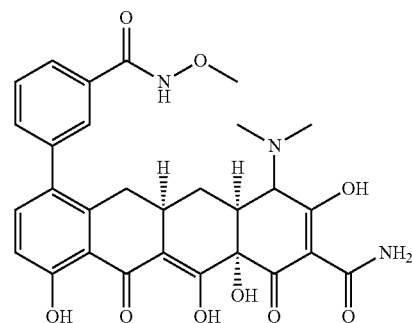
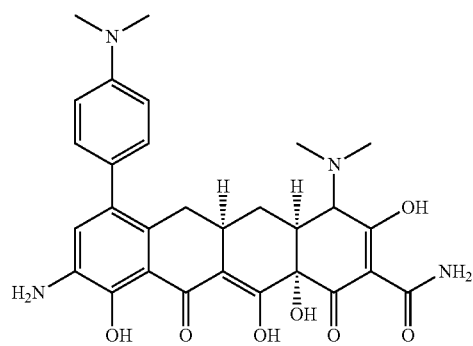
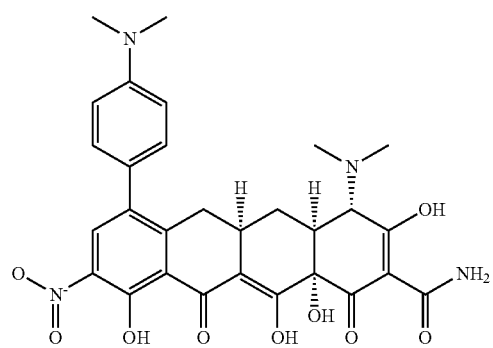
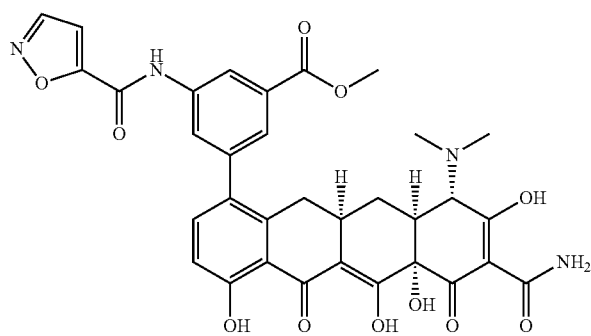

TABLE 2-continued
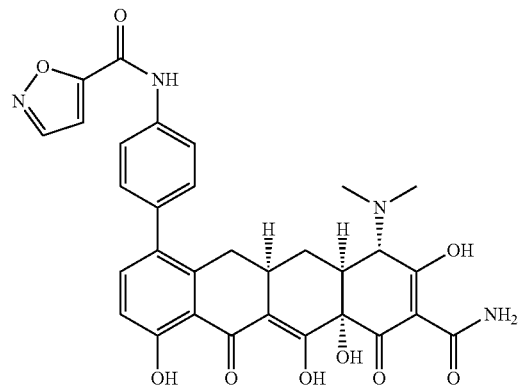
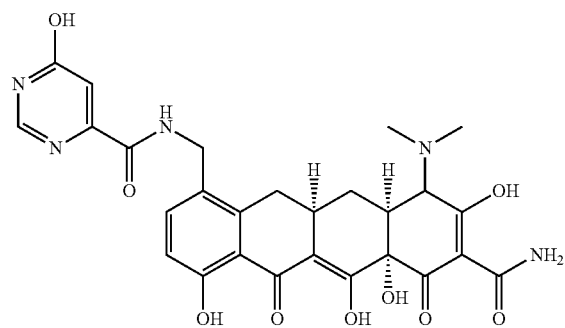
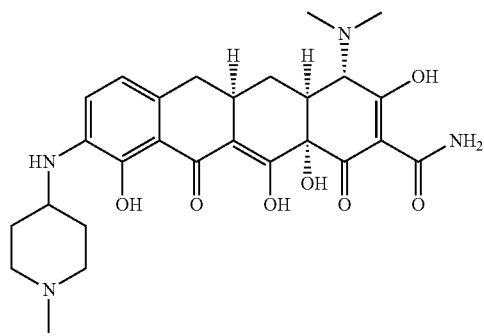
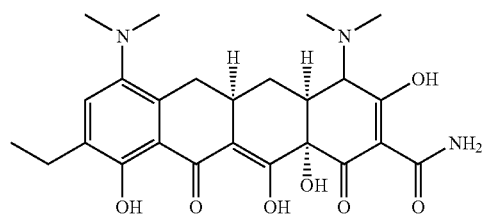
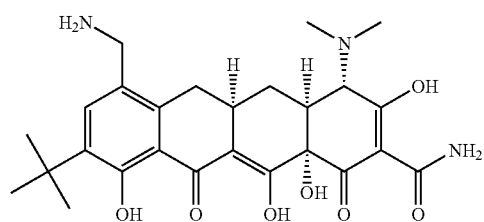

TABLE 2-continued
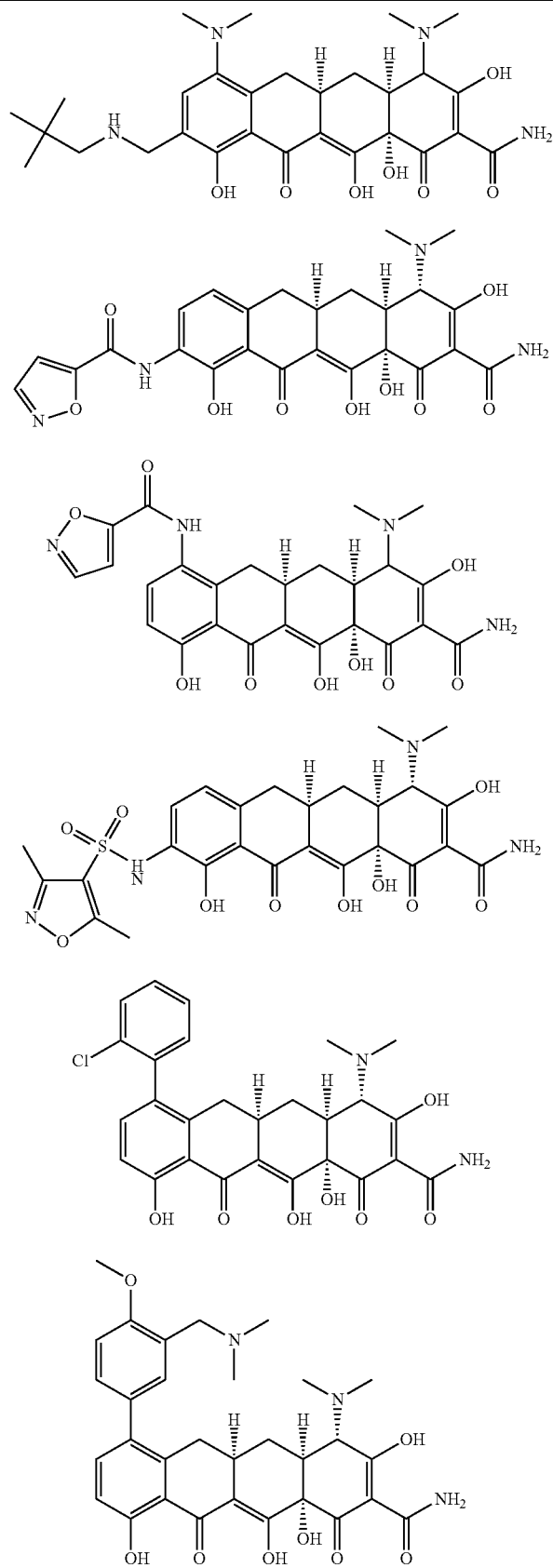

TABLE 2-continued
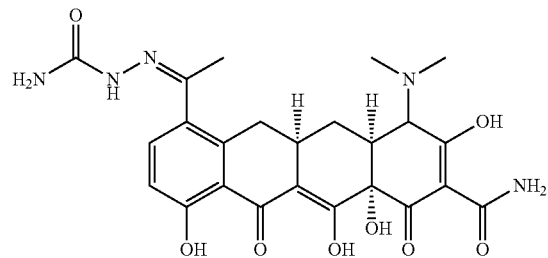
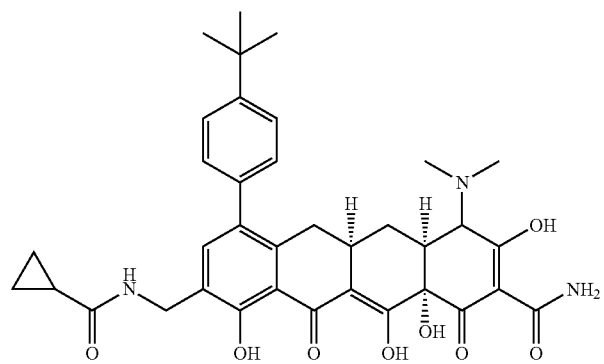
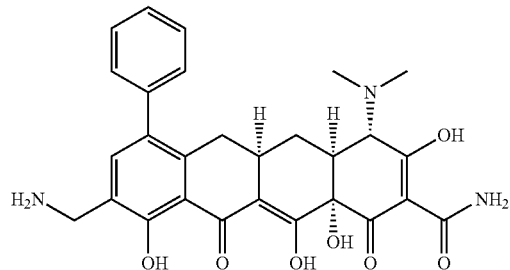
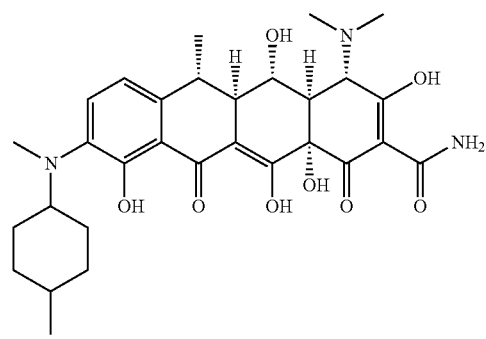
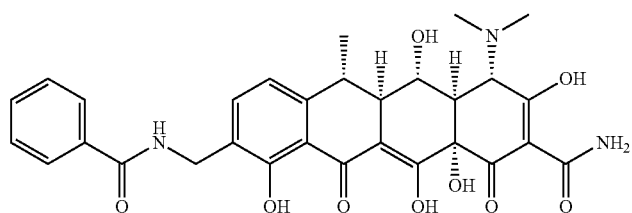

TABLE 2-continued
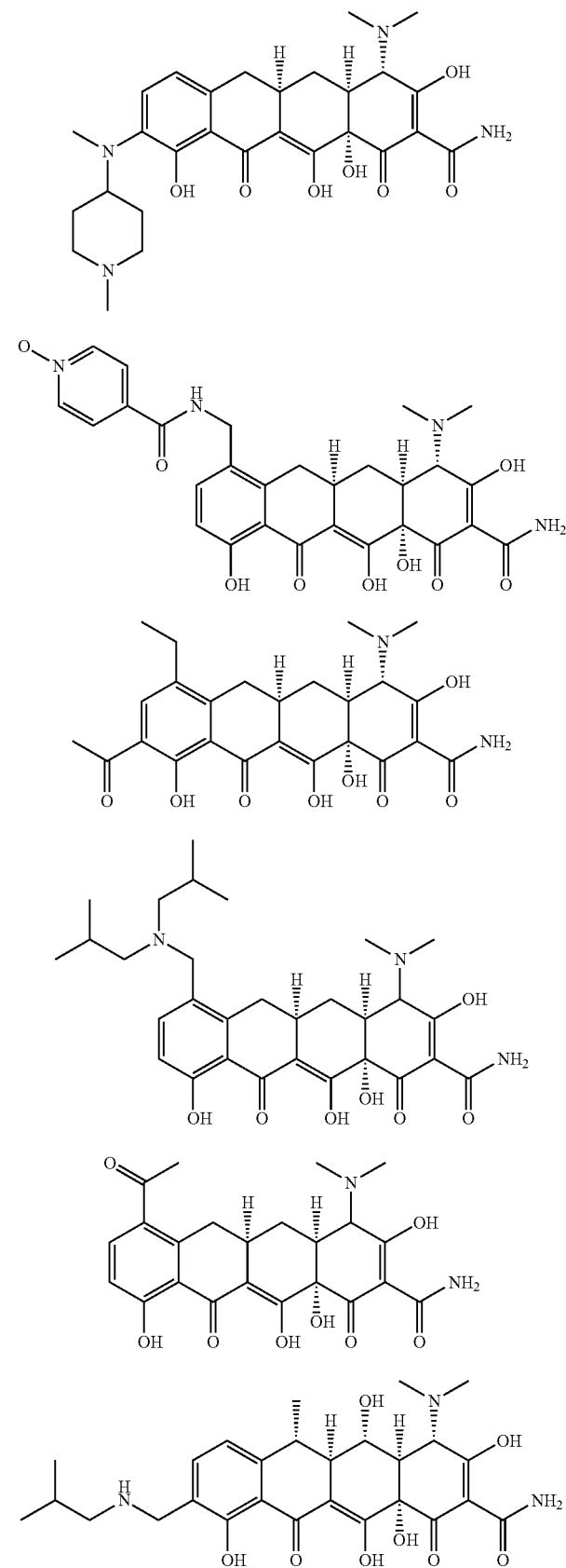

TABLE 2-continued
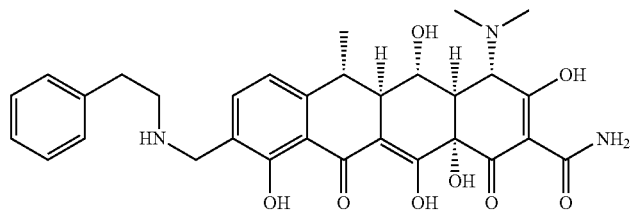
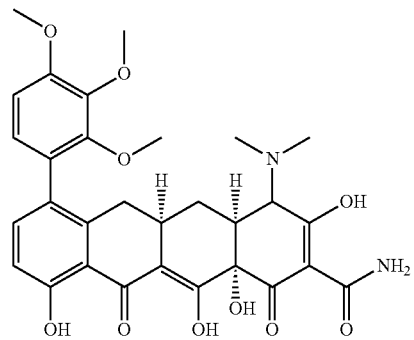
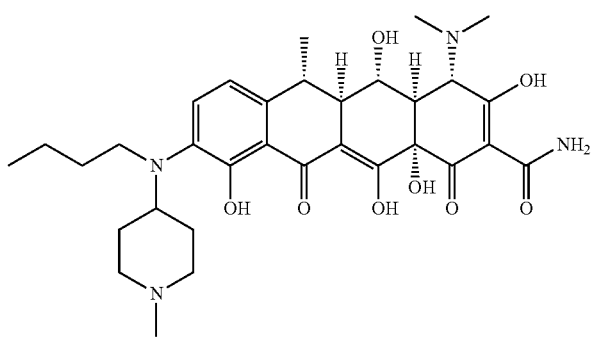
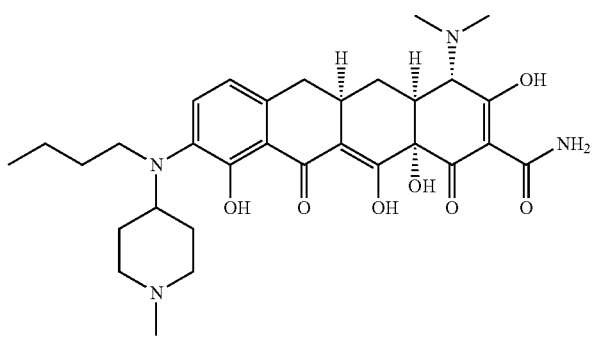
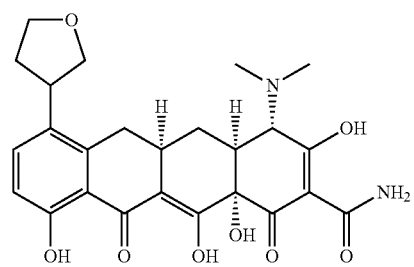

TABLE 2-continued
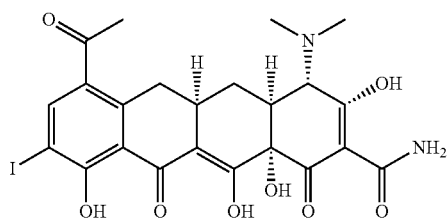
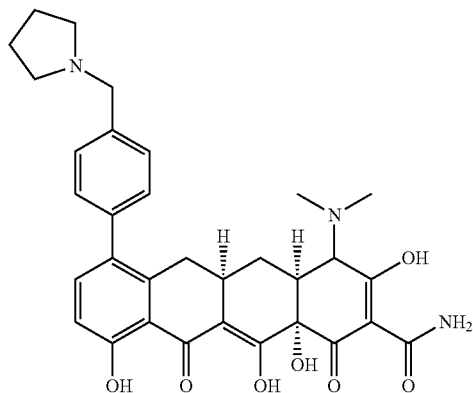
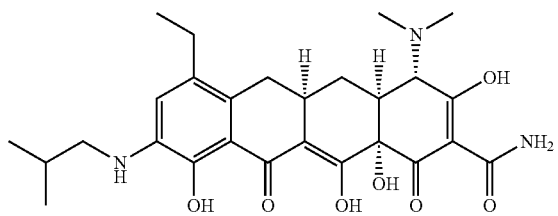
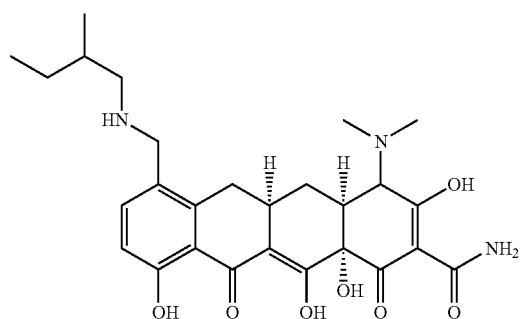
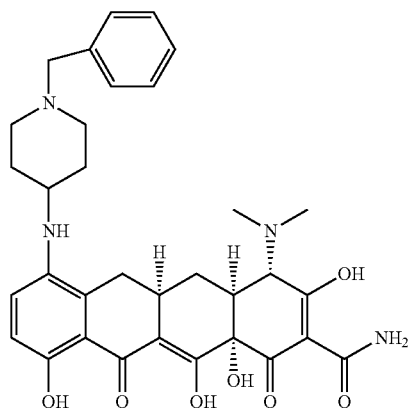

TABLE 2-continued
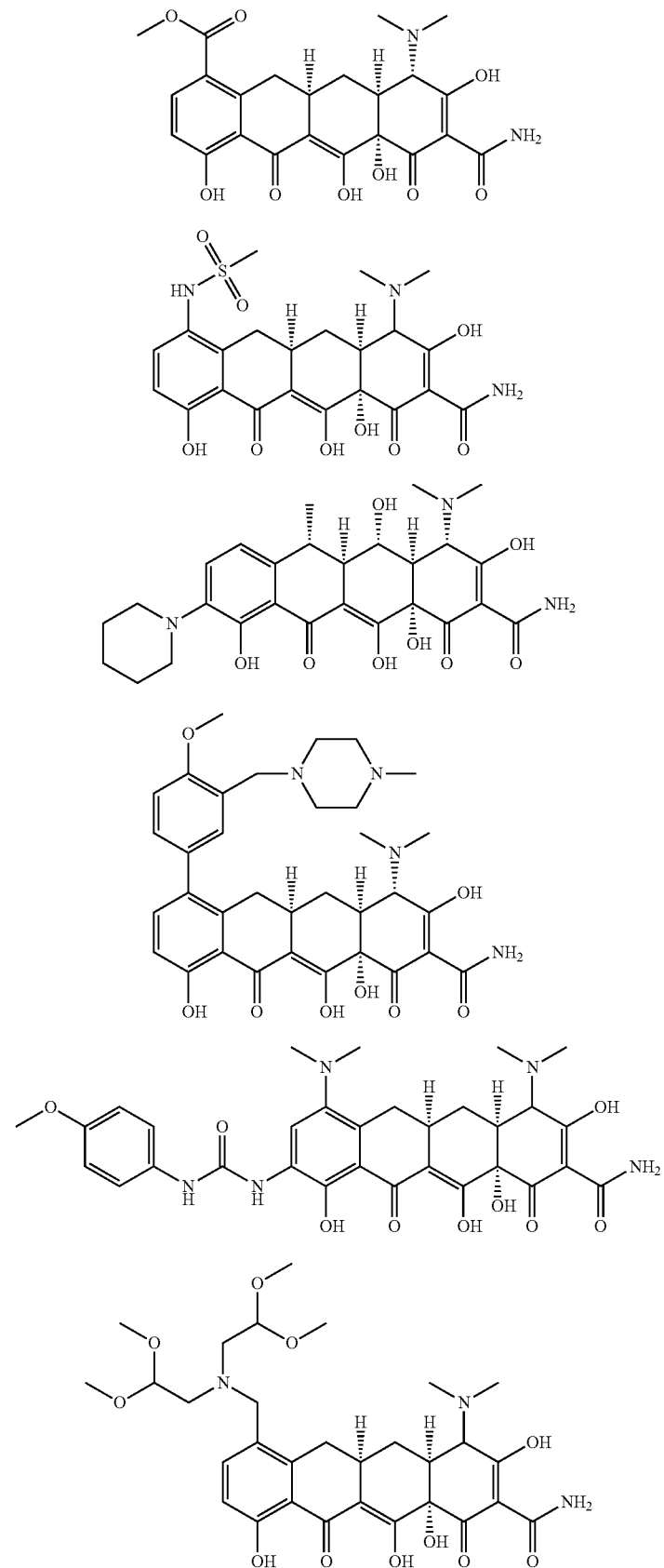

TABLE 2-continued
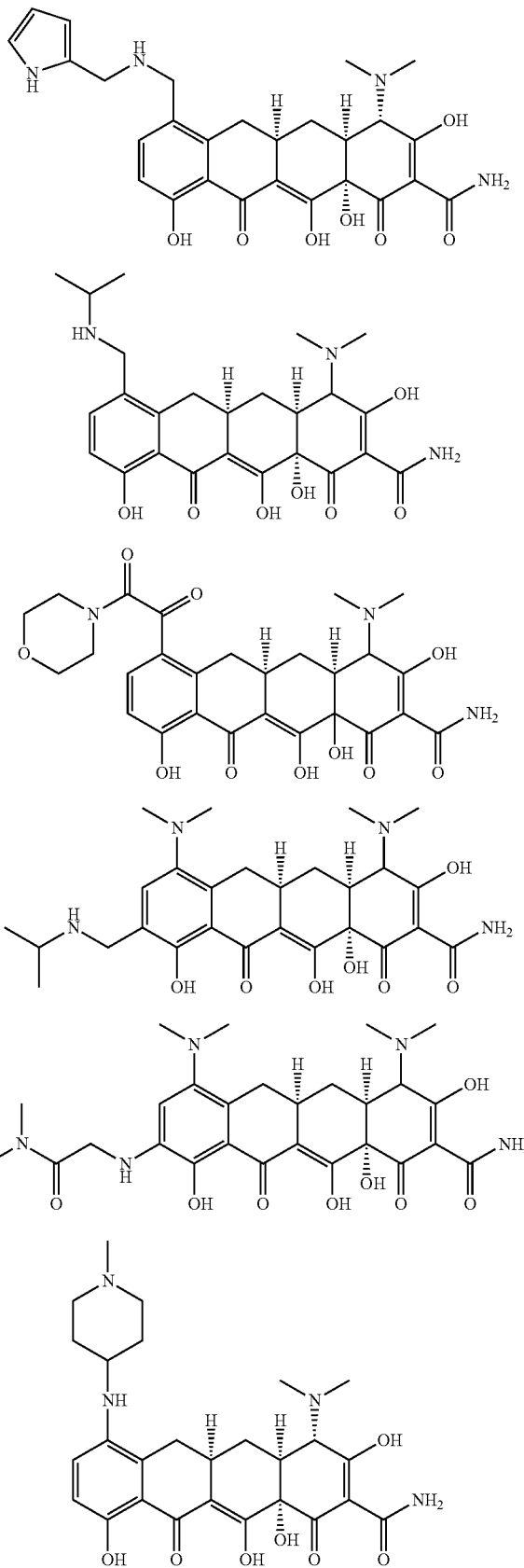

TABLE 2-continued
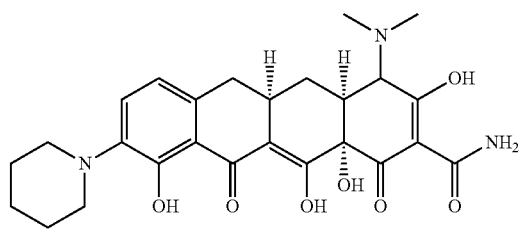
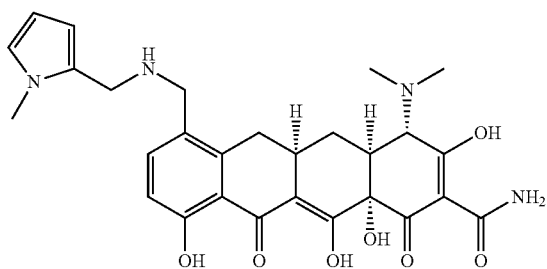
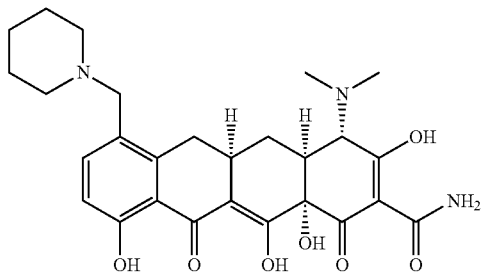
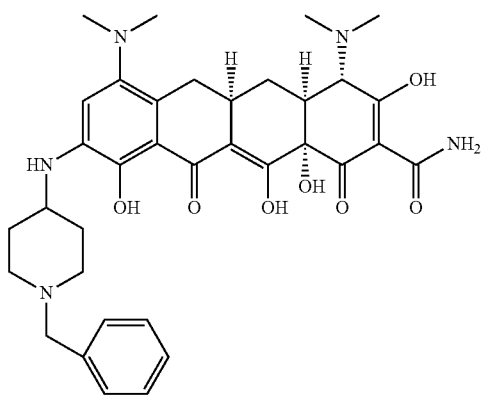
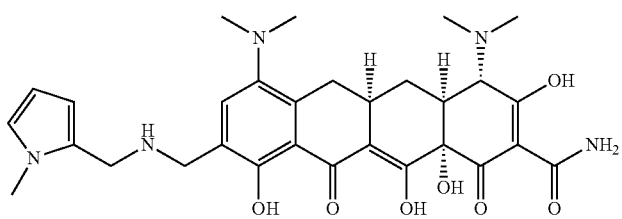

TABLE 2-continued
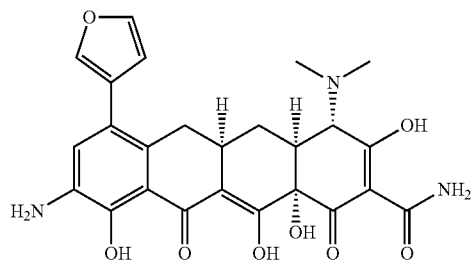
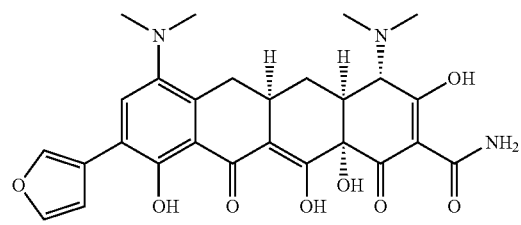
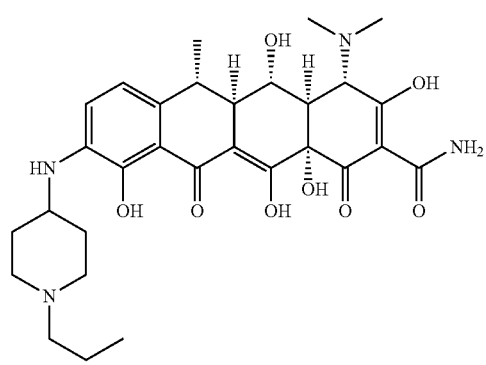
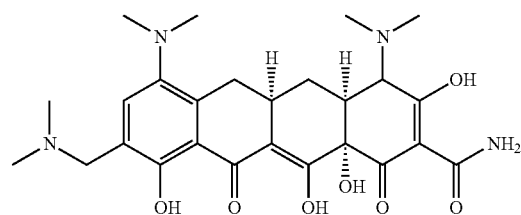
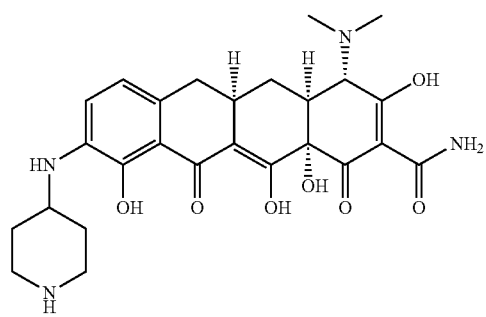

TABLE 2-continued
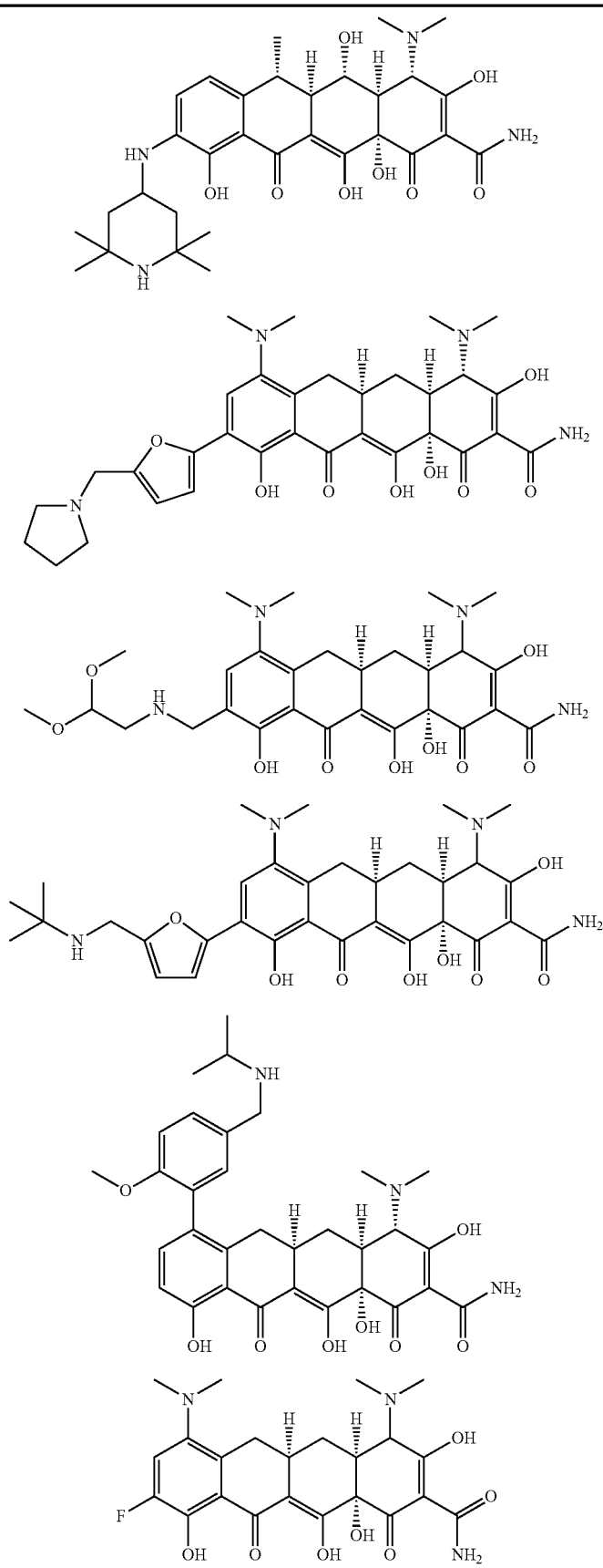

TABLE 2-continued
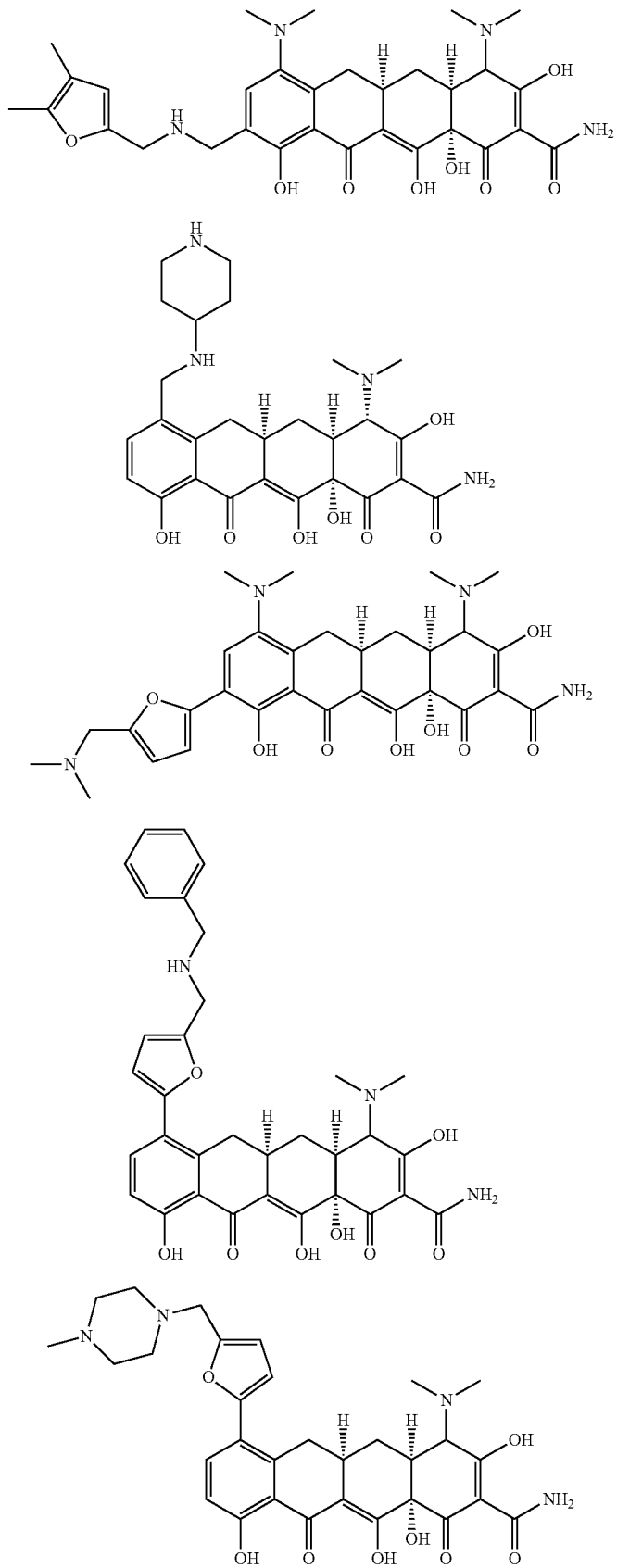

TABLE 2-continued
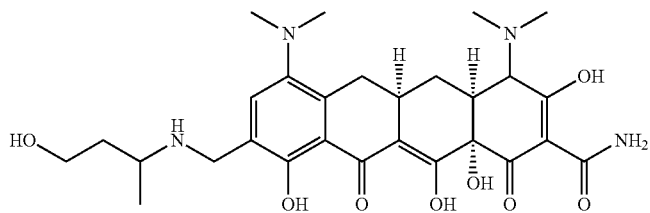
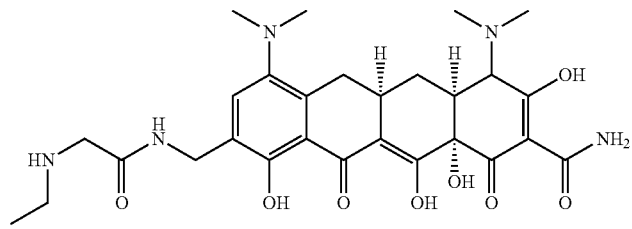
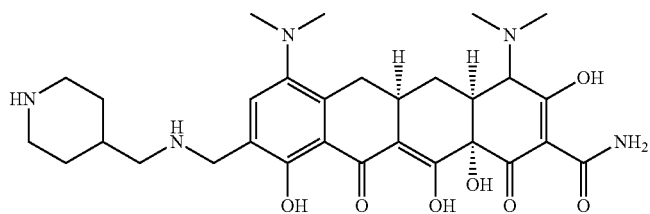
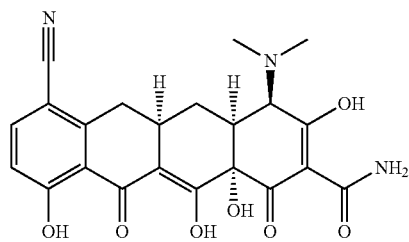
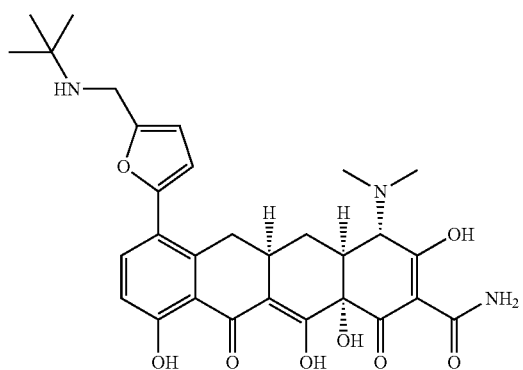

TABLE 2-continued
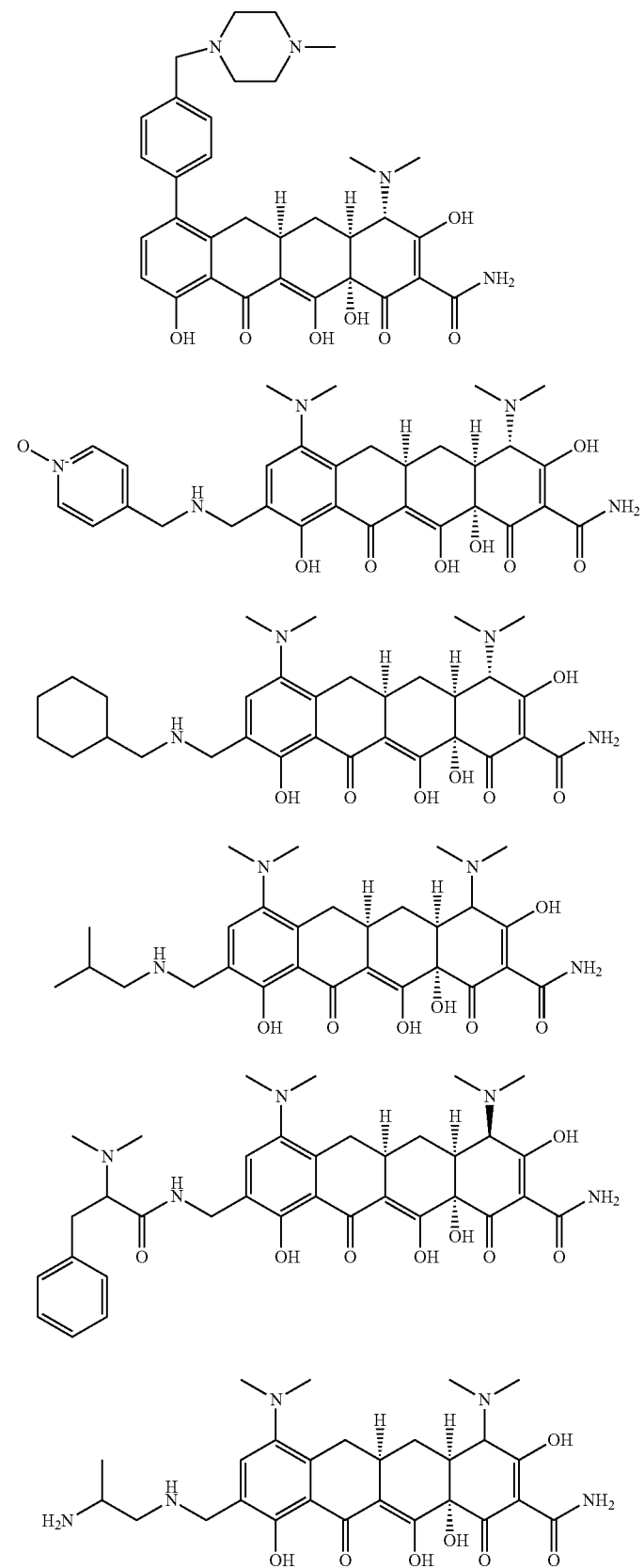

TABLE 2-continued
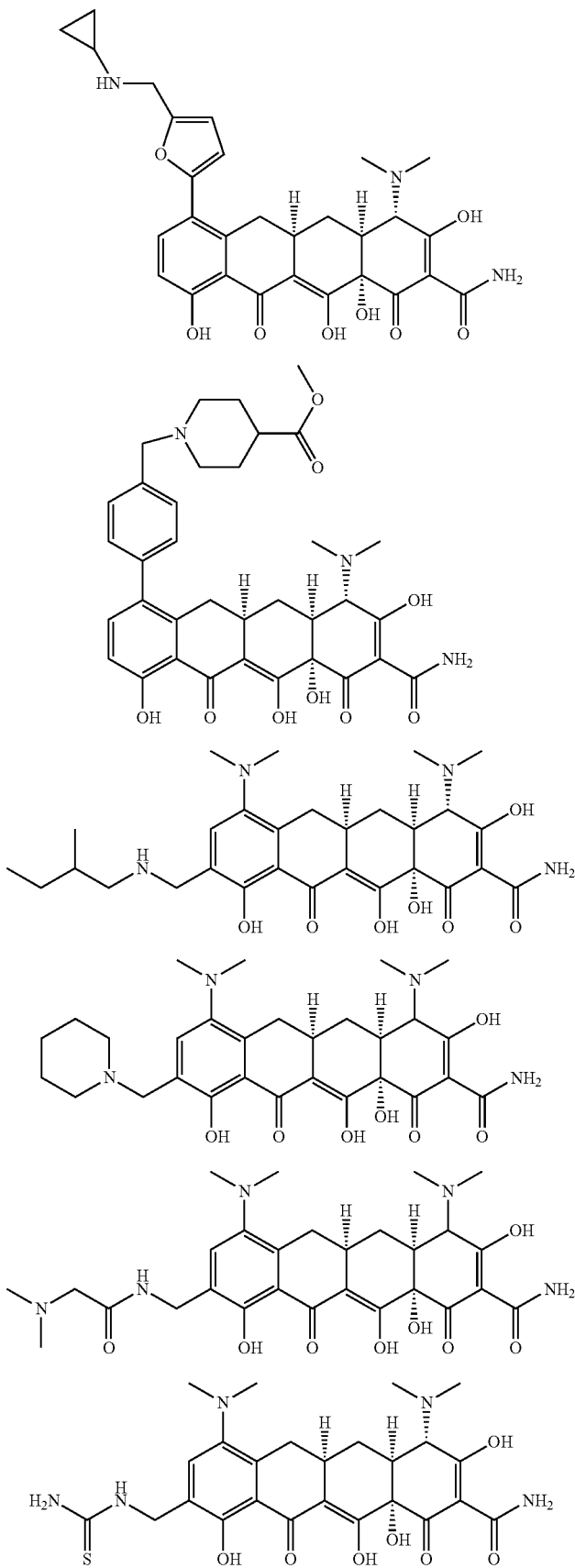

TABLE 2-continued
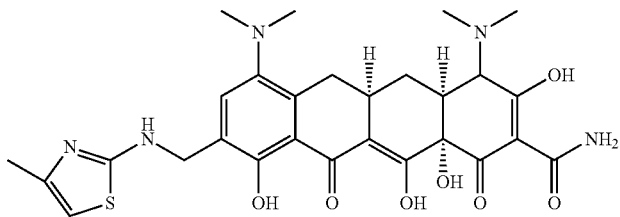
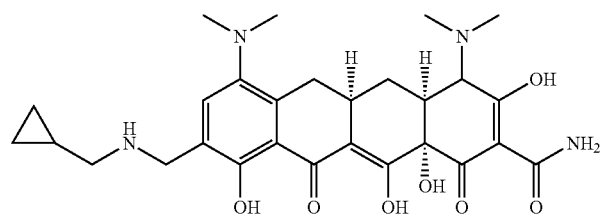
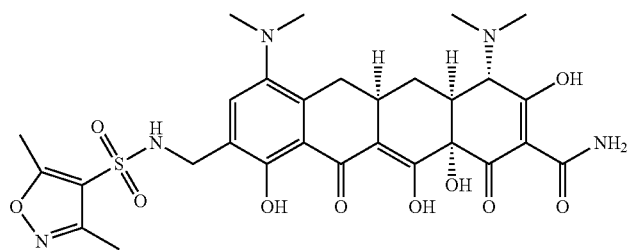
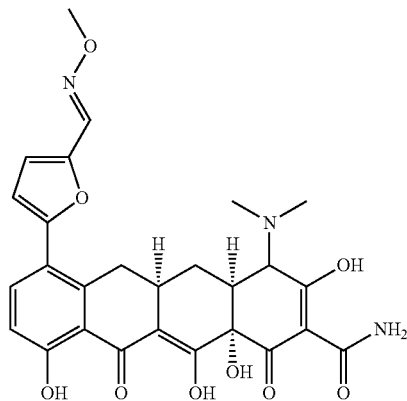
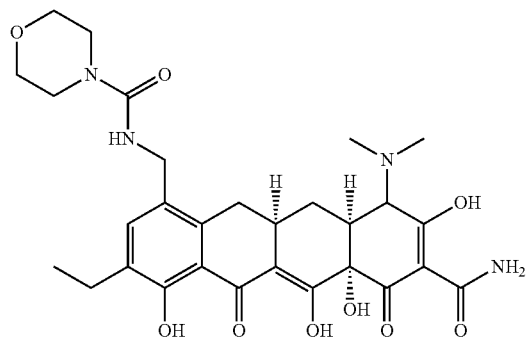

TABLE 2-continued
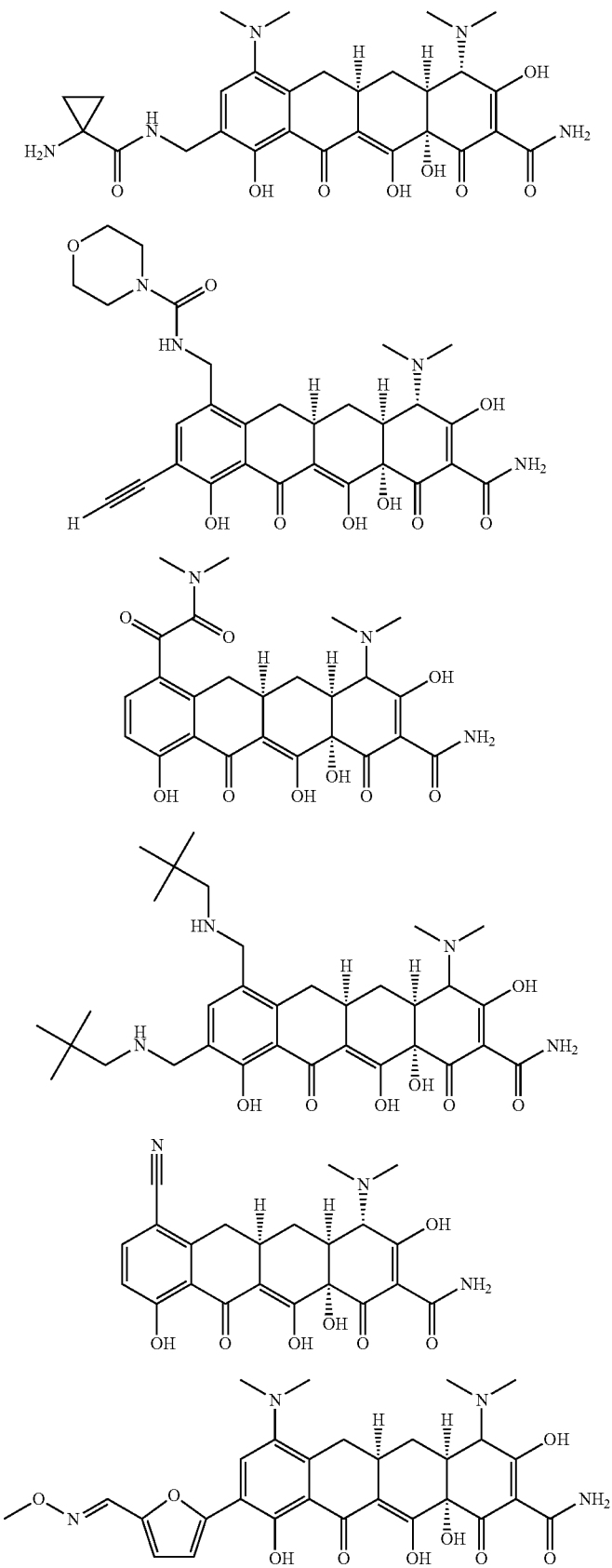

TABLE 2-continued
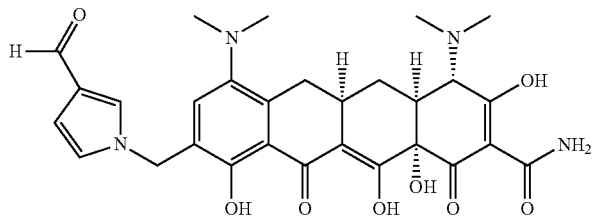
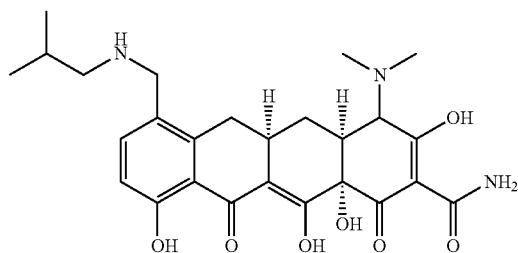
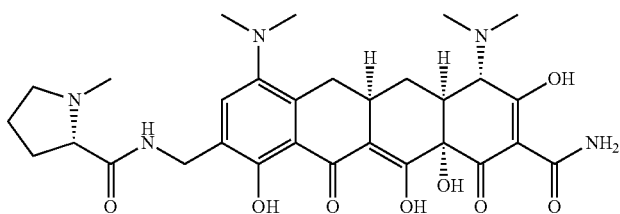
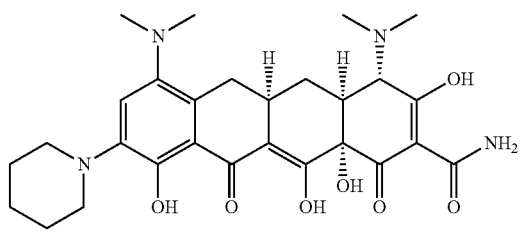
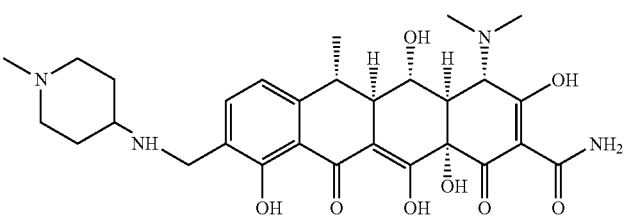
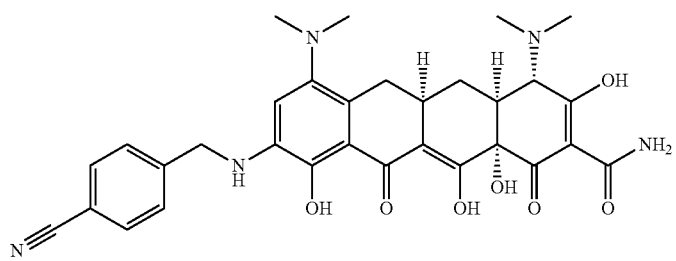

TABLE 2-continued
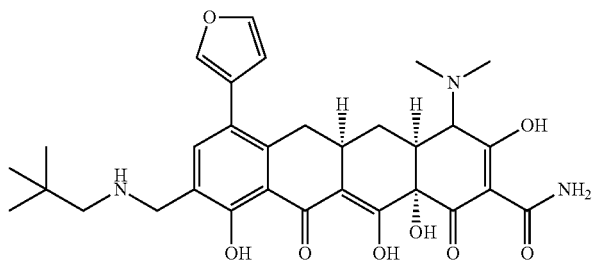
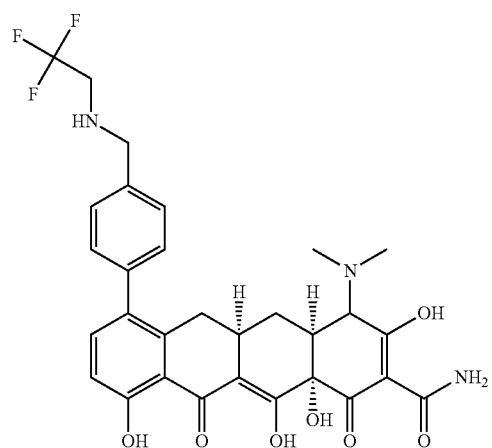
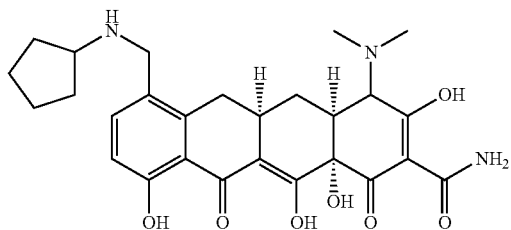
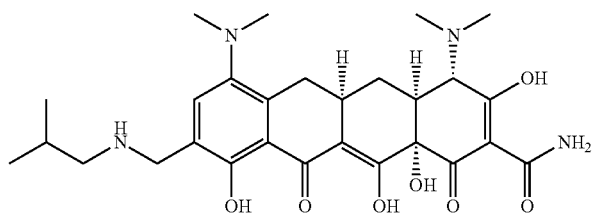
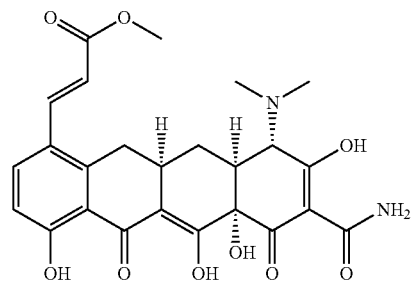

TABLE 2-continued
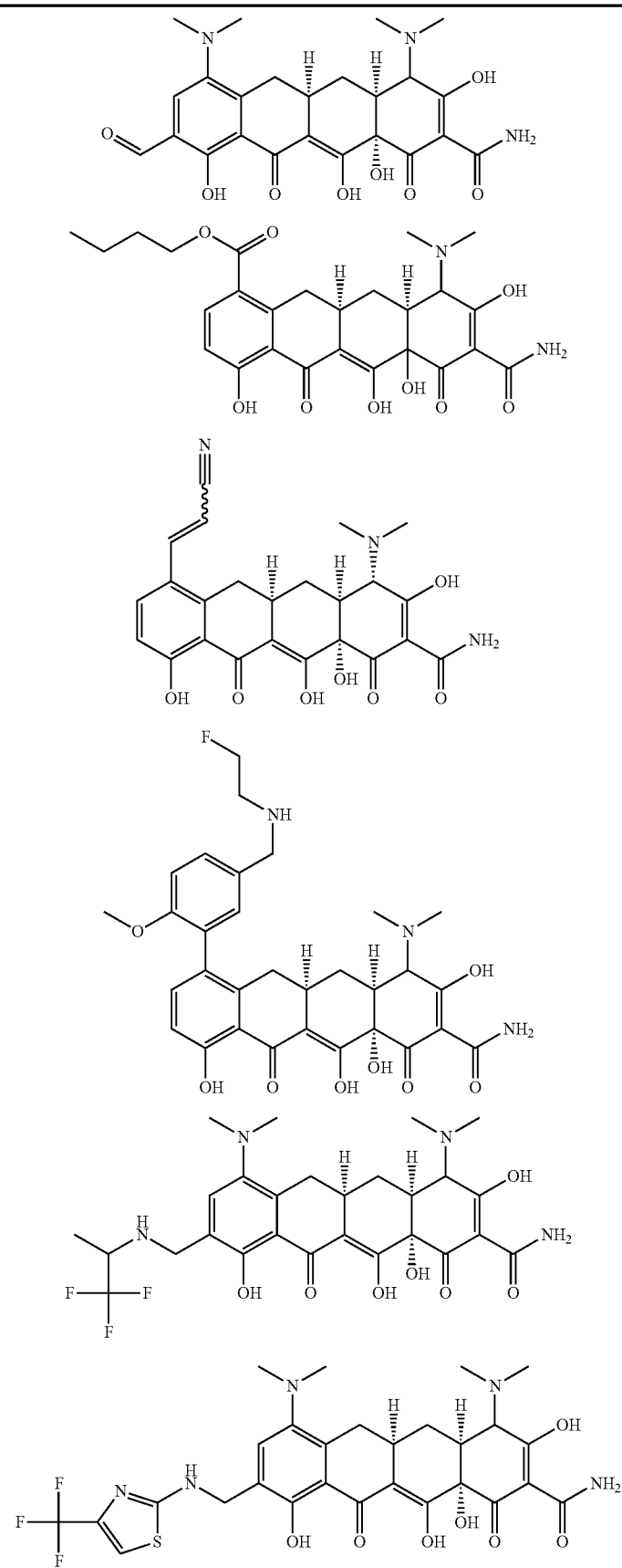

TABLE 2-continued
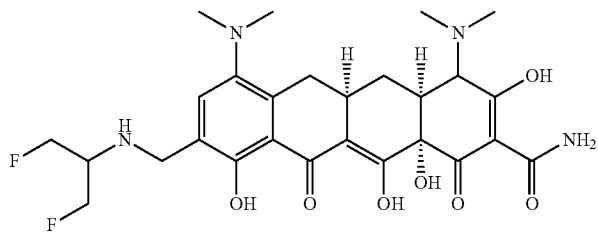
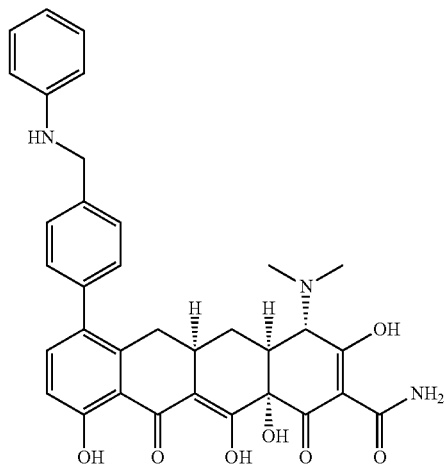
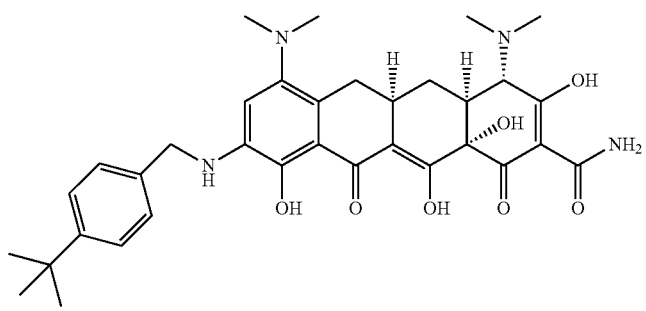
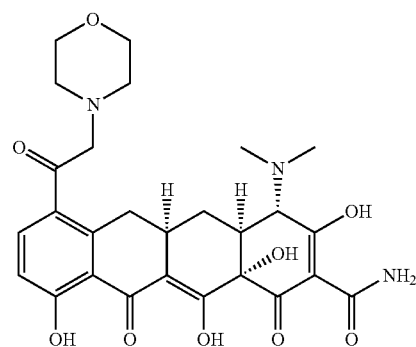

TABLE 2-continued
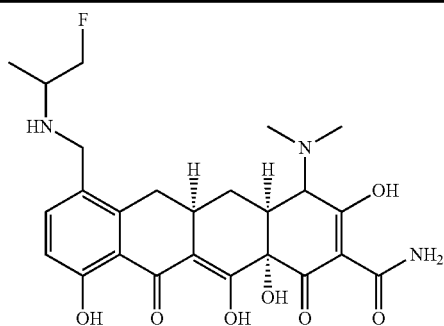
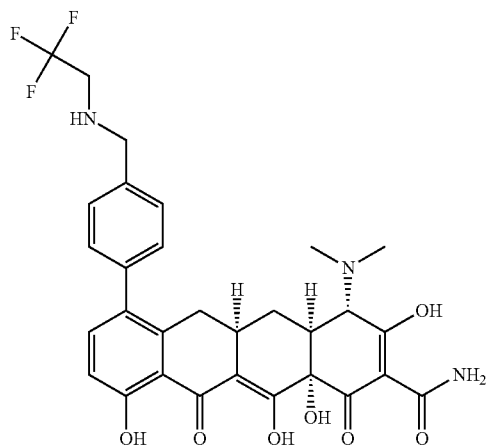
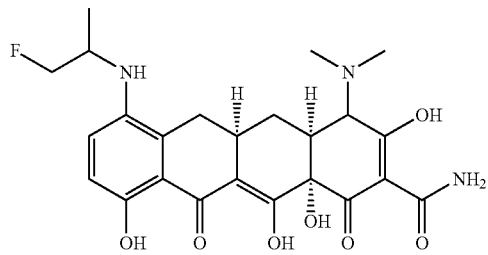
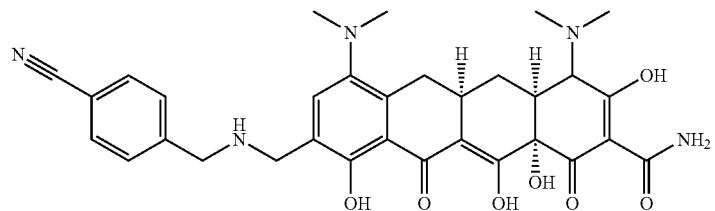
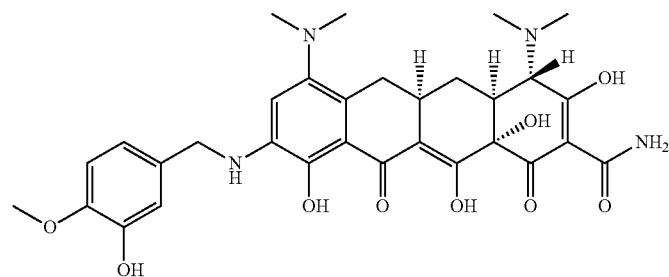

TABLE 2-continued
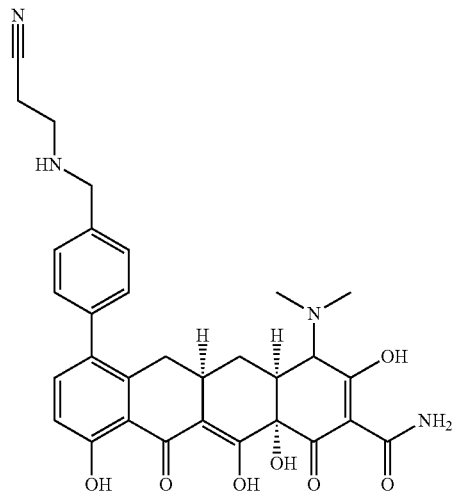
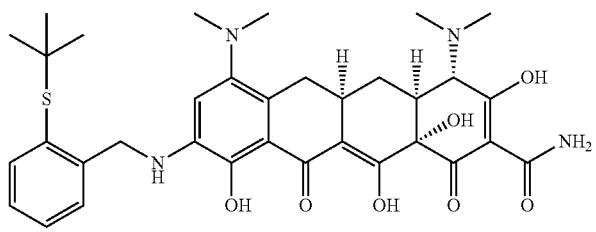
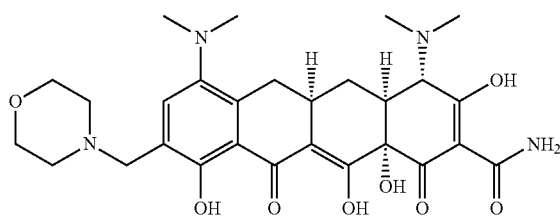
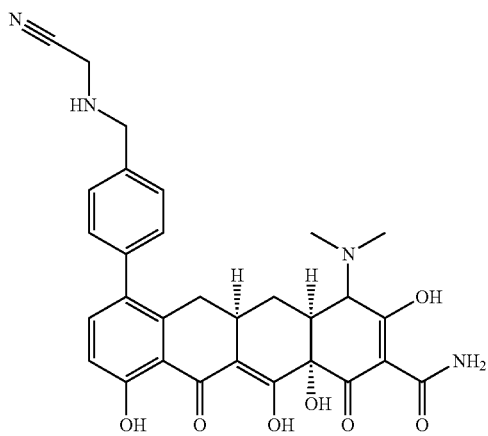

TABLE 2-continued
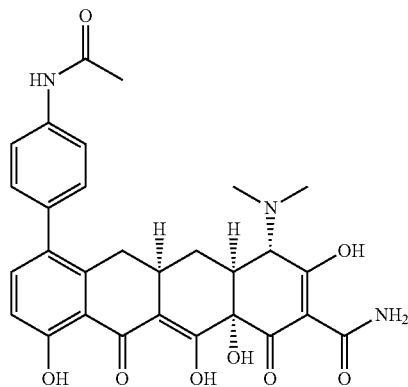
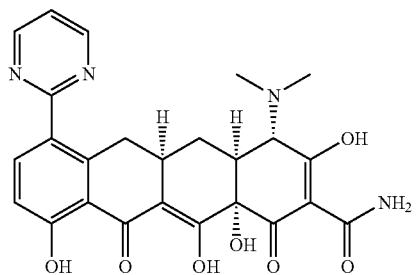
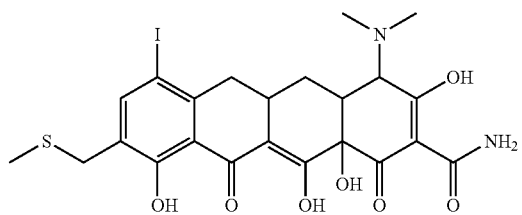
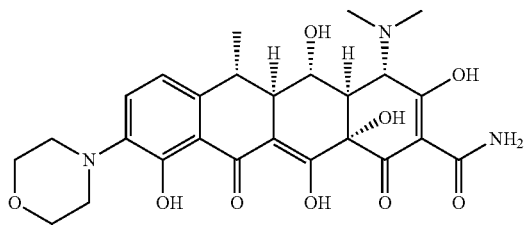
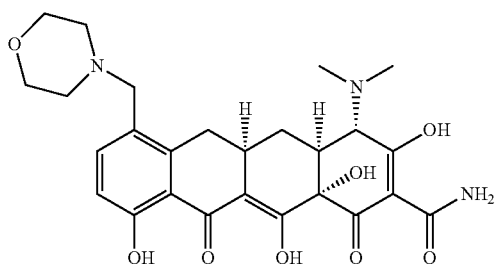

TABLE 2-continued
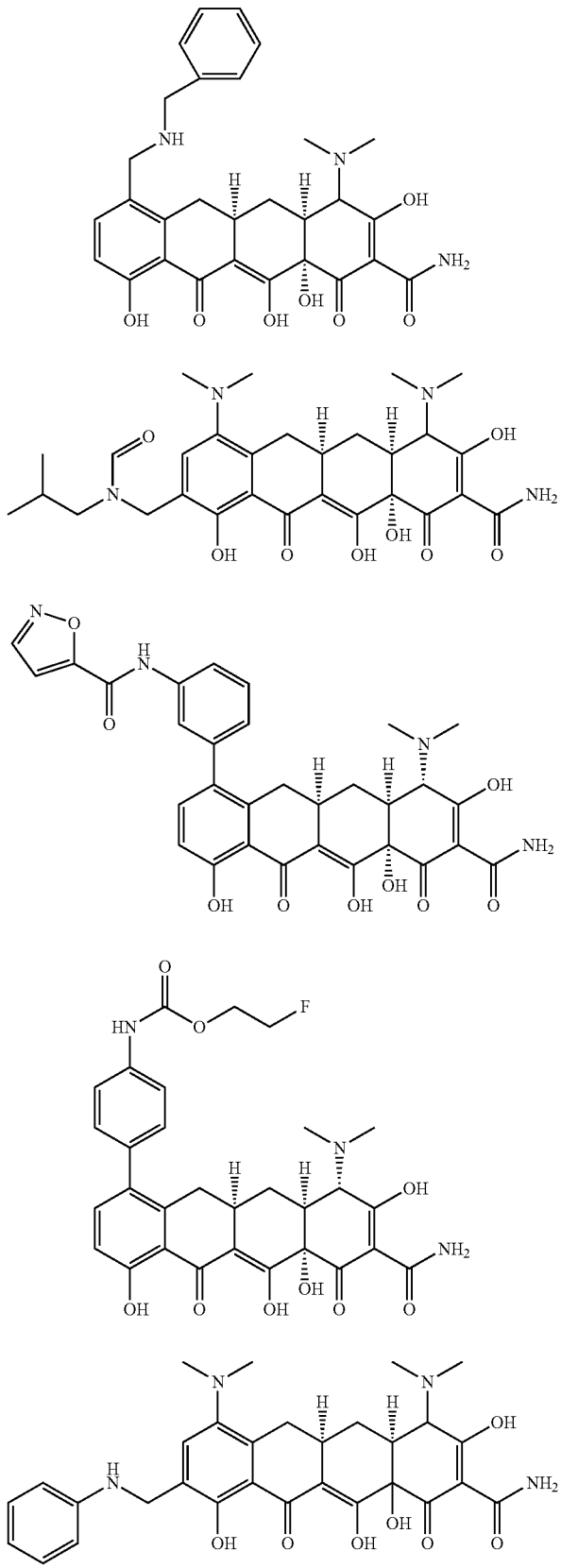

TABLE 2-continued
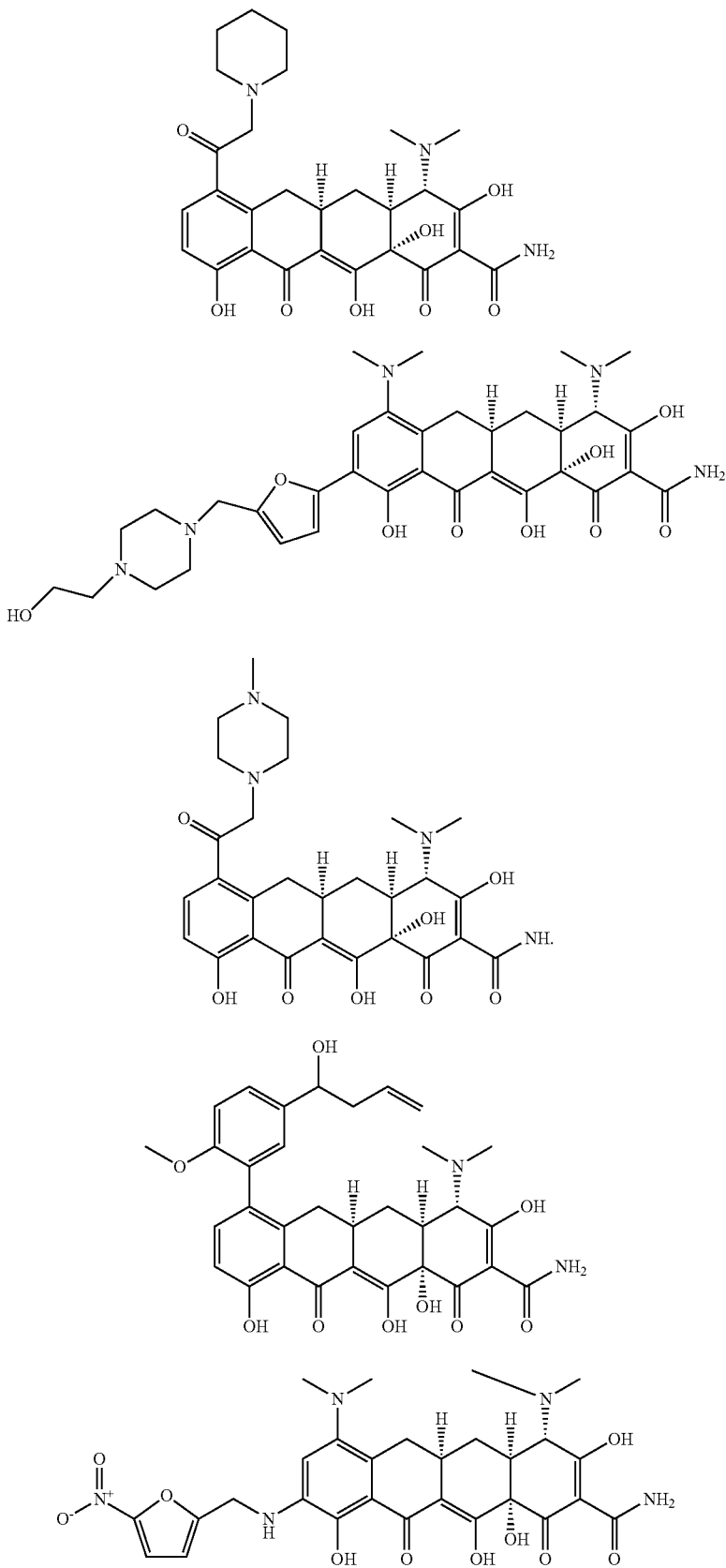

TABLE 2-continued
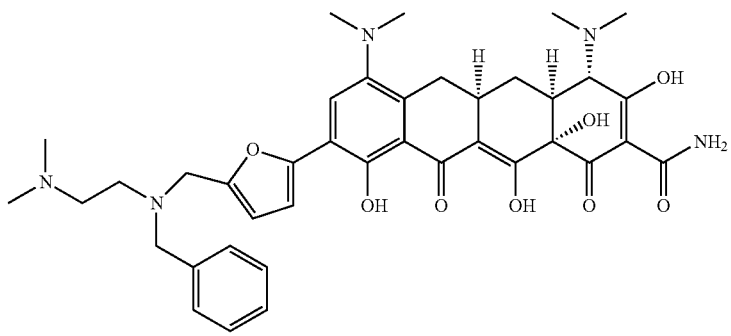
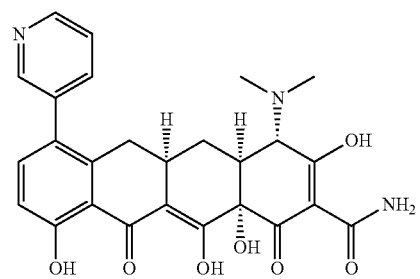
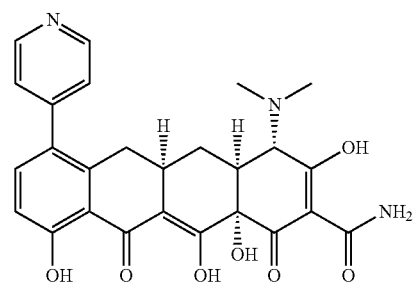
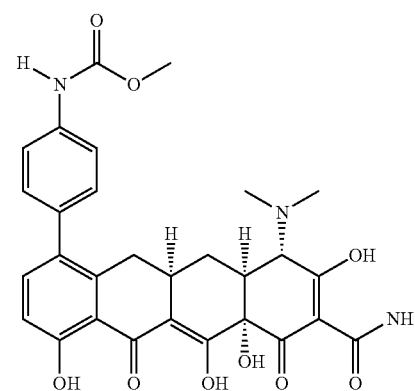

TABLE 2-continued
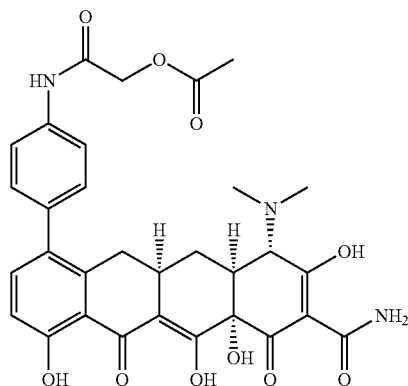
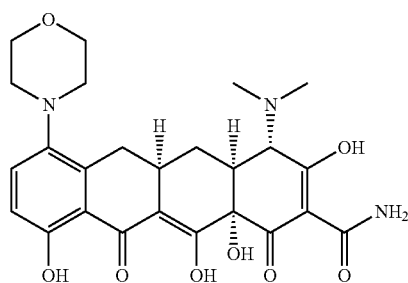
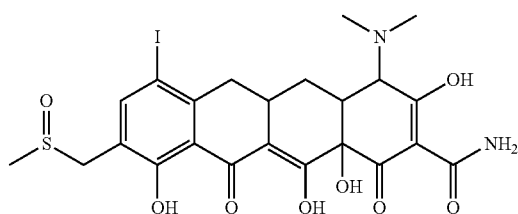
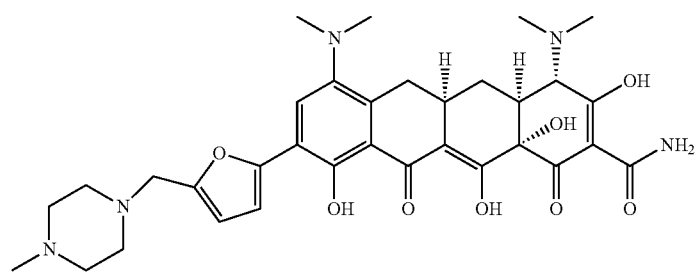
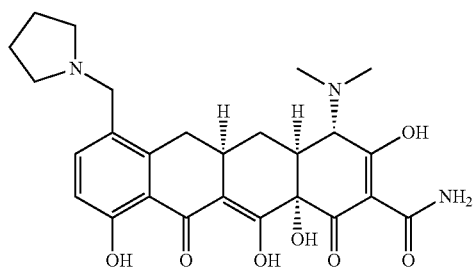

TABLE 2-continued
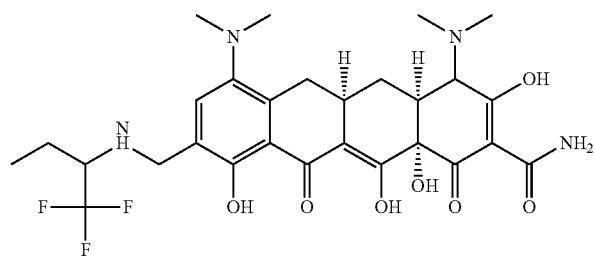
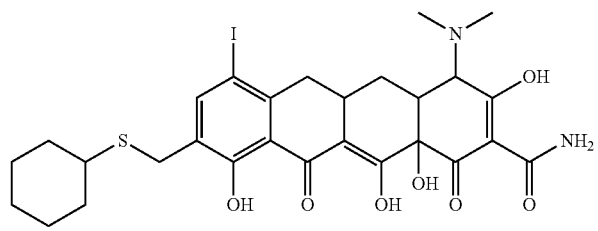
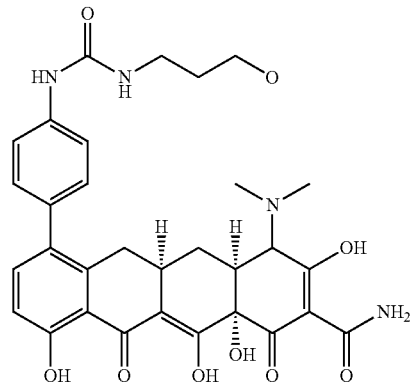
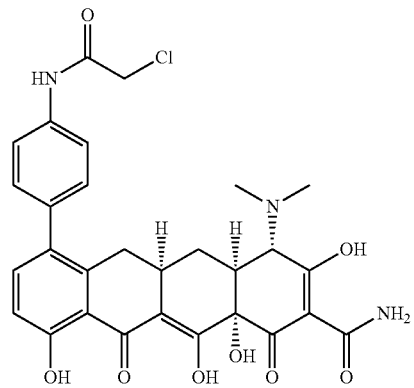
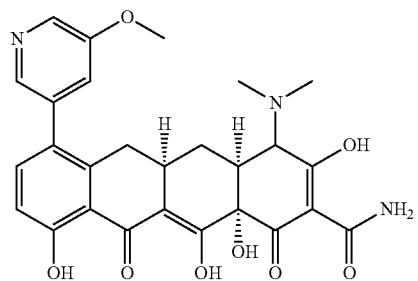

TABLE 2-continued
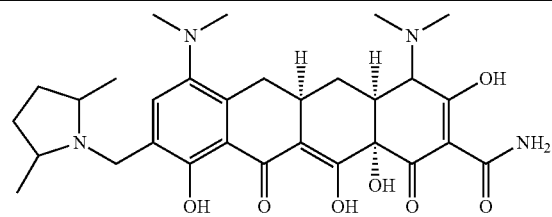
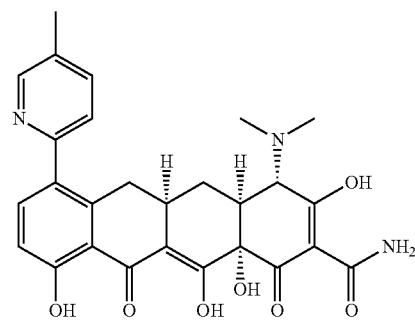
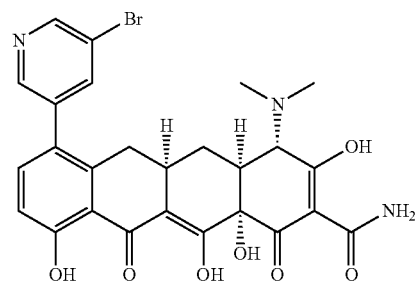
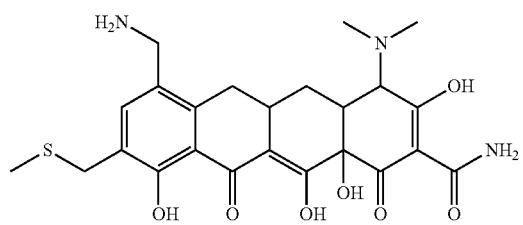
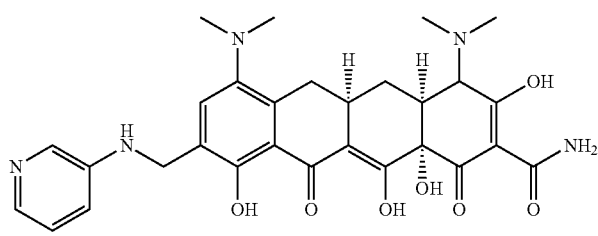
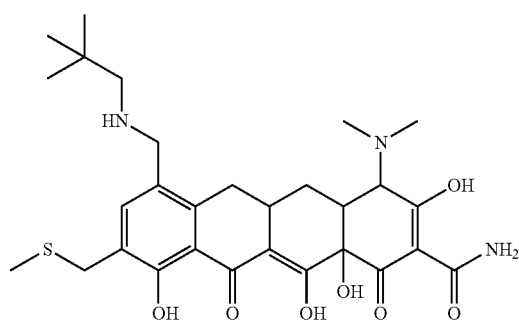

TABLE 2-continued
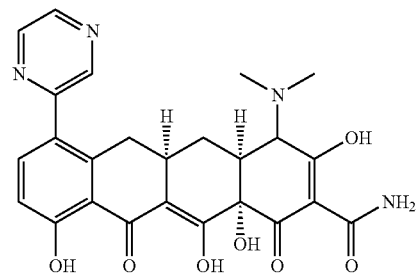
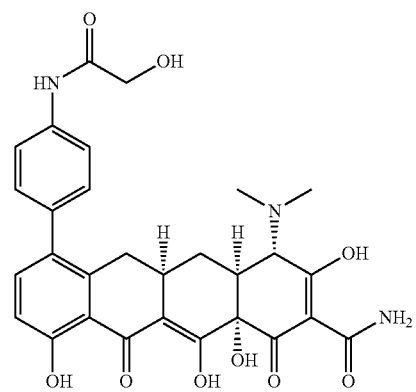
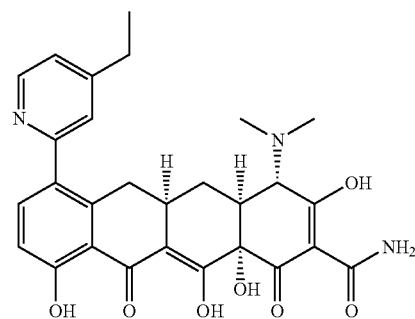
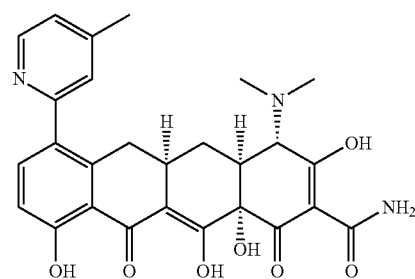
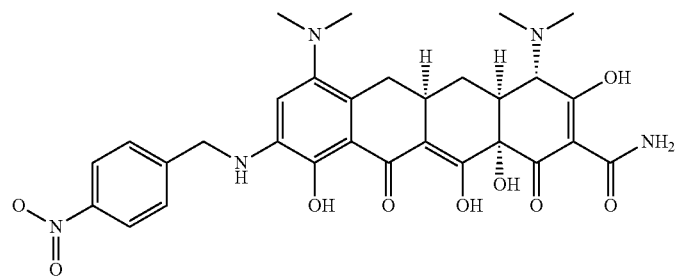

TABLE 2-continued
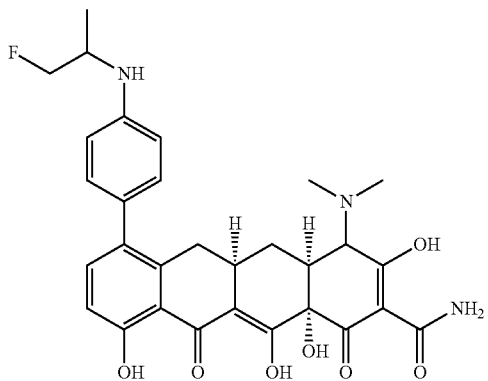
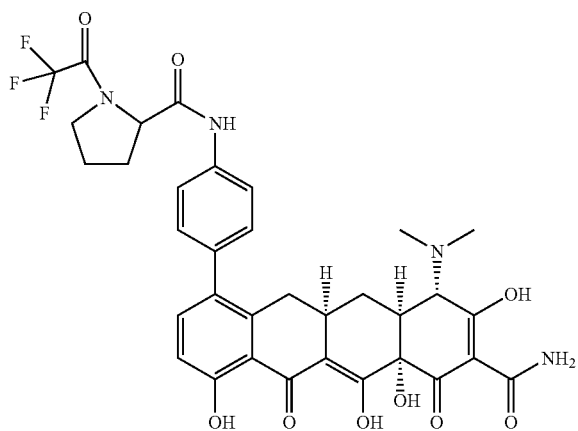
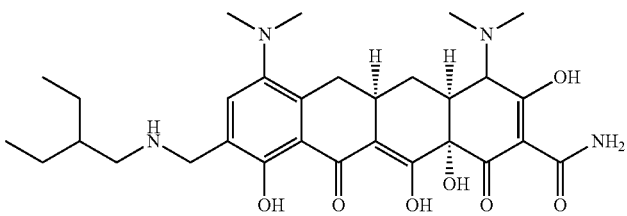
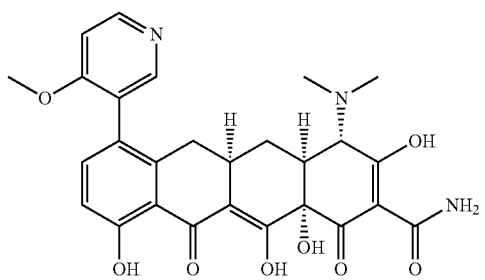
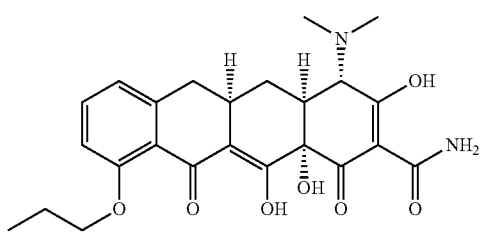

TABLE 2-continued
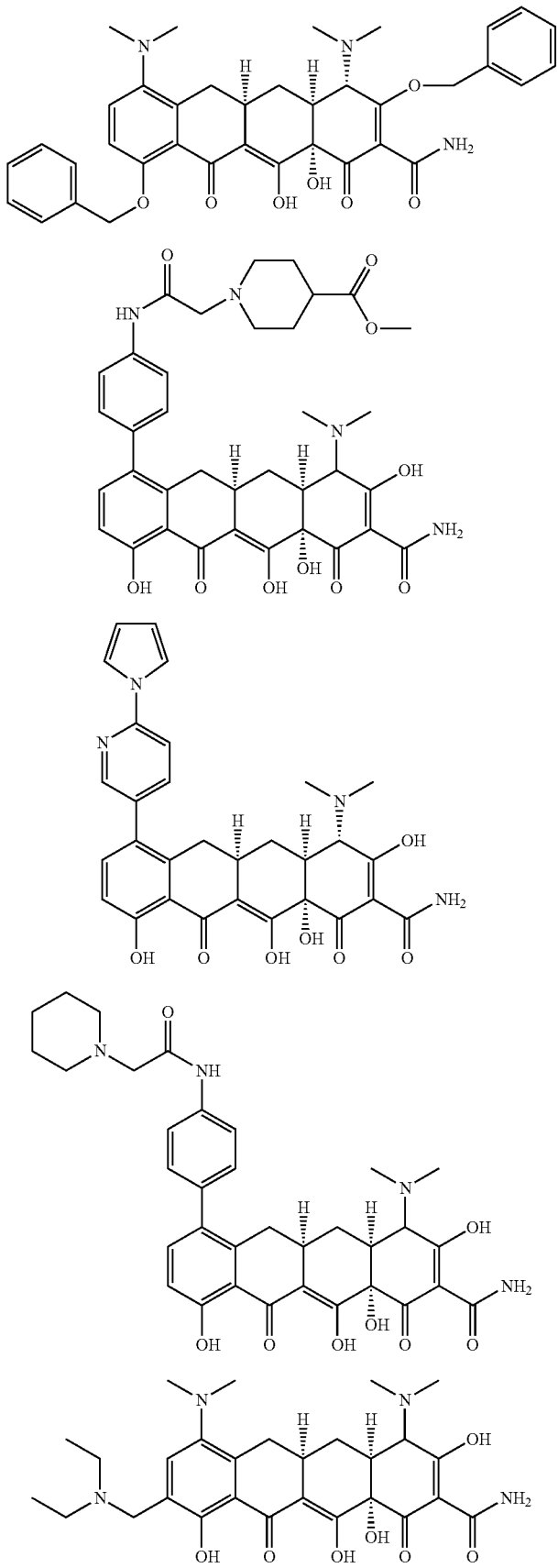

TABLE 2-continued
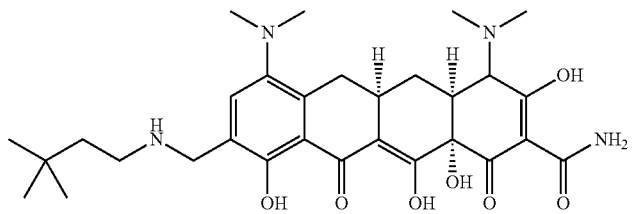
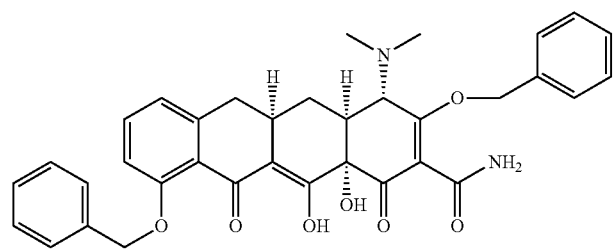
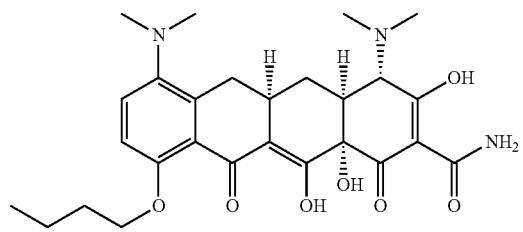
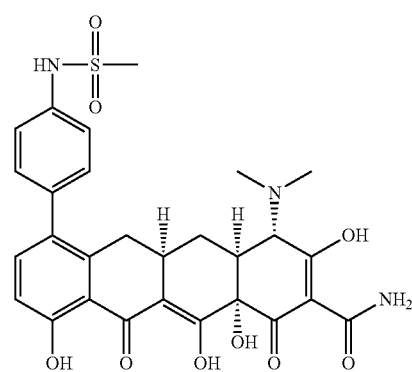
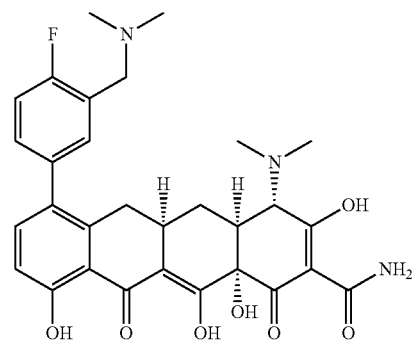

TABLE 2-continued
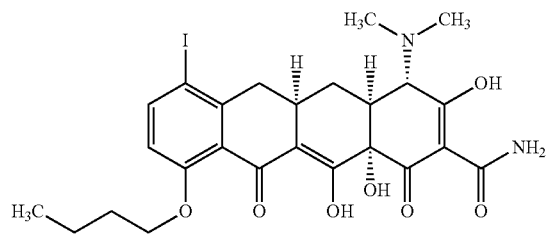
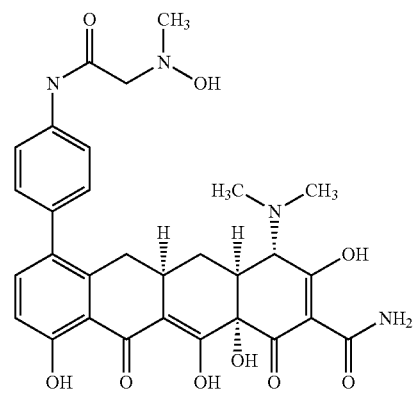
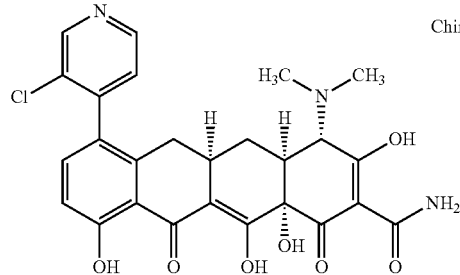
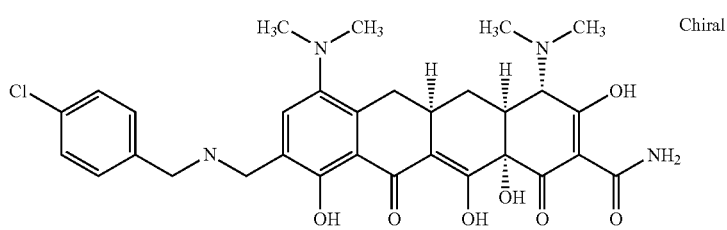
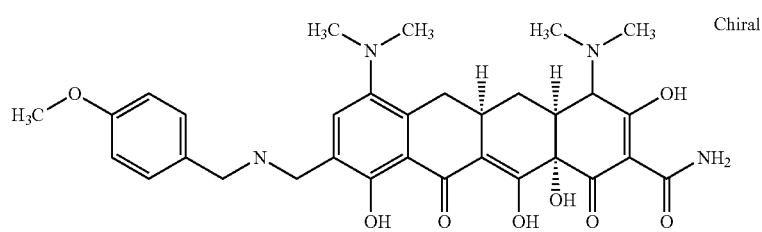

TABLE 2-continued
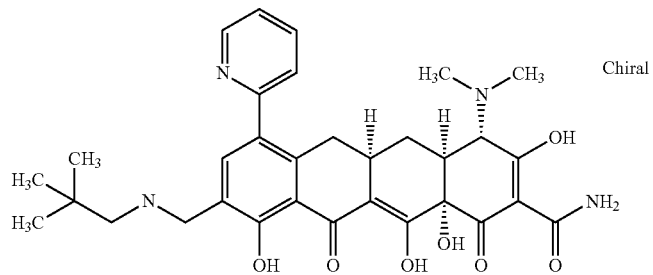
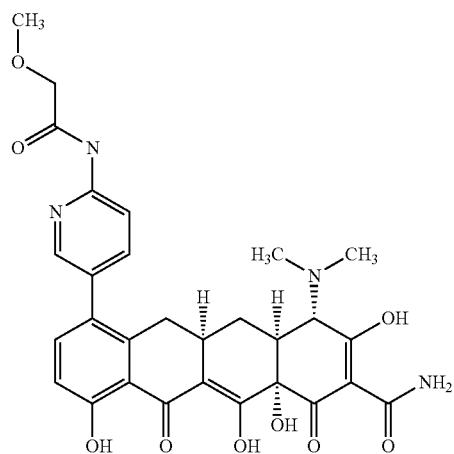
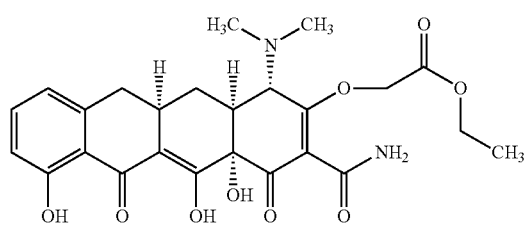
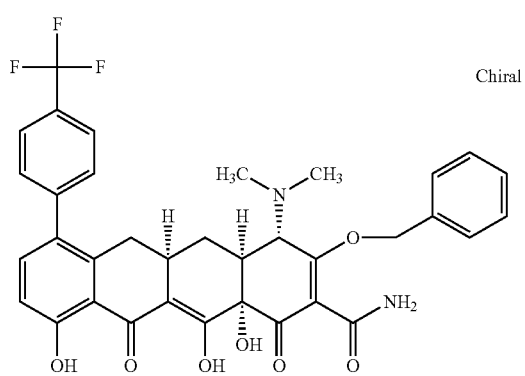

TABLE 2-continued
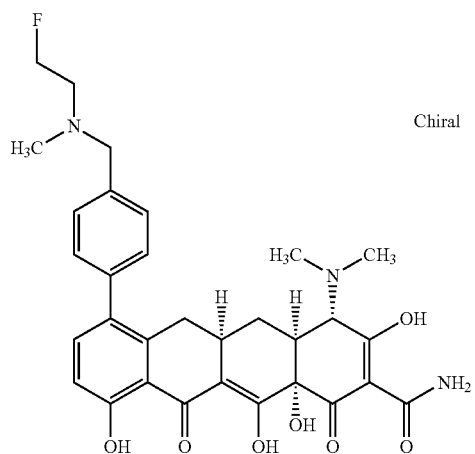
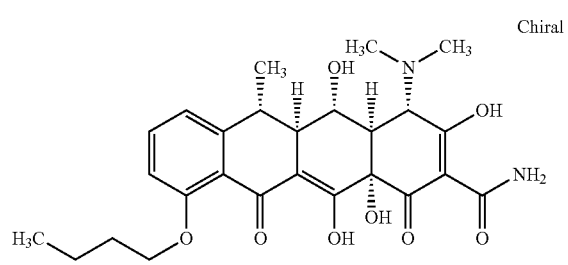
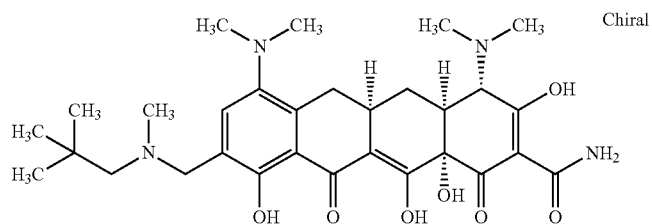
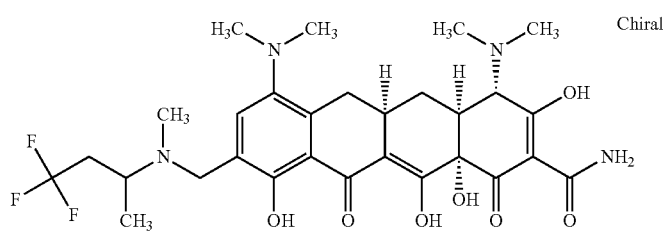
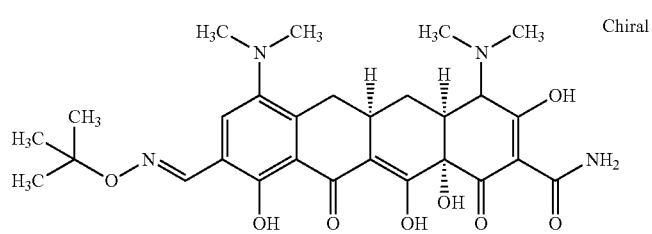

TABLE 2-continued
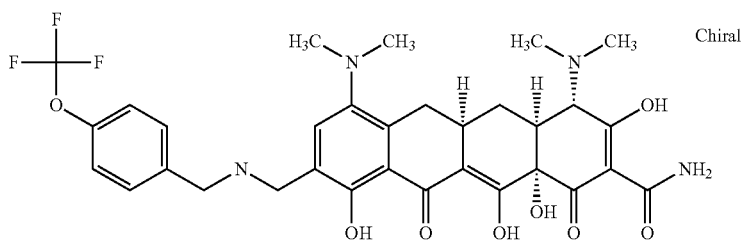
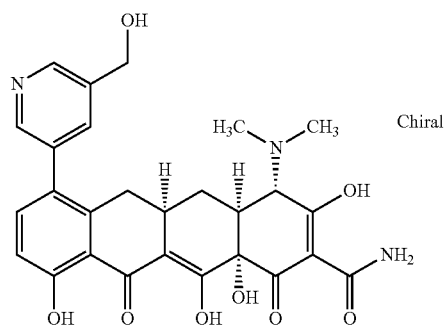
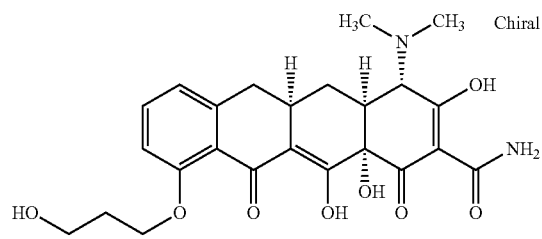
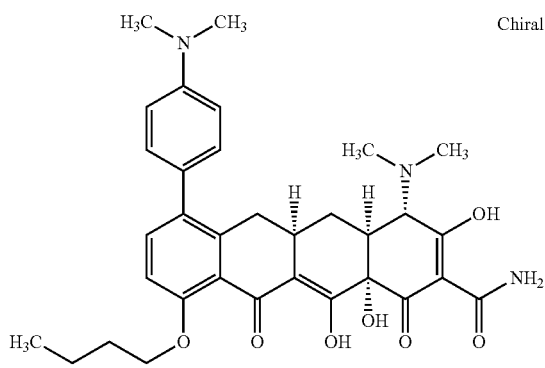
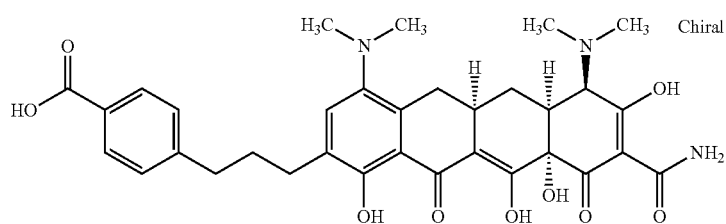

TABLE 2-continued
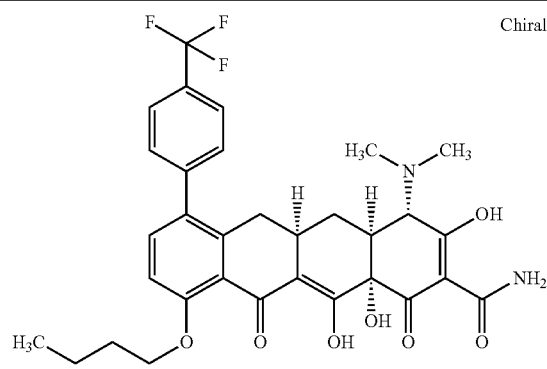
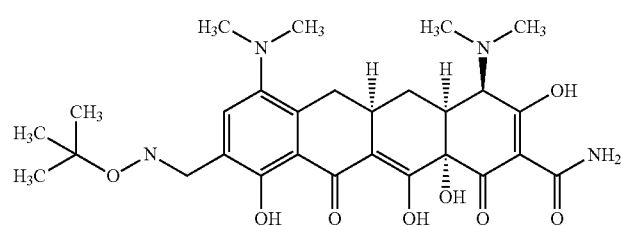
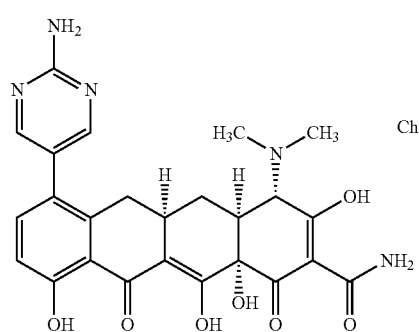
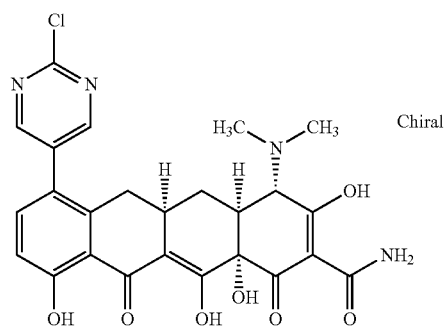
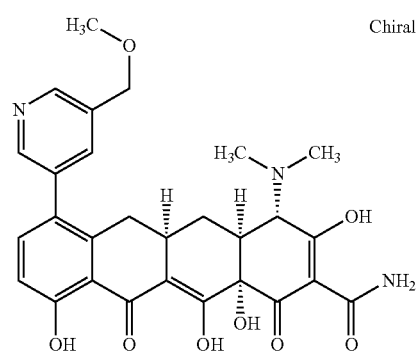

TABLE 2-continued
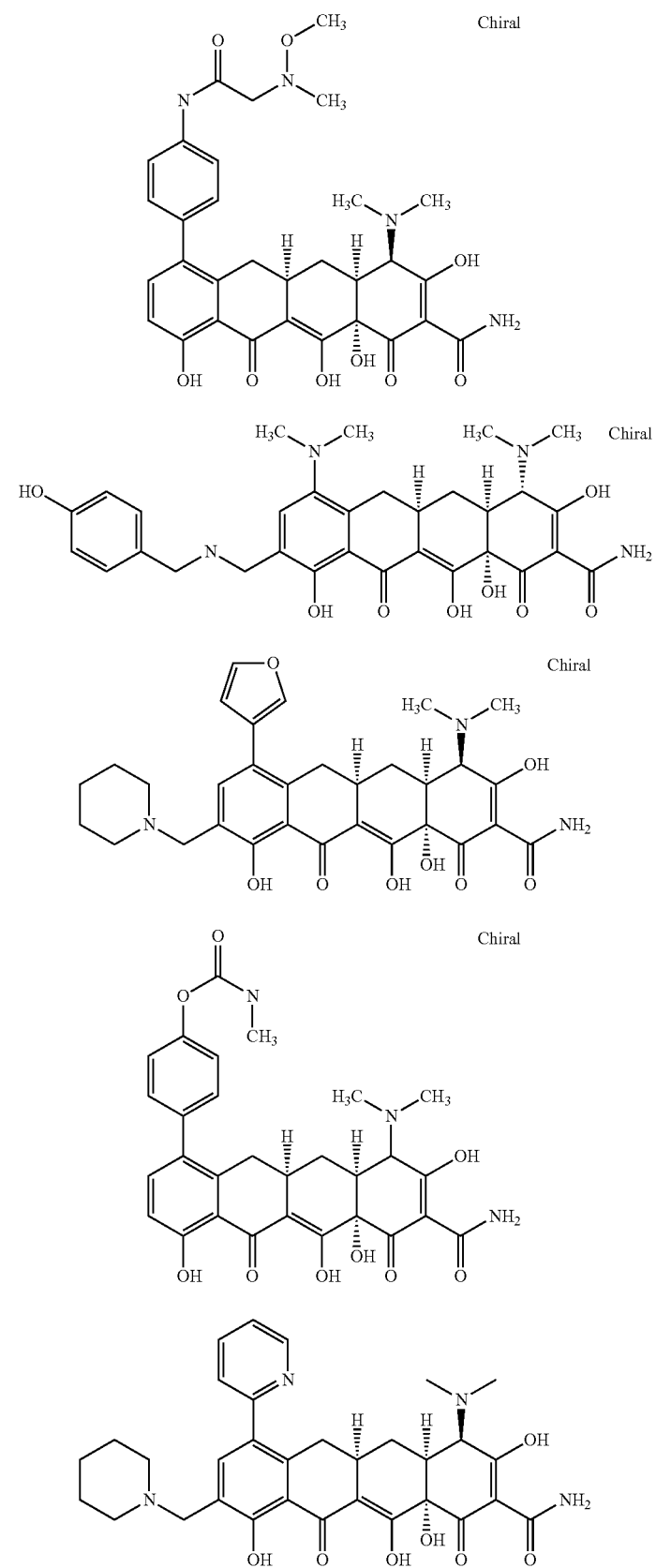

TABLE 2-continued
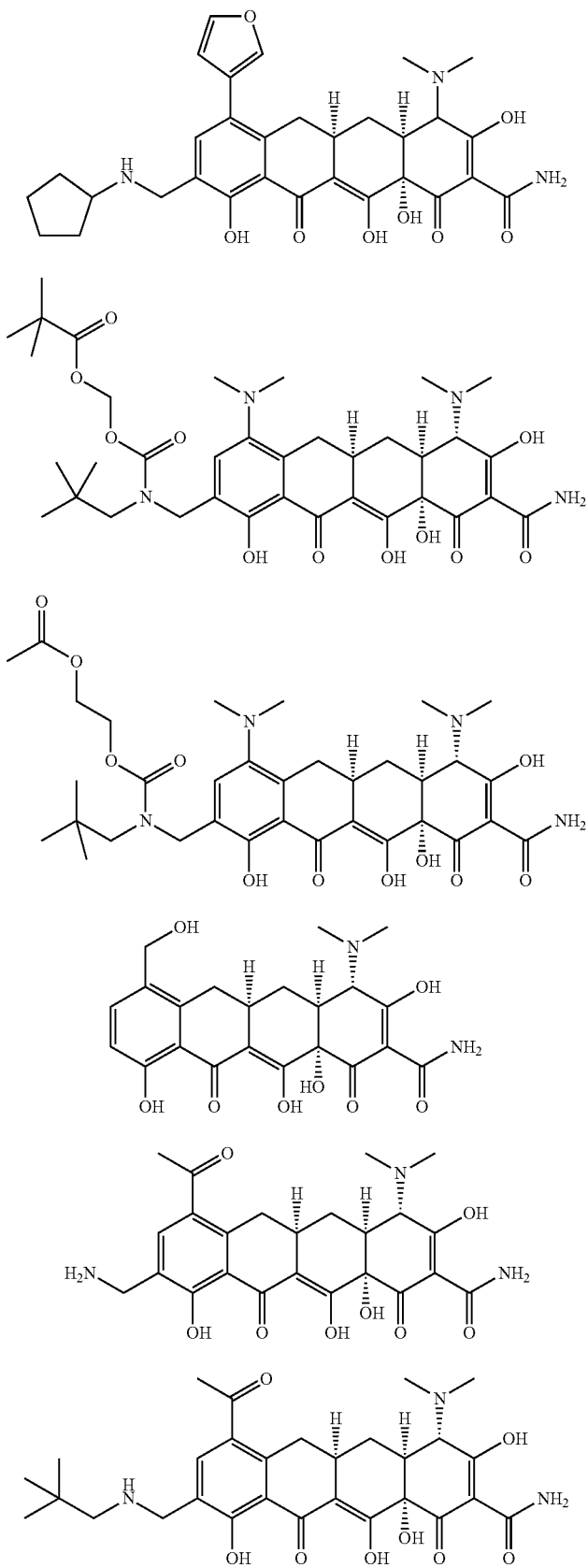

TABLE 2-continued
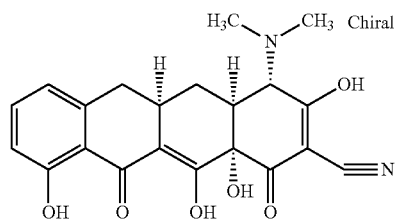
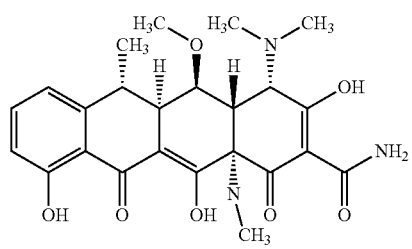
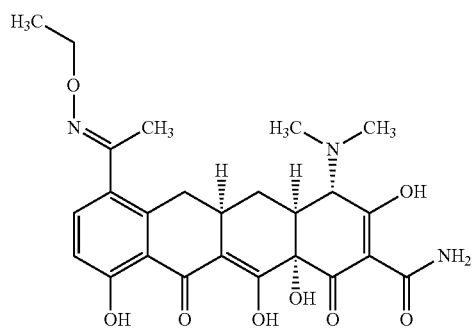
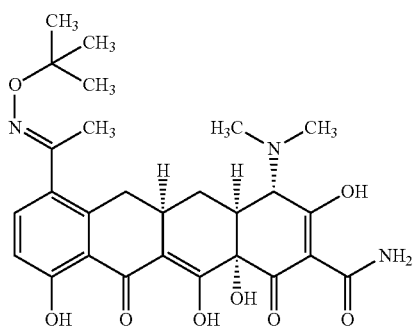
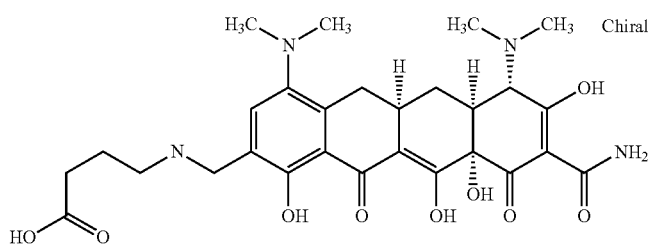
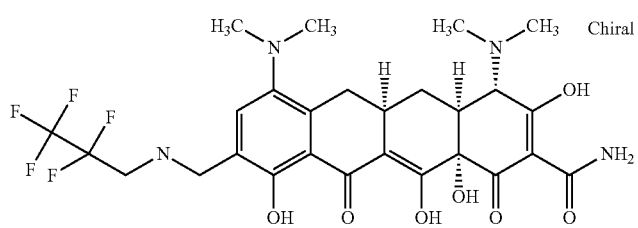

TABLE 2-continued
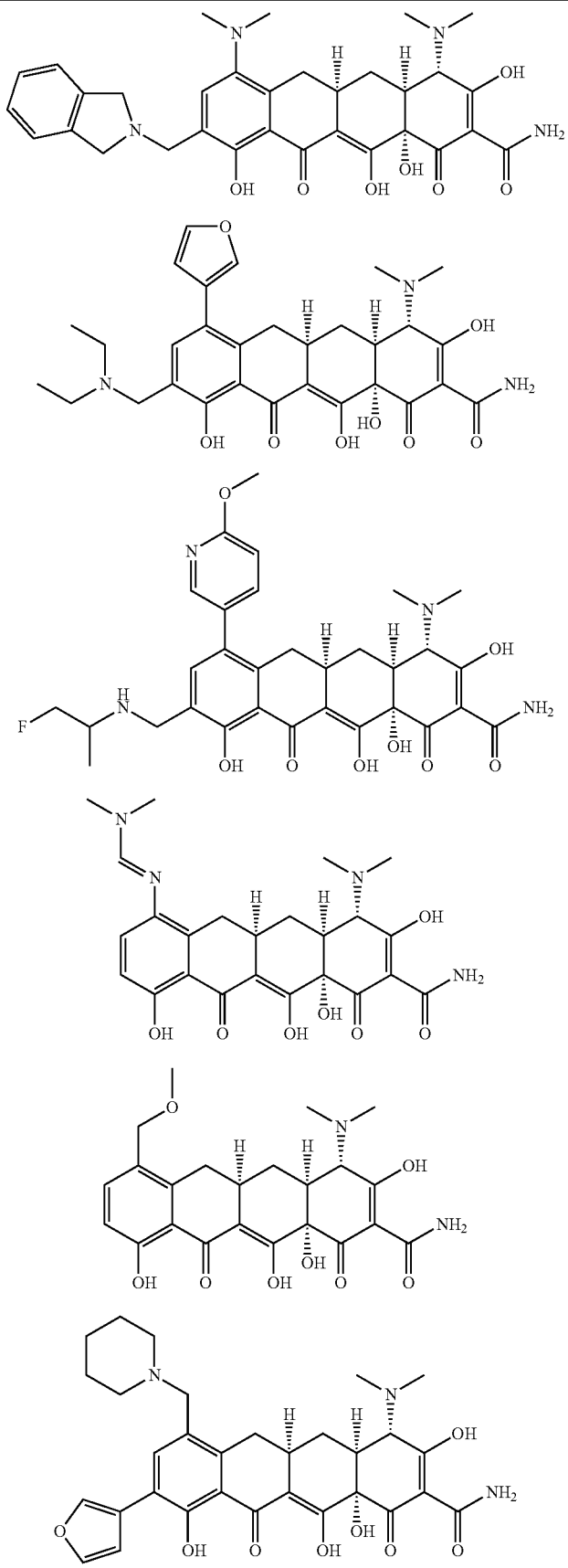

TABLE 2-continued
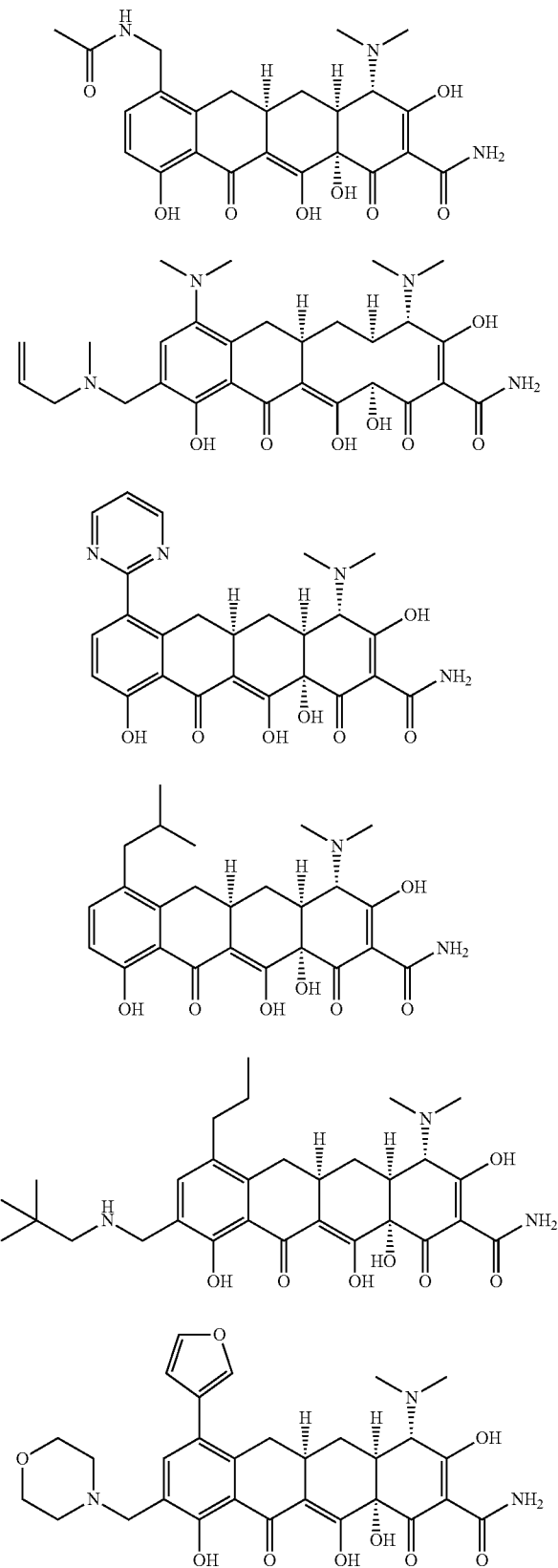

TABLE 2-continued
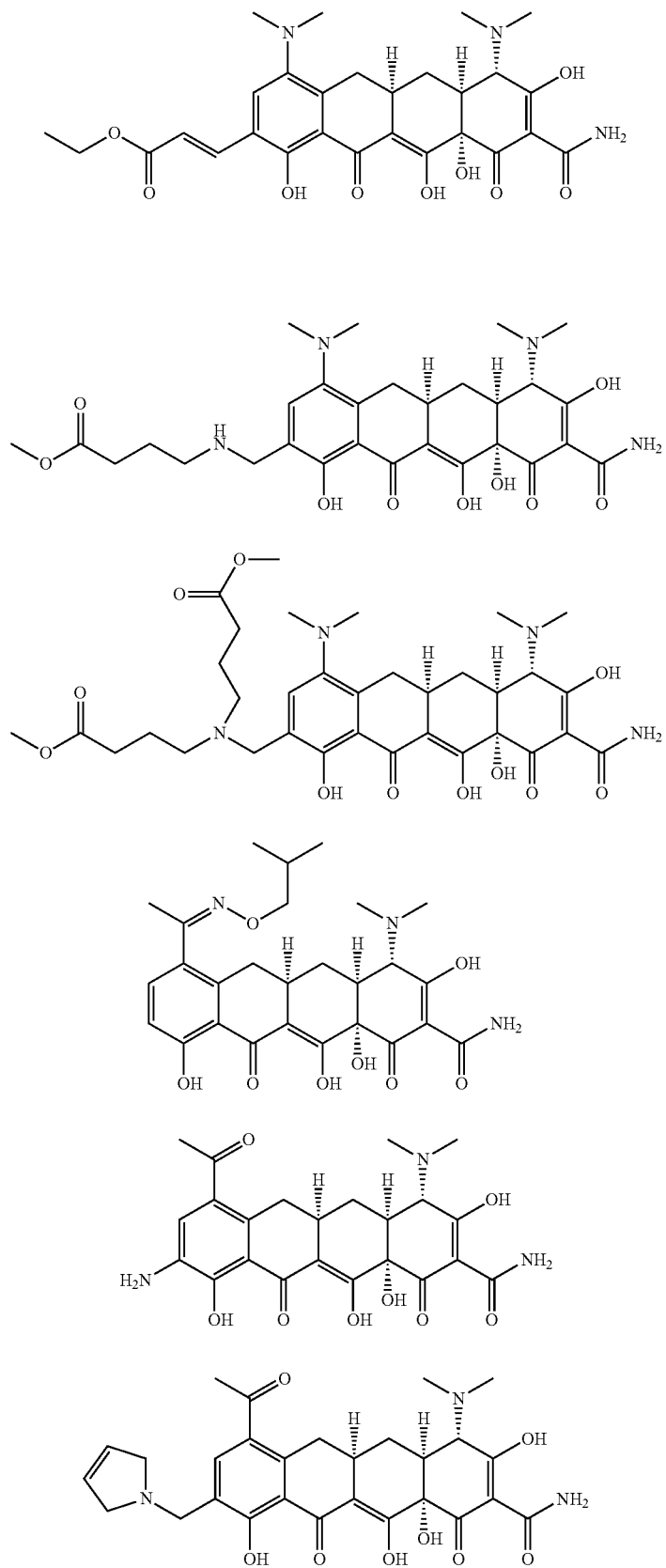

TABLE 2-continued
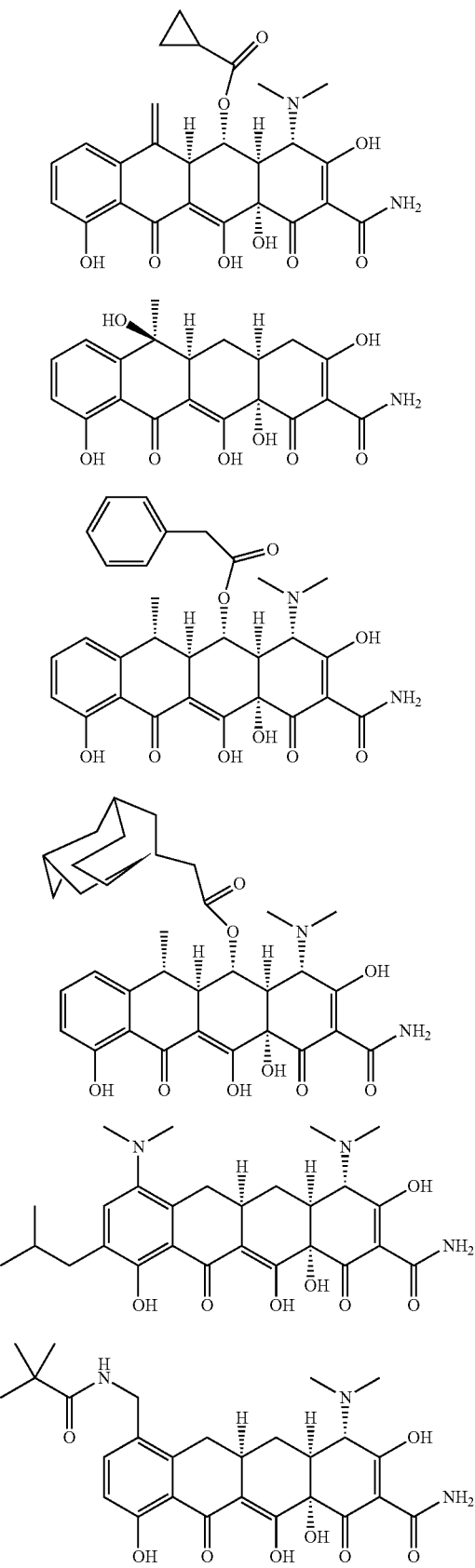

TABLE 2-continued
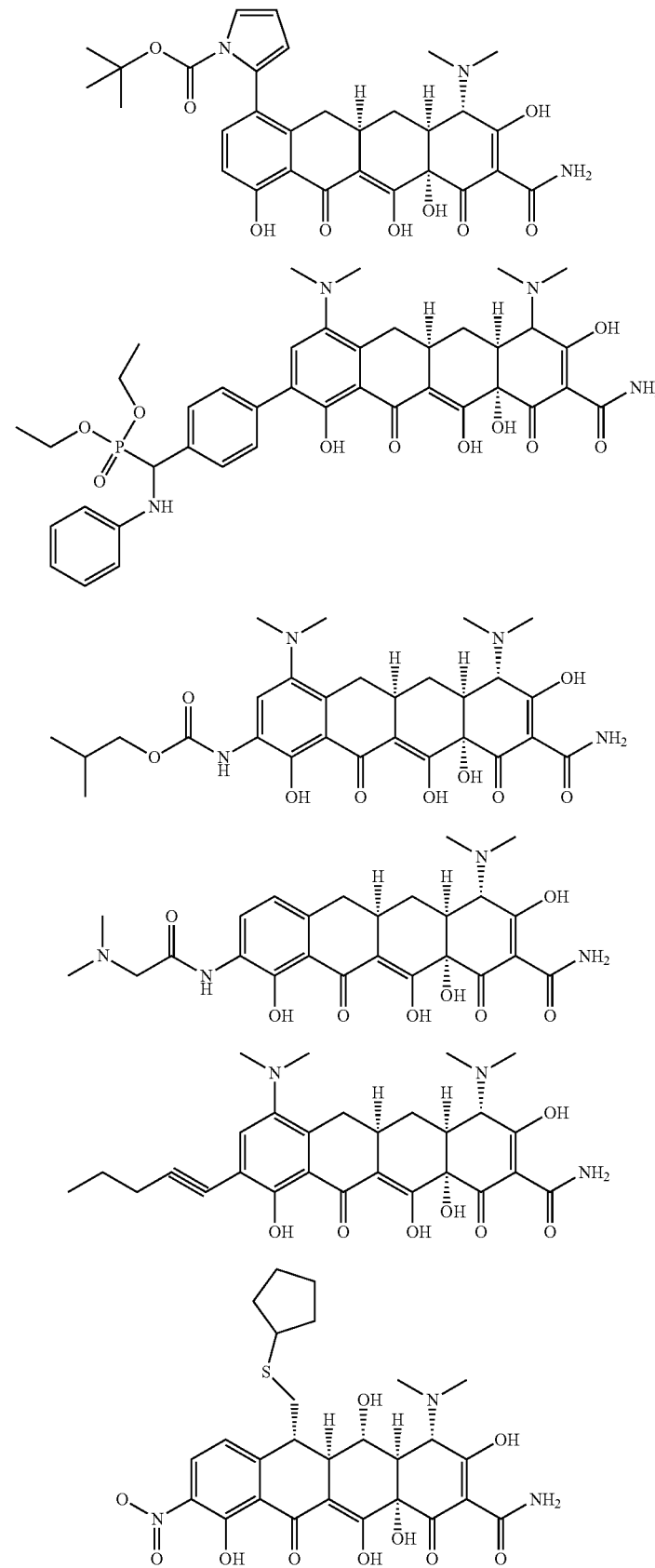

TABLE 2-continued
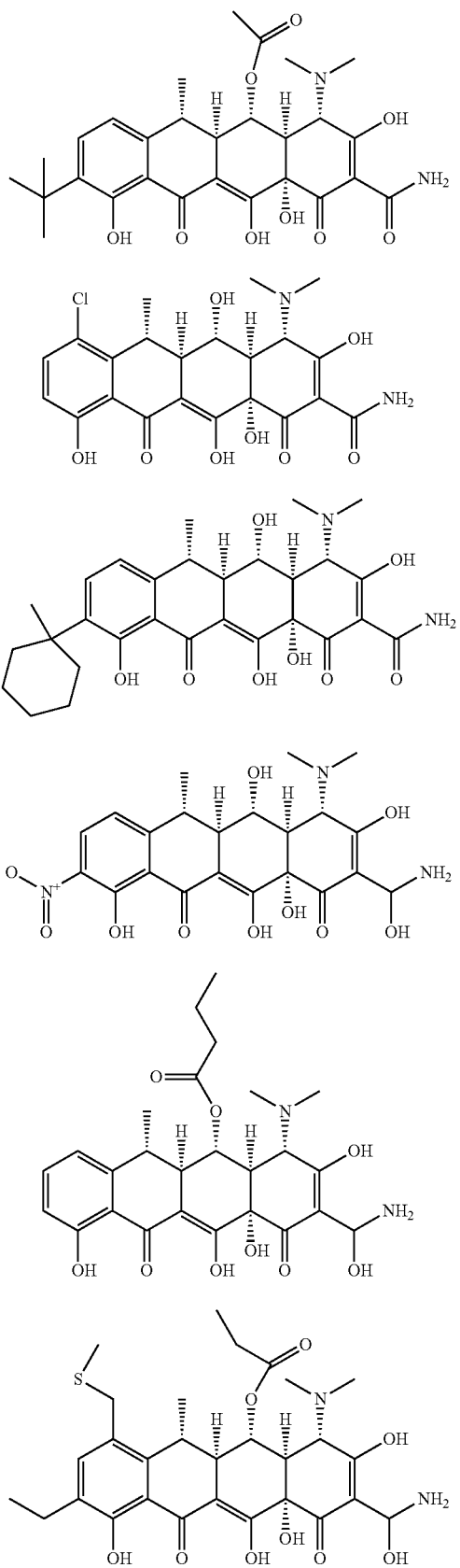

TABLE 2-continued
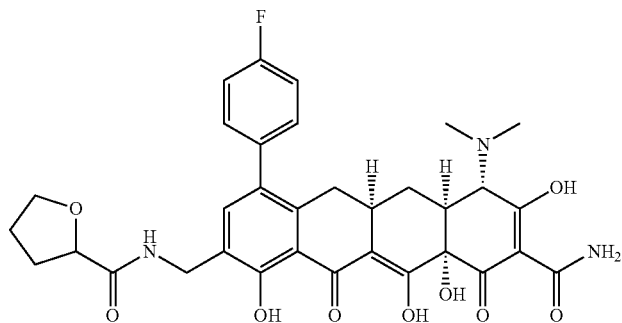
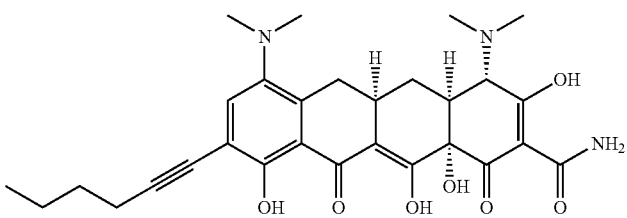
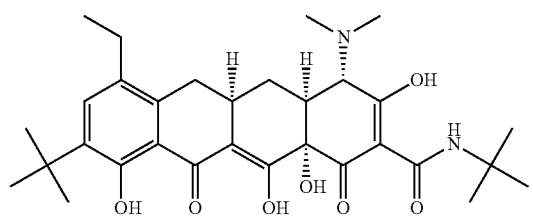
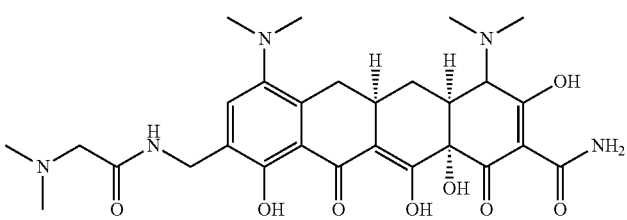
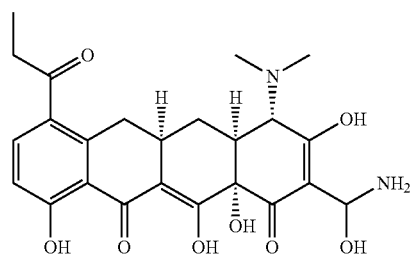
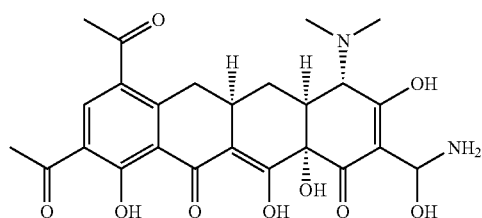

TABLE 2-continued
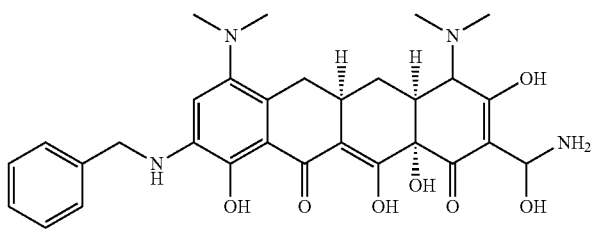
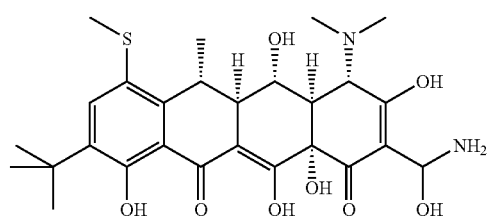
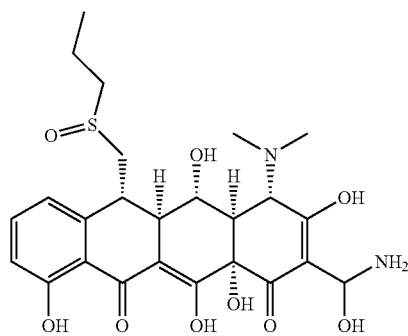
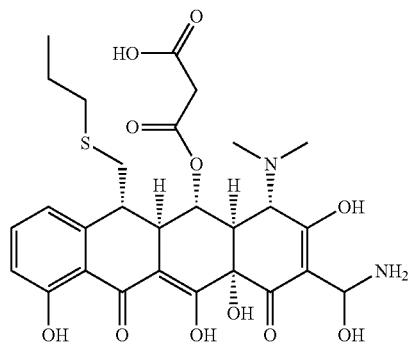
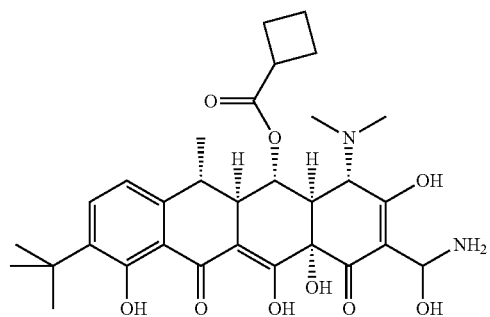

TABLE 2-continued
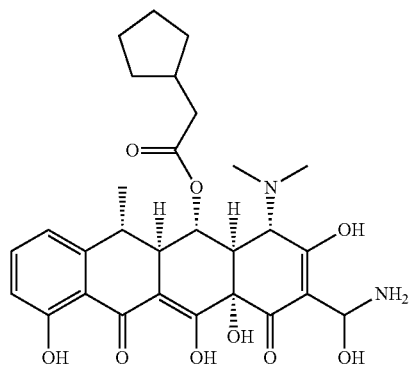
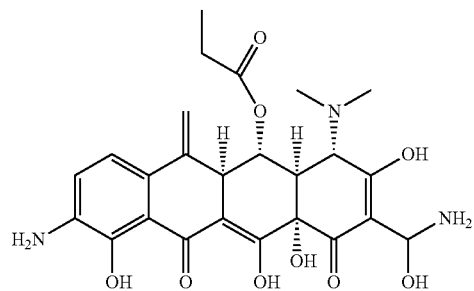
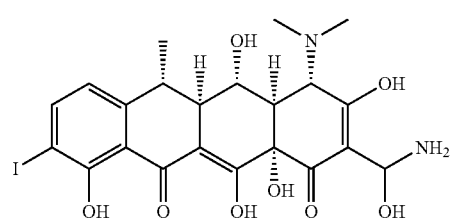
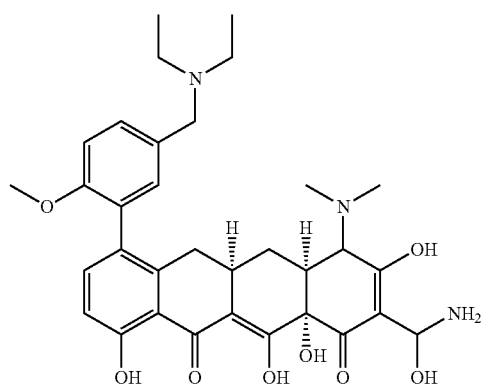

TABLE 2-continued
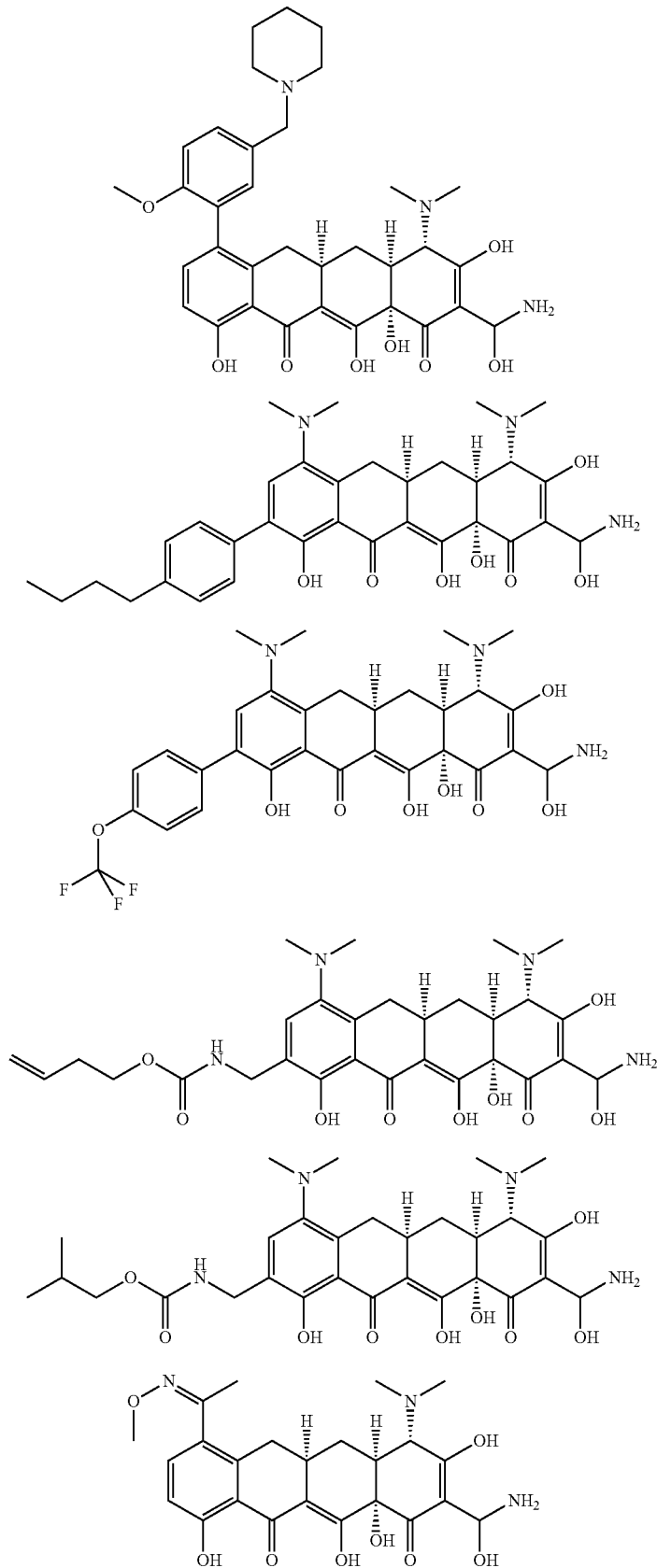

TABLE 2-continued
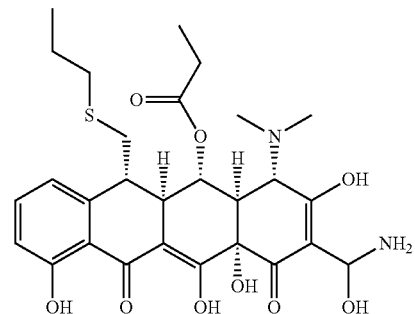
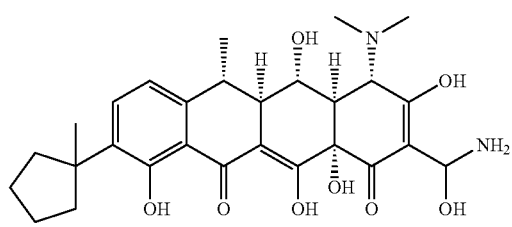
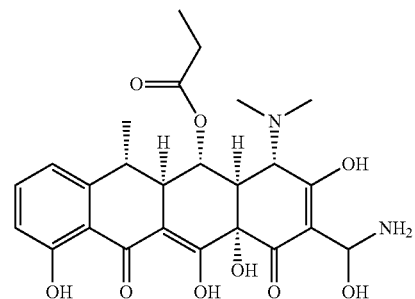
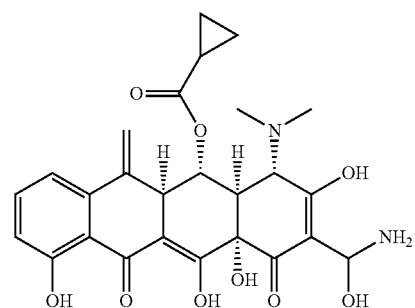
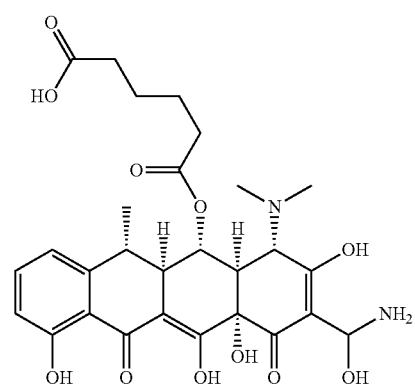

TABLE 2-continued
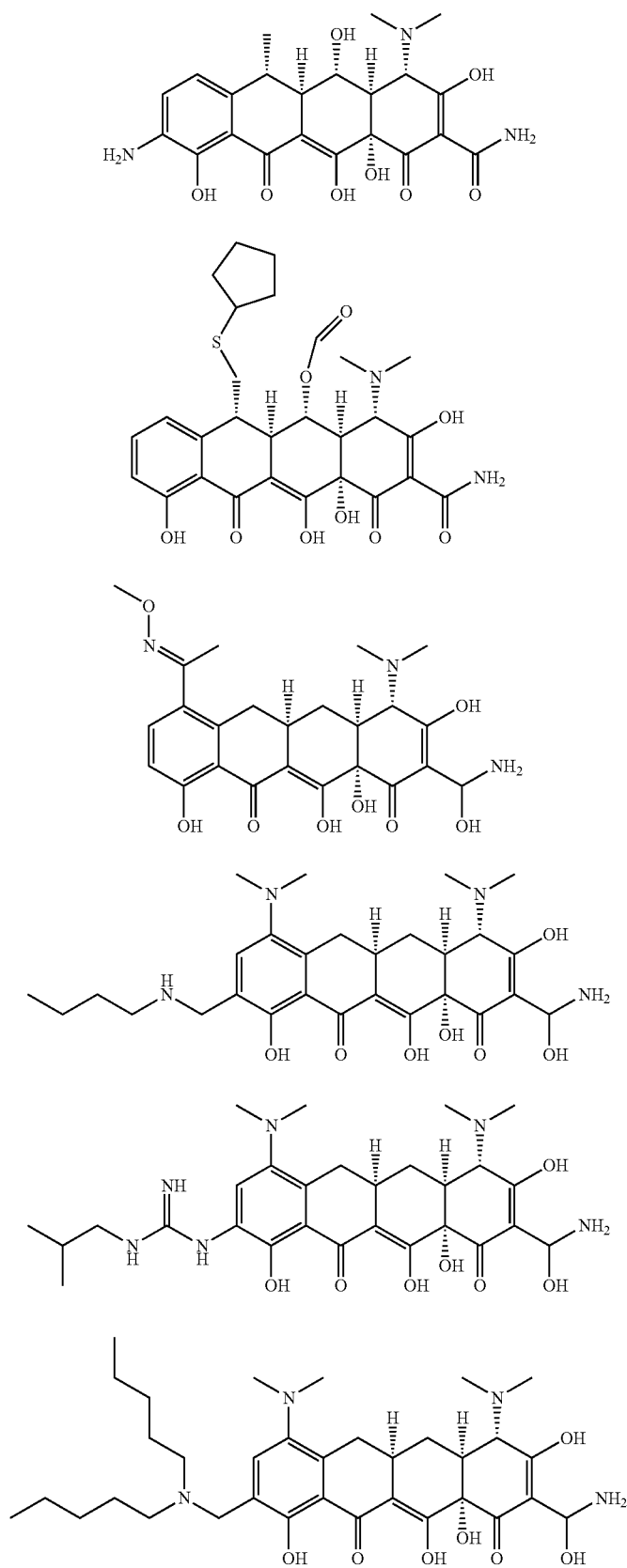

TABLE 2-continued
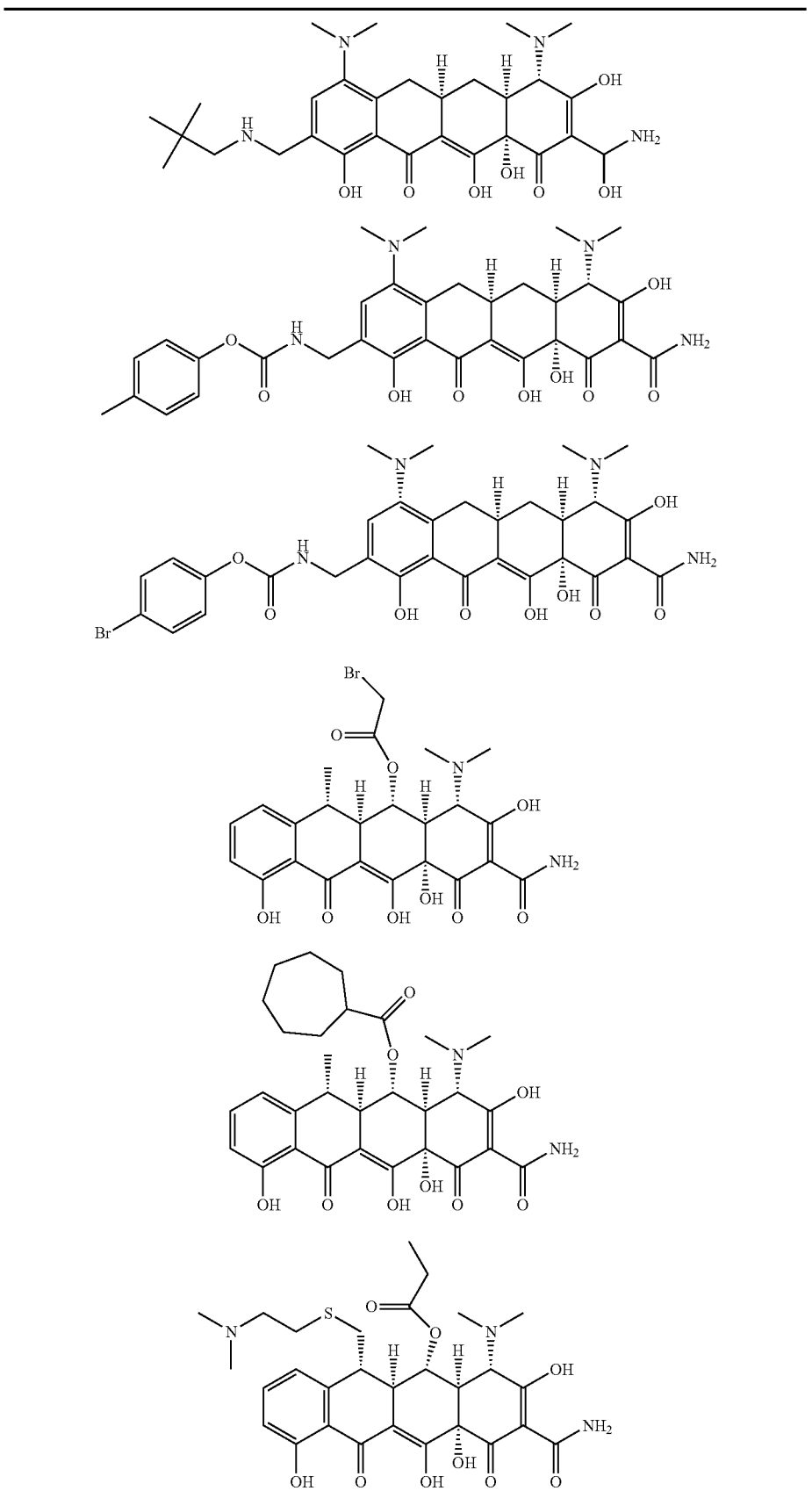

TABLE 2-continued
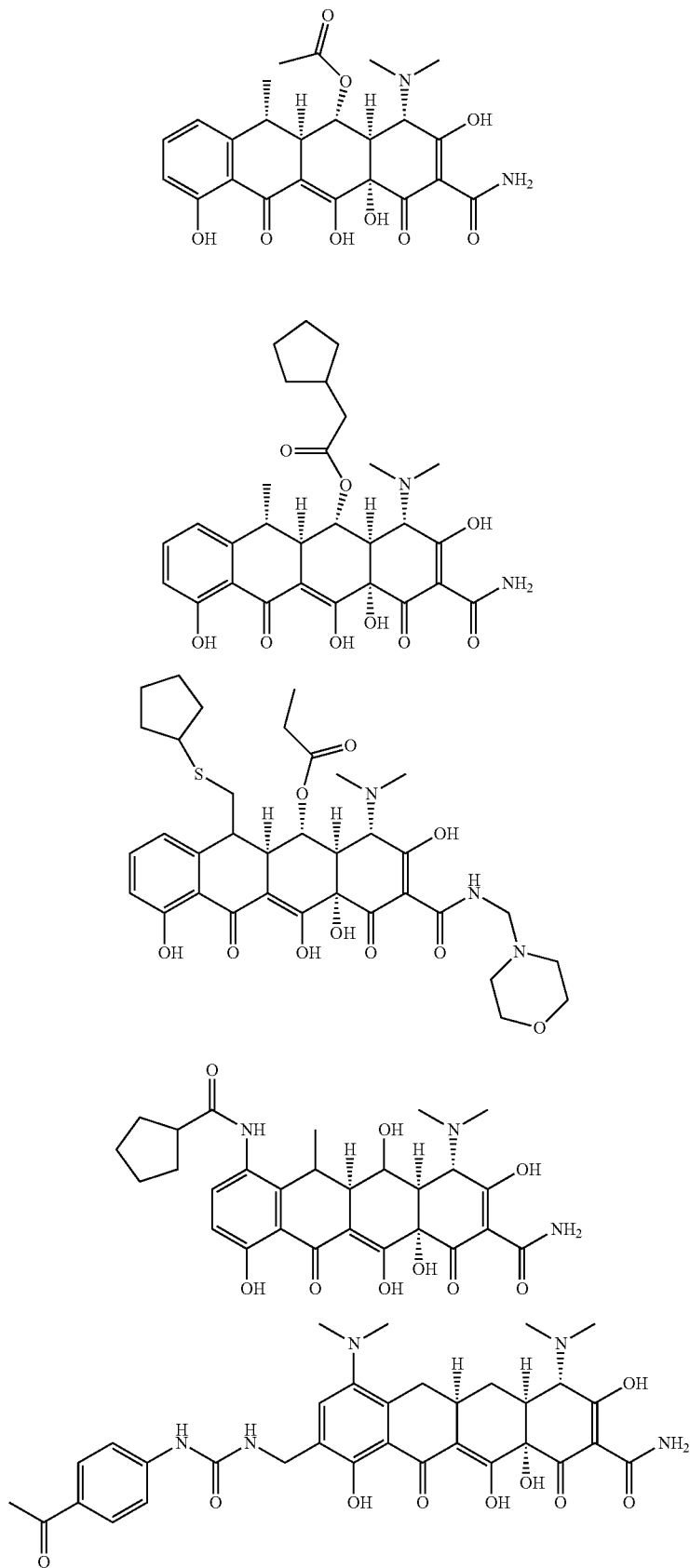

TABLE 2-continued
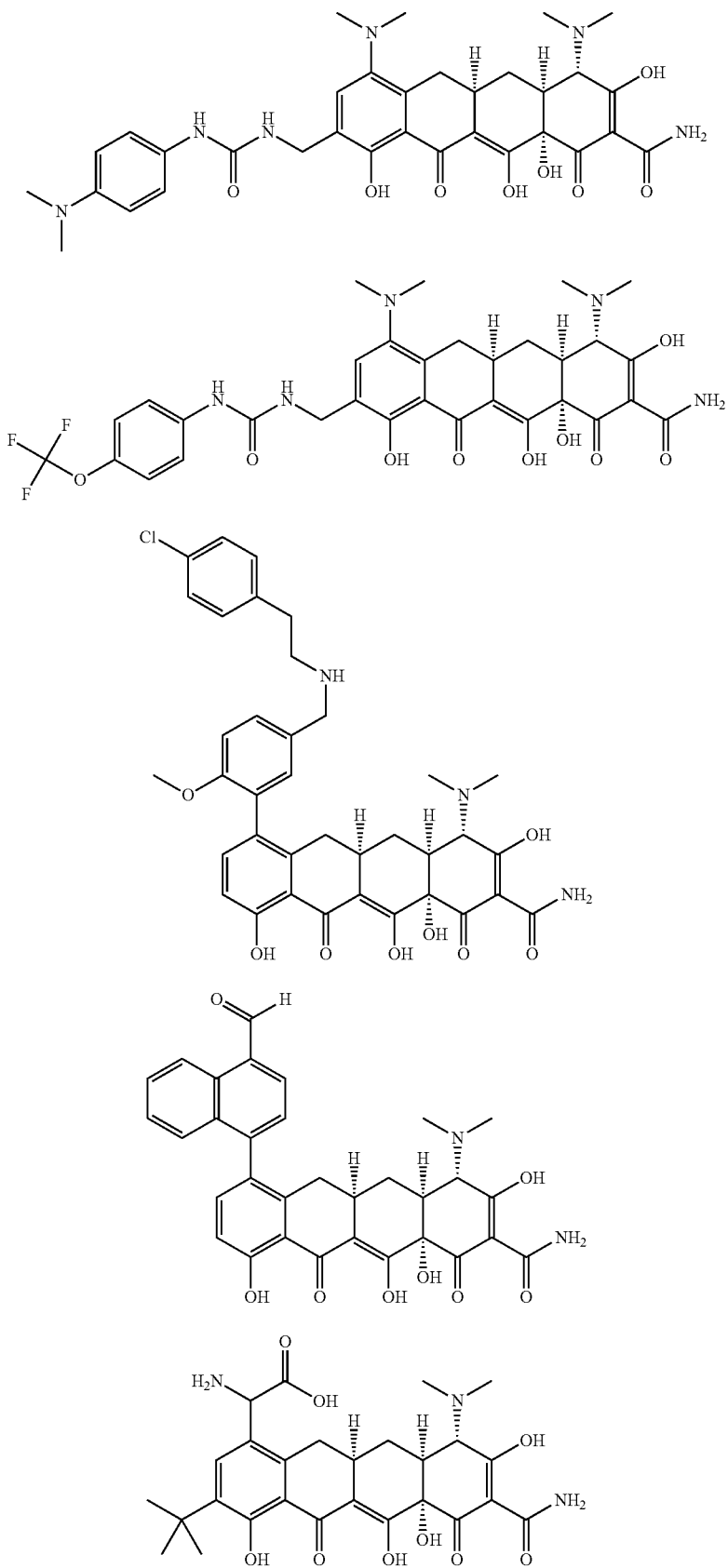

TABLE 2-continued
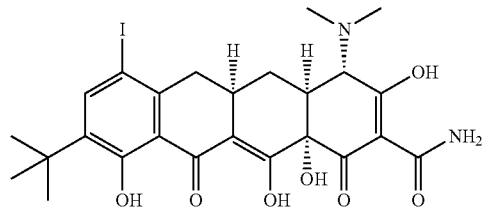
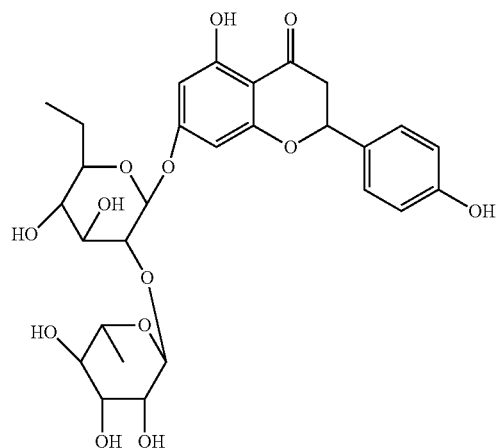
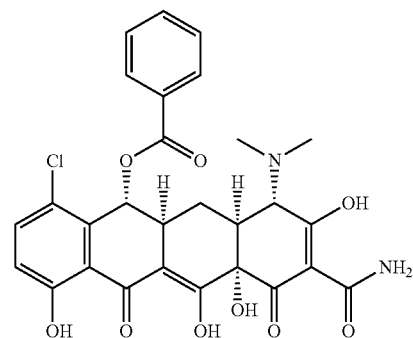
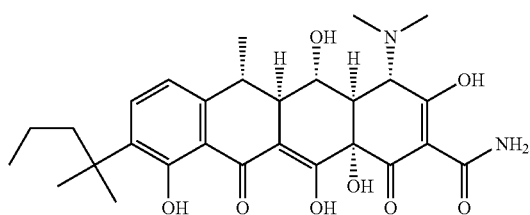
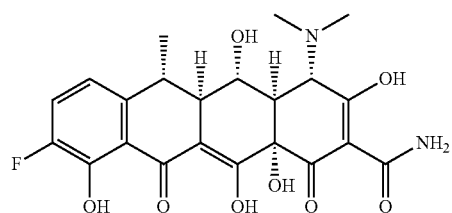

TABLE 2-continued
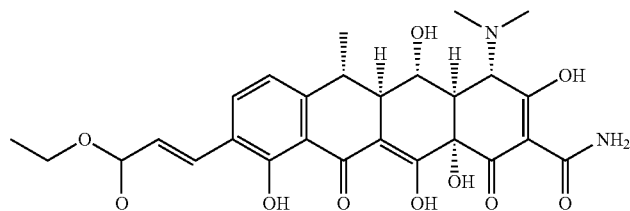
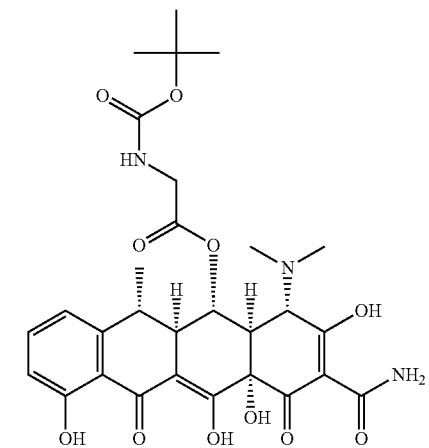
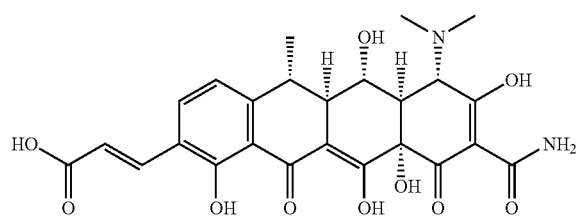
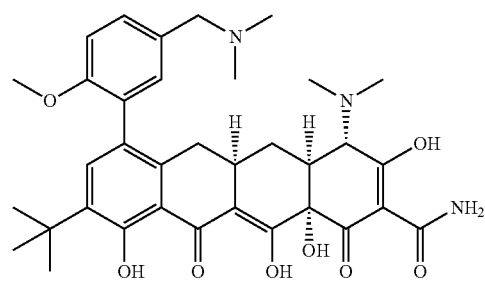
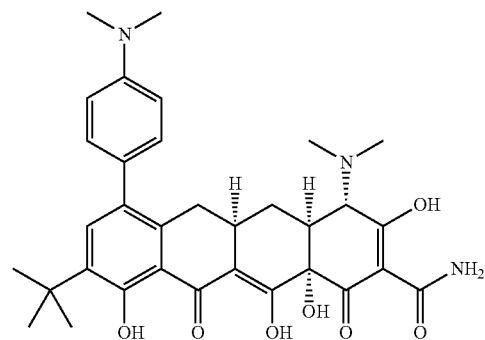

TABLE 2-continued
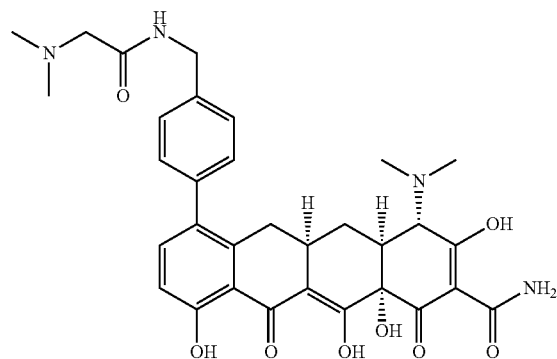
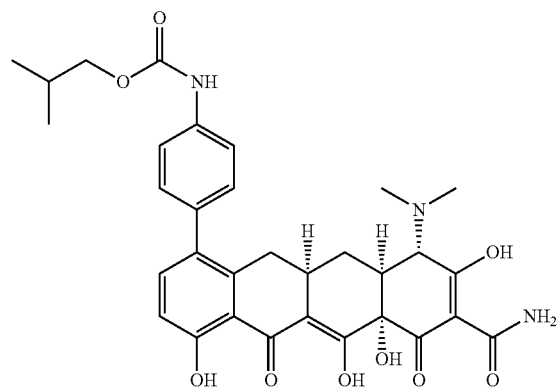
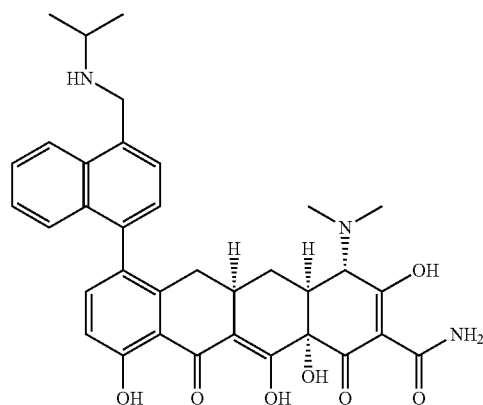
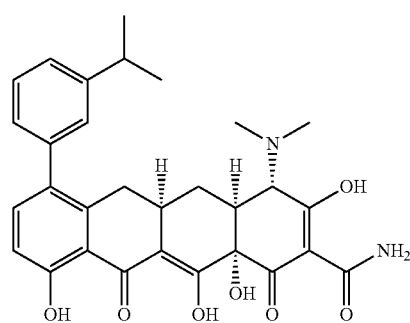

TABLE 2-continued
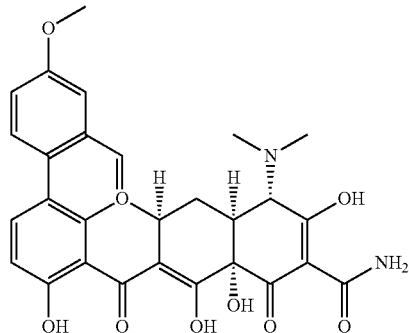
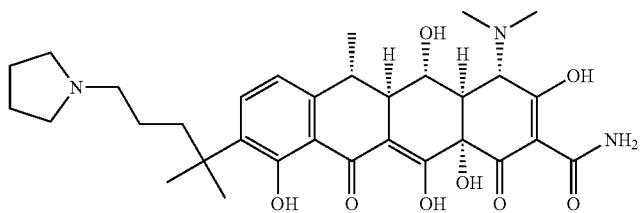
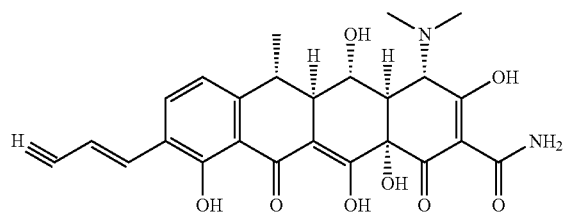
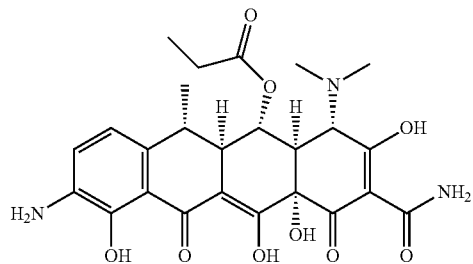
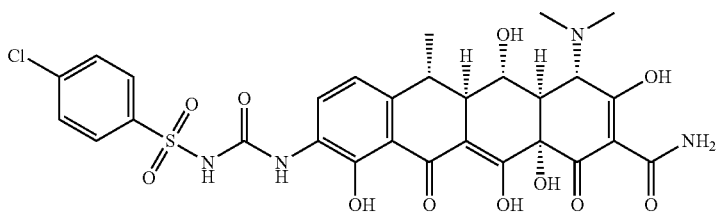
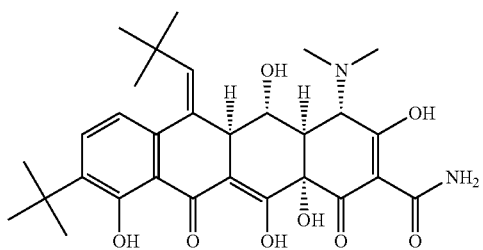

TABLE 2-continued
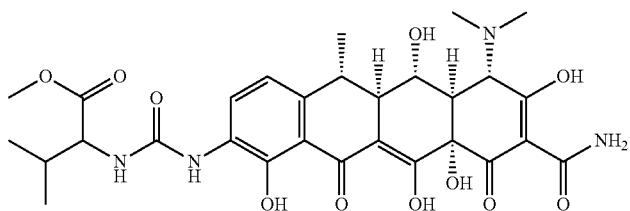
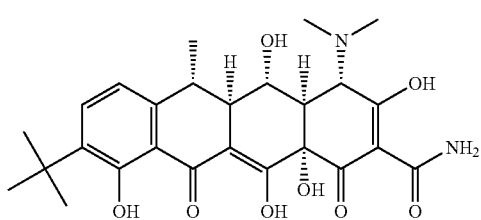
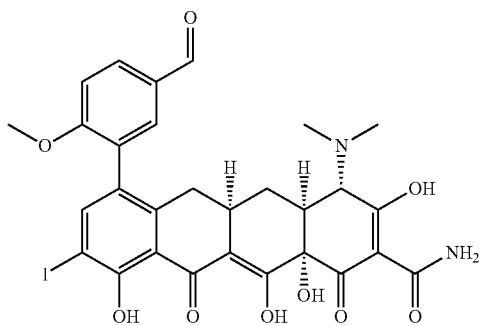
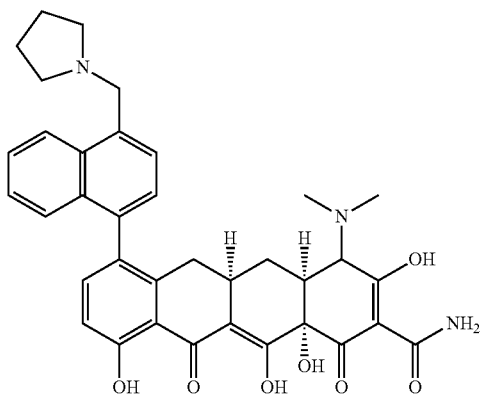
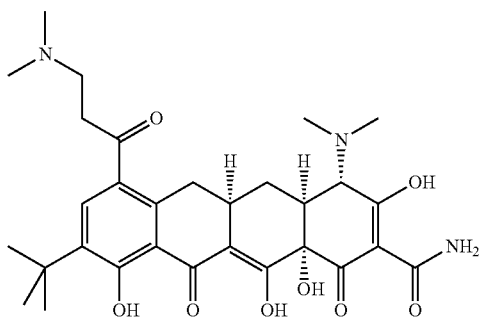

TABLE 2-continued
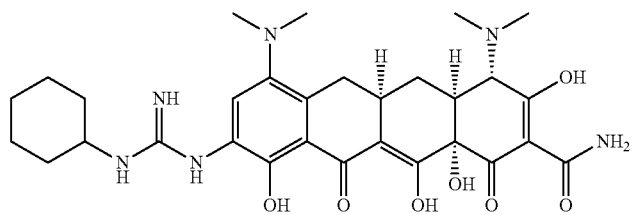
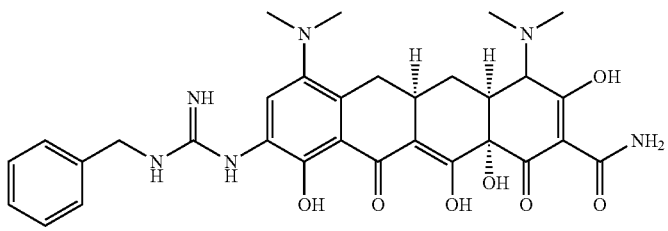
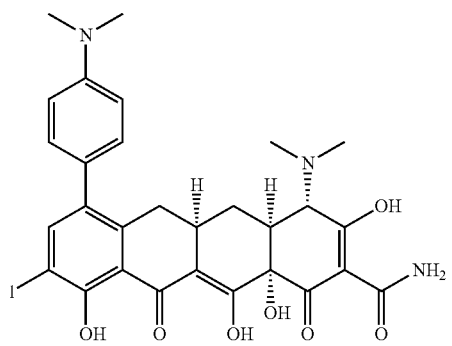
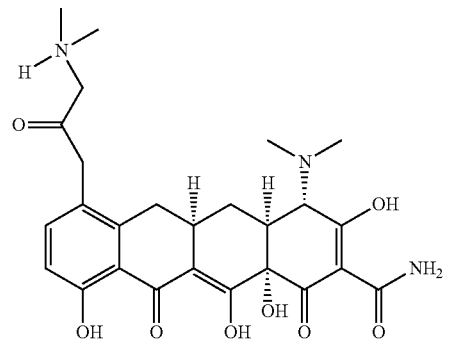
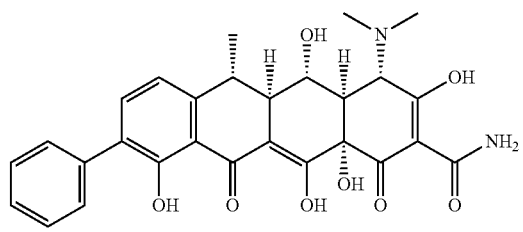
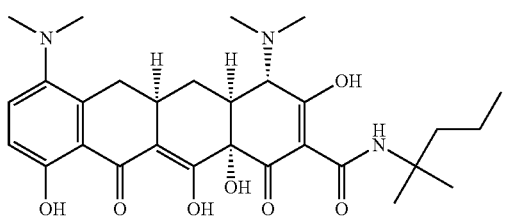

TABLE 2-continued
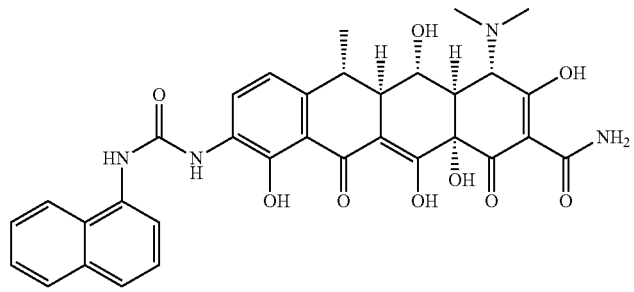
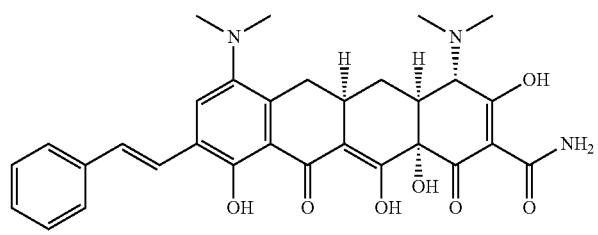
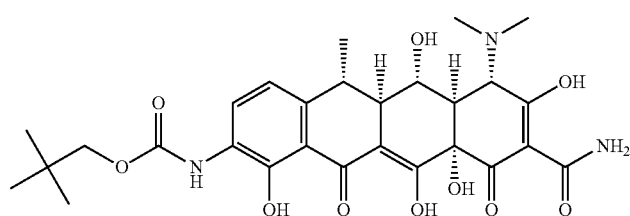
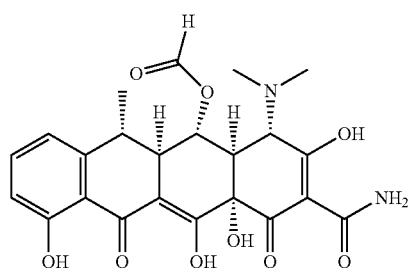
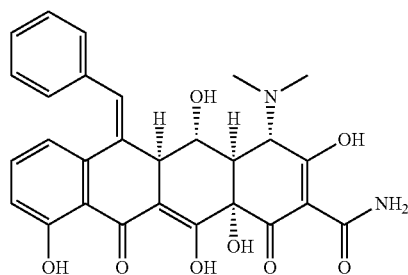

TABLE 2-continued
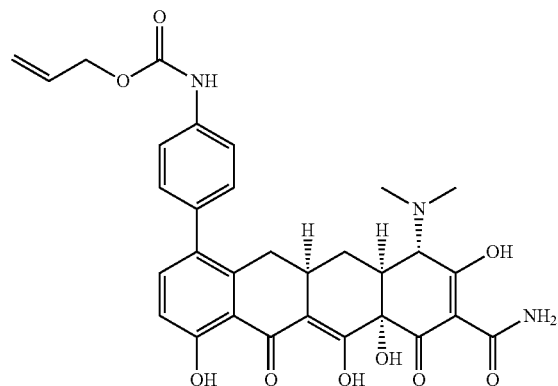
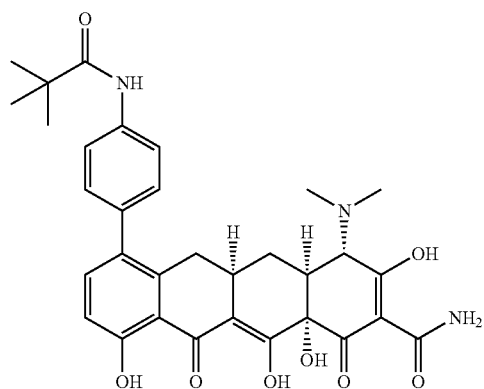
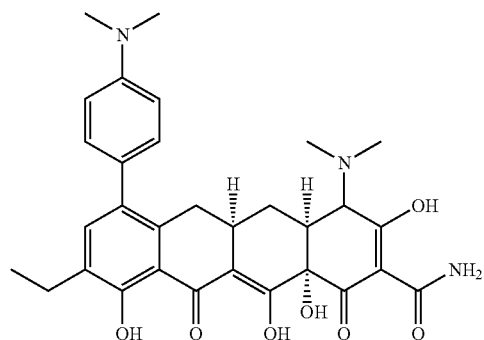
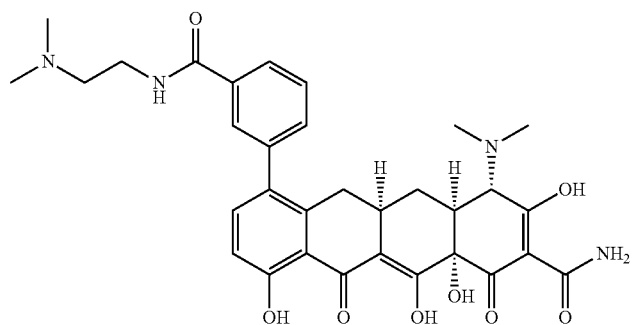

TABLE 2-continued
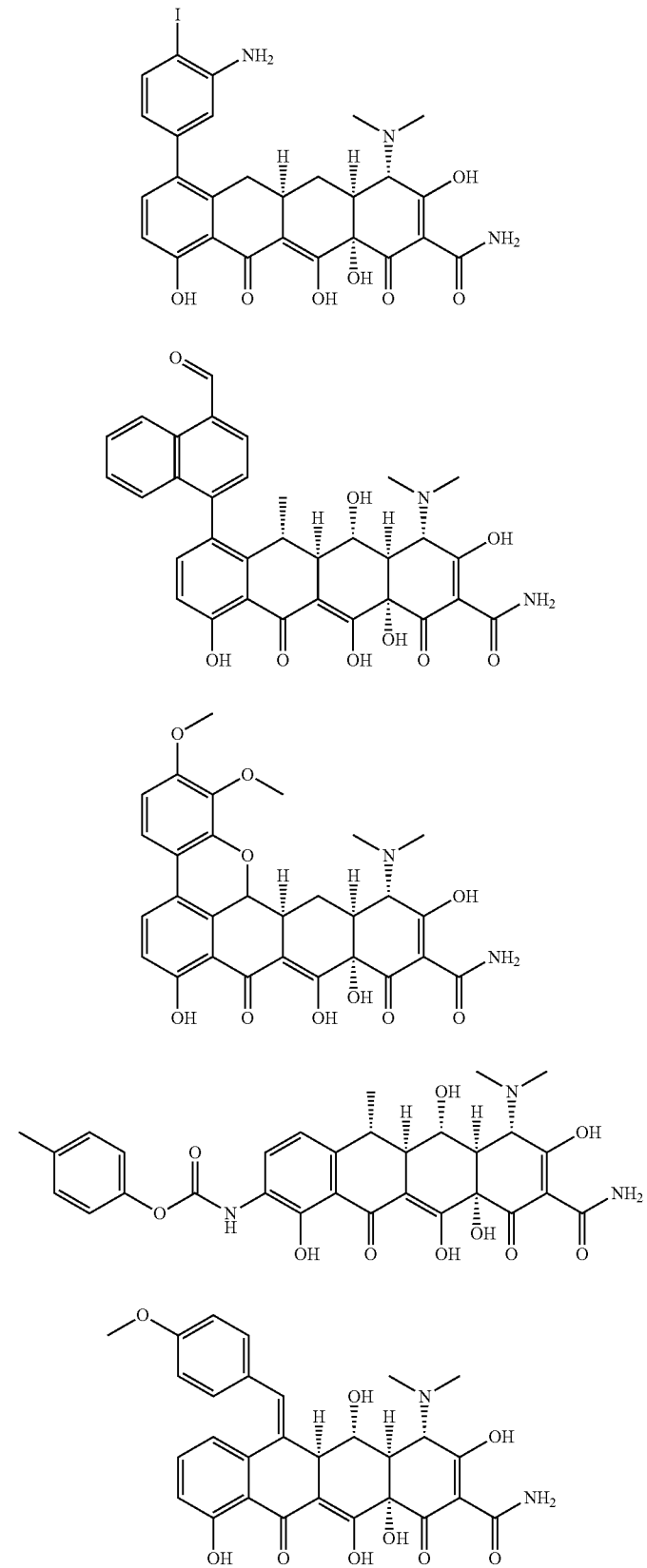

TABLE 2-continued
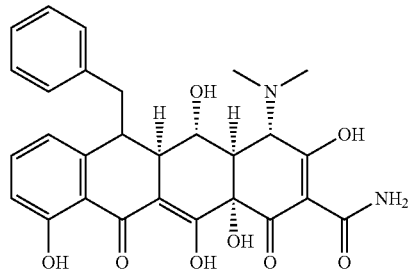
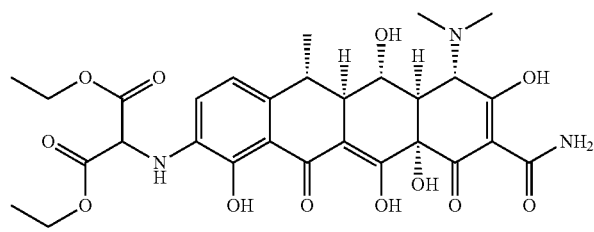
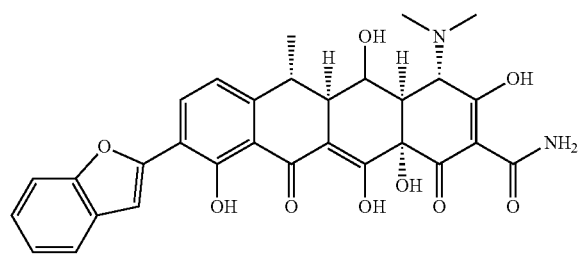
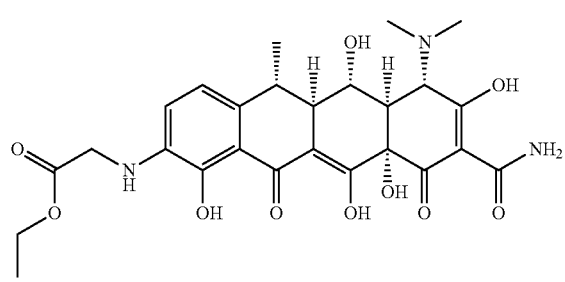
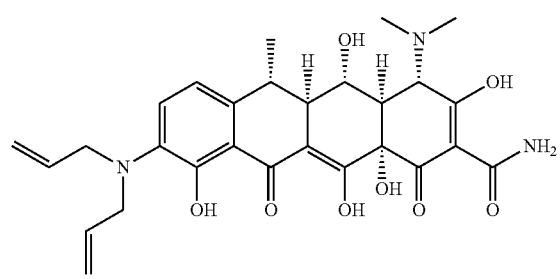

TABLE 2-continued
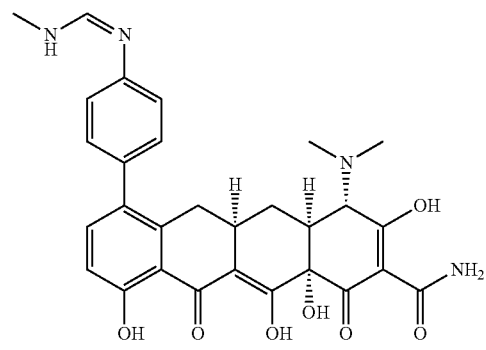
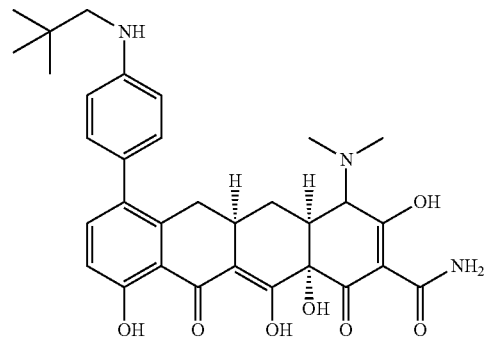
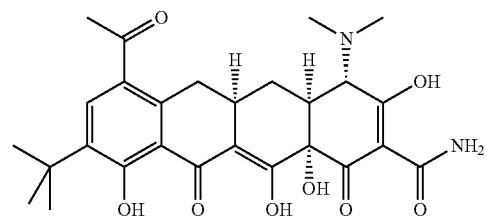
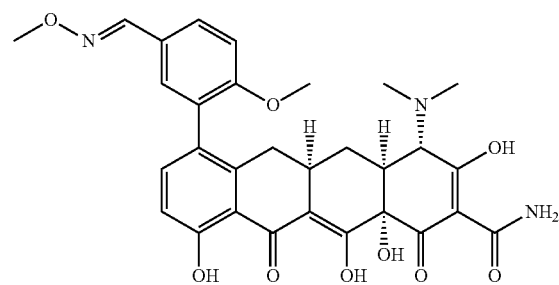
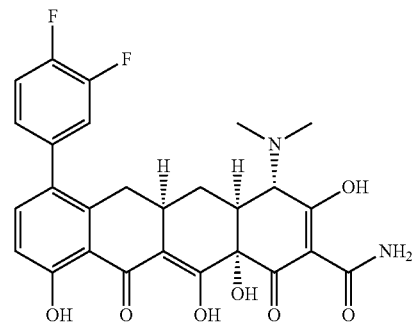

TABLE 2-continued
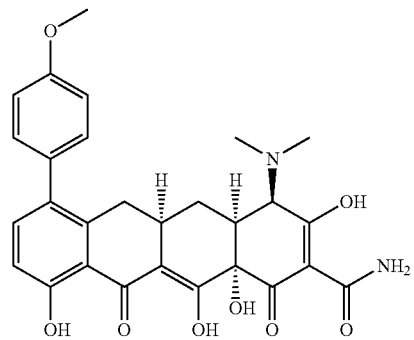
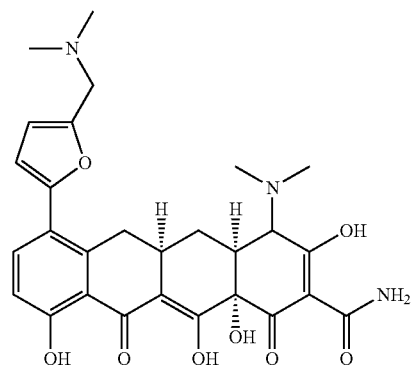
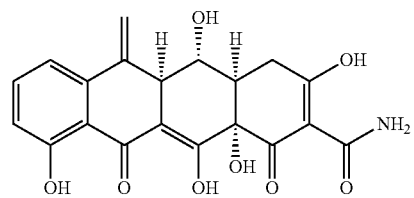
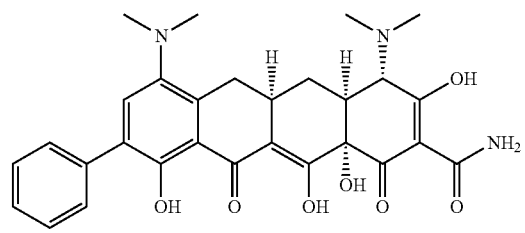
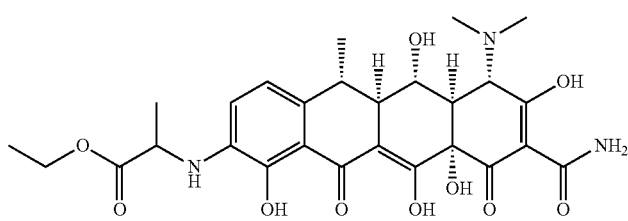
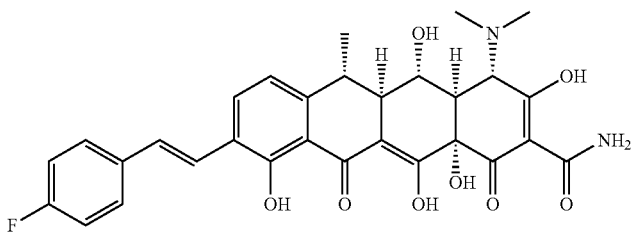

TABLE 2-continued
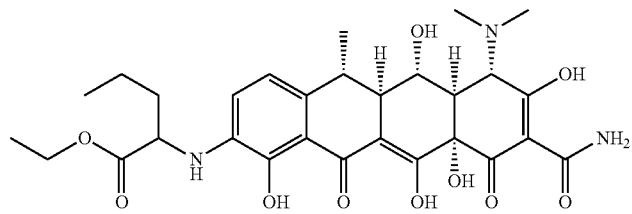
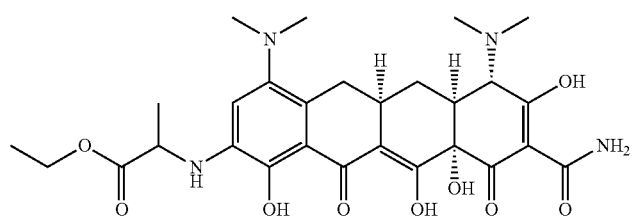
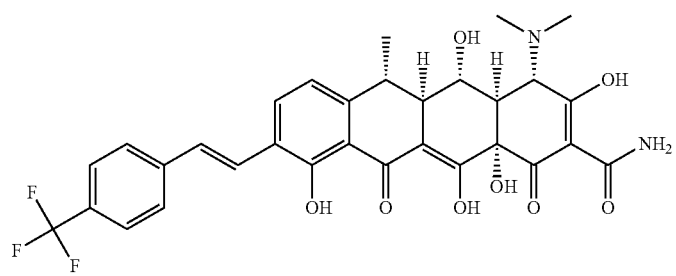
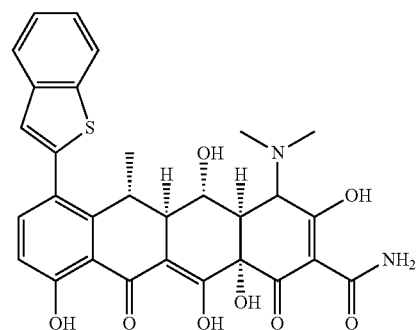
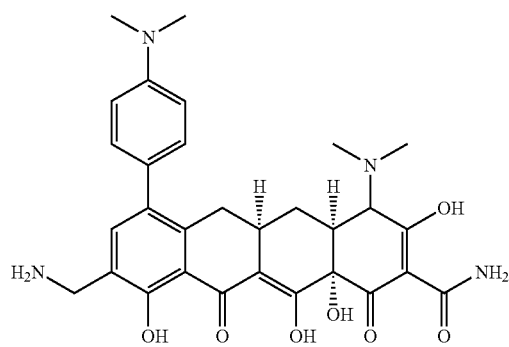

TABLE 2-continued
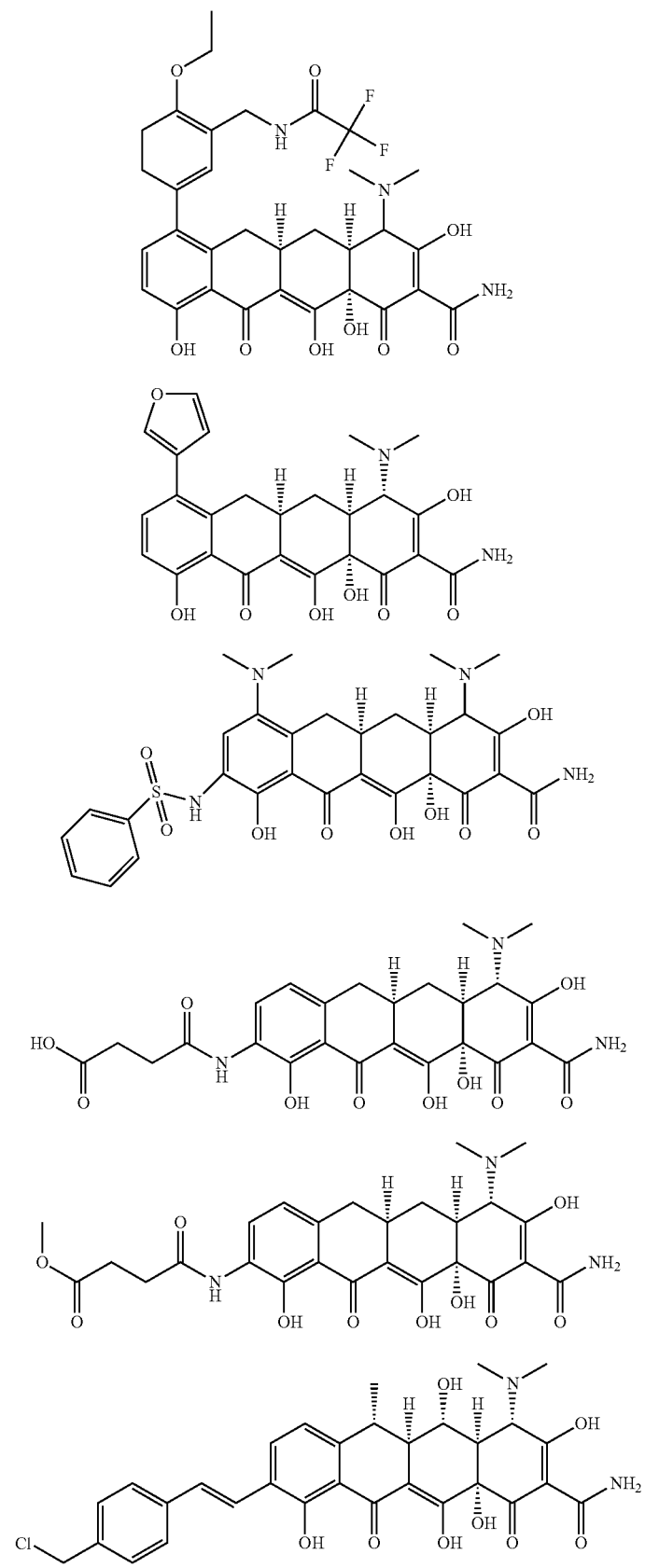

TABLE 2-continued
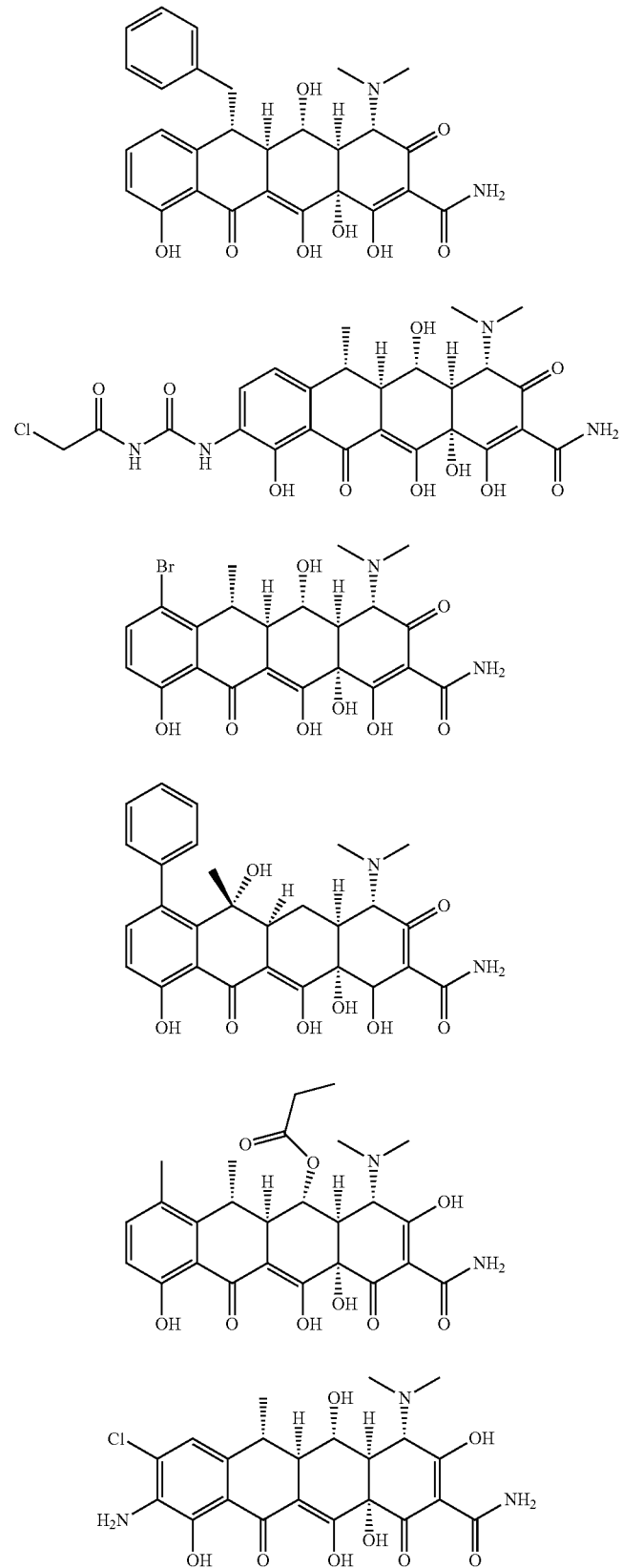

TABLE 2-continued
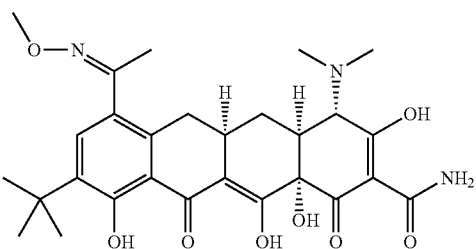
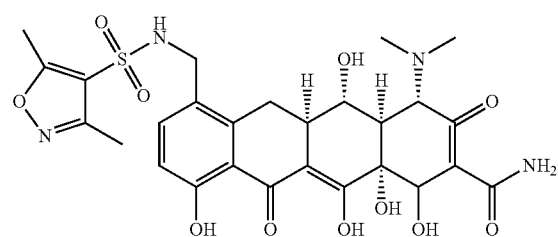
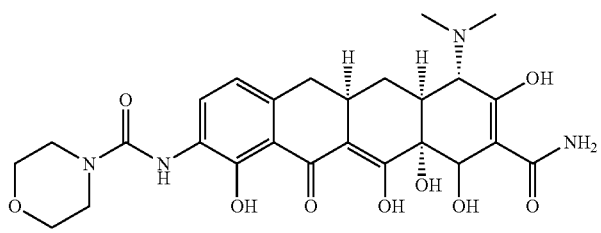
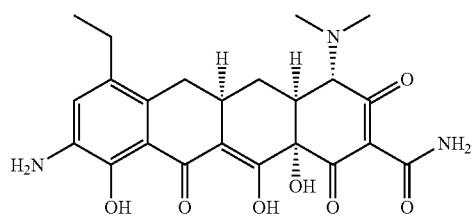
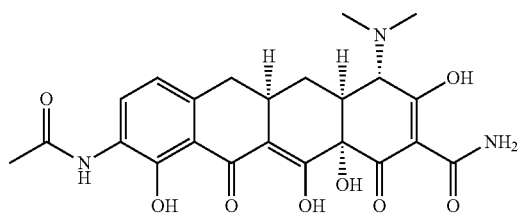
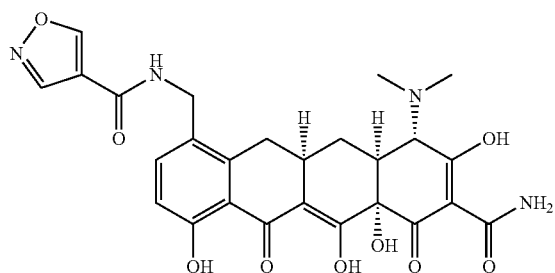

TABLE 2-continued
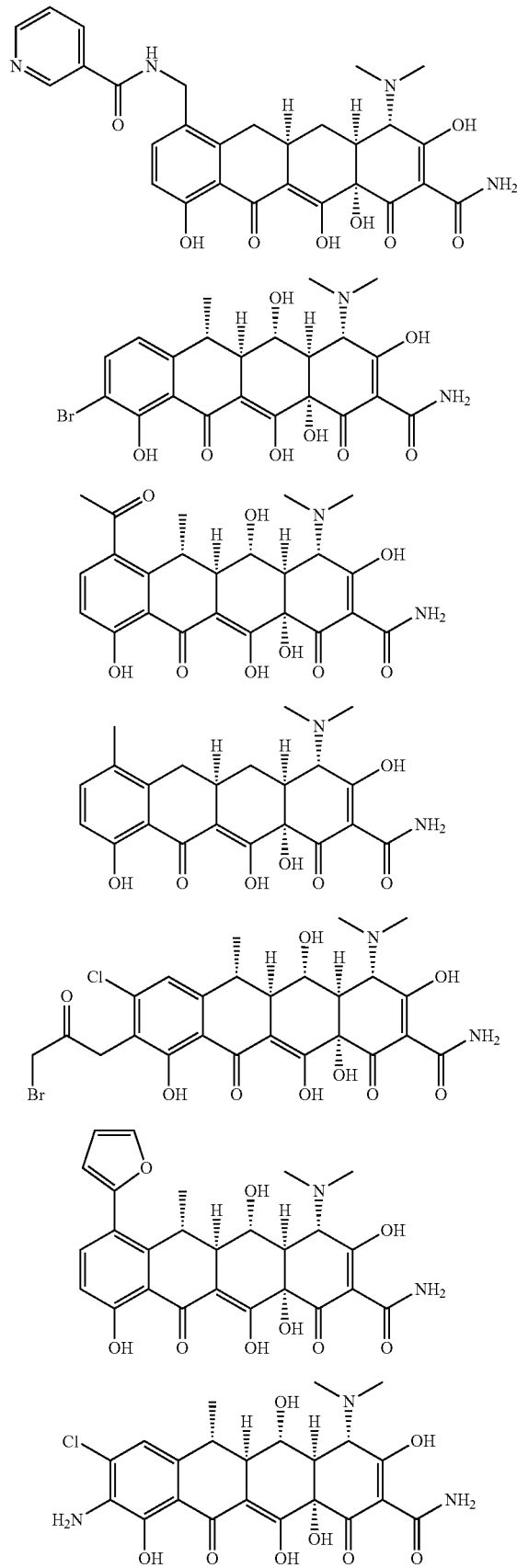

TABLE 2-continued
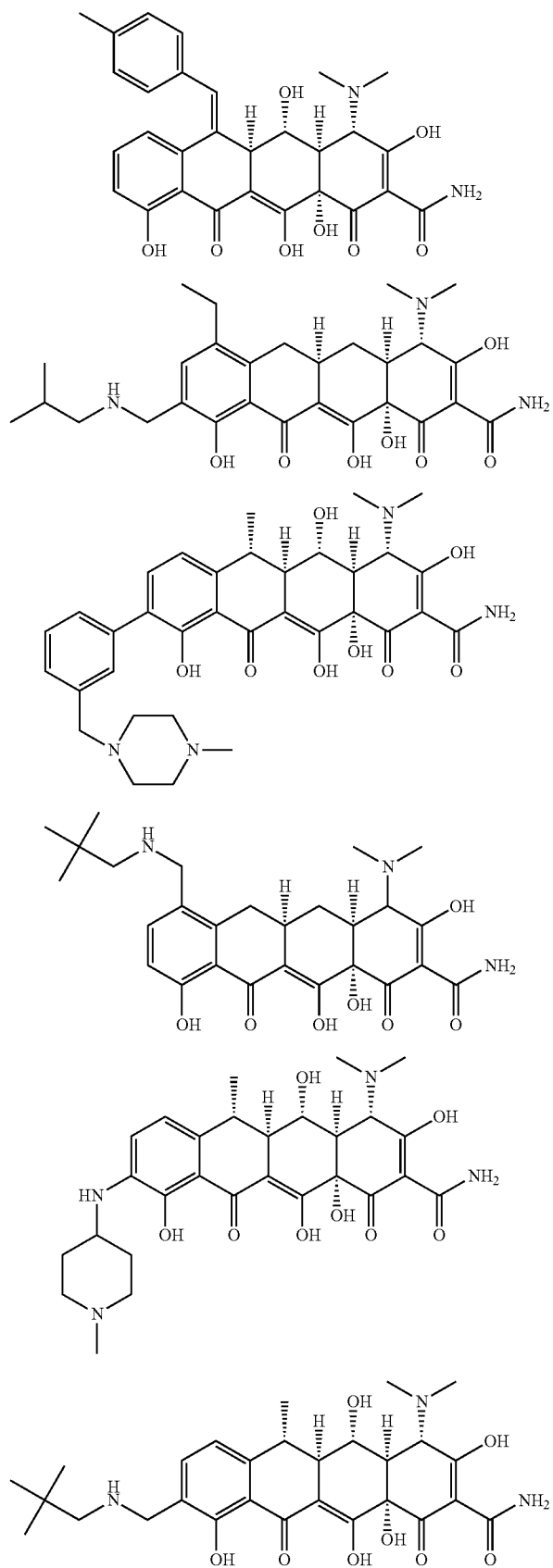

TABLE 2-continued
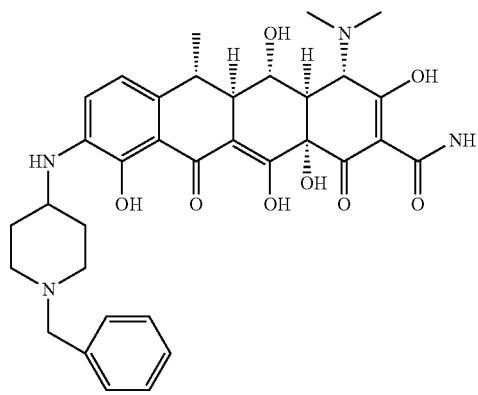
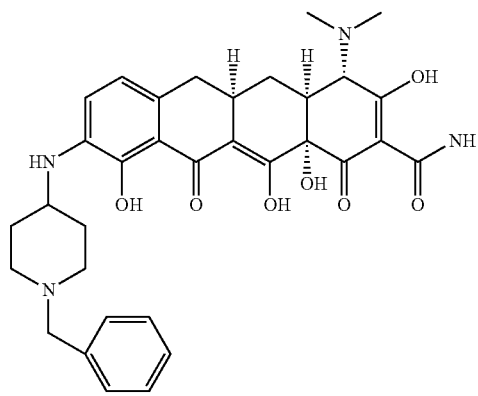
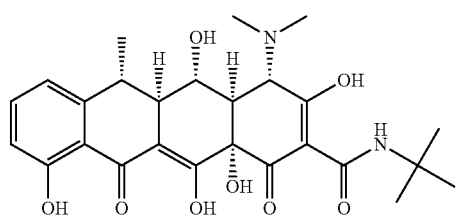
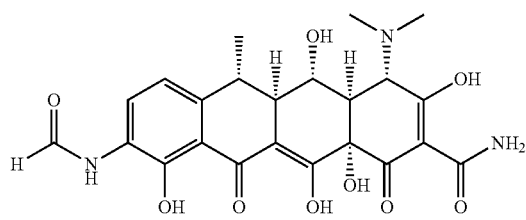
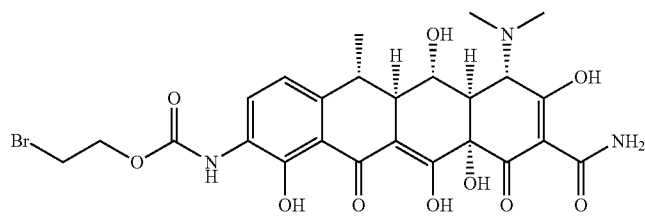

TABLE 2-continued
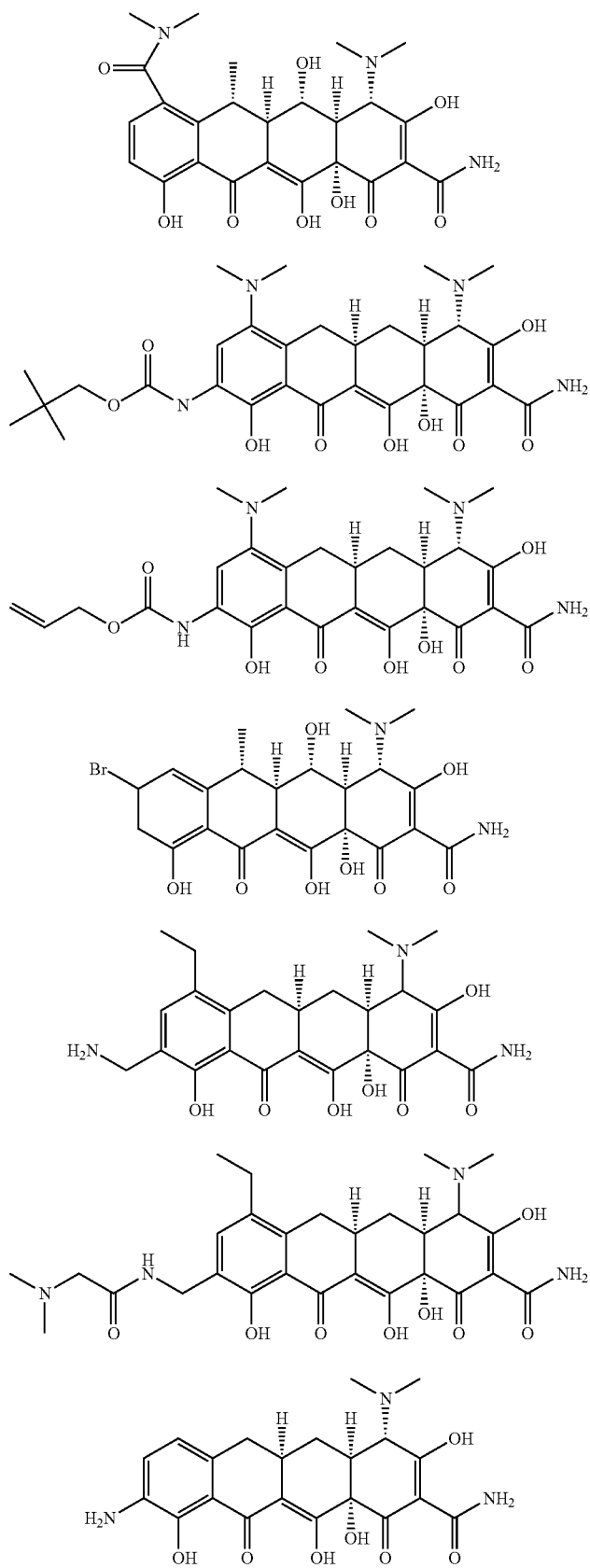

TABLE 2-continued
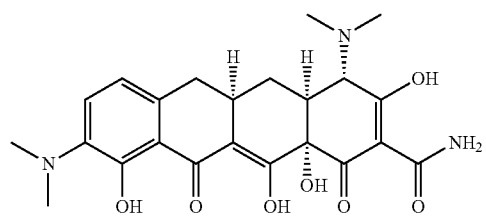
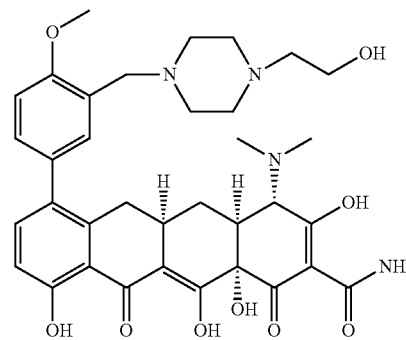
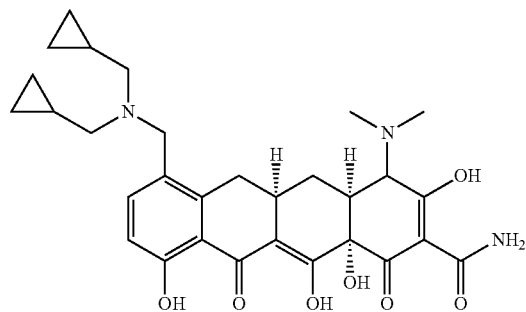
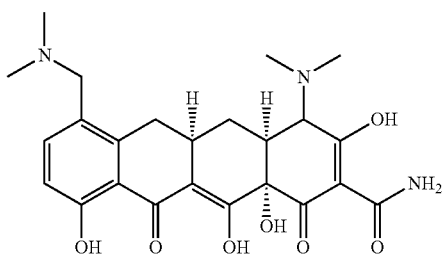
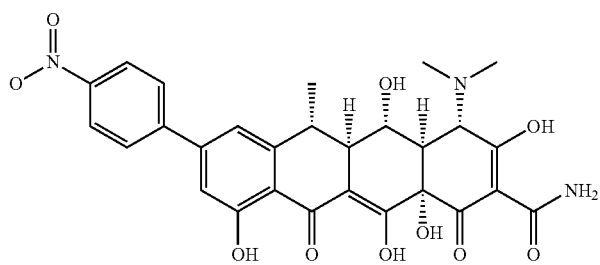
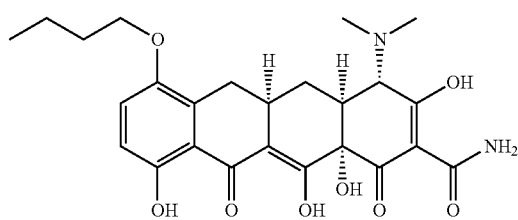

TABLE 2-continued
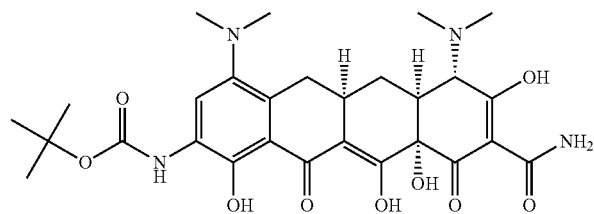
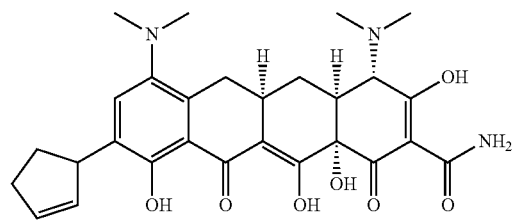
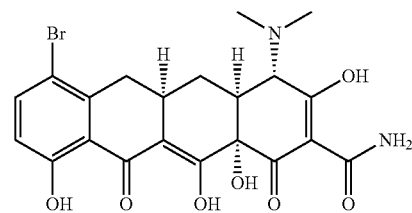
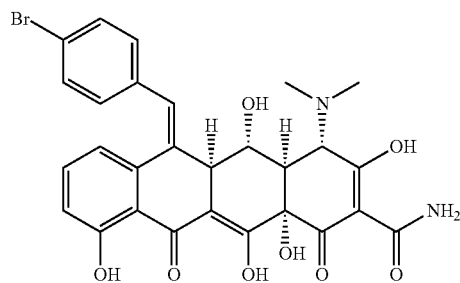
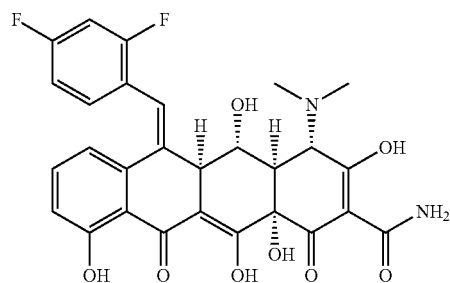
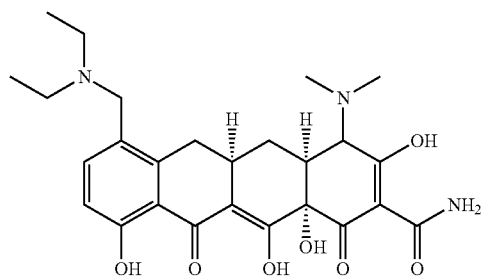

TABLE 2-continued
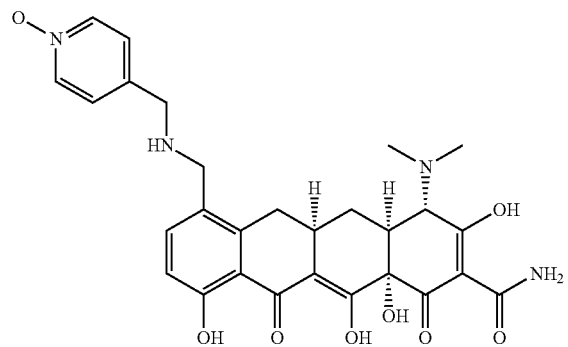
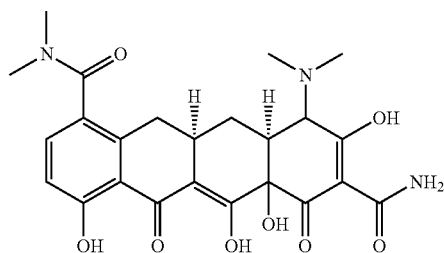
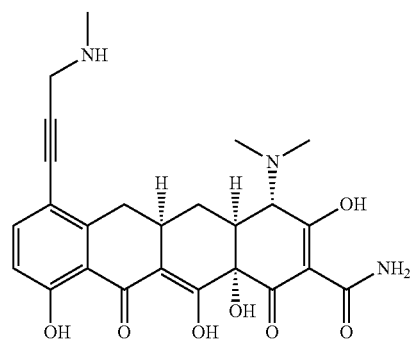
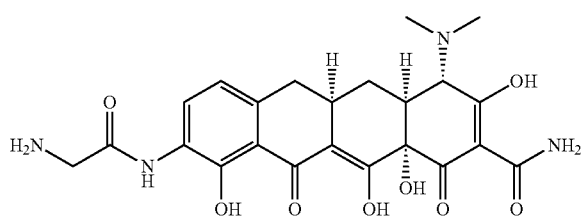
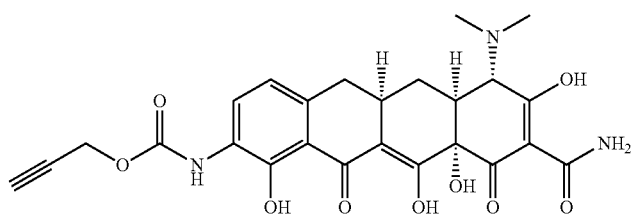

TABLE 2-continued
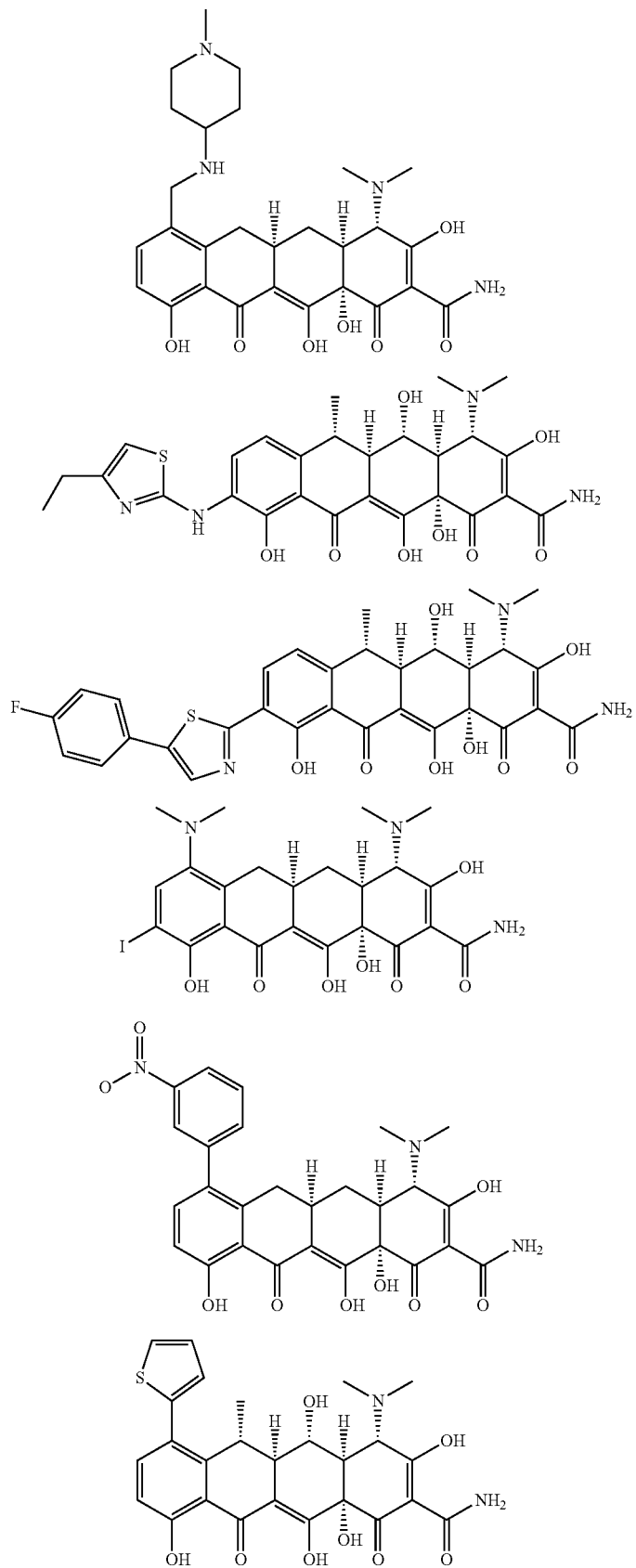

TABLE 2-continued
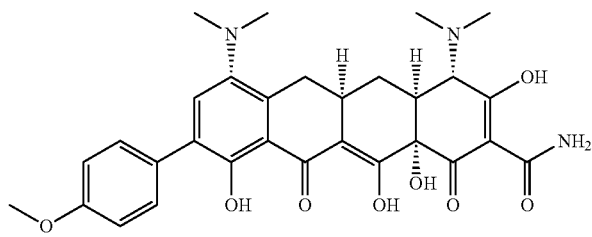
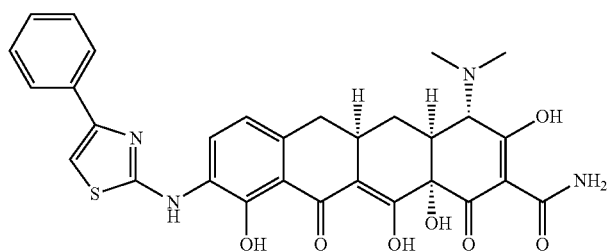
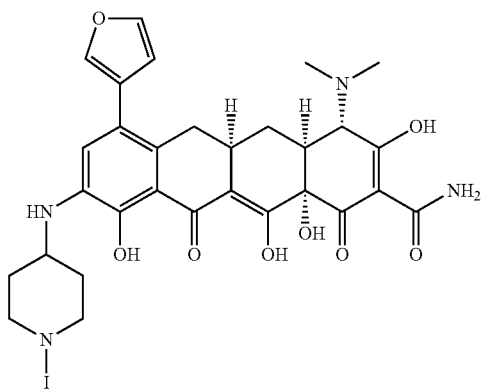
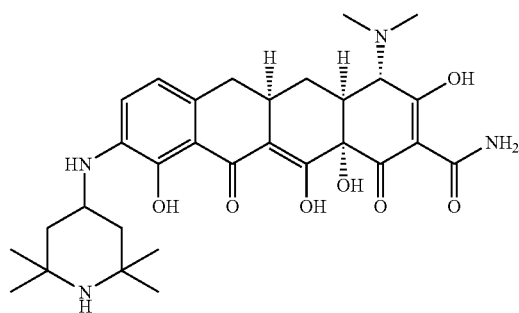
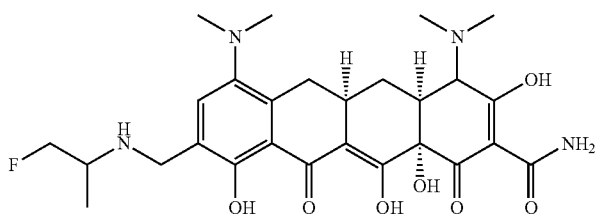

TABLE 2-continued
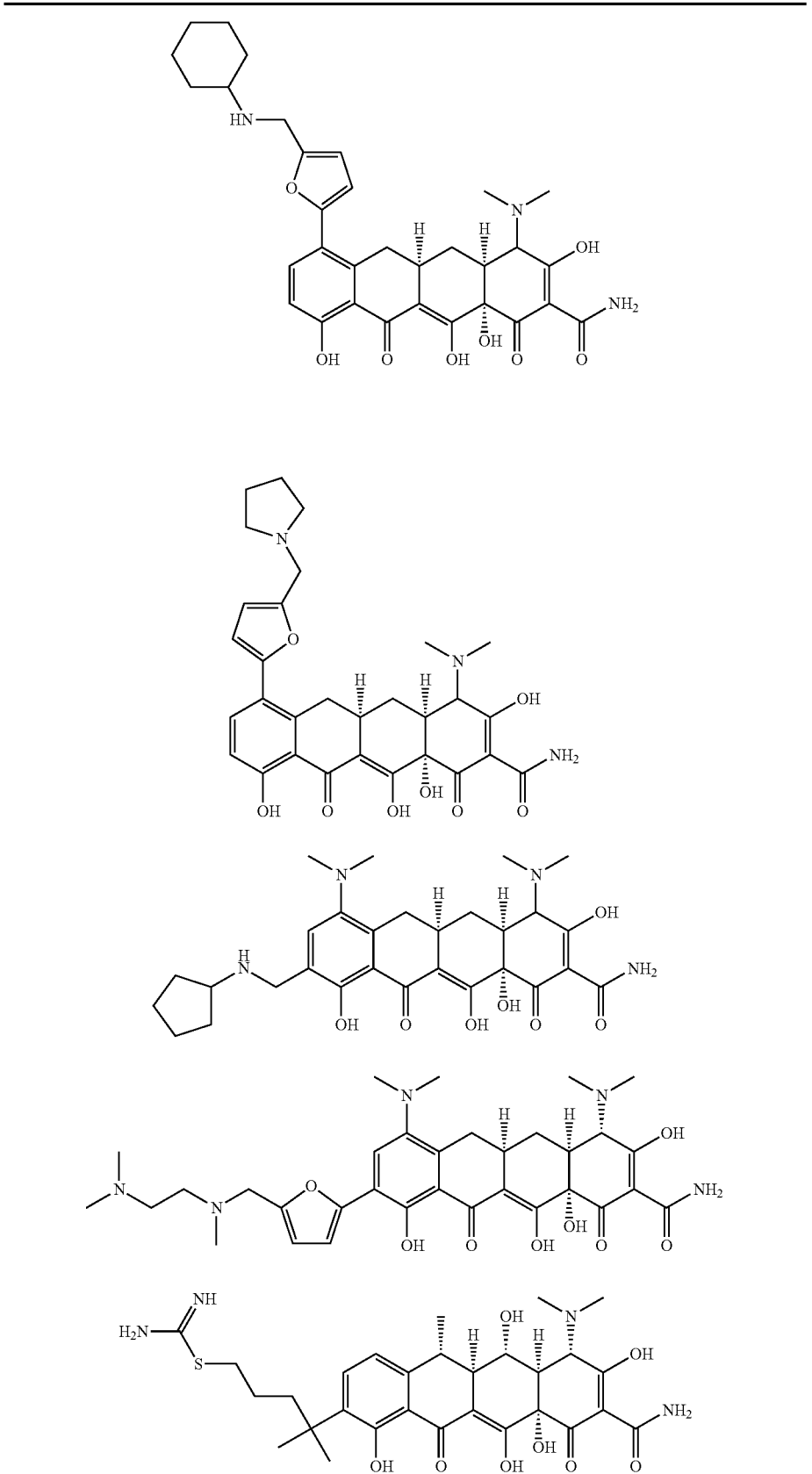

TABLE 2-continued
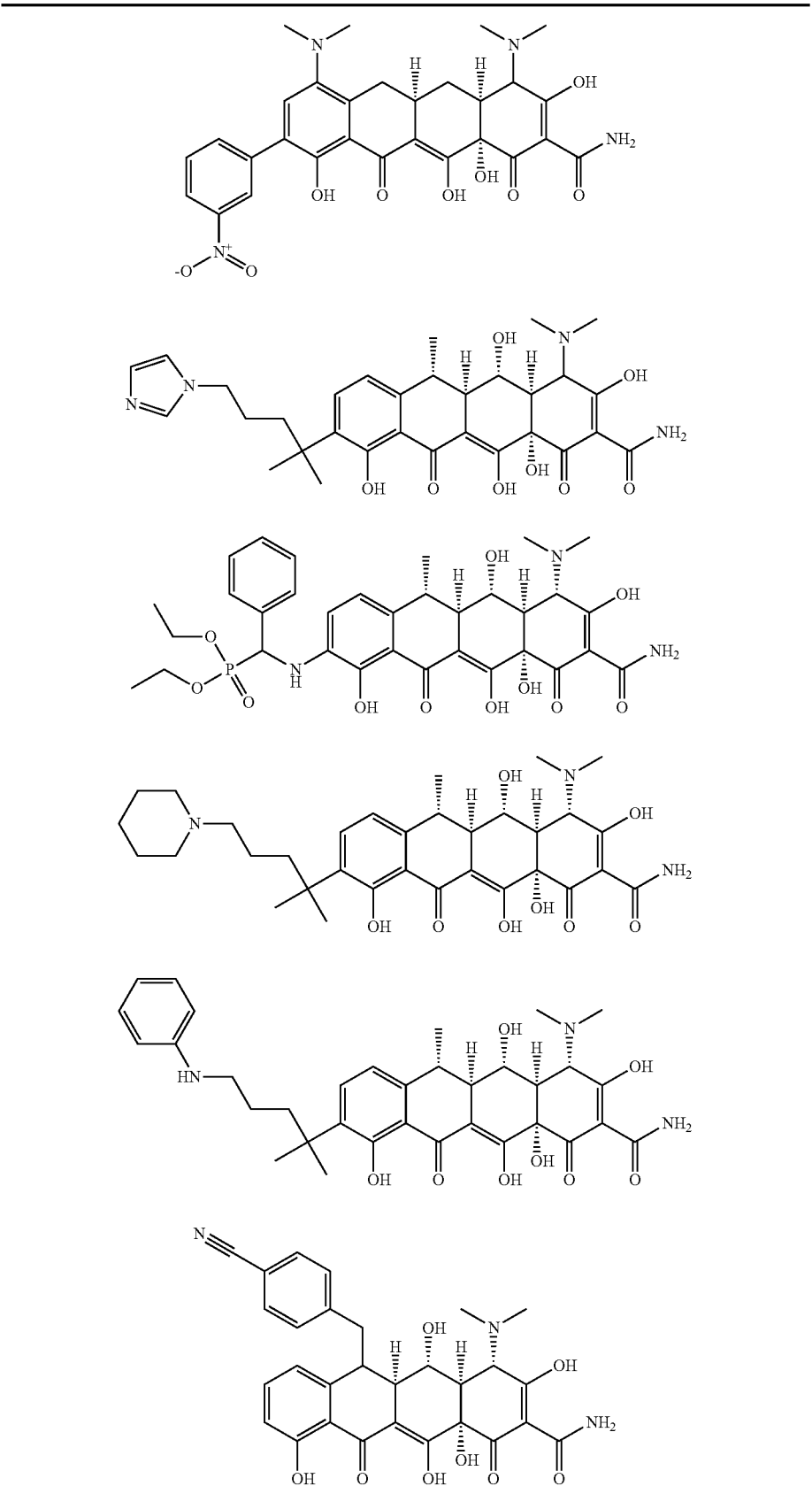

TABLE 2-continued
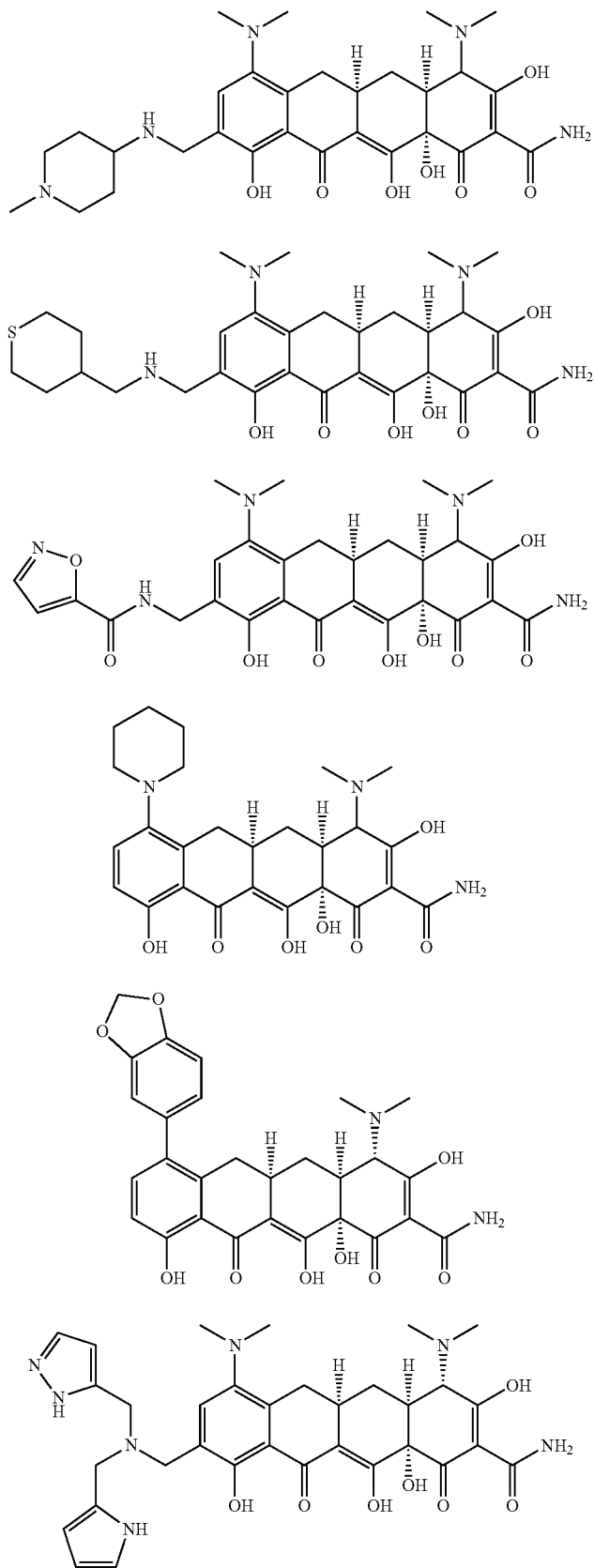

TABLE 2-continued
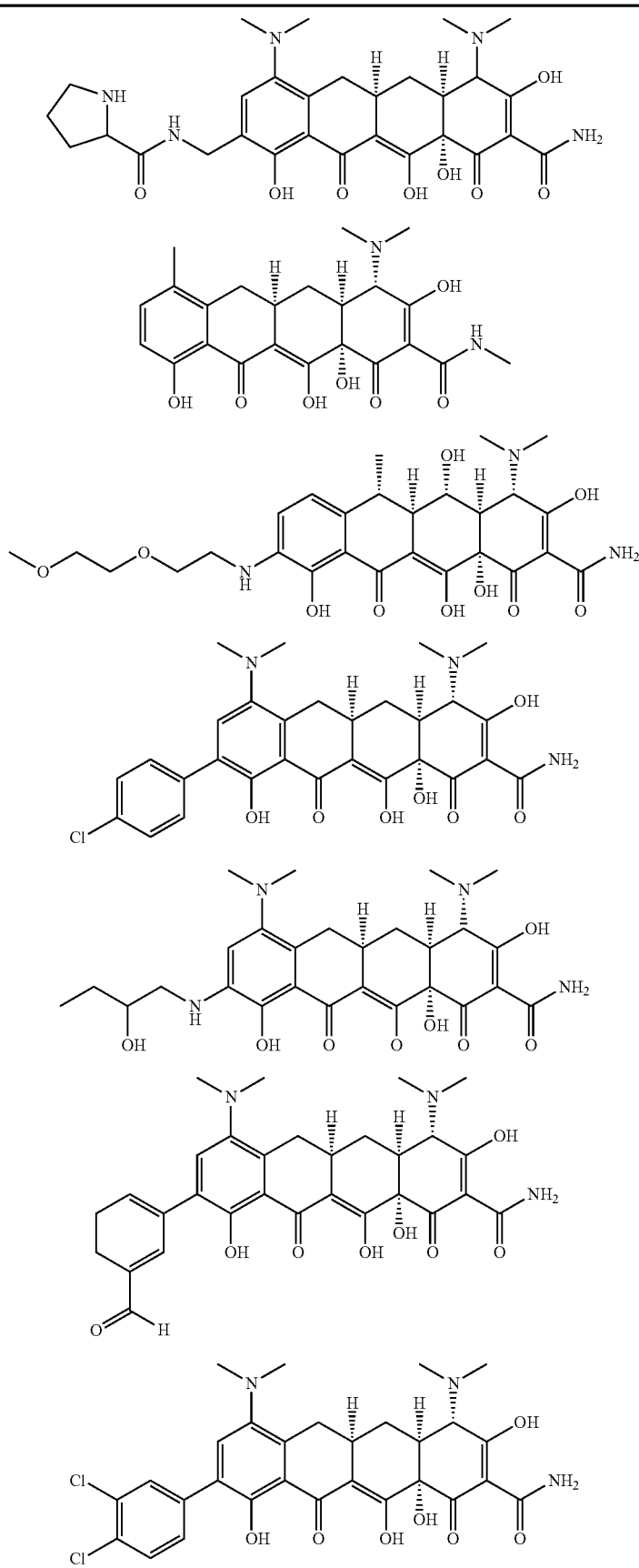

TABLE 2-continued
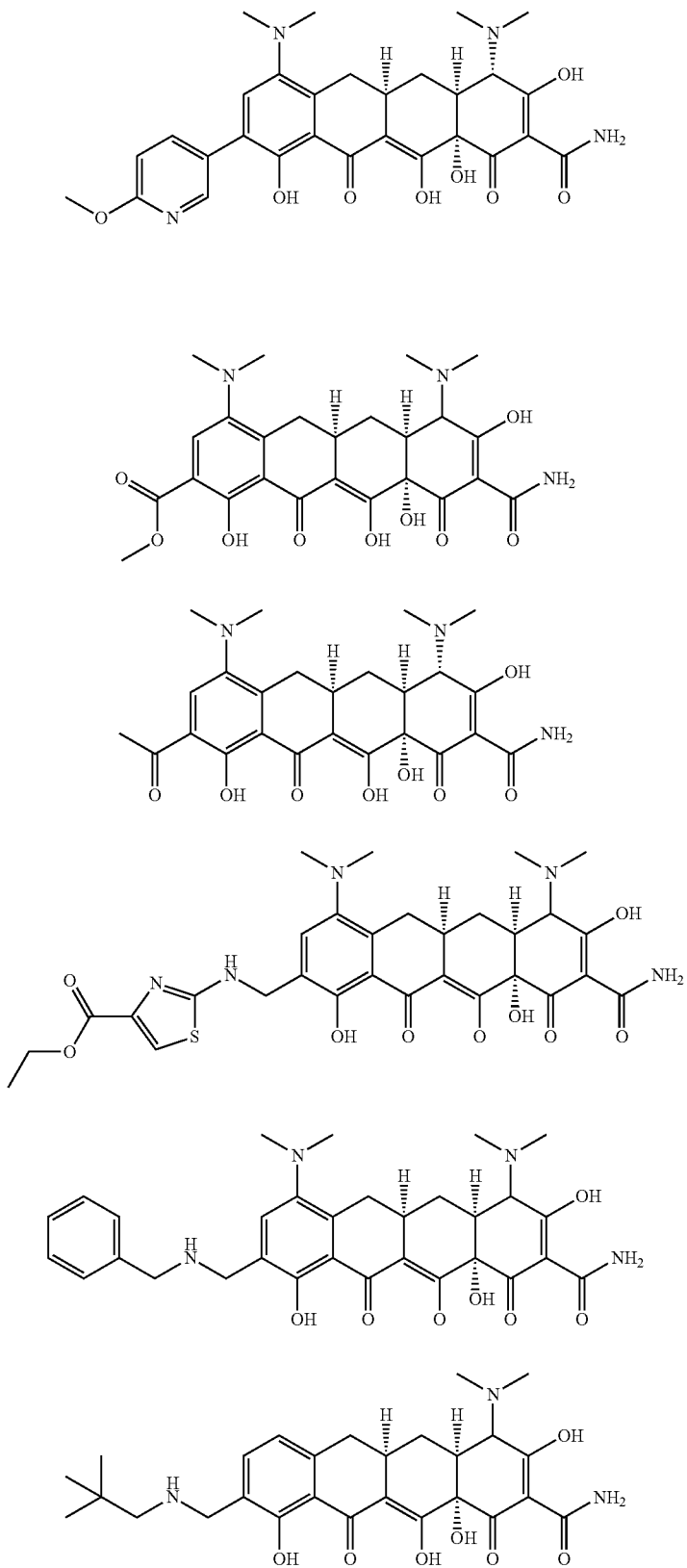

TABLE 2-continued
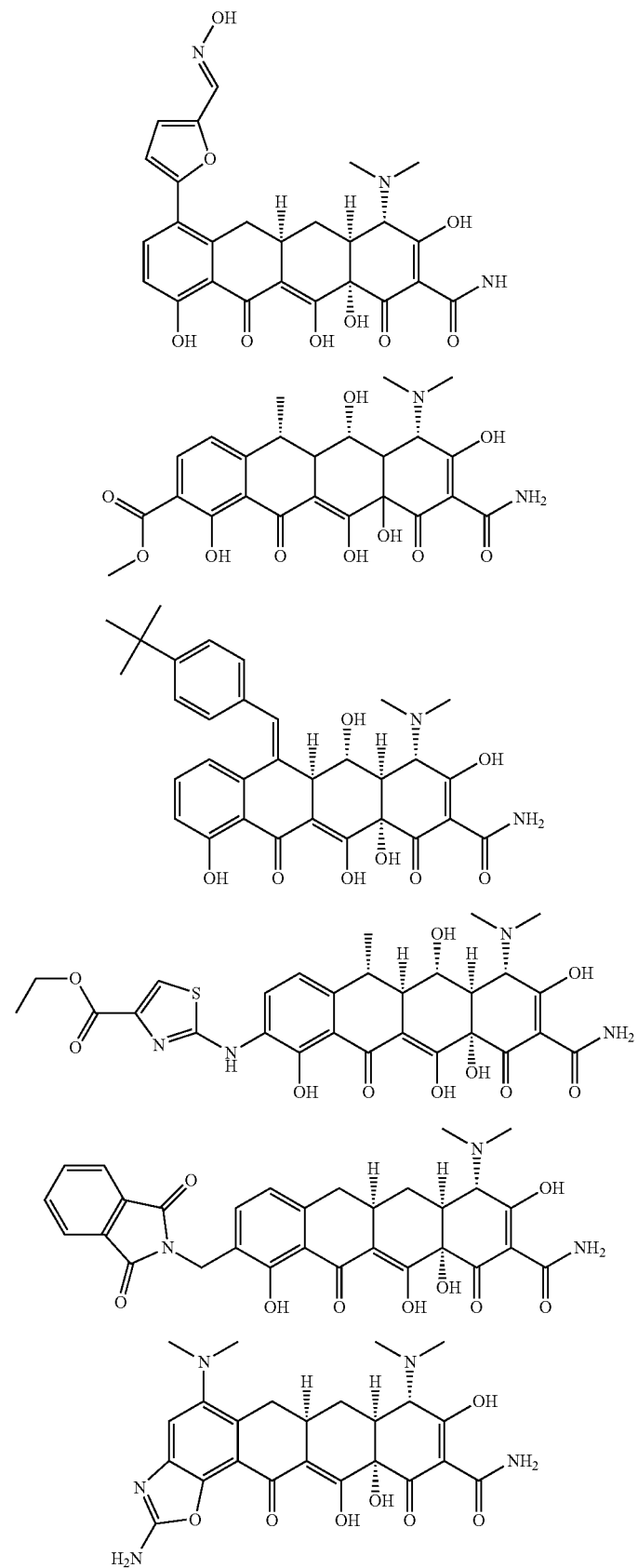

TABLE 2-continued
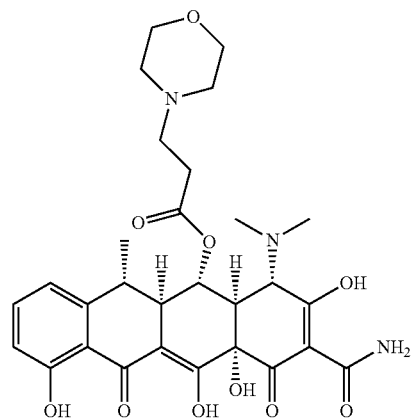
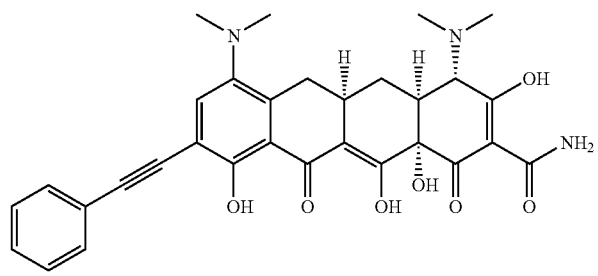
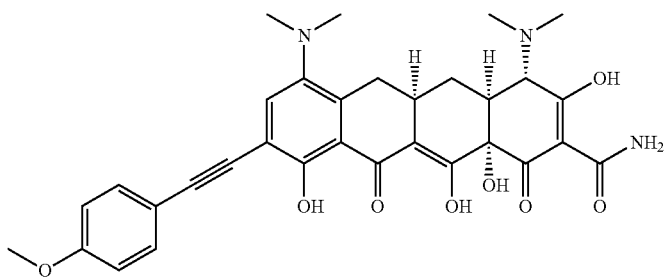
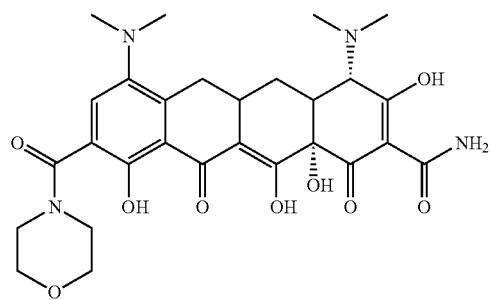
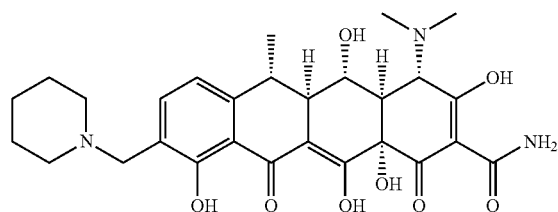

TABLE 2-continued
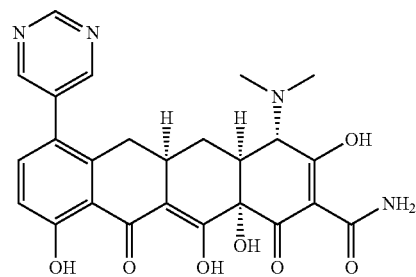
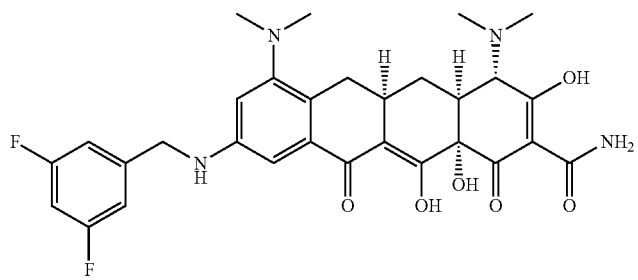
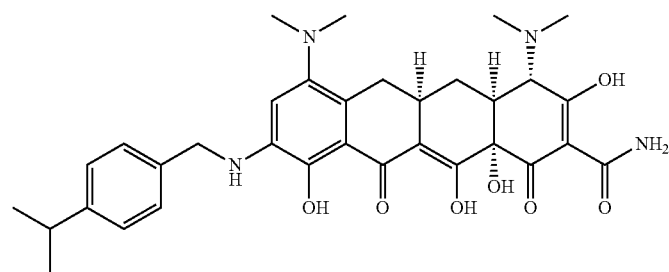
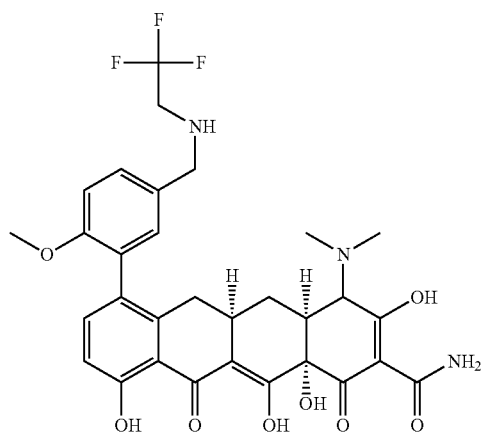
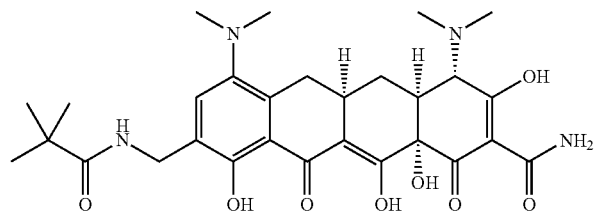

TABLE 2-continued
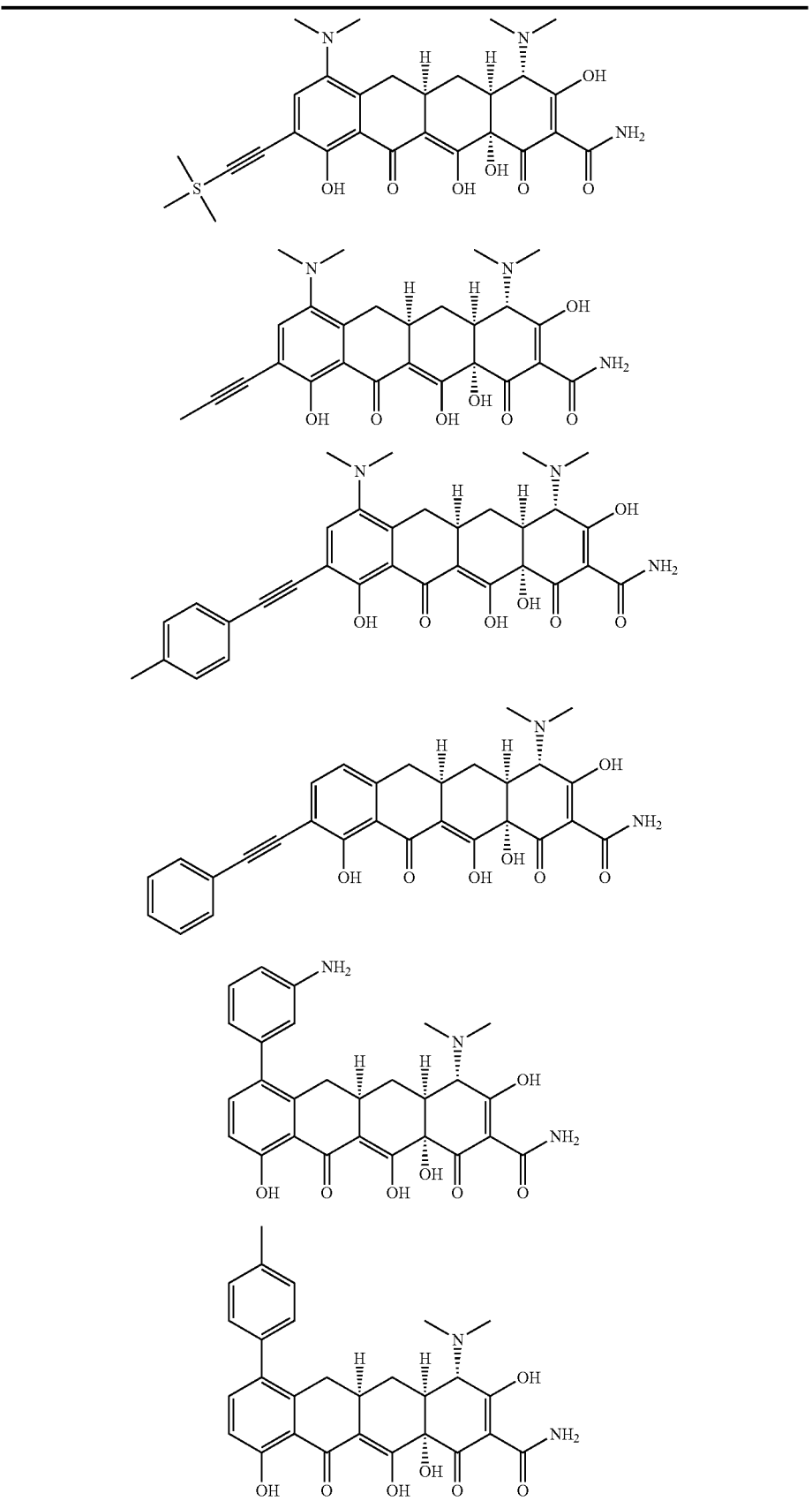

TABLE 2-continued
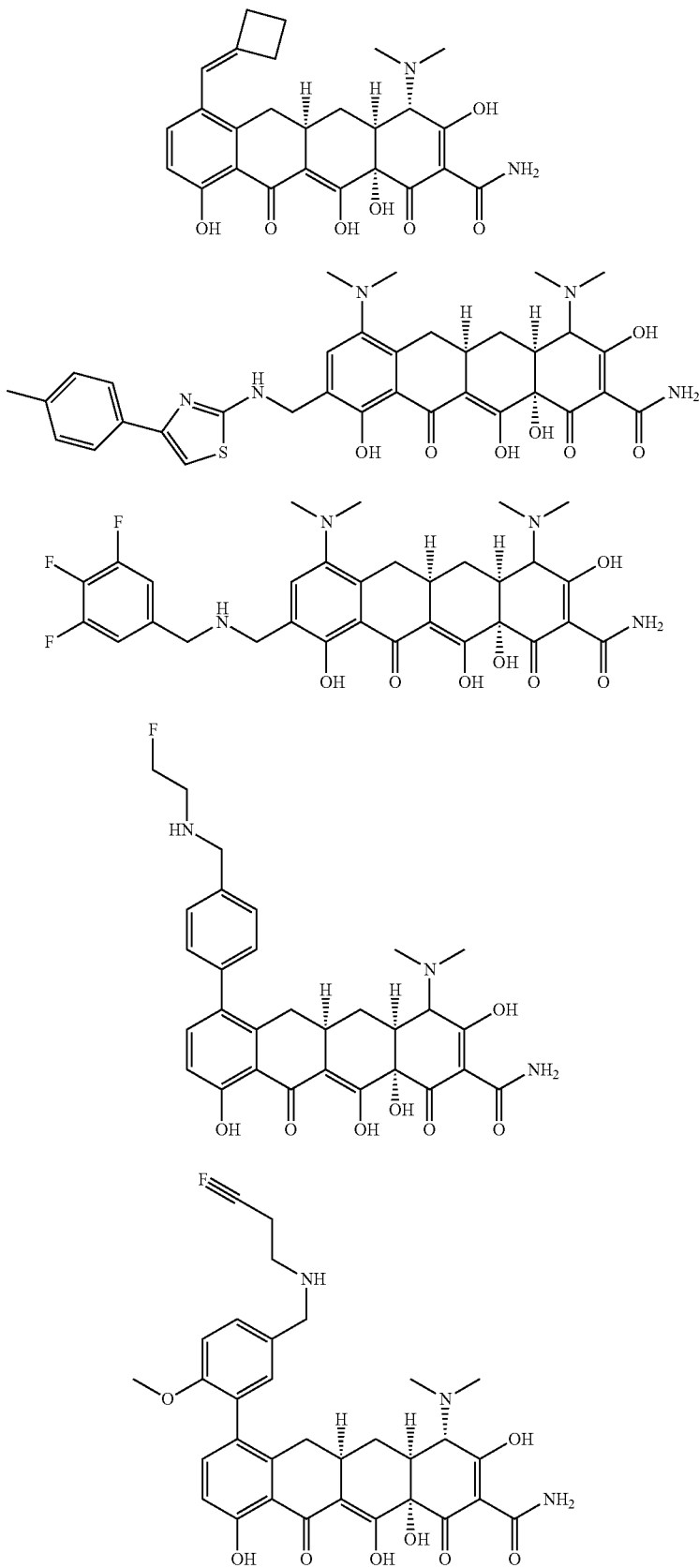

TABLE 2-continued
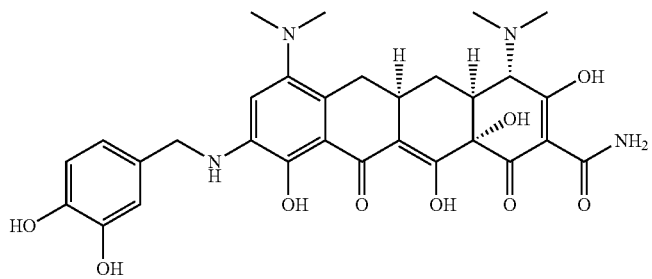
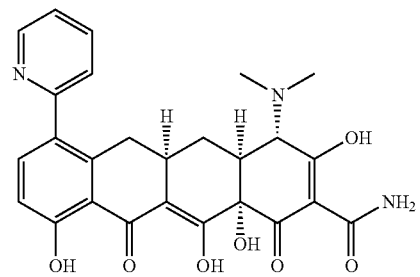
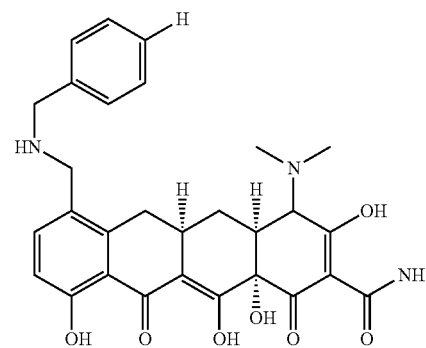
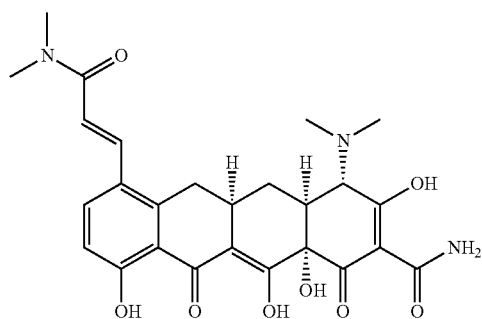
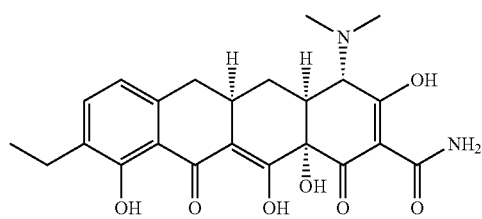

TABLE 2-continued
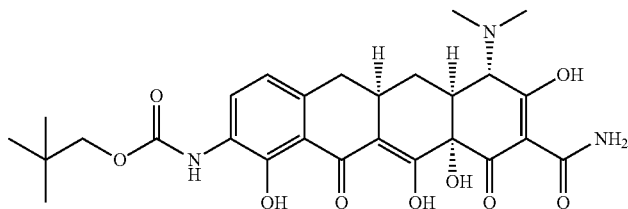
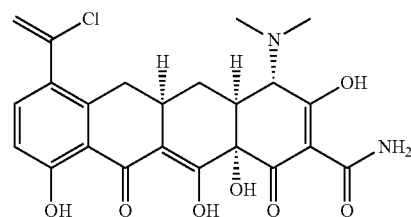
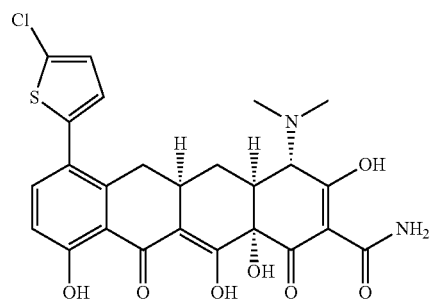
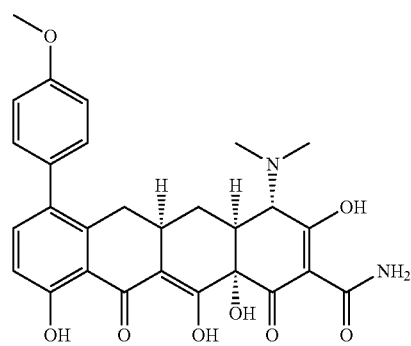
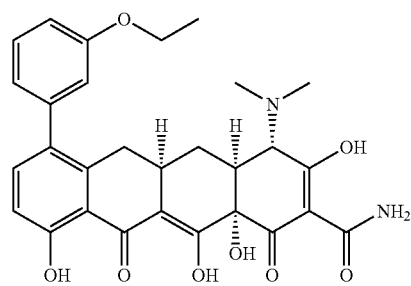

TABLE 2-continued
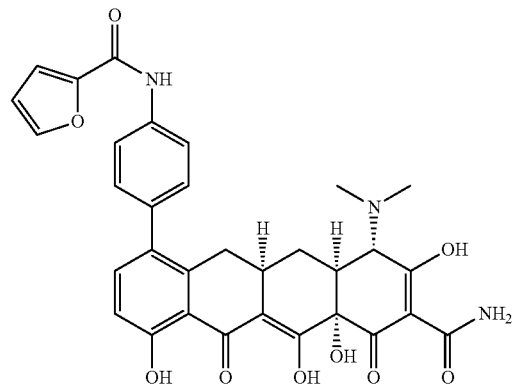
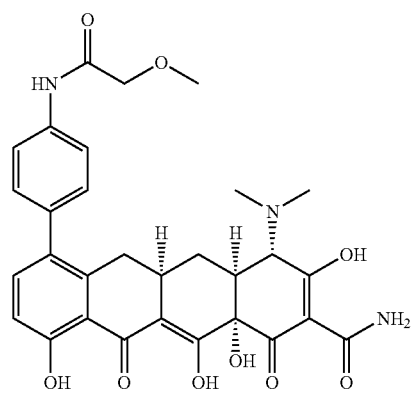
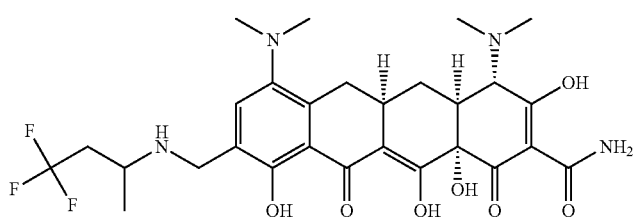
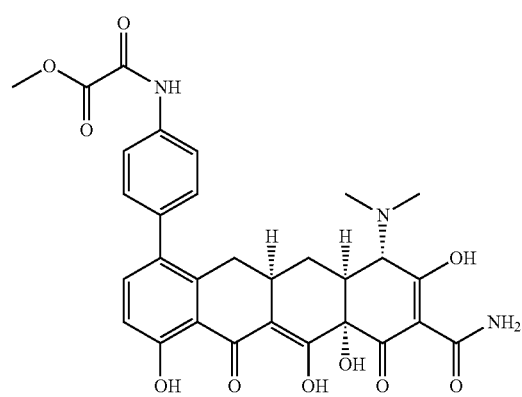
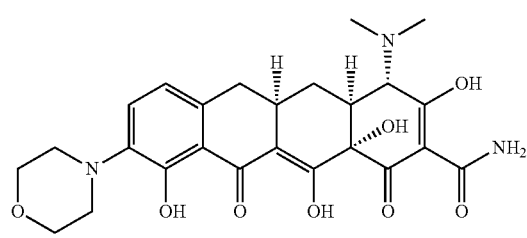

TABLE 2-continued
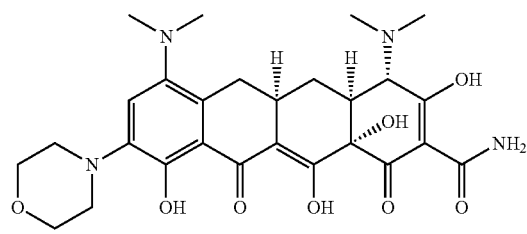
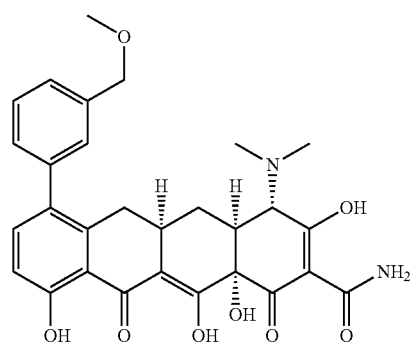
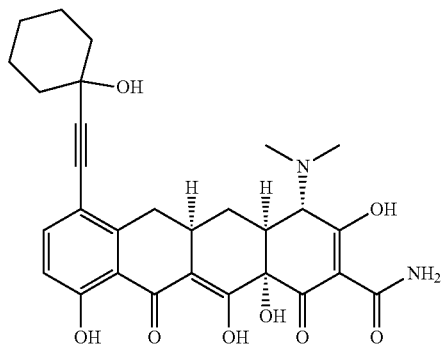
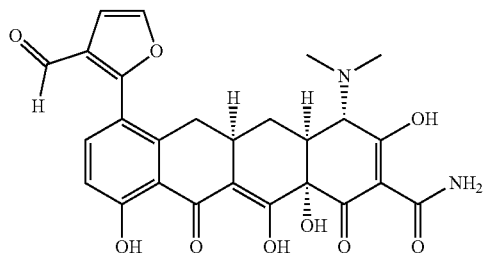
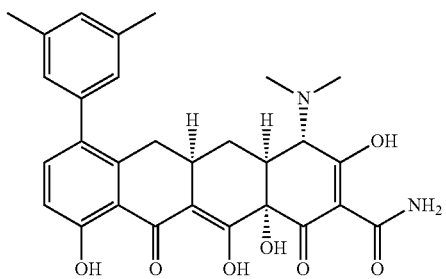

TABLE 2-continued
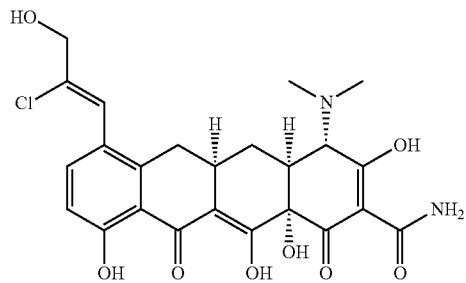
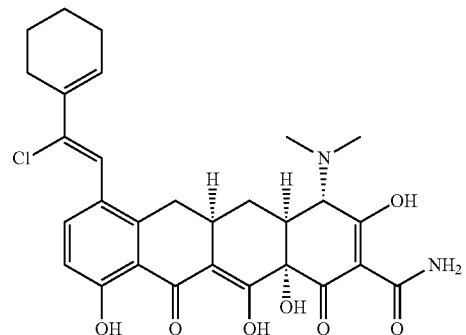
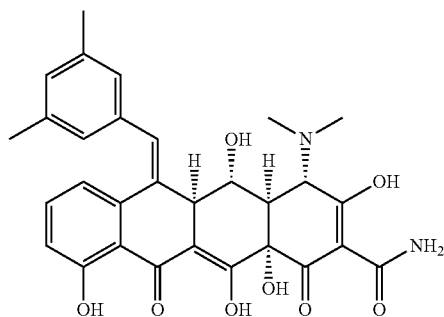
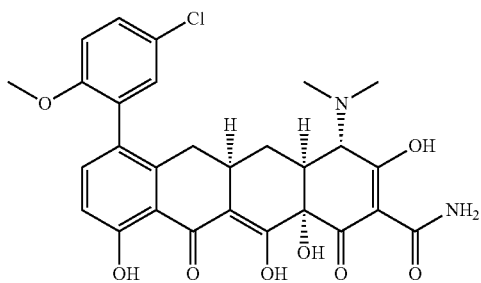
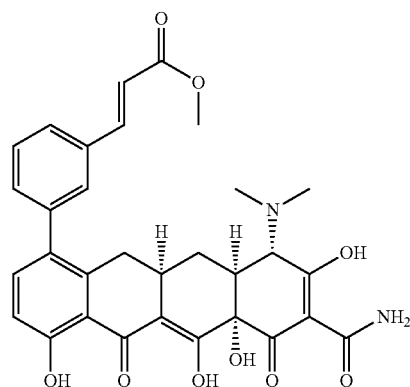

TABLE 2-continued
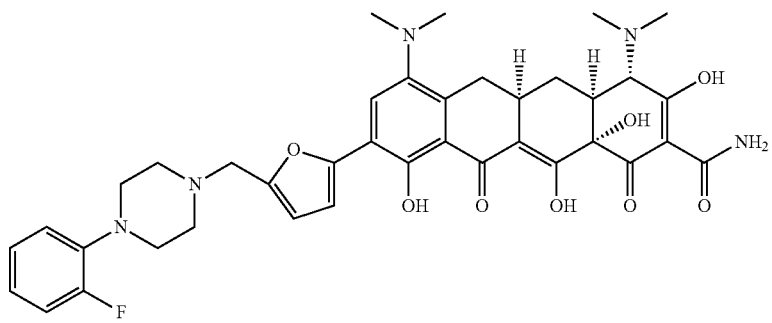
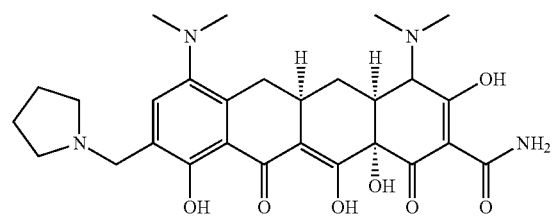
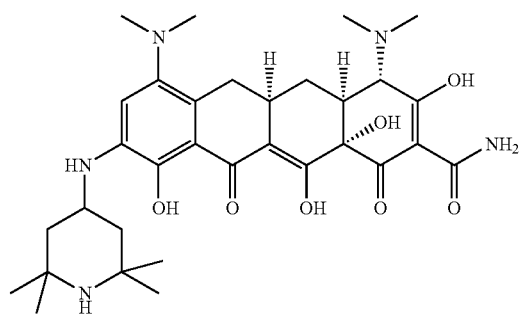
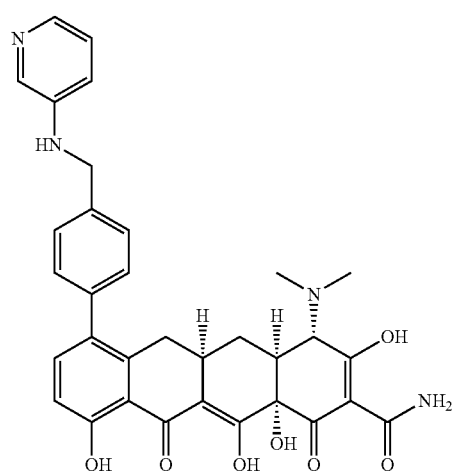

TABLE 2-continued
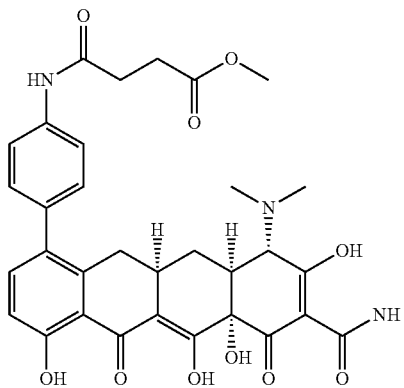
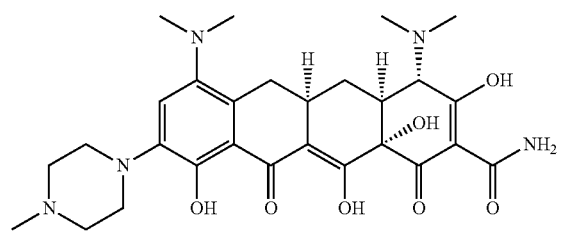
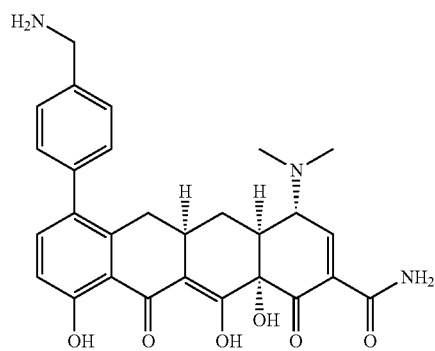
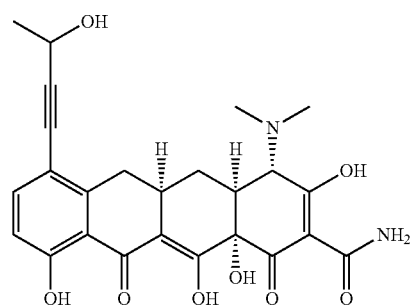
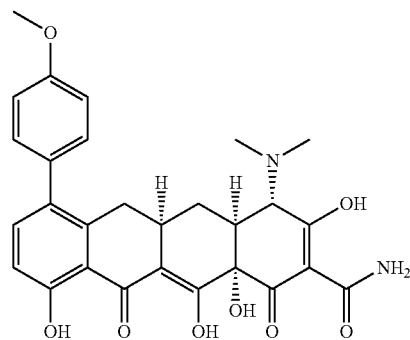

TABLE 2-continued
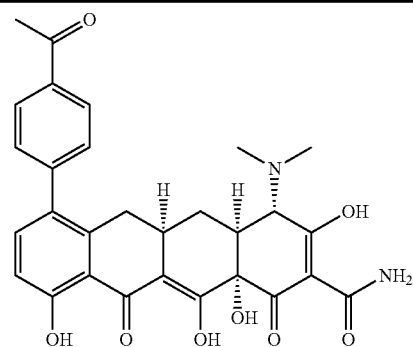
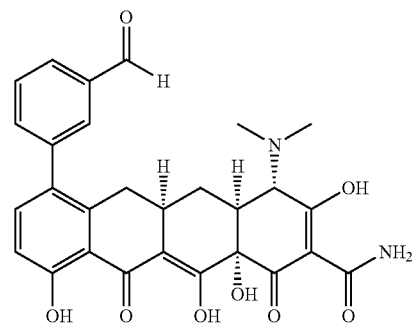
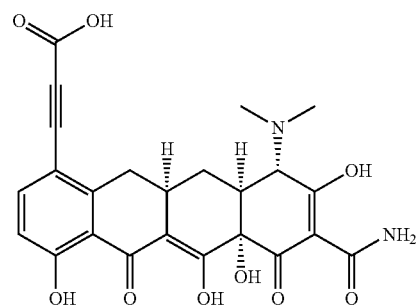
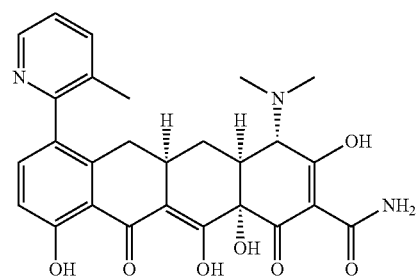
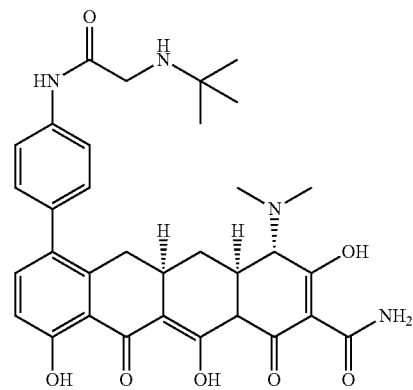

TABLE 2-continued
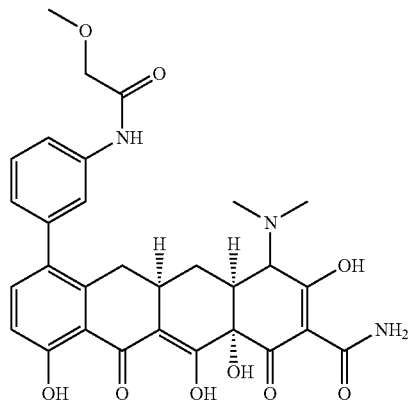
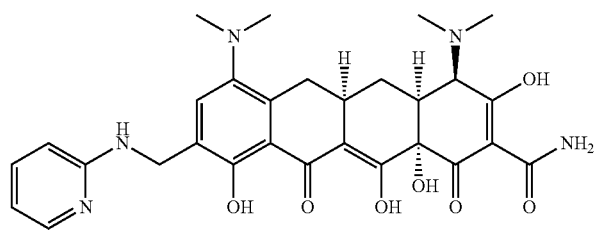
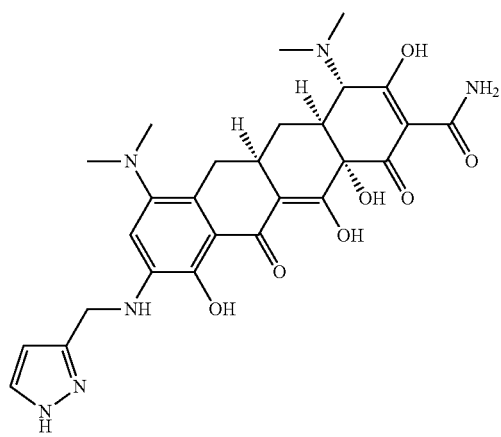
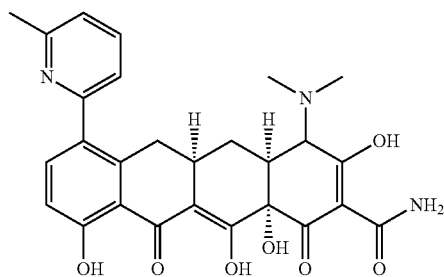

TABLE 2-continued
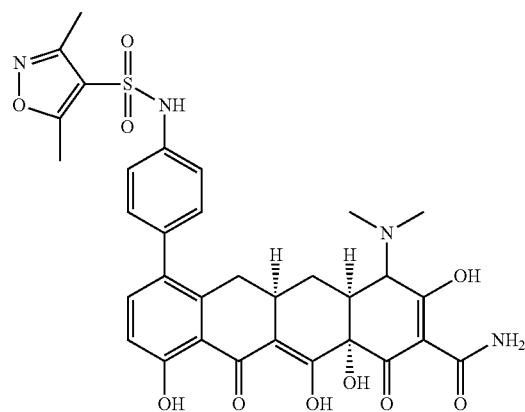
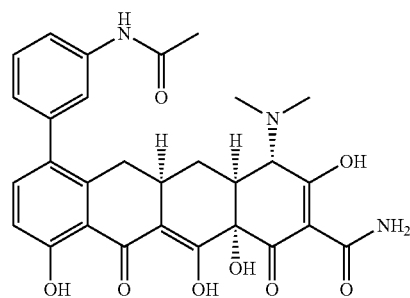
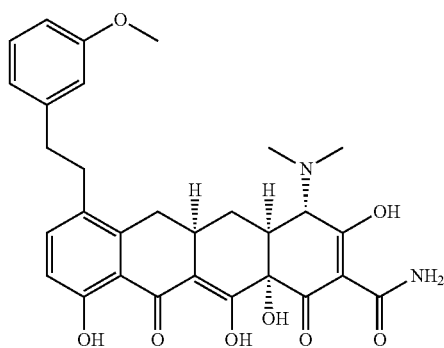
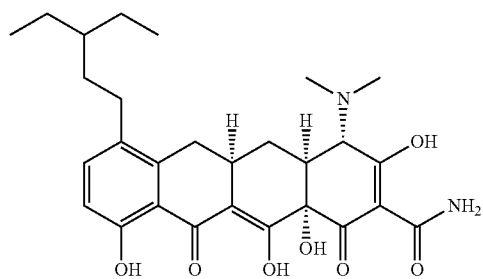

TABLE 2-continued
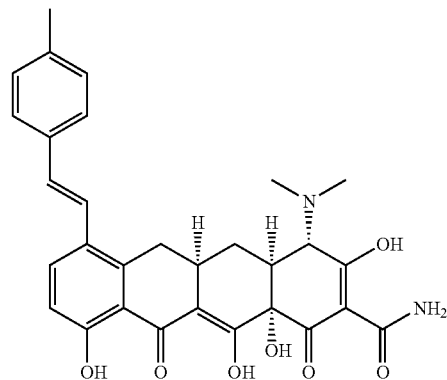
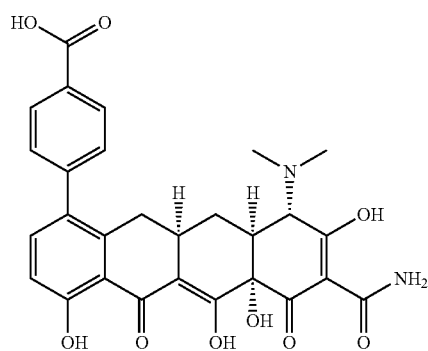
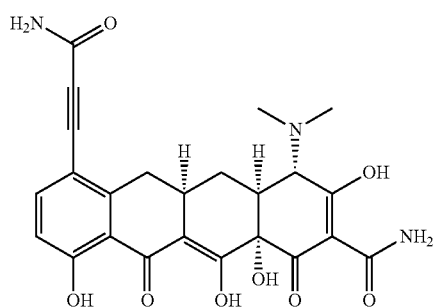
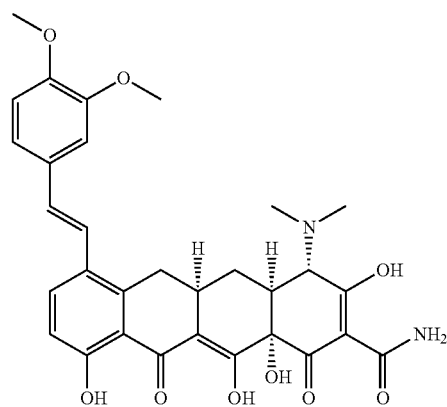
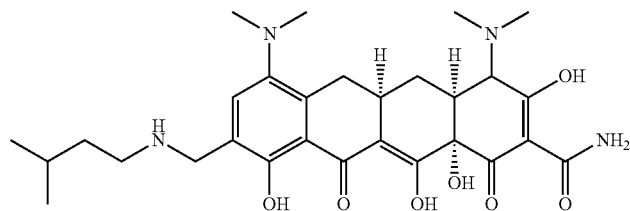

TABLE 2-continued
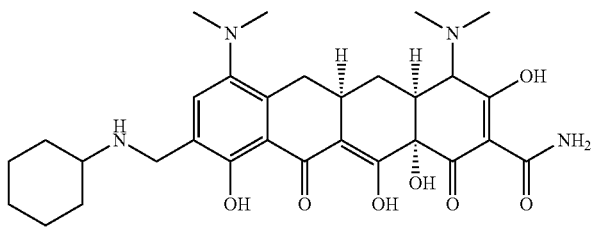
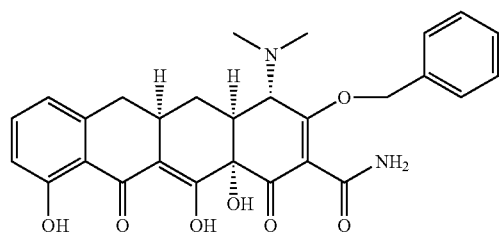
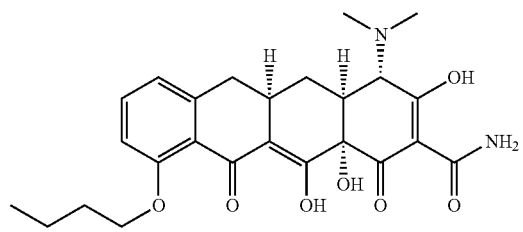
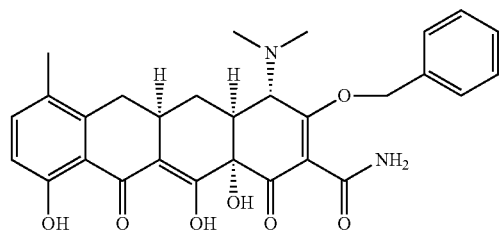
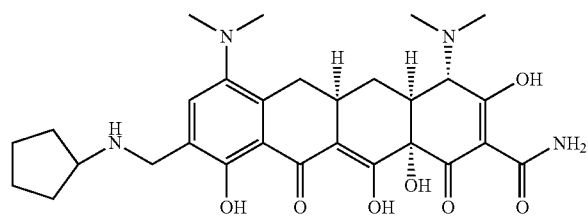
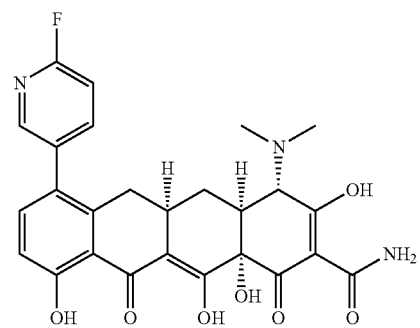

TABLE 2-continued
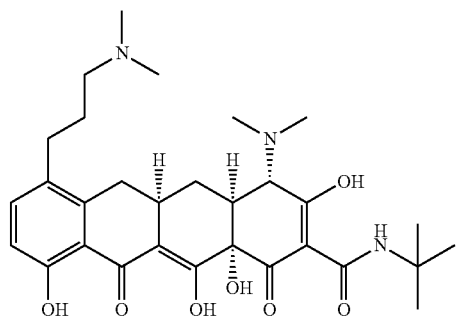
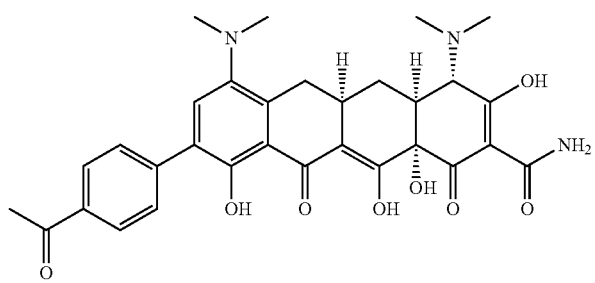
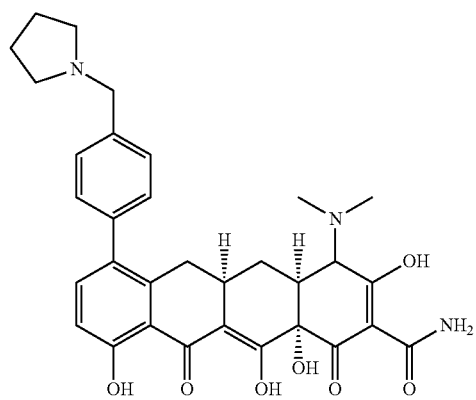
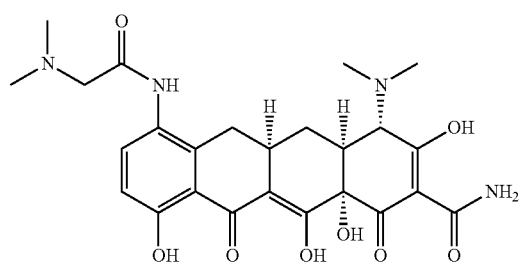
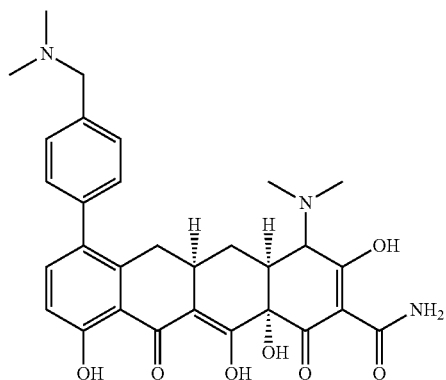

TABLE 2-continued
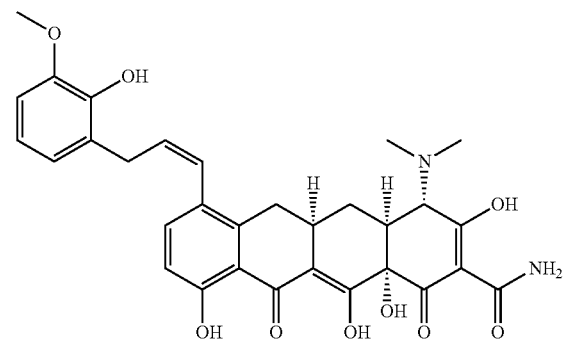
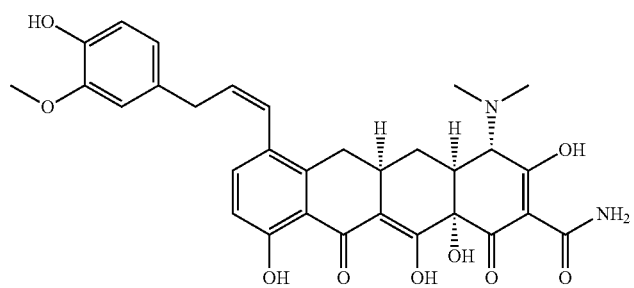
Chiral
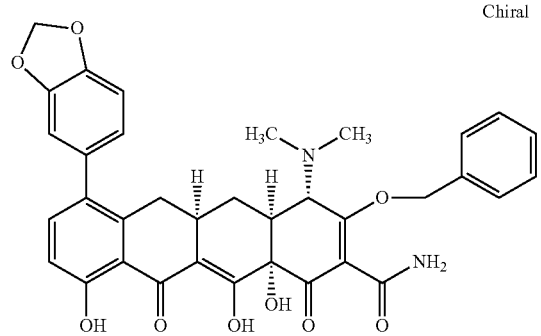
Chiral
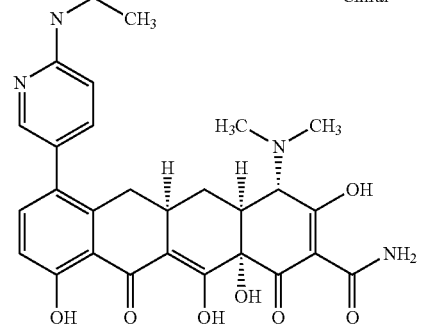
Chiral
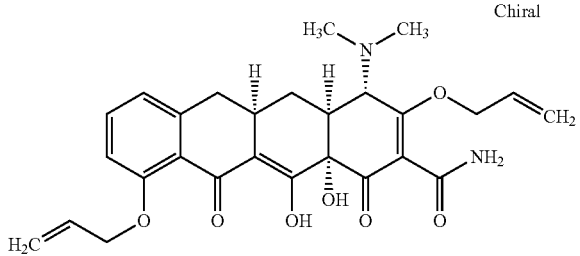

TABLE 2-continued
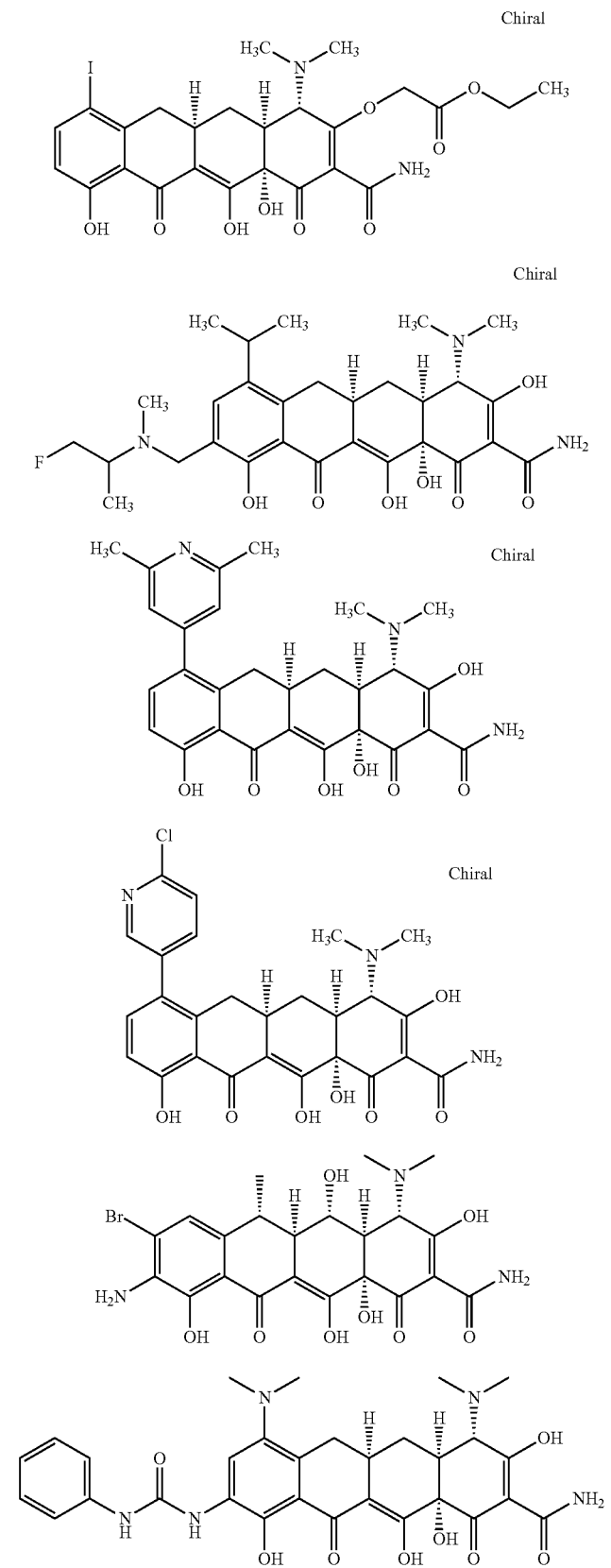

TABLE 2-continued
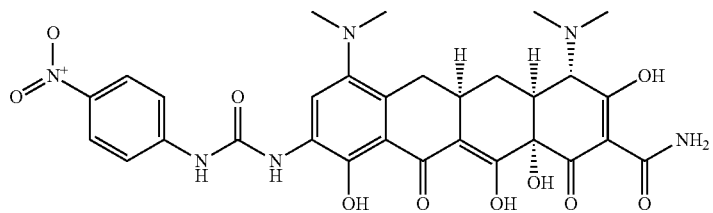
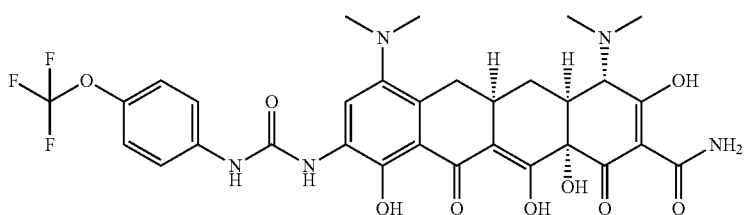
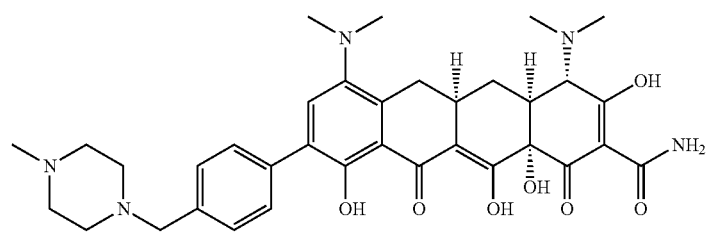
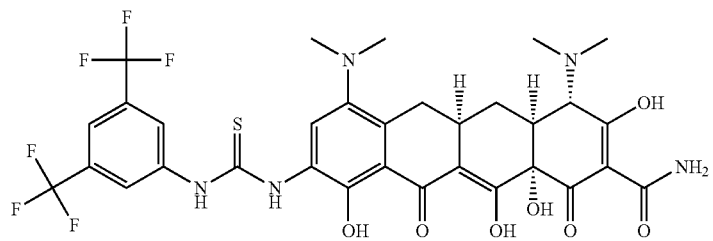
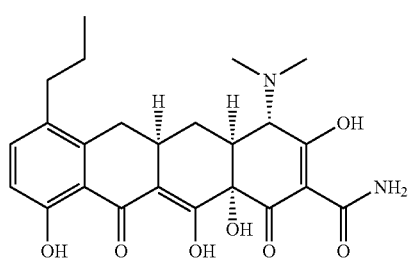
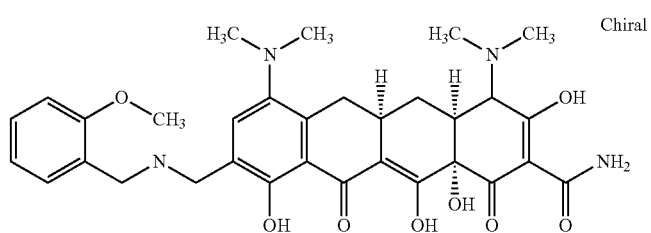

TABLE 2-continued
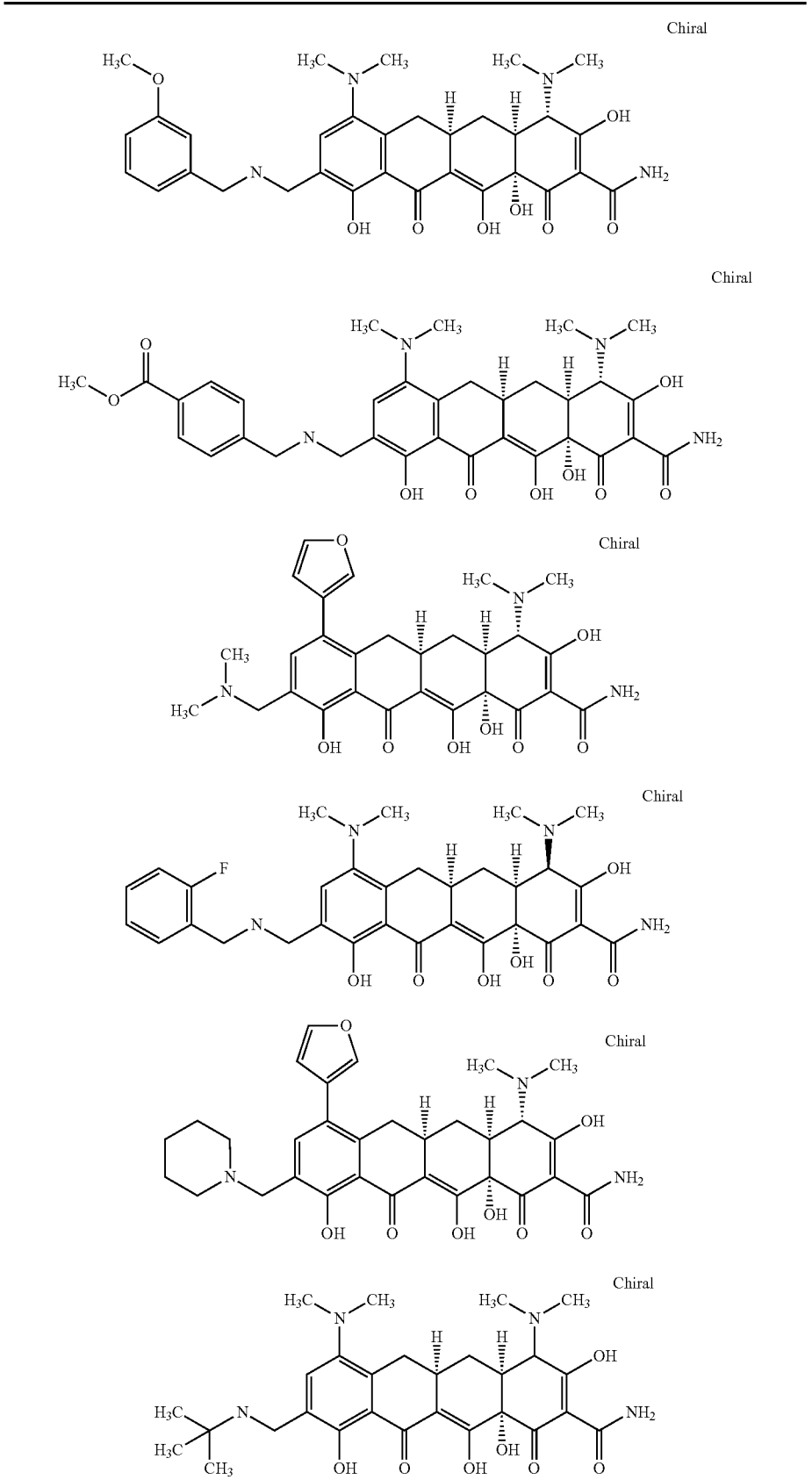

TABLE 2-continued
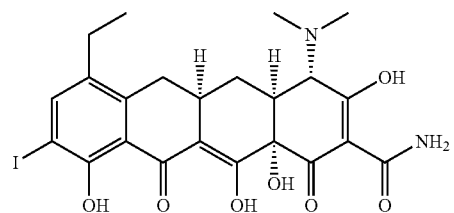
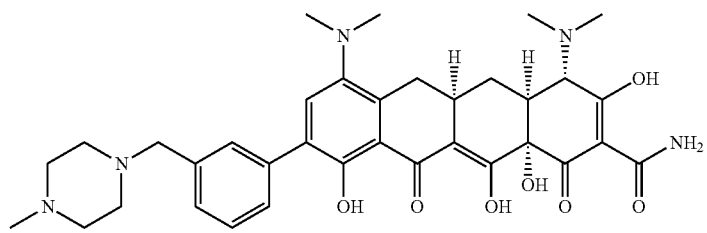
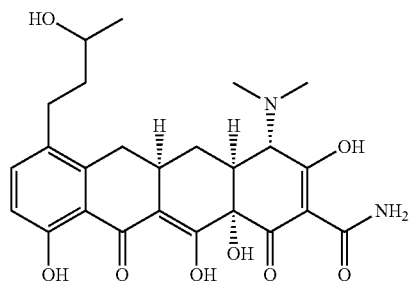
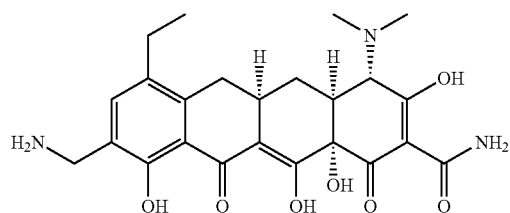
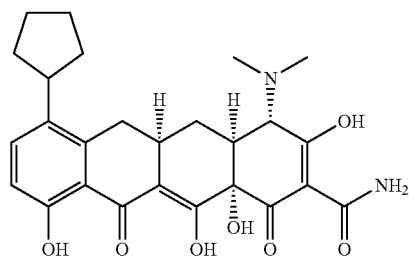
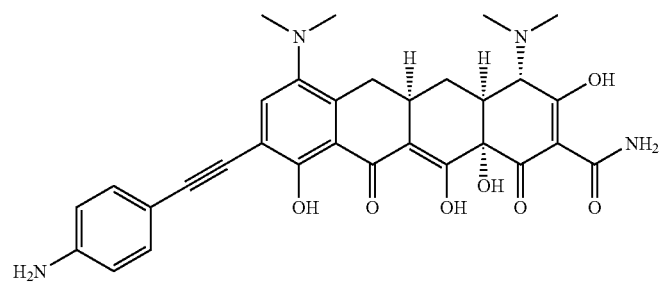

TABLE 2-continued
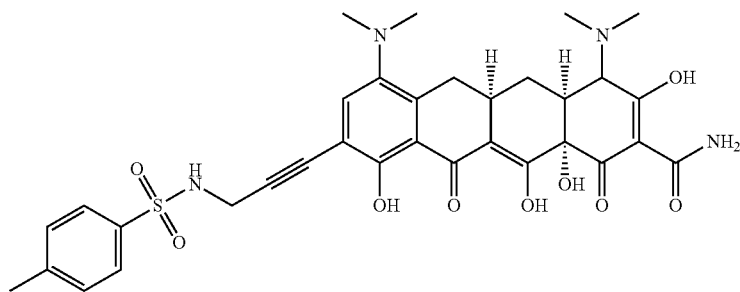
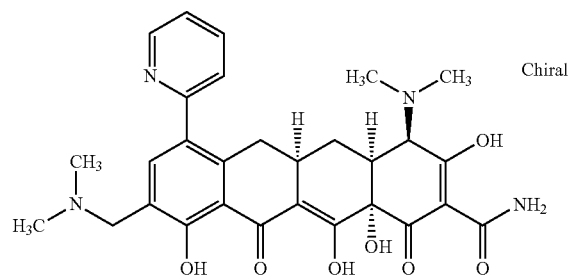
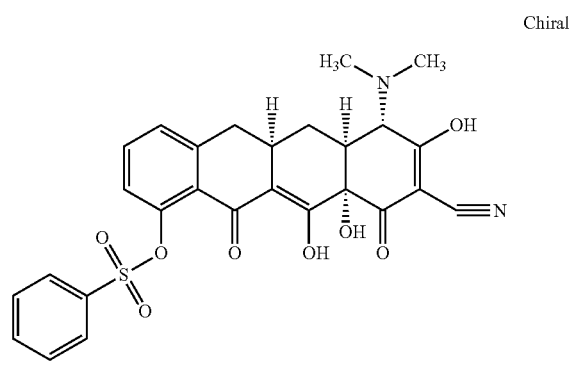
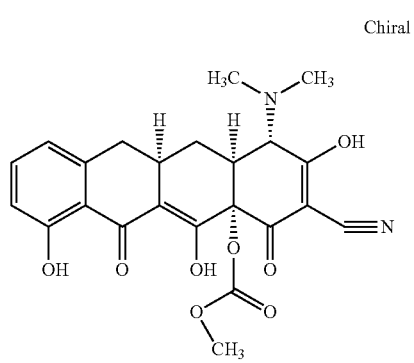
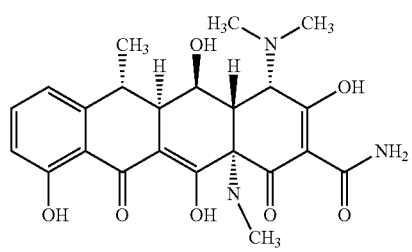

TABLE 2-continued
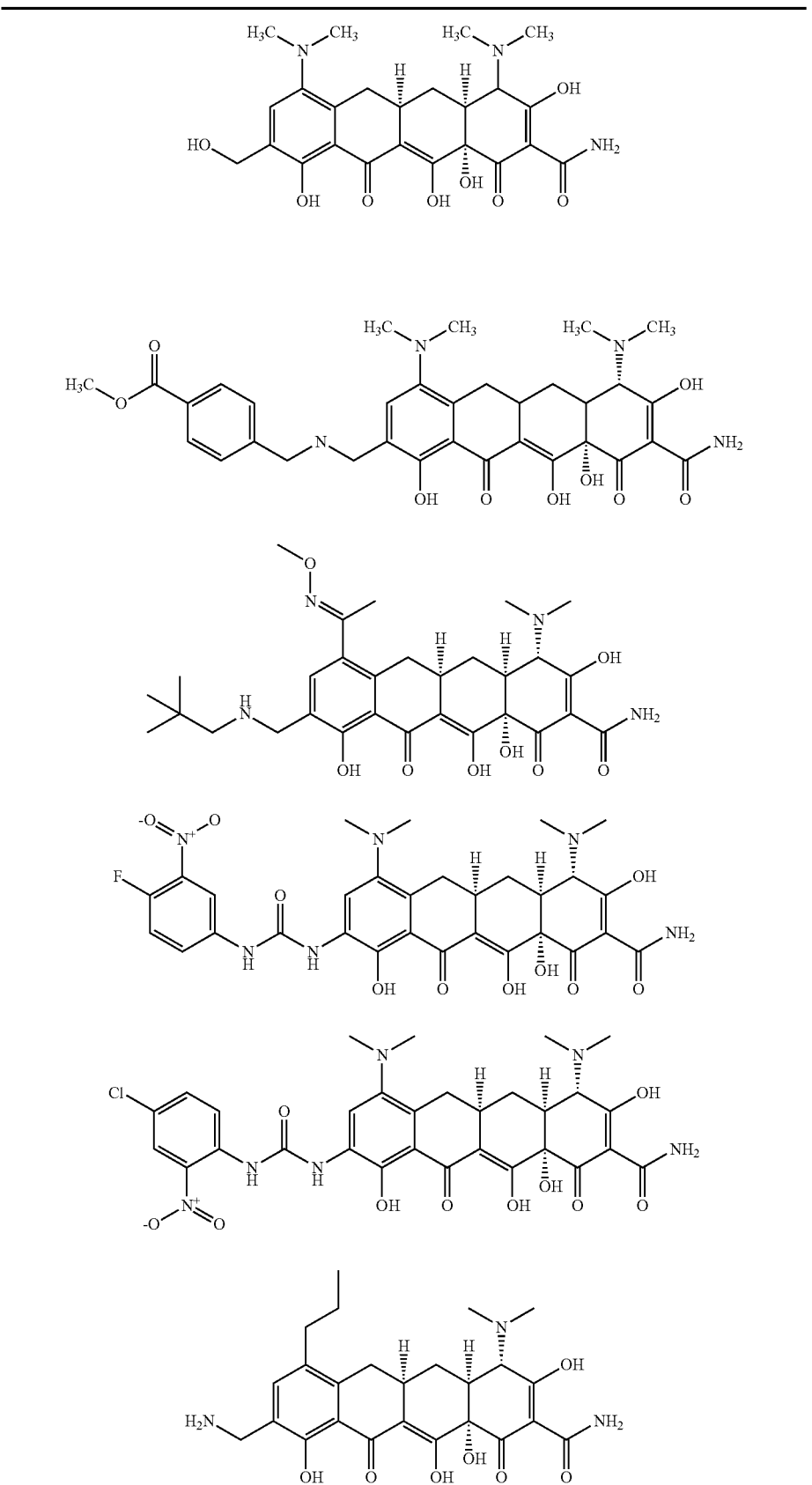

TABLE 2-continued
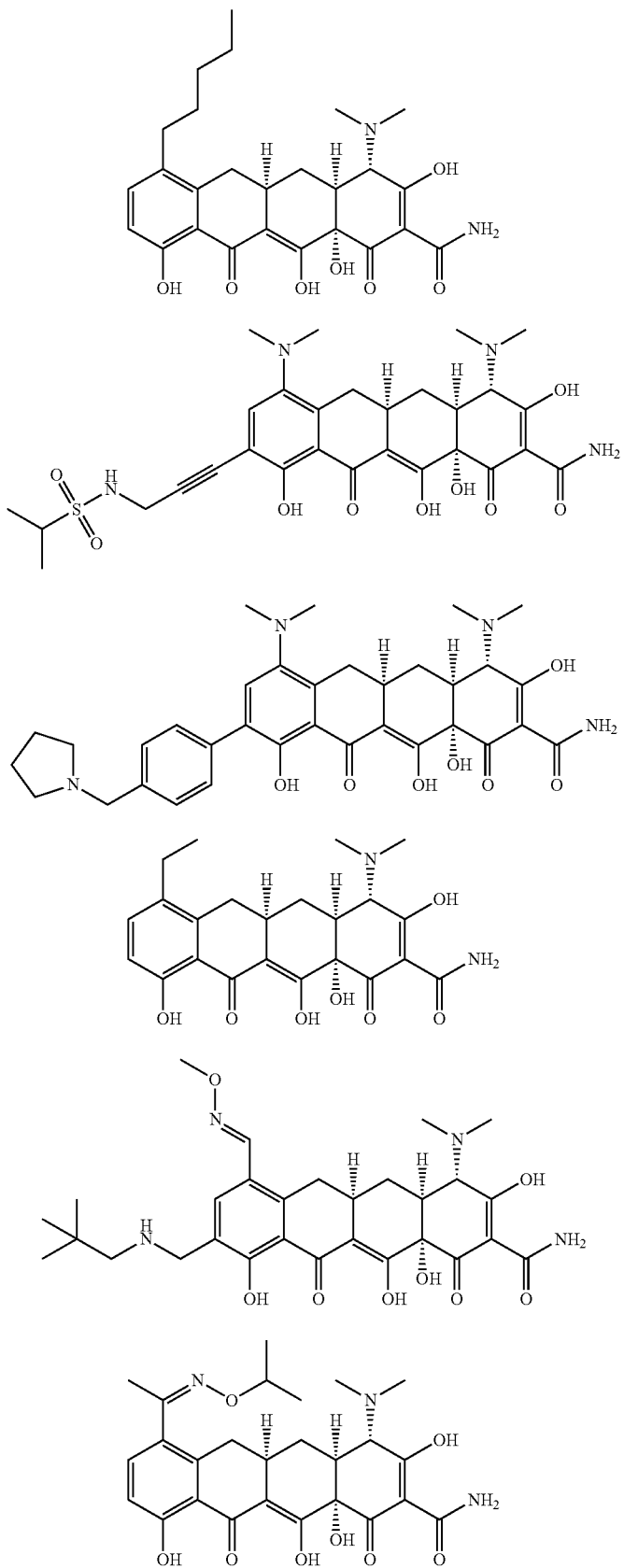

TABLE 2-continued
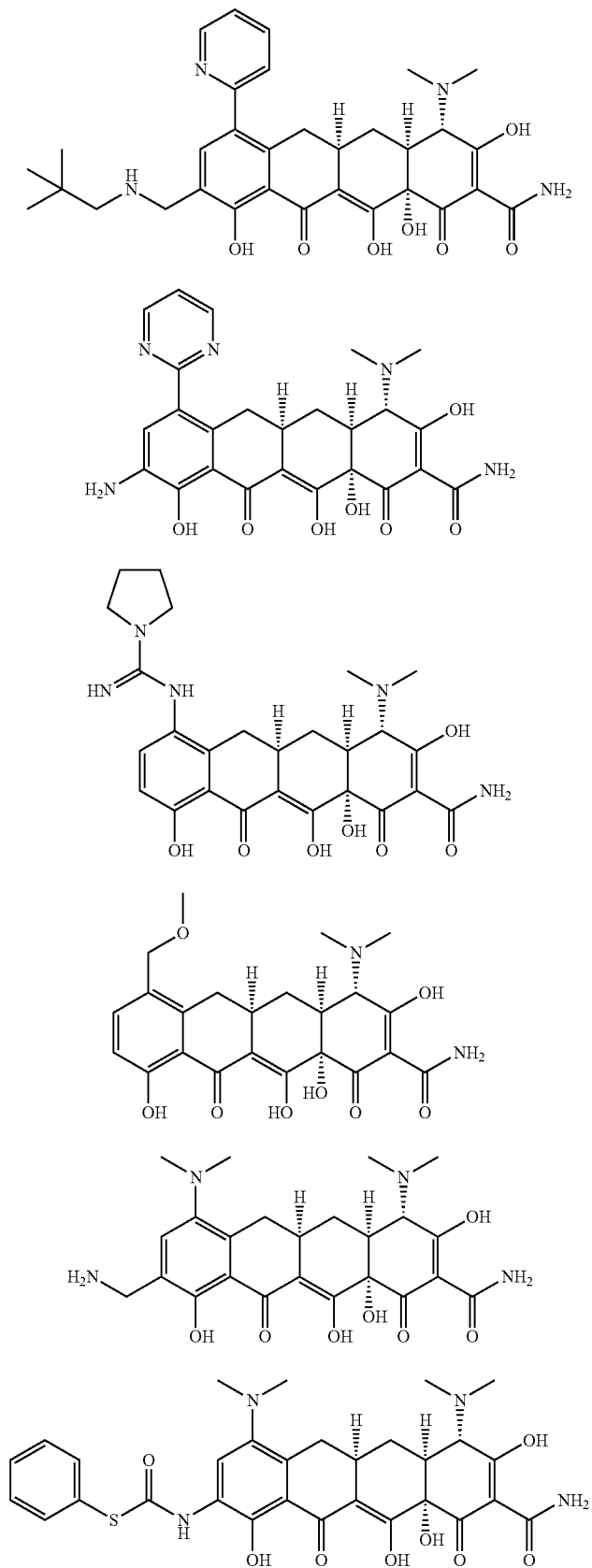

TABLE 2-continued

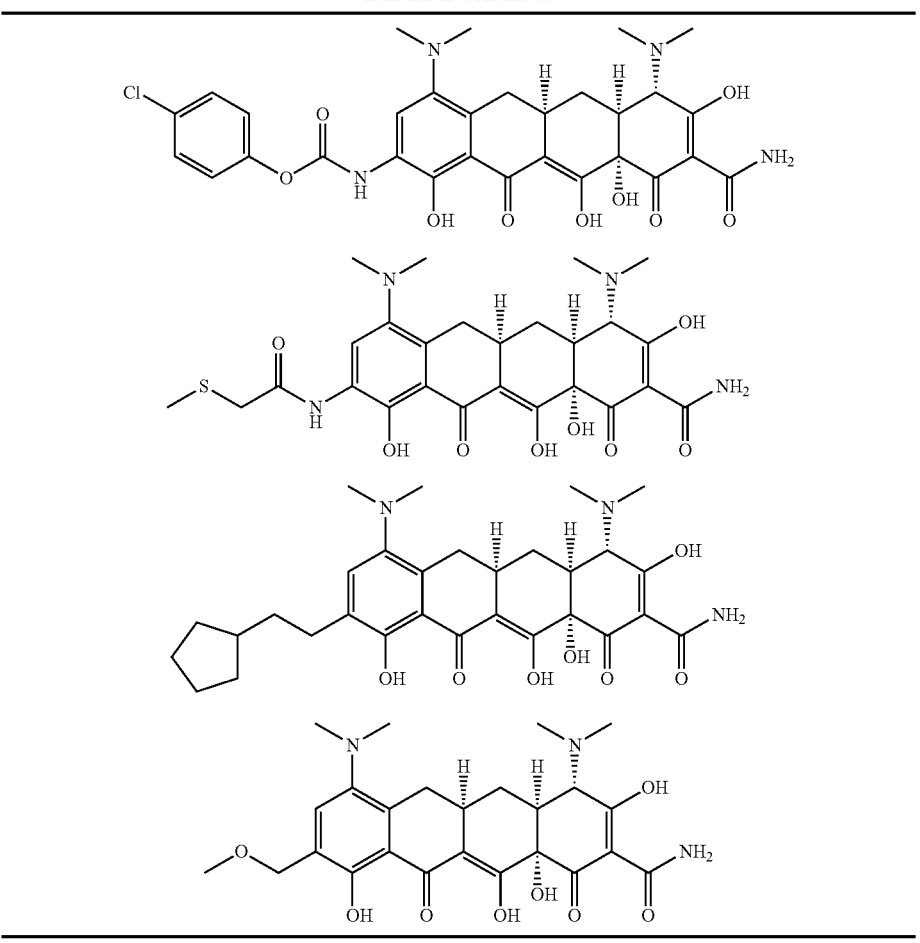

In certain embodiments, the substituted tetracycline compounds of the invention have antibacterial activity against gram+ and/or gram− bacteria. In certain embodiments, the tetracycline compounds of the invention do not have antibacterial activity against gram+ and/or gram− bacteria. In other embodiments, compounds with MIC of greater than about 2 µg/ml, greater than about 3 µg/ml, greater than about 4 µg/ml, greater than about 5 µg/ml, greater than about 6 µg/ml, greater than about 8 µg/ml, greater than about 9 µg/ml, greater than about 10 µg/ml, greater than about 11 µg/ml, greater than about 12 µg/ml, greater than about 13 µg/ml, greater than about 14 µg/ml, greater than about 15 µg/ml, greater than about 16 µg/ml, greater than about 17 µg/ml, greater than about 18 µg/ml, greater than about 19 µg/ml, greater than about 20 µg/ml, greater than about 25 µg/ml, greater than about 30 µg/ml, greater than about 40 µg/ml, or greater than about 50 µg/ml for gram+ and/or gram− bacteria are considered not to have anti-bacterial activity.

In other embodiments, compounds with MIC of less than about 50 µg/ml, less than about 40 µg/ml, less than about 30 µg/ml, less than about 25 µg/ml, less than about 20 µg/ml, less than about 15 µg/ml, less than about 14 µg/ml, less than about 13 µg/ml, less than about 12 µg/ml, less than about 11 µg/ml, less than about 10 µg/ml, less than about 9 µg/ml, less than about 8 µg/ml, less than about 6 µg/ml, less than about 5 µg/ml, less than about 4 µg/ml, less than about 3 µg/ml, less than about 2 µg/ml, less than about 1 µg/ml, or less than about 0.5 µg/ml for gram+ and/or gram− bacteria are considered to have anti-bacterial activity.

In one embodiment, the tetracycline compound of the invention may retain antibiotic, antibacterial, or antimicrobial activity, it may have decreased antibiotic, antibacterial, or antimicrobial activity, or, it may have little to no antibiotic, antibacterial or antimicrobial activity. In an embodiment, the substituted tetracycline compound is substituted at the 1, 2, 3, 4, 5, 6, 7, 8, 9, 10, 11, 11a, 12, 12a and/or 13 position. In certain embodiments, the tetracycline compounds of the invention are 7 and/or 9 substituted, e.g., 7 and/or 9-substituted tetracycline compounds (e.g., compounds wherein $R^7$ and/or $R^9$ are not both hydrogen). In yet a further embodiment, the tetracycline compounds of the invention are 7 and/or 9 substituted sancycline compounds. Other examples of tetracycline compounds which may be used in the methods of the invention include those otherwise described herein or incorporated by reference.

The substituted tetracycline compounds of the invention can be synthesized using the methods described in Example 1, in the following schemes and/or by using art recognized techniques. All novel substituted tetracycline compounds described herein are included in the invention as compounds.

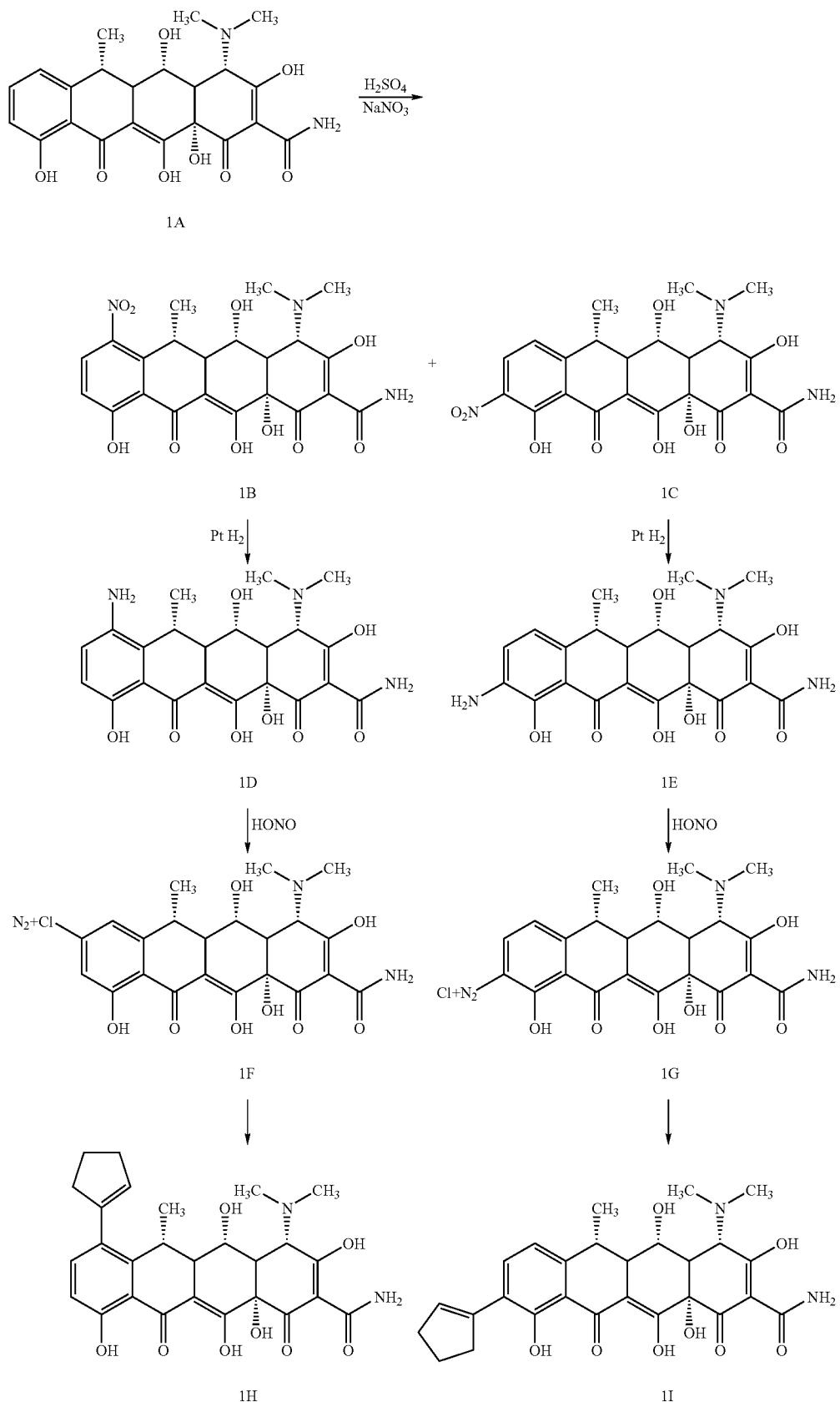
SCHEME 1

9- and 7-substituted tetracyclines can be synthesized by the method shown in Scheme 1. As shown in Scheme 1,9- and 7-substituted tetracycline compounds can be synthesized by treating a tetracycline compound (e.g., doxycycline, 1A), with sulfuric acid and sodium nitrate. The resulting product is a mixture of the 7-nitro and 9-nitro isomers (1B and 1C, respectively). The 7-nitro (1B) and 9-nitro (1C) derivatives are treated by hydrogenation using hydrogen gas and a platinum catalyst to yield amines 1D and 1E. The isomers are separated at this time by conventional methods. To synthesize 7- or 9-substituted alkenyl derivatives, the 7- or 9-amino tetracycline compound (1E and 1F, respectively) is treated with HONO, to yield the diazonium salt (1G and 1H). The salt (1G and 1H) is treated with an appropriate reactive reagent to yield the desired compound (e.g., in Scheme 1,7-cyclopent-1-enyl doxycycline (1H) and 9-cyclopent-1-enyl doxycycline (1I)).

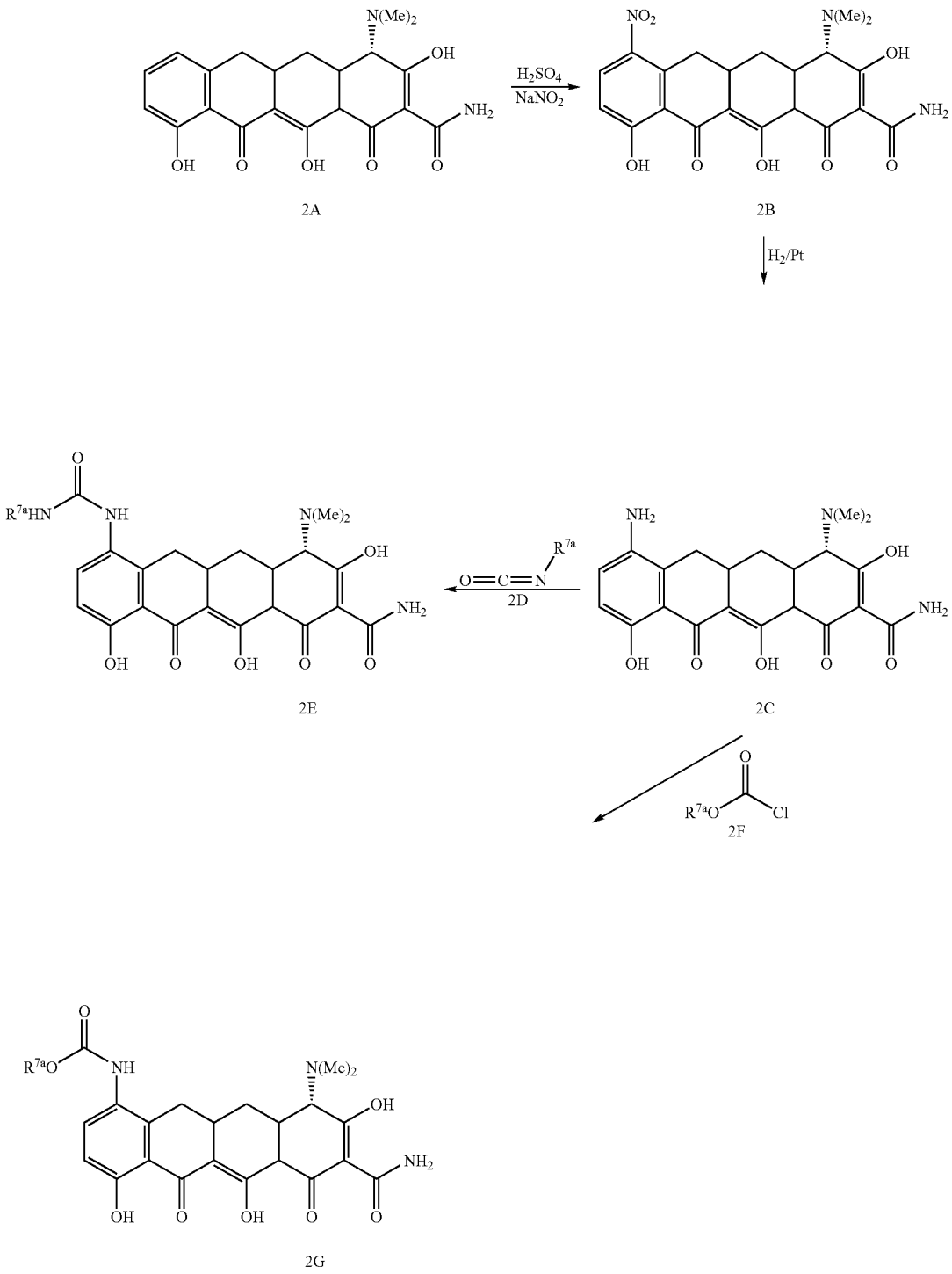

As shown in Scheme 2, tetracycline compounds of the invention wherein $R^7$ is a carbamate or a urea derivative can be synthesized using the following protocol. Sancycline (2A) is treated with $NaNO_2$ under acidic conditions forming 7-nitro sancycline (2B) in a mixture of positional isomers. 7-nitrosancycline (2BY is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

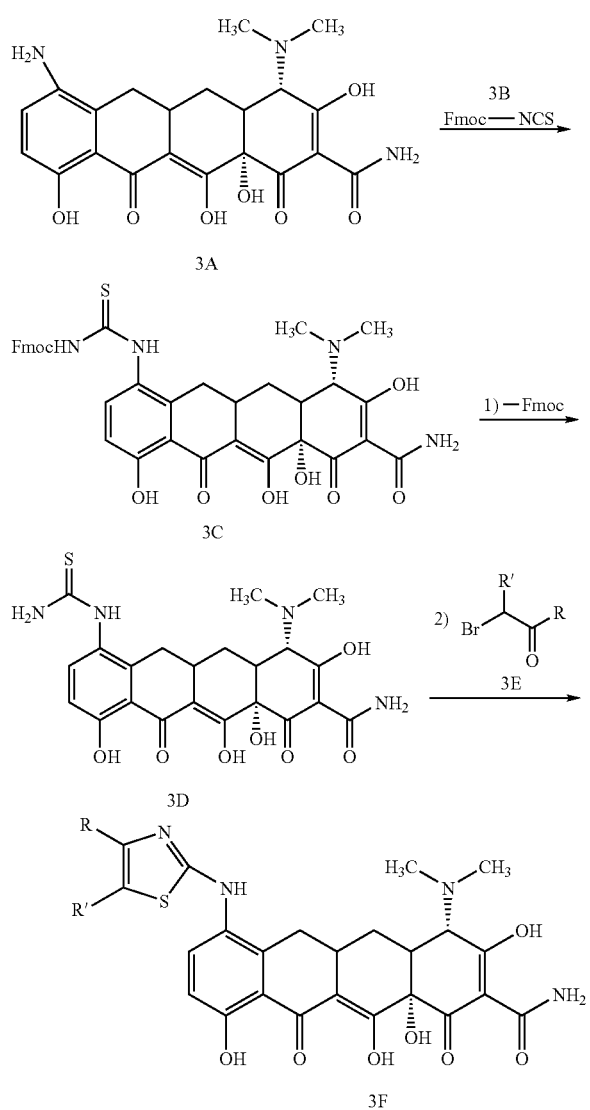

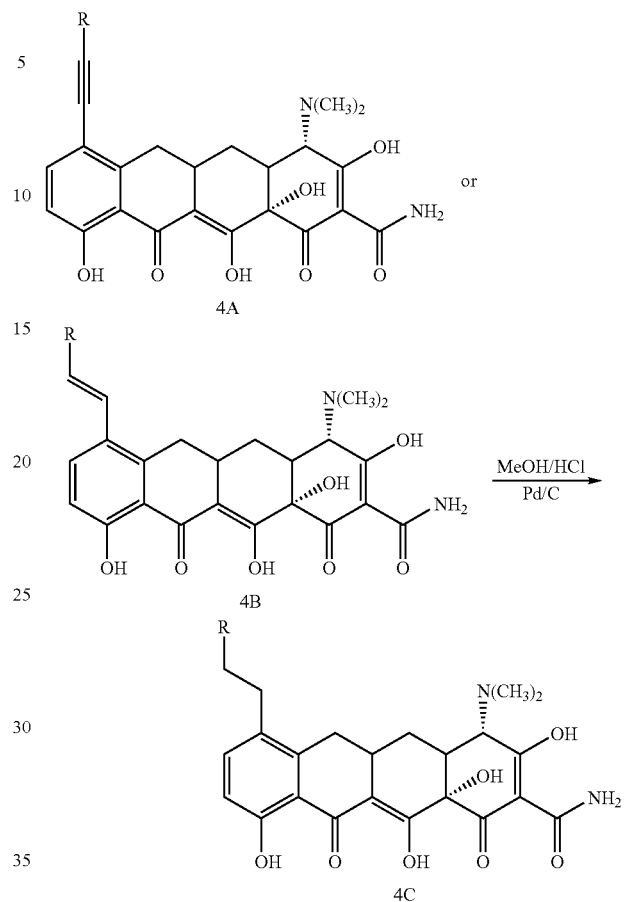

7-alkenyl tetracycline compounds, such as 7-alkynyl sancycline (4A) and 7-alkenyl sancycline (4B), can be hydrogenated to form 7-alkyl substituted tetracycline compounds (e.g., 7-alkyl sancycline, 4C). Scheme 4 depicts the selective hydrogenation of the 7-position double or triple bond, in saturated methanol and hydrochloric acid solution with a palladium/carbon catalyst under pressure, to yield the product.

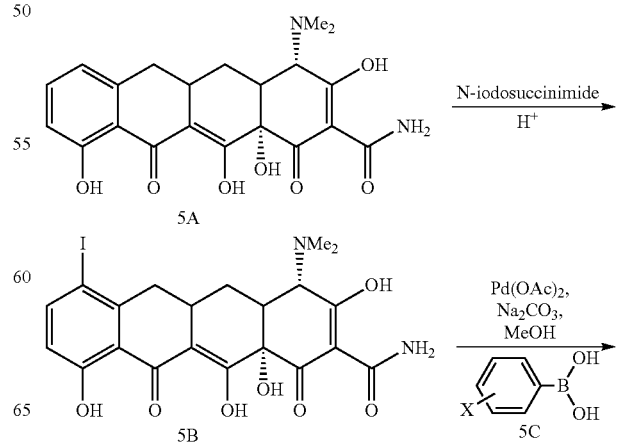

As shown in Scheme 3, tetracycline compounds of the invention, wherein $R^7$ is a heterocyclic (i.e. thiazole) substituted amino group can be synthesized using the above protocol. 7-amino sancycline (3A) is reacted with Fmoc-isothiocyanate (3B) to produce the protected thiourea (3C). The protected thiourea (3C) is then deprotected yielding the active sancycline thiourea (3D) compound. The sancycline thiourea (3D) is reacted with an α-haloketone (3E) to produce a thiazole substituted 7-amino sancycline (3F).

-continued

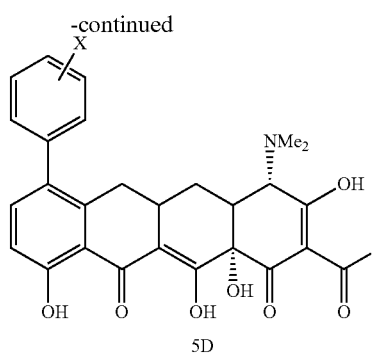

5D

In Scheme 5, a general synthetic scheme for synthesizing 7-position aryl derivatives is shown. A Suzuki coupling of an aryl boronic acid with an iodosancycline compound is shown. An iodo sancycline compound (5B) can be synthesized from sancycline by treating sancycline (5A) with at least one equivalent N-iodosuccinimide (NIS) under acidic conditions.

The reaction is quenched, and the resulting 7-iodo sancycline (5B) can then be purified using standard techniques known in the art. To form the aryl derivative, 7-iodo sancycline (5B) is treated with an aqueous base (e.g., $Na_2CO_3$) and an appropriate boronic acid (5C) and under an inert atmosphere. The reaction is catalyzed with a palladium catalyst (e.g., Pd$(OAc)_2$). The product (SD) can be purified by methods known in the art (such as HPLC). Other 7-aryl, alkenyl, and alkynyl tetracycline compounds can be synthesized using similar protocols.

The 7-substituted tetracycline compounds of the invention can also be synthesized using Stille cross couplings. Stille cross couplings can be performed using an appropriate tin reagent (e.g., R—$SnBu_3$) and a halogenated tetracycline compound, (e.g., 7-iodosancycline). The tin reagent and the iodosancycline compound can be treated with a palladium catalyst (e.g., Pd(PPh$_3$)$_2$Cl$_2$ or Pd(AsPh$_3$)$_2$Cl$_2$) and, optionally, with an additional copper salt, e.g., CuI. The resulting compound can then be purified using techniques known in the art.

SCHEME 6

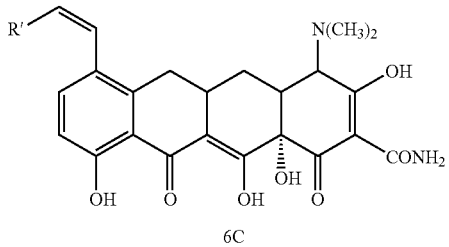

6C

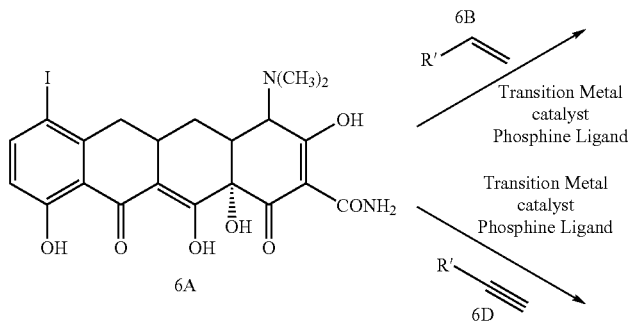

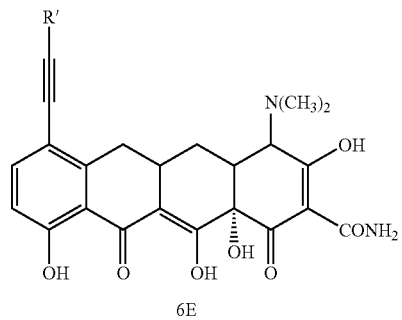

6E

The compounds of the invention can also be synthesized using Heck-type cross coupling reactions. As shown in Scheme 6, Heck-type cross-couplings can be performed by suspending a halogenated tetracycline compound (e.g., 7-iodosancycline, 6A) and an appropriate palladium or other transition metal catalyst (e.g., Pd(OAc)₂ and CuI) in an appropriate solvent (e.g., degassed acetmitrile). The substrate, a reactive alkene (6B) or alkyne (6D), and triethylamine are then added and the mixture is heated for several hours, before being cooled to room temperature. The resulting 7-substituted alkenyl (6C) or 7-substituted alkynyl (6E) tetracycline compound can then be purified using techniques known in the art.

SCHEME 7

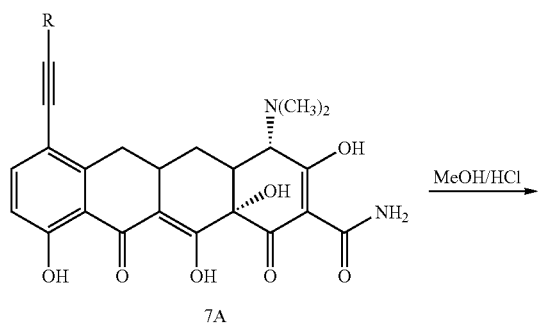

To prepare 7-(2'-Chloro-alkenyl)-tetracycline compounds, the appropriate 7-(alkynyl)-sancycline (7A) is dissolved in saturated methanol and hydrochloric acid and stirred. The solvent is then removed to yield the product (7B).

SCHEME 8

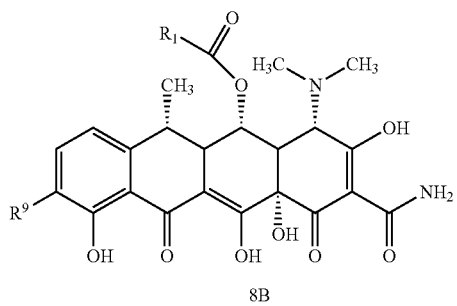

As depicted in Scheme 8, 5-esters of 9-substituted tetracycline compounds can be formed by dissolving the 9-substituted compounds (8A) in strong acid (e.g. HF, methanesulphonic acid, and trifluoromethanesulfonic acid) and adding the appropriate carboxylic acid to yield the corresponding esters (8B).

SCHEME 9

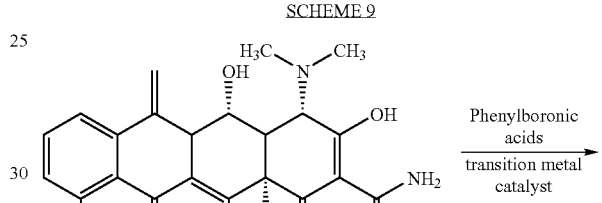

As shown in Scheme 9, methacycline (9A) can be reacted with a phenylboronic acid in the presence of a palladium catalyst such as Pd(OAc)₂ to form a 13 aryl substituted methacycline compound. The resulting compound can then be purified using techniques known in the art such as preparative HPLC and characterized.

As shown in Scheme 10 below, 7 and 9 aminomethyl tetracyclines may be synthesized using reagents such as hydroxymethyl-carbamic acid benzyl ester. The resulting aminomethyl tetracycline compounds may be further derivatized

SCHEME 10

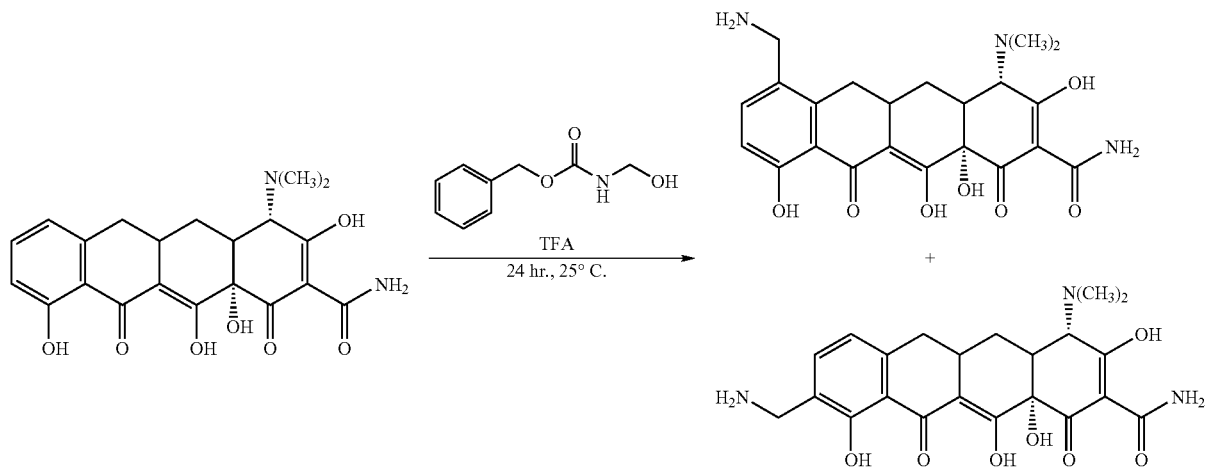

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (e.g., isopropyl, tert-butyl, isobutyl, etc.), cycloalkyl (alicyclic) groups (e.g., cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 20 or fewer carbon atoms in its backbone (e.g., $C_1$-$C_{20}$ for straight chain, $C_3$-$C_{20}$ for branched chain), and more preferably 4 or fewer. Cycloalkyls may have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxophenyl, quinoline, isoquinoline, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diairylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 20 or fewer carbon atoms in its backbone (e.g., $C_2$-$C_{20}$ for straight chain, $C_3$-$C_{20}$ for branched chain).

Likewise, cycloalkenyl groups may have from 3-8 carbon atoms in their ring structure, and more preferably have 5 or 6 carbons in the ring structure. The term $C_2$-$C_{20}$ includes alkenyl groups containing 2 to 20 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 20 or fewer carbon atoms in its backbone (e.g., $C_2$-$C_{20}$ for straight chain, $C_3$-$C_{20}$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including, e.g., alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO-$) or a carbonyl group. The term "substituted acyl" includes acyl groups where one or more of the hydrogen atoms are replaced by for example, alkyl groups, alkenyl, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "aroyl" includes compounds and moieties with an aryl or heteroaromatic moiety bound to a carbonyl group. Examples of aroyl groups include phenylcarboxy, naphthyl carboxy, etc.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "halogen" includes fluorine, bromine, chlorine, iodine, etc. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O$^-$ X$^+$, where X$^+$ is a counterion.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "thiocarbonyl" or "thiocarboxy" includes compounds and moieties which contain a carbon connected with a double bond to a sulfur atom.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "oximyl" includes moieties which comprise an oxime group.

The term "dimeric moiety" includes moieties which comprise a second tetracycline four ring structure. The dimeric moiety may be attached to the substituted tetracycline through a chain of from 1-30 atoms. The chain may be comprised of atoms covalently linked together through single, double and triple bonds. The tetracycline ring structure of the dimeric moiety may further be substituted or unsubstituted. It may be attached at the 1, 2, 3, 4, 5, 6, 7, 8, 9, 10, 11, 11a, 12, 12a, and/or 13 position.

The term "prodrug moiety" includes moieties which can be metabolized in vivo. Generally, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The structures of some of the substituted tetracycline compounds used in the methods and compositions of the invention include asymmetric carbon atoms. The isomers arising from the chiral atoms (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The method may further comprise administering the tetracycline compound in combination with a second agent, e.g., an agent which may enhance treatment of the DTMR, enhance the modulation of RNA, or the second agent may be selected for treating a different DTMR or a different disease state not related to the RNA modulation.

The language "in combination with" a second agent includes co-administration of the tetracycline compound, and with the second agent, administration of the tetracycline compound first, followed by the second agent and administration of the second agent first, followed by the tetracycline compound. The second agent may be any agent which is known in the art to treat, prevent, or reduce the symptoms of a DTMR. Furthermore, the second agent may be any agent of benefit to the patient when administered in combination with the administration of an tetracycline compound. Examples of second agents include neuroprotective agents and chemotherapeutic agents.

The language "chemotherapeutic agent" includes chemical reagents which inhibit the growth of proliferating cells or tissues wherein the growth of such cells or tissues is undesirable or otherwise treat at least one resulting symptom of such a growth. Chemotherapeutic agents are well known in the art (see e.g., Gilman A. G., et al., *The Pharmacological Basis of Therapeutics*, 8th Ed., Sec 12:1202-1263 (1990)), and are typically used to treat neoplastic diseases. Examples of chemotherapeutic agents include: bleomycin, docetaxel (Taxotere), doxorubicin, edatrexate, etoposide, finasteride (Proscar), flutamide (Eulexin), gemcitabine (Gemzar), goserelin acetate (Zoladex), granisetron (Kytril), irinotecan (Campto/Camptosar), ondansetron (Zofran), paclitaxel (Taxol), pegaspargase (Oncaspar), pilocarpine hydrochloride (Salagen), porfimer sodium (Photofrin), interleukin-2 (Proleukin), rituximab (Rituxan), topotecan (Hycamtin), trastuzumab (Herceptin), tretinoin (Retin-A), Triapine, vincristine, and vinorelbine tartrate (Navelbine).

Other examples of chemotherapeutic agents include alkylating drugs such as Nitrogen Mustards (e.g., Mechlorethamine ($HN_2$), Cyclophosphamide, Ifosfamide, Melphalan (L-sarcolysin), Chlorambucil, etc.); ethylenimines, methylmelamines (e.g., Hexamethylmelamine, Thiotepa, etc.); Alkyl Sulfonates (e.g., Busulfan, etc.), Nitrosoureas (e.g., Carmustine (BCNU), Lomustine (CCNU), Semustine (methyl-CCNU), Streptozocin (streptozotocin), etc.), triazenes (e.g. Decarbazine (DTIC; dimethyltriazenoimi-dazolecarboxamide)), Alkylators (e.g., cis-diamminedichloroplatirium II (CDDP)), etc.

Other examples of chemotherapeutic agents include antimetabolites such as folic acid analogs (e.g., Methotrexate (amethopterin)); pyrimidine analogs (e.g., fluorouracil ('5-fluorouracil; 5-FU); floxuridine (fluorode-oxyuridine); FUdr; Cytarabine (cyosine arabinoside), etc.); purine analogs. (e.g., Mercaptopurine (6-mercaptopurine; 6-MP); Thioguanine (6-thioguanine; TG); and Pentostatin (2'-deoxycoformycin)), etc.

Other examples of chemotherapeutic agents also include vinca alkaloids (e.g., Vinblastin (VLB) and Vincristine); topoisomerase inhibitors (e.g., Etoposide, Teniposide, Camptothecin, Topotecan, 9-amino-campotothecin CPT-11, etc.); antibiotics (e.g., Dactinomycin (actinomycin D), adriamycin, daunorubicin, doxorubicin, bleomycin, plicamycin (mithramycin), mitomycin (mitomycin C), Taxol, Taxotere, etc.); enzymes (e.g., L-Asparaginase); and biological response modifiers (e.g., interferon-; interleukin 2, etc.). Other chemotherapeutic agents include cis-diaminedichloroplatinum II (CDDP); Carboplatin; Anthracendione (e.g., Mitoxantrone); Hydroxyurea; Procarbazine (N-methylhydrazine); and adrenocortical suppressants (e.g., Mitotane, aminoglutethimide, etc.).

Other chemotherapeutic agents include adrenocorticosteroids (e.g., Prednisone); progestins (e.g., Hydroxyprogesterone caproate, Medroxyprogesterone acetate, Megestrol acetate, etc.); estrogens (e.g., diethylstilbestrol; ethenyl estradiol, etc.); antiestrogens (e.g. Tamoxifen, etc.); androgens (e.g., testosterone propionate, Fluoxymesterone, etc.); antiandrogens (e.g., Flutamide); and gonadotropin-releasing hormone analogs (e.g., Leuprolide).

III. Pharmaceutical Compositions for the Treatment of DTMR

The invention also pertains at least in part to pharmaceutical compositions for the treatment of DTMR. The pharmaceutical compositions comprise a tetracycline compound of the invention in combination with a pharmaceutical acceptable carrier. The composition may further comprise a second agent for the treatment of a DTMR.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal, pulmonary and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier- and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. Sprays also can be delivered by mechanical, electrical, or by other methods known in the art.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial, antiparasitic and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle. The compositions also may be formulated such that its elimination is retarded by methods known in the art.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration or administration via inhalation is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually. Other methods for administration include via inhalation.

The tetracycline compounds of the invention may also be administered to a subject via stents. The compounds may be administered through the stent or be impregnated in the stent itself.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient will range from about 0.0001 to about 100 mg per kilogram of body weight per day, more preferably from about 0.01 to about 50 mg per kg per day, and still more preferably from about 1.0 to about 100 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition. Compounds or pharmaceutical compositions can be administered in combination with other agents.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Farm. SCI.* 66:1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances includes relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying-agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.)

The invention also pertains, at least in part, to packaged compositions comprising a tetracycline compound of the invention and instructions for using said compound for the treatment of a DTMR.

The invention is further illustrated by the following examples, which should not be construed as further limiting. The contents of all references, pending patent applications and published patents, cited throughout this application are hereby expressly incorporated by reference.

EXEMPLIFICATION OF THE INVENTION

Compounds of the invention may be made as described below, with modifications to the procedure below within the skill of those of ordinary skill in the art.

Example 1

Synthesis of 7-Substituted Tetracyclines

7 Iodo Sancycline

One gram of sancycline was dissolved in 25 mL of TFA (trifluoroacetic acid) that was cooled to 0 C (on ice). 1.2 equivalents of N-iodosuccinimide (NIS) was added to the reaction mixture and reacted for forty minutes. The reaction was removed from the ice bath and was allowed to react at room temperature for an additional five hours. The mixture was then analyzed by HPLC and TLC, was driven to completion by the stepwise addition of NIS. After completion of the reaction, the TFA was removed in vacuo and 3 mL of MeOH was added to dissolve the residue. The methanolic solution was the added slowly to a rapidly stirring solution of diethyl ether to form a greenish brown precipitate. The 7-iodo isomer of sancycline was purified by treating the 7-iodo product with activated charcoal, filtering through Celite, and subsequent removal of the solvent in vacuo to produce the 7-isomer compound as a pure yellow solid in 75% yield.

MS(M+H) (formic acid solvent) 541.3.

\Rt: Hypersil C18 BDS Column, 11.73

$^1$H NMR (Methanol $d_4$-300 MHz) δ 7.87-7.90 (d, 1H), 6.66-6.69 (d, 1H), 4.06 (s, 1H), 2.98 (s, 6H), 2.42 (m, 1H), 2.19 (m, 1H), 1.62 (m, 4H), 0.99 (m, 2H)

7-Phenyl Sancycline 7-iodosancycline, 150 mg (0.28 mM), Pd(OAc)$_2$ and 10 mL of MeOH are added to a flask with a stir bar and the system degassed 3× using argon. Na$_2$CO$_3$ (87 mg, 0.8 mM) dissolved in water and argon degassed is added via syringe is added along with phenylboronic acid (68 mg, 0.55 mM) in MeOH that was also degassed. The reaction was followed by HPLC for 2 hours and cooled to room temperature. The solution was filtered, and dried to produce a crude mixture. The solid was dissolved in dimethylformamide and injected onto a preparative HPLC system using C18 reverse-phase silica. The fraction at 36-38 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product in 42% yield as a yellow solid.

Rt 21.6 min: MS (M+H, formic acid solvent): 491.3

$^1$H NMR (Methanol $d_4$-300 MHz) δ 7.87 (d, J=8.86 Hz, 1H), 7.38 (m, 5H), 6.64 (d, 8.87 Hz, 1H), 4.00 (s, 1H), 3.84 (s, 2H), 3.01 (s, 6H), 2.46 (m, 2H), 1.63 (m, 4H), 0.95 (m, 2H)

7-(4'-Chlorophenyl) Sancycline 7-iodosancycline, 500 mg (0.91 mM), Pd(OAc)$_2$ 21 mg, and 20 mL of MeOH are added to a flask with a stir bar and the system degassed 3× using argon. Na$_2$CO$_3$ (293 mg, 2.8 mM) dissolved in water and argon degassed is added via syringe is added along with 4-Cl-phenylboronic acid (289 mg, 1.85 mM) in MeOH that was also degassed. The reaction was followed by HPLC for 45 minutes and cooled to room temperature. The solution was filtered, and dried to produce a crude mixture. The solid was dissolved in dimethylformamide and injected onto a preparative HPLC system using C18 reverse-phase silica. The fraction at 39 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product in 57% yield as a yellow solid.

Rt 20.3 min: MS (M+H, formic acid solvent): 525.7

$^1$H NMR (Methanol d$_4$-300 MHz) δ 7.49-7.52 (d, J=8.54 Hz, 1H), 6.99-7.01 (d, 8.61 Hz, 1H), 4.12 (s, 1H), 3.67 (m, 1H), 3.06 (s, 6H), 2.58 (m, 2H), 1.62 (m, 4H), 1.01 (m, 2H)

7-(4'-Fluorophenyl) Sancycline 7-iodosancycline, 200 mg (0.3 mM), Pd(OAc)$_2$ 8.3 mg, and 10 mL of MeOH are added to a flask with a stir bar and the system degassed 3× using argon. Na$_2$CO$_3$ (104 mg, 1.1 mM) dissolved in water and argon degassed is added via syringe is added along with 4-F-phenylboronic acid (104 mg, 0.7 mM) in MeOH that was also degassed. The reaction was followed by HPLC for 20 minutes and cooled to room temperature. The solution was filtered, and dried- to produce a crude mixture. The solid was dissolved in dimethylformamide and injected onto a preparative HPLC system using C18 reverse-phase silica. The fraction at 19-20 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product in 47% yield as a yellow solid.

Rt 19.5 min: MS (M+H, formic acid solvent): 509.4

$^1$H NMR (Methanol d$_4$-300 MHz) δ 6.92-6.95 (d, 1H), 7.45-7.48 (d, 1H), 7.15-7.35 (m, 4H), 4.05 (s, 1H), 3.62 (m, 1H), 3.08 (s, 6H), 2.55 (m, 2H), 1.65 (m, 4H), 1.00 (m, 2H)

7-(4'-Iodo-1',3'-carboethoxy-1',3'-butadiene) Sancycline

7-I-Sancycline (1 gm, 1.86 mmol), was dissolved in 25 mL of acetonitrile and was degassed and purged with nitrogen (three times). To this suspension Pd(OAc)$_2$ (20 mg, 0.089 mmol), CuI (10 mg, 0.053 mmol), (o-tolyl)$_3$P (56 mg, 0.183 mmol) were added and purged with nitrogen. Ethyl propiolate (1 mL) and triethylamine (1 mL) were added to the suspension. It turned to a brown solution upon addition of Et$_3$N. The reaction mixture was then heated to 70 degrees C. for two hours. Progress of the reaction was monitored by HPLC. It was then cooled down to room temperature and was filtered through celite. Evaporation of the solvent gave a brown solid, which was then purified on preparative HPLC to give a yellow solid.

7-(2'-Chloroethenyl)-Sancycline

To a solution/suspension of 0.65 g (1 mmol) of 7-iodo sancycline, 0.05 g tetrakis triphenyl phosphinato palladate, 0.012 g palladium acetate, 0.05 g copper (I) iodide in 10 mL acetonitrile, 2 mL triethylamine and 0.5 g trimethylsilyl acetylene was added at room temperature. The reaction proceeded for two hours before being filtered through a celite bed and concentrated. The crude product was purified by preparative HPLC. The collected fractions were concentrated and the residue was taken up in about 1 mL of methanol and 2 mL of HCl saturated methanol. The product was precipitated with ether. The solids were filtered off and dried under reduced pressure. NMR spectroscopy and LC-MS showed that the compound was 7-(2-chloroethenyl) sancycline.

7-(4'-aminophenyl) Sancycline

To a solution of 200 mg of 7-(4-nitrophenyl) sancycline in 50 mL methanol, 10 mg of 10% palladium on charcoal catalyst was added. The reaction mixture was shaken under 40 psi hydrogen pressure for 2 hours and was then filtered followed by concentration. The residue was further purified by preparative HPLC. 35 mg was isolated as the HCl salt and the structure was proved by NMR and LC-MS to be 7-(4-aminophenyl) sancycline.

7-(NN-Dimethylpropynyl)-Sancycline

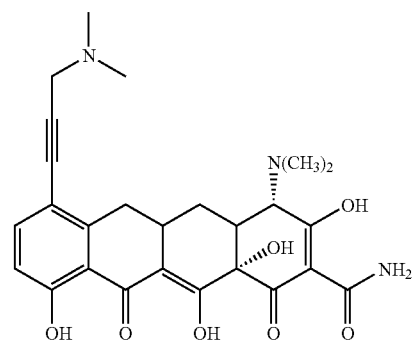

7-I-Sancycline (1 gm, 1.86 mmol), taken in 25 mL of acetonitrile was degassed and purged with nitrogen (three times). To this suspension Pd(OAc)$_2$ (20 mg, 0.089 mmol), CuI (10 mg, 0.053 mmol), (o-tolyl)$_3$P (56 mg, 0.183 mmol) were added and purged with nitrogen for few minutes. NN-Dimethylpropyne (308 mg, 3.72 mmol) and triethylamine (1 mL) were added to the suspension. It was turned into a brown solution upon addition of Et$_3$N. The reaction mixture was then heated to 70° C. for 3 hours. Progress of the reaction was monitored by HPLC. It was then cooled down to room temperature and was filtered through celite. Evaporation of the solvent gave a brown solid, which was then purified on preparative HPLC to give a yellow solid. The structure of this compound has been characterized using 1H NMR, HPLC, and MS.

7-(2'-Chloro-3-Hydroxypropenyl)-Sancycline

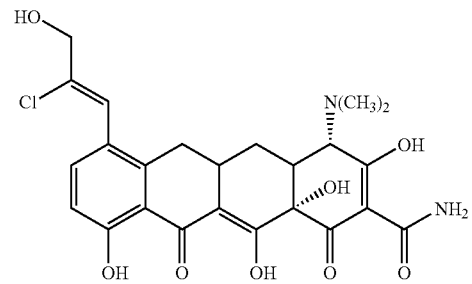

7-(alkynyl)-sancycline (100 mg) was taken in 20 ml of saturated MeOH/HCl and stirred for 20 min. The solvent was 7-(3'-Methoxyphenylethyl)-Sancycline

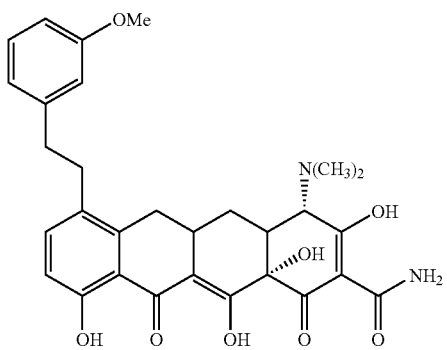

7-(3'-Methoxyphenylethynyl)-sancycline (1 mmol) was taken in saturated solution of MeOH/HCl. To this solution 10% Pd/C was added and was subjected to hydrogenation at 50 psi for 12 hrs. It was then filtered through celite. The solvent was evaporated to give a yellow powder. Finally, it was precipitated from MeOH/diethylether. The structure of this compound has been characterized using 1H NMR, HPLC, and MS.

(2-Dimethylamino-Acetylamino)-Sancycline

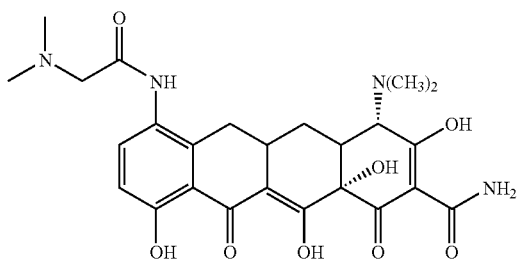

NN-Dimethylglycine (1.2 mmol) was dissolved in DMF (5 mL) and O-Benzotriazol-1-yl-N,N,N',N',-tetramethyluronium hexafluorophosphate (HBTU, 1.2 mmol) was added. The solution was then stirred for 5 minutes at room temperature. To this solution, 7-aminosancycline (1 mmol) was added, followed by the addition of diisopropylethyl amine (DIEA, 1.2 mmol). The reaction was then stirred at room temperature for 2 hours. The solvent, DMF, was removed on vacuum. The crude material was dissolved in 5 mL of MeOH and filtered using autovials and purified using preparative HPLC. The structure of the product has been characterized using 1H NMR, HPLC, and MS.

7-(N-Methylsulphonamidopropargylamine) Sancycline

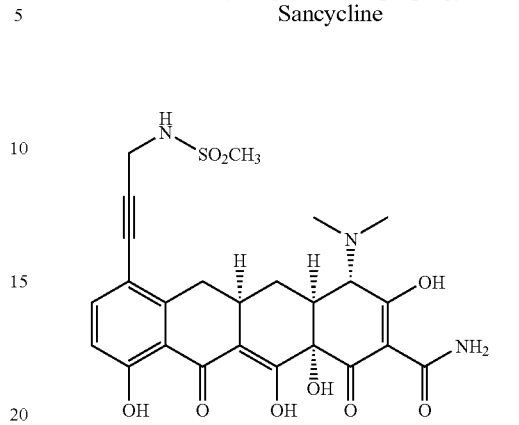

To a mixture of 7-iodosancycline mono trifluoroacetic acid salt (1 g; 1.53 mmoles), palladium II acetate (17.2 mg; 0.076 mmoles), tetrakis triphenylphosphine palladium (176.8 mg; 0.153 mmoles), and copper (I) iodide (49 mg; 0,228 mmoles) was added 15 ml of reagent grade acetonitrile in a clean dry 2 necked round bottom flask. The reaction was purged with a slow steam of argon gas, with stirring, for 5 minutes before the addition (in one portion as a solid) of N-methylsulphonamidopropargyl amine. The sulphonamide was prepared by a method known in the art (J. Med. Chem 31(3) 1988; 577-82). This was followed by one milliliter of triethylamine (1 ml; 0.726 mg; 7.175 mmoles) and the reaction was stirred, under an argon atmosphere, for approximately 1.0 hour at ambient temperature. The reaction mixture was suctioned filtered through a pad of diatomaceous earth and washed with acetonitrile. The filtrates were reduced to dryness under vacuo and the residue was treated with a dilute solution of trifluroroacetic acid in acetonitrile to adjust the pH to approximately 2. The residue was treated with more dilute trifluoroacetic acid in acetonitrile, resulting in the formation of a precipitate, which was removed via suction filtration. The crude filtrates were purified utilizing reverse phase HPLC with DVB as the solid phase; and a gradient of 1:1 methanol/acetonitrile 1% trifluoroacetic acid and 1% trifluoroacetic acid in water. The appropriate fractions were reduced to dryness under reduced pressure and solid collected. The product was characterized via $^1$H NMR, mass spectrogram and LC reverse phase.

7-(2'-methoxy-5'-formylphenyl)sancycline

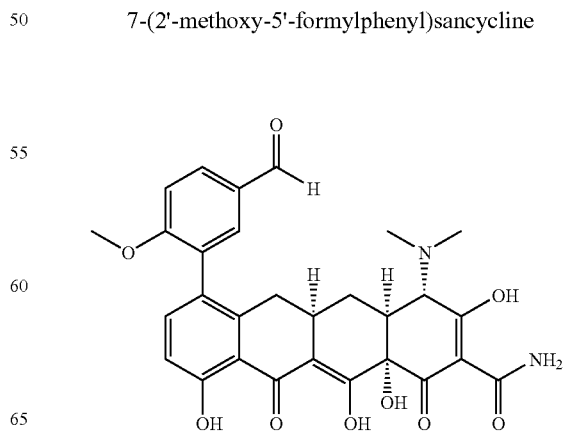

7-iodo-sancycline (1 g, 1.53 mmol), Pd(OAc)$_2$ (34 mg, 0.153 mmol), and MeOH (50 mL) were combined in a 250 mL 2 neck round bottom flask equipped with a condenser and argon line. The solution was then purged with argon (15 min) while heated in an oil bath to approximately 70° C. Sodium carbonate (482 mg, 4.58 mmol) was dissolved in water (3-5 mL) and added to reaction flask. The flask was then purged with argon for another 5 minutes. 2-Methoxy-5-formylphenyl boronic acid (333 mg, 1.83 mmol) was dissolved in MeOH (5 mL) and added to reaction flask. The flask was then purged again with argon for 10 minutes. The reaction was monitored to completion within 3 hours. The contents of the flask were filtered through filter paper and the remaining solvent was evacuated. To make the hydrochloric acid salt, the residue was dissolved in MeOH (sat. HCl) to make the HCl salt. The solution was then filtered and the solvent was evacuated. The product was then characterized by $^1$H NMR, LC-MS.

7-(2'-Methoxy-5'-N,N'-Dimethylaminomethylphenyl)Sancycline

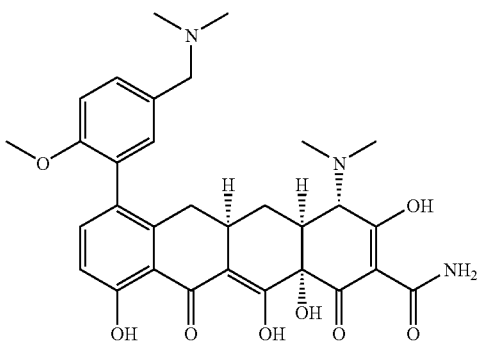

7-(2'-methoxy-5'-formylphenyl)sancycline (1 g, 1.82 mmol), dimethylamine HCl (297 mg, 3.64 mmol), triethylamine (506 µL, 3.64 mmol), and 1,2-DCE (7 mL) were combined in a 40 mL vial. The contents were dissolved within several minutes of shaking or stirring. Sodium triacetoxyborohydride (772 mg, 3.64 mmol) was then added as a solid. The reaction was monitored by HPLC and LC-MS and was complete within 3 hours. The reaction was quenched with MeOH (20 mL) and the solvent was subsequently evacuated. The residue was redissolved in 3 mL DMF and separated on a C-18 column. Fractions from the prep column dried down in-vacuo and the HCl salt was made by dissolving contents in methanol (sat. HCl). The solvent was reduced and a yellow powder obtained. Characterized by $^1$H NMR, LC-MS, HPLC.

7-Furanyl Sancycline 7-iodo sancycline (1.3 mg) and Pd(OAc)$_2$ were taken in 100 mL of methanol and purged with argon for five minutes at 70° C. To this solution was added a solution of sodium carbonate (44 mg) in water (previously purged with argon). A yellow precipitate was obtained and the mixture was heated for another ten minutes. 3-Furanyl boronic acid (333 mg, solution in DMF, purged with argon) was then added and the mixture was heated for another two hours at 70° C. The reaction was monitored by MPLC/MS. When the reaction was complete, the mixture was filtered through celite and the solvent was removed to give a crude material. The crude material was purified by precipitating it with ether (200 ml). The yellow precipitate was filtered and purified using preparative HPLC. The hydrochloride salt was made by dissolving the material in MeOH/HCl and evaporating to dryness. The identity of the resulting solid was confirmed using HPLC, MS, and NMR.

4S-(4α,12aα)]-4-Dimethylamino-7-ethynyl-3,10,12,12a-tetrahydroxy-1,11-dioxo-1,4,4a,5,5a,6,11,12a-octahydro-naphthacene-2-carboxamide 300 mg of 7-iodosancycline 6A was dissolved in 20 mL of acetonitrile and 2.0 mL triethylamine, 50.0 mg Pd(PPh$_3$)$_4$, 50 mg CuI, 12.5 mg Pd(OAc)$_2$ was added followed by 0.5 mL of trimethylsilylacetylene. The reaction was stirred at room temperature for 4 hours, filtered through a divinyl-benzene cartridge (25 g), and concentrated in vacuo to yield 280 mg of the crude material (monitored by LC/MS). The TMS group was removed by dissolving the crude material in methanol, and adding 250 mg of K$_2$CO$_3$ while stirring for 4 hours at room temperature to yield compound 6E (Scheme 11). The mixture was filtered through a divinylbenzene cartridge. The solvent was removed in vacuo to yield the 7-ethynyl sancycline 6E (Scheme 11) in 60% yield by HPLC.

General Method for Synthesis of 7-acetyl sancycline and 7-carbonylalkyl Derivatives of Sancycline 7-ethynyl sancycline 6E (Scheme 11,300 mg) or ethynyl substituted derivatives of 7-ethynyl sancycline are dissolved in 0.1 mL water, 2 mL of H$_2$SO$_4$, optionally with HgSO$_4$ (170 mg) and stirred overnight at room temperature. The aqueous layer is extracted into butanol, CH$_2$Cl$_2$ or an equivalent and the solvent is removed to yield the crude compound 11A (Scheme 11). 7-acetyl sancycline (11A, Scheme 11) is isolated via C18 reverse-phase HPLC or by other methods in the art to yield pure compound in good yield. M+H=457.4

Conversion of 7-acetyl or 7-carbonylalkyl derivatives of sancycline to oximes or O-alkyl oximes 1 gram of 7-acetyl or 7-carbonylalkyl derivatives of sancycline 11A (Scheme 11, 2 mmol) and hydroxylamine HCl are dissolved in methanol or ethanol and stirred at room temperature for 2 or more hours. The compounds are isolated as the syn and anti isomers appropriately by preparative C18-HPLC or by other methods in the art to yield 7-oximecarbonyl alkyl derivatives of sancycline or 7-O-substituted oximecarbonyl derivatives in good yield. 7-acetyl-oxime (Scheme 11, 11B); M+H=473.5. 11C 7-acetyl-oxime-O-methyl ether; M+H=487.5. The syn or anti isomers are both attainable by fractionation of HPLC solvent volumes.

General Methods and Conversion of 7-acetyl or 7-carbonylalkyl Derivatives of sancycline to 7-carbonyl-α-amino Derivatives 1 gram of 7-acetyl or 7-carbonylalkyl derivatives of sancycline 11A (Scheme 11, 2 mmol) is reacted with bromine (4 mmol) or typical halogenating agent (NBS, NCS or equivalent, 24 mmol) to produce the α-halogenated derivative 11D (Br, Cl) as crude solid. This compound is isolated by extraction or other methods in the art and may be reacted with nucleophilic amines (24 mmol) or other nucleophiles (C or O-based) to yield α-amino derivatives of 7-acetyl 11E or other 7-carbonylalkyl derivatives of sancycline.

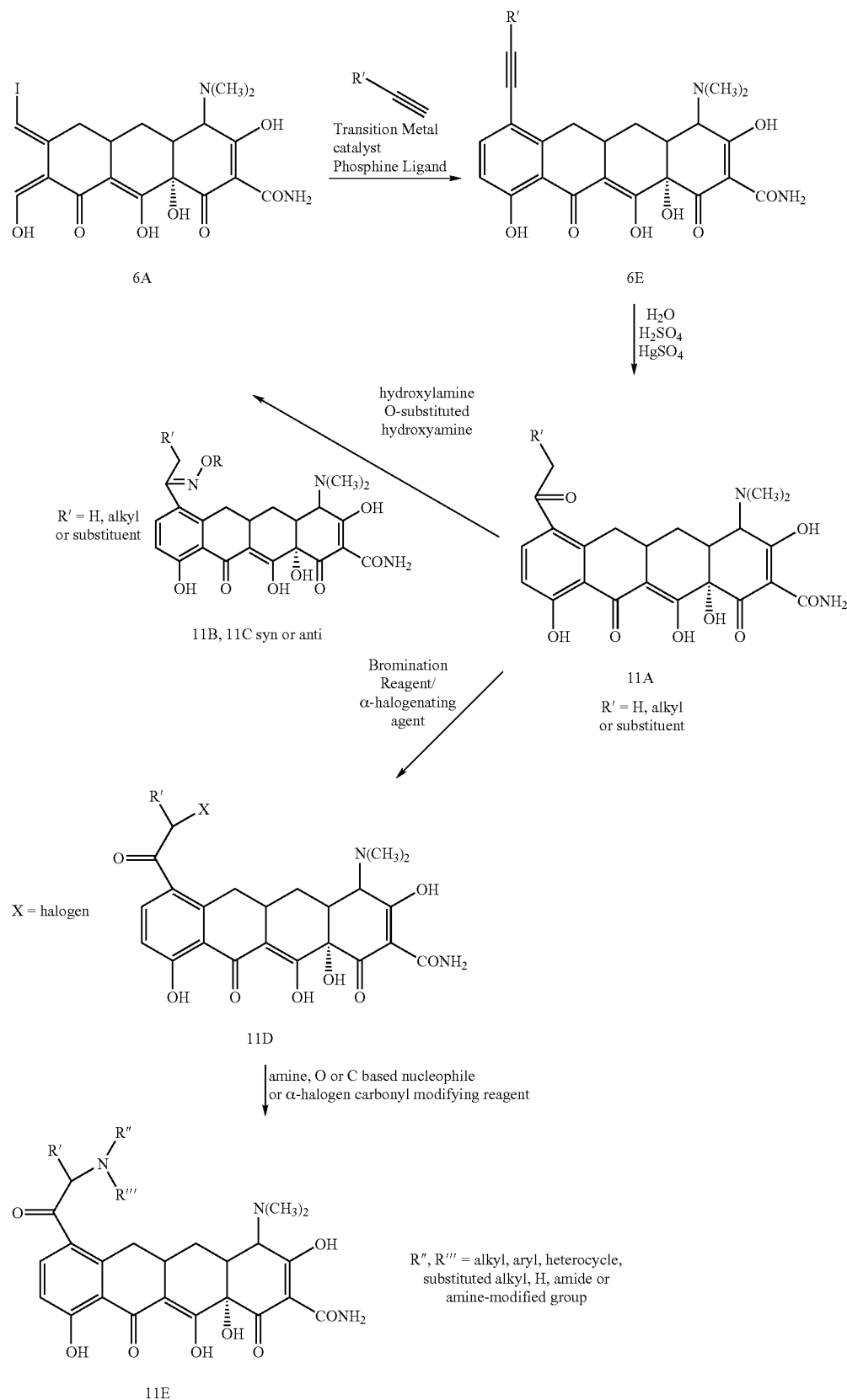
Scheme 11

Example 2

Preparation of 9-Substituted Minocyclines

Preparation of 9-Iodominocycline

To 200 ml of 97% methanesulfonic acid was slowly added, at ambient temperature, portionwise [30 g; 56.56 mM] of minocycline-bis-hydrochloride salt. The dark yellow brown solution was then stirred at ambient temperature while [38 g; 169.7 mM] of N-iodosuccinimide was added, in six equal portions, over 3.0 hours time. The reaction was monitored via analytical LC, noting the disappearance of the starting material.

The reaction was slowly quenched into 2 L of ice cold water containing [17.88 g; 1134.1 mM] of sodium thiosulfate with rapid stirring. This quench was stirred for approximately 30 minutes at ambient temperature. The aqueous layer was then extracted with 6×200 ml of ethyl acetate before the aqueous was poured onto [259.8 g; 3.08M] of sodium hydrogen carbonate containing 300 ml of n-butanol. The phases were split and the aqueous extracted with 4×250 ml of n-butanol. The organic fractions were combined and washed with 3×250 ml of water and once with 250 ml of saturated brine. The resulting organic phase was reduced to dryness under reduced pressure. The residue was suspended in methanol (~600 ml) and anhydrous HCl gas was bubbled into this mixture until solution occurred This solution was reduced to dryness under reduced pressure. The filtrates were reduced to dryness under reduced pressure. The resulting material was triturated with 300 ml of methyl t-butyl ether and isolated via filtration. This material was redissolved in 300 ml of methanol and treated with 0.5 g of wood carbon, filtered and filtrates reduced to dryness under reduced pressure. The material was again powdered under methyl t-butyl ether, isolated via suction filtration and washed with more ether, and finally hexanes. The material was vacuum dried to give 22.6 g of a light yellow brown powder.

General Procedure for Preparation of 9-Alkynyl Minocycline Compounds 1 mmol 9-iodo minocycline, 50 mg tetrakis triphenylphosphinato palladate, 12 mg palladium acetate, 32 mg copper (I) iodide are dissolved/suspended in 10 ml acetonitrile. 2 to 5 ml triethylamine and 3 to 5 mmol alkynyl derivative is added. The reaction mixture is vigorously stirred between ambient temperature to 70° C. The reaction time is 2-24 hours. When the reaction is completed the dark suspension is filtered through a celite bed and concentrated. The crude product is purified by prep HPLC. The combined fractions are concentrated and taken up in ~1 ml methanol. ~3 ml HCl saturated methanol is added, and the product is precipitated with ether.

General Procedure for Preparation of 9-Aryl Minocycline Compounds 0.15 mmol of 9-iodominocycline, PdOAc (3.2 mg), 229 μl 2M $Na_2CO_3$ and 2 equivalents of phenyl boronic acid were dissolved/suspended in 10 ml methanol. The reaction flask was purged with argon and the reaction run for a minimum of four hours or until HPLC monitoring shows consumption of starting material and/or the appearance of products. The suspension was filtered through celite; and subject to purification by prep HPLC on a divinylbenzene or CIE reverse-phase column.

9-(4-Trifluoromethoxyphenylureido)-Methyl Minocycline

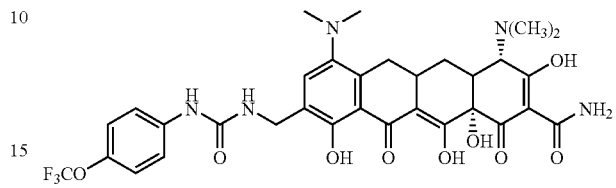

To 3 mL of dimethylformamide was added 150 mg (0.25 mmol) of 9-methyl aminominocyline trihydrochloride and 67 mL (0.50 mmol) of triethylamine at 25° C. With stirring, 75 mL (0.50 mmol) of 4-trifluoromethoxyphenylisocyanate was added and the resulting reaction mixture was stirred at 25° C. for two hours. The reaction was monitored by analytical HPLC (4.6×50 mm reversed phase Luna C18 column, 5 minute linear gradient 1-100% B buffer, A buffer was water with 0.1% trifluoroacetic acid, B buffer was acetonitrile with 0.1% trifluoroacetic acid). Upon completion, the reaction was quenched with 1 mL of water and the pH adjusted to approximately 2.0 with concentrated HCl. The solution was filtered and the compound purified by preparative HPLC. The product yield was 64 mg (37% yield). The purity of the product was 95%, as determined by LCMS (M+1=690).

9-(4'Carboxy phenyl) Minocycline

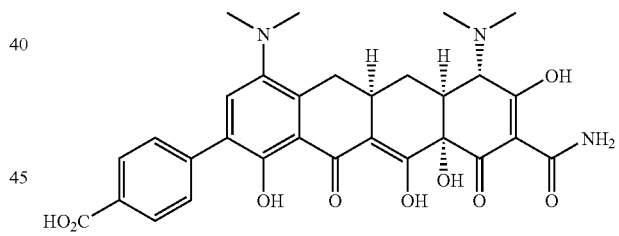

In a clean, dry reaction vessel, was placed 9-iodominocycline [500 mg; 0.762 mmoles]bis HCl salt, palladium (II) acetate [17.2 mg; 0.076 mmoles] along with 10 ml of reagent grade methanol. The solution was immediately purged, with stirring, with a stream of argon gas for approximately 5 minutes. The reaction vessel was brought to reflux and to it was sequentially added via syringe 2M potassium carbonate solution [1.91 ml; 3.81 mmoles], followed by a solution of p-carboxyphenyl boronic acid [238.3 mg; 1.53 mmoles] in 5 ml of reagent DMF. Both of these solutions were previously degassed with argon gas for approximately 5 minutes. The reaction was heated for 45 minutes, the progress was monitored via reverse phase HPLC. The reaction was suctioned filtered through a pad of diatomaceous earth and washed with DMF. The filtrates were reduced to an oil under vacuum and residue treated with t-butylmethyl ether. Crude material was purified via reverse phase HPLC on DVB utilizing a gradient of water and methanol/acetonitrile containing 1.0% trifluoroacetic acid. Product confirmed by mass spectrum: found M+1 578.58; the structure corroborated with 1H NMR.

Example 3

Modulation of Murine Macrophage mRNAs Using Tetracyclines

Materials and Methods

Two murine macrophage cell lines were used: J774.2 (gift from Peter Lambert, Aston University, UK), and RAW 264.7 (ATCC item number TIB-71). Cells were harvested from nearly confluent culture flasks and seeded into 6 well plates at a density of $5 \times 10^6$ cells well$^{-1}$ in a volume of 3 ml Dulbecco's modified essential medium supplemented with 10% fetal calf serum. After 2 hours, cells were exposed to the following conditions:
1) control (J774 cells on two separate occasions, and RAW 264.7 cells)
2) 50 µg/ml minocycline (J774 cells on two separate occasions, and RAW 264.7 cells)
3) 100 ng/ml LPS (J774 cells on two separate occasions, and RAW 264.7 cells)
4) 50 µg/ml minocycline+100 ng/ml LPS (J774 cells on two separate occasions, and RAW 264.7 cells)
5) 50 µg/ml Compound A+100 ng/ml LPS (J774 cells only)
6) 50 µg/ml Compound B+100 ng/ml LPS (J774 cells only)

The tetracycline compounds were added 1.5 hours post seeding, thirty minutes before the addition of LPS. The plates were incubated at 37° C. at 5% $CO_2$ in a humidified incubator.

Sample Processing, Hybridization, and Scanning 24 hours after incubation under experimental conditions, media was removed from the wells, and total RNA was purified from each sample using QIAGEN RNeasy® Mini columns. The manipulations which were then performed on the total RNA samples were as outlined in The Affymetrix® GeneChip® Expression Analysis technical manual, sections 2, chapter 1, entitled *Eukaryotic Target Preparation*. Briefly, RNA was reverse transcribed into double stranded cDNA with an oligo dT primer containing a T7 promoter. The product was then purified by phenol:chloroform:isoamyl extraction and ethanol precipitation, and then used in an in vitro translation reaction to synthesize biotin-labelled antisense cRNA (Affymetrix controls of *B. subtilis* genes excised from pBluescript plasmid with Xho I digestion were added at this stage to control for correct translation and biotin incorporation). The cRNA was then cleaned using QIAGEN RNeasy® Mini columns, and the resulting cRNA solution fragmented using metal-induced hydrolysis.

Samples were prepared for hybridization with the Affymetrix murine genome chips U74AV2 according to the directions in the Affymetrix® GeneChip® Expression Analysis technical manual, sections 2, chapters 3 and 4, entitled *Eukaryotic Target Hybridization* and *Eukaryotic Arrays: Washing, Staining and Scanning*. Briefly, 15 ug Fragmented cRNA was mixed with Affymetrix hybridization controls, herring sperm DNA, BSA, and concentrated hybridization buffer, boiled for 5 minutes, centrifuged at 14000×g for 5 minutes to obtain a precipitated-free solution, and hybridized with the array for 16 hours. Following hybridization, the Affymetrix washing and staining procedure was used entitled *Washing and Staining Procedure 2: Antibody Amplification for Eukaryotic Targets*.

Data Analysis

I. Finding mRNAs Which are Up-Regulated or Down-Regulated by Minocycline

For both J774.2 and RAW264.7 cells, two lists were generated, one of mRNAs which were increased at lease 2-fold by minocycline, and one of mRNAs which were decreased at least 2-fold by minocycline. In the case of mRNAs which were increased, the mRNAs had to be statistically 'Present' in the samples which contained minocycline ('Present' as determined by the Affymetrix microarray suite software). In the case of mRNAs which were decreased, the mRNAs had to be statistically 'Present' in the samples which did not contain minocycline.

The three experimental conditions produced three lists of increased mRNAs, and three lists of decreased mRNAs. The mRNAs common to all three lists are tallied in Table 2, below.

II. Finding mRNAs Which are Up-Regulated or Down-Regulated by Minocycline in Samples Which are Stimulated With LPS For both J774.2 and RAW264.7 cells stimulated by LPS, two lists were generated, one of mRNAs which were increased at lease 2-fold by minocycline, and one of mRNAs which were decreased at least 2-fold by minocycline. In the case of mRNAs which were increased, the mRNAs had to be statistically 'Present' in the samples which contained minocycline ('Present' as determined by the Affymetrix microarray suite software). In the case of mRNAs which were decreased, the mRNAs had to be statistically 'Present' in the samples which did not contain minocycline.

The three experimental conditions produced three lists of increased mRNAs, and three lists of decreased mRNAs. The mRNAs common to all three lists are tallied in Table 2, below.

III. Finding mRNAs Which are Up-Regulated or Down Regulated by Compounds A and B in Samples Also Stimulated With LPS For J774.2 cells stimulated by LPS, two lists were generated, one of mRNAs which were increased at lease 2-fold by Compounds A and/or B, and one of mRNAs which were decreased at least 2-fold by Compounds A and/or B. In the case of mRNAs which were increased, the mRNAs had to be statistically 'Present' in the samples which contained Compounds A and/or B ('Present' as determined by the Affymetrix microarray suite software). In the case of mRNAs which were decreased, the mRNAs had to be statistically 'Present' in the samples which did not contain Compounds A and/or B. The structures of compounds A and B are shown beneath Table 3.

mRNAs were found which were up-regulated by both Compounds A and B, and mRNAs were found which were down-regulated by both compounds. Results are tallied in Table 3, below.

TABLE 3

| | Numbers of mRNAs with levels significantly altered by minocycline (in J774.2 and RAW264.7 cells) | Numbers of mRNAs with levels significantly altered by minocycline, in the presence of LPS (in J774.2 and RAW264.7 cells) | Numbers of mRNAs with levels significantly altered by both Compounds A and B, in the presence of LPS (in J774.2 only) |
| --- | --- | --- | --- |
| Increased | 21 | 28 | 133 |
| Decreased | 4 | 9 | 108 |

Compound A

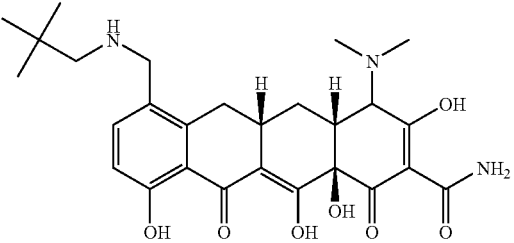

Compound B

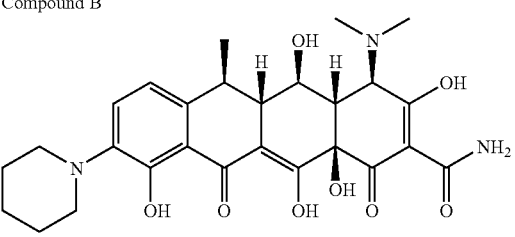

Example 4

Modulation of Inducible Nitric Oxide Synthase (iNOS) with Minocycline

Materials and Methods

Mouse macrophage J774.2 cells were seeded into 6 well plates as described above, and exposed to either minocycline alone, or in combination with LPS as above (untreated and LPS-alone conditions were used as controls). Data representing the modulation of iNOS mRNA was extracted from the Affymetrix data, described above.

Nitrite levels were measured in the supernatants of the samples using the Greiss reaction. Briefly, 100 µl singlicates of supernatant were incubated in the dark for 10 minutes with sulfanilamide solution (1% sulfanilamide in 5% $H_2PO_4$). Then 50 µl of NED (0.1% N-1-napthylethylenediamine dihydrochloride in water) was added, and the samples incubated for a further 10 minutes in the dark. Samples were read in a Wallac Victor V plate reader at 535 nm.

Protein levels were measured by Western analysis. Cells were lysed in 10 mM Tris HCl, pH 7.4, 1 mM EDTA, 0.5% SDS, protease inhibitors and DNAse. The antibody used to detect the iNOS protein was an anti iNOS antibody from Transduction laboratories. The results of the experiment are shown in FIG. 1.

Example 5

Mammalian Cytotoxicity Assay

COS-1 and CHO-K1 cell suspensions were prepared, seeded into 96-well tissue culture treated black-walled microtiter plates (density determined by cell line), and incubated overnight at 37° C., in 5% $CO_2$ and approximately 95% humidity. The following day, serial dilutions of drug were prepared under sterile conditions and transferred to cell plates. Cell/Drug plates were incubated under the above conditions for 24 hours. Following the incubation period, media/drug was aspirated and 50 µl of Resazurin (0.042 mg/ml in PBS w/Ca and Mg) was added. The plates were then incubated under the above conditions for 2 hours and then in the dark at room temperature for an additional 30 minutes. Fluorescence measurements were taken (excitation 535 nm, emission 590 nm). The $IC_{50}$ (concentration of drug causing 50% growth inhibition) was then calculated. The cytotoxicity of both unsubstituted minocycline and doxycycline were found to be greater than 25 µg/ml. Each of the compounds tested was found to have an acceptable cytotoxicity.

Example 6

In Vitro Anti-Bacterial Activity Assay

The following assay was used to determine the efficacy of the tetracycline compounds against gram positive (*S. aureus* RN450) and gram negative (*E. coli* ML308 225) bacteria. 2 mg of each compound was dissolved in 100 µl of DMSO. The solution was then added to cation-adjusted Mueller Hinton broth (CAMHB), which resulted in a final compound concentration of 200 µg per ml. The tetracycline compound solutions were diluted to 50 µL volumes, with a test compound concentration of 0.098 µg/ml. Optical density (OD) determinations were made from fresh log-phase broth cultures of the test strains. Dilutions were made to achieve a final cell density of 1×10⁶ CFU/ml. At OD=1, cell densities for different genera were approximately:

| | |
|---|---|
| *E. coli* | $1 \times 10^9$ CFU/ml |
| *S. aureus* | $5 \times 10^8$ CFU/ml |

50 μl of the cell suspensions were added to each well of microtiter plates. The final cell density was approximately 5×10⁵ CFU/ml. These plates were incubated at 35° C. in an ambient air incubator for approximately 18 hours. The plates were read with a microplate reader and were visually inspected when necessary. The MIC was defined as the lowest concentration of the tetracycline compound that inhibits growth.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

All patents, patent applications, and literature references cited herein are hereby expressly incorporated by reference.

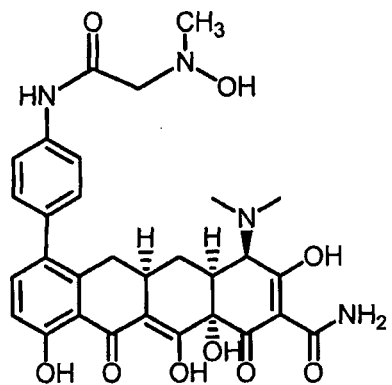

The invention claimed is:

1. A method for treating a subject for a disease treatable by modulation of RNA (DTMR) associated with splicing of nuclear RNA, comprising: administering to said subject an effective amount of a tetracycline compound of formula (I):

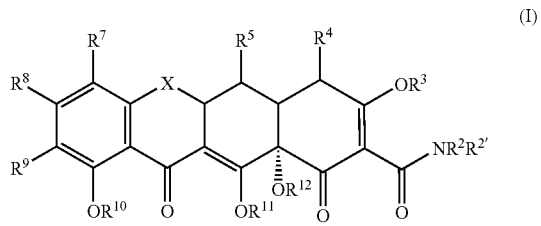

wherein
$R^2$, $R^{2'}$, $R^{4'}$, and $R^{4''}$ are each independently hydrogen or alkyl;
$R^3$, $R^{10}$, $R^{11}$ and $R^{12}$ are each hydrogen;
$R^4$ is $NeR^{4'}R^{4''}$;
$R^5$ is hydrogen;
$R^6$ and $R^{6'}$ are each hydrogen;
$R^7$ is substituted alkenyl, substituted alkynyl, substituted phenyl, substituted or unsubstituted furanyl, acyl, or aminoalkyl;
$R^8$ is hydrogen;
$R^9$ is hydrogen; and
X is $CR^{6'}R^6$;
or a pharmaceutically acceptable salt, ester or enantiomer thereof;
such that said DTMR associated with splicing of nuclear RNA is treated, wherein said DTMR associated with splicing of nuclear RNA is spinal muscular atrophy, and further wherein said effective amount is effective to modulate splicing of said subject's nuclear RNA.

2. The method of claim 1, wherein $R^2$ and $R^{2'}$ are each hydrogen and $R^{4'}$ and $R^{4''}$ are each methyl.

3. The method of claim 2, wherein $R^7$ is substituted or unsubstituted furanyl.

4. The method of claim 2, wherein $R^7$ is substituted phenyl.

5. The method of claim 4, wherein said substituted phenyl is substituted with one or more substituents and further wherein said substituents are each independently alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl or heterocyclic moiety.

6. The method of claim 2, wherein $R^7$ is substituted alkenyl.

7. The method of claim 2, wherein $R^7$ is substituted alkynyl.

8. The method of claim 2, wherein $R^7$ is acyl.

9. The method of claim 2, wherein $R^7$ is aminoalkyl.

10. The method of claim 1, wherein said tetracycline compound is:

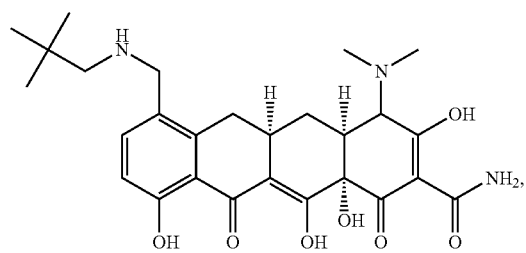

or a pharmaceutically acceptable salt thereof.

11. The method of claim 1, wherein said modulation of splicing increases splicing of RNA.

12. The method of claim 1, wherein said modulation of splicing decreases splicing of RNA.

13. The method of claim 1, wherein said subject is a mammal.

14. The method of claim 13, wherein said mammal is a human.

15. The method of claim 1, wherein said modulation of splicing is activation of cryptic splice sites, silencing of consensus splice sites, silencing of exonic or intronic splicing enhancers (ESEs or ISEs), silencing of exonic or inronic splicing silencers (ESSs or ISSs), alteration of the binding or a component of the splicing machinery to the RNA, or the affecting of intermolecular interactions between components of the splicing machinery.

16. The method of claim 1, wherein said tetracycline compound is:

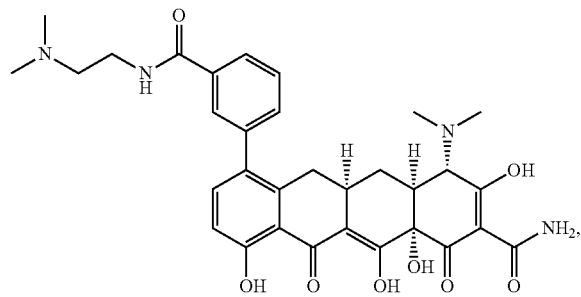

or a pharmaceutically acceptable salt thereof.

17. A method for treating a subject for a DTMR associated with splicing of nuclear RNA, comprising: administering to said subject an effective amount of a tetracycline compound; wherein said tetracycline compound is a tetracycline compound selected from the group consisting of:

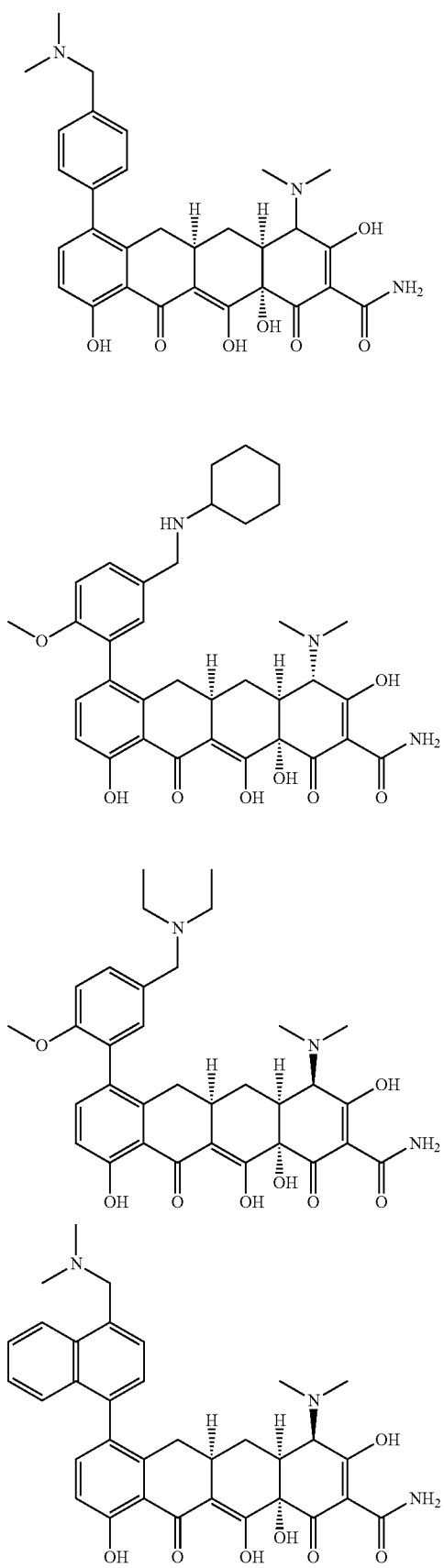

925
-continued
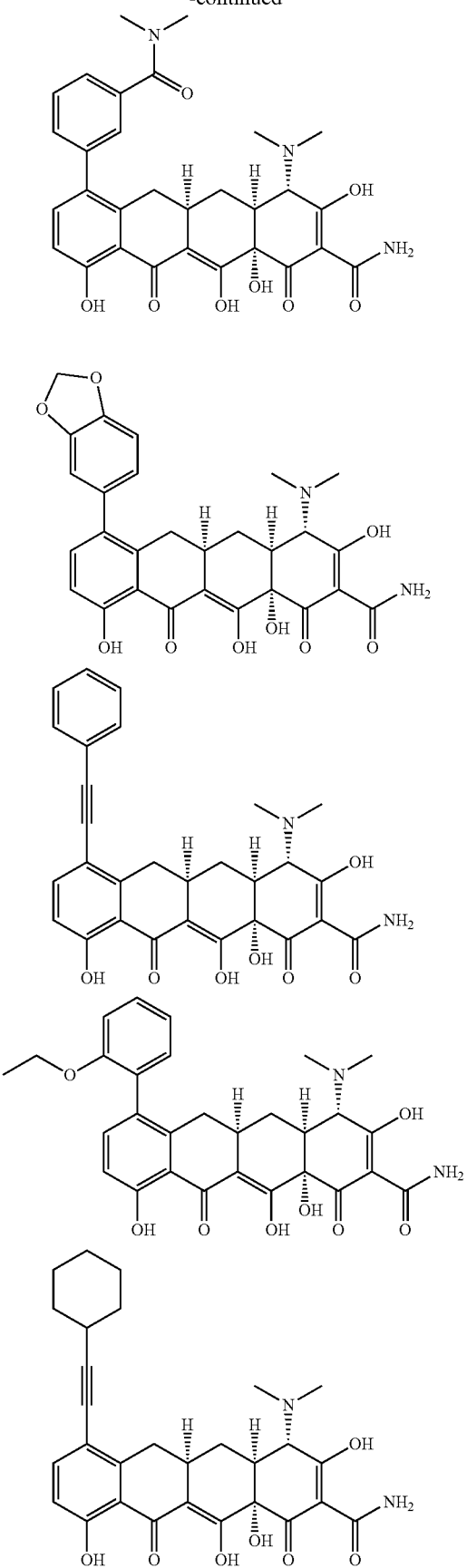
926
-continued
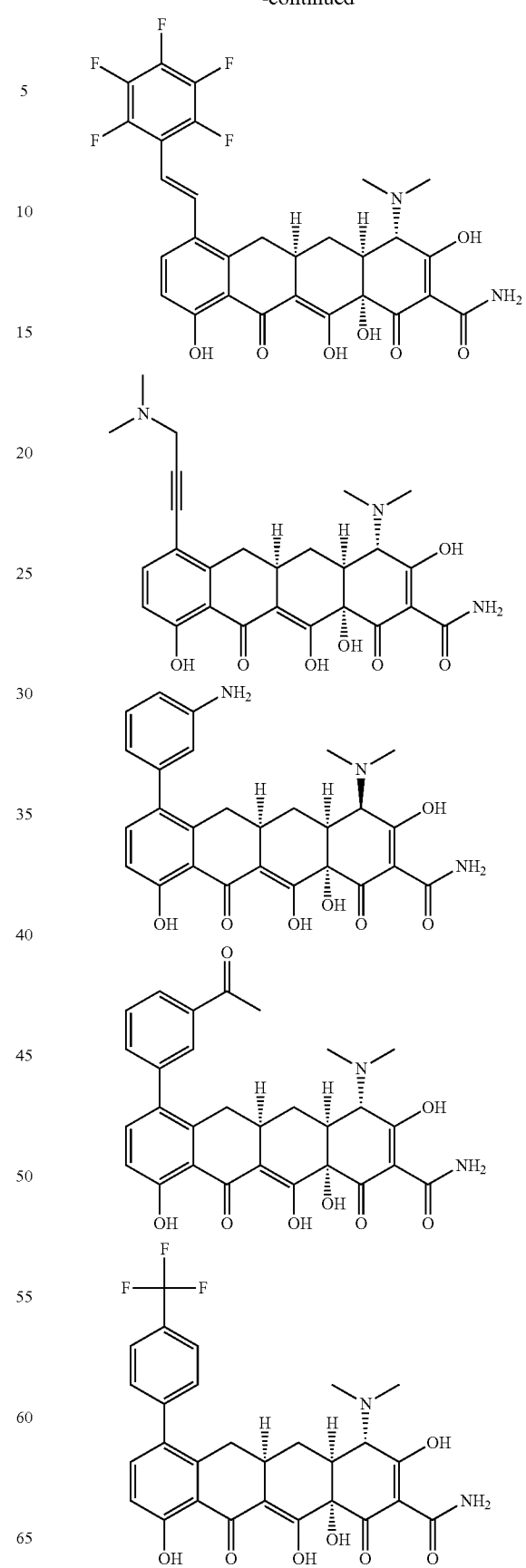

927
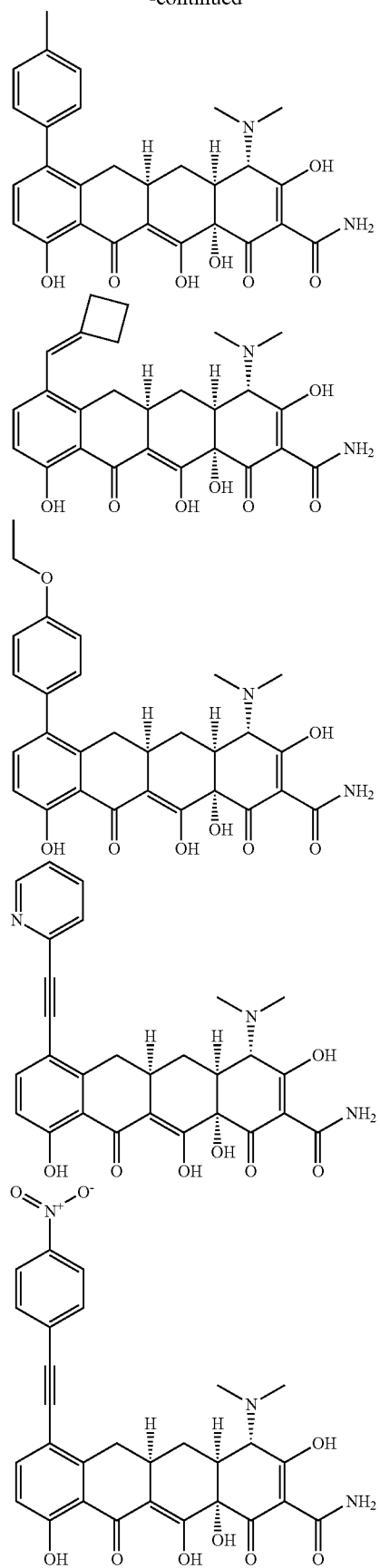
928
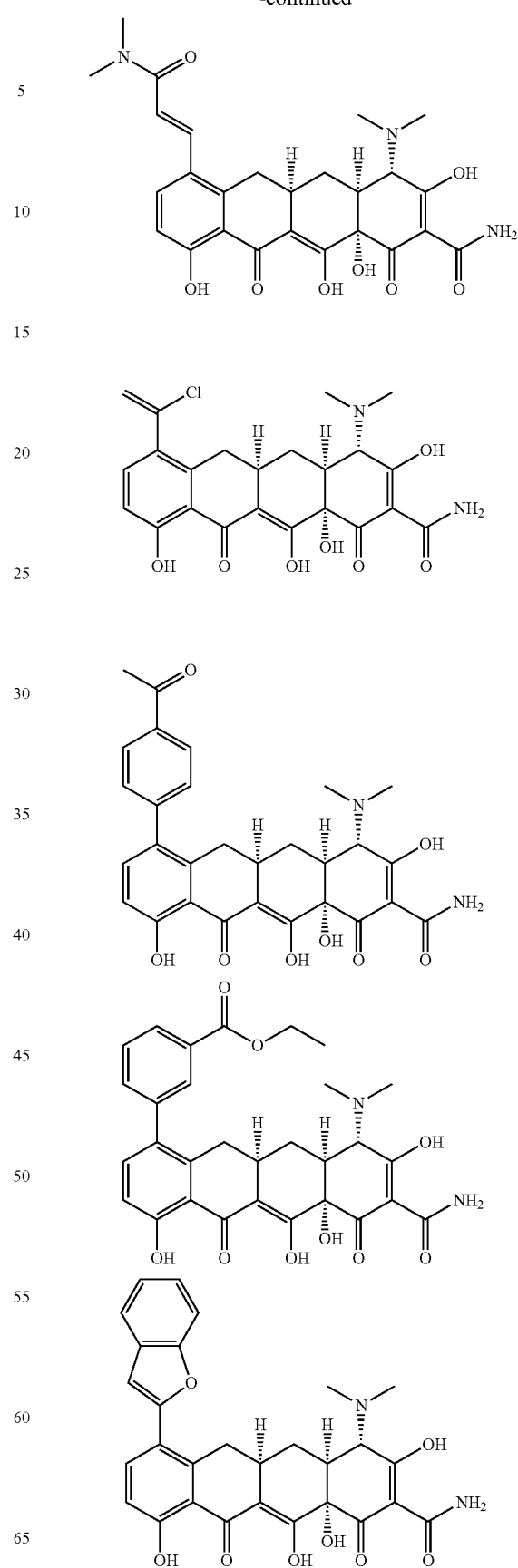

929
-continued
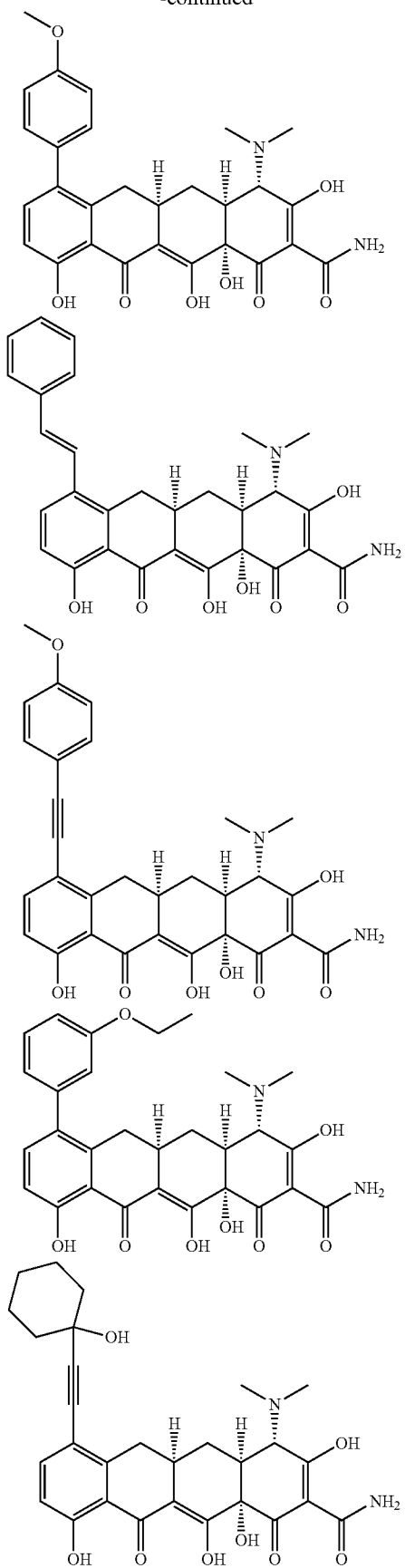
930
-continued
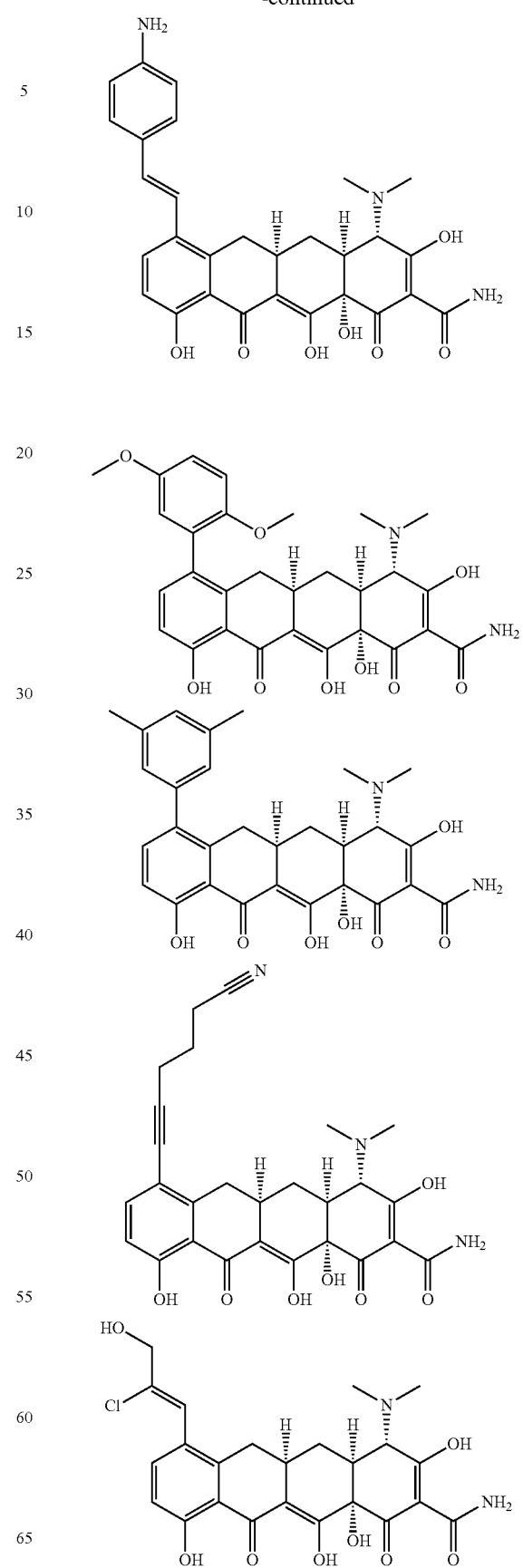

931
-continued
932
-continued
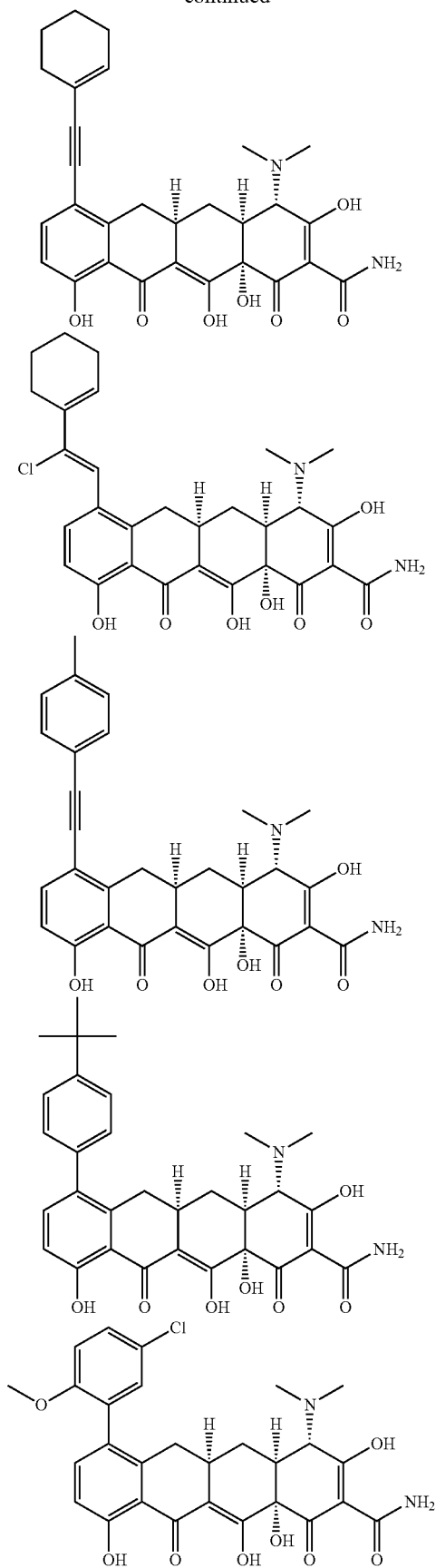
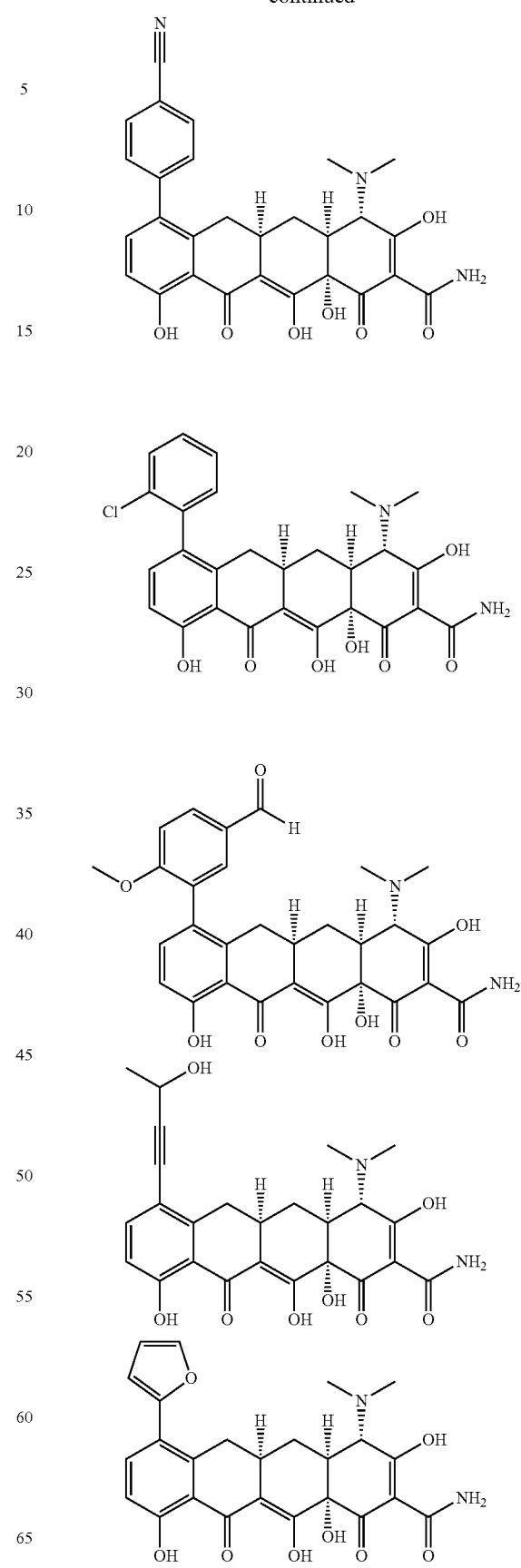

933
-continued
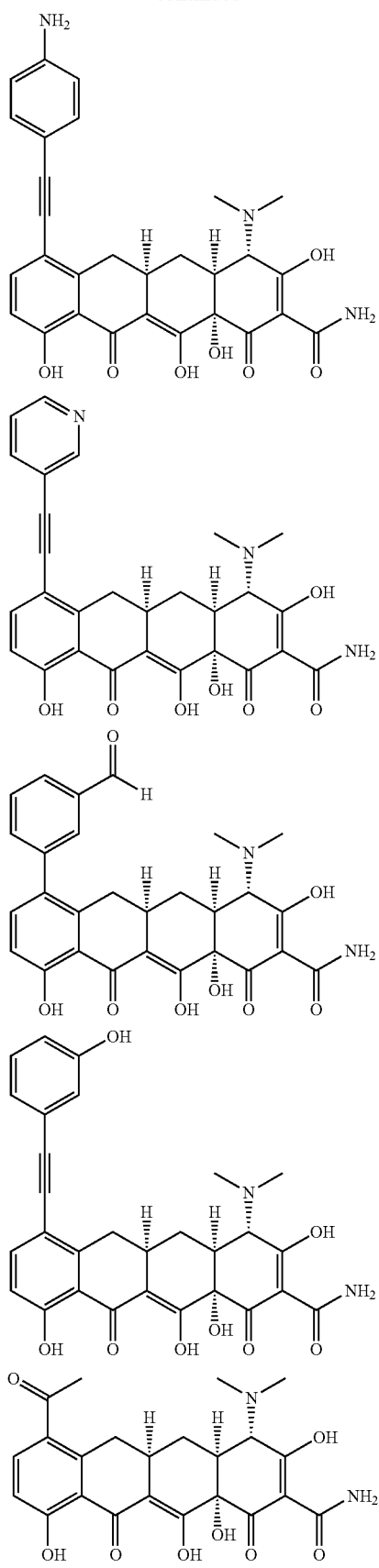
934
-continued
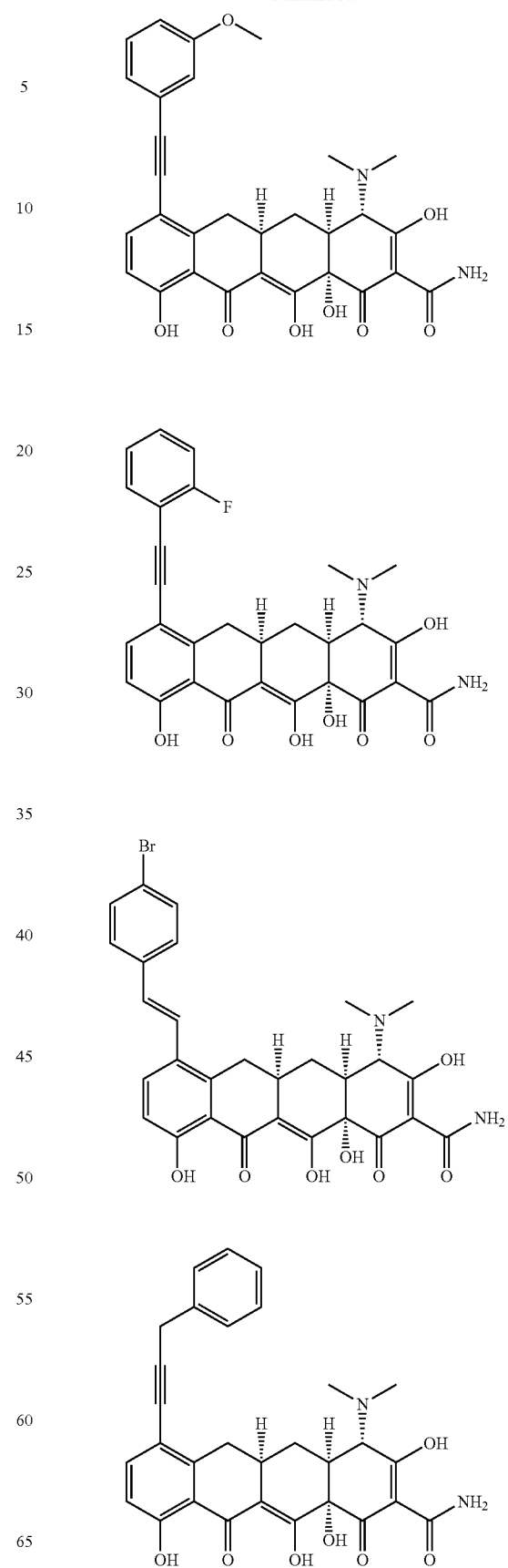

935
-continued
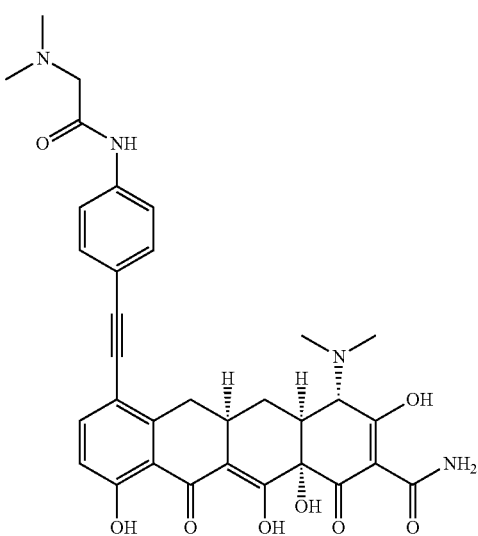
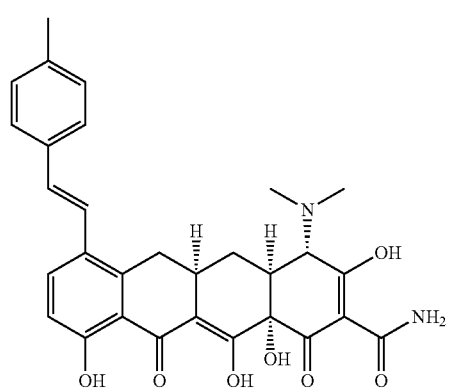
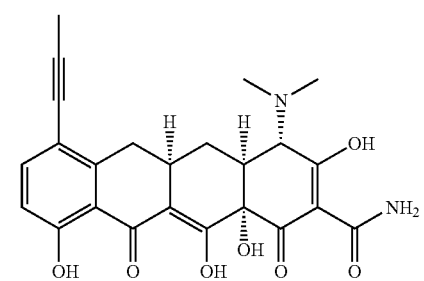
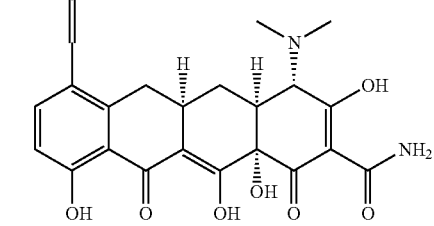
936
-continued
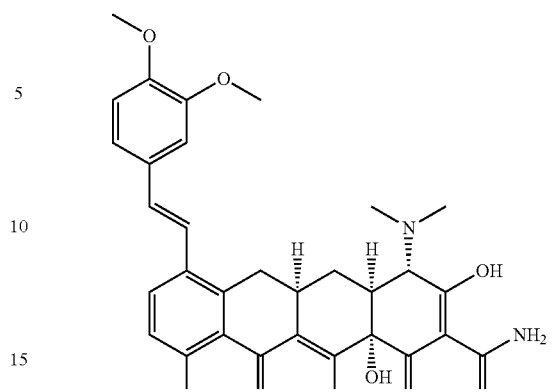
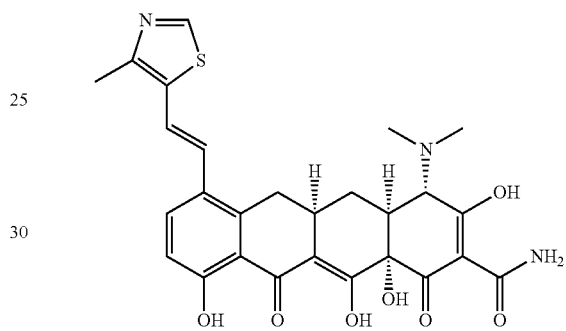
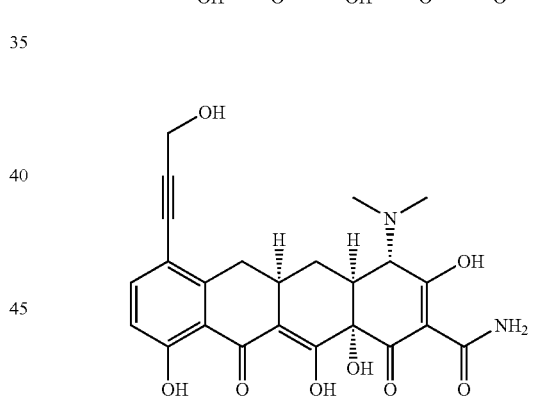
Chiral
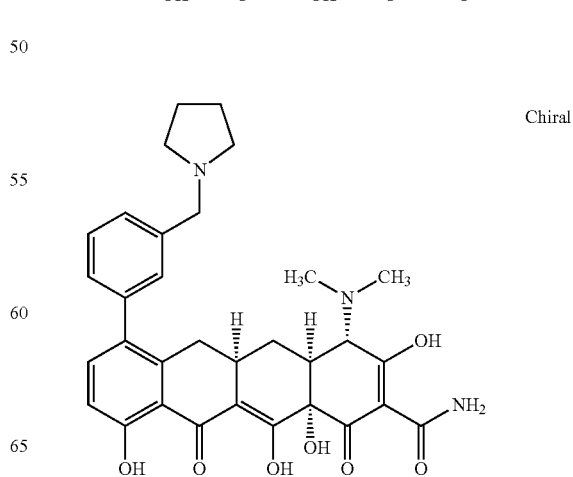

937
-continued
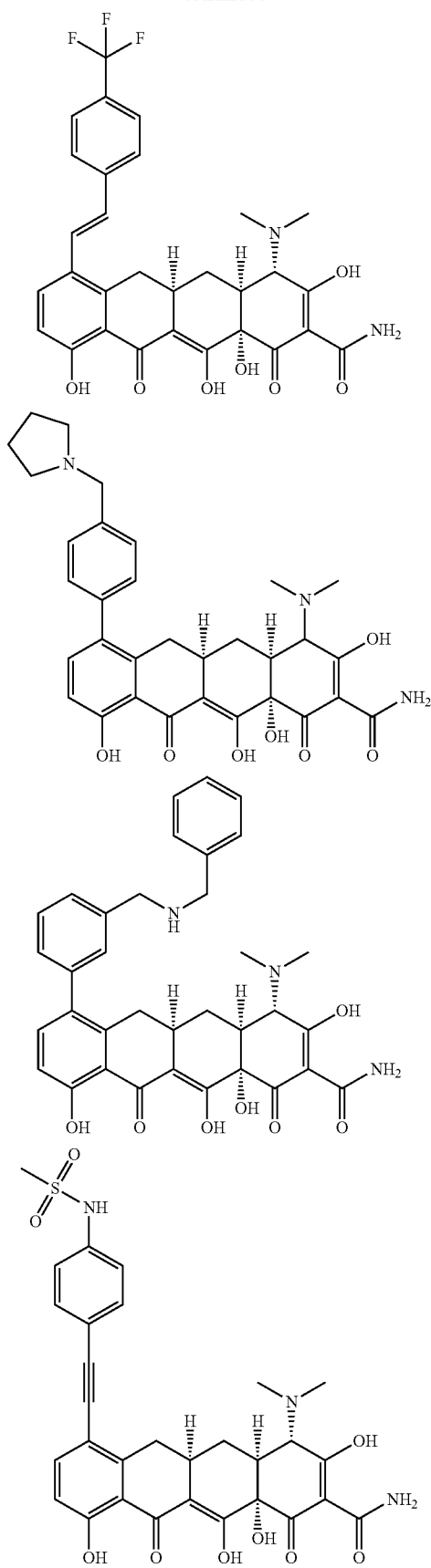
938
-continued
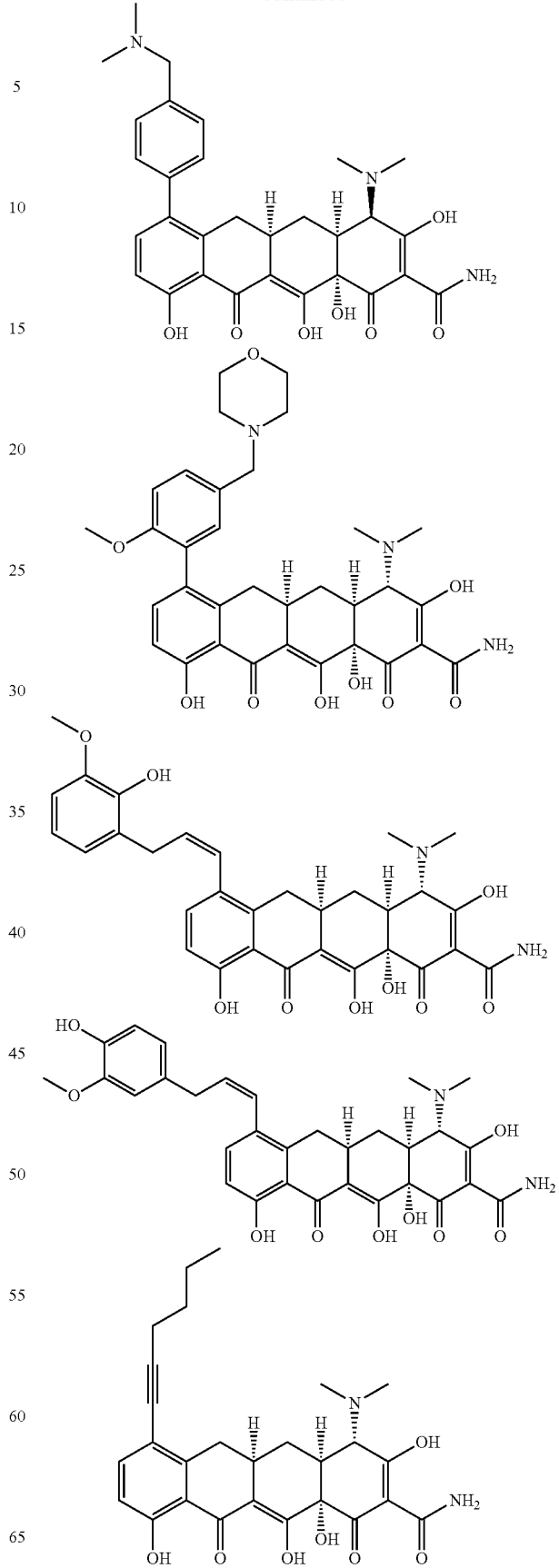

939
-continued
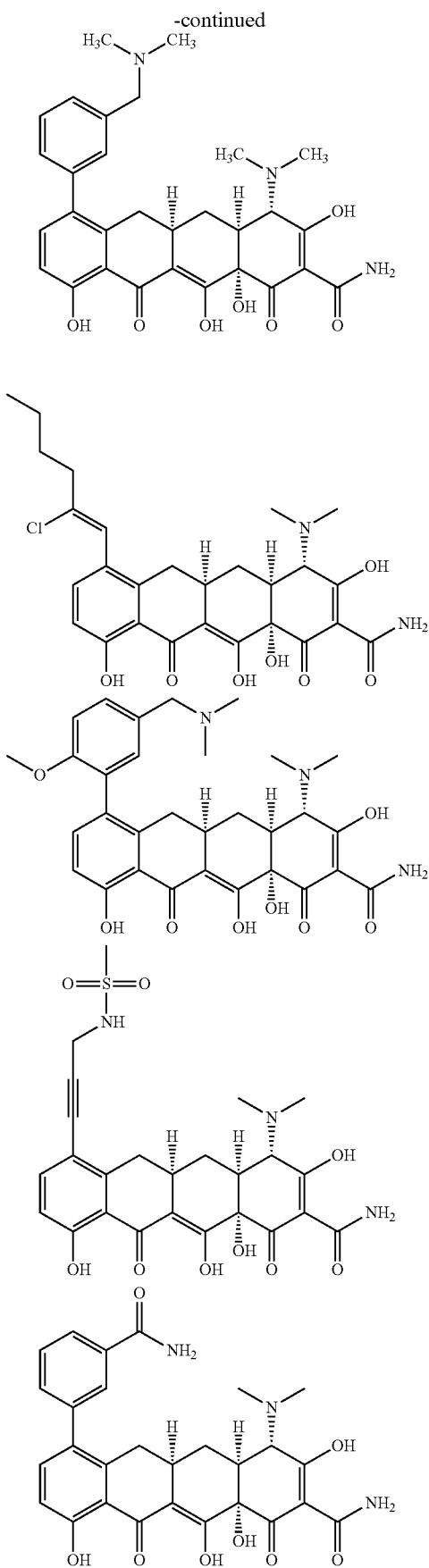
940
-continued
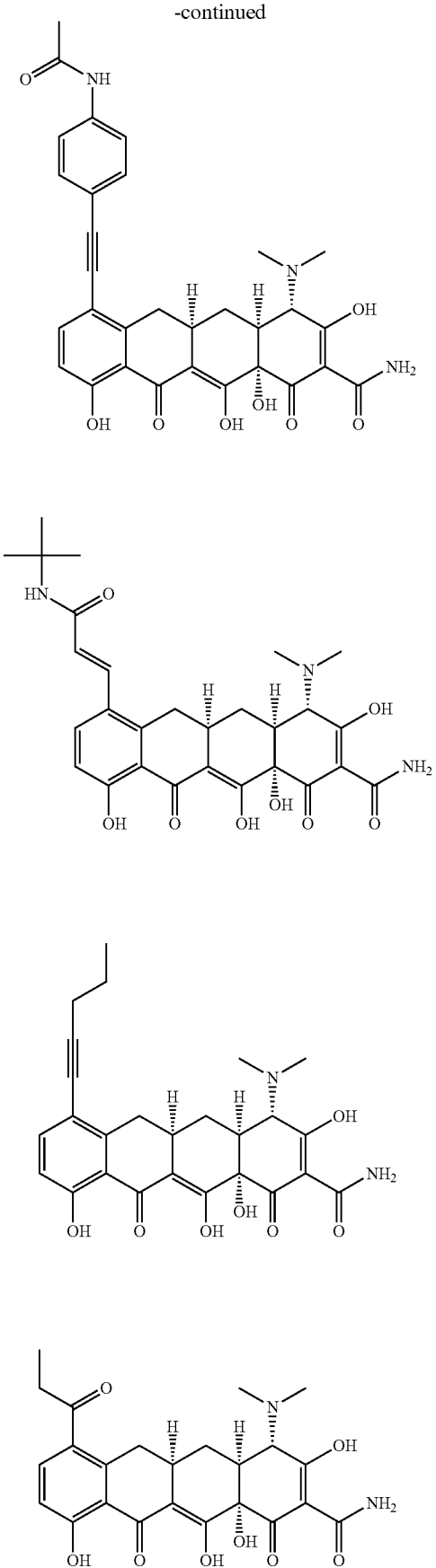

| 941 | 942 |
|---|---|
| -continued | -continued |
| 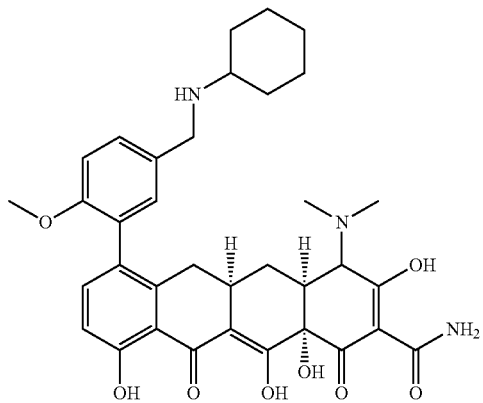 | 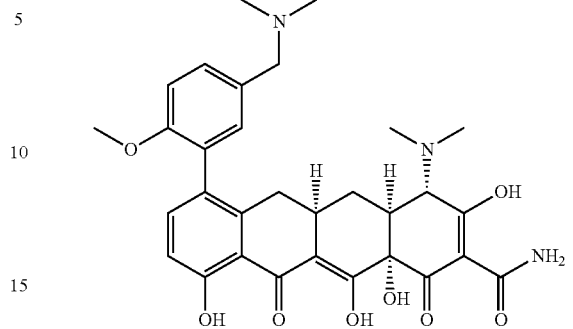 |
| 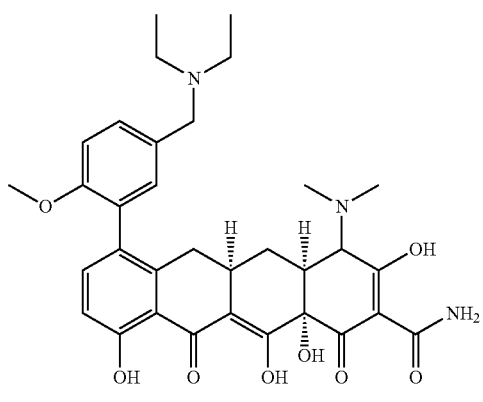 | 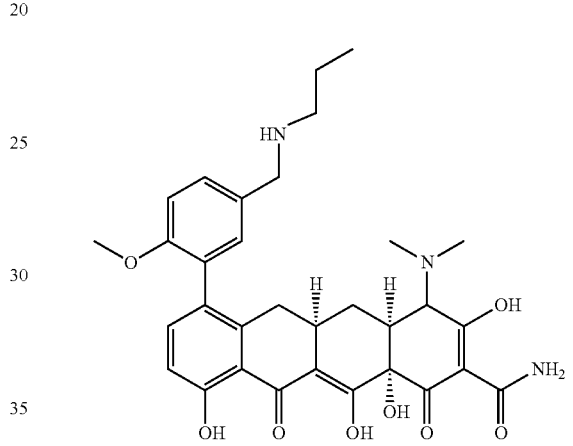 |
| 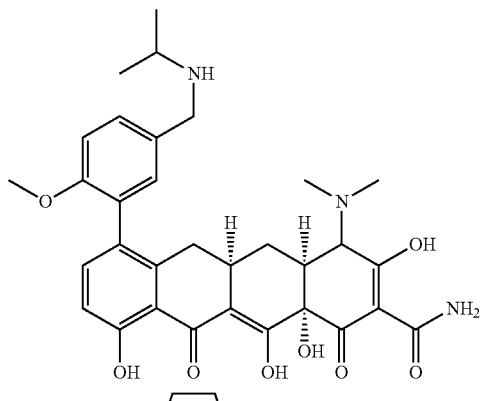 | 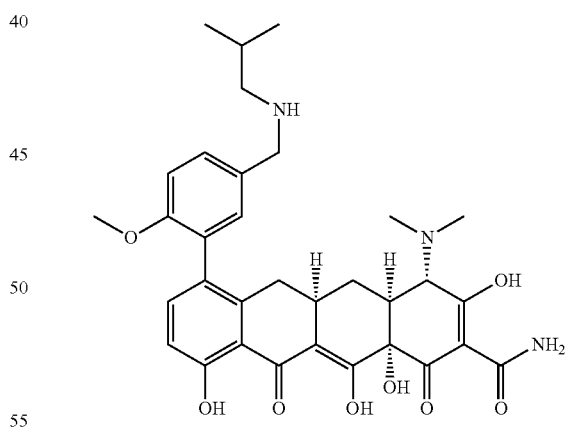 |
| 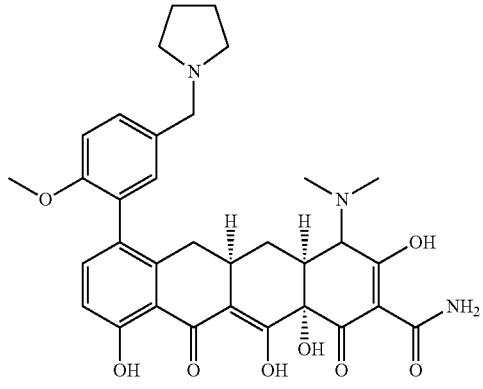 | 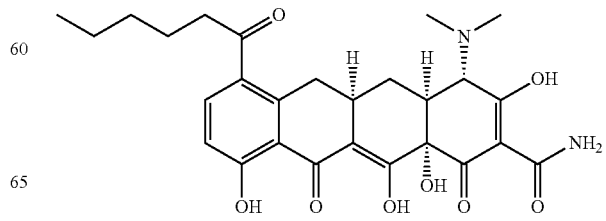 |

943
-continued
944
-continued
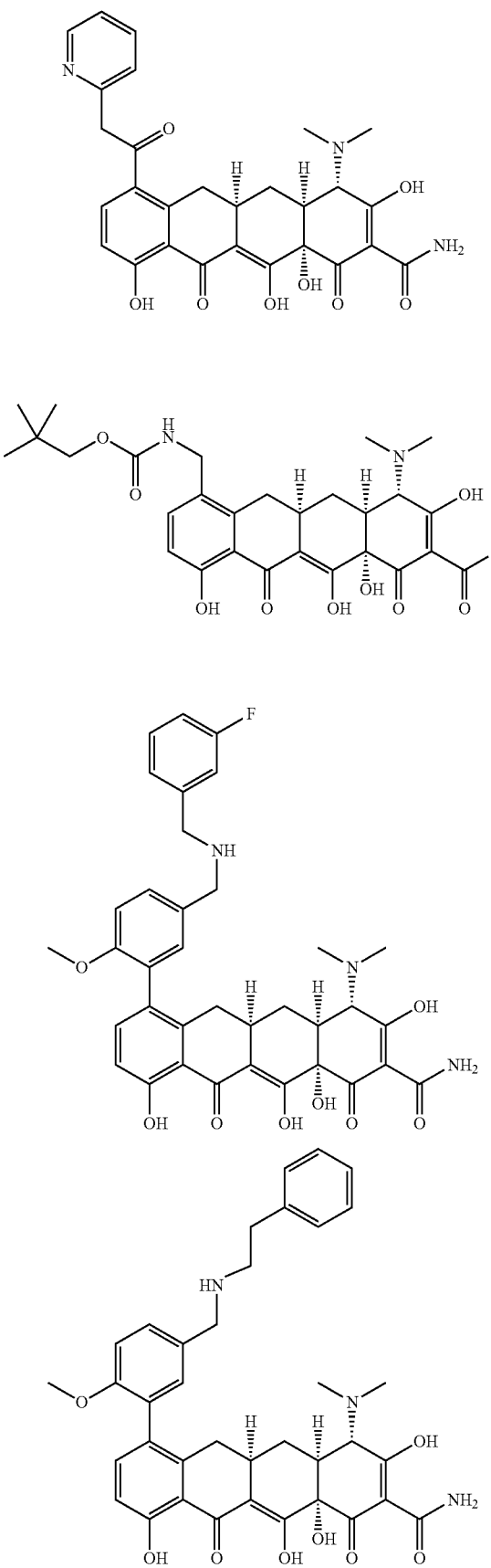
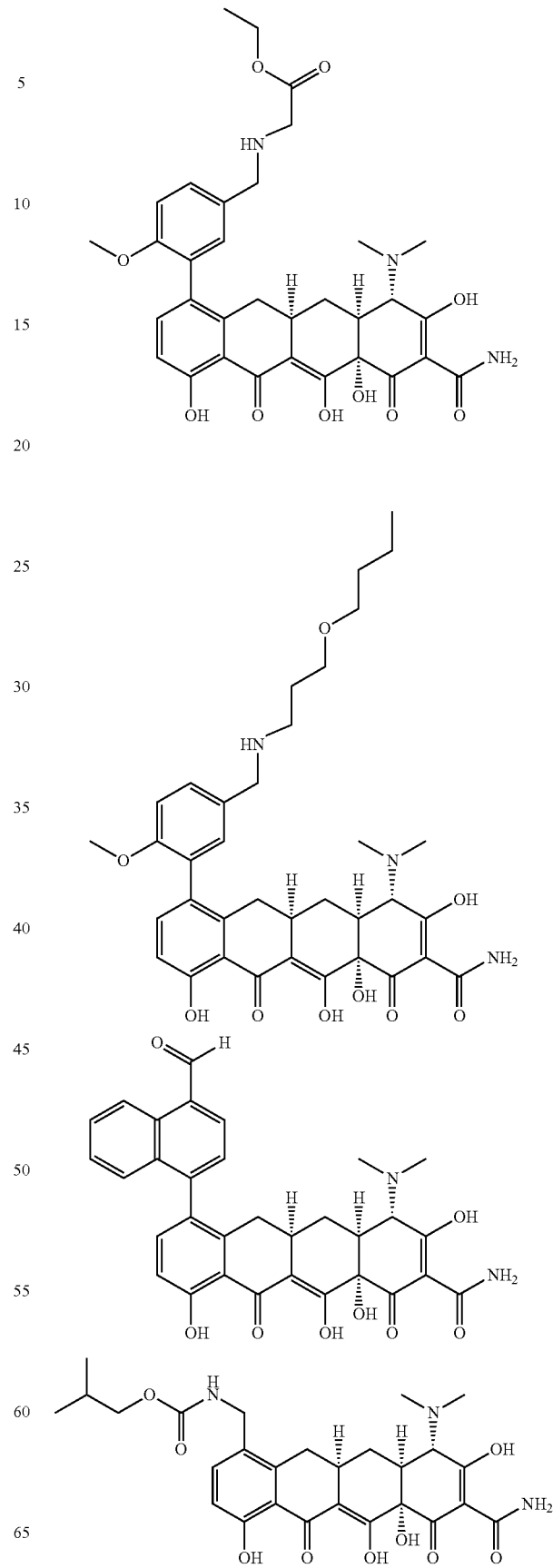

945
-continued
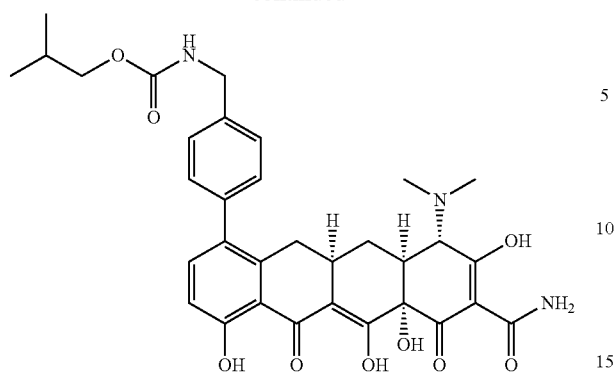
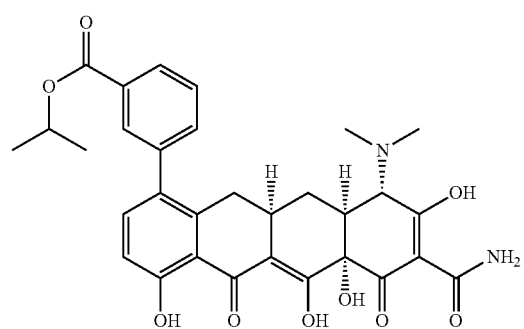
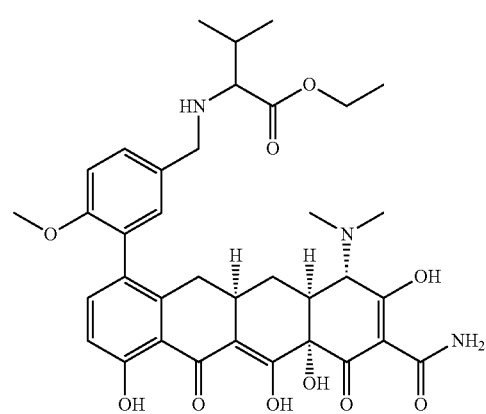
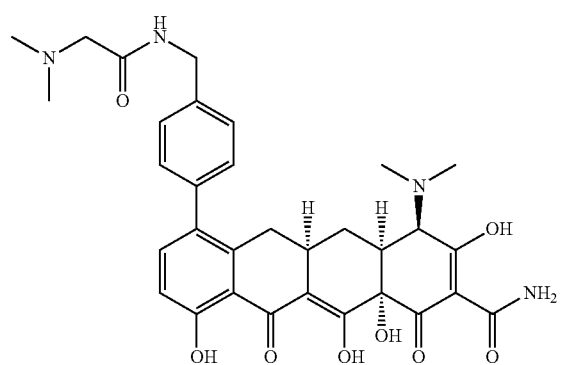
946
-continued
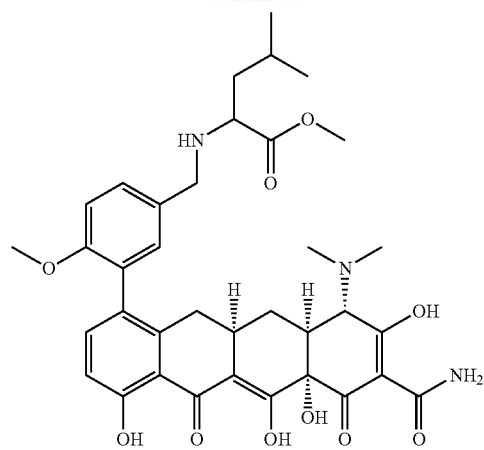
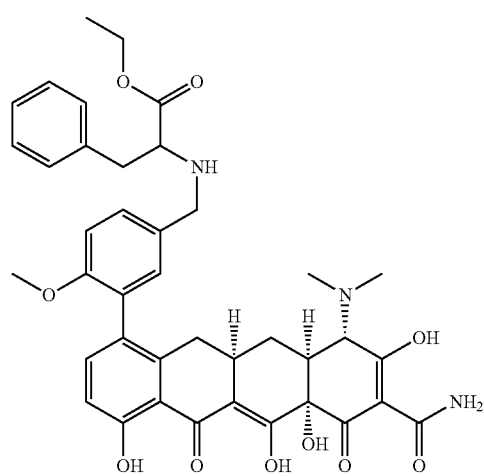
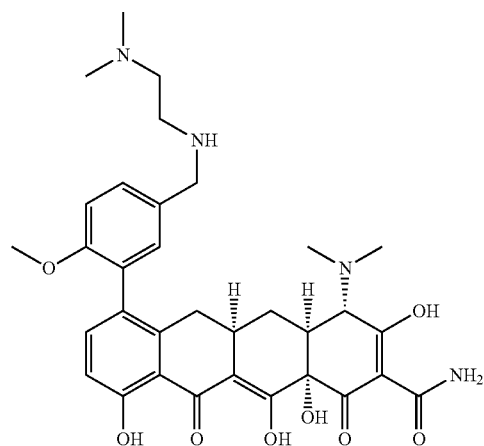

947
-continued
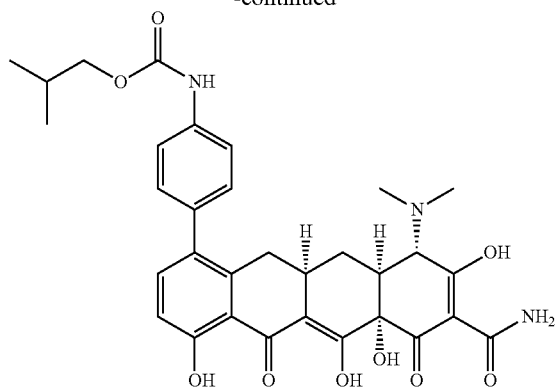
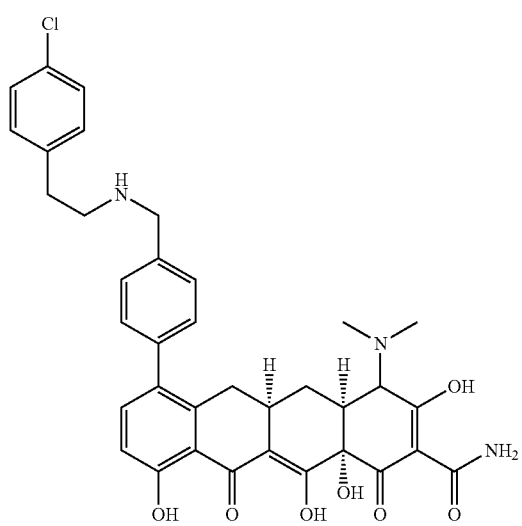
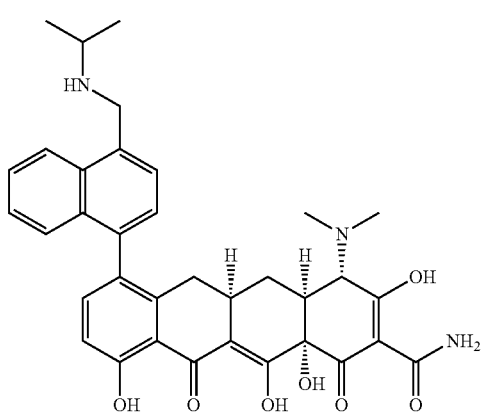
948
-continued
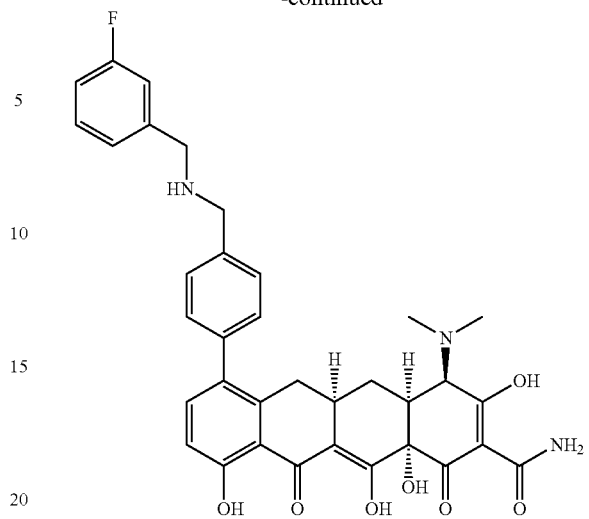
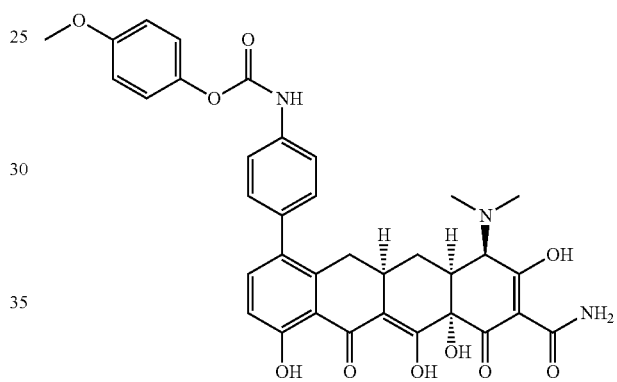
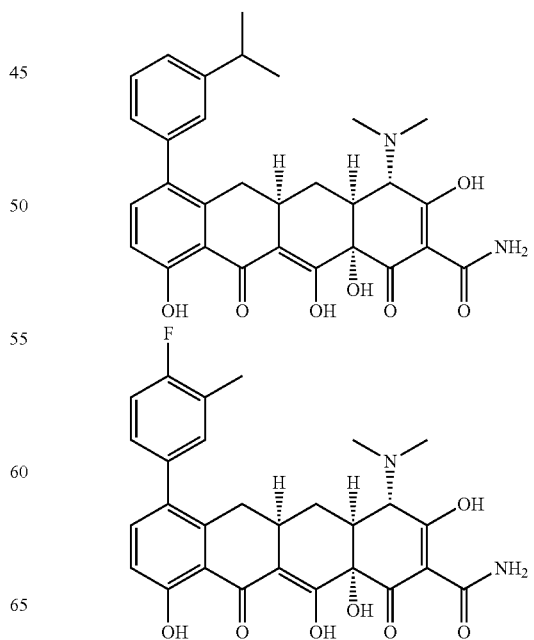

949
-continued
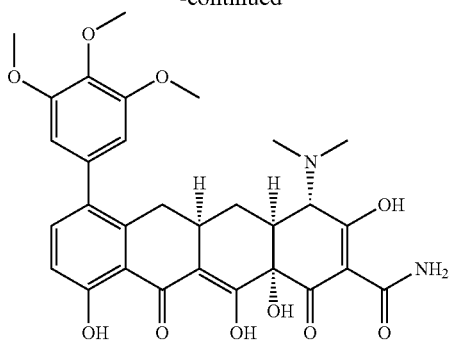
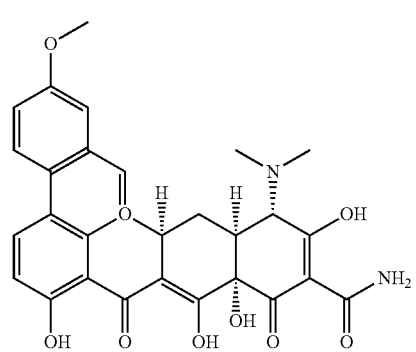
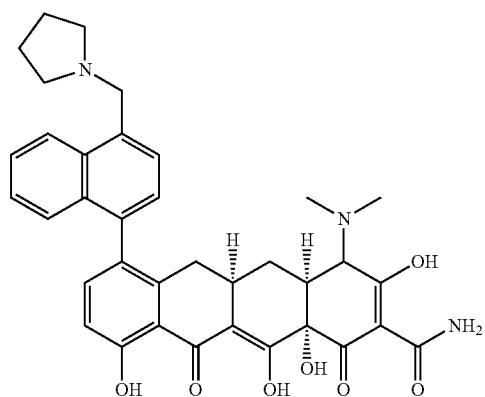
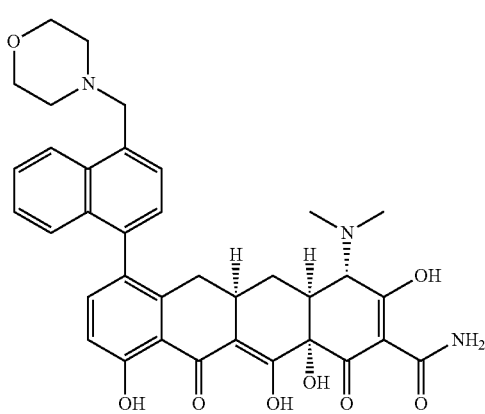
950
-continued
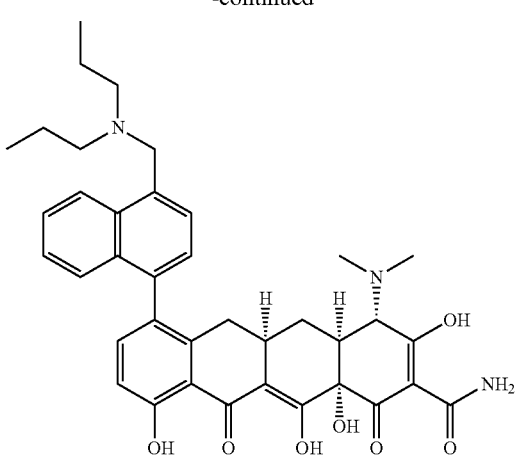
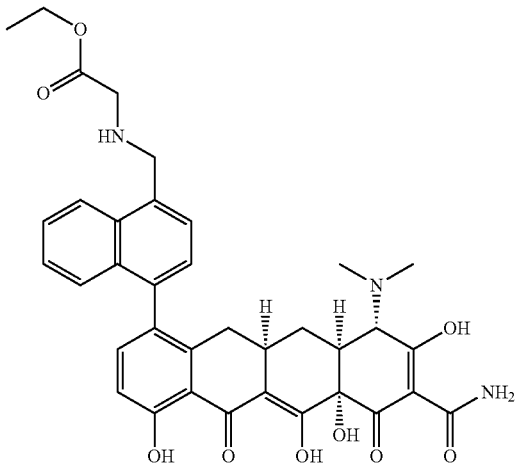
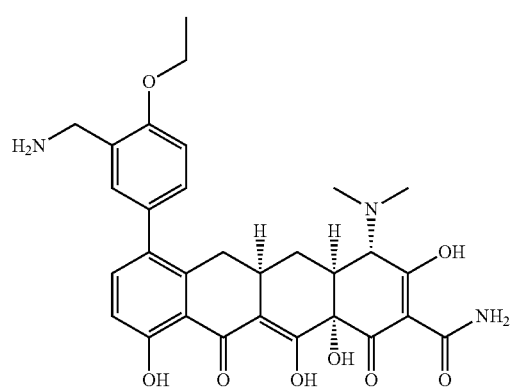

951
-continued
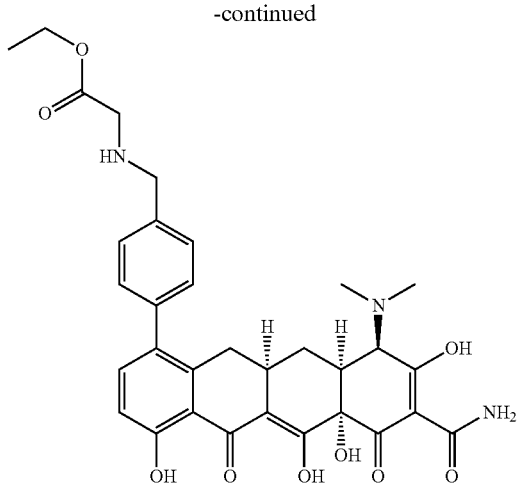
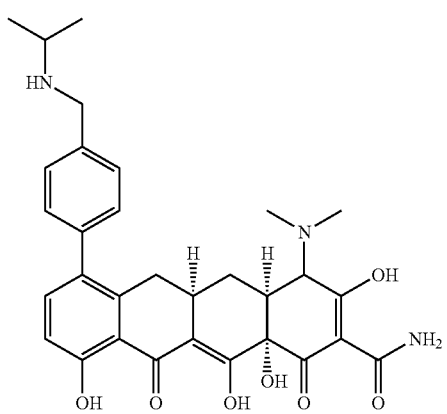
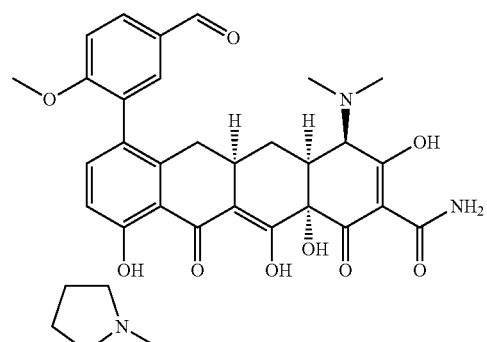
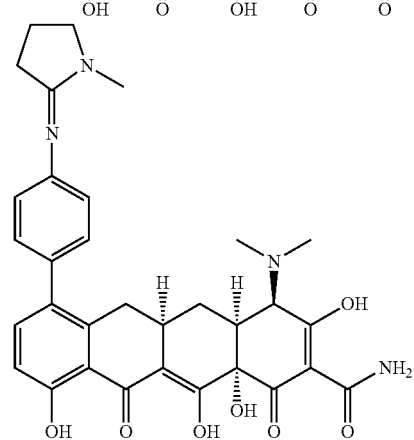
952
-continued
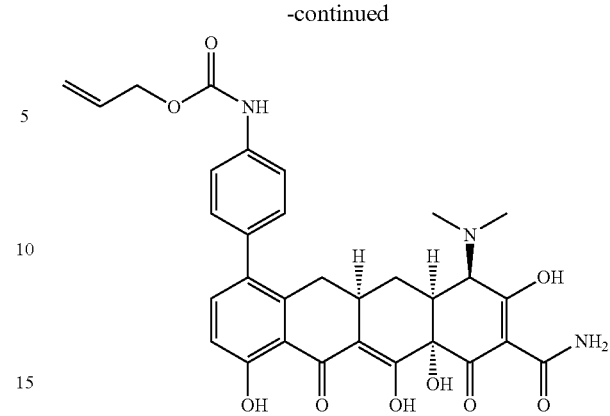
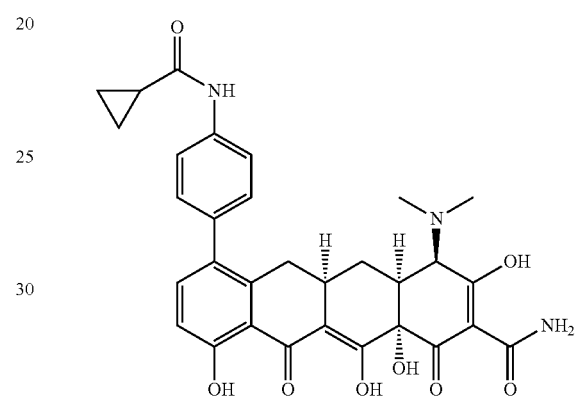
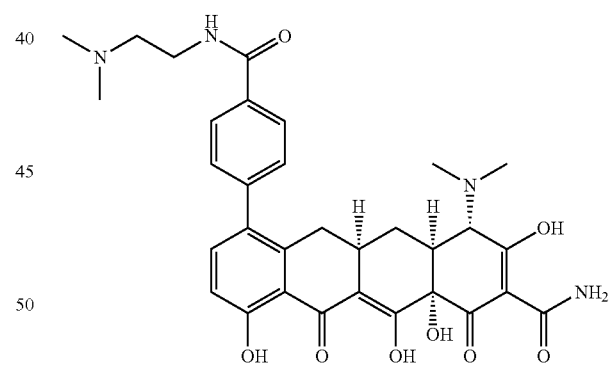
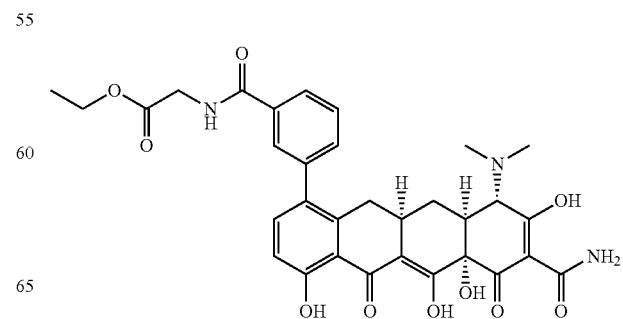

953
-continued
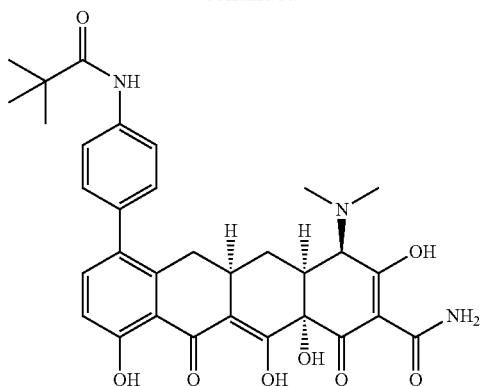
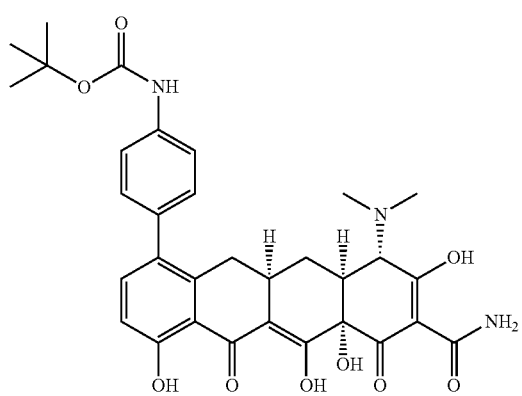
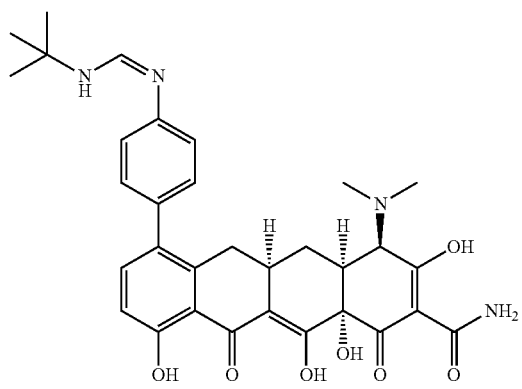
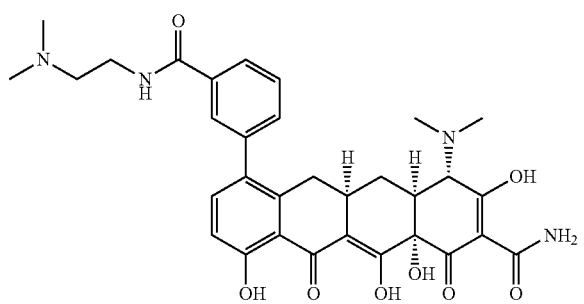
954
-continued
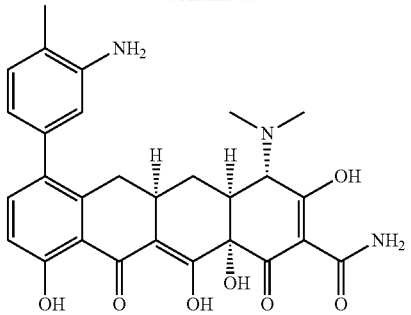
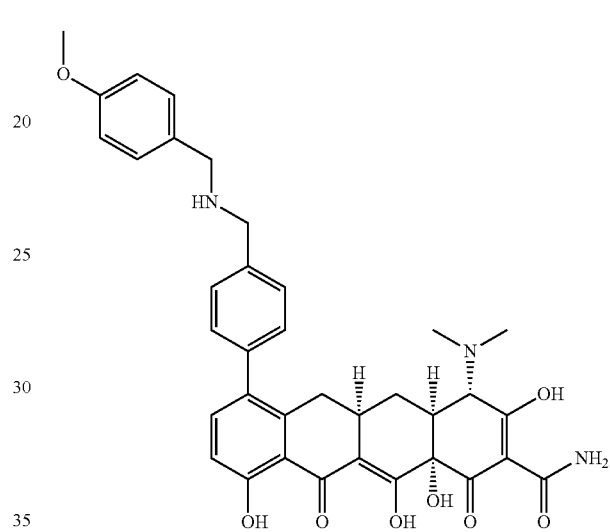
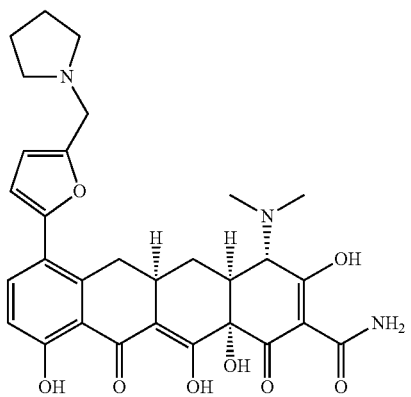
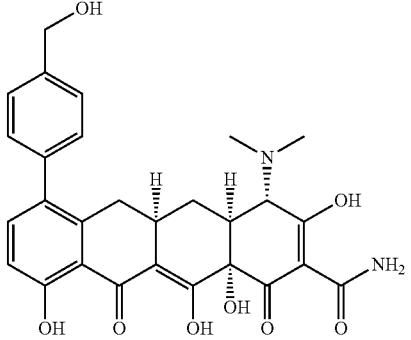

955
-continued
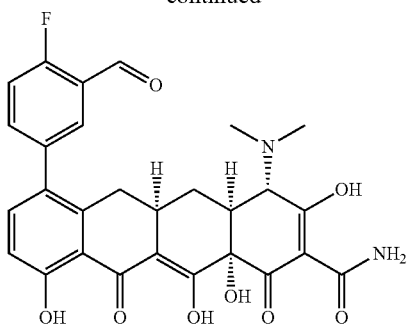
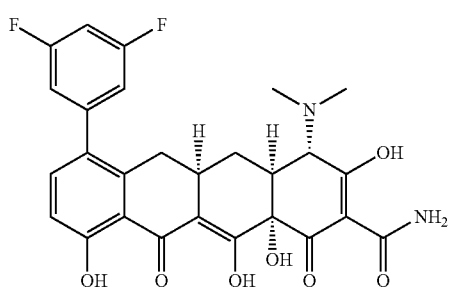
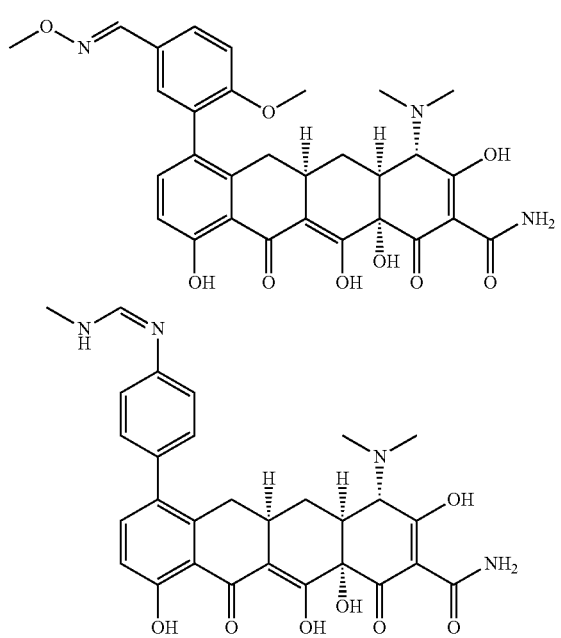
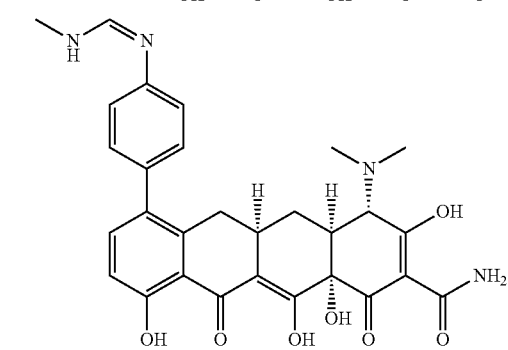
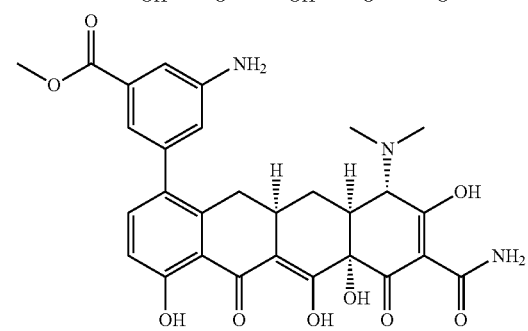
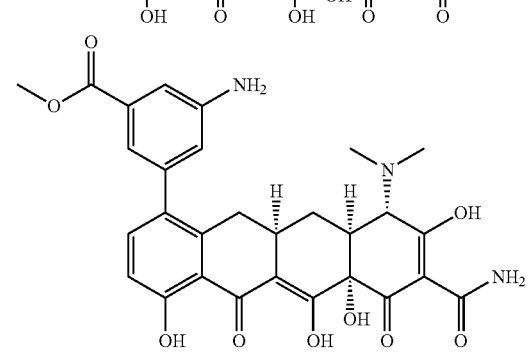
956
-continued
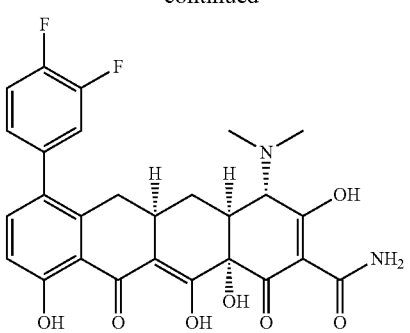
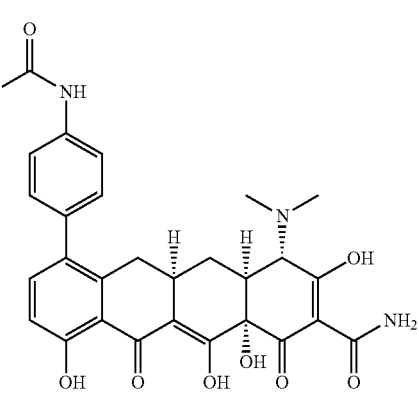
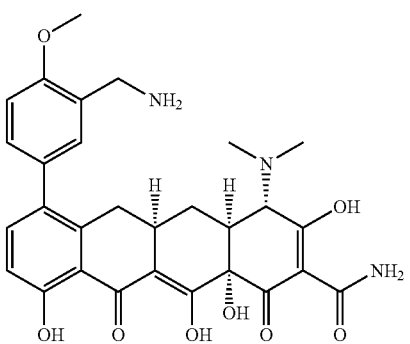
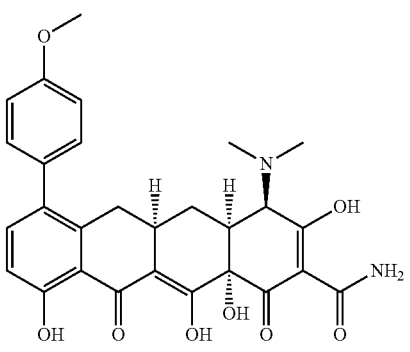

957 -continued
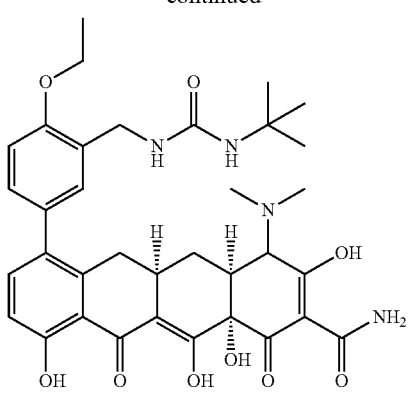
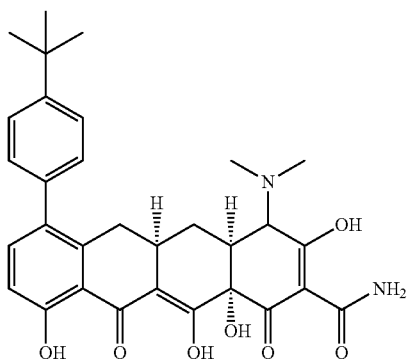
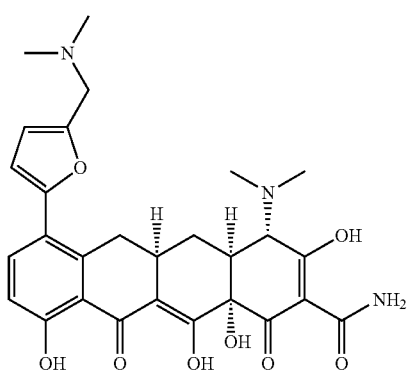
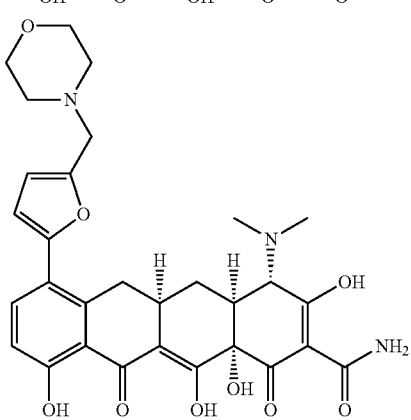
958 -continued
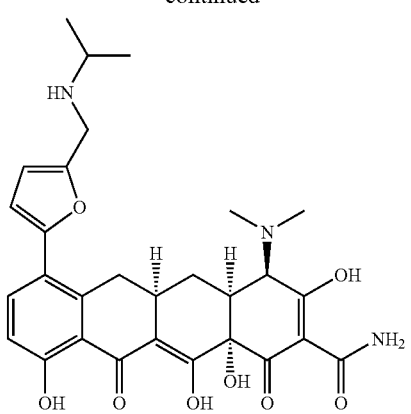
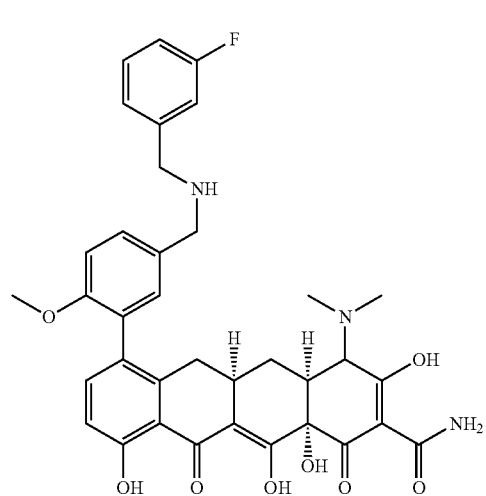
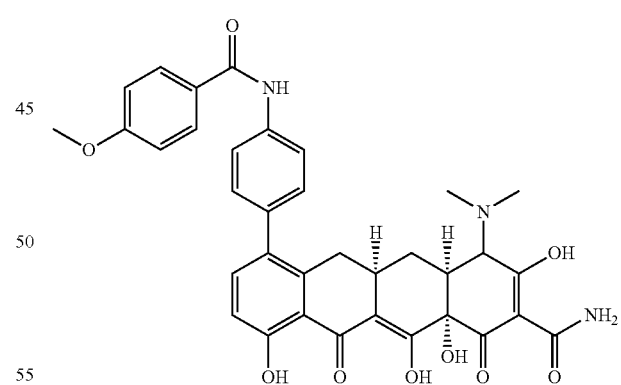
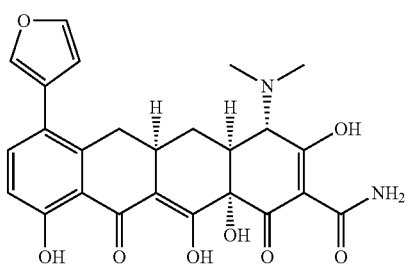

| 959 -continued | 960 -continued |
|---|---|
| 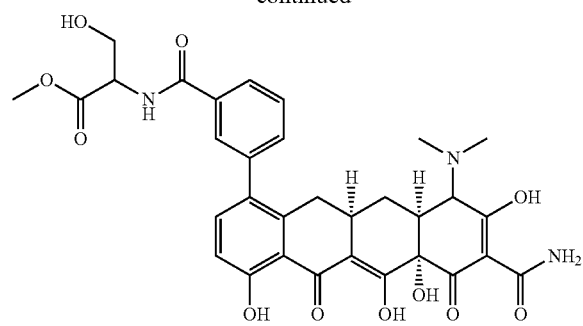 | 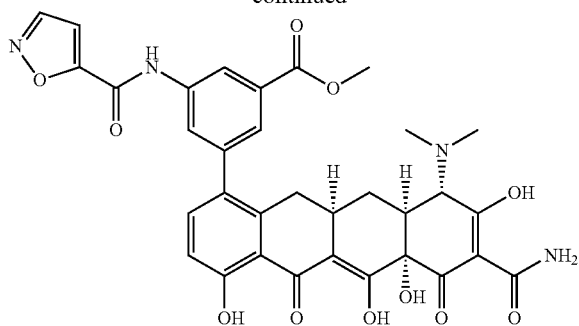 |
| 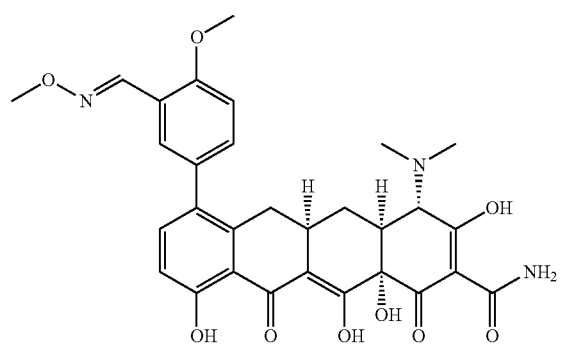 | 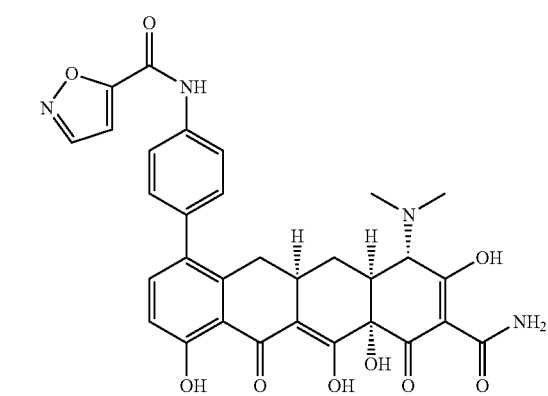 |
| 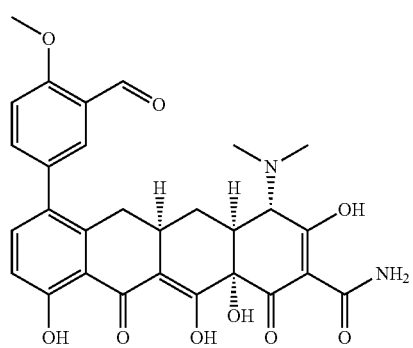 | 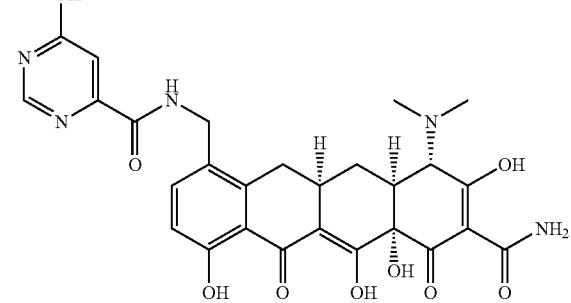 |
| 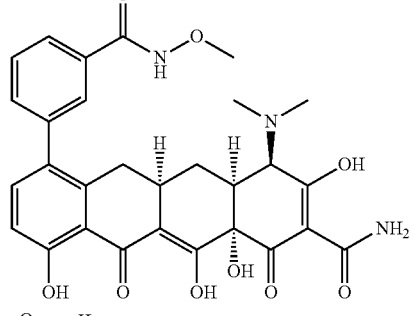 | 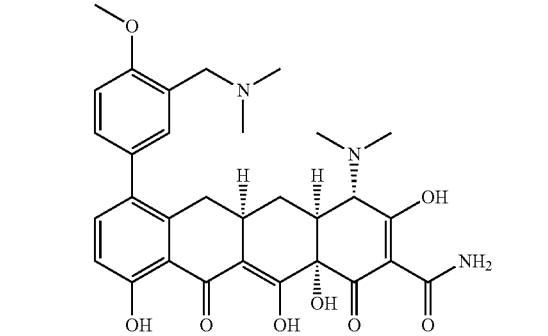 |
| 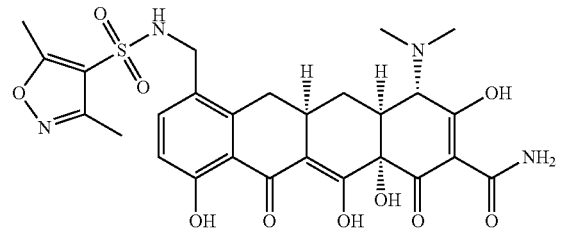 | 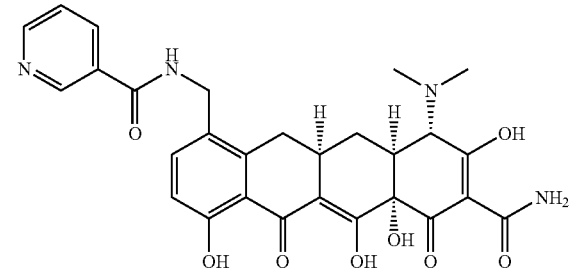 |

961
-continued
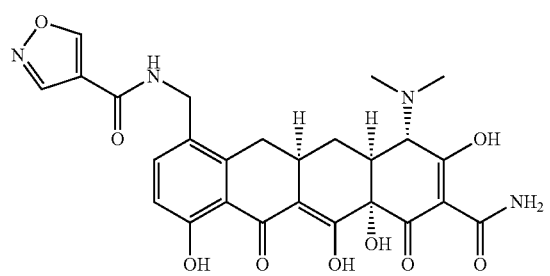
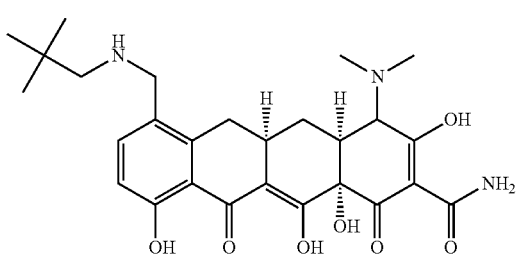
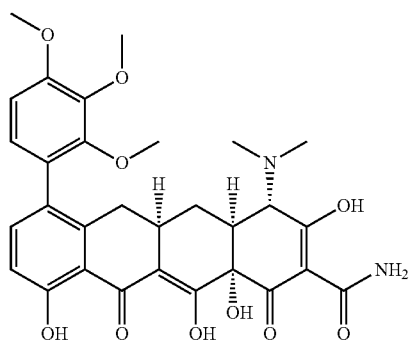
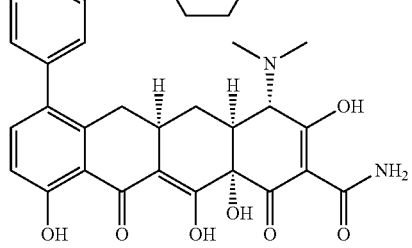
962
-continued
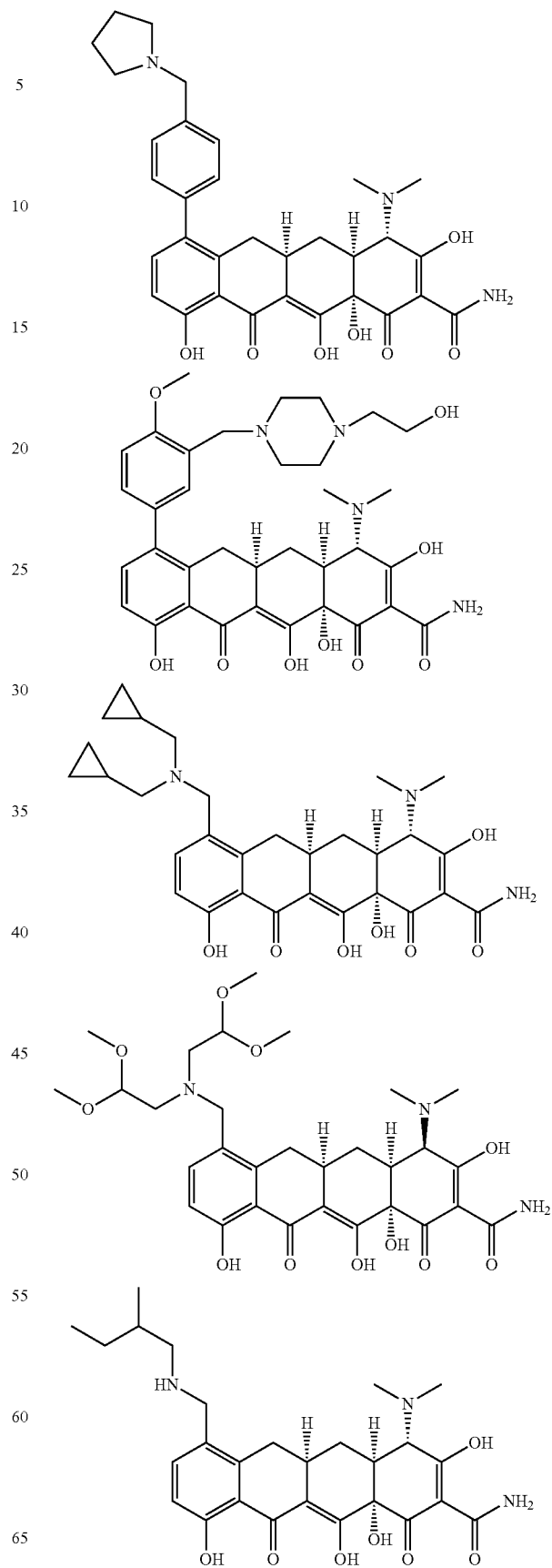

963
-continued
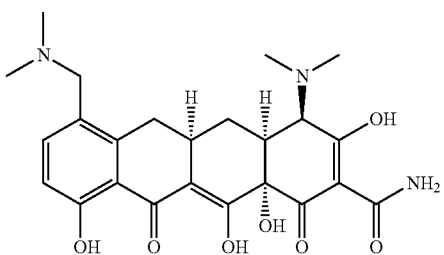
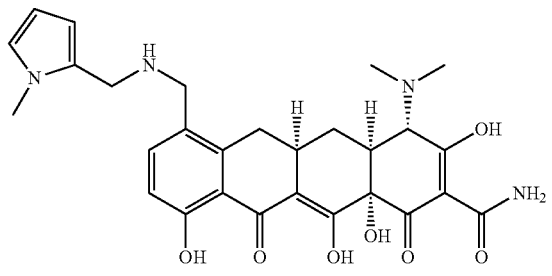
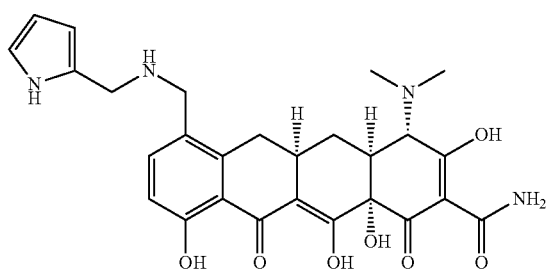
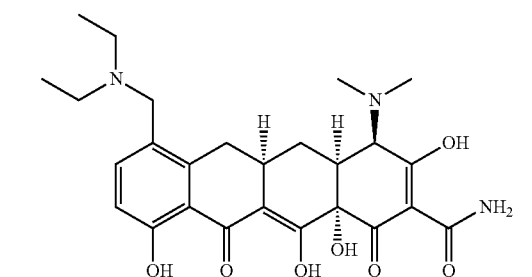
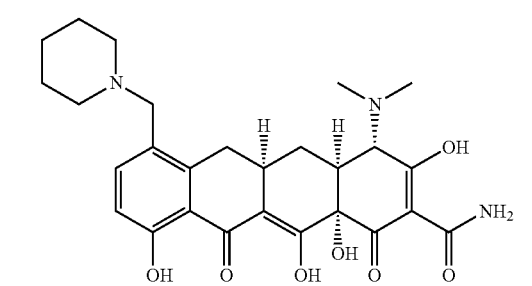
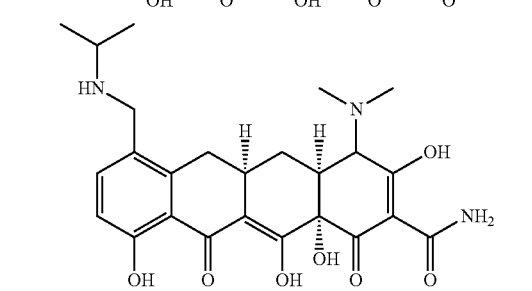
964
-continued
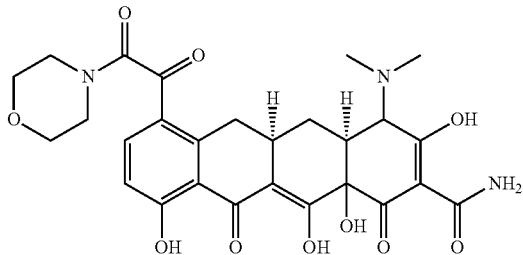
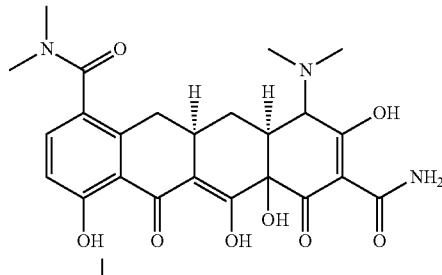
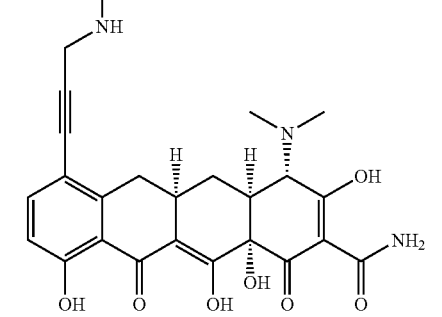
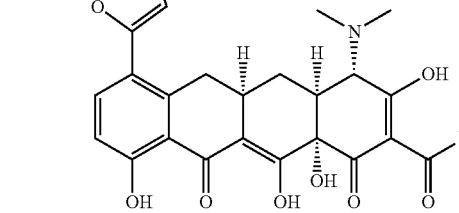
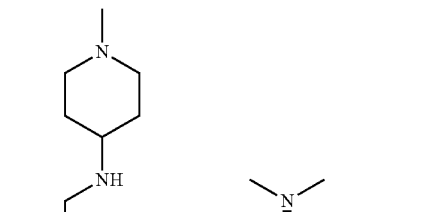
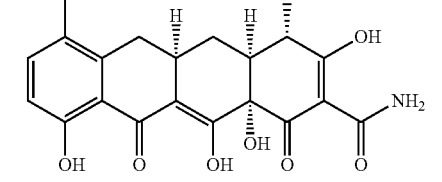

965
-continued
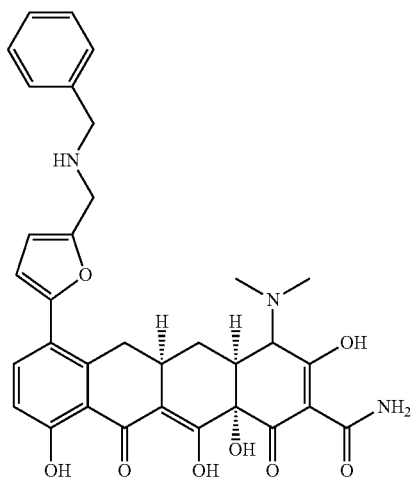
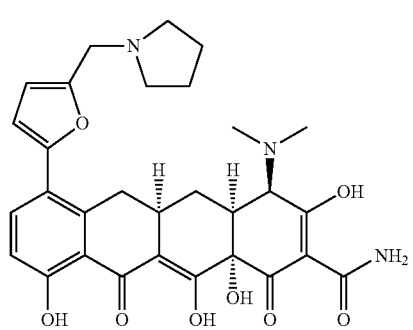
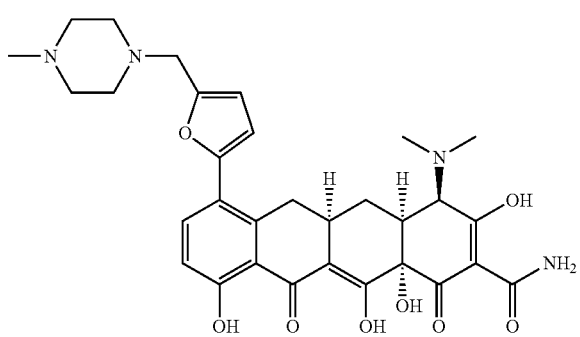
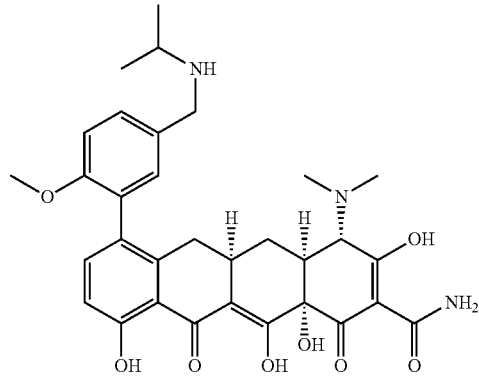
966
-continued
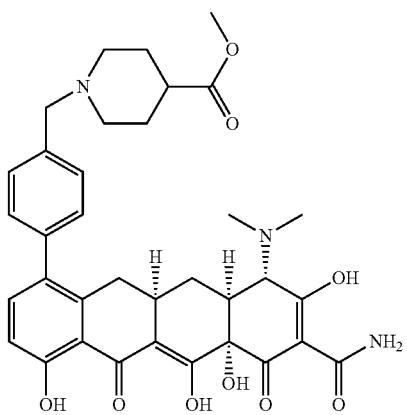
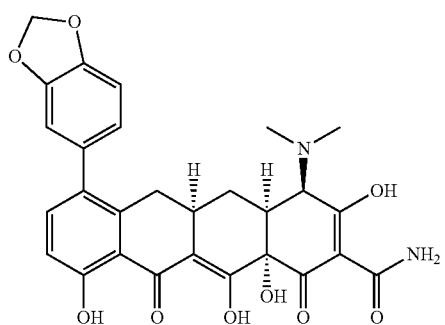
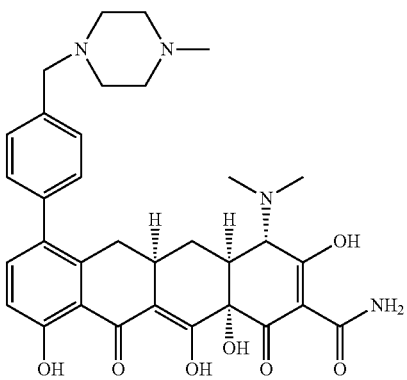
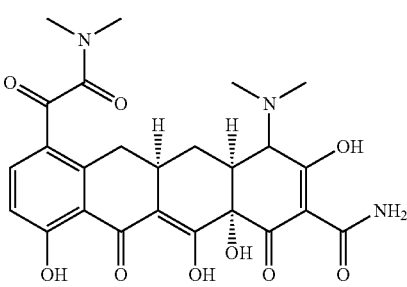

967
-continued
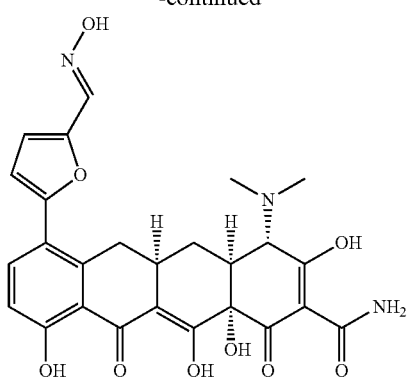
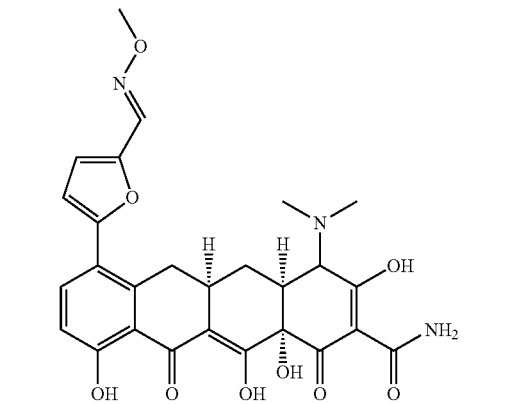
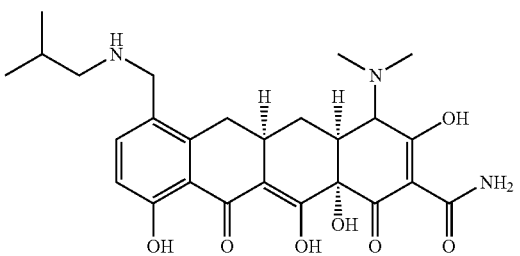
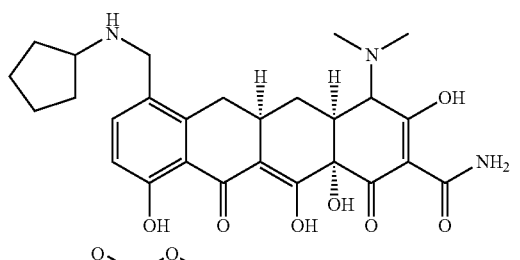
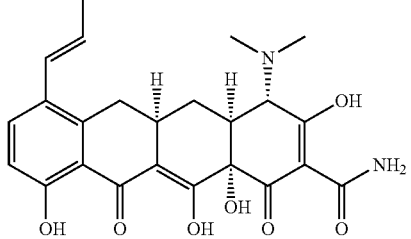
968
-continued
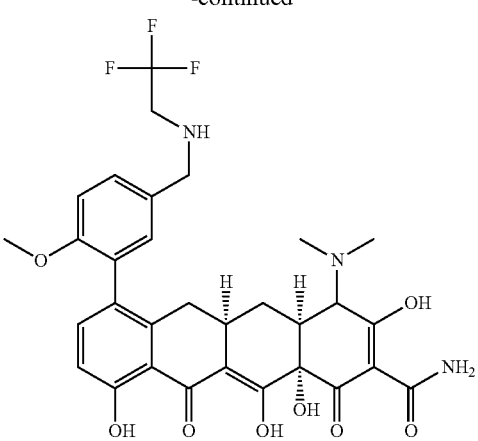
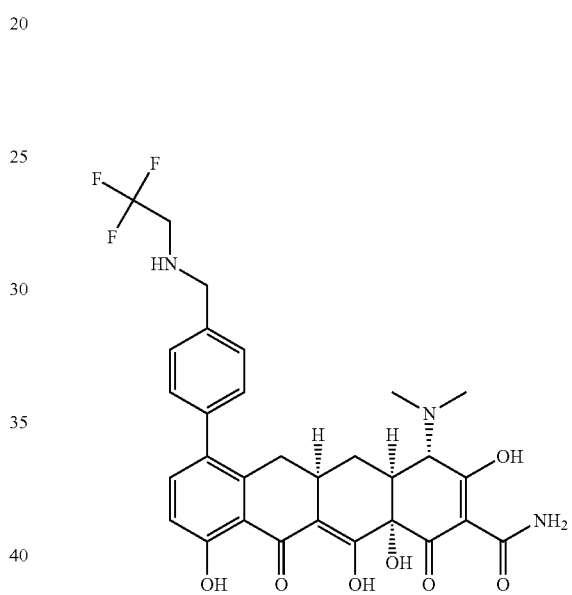
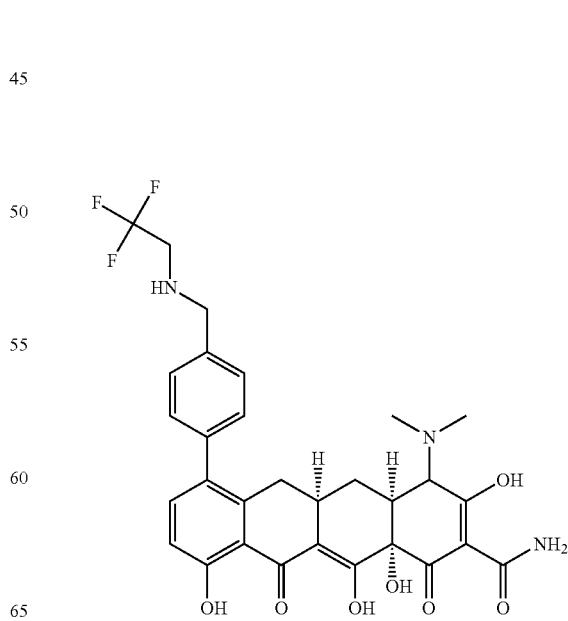

| 969 | 970 |
|---|---|
| -continued | -continued |
| 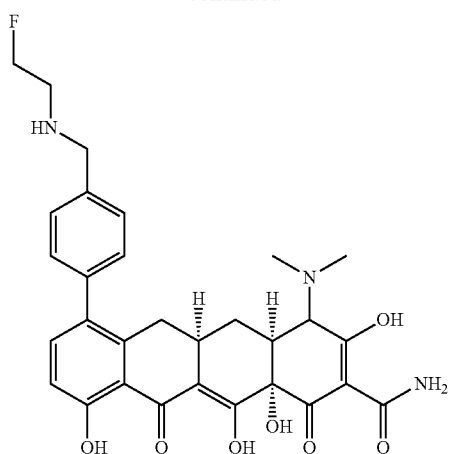 | 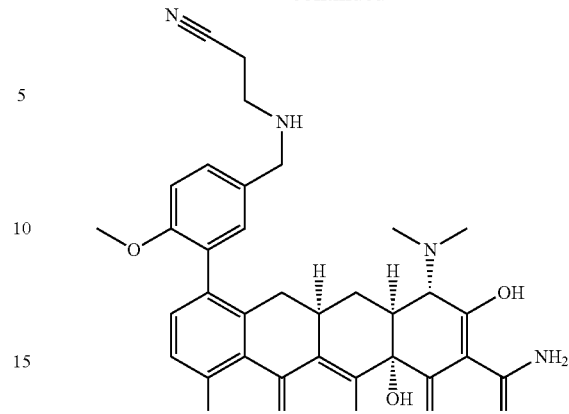 |
| 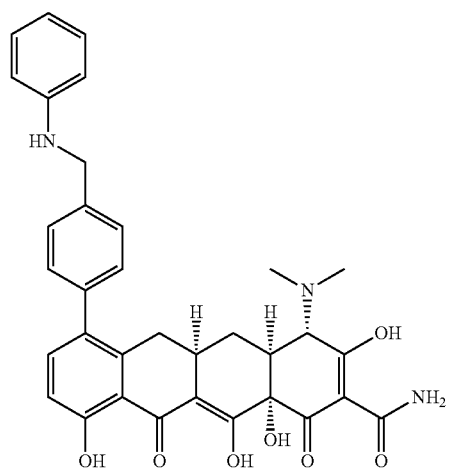 | 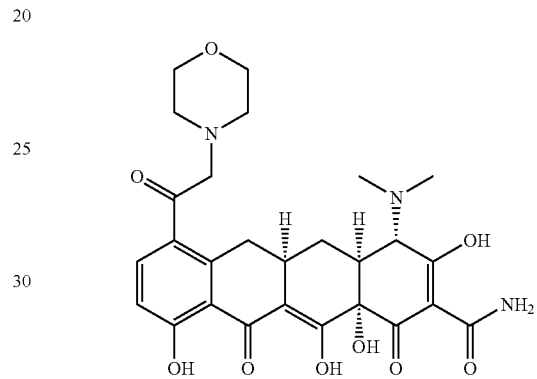 |
| | 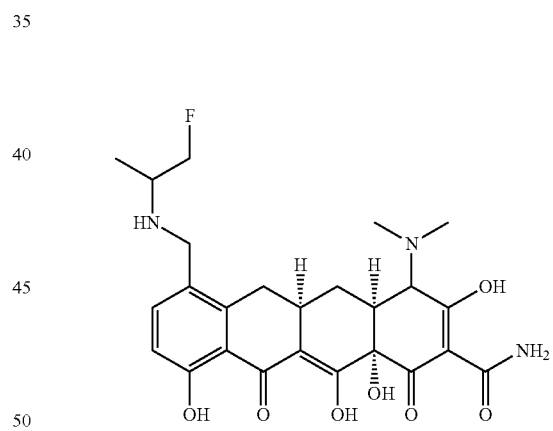 |
| 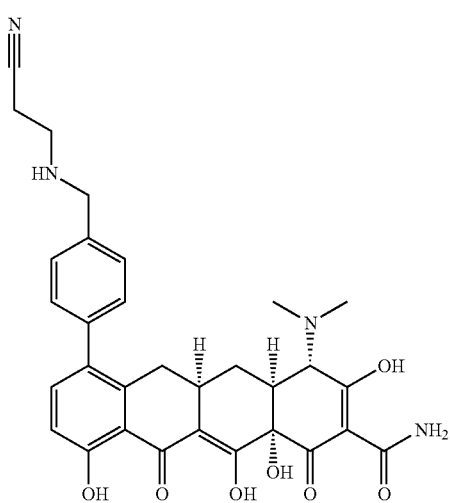 | 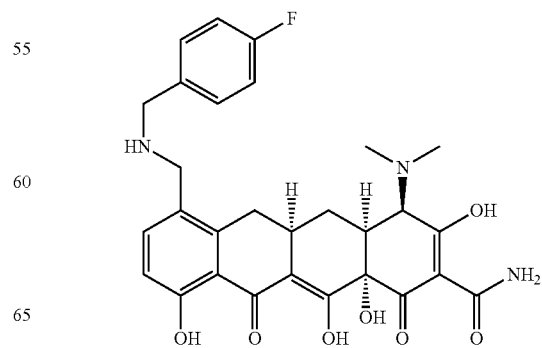 |

971
-continued
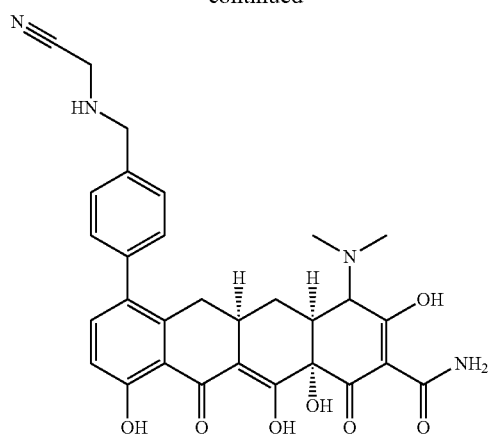
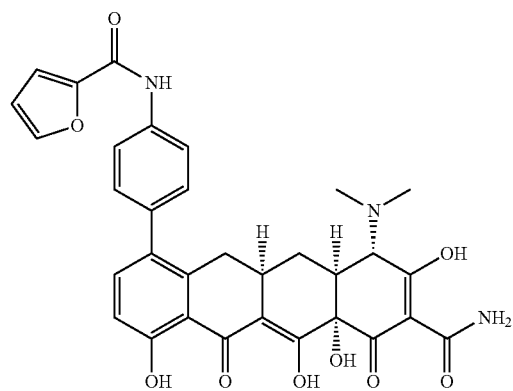
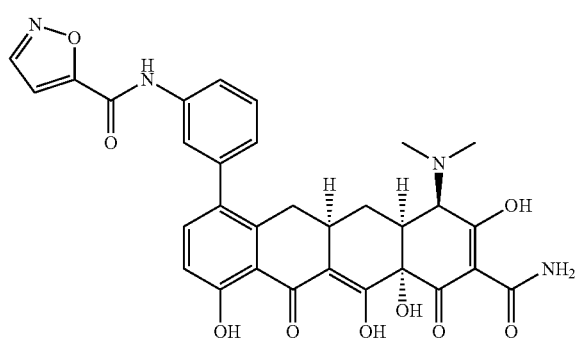
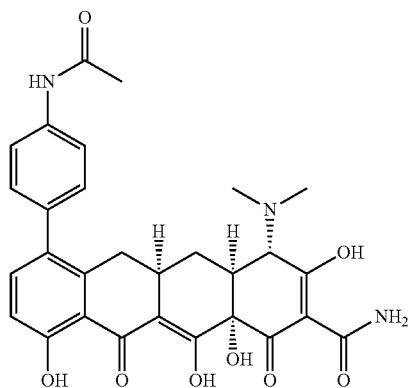
972
-continued
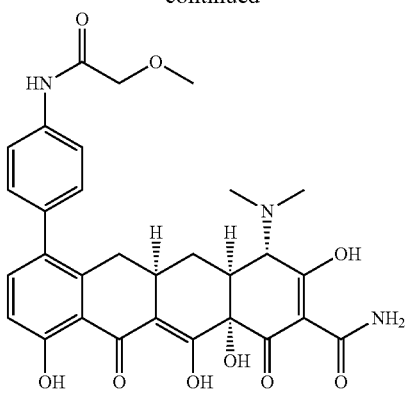
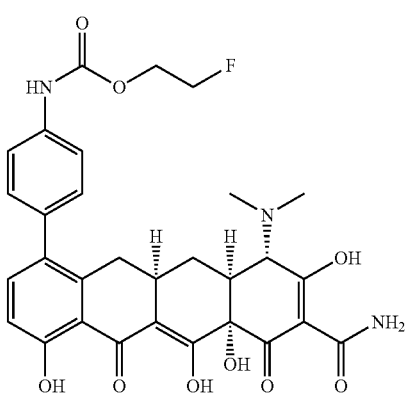
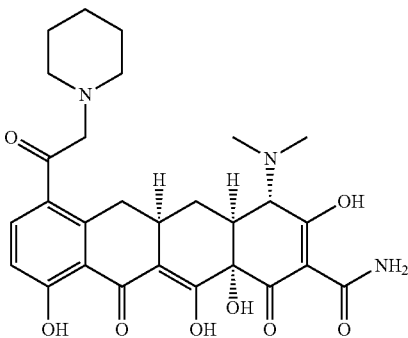
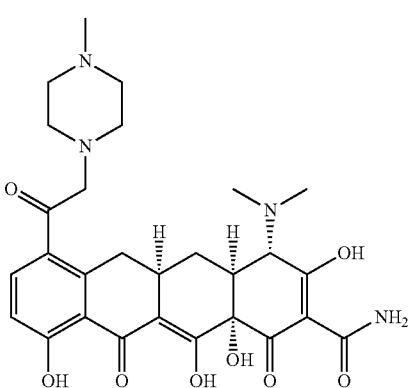

973
-continued
974
-continued
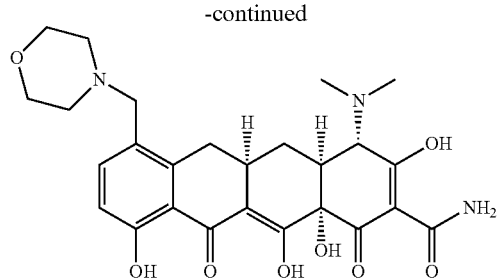
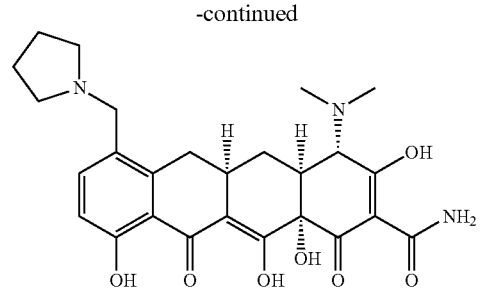
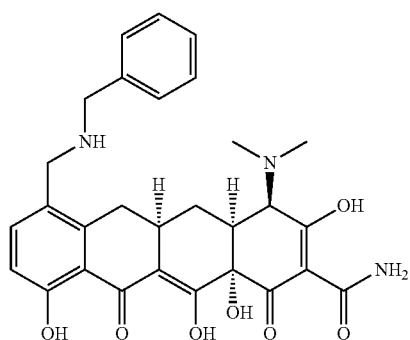
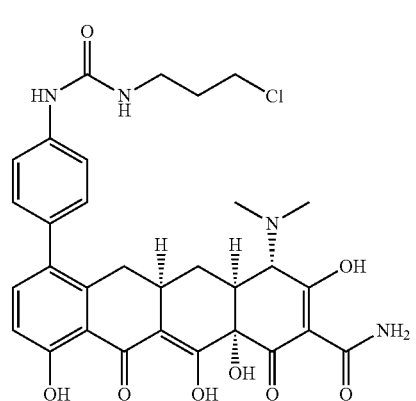
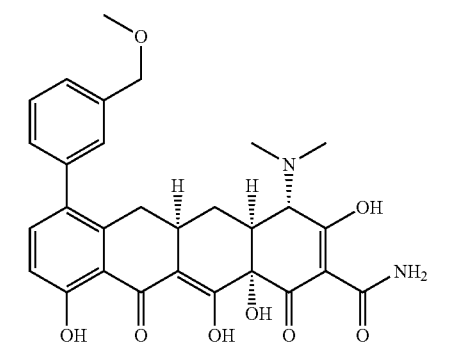
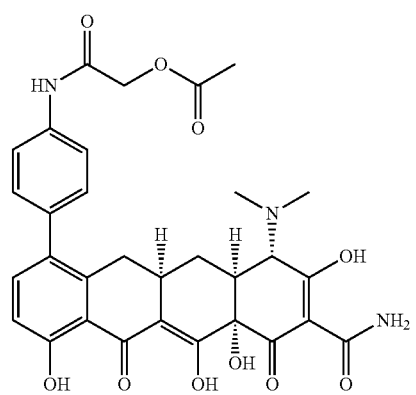
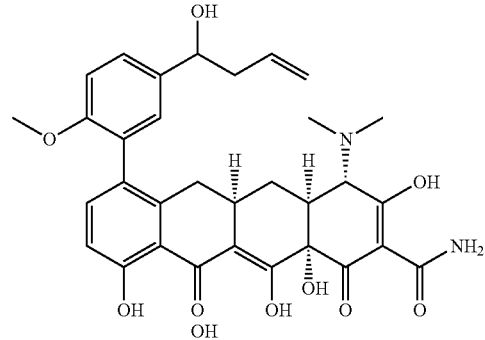
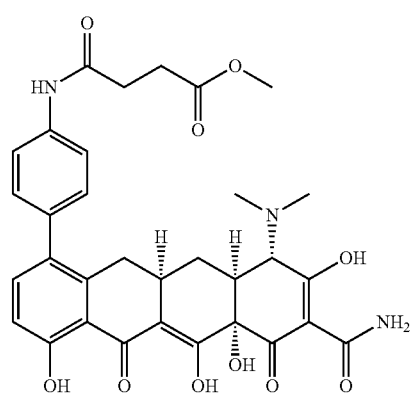
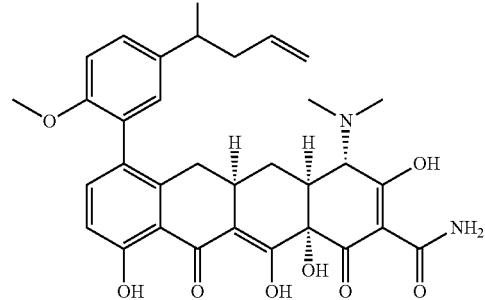

975
-continued
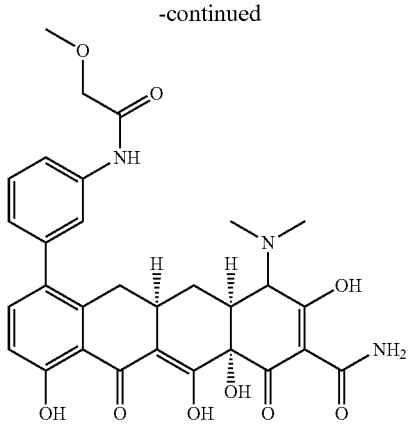
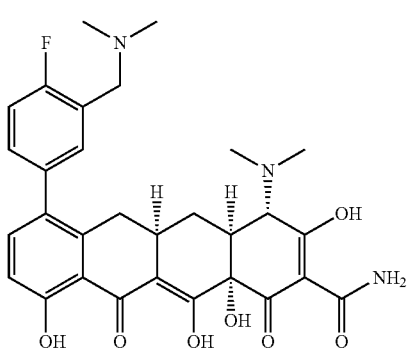
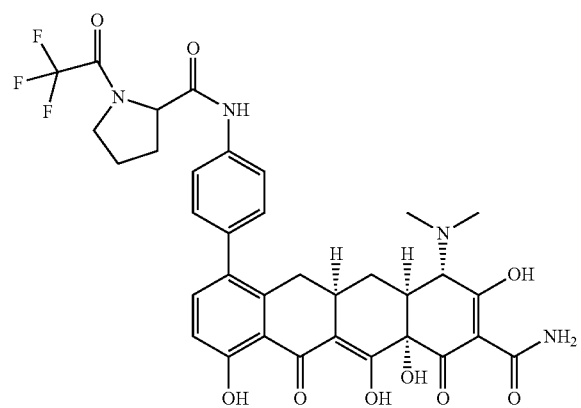
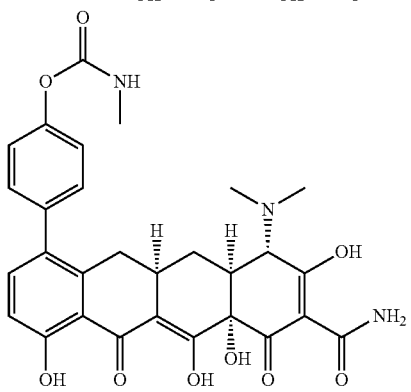
976
-continued
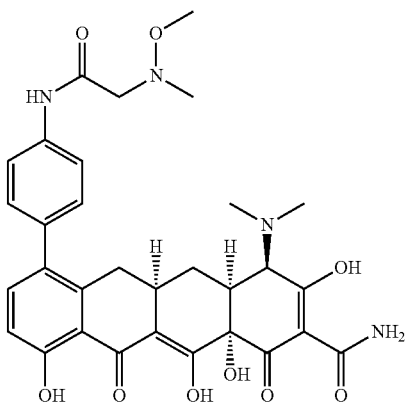
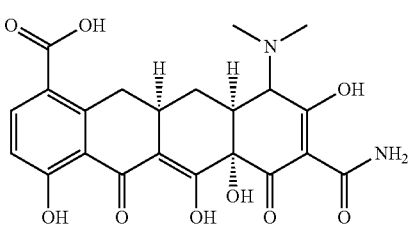
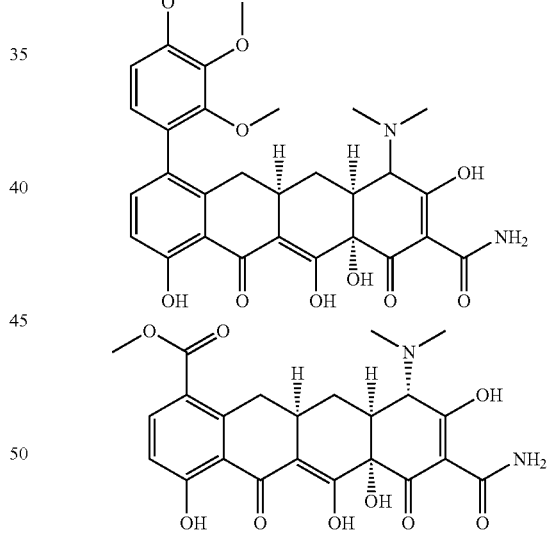
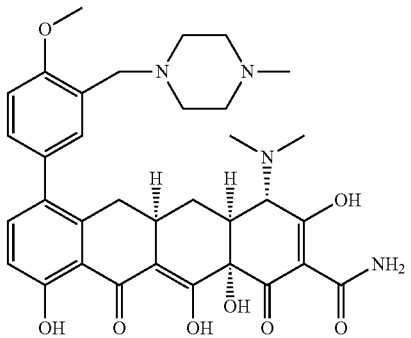

977
-continued
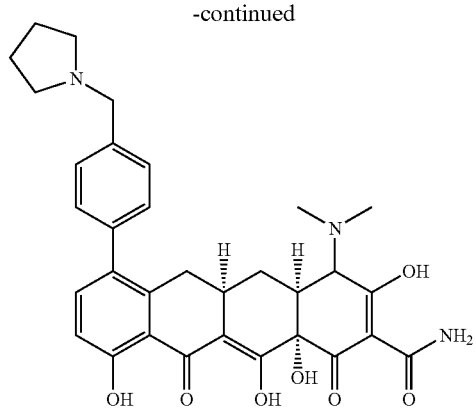
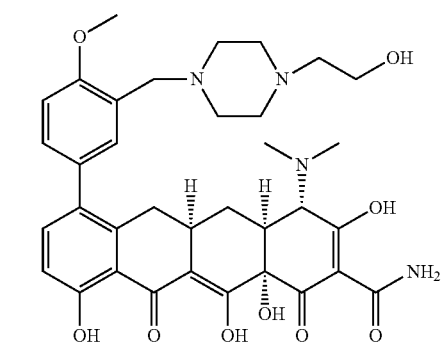
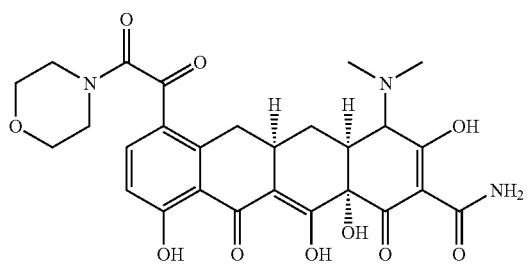
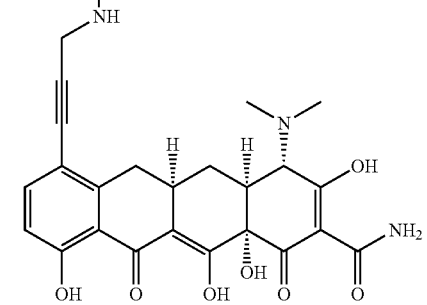
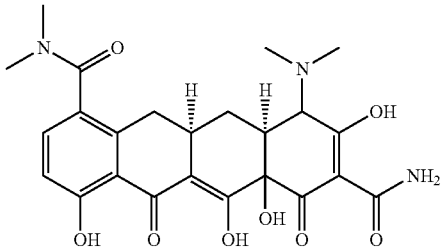
978
-continued
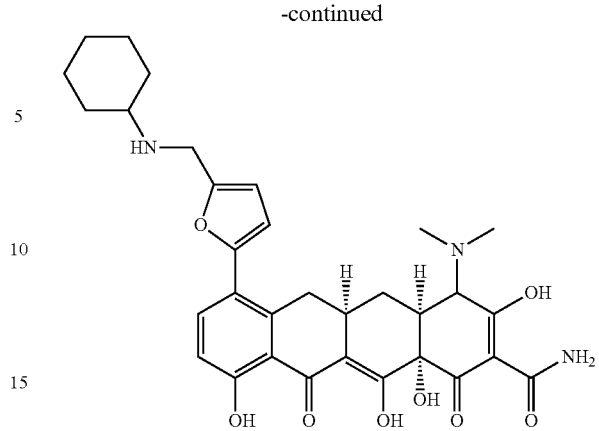
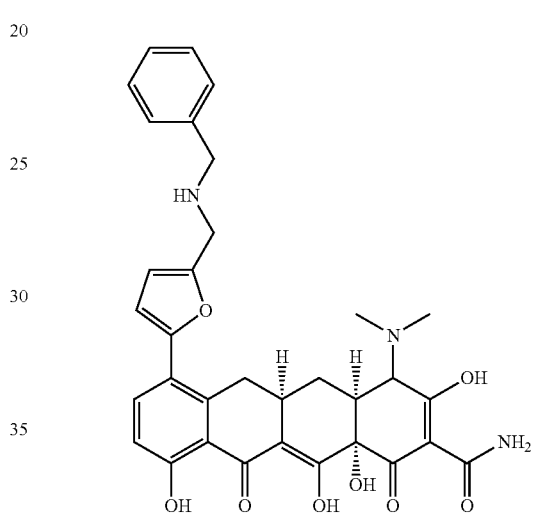
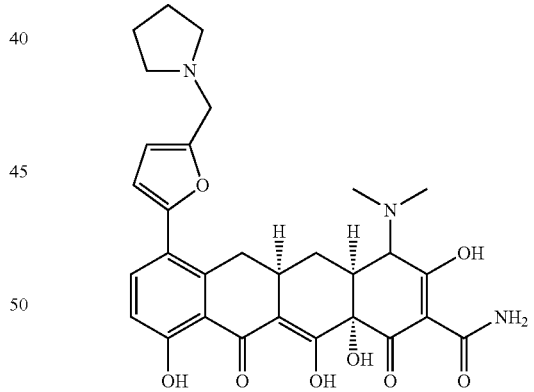
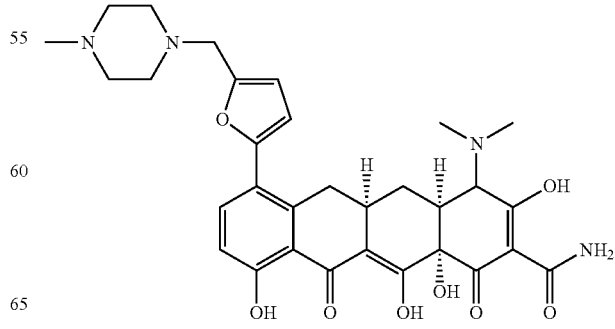

979
-continued
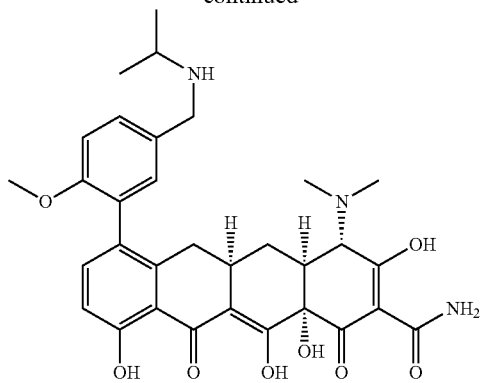
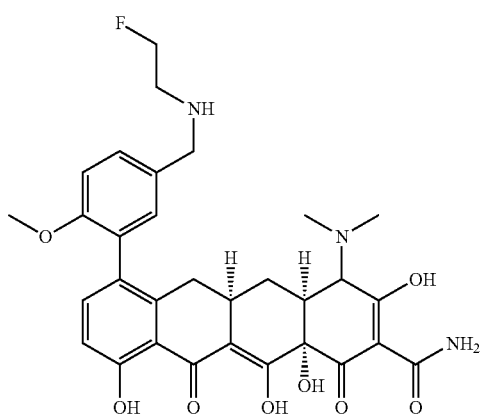
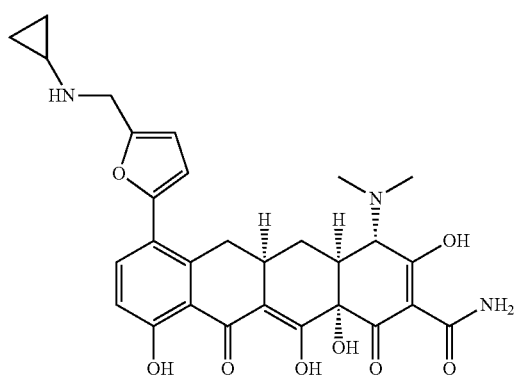
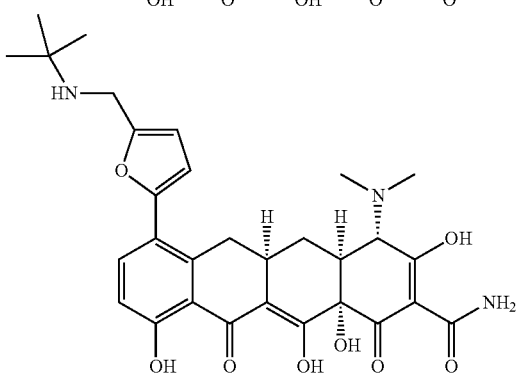
980
-continued
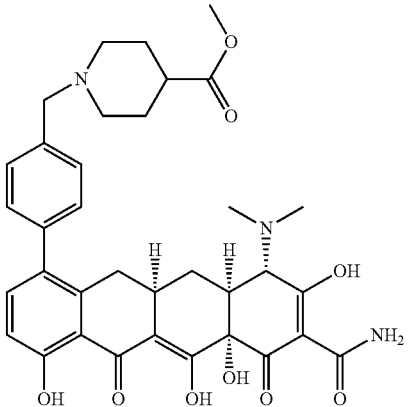
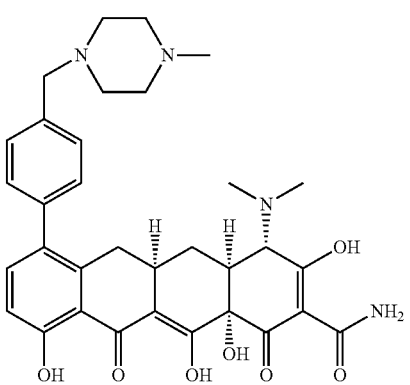
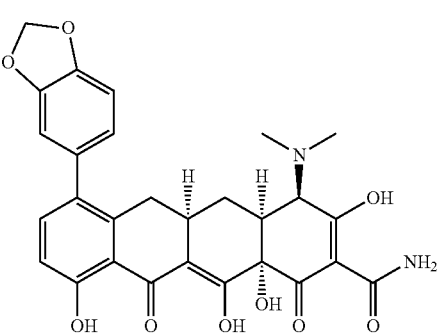
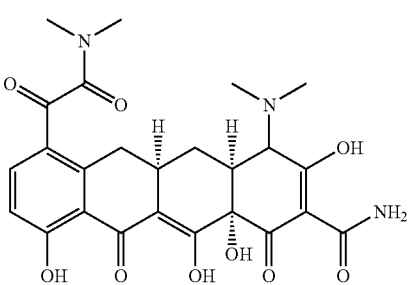

981
-continued
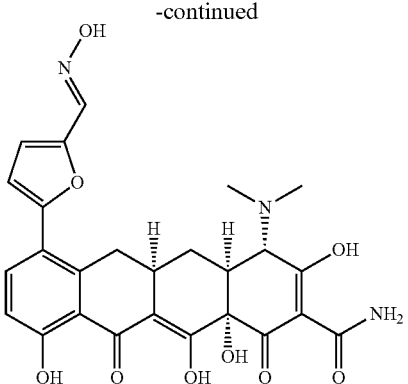
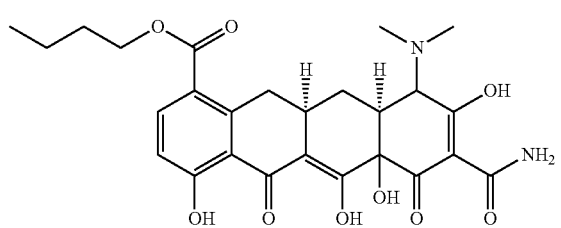
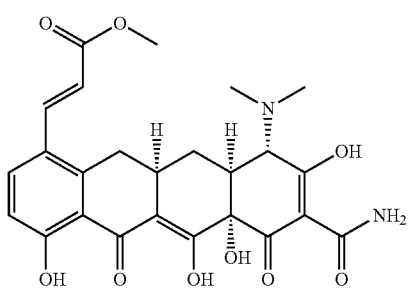
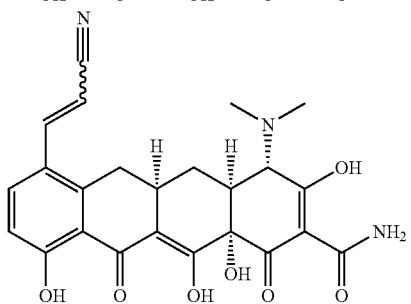
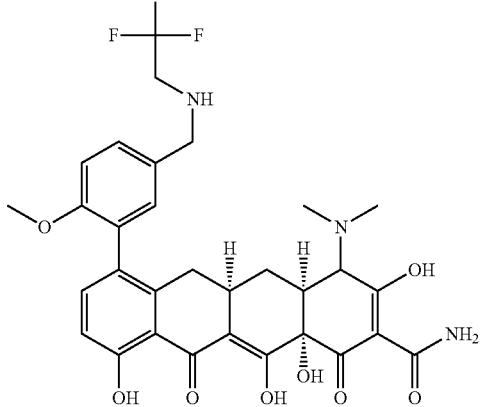
982
-continued
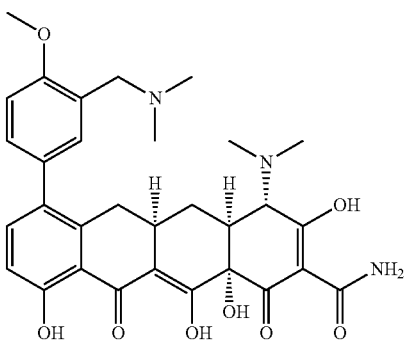
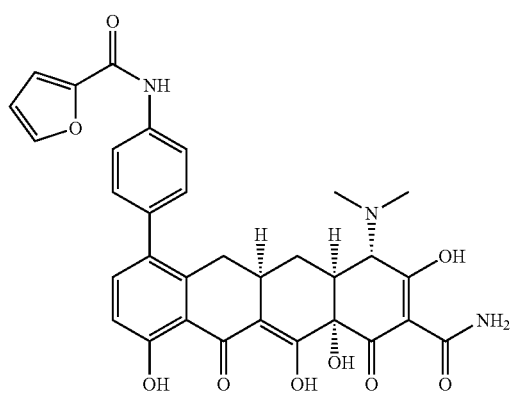
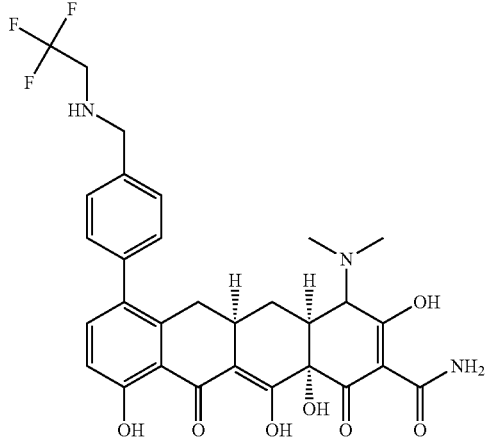
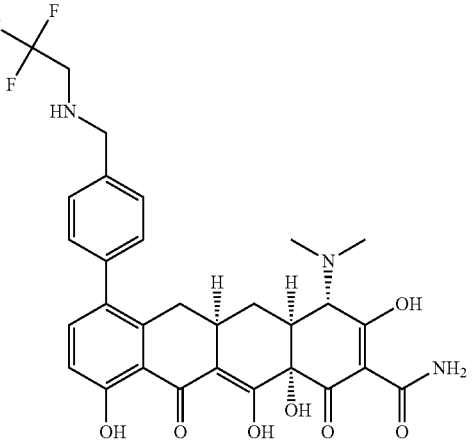

983
-continued
984
-continued
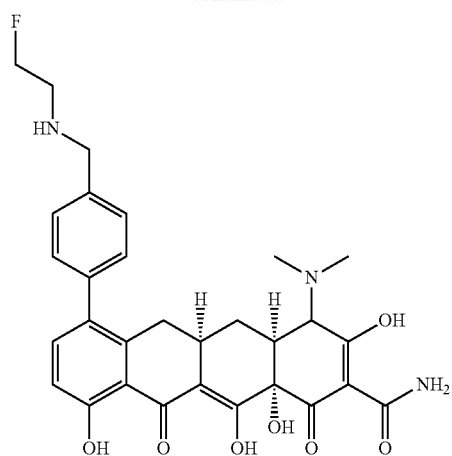
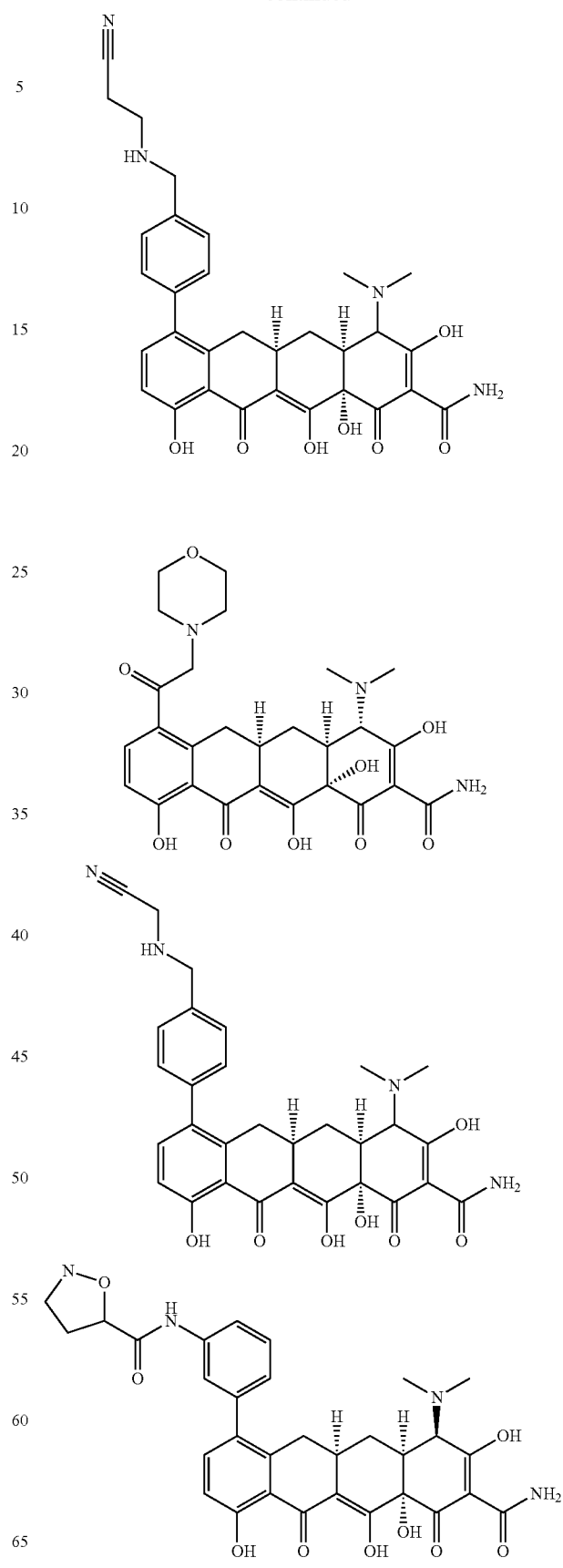
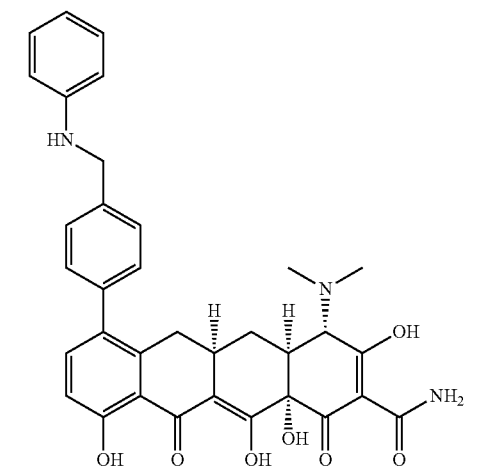
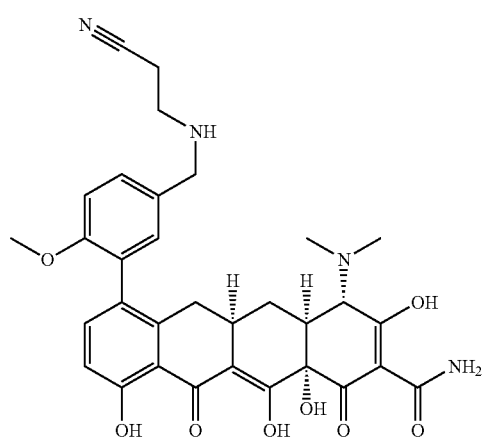

| 985 -continued | 986 -continued |
|---|---|
| 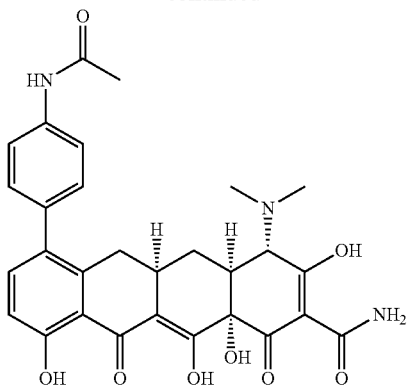 | 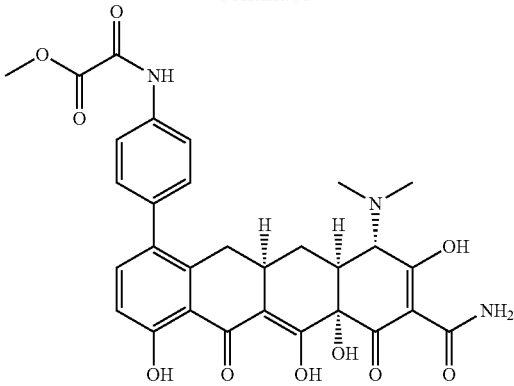 |
| 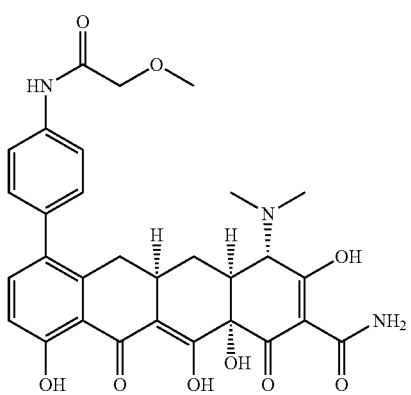 | 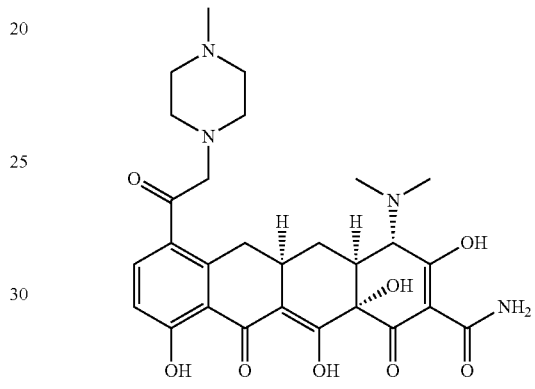 |
| 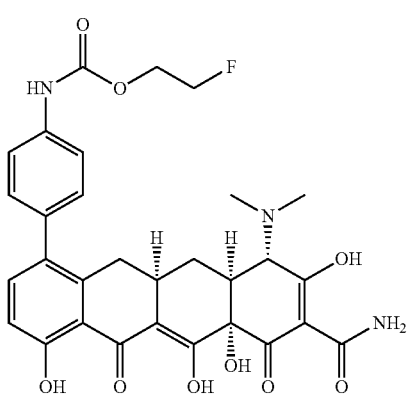 | 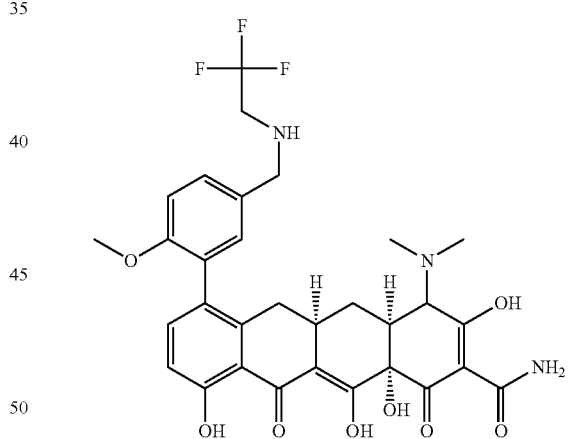 |
| 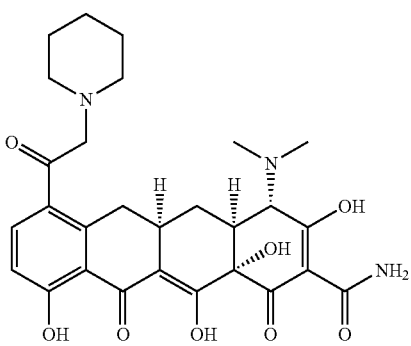 | 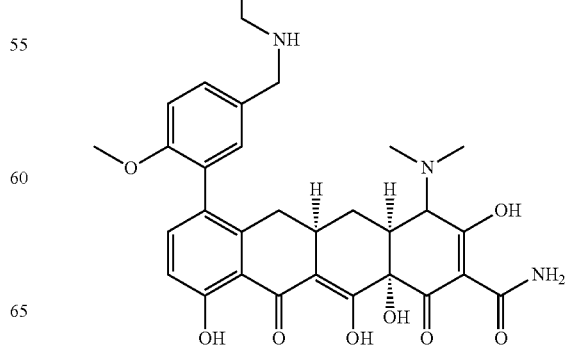 |

987
-continued
988
-continued
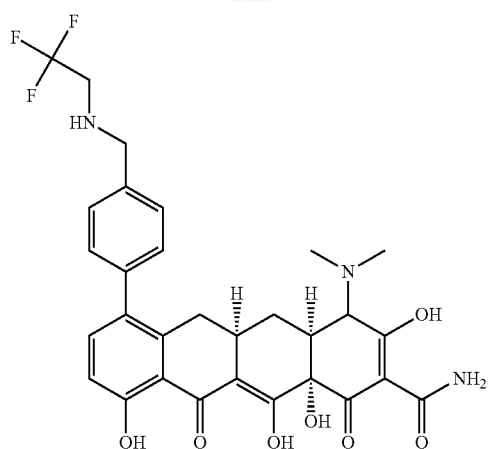
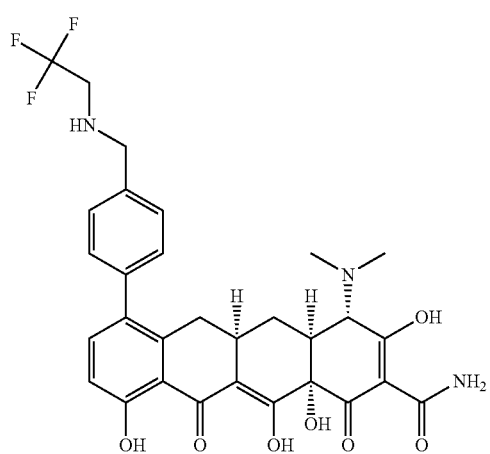
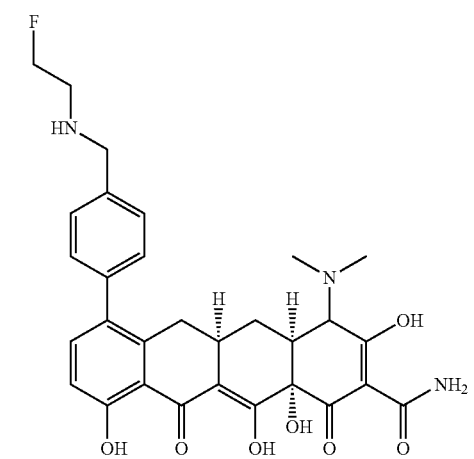
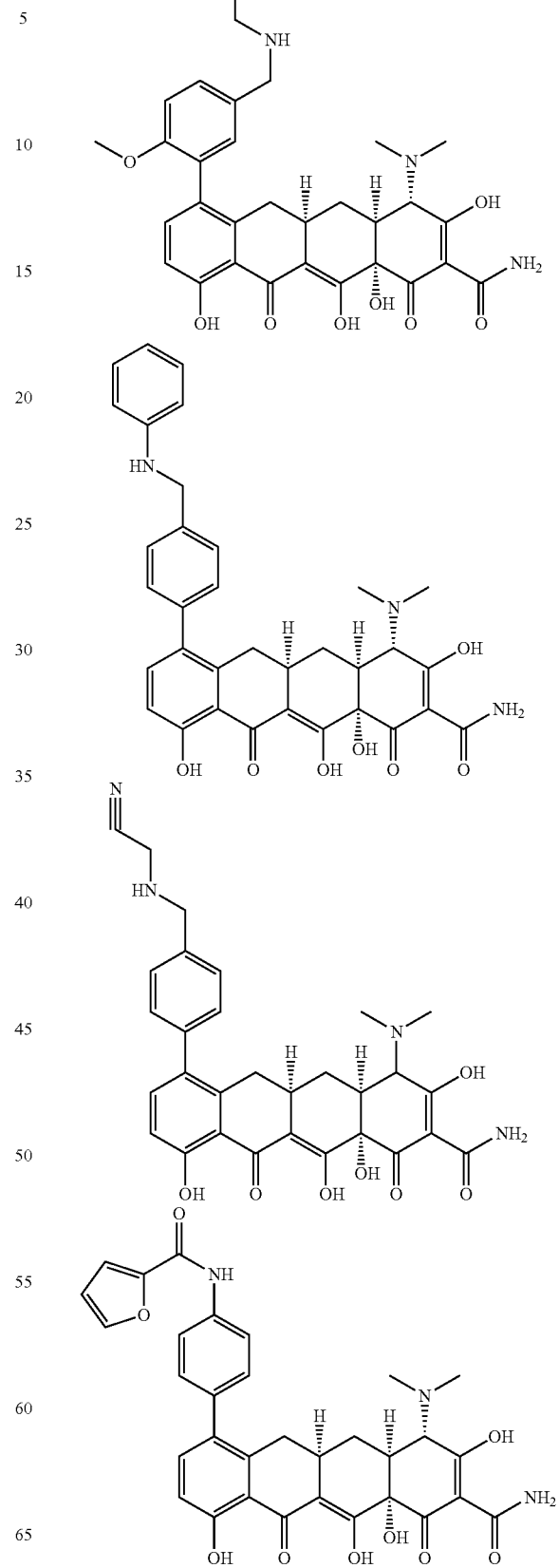

989
-continued
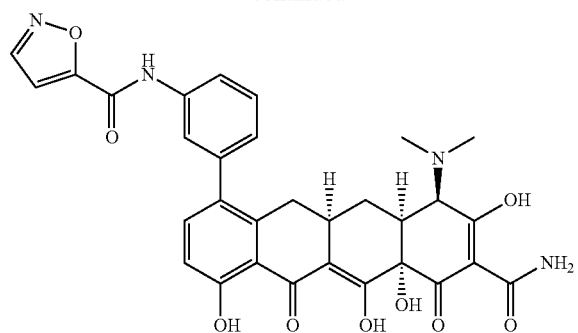
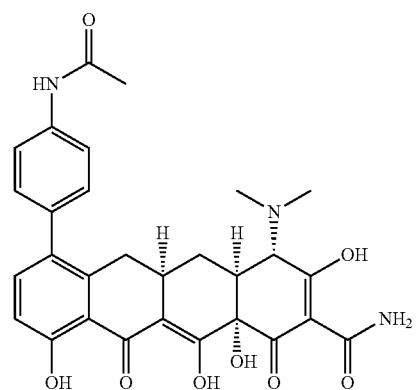
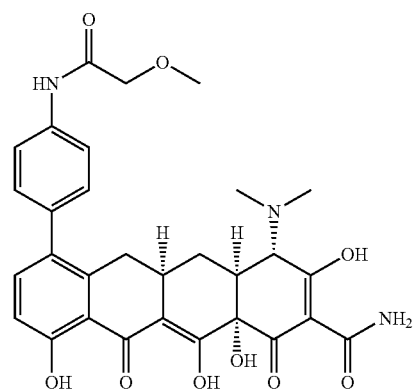
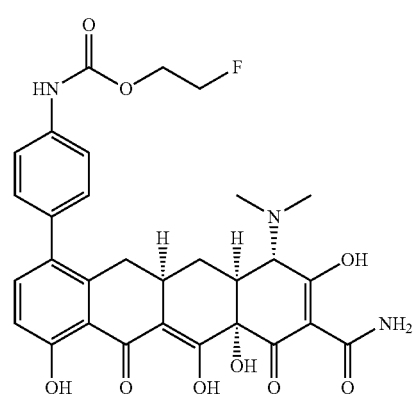
990
-continued
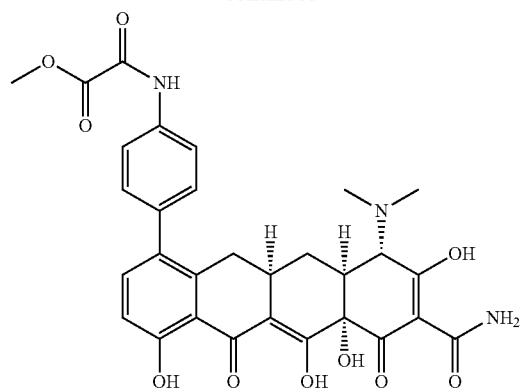
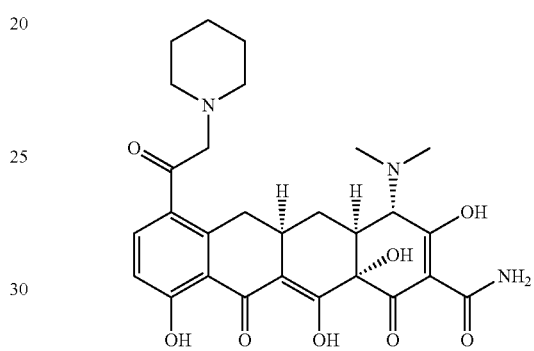
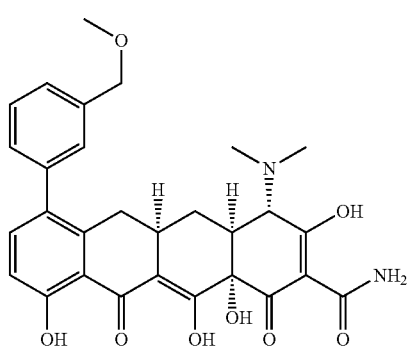
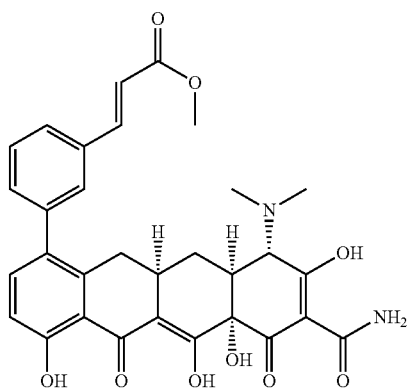

991
-continued
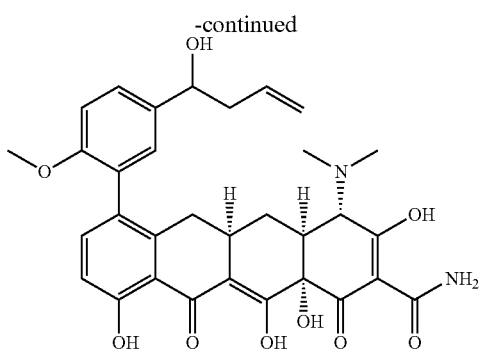
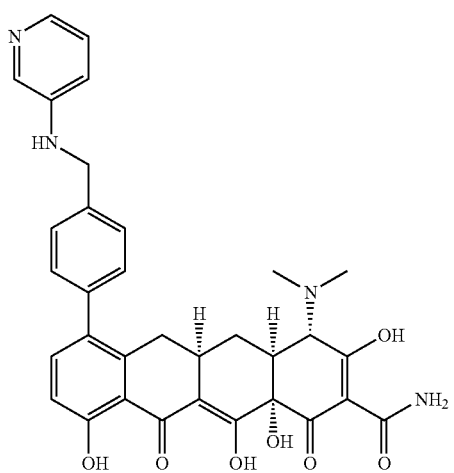
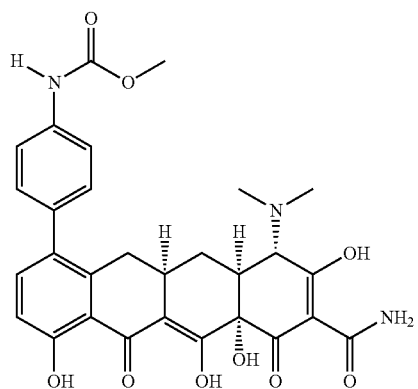
992
-continued
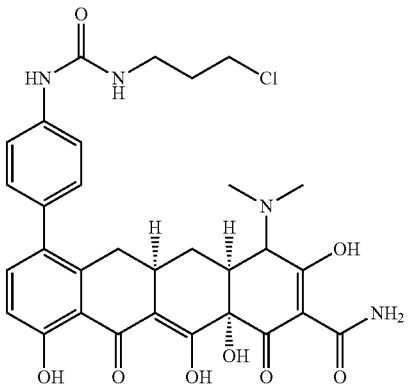
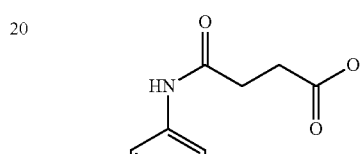
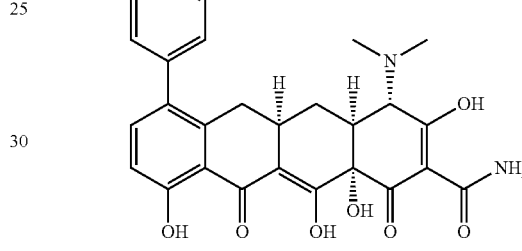
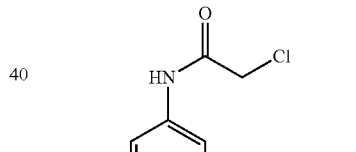
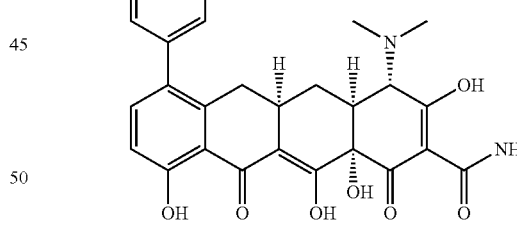
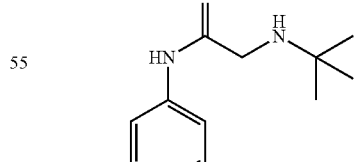
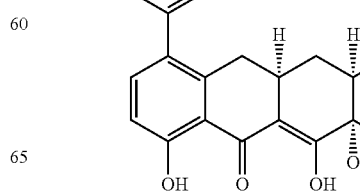
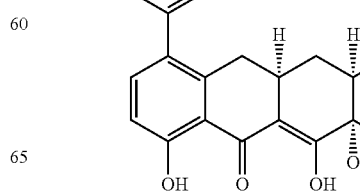

| 993 | 994 |
|---|---|
| -continued | -continued |
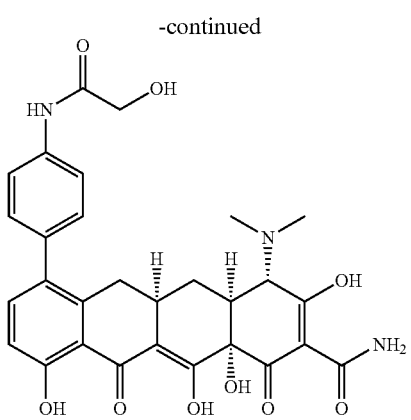
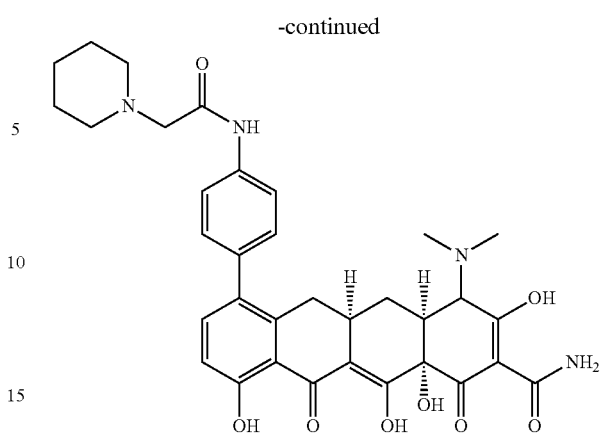
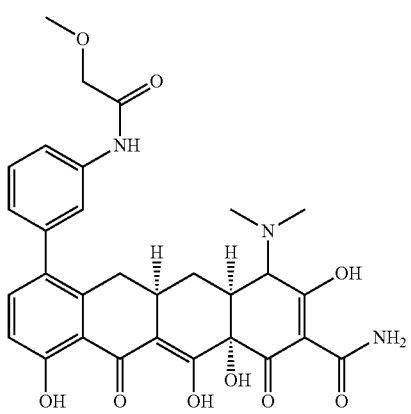
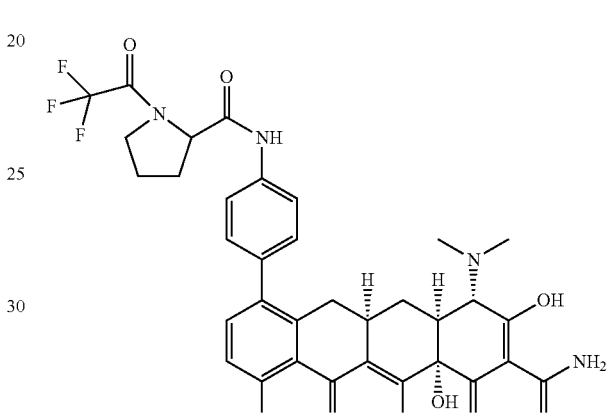
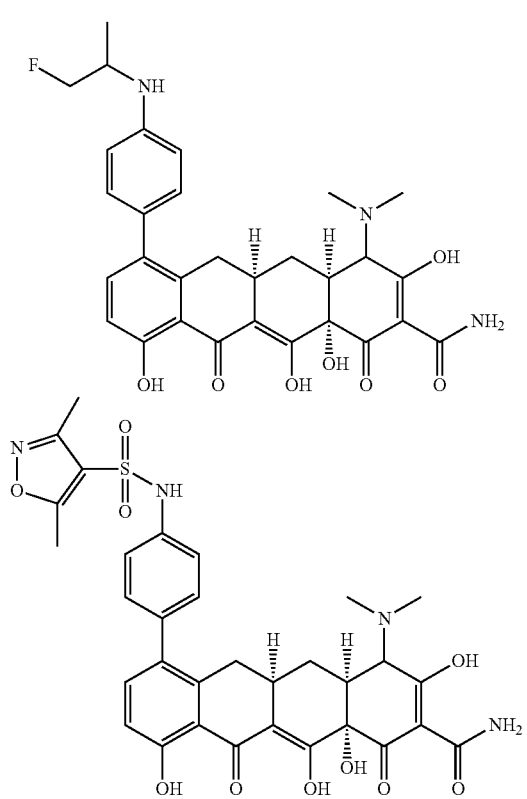
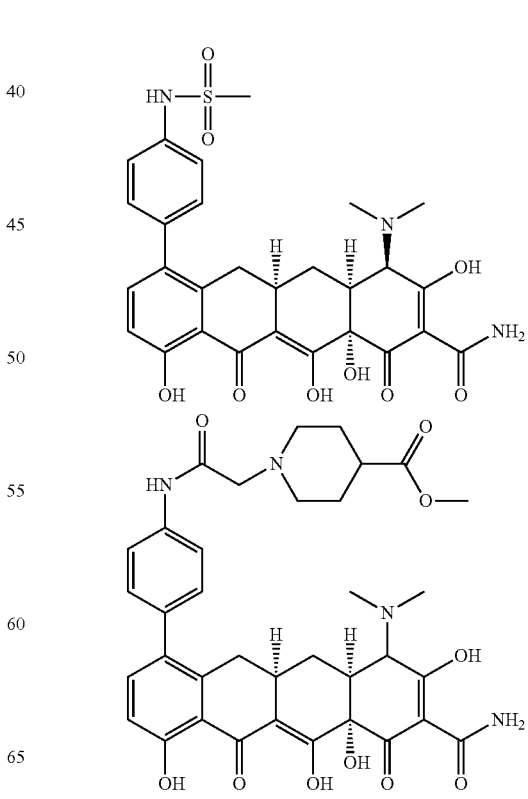

995
-continued
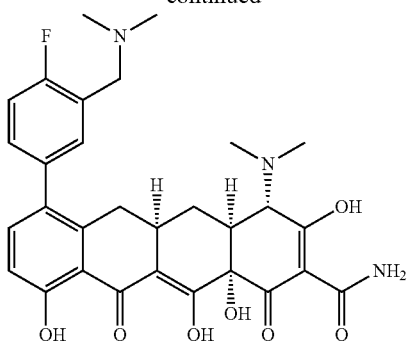
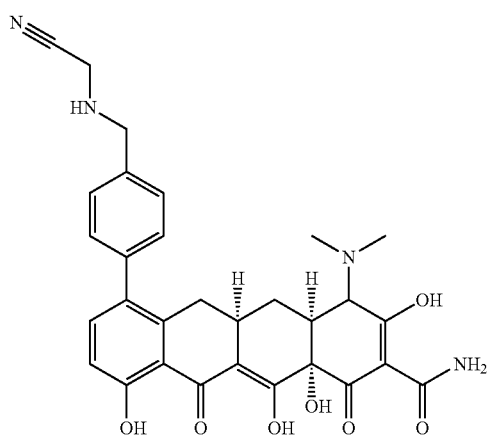
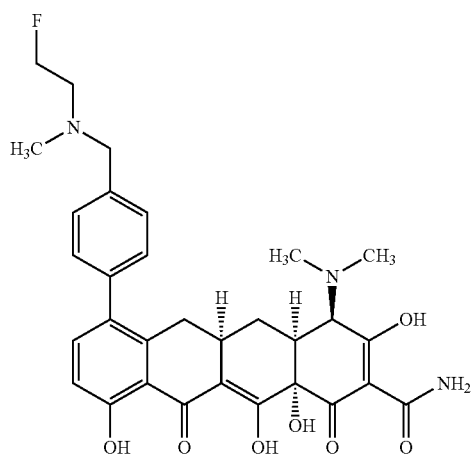
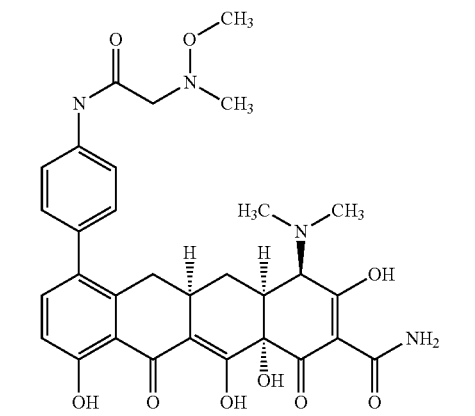
996
-continued
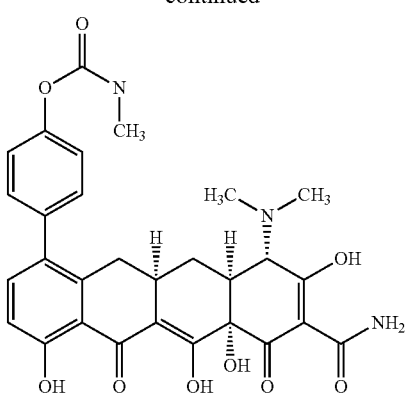
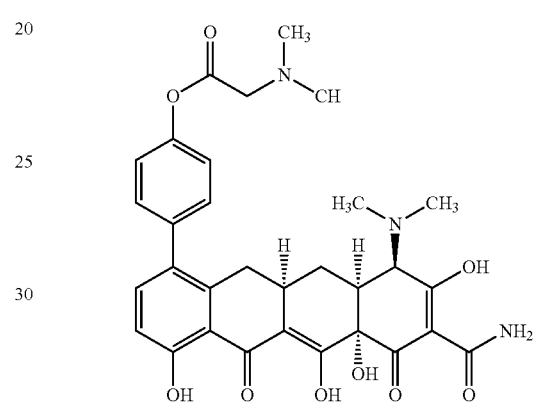
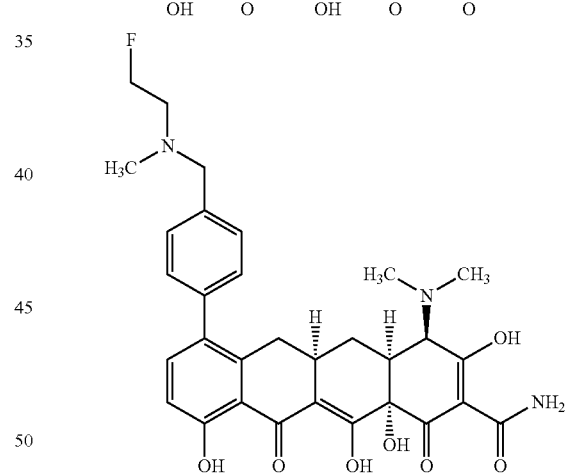
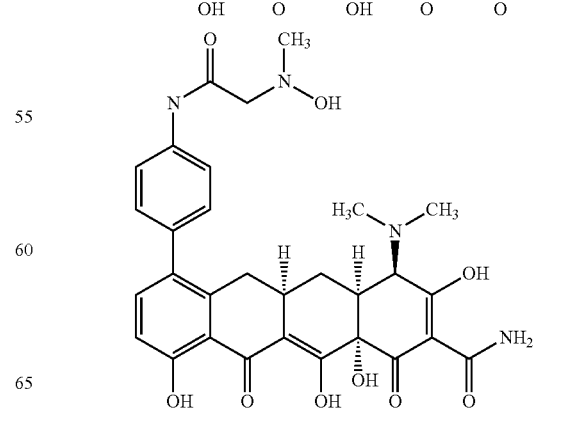

997 998
-continued -continued
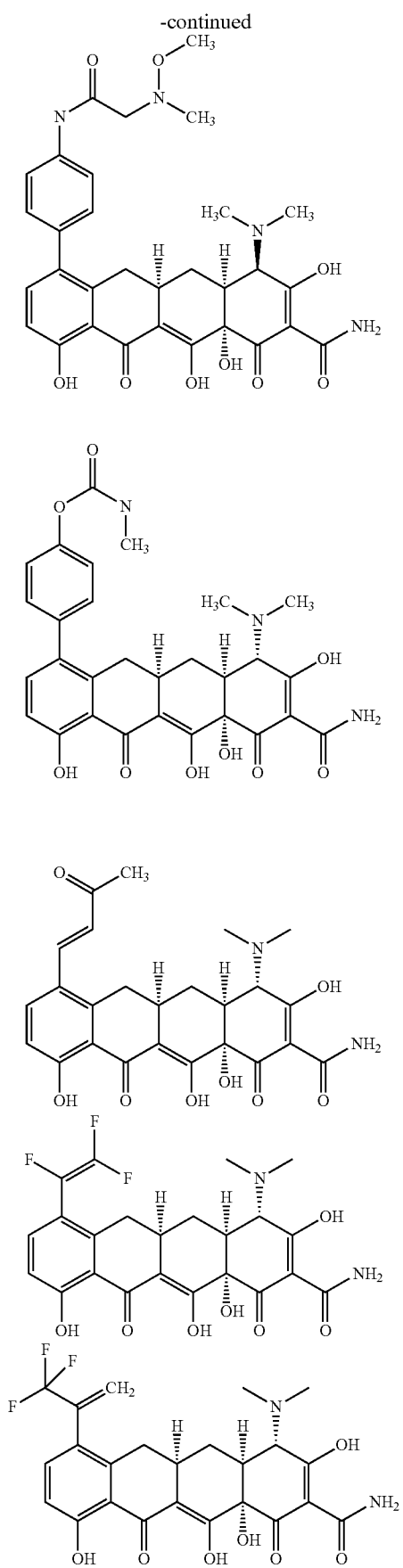
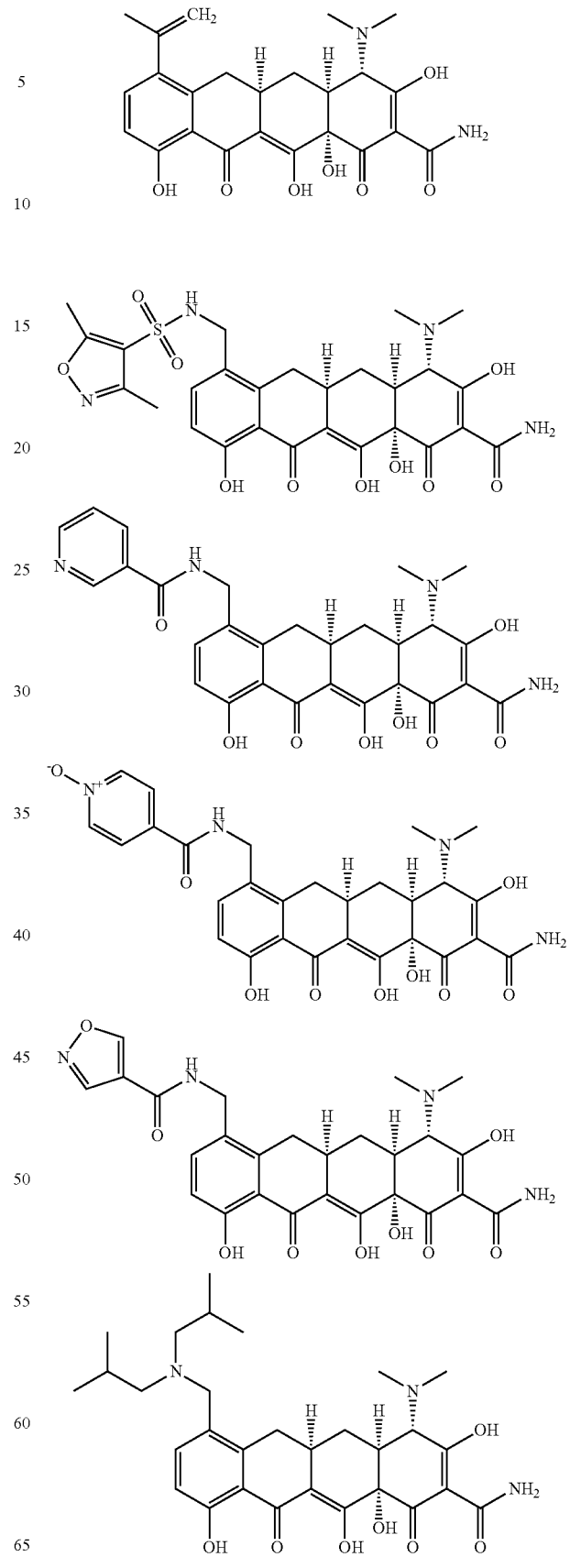

| 999 -continued | 1000 -continued |
|---|---|
| 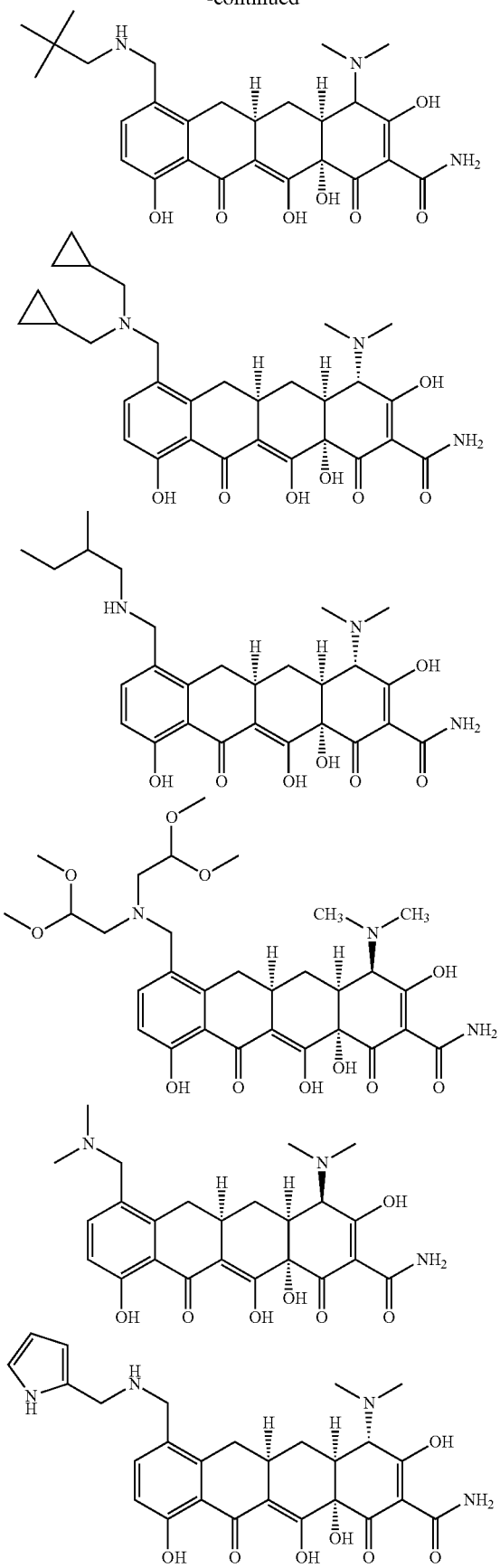 | 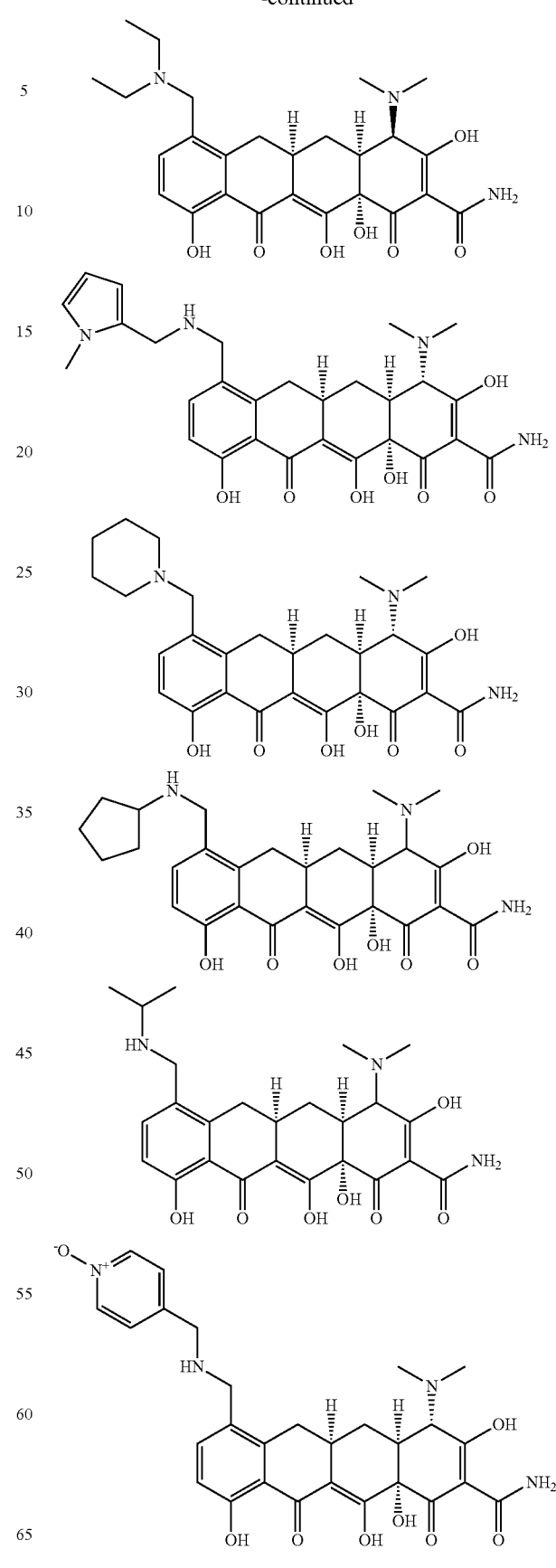 |

1001
-continued

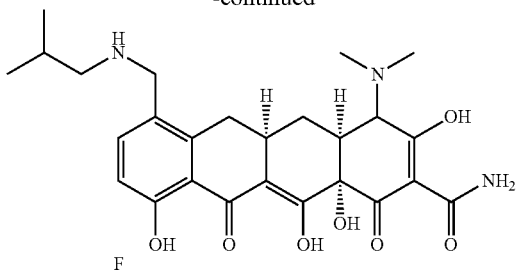

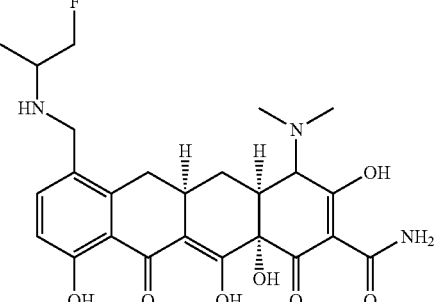

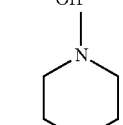

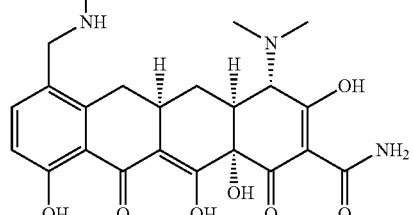

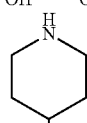

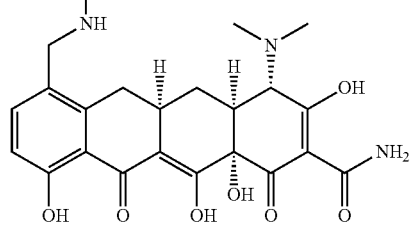

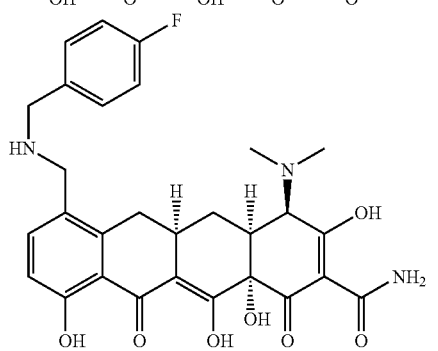

1002
-continued

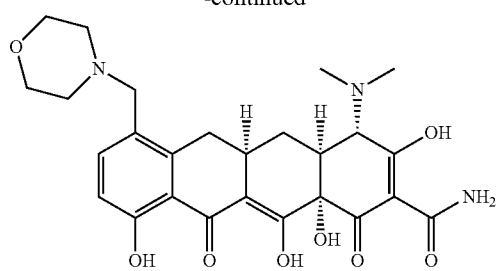

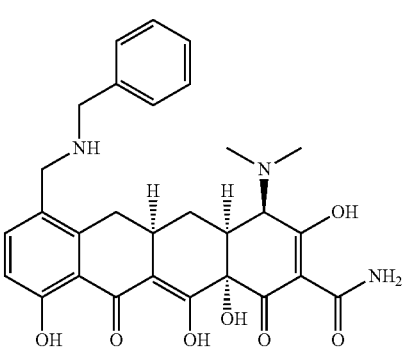

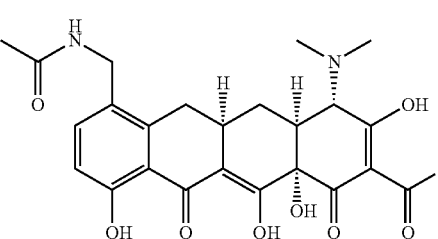

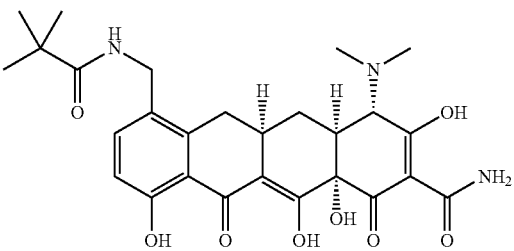

and pharmaceutically acceptable salts, esters and enantiomers thereof; such that said DTMR associated with splicing of nuclear RNA is treated, wherein said DTMR associated with splicing of nuclear RNA is spinal muscular atrophy, and further wherein said effective amount is effective to modulate splicing of said subject's nuclear RNA.

\* \* \* \* \*

UNITED STATES PATENT AND TRADEMARK OFFICE
CERTIFICATE OF CORRECTION

PATENT NO. : 8,173,624 B2
APPLICATION NO. : 10/692764
DATED : May 8, 2012
INVENTOR(S) : Stuart B. Levy et al.

Page 1 of 2

It is certified that error appears in the above-identified patent and that said Letters Patent is hereby corrected as shown below:

In the Claims

In claim 1, at column 921, line 40, "$R^4$ is $NeR^{4'}R^{4''}$" should read -- $R^4$ is $NR^4R^{4''}$ --, In claim 17, at column 949, lines 15 to 30, the formula should appear as follows:

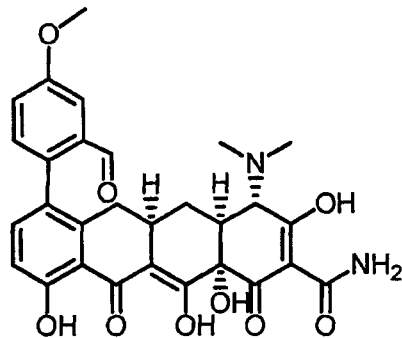

In claim 17, at column 984, lines 53 to 65, the formula should appear as follows:

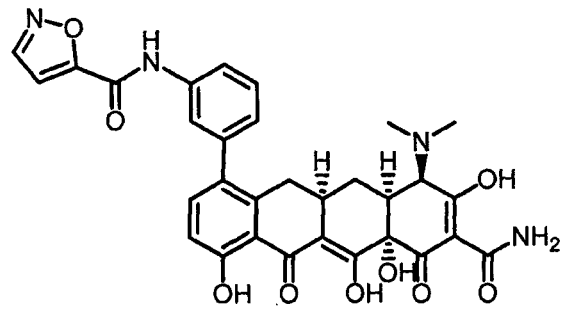

Signed and Sealed this
Third Day of June, 2014

Michelle K. Lee
*Deputy Director of the United States Patent and Trademark Office*

CERTIFICATE OF CORRECTION (continued)
U.S. Pat. No. 8,173,624 B2

In claim 17, at column 996, lines 20 to 34, the formula should appear as follows: